United States Patent
Weng et al.

(10) Patent No.: US 10,434,182 B2
(45) Date of Patent: Oct. 8, 2019

(54) EIGHT-ARM POLYETHYLENE GLYCOL DERIVATIVE, PRODUCTION METHOD THEREFOR, AND MODIFIED BIO-RELATED SUBSTANCE THEREOF

(71) Applicant: XIAMEN SINOPEG BIOTECH CO., LTD., Xiamen (CN)

(72) Inventors: Wengui Weng, Xiamen (CN); Chao Liu, Xiamen (CN); Ce Yan, Xiamen (CN); Huihuang Su, Xiamen (CN); Chun Zhou, Xiamen (CN)

(73) Assignee: Xiamen Sinopeg Biotech Co., Ltd., Xiamen (CN)

( * ) Notice: Subject to any disclaimer, the term of this patent is extended or adjusted under 35 U.S.C. 154(b) by 85 days.

(21) Appl. No.: 15/738,761

(22) PCT Filed: Jun. 8, 2016

(86) PCT No.: PCT/CN2016/085286
§ 371 (c)(1),
(2) Date: Dec. 21, 2017

(87) PCT Pub. No.: WO2016/206540
PCT Pub. Date: Dec. 29, 2016

(65) Prior Publication Data
US 2018/0214561 A1    Aug. 2, 2018

(30) Foreign Application Priority Data

Jun. 23, 2015    (CN) .......................... 2015 1 0349134

(51) Int. Cl.
*A61K 47/60*    (2017.01)
*C08G 65/334*    (2006.01)
(Continued)

(52) U.S. Cl.
CPC .............. *A61K 47/60* (2017.08); *A61K 47/10* (2013.01); *A61K 47/50* (2017.08); *C08G 65/332* (2013.01);
(Continued)

(58) Field of Classification Search
CPC .............................. A61K 47/60; C08G 83/002
See application file for complete search history.

(56) References Cited

U.S. PATENT DOCUMENTS

| 5,811,510 A | 9/1998 | Papisov |
|---|---|---|
| 7,790,150 B2 | 9/2010 | Papisov et al. |

(Continued)

FOREIGN PATENT DOCUMENTS

| CN | 1381512 A | 11/2002 |
|---|---|---|
| CN | 1569892 A | 1/2005 |

(Continued)

OTHER PUBLICATIONS

Im et al., Biomaterials, 34(8):2098-106 (2013).
(Continued)

*Primary Examiner* — Kyle A Purdy
(74) *Attorney, Agent, or Firm* — RatnerPrestia

(57) ABSTRACT

Disclosed are an eight-arm polyethylene glycol (PEG) derivative (formula I), production method therefor and modified bio-related substance thereby. Wherein, one tetravalent group U together with four trivalent groups $E_c$ form a highly symmetrical octavalent group $CORE_0$; $L_c$ connects the octavalent group to eight PEG chains having polydispersity or monodispersity and having $n_1$ to $n_8$ as the degree of polymerization thereof; the terminal of one PEG chain is connected to at least one functional group F ($k \geq 1$); said PEG chain and F therebetween can be directly connected ($g=0$) or be indirectly connected via a linking group $L_0$ to a terminal end-branching group G ($g=1$); the latter provides more reactive sites for binding more drug molecules and increases the drug loading. The eight-arm polyethylene glycol derivative has a centrosymmetric or approximately centrosymmetric structure, and leads to more precise control of the molecular weight in large-scale production and much narrower distribution of molecular weight for products. The modified bio-related substance thereby has a more uniform and controllable performance.

(1c)

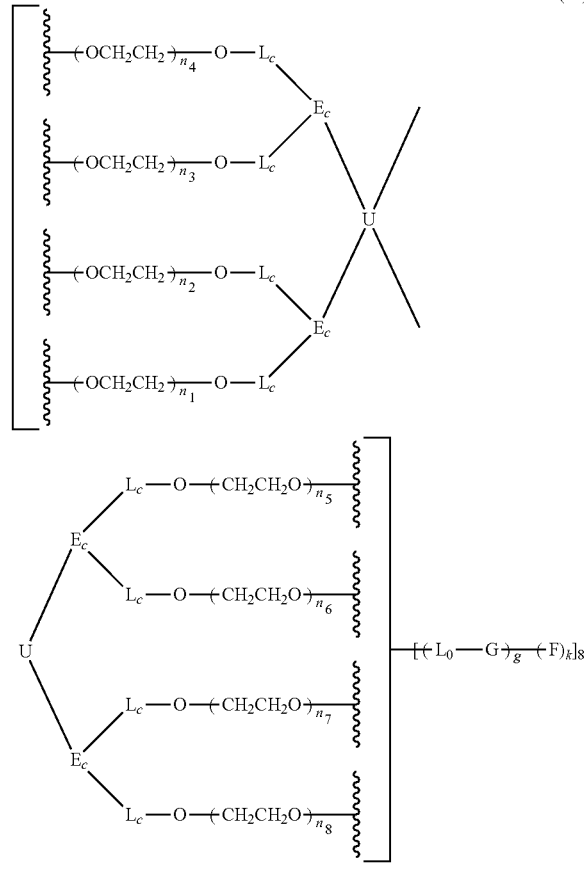

(Continued)

-continued

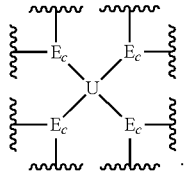

40 Claims, No Drawings

(51) Int. Cl.

| | |
|---|---|
| *C08G 65/332* | (2006.01) |
| *C08G 65/333* | (2006.01) |
| *A61K 47/50* | (2017.01) |
| *C08G 83/00* | (2006.01) |
| *A61K 47/10* | (2017.01) |

(52) U.S. Cl.
CPC ......... *C08G 65/333* (2013.01); *C08G 65/334* (2013.01); *C08G 65/33306* (2013.01); *C08G 65/33324* (2013.01); *C08G 83/002* (2013.01); *C08G 2650/32* (2013.01)

(56) References Cited

U.S. PATENT DOCUMENTS

| | | |
|---|---|---|
| 7,838,619 B2 | 11/2010 | Papisov |
| 9,315,445 B2 | 4/2016 | Urban et al. |
| 9,555,123 B2 | 1/2017 | Zhao et al. |
| 2005/0265922 A1 | 12/2005 | Nie et al. |
| 2011/0286956 A1 | 11/2011 | Zhao et al. |
| 2011/0305751 A1 | 12/2011 | Gaillard |
| 2015/0119281 A1 | 4/2015 | Hermanson et al. |
| 2017/0082642 A1 | 3/2017 | Korchagina et al. |

FOREIGN PATENT DOCUMENTS

| | | |
|---|---|---|
| CN | 1969190 A | 5/2007 |
| CN | 101679849 A | 3/2010 |
| CN | 101724144 A | 6/2010 |
| CN | 101831065 A | 9/2010 |
| CN | 102316902 A | 1/2012 |
| CN | 102367291 A | 3/2012 |
| CN | 103755949 A | 4/2014 |
| CN | 104530413 A | 4/2015 |
| CN | 104530415 A | 4/2015 |
| CN | 104530417 A | 4/2015 |
| CN | 104877127 A | 9/2015 |
| EP | 1 479 711 A1 | 11/2004 |
| EP | 2 360 203 A1 | 8/2011 |
| EP | 2 518 098 A1 | 10/2012 |
| WO | WO 2006/024953 A2 | 3/2006 |
| WO | WO 2008/066787 A2 | 6/2008 |

OTHER PUBLICATIONS

Abbasi et al., Nanoscale Research Letters, 9(247):1-10 (2014).
Ahmed and Tanaka, J. Org. Chem., 71:9884-86 (2006).
Albertazzi et al., Biomacromolecules, 13:4089-97 (2012).
Bailon and Berthold, Pharm Sci Technol Today, 1(8):352-6 (1998).
Bailon and Won, Expert Opinion Drug Deliver, 6(1):1-16 (2009).
Brocchini et al., Advanced Drug Delivery Reviews, 60:3-12 (2008).
Chan et al., Macromolecules, 43:4937-42 (2010).
Chang et al., Macromolecules, 33:4496-500 (2000).
Chang-Gong, Chinese Journal of Spectroscopy Laboratory, 30(5):2539-42 (2013) with English Abstract.
Cheng et al., Chem. Soc. Rev., 40:2673-703 (2011).
Conte et al., Chem. Commun., 47:11086-88 (2011).
Delius, Synlett, 27(02):177-80 (2016).
French et al., Angew. Chem., 121:1274-78 (2009).
Geschwind and Frey, Macromolecules, 46:3280-87 (2013).
Greenwald et al., J. Org. Chem., 60:331-36 (1995).
Hoogenboom, Angew. Chem. Int. Ed., 49:3415-17 (2010).
Ihre et al., J. Am. Chem. Soc., 123(25):5908-17 (2001).
International Preliminary Report on Patentability for Application No. PCT/CN2016/085286 dated Dec. 26, 2017.
International Search Report for International Application No. PCT/CN2016/085286 dated Aug. 29, 2016.
Ji et al., ACS Macro Letters, 5(1):78-82 (2016).
Kahveci et al., Macromol. Chem. Phys., 215:566-71 (2014).
Khire et al., J. Polymer Science: Part A: Polymer Chemistry, 46:6896-906 (2008).
Kim et al., Bioorganic & Medicinal Chemistry Letters, 25:38-42 (2015).
Lehn, Top Curr Chem, 322:1-32 (2012).
Li et al., Macromol. Biosci., 11:1570-78 (2011).
Mahou and Wandrey, Polymers, 4:561-89 (2012).
Mangold et al., Polym. Chem., 3:1714-21 (2012).
Maranski et al., Angew. Chem. Int. Ed., 53:6411-13 (2014).
Martin and Coller, Molecular Cell, 59:716-17 (2015).
Meguellati and Ladame, Top Curr Chem, 322:291-314 (2012).
Mommer et al., Macromol. Rapid Commun., 35:1986-93 (2014).
Monfardini et al., Bioconjugate Chem., 6:62-69 (1995).
Movellan et al., Biomaterials, 35:7940-50 (2014).
Pasut and Veronese, Journal of Controlled Release, 161:461-72 (2012).
Plas et al., Chem. Commun., 51:16338-41 (2015).
Povoski et al., Expert Rev. Mol. Diagn., 13(4):315-19 (2013).
Rajan et al., J. Controlled Release, 194:301-9 (2014).
Rocard et al., Angew. Chem. Int. Ed., 54:15739-43 (2015).
Rowan et al., Angew. Chem. Int. Ed., 41:898-952 (2002).
Schömer and Frey, Macromolecules, 45:3039-46 (2012).
Schömer et al., J. Polymer Science: Part A: Polymer Chemistry, 51:995-1019 (2013).
Vardhan, RSC Advances, 5:1-41 (2015).
Wang et al., Macromolecular Bioscience, 11:1553-62 (2011).
Wilms et al., Macromolecular Rapid Communications, 31:1811-15 (2010).
Wojtecki et al., J. Am. Chem. Soc., 137:14248-51 (2015).
Xi et al., Advanced Functional Materials, 24:2572-90 (2014).
Yuehua et al., Progress in Chemistry, 22(10): 1929-39 (2010) with English Abstract.
Zhang and Matile, Angew. Chem. Int. Ed., 54:8980-83 (2015).
Zhang et al., Angew. Chem. Int. Ed., 54:3763-67 (2015).
Zhu et al., Langmuir, 26(11):8875-81 (2010).

EIGHT-ARM POLYETHYLENE GLYCOL DERIVATIVE, PRODUCTION METHOD THEREFOR, AND MODIFIED BIO-RELATED SUBSTANCE THEREOF

CROSS-REFERENCE TO RELATED APPLICATIONS

This application is a U.S. national phase application of International Application No. PCT/CN2016/085286, filed Jun. 8, 2016 claiming the benefit of Chinese Application No. 201510349134.9, filed Jun. 23, 2015, the content of each of which is incorporated herein by its entirety for all purposes.

TECHNICAL FIELD

The present invention relates to the field of polymer synthesis. In particular, the invention relates to, among other things, an eight-arm polyethylene glycol derivative, production methods therefor and modified bio-related substances thereof.

BACKGROUND

PEGylation has been widely recognized as one of the most important approaches for drug modification. Wherein, functional polyethylene glycols (PEGs), owing to their reactive groups, are capable of modifying therapeutic drugs and other bio-related substances by covalently binding to target molecules, generally small molecule organic drugs or biomolecules, including proteins, peptides, saccharides, lipids, oligonucleotides, affinity ligands, cofactors, liposomes, biomaterials and the like. The pegylated drugs can be endowed with many beneficial properties in the aspect of hydrophilicity, flexibility, antithrombogenicity, etc. Meanwhile, due to the steric repulsion effect, pharmaceutical drugs modified with polyethylene glycol can avoid the filtration through glomeruli in the kidney and the bio-reactions such as immunoreactions, so that longer half-life in blood is achieved compared with the unmodified form. For example, it has been reported that paclitaxel, a water-insoluble drug, when coupled to polyethylene glycol, becomes water-soluble (Greenwald et al., J. Org. Chem. 1995, 331-336).

In 1995, Monfardini and coworkers synthesized a branched polyethylene glycol derivative with two arms, also denoted as "V-shaped" PEG, wherein, two linear monomethoxy polyethylene glycol chains were directly linked to the two amino groups of lysine followed by activation of the α-carboxyl group of lysine into a succinimidyl ester group, and thereafter investigated modification of proteins with the branched polyethylene glycol (Bioconjugate Chem. 1995, 6, 62-69). Since then, it has gained popularity as a tool to produce a monofunctional branched polyethylene glycol and drug derivatives thereof, and has already been applied in three commercially available pharmaceutical products. Compared with a linear polyethylene glycol having the same molecular weight, a branched polyethylene glycol, in virtue of its particular molecular structure, can provide an "umbrella-like" protective coverage around protein surface which increases steric hindrance around the drug molecule, inhibit the attack from other macromolecules in vivo more effectively so as to decrease inactivation and enzymolysis in body and therefore extend the circulation time of pegylated drugs.

In addition to linear monofunctional and linear bifunctional polyethylene glycols, multiarm polyethylene glycols such as three-arm, four-arm, six-arm and eight-arm polyethylene glycols, thanks to their advantages in structure and drug loading, have also occupied a place in the commercial market. Especially for small molecule drugs, the drawbacks including low solubility and high toxicity greatly limit their clinical applications. When using traditional linear polyethylene glycol for modification, no matter monofunctional or bifunctional polyethylene glycols, improved solubility and reduced toxic side effect can be achieved, but because drug molecules are probably embeded by the PEG chain, the drug activity may be greatly reduced. Compared with linear polyethylene glycol derivatives, multiarm branched polyethylene glycol derivatives can simultaneously achieve increasement in solubility, decreasement in toxic side effect and high maintenance of drug activity. Additionally, the multiarm structure also leads to reduced viscosity and facilitates better pharmacokinetics. So far, there are two cases of four-arm PEG-modified small molecule drugs into the clinical stage II or III.

Compared with four-arm polyethylene glycol derivatives, eight-arm polyethylene glycol derivatives provide higher drug loading, better solubility and higher drug activity. Regarding eight-arm polyethylene glycol derivatives, two kinds of octavalent central groups including —O[CH$_2$CH(O—)CH$_2$O]$_6$— of a tripentaerythritol type and —O[CH$_2$CH(O—)CH$_2$O]$_6$— of a hexaglycerol type have been disclosed. To the best of our knowledge, they have not yet entered preclinical study or clinical trials Since the intramolecular ether bond inside the PEG structure (CH$_2$CH—O—CH$_2$CH$_2$) is relatively stable, the eight-arm polyethylene glycol molecules of the above two kinds are considered to be undegradable. Moreover, the asymmetry of the octavalent central groups may cause a difference in the reactivity of the eight active sites when initiating polymerization of ethylene oxide, and thus result in different PEG chain lengths and undesired homogeneity of the molecular weight.

SUMMARY OF THE INVENTION

The present invention involves an eight-arm polyethylene glycol derivative (also denoted as an eight-arm functional polyethylene glycol), production methods therefor and modified bio-related substances thereof. The involved eight-arm functional polyethylene glycol has a centrosymmetric or approximately centrosymmetric structure, and therefore more precise control of molecular weight and molecular distribution during synthesis process can be achieved. Degradable moieties are allowed to be introduced into the molecular structure, so that pegylated drugs thereof can be degraded in a specific environment to release the loaded drug molecules, be endowed with enhanced active drug targeting and can be used for producing environmentally responsive drugs.

The invention involves the following technical solutions.

An eight-arm polyethylene glycol derivative was disclosed. An eight-arm polyethylene glycol derivative has eight PEG chains and an octavalent central group CORE$_8$ as represented by

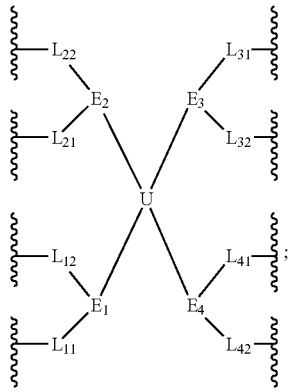
CORE₈
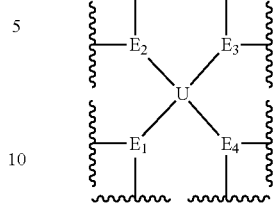
wherein, the moiety
is denoted as "CORE"; wherein, each PEG chain bears at least one terminal functional group F.
An eight-arm polyethylene glycol derivative can have a structure represented by the general formula (1):
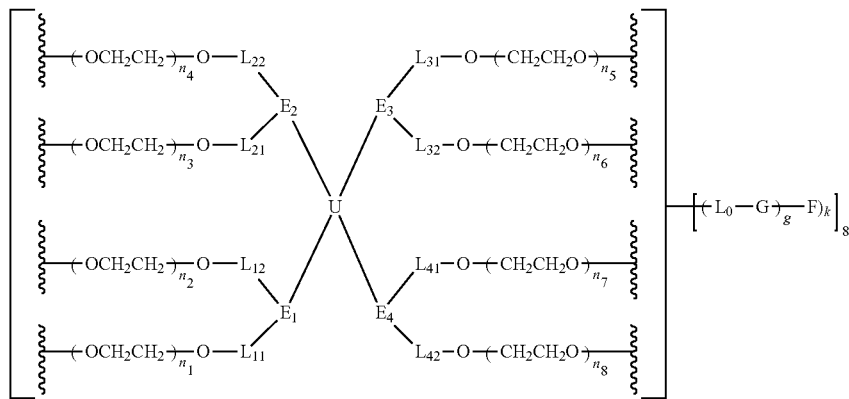
(1)
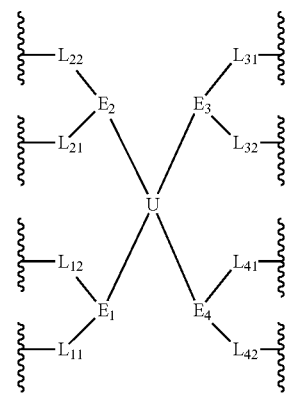
CORE₈ wherein, the eight-arm polyethylene glycol derivative has eight PEG chains and one octavalent

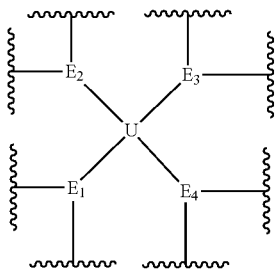

central group $CORE_8$; the octavalent central group contains a moiety of denoted as "CORE" which consists of one tetravalent central group U and four trivalent branching groups $E_1$, $E_2$, $E_3$ and $E_4$; wherein, U is a tetravalent central group; $E_1$, $E_2$, $E_3$ and $E_4$ are trivalent branching groups that are connected to the tetravalent central group U, and can be each independently identical or not identical in one molecule; one of the preferred embodiments is that $E_1$, $E_2$, $E_3$ and $E_4$ have the same structure in one molecule, denoted by $U_c$;

wherein, $L_{11}$, $L_{12}$, $L_{21}$, $L_{22}$, $L_{31}$, $L_{32}$, $L_{41}$ and $L_{42}$ are divalent linking groups that respectively attaches a PEG chain to one of the eight termini of CORE; $L_{11}$, $L_{12}$, $L_{21}$, $L_{22}$, $L_{31}$, $L_{32}$, $L_{41}$ and $L_{42}$ are each independently present or absent, and can be each independently identical or not identical in one molecule; one of the preferred embodiments is that $L_{11}$, $L_{12}$, $L_{21}$, $L_{22}$, $L_{31}$, $L_{32}$, $L_{41}$ and $L_{42}$ have the same structure in one molecule, denoted as L;

wherein, $n_1$, $n_2$, $n_3$, $n_4$, $n_5$, $n_6$, $n_7$ and $n_8$ represent the degree of polymerization of the eight PEG chains, respectively; they are each independently a value from 2 to about 2000, and can be each independently identical or not identical in one molecule; one of the preferred embodiments is that $n_1$, $n_2$, $n_3$, $n_4$, $n_5$, $n_6$, $n_7$ and $n_8$ are each independently a value from 2 to about 1000;

PEG chains corresponding to $n_1$, $n_2$, $n_3$, $n_4$, $n_5$, $n_6$, $n_7$ and $n_8$ are each independently polydisperse or monodisperse;

wherein, G is an end-branching group of trivalence or higher valence which can connect one PEG chain with terminal functional groups; $L_0$ is a divalent linking group which connects the PEG chain with the end-branching group G;

wherein, g is 0 or 1; k is an integer of 1 or an integer from 2 to 250; when all the k values of the eight PEG chain terminals are greater than 2, those k values can be each independently equal or different;

when g is 0, k is equal to 1, meanwhile both $L_0$ and G are absent;

when g is 1, G is present, meanwhile $L_0$ can be present or absent, and k is an integer from 2 to 250;

wherein, the terminal functional group F contains a functional end-group, and the structure of F is represented by

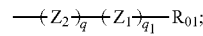

herein, q and $q_1$ are each independently equal to 0 or 1; $Z_1$ and $Z_2$ are each independently a divalent linking group; $R_{01}$ is a functional end-group capable of interreacting with a bio-related substance;

the eight-arm polyethylene glycol derivative can remain stable or be degraded (stable or degradable); in one molecule, U, $E_1$, $E_2$, $E_3$, $E_4$, $L_{11}$, $L_{12}$, $L_{21}$, $L_{22}$, $L_{31}$, $L_{32}$, $L_{41}$, $L_{42}$, $L_0$, G and $(Z_2)_q$—$(Z_1)_{q1}$ can be each independently either stable or degradable, and the joint linking group formed by any aforesaid group with its adjacent group can be each independently either stable or degradable.

The invention also discloses a substance comprising the eight-arm polyethylene glycol derivative, which can be polydisperse or monodisperse.

The invention also discloses a bio-related derivative of the eight-arm polyethylene glycol derivative. Wherein, the eight-arm functional polyethylene glycol also binds a bio-related substance to form a covalent linkage L, and the number of the bio-related substance residue D in one molecule is at least one.

The invention also discloses a bio-related substance modified by the eight-arm polyethylene glycol derivative, and the resulting eight-arm polyethylene glycol modified bio-related substance is represented by the general formula (2):

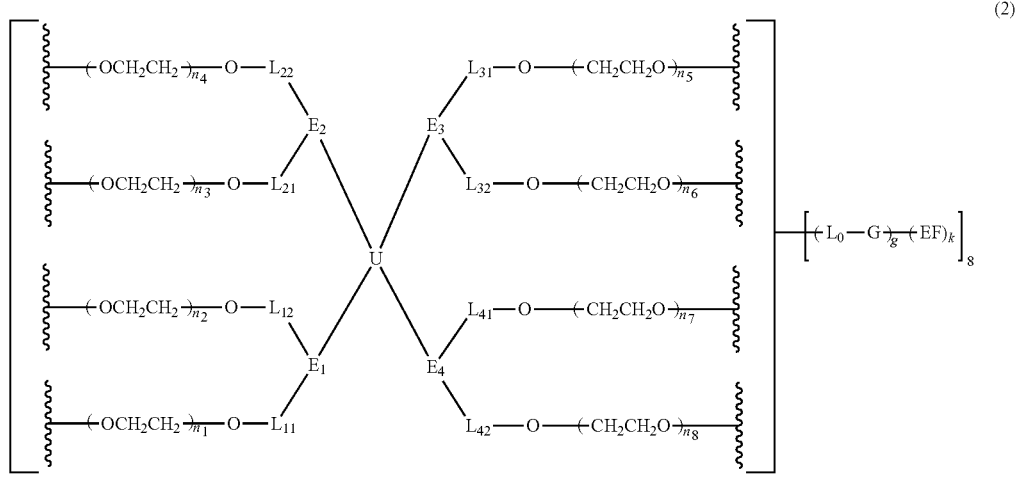

wherein, g is equal to 0 or 1; EF is represented as ED (with a structure of

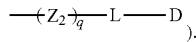

).

or $EF_1$ (with a structure of

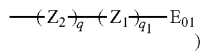

), wherein, D is different from $E_{01}$. Wherein, D represents the resulting residue of a bio-related substance to be modified after said bio-related substance reacting with the eight-arm polyethylene glycol derivative; $E_{01}$ is selected from the group consisting of $R_{01}$, protected $R_{01}$, deprotected $R_{01}$ and end-capped $R_{01}$; $R_{01}$ is a reactive group capable of reacting with a bio-related substance; L is the linking group formed after the reaction between the reactive group of the eight-arm polyethylene glycol derivative and the bio-related substance. The number of D at one PEG chain terminal is denoted as $k_D$, wherein, $0 \le k_D \le k$, and the $k_D$ values of different PEG chains in one molecule are each independently identical or not identical. Moreover, the total number of D in one molecule is at least 1, and preferably at least 8. When g is equal to 1, $G\text{-}(EF)_k$ can be represented as D

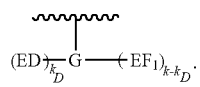

Wherein, the definitions of U, $E_1$, $E_2$, $E_3$, $E_4$, $L_{11}$, $L_{12}$, $L_{21}$, $L_{22}$, $L_{31}$, $L_{32}$, $L_{41}$, $L_{42}$, $L_0$, G, $n_1$, $n_2$, $n_3$, $n_4$, $n_5$, $n_6$, $n_7$, $n_8$, k, $Z_1$, $Z_2$, q and $q_1$ are the same as those in the general formula (1), and no more repeated here.

The bio-related substance modified by the eight-arm polyethylene glycol derivative can remain stable or be degraded (i.e. stable or degradable); in one molecule, U, $E_1$, $E_2$, $E_3$, $E_4$, $L_{11}$, $L_{12}$, $L_{21}$, $L_{22}$, $L_{31}$, $L_{32}$, $L_{41}$, $L_{42}$, $L_0$, G, $(Z_2)_q\text{-}(Z_1)_{q1}$ and $(Z_2)_q\text{-}L$ can be each independently either stable or degradable, and the joint linking group formed by any aforesaid group with its adjacent group can be each independently either stable or degradable.

For translation, the phrase "be different" used in the present invention means "be not identical" and allows the presence of two identical objects as far as that there exist at least two different objects.

Compared with the prior art, the present invention brings the following beneficial effects:

(1) The involved eight-arm functional polyethylene glycol (i.e. eight-arm polyethylene glycol derivative) has a centrosymmetric structure or an approximately centrosymmetric structure. When the eight polyethylene glycol chains are introduced via polymerization, the reaction rate of the eight initiating sites of an octa-ol initiator (OctaIN, $CORE_8$ $(OH)_8$) is close or even equal, which can lead to better homogeneity in the molecular weight of different polyethylene glycol chains, narrower distribution of molecular weight, and thus improved performance of product compared with the methods using tripentaerythritol or hexaglycerol as an initiator. (2) Compared with linear, three-arm, four-arm and six-arm polyethylene glycols, the eight-arm structure has a much smaller viscosity coefficient which beneficially improves the pharmacokinetics, increases the number of active groups and boosts the drug loading. (3) A terminal end-branching group of trivalence or higher valence can be introduced between the terminal functional group and the corresponding PEG chain, which can further increase the number of active groups, greatly boost the drug loading and further enhance drug efficacy. (4) With respect to the introduction of the eight PEG chains, in addition to direct polymerization of ethylene oxide initiated by an octa-ol initiator, covalent reactions can also be used to couple eight polyethylene glycol chains to the eight ends of an octafunctional small molecule (OctaSM). Along with the redistribution of molecular weights into a combination, the high-molecular-weight conjugate product can have more uniform mass and lower polydispersity index (PDI). With respect to high-molecular-weight eight-arm polyethylene glycol derivative, a single-chain PEG reagent with a low PDI value can also contribute to a narrower molecular weight distribution. (5) When the single-chain PEG reagent is monodisperse, a single-molecular-weight product with a PDI value equal to 1 can be obtained, and the corresponding eight-arm polyethylene glycol derivative and modified bio-related substances thereof can have a definite structure and definite molecular weight, which can facilitate the standardization for control and production. (6) Regarding modified bio-related substances by the eight-arm polyethylene glycol derivative, positions including the octavalent central group ($CORE_8$) and the linkages between the functional group (F) and the corresponding polyethylene glycol chain can each independently allow the presence of degradable linkages, which can lead to the release of loaded drugs along with degradation in a specific environment, improvement of tissue distribution of drugs, increasement of drug accumulation at the lesion site and enhancement of drug efficacy.

In order to better illustrate the difference between the involved eight-arm polyethylene glycol derivative and the conventional eight-arm polyethylene glycols, the following parameters are introduced. The maximum chain length $D_{Emax}$ refers to the largest number of skeleton atoms between two trivalent branching centers of the four trivalent branching groups $E_i$ (i=1, 2, 3, 4), wherein, the skeleton atoms between two trivalent branching centers cross U, but exclude the two branching points; similarly, $D_{Emin}$ refers to the minimum chain length between two trivalent branching centers of $E_i$ (i=1, 2, 3, 4); $d_{DE}$ refers to the difference between $D_{Emax}$ and $D_{Emin}$; the two branch lengths towards the PEG chain side of one trivalent branching center of $E_i$ (i=1, 2, 3, 4) refer to the skeleton atom numbers respectively from that trivalent branching center to the oxygen atoms of the two corresponding PEG chains; the shorter $D_{Emax}$ is, the smaller $d_{DE}$ is, and the closer the two branch lengths of one trivalent branching center are, the more uniform the structural topologicity of the eight termini of $CORE_8$ is. When introducing PEG chains by polymerization, the closer the lengths of the eight polyethylene glycol chains are, the more homogenous the quality of the modified product is and the higher the performance is; when using coupling methods, the lower the content of the by-product that consists of less than eight PEG chains is. One of the preferred embodiments is that the eight divalent linking groups $L_{i1}$ (i=1, 2, 3, 4) and $L_{i2}$ (i=1, 2, 3, 4) are completely identical.

The present invention can cover those eight-arm polyethylene glycol derivatives represented by the general formula (1) in which $D_{Emax}$, $d_{DE}$ and $d_{E2}$ are not particularly limited. With respect to $D_{Emax}$, preferably $D_{Emax} \le 100$, more preferably $D_{Emax} \le 50$, more preferably $D_{Emax} \le 30$, more preferably $D_{Emax} \le 20$, and more preferably $D_{Emax} \le 15$. The embodiments with minimum $D_{Emax}$ appear in the general formulas (8) and (9), corresponding to $D_{Emax}=5$ and $d_{DE}=0$. With respect to $d_{DE}$, preferably $d_{DE} \leq 21$, more preferably $d_{DE} \leq 10$, more preferably $d_{DE} \leq 6$, more preferably $d_DE \leq 4$, more preferably $d_{DE} \leq 2$, and most preferably $d_{DE}=0$. What should be illustrated is that, when two trivalent branching centers of the four trivalent branching groups $E_i$ (i=1, 2, 3, 4) cross a cyclic structure, the length of the whole cyclic structure is considered as 2; take

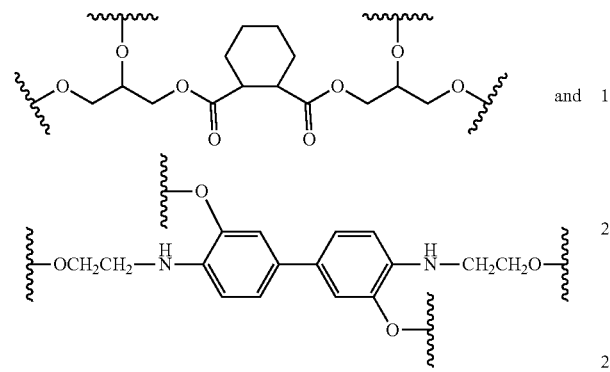

and for example, provided that both two terminal oxygen atoms directly connect to a trivalent branching center, then $D_{Emax}$ is 14 and 12, respectively, and $d_{DE}$ is 10 and 6, respectively.

The length difference between the two branches which respectively starts from one branching center of $E_i$ to two oxygen atoms of the two corresponding PEG chains is denoted as $d_{E2}$, and $d_{E2} \leq 10$, preferably $d_{E2} \leq 5$, more preferably $d_{E2} \leq 4$, more preferably $d_{E2} \leq 3$, more preferably $d_{E2} \leq 2$, more preferably $d_{E2} \leq 1$, and most preferably $d_{E2}=0$. When $L_{i1}$ and $L_{i2}$ are identical as well as $E_i$ (i=1, 2, 3, 4 has a symmetrically branched structure, $d_{E2}$ is equal to 0. Examples of $E_i$ for $d_{E2}=0$ include

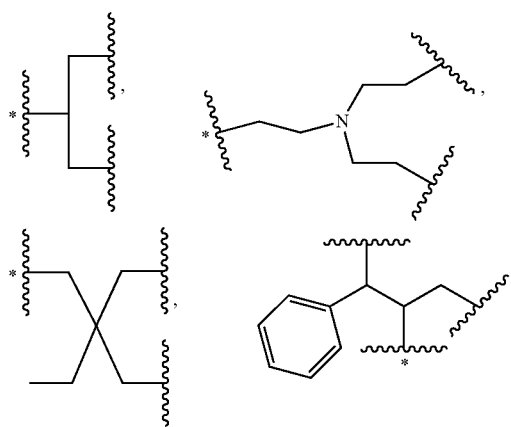

and the like (wherein, the asterisk symbols indicate the direction towards U). What should be noted is that, when $d_{E2}=0$, it only indicates that the lengths of the two branches of one $E_i$ center are equal, either symmetrically or asymmetrically, wherein, whether or not being symmetrical relies on whether or not the two branches have the same chemical structure. When $d_{E2} \geq 1$, $E_i$ (i=1, 2, 3, 4) have asymmetrical structures. Take the embodiment in which $L_{i1}$ and $L_{i2}$ have different lengths for example, examples with $d_{E2}=1$ include

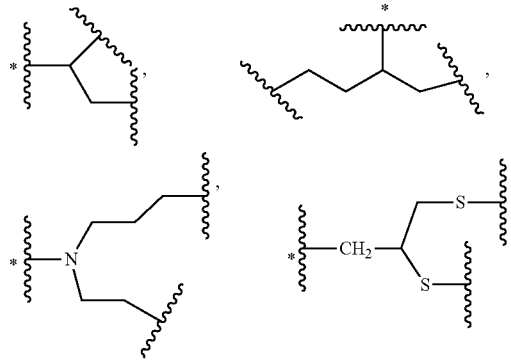

and the like, examples with $d_{E2}=2$ include

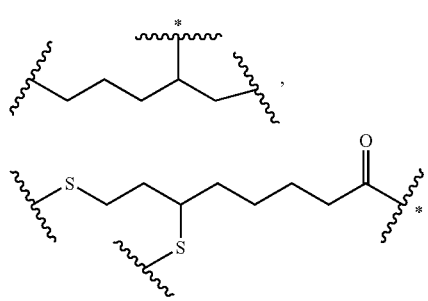

and the like, examples with $d_{E2}=3$ include

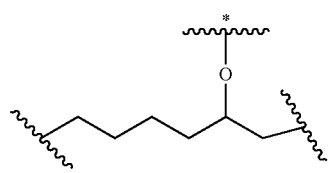 [SMILES: *CCCCC(C*)O*]

and the like, and examples with $d_{E2}=4$ include

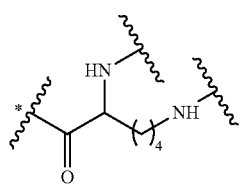

and the like.

The combination of $D_{Emax}$, $d_{DE}$ and $d_{E2}$ of the eight-arm polyethylene glycol derivative, most preferably but not limited to, satisfies at least one of the following formulas: $D_{Emax} \leq 15$, $d_{DE} \leq 2$ or $d_{E2} \leq 1$.

The values of ($D_{Emax}$, $d_{DE}$, $d_{E2}$) of the general formulas (6) and (7), the general formulas (8) and (9), the general formulas (10) and (11), the general formulas (12) and (13), the general formulas (14) and (15), the general formulas (16) and (17), the general formulas (18) and (19), the general formulas (20) and (21), the general formulas (22) and (23), the general formulas (24) and (25), the general formulas (26) and (27), the general formulas (28) and (29), the general formulas (30) and (31), the general formulas (32) and (33), and the general formulas (34) and (35), are (7, 0, 1), (5, 0, 0), (6, 2, 0), (8, 2, 1), (11, 4, 1), (9, 4, 0), (11, 5, 1), (9, 5, 0), (7, 2, 0), (9, 2, 1), (9, 2, 0), (11, 5, 0), (10, 3, 0), (14, 7, 0) and (17, 11, 0), respectively. With respect to tripentaerythritol (—O[CH$_2$C(CH$_2$O—)$_2$CH$_2$O]$_3$—) and hexaglycerol (—O[CH$_2$CH(O—)CH$_2$O]$_6$—), the distance between the farthest two branching points, the distance between the nearest two branching points, and the difference between distances from the hydroxyl oxygen atoms to the terminal end-branching center, are similar to the above-defined parameters $D_{Emax}$, $d_{DE}$ and $d_{E2}$, respectively, and correspond to (6, 3, 0) for tripentaerythritol and (19, 16, 1) for hexaglycerol respectively. According to the comparison, the eight-arm polyethylene glycol derivatives provided in the present invention can be imparted with better over-all performance.

DETAILED DESCRIPTION

Definitions of Terms

Most terms of the present invention are defined in the following part, while some others are defined elsewhere.

Most of the terms involved in the present invention have been disclosed in the documents CN104530413A (paragraphs from [0024] to [0145]), CN104530415A (paragraphs from [0042] to [0163]) and CN104530417A (paragraphs from [0021] to [0142]), no more repeated again. Herein, definitions, embodiments and examples of cited terms are all incorporated into the present invention by reference, but referring to what is disclosed in the present invention if different.

Referring to the documents CN104530413A, CN104530415A and CN104530417A, in summary, cited terms related to compounds and structures include but are not limited to hydrocarbons, aliphatic hydrocarbons, aromatic hydrocarbons (or aryl hydrocarbons, or arenes), arylalkanes (or aralkanes), saturated hydrocarbons, alkanes, saturated aliphatic hydrocarbons, unsaturated hydrocarbons, unsaturated aliphatic hydrocarbons, alkenes, alkynes, dienes (or alkadienes), open-chain hydrocarbons, linear structures (or straight structures) which have no pendant group, linear hydrocarbons, linear aliphatic hydrocarbons, branched hydrocarbons, branched structures which bear the pendant group), branched aliphatic hydrocarbons, cyclic hydrocarbons (or cyclohydrocarbons), cyclic structures (which contain at least one ring), dendritic structures, comb-like structures, hyperbranched structures, ring-membering atoms, ring skeletons, carbon rings, alicyclic hydrocarbons, alicyclic rings, saturated alicyclic rings, saturated alicyclic hydrocarbons (cycloalkanes), unsaturated alicyclic rings, unsaturated alicyclic hydrocarbons, cycloalkenes (or cycloolefins, or cyclic alkenes), cycloalkynes (or cyclic alkynes), cyclodienes (or cyclic dienes), phenyl rings, aryl rings (or aromatic all-carbon rings), condensed rings (or condensed cyclic rings, or fused rings), structural units to constitute a ring skeleton, cyclic structures with nested cyclic moieties or not, heteroatoms, the species of heteroatoms, heterorings, aliphatic-derived heterorings, aromatic-derived heterorings (also aromatic heterorings), hetero-aliphatic rings (or heterosubstituted aliphatic rings), hetero-aromatic rings (or heteroaryl rings), oxa-, aza-, thia-, phospha-, the number of heteroatoms, aza-oxa compounds, aza-thia compounds, the position of heteroatoms, the number of cyclic structures, monocyclic rings (or monorings), polycyclic rings (or polyrings), monocyclic compounds, polycyclic compounds, the number of rings, bicyclic compounds, tricyclic compounds, tetracyclic compounds, the linking manner between two or more cyclic rings of polycyclic rings, spirocyclic rings (or spiro-rings), bridged cyclic rings (or bridged rings), any two connected rings of polycyclic rings, heterosubstituted monocyclic rings or heteromonocyclic rings or heterosubstituted monorings or heteromonorings (monocyclic heterorings), heterosubstituted polycyclic rings (or heteropolycyclic rings, or heteropolyrings), heterospirocyclic rings, heterobridged cyclic rings, hetero-condensed rings (or heterocondensed cyclic rings, or heterosubstituted condensed rings, or heterosubstituted fused rings), condensed aryl rings (or fused aryl rings), condensed heterorings or fused heterorings (hetero-condensed rings), aryl-condensed heterorings (aryloheterorings), benzoheterorings, heterocondensed heterorings (or heterofused heterorings), heterocondensed aromatic rings, monocyclohydrocarbons (or monocyclic hydrocarbons), polycyclohydrocarbons (or polycyclic hydrocarbons), spirohydrocarbons, bridged hydrocarbons, condensed cyclic hydrocarbons (or condensed cyclohydrocarbons, or condensed ring hydrocarbons, or fused cyclic hydrocarbons, or fused ring hydrocarbons), condensed aromatic hydrocarbons (or condensed aryl hydrocarbons, or fused aromatic hydrocarbons), saturated cyclic hydrocarbons (cycloalkanes), unsaturated cyclic hydrocarbons, heterohydrocarbons (or heterosubstituted hydrocarbons), open-chain heterohydrocarbons, heterocyclic hydrocarbons (or cyclic heterohydrocarbons, or heterocyclohydrocarbons), aliphatic-derived heterosubstituted hydrocarbons (or aliphatic-derived heterohydrocarbons, or heterosubstituted aliphatic hydrocarbons), aromatic-derived heterosubstituted hydrocarbons (or aromatic-derived heterohydrocarbons, or heterosubstituted aromatic hydrocarbons), aliphatic-derived heterocyclic hydrocarbons (or aliphatic-derived heterocyclohydrocarbons, or heterosubstituted alicyclic hydrocarbons, or heterosubstituted aliphatic cyclohydrocarbons), aliphatic-derived open-chain heterosubstituted hydrocarbons (or heterosubstituted aliphatic open-chain heterohydrocarbons), saturated aliphatic-derived heterohydrocarbons (heteroalkanes), heteroaromatics (or hetero-aromatic hydrocarbons, or heteroarylhydrocarbons), condensed heterohydrocarbons (or condensed heterosubstituted hydrocarbons, or fused heterohydrocarbons), condensed heterocyclic hydrocarbons (or condensed heterocyclohydrocarbons, or fused heterocyclohydrocarbons), aryl-condensed heterocyclic hydrocarbons, heterocondensed heterocyclic hydrocarbons (or heterocondensed heterocyclohydrocarbons, or heterofused heterocyclic hydrocarbons), heteroarylalkanes (or heteroaralkanes) and the like.

In the present invention, heteroatoms are not particularly limited, including but not limited to O, S, N, P, Si, F, Cl, Br, I, B, etc.

In the present invention, rings deriving from hydrocarbons include but are not limited to alicyclic rings, aryl rings, monocyclic rings, polycyclic rings, spirorings, bridged rings, condensed rings, condensed aryl rings, condensed heterorings, aryl-condensed heterorings, aryloheterorings, benzoheterorings, heterocondensed heterorings, carbon rings, heterorings, aliphatic-derived heterorings, aromatic-derived heterorings, heterosubstituted monocyclic rings, heterosubstituted polycyclic rings, hetero-spirorings, heterobridged rings, hetero-condensed rings, hetero-aliphatic rings, hetero-aromatic rings, saturated alicyclic rings, unsaturated alicyclic rings, the like, and the combination of any two or more types of aforesaid rings, wherein, the number of rings in the combination is not particularly limited. According to whether aryl rings or heteroaromatic rings are contained, rings in the present invention can be generally classified into two types.

In the present invention, hydrocarbons with the carbon atom of any position to be replaced by a heteroatom are generally referred to as heterosubstituted hydrocarbons (or heterohydrocarbons).

Referring to the documents CN104530413A, CN104530415A and CN104530417A, in summary, terms related to groups include but are not limited to groups, residue groups, the valence of a group, monovalent groups, divalent groups, trivalent groups, tetravalent groups, . . . hectovalent groups, linkages (or linking groups), an oxy group, a thioxy group, hydrocarbon groups, monovalent hydrocarbon groups (removing one hydrogen atom, also denoted as hydrocarbyl groups), divalent hydrocarbon groups (removing two hydrogen atoms, including hydrocarbylene groups or hydrocarbylidene groups), trivalent hydrocarbon groups (removing three hydrogen atoms), an atom substituent (or a substituting atom), a group substituent (or a substituting group), a hydrocarbon substituent (e.g., a hydrocarbyl substituent), heteroatom-containing groups, heterohydrocarbon groups, heteroatom-containing substituents, acyl groups, a carbonyl group, non-carbonyl acyl groups, a hydrocarbyloxy group (or a hydrocarbonoxy group), a hydrocarbylthio group (or a hydrocarbylthioxy group), acyloxy groups (acyloxyl groups), oxyacyl groups, aminoacyl groups, acylamino groups, substituted hydrocarbon groups, hydrocarbyl-substituted hydrocarbon groups (still falling into the scope of hydrocarbon groups), saturated hydrocarbon groups (alkyl groups), unsaturated hydrocarbon groups, alkenyl groups, alkynyl groups, dienyl groups (or alkadienyl groups), alkenyl-hydrocarbyl groups, alkynyl-hydrocarbyl groups, dienyl-hydrocarbyl groups, open-chain hydrocarbon groups, linear hydrocarbon groups, branched hydrocarbon groups, cyclohydrocarbon groups (or cyclic hydrocarbon groups), aliphatic hydrocarbon groups, alicyclic hydrocarbon groups, cycloalkyl groups, unsaturated alicyclic hydrocarbon groups, monocyclohydrocarbon groups (or monocyclic hydrocarbon groups), polycyclohydrocarbon groups (or polycyclic hydrocarbon groups), aryl groups, aryl-hydrocarbyl groups, arylalkyl groups (or aralkyl groups), heterohydrocarbyl-substituted hydrocarbon groups (falling into the scope of heterohydrocarbon groups), aliphatic-derived heterohydrocarbon groups, heteroalkyl groups, open-chain heterohydrocarbon groups, aliphatic-derived heterocyclohydrocarbon groups, heterocyclohydrocarbon groups (or heterocyclic hydrocarbon groups), heteroring-substituted hydrocarbon groups, aromatic-derived heterohydrocarbon groups, heteroaryl groups, heteroarylhydrocarbyl groups, heteroarylalkyl groups (or heteroaralkyl groups), condensed cyclohydrocarbon groups, condensed aromatic hydrocarbon groups, condensed heterocyclohydrocarbon groups, aryl-condensed heterocyclohydrocarbon groups, heterocondensed heterocyclohydrocarbon groups, oxa-hydrocarbyl groups, aza-hydrocarbyl groups, thia-hydrocarbyl groups, phospha-hydrocarbyl groups, monoheterosubstituted hydrocarbyl groups, diheterosubstituted hydrocarbyl groups, multiheterosubstituted hydrocarbyl groups, alkylene groups, the source of hydrocarbylene groups, hydrocarbylene groups derived from unsaturated aliphatic hydrocarbons, cyclohydrocarbylene groups, alicyclic hydrocarbylene groups, arylene groups, arylhydrocarbylene groups, a cyclic structure as a group substituent, that hydrocarbylene groups can contain or do not contain substituting groups or pendant groups, the two radical positions of hydrocarbylene groups to connect with other groups, protecting groups (or protective groups), mercapto protecting groups (or thiol protecting groups), alkynyl protecting groups, hydroxyl protecting groups, amino protecting groups, amino groups, divalent linking groups (or divalent linkages) and the like.

One or more hydrogen atoms of the above-described compounds including hydrocarbons, aliphatic hydrocarbons, aromatic hydrocarbons (or aryl hydrocarbons, arenes), arylalkanes (or aralkanes), saturated hydrocarbons, alkanes, unsaturated hydrocarbons, alkenes, alkynes, dienes, open-chain hydrocarbons, linear hydrocarbons (linear aliphatic hydrocarbons), branched hydrocarbons (branched aliphatic hydrocarbons), cyclohydrocarbons (or cyclic hydrocarbons), alicyclic hydrocarbons, cycloalkanes, unsaturated alicyclic hydrocarbons, cycloalkenes (or cycloolefins, or cyclic alkenes), cycloalkynes (or cyclic alkynes), cyclodienes (or cyclic dienes), monocyclohydrocarbons (or monocyclic hydrocarbons), polycyclohydrocarbons (or polycyclic hydrocarbons), spirohydrocarbons, bridged hydrocarbons, condensed cyclic hydrocarbons (or condensed cyclohydrocarbons, or condensed ring hydrocarbons, or fused cyclic hydrocarbons, or fused ring hydrocarbons), condensed aromatic hydrocarbons (or condensed aryl hydrocarbons, or fused aromatic hydrocarbons), heterohydrocarbons (or heterosubstituted hydrocarbons), aliphatic-derived heterosubstituted hydrocarbons (or heterosubstituted aliphatic hydrocarbons, or aliphatic-derived heterohydrocarbons), open-chain heterohydrocarbons, heterocyclic hydrocarbons (or cyclic heterohydrocarbons, or heterocyclohydrocarbons), aliphatic-derived heterocyclic hydrocarbons (or aliphatic-derived heterocyclohydrocarbons, or heterosubstituted alicyclic hydrocarbons, heterosubstituted aliphatic cyclohydrocarbons), aromatic-derived heterosubstituted hydrocarbons (or heterosubstituted aromatic hydrocarbons, aromatic-derived heterohydrocarbons), heteroaromatics (or heteroarylhydrocarbons), heteroarylalkanes (or heteroaralkanes), condensed heterocyclic hydrocarbons (or condensed heterocyclohydrocarbons, or fused heterocyclic hydrocarbons), aryl-condensed heterocyclic hydrocarbons (or aryl-condensed heterocyclohydrocarbons, or aryl-fused heterocyclic hydrocarbons), heterocondensed heterocyclic hydrocarbons (heterocondensed heterocyclohydrocarbons, or heterofused heterocyclic hydrocarbons) and the like, can be substituted by any suitable substituents (a heteroatom substituent or a group substituent), corresponding to substituted hydrocarbons, substituted aliphatic hydrocarbons, substituted aromatic hydrocarbons, substituted arylalkanes, substituted saturated hydrocarbons, substituted alkanes, substituted unsaturated hydrocarbons, substituted alkenes, substituted alkynes, substituted dienes, substituted open-chain hydrocarbons, substituted linear hydrocarbons (substituted linear aliphatic hydrocarbons), substituted branched hydrocarbons (substituted branched aliphatic hydrocarbons), substituted cyclohydrocarbons (or substituted cyclic hydrocarbons), substituted alicyclic hydrocarbons, substituted cycloalkanes, substituted unsaturated alicyclic hydrocarbons, substituted cycloalkenes, substituted cycloalkynes, substituted cyclodienes, substituted monocyclohydrocarbons, substituted polycyclohydrocarbons, substituted spirohydrocarbons, substituted bridged hydrocarbons, substituted condensed cyclic hydrocarbons (or substituted condensed cyclohydrocarbons), substituted condensed aromatic hydrocarbons, substituted heterohydrocarbons, substituted aliphatic-derived heterohydrocarbons, substituted open-chain heterohydrocarbons, substituted heterocyclic hydrocarbons (or substituted heterocyclohdrocarbons), substituted heteroarylalkanes, substituted aliphatic-derived heterocyclic hydrocarbons, substituted aromatic-derived heterohydrocarbons, substituted heteroaromatics, substituted condensed heterocyclic hydrocarbons, substituted aryl-condensed heterocyclic hydrocarbons, substituted heterocondensed heterocyclic hydrocarbons and the like, respectively. In the present invention, a heteroatom used for substituting is referred to as "an atom substituent" (or "a substituting atom"), and a group used for substituting is referred to as "a group substituent" (or "a substituting group"). A substituent can be an atom substituent or a group substituent.

In the present invention, besides heterohydrocarbon groups, heteroatom-containing substituents also include but are not limited to substituents selected from the group consisting of a haloalkyl group, a nitro group, a silyl group (e.g., a trimethylsilyl group, a t-butyldimethylsilyl group, a trimethoxysilyl group and the like), a group substituent formed by directly linking a hydrocarbon group or a heterohydrocarbon group to a heteroatom-containing linkage such as an oxy group (a divalent oxygen linkage), a thioxy group (a divalent sulfur linkage), an acyl linkage, an acyloxy linkage, an oxyacyl linkage, —NH—C(=O)—, —C(=O)—NH— and the like, etc. Take a hydrocarbyl group for example, the resulting substituents correspond to a hydrocarbyloxy group, a hydrocarbylthio group, an acyl group, an acyloxy group, a hydrocarbyloxy-acyl group, an aminoacyl group, an acylamino group and the like, respectively.

The acyl group in the present invention can be a carbonyl group or a non-carbonyl acyl group. For example, the acyl group can be but not limited to a carbonyl group, a sulfonyl group, a sulfinyl group, a phosphoryl group, a phosphiryl group, a phosphinyl group, a nitroxyl group, a nitrosyl group, a thiocarbonyl group, an imidoyl group, a thiophosphoryl group, a dithiophosphoryl group, a trithiophosphoryl group, a thiophosphiryl group, a dithiophosphiryl group, a thiophosphinyl group, a thiophosphono group, a dithiophosphono group, a thiophosphino group or the like, and preferably a carbonyl group, a thiocarbonyl group, a sulfonyl group or a sulfinyl group. Herein, an acyl group particularly refers to a carbonyl group if without particular illustrations.

With respect to a compound, a group or an atom, it can be both substituted and heterosubstituted in one molecule, e.g., a nitrophenyl substituent to replace a hydrogen atom, or a group —$CH_2$—S—$CH(CH_3)$— derived from —$CH_2$—$CH_2$—$CH_2$— after being both substituted and heterosubstituted. For translation, the term of "heterosubstituted" means a carbon atom to be replaced into a heteroatom, referred to as a skeleton-membering heteroatom, typically a ring-membering heteroatom. What should be noted is that, a hydrogen atom to be replaced into a substituent is described as "substituted"; when the substituent contains a heteroatom, it is also referred to as "heterosubstituted". In summary, "heterosubstituted" include substitution of a hydrogen atom with a heteroatom-containing substituent and replacement of a carbon atom with a heteroatom, and can generally refer to structural changes with introduction of heteroatoms.

In the present invention, the sources of divalent hydrocarbon groups, mainly involving hydrocarbylene groups, are not particularly limited. For example, they can be derived from aliphatic hydrocarbons or aromatic hydrocarbons, or be derived from saturated hydrocarbons or unsaturated hydrocarbons, or be derived from linear hydrocarbons, branched hydrocarbons or cyclic hydrocarbons, or be derived from hydrocarbons or heterohydrocarbons, etc. According to the degree of saturation, e.g., they can be derived from alkanes, alkenes, alkynes, dienes, etc. With respect to cyclic hydrocarbons, e.g., they can be derived from alicyclic hydrocarbons or aromatic hydrocarbons, or be derived from monocyclic hydrocarbons or polycyclic hydrocarbons. With respect to heterocyclic hydrocarbons, e.g., they can be derived from aliphatic-derived heterocyclic hydrocarbons or aromatic-derived heterocyclic hydrocarbons.

The protecting groups (protective groups) involved in the present invention, such as mercapto protecting groups (or thiol protecting groups), alkynyl protecting groups, hydroxyl protecting groups, amino protecting groups and the like, are not particularly limited. All the protecting groups described in the published patent documents and references, including documents CN104530413A, CN104530415A and CN104530417A, are incorporated into the present invention by reference. Wherein, hydroxyl groups to be protected are not particularly limited, e.g., alcoholic hydroxyl groups, phenolic hydroxyl groups and the like. Wherein, amino groups to be protected are not particularly limited, e.g., amino groups derived from primary amines, secondary amines, hydrazines, amides and the like. The amino group in the present invention is not particularly limited, can be but not limited to a primary amino group, a secondary amino group, a tert-amino group or an ammonium ion.

For the sake of simplicity, the value range of the carbon-atom number of a group can also be marked as a subscript of a carbon atom ("C") to represent the available number of carbon atoms. For example, $C_{1-10}$ represents "having 1 to 10 carbon atoms", $C_{3-20}$ indicates "having 3 to 20 carbon atoms". "A substituted $C_{3-20}$ hydrocarbyl group" represents the resulting group derived from a $C_{3-20}$ hydrocarbyl group after one or more hydrogen atoms are substituted. "A $C_{3-20}$ substituted hydrocarbyl group" means that the carbon-atom number of the resulting group formed by substituting one or more hydrogen atoms of a hydrocarbyl group varies from 3 to 20. For another example, when a group can be a $C_{1-10}$ hydrocarbyl group, it can be a hydrocarbyl group with a carbon-atom number optionally selected from the value range as denoted by the subscript, i.e. it can be a hydrocarbyl group selected from the group consisting of $C_1$, $C_2$, $C_3$, $C_4$, $C_5$, $C_6$, $C_7$, $C_8$, $C_9$ and $C_{10}$ hydrocarbyl groups. In the present invention, the subscript as an interval represents that the number can be any integer in the range, with the two endpoints included if without particular illustrations.

With respect to the phrase "each independently preferably" related to two or more objects, when multi-level sets involving at least two preferable sets are concerned, those objects not necessarily come from the same preferable set. For example, one object comes from a preferable set with a larger range while another object comes from a preferable set with a smaller range, one object comes from a preferable set with a largest range while another object can come from any one of the preferable sets, or both objects come from the same preferable set. For example, with respect to "the carbon-atom numbers of $R_8$, $R_9$, $R_{10}$, $R_{11}$ and $R_{12}$ are each independently preferably from 1 to 20, and more preferably form 1 to 10", the carbon-atom numbers can be both from 1 to 20, both from 1 to 10, or some from 1 to 20 while the others from 1 to 10.

Regarding the divalent linking groups in the present invention, e.g., a hydrocarbylene group, an alkylene group, an arylene group, an amide bond and the like, either radical terminus of the two termini can be optionally linked to another group, if without particular limitations. For example, when an amide bond serves as a divalent linking group between A-$CH_2CH_2$— and —$CH_2$—B, both A-$CH_2CH_2$—C(=O)NH—$CH_2$—B and A-$CH_2CH_2$—NHC(=O)—$CH_2$—B can be a candidate. Some chemical formulas are marked with asterisks to denote an oriented terminus and to indicate the available radical terminus to be directionally connected.

When a structure has isomers, it can refer to any form of the isomers if without particular instructions. For example, when cis- and trans-isomers are present, it can refer to a cis-structure or a trans-structure. Regarding an alkyl group, if without particular instructions, it refers to a hydrocarbyl group which is formed via removing a hydrogen atom from any position of a hydrocarbon. Specific examples include that a propyl group can refer to a 1-propyl group or an isopropyl group, and that a propylene group can refer to a 1,3-propylene group or a 1,2-propylene group (an isopropylene group).

As for a structural formula, when the terminal radical of a linkage is likely confused with the terminal substituent, e.g.,

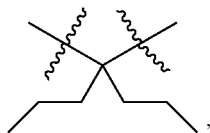

we use "〜〜" to mark the radical positions for connecting other groups. If no ambiguity is caused, formulas are also allowed not to be particularly marked, such as phenylene groups like

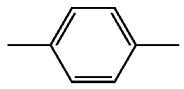 and 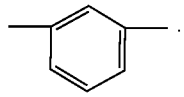.

In the present invention, cyclic structures can be represented by circles (rings), and be respectively marked according to different characteristics of cyclic structures. For example,

represents a cyclic structure of any type;

represents a cyclic structure deriving from aliphatics which contain neither aryl rings nor heteroaromatic rings of any type, and is also denoted as an aliphatic ring;

represents a cyclic structure deriving from aromatics and containing at least one aryl ring or heteroaromatic ring, and is also denoted as an aromatic ring (either all-carbon or heteroatom-containing).

(Sug)

represents a skeleton deriving from saccharides or derivatives thereof which contains one or more cyclic monosaccharide skeletons, and is also denoted as a sugar ring.

(Con)

represents a ring which contains at least one type of chemical bonds selected from the group consisting of an amide bond, an ester bond, an imide bond, an anhydride bond and the like, and is also denoted as a condensed ring.

(POLY)

represents a cyclic skeleton of watersoluble polymers, and is also denoted as a polymeric ring, wherein, the molecular weight of the watersoluble polymers is not particularly limited.

For example, formulas including

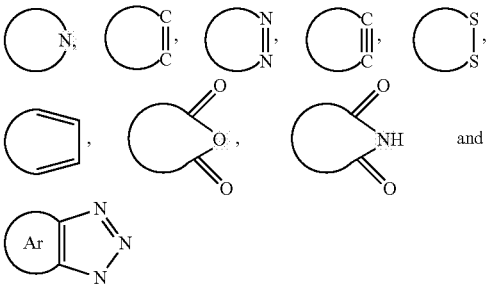

correspond to cyclic structures which contain a nitrogen atom, a double carbon-carbon bond, an azo group, a triple carbon-carbon bond, a disulfide bond, a conjugated dienyl bond, an anhydride moiety, an imide moiety and a triazole moiety, respectively.

If without particular illustrations, cyclic structures in the present invention include but are not limited to aliphatic rings (Ali), aromatic rings (Ar), sugar rings

, condensed rings

and polymeric rings

.

The related embodiments and examples described in the documents CN104530413A, CN104530415A and CN104530417A are all incorporated into the present invention by reference.

Aliphatic rings include alicyclic rings (all-carbon) and aliphatic-derived heterorings (heteroatom-containing), including but not limited to cyclic structures selected from the group consisting of cyclopropane, ethylene oxide, aziridine, cyclobutane, cyclobutene, squaric acid, cyclobutanedione, semi-squaric acid, cyclopentane, cyclopentadiene, tetrahydrofuran, pyrrolidine, thiazolidine, dihydroisoxazole, oxazolidine, cyclohexane, cyclohexene, tetrahydropyran, piperidine, 1,4-dioxane, norbornane, norbornene, norbornadiene, 1,4,7-triazacyclononane, cycleanine and the like. What should be noted is that, rings showing weak aromaticity, such as furan, thiophene, pyrrole, imidazole, oxazole, isoxazole, thiazole, isothiazole, pyrazole and the like, also belong to aliphatic rings. Similarly, triazole can also be classified here into aliphatic-derived heterorings.

Examples of sugar rings include but are not limited to furanose rings, pyranose rings, cyclodextrins, etc.

Aromatic rings include aryl rings (all-carbon) and aromatic-derived heterorings, including but not limited to benzene, pyridine, pyridazine, pyrimidine, pyrazine, 1,3,5-triazine, tetrazine (1,2,3,4-, 1,2,4,5- and 1,2,3,5-isomers), indene, indane, indole, isoindole, purine, naphthalene, dihydroanthracene, xanthene, thioxanthene, dihydrophenanthrene, 10,11-dihydro-5H-dibenzo[a,d]cycloheptane, dibenzocycloheptene, 5-dibenzosuberenone, quinoline, isoquinoline, fluorene, carbazole, iminodibenzyl, acenaphthene (or 1,2-dihydroacena-phthylene), dibenzocyclooctyne, aza-dibenzocyclooctyne, the like, substituted forms of any aforesaid group and heterosubstituted forms of any aforesaid group. Wherein, a nitrogen atom of the ring skeleton can also be present in the form of a cation ion. For example, pyridine, pyridazine, pyrimidine and pyrazine are aza-forms of benzene, indole and isoindole are aza-forms of indene, carbazole is an aza-form of fluorene, xanthene is an oxa-form of dihydroanthracene, thioxanthene is a thia-form of dihydroanthracene, 9H-thioxanthene-10,10-dioxide is a sulfone derivative of dihydroanthracene. Pyridinium is a substituted form of pyridine, wherein, the nitrogen atom is present as a cation ion. Besides the structures disclosed in paragraphs from [130] to [131] in the document CN104530417A, aromatic rings also include those disclosed in paragraphs from [267] to [284]. What should be noted is that, trivalent diphenyl group is not a net cyclic core structure, but is regarded as the combination of a trivalent phenyl group (which can be regarded as a net cyclic core structure) and a divalent phenyl group; a trivalent diphenylmethane group is similar to the trivalent biphenyl group.

Condensed rings include but are not limited to lactones (e.g., β-propiolactone), cyclic diesters of hydroxycarboxylic acids (e.g., lactide of lactic acid), lactams (e.g., β-lactam), cyclic imides (e.g., maleimide, succinimide, 3H-1,2,4-triazoline-3,5-dione), cyclic anhydride, cyclic peptide and the like.

Regarding the term "substituted" in the present invention, for example, a "substituted hydrocarbyl group" means that any one or more hydrogen atoms at any position of the hydrocarbyl group to be substituted can be substituted by any atom or group substituent. If without particular limitations, the atom substituent is not particularly limited and is preferably a halogen atom. If without particular limitations, the group substituents are not particularly limited, including but not limited to all the above-described group substituents in the term-defining section, and can be selected from all above-described hydrocarbon substituents and heteroatom-containing substituents.

In the description, we directly illustrate available combination of atom substituents and group substituents such as "the atom or group substituent can be a halogen atom, a hydrocarbyl substituent or a heteroatom-containing substituent."

The terms regarding a group "be stable" (or "can remain stable") and "be degradable" (or "can be degraded") are a pair of relative concepts in the present invention.

The term "degradation", the noun form of the term "degradable", means the breakage of a chemical bond into at least two individual residues. If a linking group has a changed structure after undergoing chemical reactions but remains as a whole linkage, such a linking group still falls into the scope of "stable groups". The condition "to be degradable" or "to degrade" or "to be degraded" is not particularly limited, and can be a physiological condition in vivo, a simulated physiological environment in vitro or other conditions, preferably a physiological condition in vivo or a simulated physiological environment in vitro. The physiological condition is not particularly limited, including but not limited to physiological environments of serum, heart, liver, spleen, lung, kidney, bone, muscle, fat, brain, lymph node, small intestine, gonads, etc. The above-described physiological conditions can be intracellular or in the extracellular matrix, or can be in normal tissues or in pathologic tissues (such as tumor, inflammation sites, etc.). The simulated physiological environment in vitro is not particularly limited, including but not limited to physiological saline, buffer, culture medium and the like. The degradation rate is not particularly limited, such as rapid degradation via enzymolysis, slow degradation via physiological hydrolysis, etc. The physiological conditions in vivo include physiological conditions during therapeutic treatment, such as ultraviolet irradiation, hyperthermia, etc. The condition "to be degradable" or "to degrade" or "to be degraded" can be but not limited to a condition such as light illumination, heat, low temperature, an enzymatic condition, an oxidation-reduction condition, an acidic condition, a basic condition, a physiological condition, a simulated physiological environment in vitro or the like, preferably a condition such as light illumination, heat, an enzymatic condition, an oxidation-reduction condition, an acidic condition, a basic condition or the like. Herein, "be degradable" or "be degraded" means that degradation reactions can take place under the stimulation of one of the above-described conditions. The light illumination condition can be but not limited to visible light, ultraviolet light, infrared light, near-infrared light, mid-infrared light, etc. The heat condition means a temperature higher than normal physiological temperature, and, generally but not limited, means a temperature higher than 37° C. and also, generally but not limited, below 45° C., preferably below 42° C. One example of the low temperature condition is the low temperature during liquid nitrogen therapy. The enzymatic condition is not particularly limited, and all enzymes that can be physiologically generated are incorporated, e.g., peptidases, proteases, lyases, etc. The oxidation-reduction condition is not particularly limited, such as the condition for redox transition or hydrogenation/reduction transition between a mercapto group and a disulfide bond. The acidic condition and basic condition mainly refer to the pH condition of normal tissues, diseased tissues, organs or tissues under therapeutic treatment and other sites in vivo, e.g., the stomach has an acidic condition, and the tumor site is usually meta-acidic. "Degradation" herein mainly includes degradation via metabolic processes in vivo (e.g., physiological process, enzymolysis, redox, etc.), degradation under stimulation of microenvironment at given sites in vivo (e.g., acidic stimulation, basic stimulation), degradation under stimulation of clinical treatment (such as light illumination, heat, low temperature) and so on.

What should be noted is that, some conditions in organic chemistry which are relatively extreme for living organisms, such as strong acid, strong base, high temperature (e.g., above 100° C.) and the like, and under which breakage degradation of bond can take place, do not belong to the scope of "degradable" conditions in the present invention. For another example, the ether bond is always classified as a stable linking group in the present invention, although it can be cleaved under strongly acidic conditions such as hydrobromic acid.

Contrarily, as long as a linking group can keep as a whole linkage (i.e. a linking group which can stay covalently connected with the adjacent groups), it is defined as "a stable group", and herein chemical changes through which the wholeness of the linking group is still maintained are allowed. The chemical changes are not particularly limited, including but not limited to isomerization transition, oxidation, reduction, ionization, protonation, deprotonation, substitution reactions, etc. The condition "to be stable" or "to remain stable" is not particularly limited, can be but not limited to light illumination, heat, low temperature, an enzymatic condition, an oxidation-reduction condition, a neutral condition, an acidic condition, a basic condition, a physiological condition, a simulated physiological environment in vitro or the like, and preferably light illumination, heat, an enzymatic condition, an oxidation-reduction condition, an acidic condition, a basic condition or the like. Herein, "be stable" or "remain stable" means that a connection can remain stably connected throughout the metabolic processes in vivo without particular stimulation (such as pH conditions at special sites, therapeutic conditions of light illumination, heat, low temperature, etc.), and no decrease of the molecular weight happens even some bonds may be broken as long as the wholeness are kept.

In addition, for one linking group, the scope of "stable" is not strictly absolute. For example, an amide bond is much more stable than an ester bond under an acidic or basic condition, and accordingly, "stable" linking groups in the present invention include the amide bond. However, a peptide bond (a kind of amino bond) can also be broken when suffering from specific enzymatic conditions, and therefore it can also be incorporated into "degradable" linking groups. Similarly, a urethane group (a carbamate group), a thiourethane group (a thiocarbamate group) and the like can be either a "stable" linking group or a "degradable" linking group. More generally, the carbamate group and the thiocarbamate group tend to degrade slowly, whereas the amide bonds of non-peptide-bond type can be stable during in vivo circulation. For example, a commonly known ester bond can be degraded under acidic or basic conditions, and ester bonds in some special structures can also be degraded under an ultraviolet light condition.

In order to illustrate the structure of compounds more clearly, a reference criterion for distinguish "be stable" and "be degradable" is provided in the present invention, wherein, the suggested boundary is 90% for objective chemical bonds that go through a limited time interval, generally referring to pharmacokinetics profile of the pegylated product and based on the dose meeting the clinical evaluation criteria. For example, with respect to pegylated drugs for intravenous administration, when the plasma concentration (in terms of effective drug ingredients, including undegraded pegylated moieties and degraded non-pegylated moieties) is less than 15% of the initial concentration (or a percentage more in line with clinical evaluation of the drug), based on the remaining 85% moieties, in terms of a specific linking group, if the proportion that remains chemically bonded exceeds 90%, said linking group is considered as a stable group in the present invention, otherwise, it is considered as a degradable group if the proportion is less than 90%.

Conditions for hydrolytically stability, enzymatic degradation and the like in the prior art are also incorporated into the present invention by reference. The hydrolytically stability herein, preferably but not limited, corresponds to a hydrolysis rate less than 1-2% per day by mass or by mole under physiological conditions. The hydrolysis rate of typical chemical bonds can refer to handbooks of chemistry.

In the present invention, the structure type of an amino acid is not particularly limited if without particular illustrations, and can be $_L$-type, $_D$-type or the mixture of $_L$-type and $_D$-type.

The definitions, embodiments and examples related to amino acid skeletons, amino acid derivative skeletons and the skeleton of a cyclic monosaccharide in the references CN104530413A, CN104530415A and CN104530417A are incorporated into the present invention by reference. Wherein, the amino acid skeleton refers to a residue group having typical characteristics of an amino acid, and specifically means a residue group formed after removal of carboxylic hydroxyl group (including all the C-terminal carboxylic hydroxyl groups as well as carboxylic hydroxyl group of the pendant group of aspartic acid and glutamic acid), hydrogen atom of hydroxyl group, hydrogen atom of phenolic hydroxyl group (e.g., tyrosine), hydrogen atom of mercapto group (e.g., cysteine), hydrogen atoms bonded to a nitrogen atom (including all the N-terminal hydrogen atoms as well as hydrogen atoms of pendant amino groups, such as hydrogen atoms of ε-amino group of lysine, hydrogen atoms of amino group of pendant ring of histidine and tryptophan and the like), amino group of terminal amide group (e.g., asparagine, glutamine, etc.), or amino group or hydrogen atoms of amino group of pendant group of guanidino group. The skeleton of an amino acid derivative include not only corresponding amino acid skeleton but also the characteristic atoms and groups. The skeleton of a monosaccharide refers to the residue group formed by the removal of all hydroxyl groups of a monosaccharide, including the skeleton of an open-chain monosaccharide and the skeleton of a cyclic monosaccharide (such as a furanose ring and a pyranose ring).

The molecular weight involving the term "approximately" or "about" or "substantially", generally but not limited, refers to a range within ±10% of the value, for example, a molecular weight of about 5000 Da usually refers to a value range from 4500 to 5500 Da.

1.1 An Eight-Arm Polyethylene Glycol Derivative Containing Active Functional Groups is Represented by the Following General Formula (1):
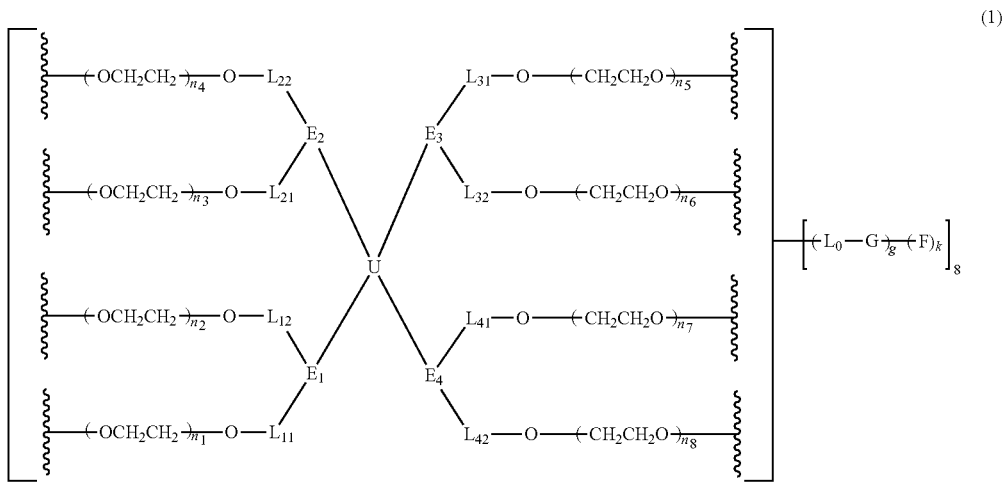
(1)
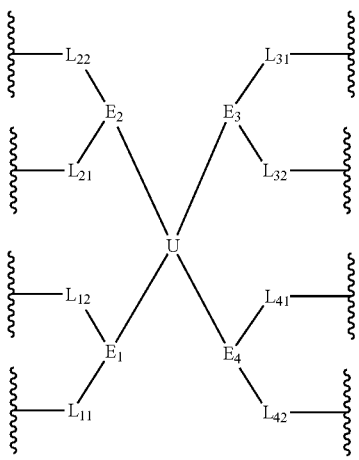
CORE$_8$
Wherein, the eight-arm polyethylene glycol derivative has eight PEG chains and one octavalent central group CORE$_8$; the octavalent central group contains a moiety of
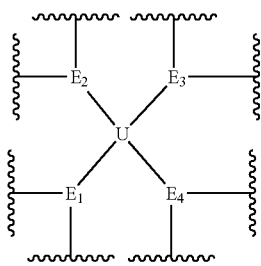

denoted as CORE which consists of one tetravalent central group U and four trivalent branching groups $E_1$, $E_2$, $E_3$ and $E_4$; wherein, U is a tetravalent central group; $E_1$, $E_2$, $E_3$ and $E_4$ are trivalent branching groups that are connected to the tetravalent central group U, and can be each independently identical or not identical in one molecule; preferably, $E_1$, $E_2$, $E_3$ and $E_4$ have the same structure in one molecule, denoted by $U_c$, wherein, the general formula (1) can be represented by formula (1a), and CORE can be represented by $CORE_0$.

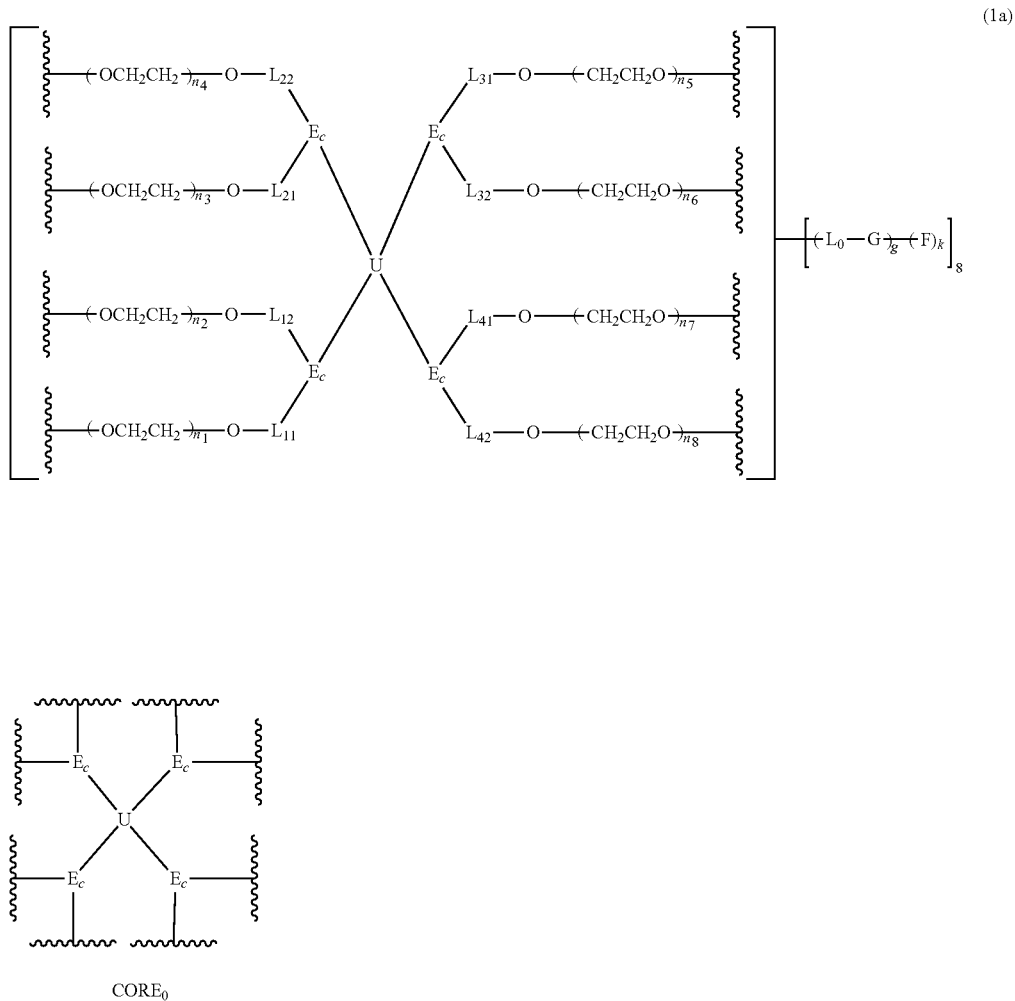

$CORE_0$

Wherein, $L_{11}$, $L_{12}$, $L_{21}$, $L_{22}$, $L_{31}$, $L_{32}$, $L_{41}$ and $L_{42}$ are divalent linking groups that respectively connects a PEG chain to the corresponding terminus of CORE with eight termini; $L_{11}$, $L_{12}$, $L_{21}$, $L_{22}$, $L_{31}$, $L_{32}$, $L_{41}$ and $L_{42}$ are each independently present or absent, and can be each independently identical or not identical in one molecule; one of the preferred embodiments is that $L_{11}$, $L_{12}$, $L_{21}$, $L_{22}$, $L_{31}$, $L_{32}$, $L_{41}$ and $L_{42}$ have the same structure in one molecule, denoted as $L_0$, wherein, they are all present or all absent, and the general formula (1) can be represented by formula (1b).

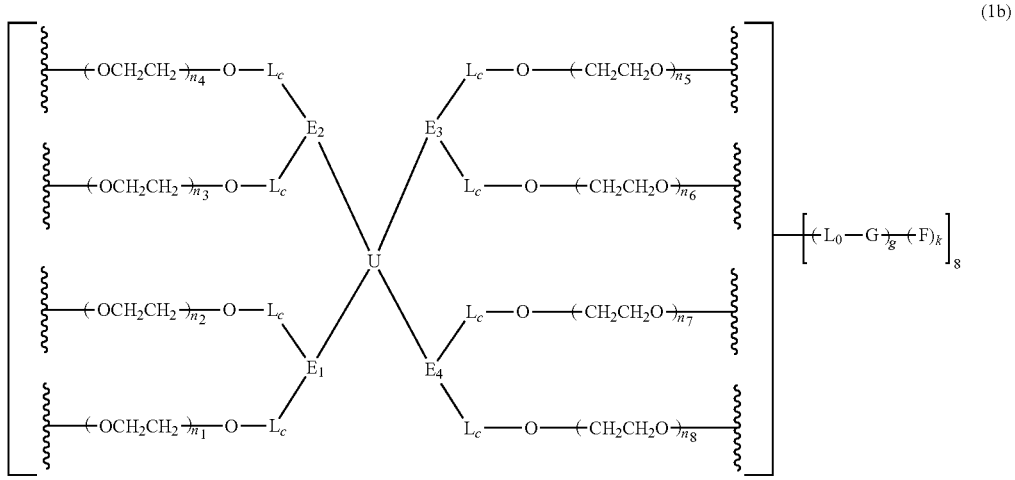

(1b)

One preferable embodiment is that $E_1$, $E_2$, $E_3$ and $E_4$ are identical, and $L_{11}$, $L_{12}$, $L_{21}$, $L_{22}$, $L_{31}$, $L_{32}$, $L_{41}$ and $L_{42}$ are identical, wherein, the general formula (1) can be represented by formula (1c).

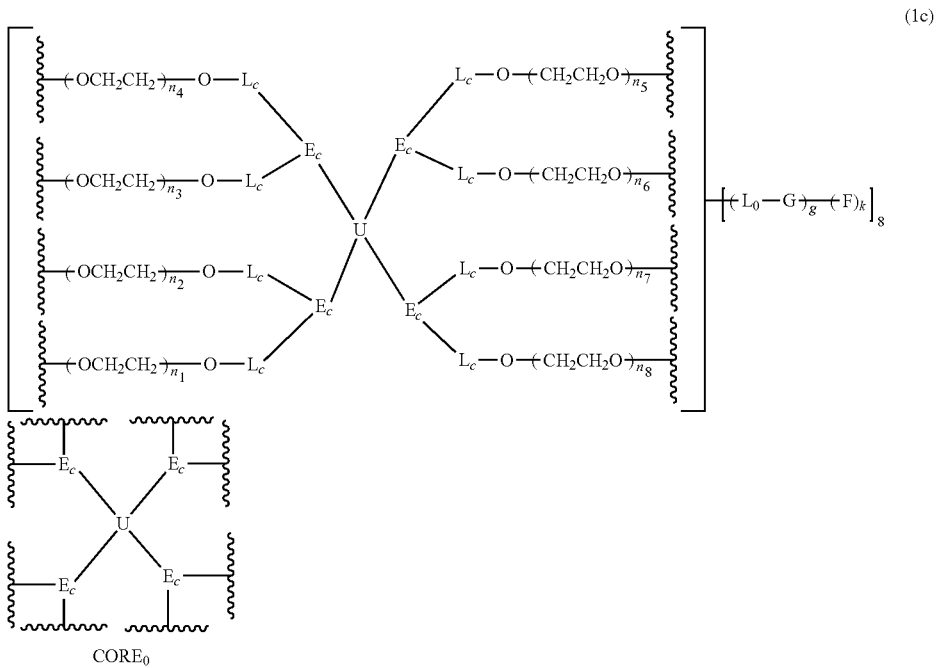

(1c)

CORE$_0$

Wherein, $n_1$, $n_2$, $n_3$, $n_4$, $n_5$, $n_6$, $n_7$ and $n_8$ represent the degree of polymerization of the eight PEG chains, respectively; they are each independently a value from 2 to about 2000, and can be each independently identical or not identical in one molecule;

PEG chains corresponding to $n_1$, $n_2$, $n_3$, $n_4$, $n_5$, $n_6$, $n_7$ and $n_8$ are each independently polydisperse or monodisperse;

wherein, G is an end-branching group of trivalence or higher valence which can connect one PEG chain with two or more terminal functional groups; $L_0$ is a divalent linking group which can connect the PEG chain with the end-branching group G;

wherein, g is 0 or 1; k is an integer of 1 or an integer from 2 to 250; when all the k values of eight PEG chain terminals are all greater than 2, those k values can be each independently equal or different;

when g is 0, k is equal to 1, meanwhile both $L_0$ and G are absent;

when g is 1, G is present, meanwhile $L_0$ can be present or absent, and k is an integer from 2 to 250;

wherein, the terminal functional group F contains a functional end-group, and the structure of F is represented by

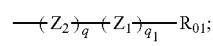

wherein, q and $q_1$ are each independently equal to 0 or 1; $Z_1$ and $Z_2$ are each independently a divalent linking group; $R_{01}$ is a functional end-group which can interreact with a bio-related substance;

the eight-arm polyethylene glycol derivative can remain stable or be degraded (stable or degradable); in one molecule, U, $E_1$, $E_2$, $E_3$, $E_4$, $L_{11}$, $L_{12}$, $L_{21}$, $L_{22}$, $L_{31}$, $L_{32}$, $L_{41}$, $L_{42}$, $L_0$, G and $(Z_2)_q$—$(Z_1)_{q1}$ can be each independently either stable or degradable, and the joint linking group formed by any aforesaid group with its adjacent group can be each independently either stable or degradable.

1.1.1. The Degree of Polymerization and Dispersity of Polyethylene Glycol Chains In the general formula (1), $n_1$, $n_2$, $n_3$, $n_4$, $n_5$, $n_6$, $n_7$ and $n_8$ represent the degree of polymerization of the eight PEG chains, respectively; they are each independently a value from 2 to about 2000, and can be each independently identical or not identical in one molecule. The number of oxyethylene units (also referred to as EO-unit number, or oxyethylene-unit number) of the eight PEG chains can be each independently identical or not identical in one molecule, while the degree of polymerization of the eight PEG chains can also be each independently identical or not identical in the macroscopic polymeric substance. PEG chains corresponding to $n_1$, $n_2$, $n_3$, $n_4$, $n_5$, $n_6$, $n_7$ and $n_8$ are each independently polydisperse or monodisperse. PEG chains corresponding to $n_i$ (i=1, 2, 3, 4, 5, 6, 7 and 8) can be all monodisperse, be all polydisperse, or be the optional combination of polydisperse and monodisperse chains.

What should be noted is that, if without particular illustration, the "molecular weight" in the present invention corresponds to "number average molecular weight" ($M_n$), and it can refer to that of a polydisperse block or substance, or refer to that of a monodisperse block or substance. Herein, if without particular illustration, the molecular weight or number average molecular weight generally corresponds to polydisperse polymers. If without particular description, the unit is Dalton, abbreviated as Da.

With respect to a polydisperse PEG chain corresponding to $n_i$ (i=1, 2, 3, 4, 5, 6, 7 or 8), the number average degree of polymerization is preferably a value from 2 to about 1500, more preferably a value from 2 to about 1000, more preferably a value from 2 to about 500, more preferably a value from 5 to about 500, more preferably a value from about 11 to about 500, more preferably a value from about 22 to about 500, more preferably a value from about 30 to about 250, and more preferably a value from about 34 to about 150. With respect to these preferable ranges, the more conventional the corresponding molecular weight of PEG segment is, the simpler and more controllable the production method is, also the narrower the PDI (polydispersity index) of molecular weight is, and also the more uniform the performance is. The number average molecular weight of linear PEG chains obtained by polymerization methods is commonly from about 2 kDa to about 40 kDa. In the present invention, the corresponding number average molecular weight in units of Da is preferably about 500, 600, 700, 800, 900, 1000, 1500, 2000, 2500, 3000, 3350, 3500, 4000, 5000, 5500, 6000, 6500, 7000, 7500, 8000, 8500, 9000, 9500, 10000, 11000, 12000, 13000, 14000, 15000, 16000, 17000, 18000, 19000 or about 20000 Da, more preferably about 1000, 1500, 2000, 2500, 3000, 3350, 3500, 4000, 5000, 5500, 6000, 6500, 7000, 7500, 8000, 8500, 9000, 9500, 10000, 11000 or about 12000 Da, more preferably about 1000, 1500, 2000, 3000, 3350, 3500, 4000, 5000, 6000, 7000, 8000, 9000 or about 10000 Da, and more preferably about 1000, 1500, 2000, 3350, 3500, 4000, 5000 or about 6000 Da.

With respect to a monodisperse PEG block corresponding to $n_i$ (i=1, 2, 3, 4, 5, 6, 7 or 8), the molecular weight is described by the number of oxyethylene units (also referred to as EO-unit number or oxyethylene-unit number). The EO-unit numbers of monodisperse polyethylene glycols by using conventional techniques in the prior art range between 1 and about 70, including but not limited to the EO-unit numbers listed in the references "Expert Rev. Mol. Diagn. 2013, 13 (4), 315-319", "J. Org. Chem. 2006, 71, 9884-9886", "Angew. Chem. 2009, 121, 1274-1278", "Bioorganic & Medicinal Chemistry Letters, 2015, 25: 38-42", "Angew. Chem Int Ed, 2015, 54: 3763-3767" and cited references in the aforesaid reference. Typical EO-unit number of monodisperse PEGs can be but not limited to 1, 2, 3, 4, 5, 6, 7, 8, 9, 10, 12, 13, 16, 20, 22, 24, 27, 29, 36, 44, 48, 56, 62, 64, 67, etc. What should be noted is that, monodispersity herein not only can refer to a single component having only one kind of EO-unit number, but also can refer to a monodisperse mixture. With respect to a monodisperse mixture, the relative contents of different components should be a fixed value in order to generate a PDI of 1 for the mixture as a whole, and herein the corresponding number average degree of polymerization can be either an integer or a non-integer value. With respect to the mixture of monodisperse blocks or substances, if the relative contents of the components are not fixed, the whole PDI becomes greater than 1, and the mixture corresponds to a polydisperse block or substance. The EO-unit number of a monodisperse PEG block is preferably from 2 to 70, more preferably from 3 to 70, more preferably from 3 to 50, and more preferably from 3 to 25. The more preferable the EO-unit number is, the more diverse production methods therefor are. The EO-unit number of a monodisperse PEG chain is preferably selected from the group consisting of 2, 3, 4, 5, 6, 7, 8, 9, 10, 11, 12, 13, 14, 15, 16, 18, 20, 22, 24, 26, 27, 28, 29, 30, 32, 34, 36, 38, 40, 42, 44, 45, 46, 48, 50, 52, 54, 56, 58, 60, 62, 64, 66, 67, 68 and 70.

According to the difference in the dispersity of the eight PEG chains, the eight-arm polyethylene glycol derivatives represented by the general formula (1) include but are not limited to the following three embodiments: (a) wherein, the PEG chains corresponding to $n_1$, $n_2$, $n_3$, $n_4$, $n_5$, $n_6$, $n_7$ and $n_8$ are all polydisperse; in the general formula (1), preferably $n_1 \approx n_2 \approx n_3 \approx n_4 \approx n_5 \approx n_6 \approx n_7 \approx n_8$; (b) wherein, the PEG chains corresponding to $n_1$, $n_2$, $n_3$, $n_4$, $n_5$, $n_6$, $n_7$ and $n_8$ are all monodisperse; in the general formula (1), preferably $n_1 = n_2 = n_3 = n_4 = n_5 = n_6 = n_7 = n_8$; (c) wherein, one to seven chains of the PEG chains corresponding to $n_1$, $n_2$, $n_3$, $n_4$, $n_5$, $n_6$, $n_7$ and $n_8$ are polydisperse, while the other chains are monodisperse, and the molecular weight of the eight PEG chains are close (i.e. substantially equal) or equal.

The above description for dispersity mainly refers to the PEG chains of the general formula (1). With respect to the whole eight-arm polyethylene glycol derivative, its polydispersity index can be the same as or different from an individual PEG chain. With respect to the PDI value of the whole compound, the lower the better. With respect to the chain length distribution of the eight PEG chains of the eight-arm polyethylene glycol derivative represented by the general formula (1), it is preferably that $n_1 \approx n_2 \approx n_3 \approx n_4 \approx n_5 \approx n_6 \approx n_7 \approx n_8$ (wherein, the number average molecular weights of the eight PEG chains is each independently the same or close) or $n_1 = n_2 = n_3 = n_4 = n_5 = n_6 = n_7 = n_8$ (wherein, the molecular weights of the eight PEG chains are fixed and equal). Herein, the chain lengths of the PEG chains are equal or close, and the modified bio-related substance thereof is more likely to show a homogeneous structure, which is beneficial for improving the purity and performance of the product. The embodiments with $n_1 \approx n_2 \approx n_3 \approx n_4 \approx n_5 \approx n_6 \approx n_7 \approx n_8$ are applicable for polydisperse structures having a polydispersity, and can meet the need for different molecular weights; while the embodiments with $n_1 = n_2 = n_3 = n_4 = n_5 = n_6 = n_7 = n_8$ are applicable for monodisperse structures having a monodispersity, and the control of the product structure can be more precise and the quality of the modified product can be better.

1.1.2. Degradability

The eight-arm polyethylene glycol derivative can be either stable or degradable. When being degradable, in one molecule, the number of degradable sites can be one or more. With respect to the degradable positions: (1) the degradable sites can be contained within one degradable group selected from U, $E_1$, $E_2$, $E_3$, $E_4$, $L_{11}$, $L_{12}$, $L_{21}$, $L_{22}$, $L_{31}$, $L_{32}$, $L_{41}$, $L_{42}$, $L_0$, G and $(Z_2)_q$—$(Z_1)_{q1}$; (2) the degradable sites can also be located at the connection between any aforesaid group and its adjacent group, but the degradability of the connection $Z_1$—$R_{01}$ is not limited. In the first case, the degradable groups should contain at least one degradable divalent linking group such as an ester group, a carbonate group or the like. In the second case, at least one connection position selected from U-$E_i$ (i=1, 2, 3 or 4), $E_i$-$L_{i1}$ (i=1, 2, 3 or 4), $E_i$-$L_{i1}$ (i=1, 2, 3 or 4), $L_{i2}$ (i=1, 2, 3 or 4)-O, $L_{i2}$ (i=1, 2, 3 or 4)-O, O-$L_0$, $L_0$-G, G-$Z_2$ and $Z_2$—$Z_1$ can be degraded.

The number and position of degradable sites of the eight-arm polyethylene glycol derivative have a great influence on the stability of polymer and drug releasability of modified drugs thereof. (1) When a degradable position exists between the terminal functional end-group of one PEG chain (eight chains in total) and the corresponding polyethylene glycol chain, such as the position at —$(Z_2)_q$—$(Z_1)_{q1}$—, the pegylated drug molecule can be separated from the polyethylene glycol moiety to expose its active site to a maximum extent, and thus the drug molecule can turn towards its unmodified form to a maximum extent when undergoing degradation. (2) When a degradable position exists at the octavalent group $CORE_8(O—)_8$, wherein, the degradable position can be selected from U, $E_1$, $E_2$, $E_3$, $E_4$, $L_{11}$, $L_{12}$, $L_{21}$, $L_{22}$, $L_{31}$, $L_{32}$, $L_{41}$, $L_{42}$, U-$E_i$ (i=1, 2, 3 or 4), $E_i$-$L_{i1}$ (i=1, 2, 3 or 4), $E_i$-$L_{i2}$ (i=1, 2, 3 or 4), $L_{i1}$ (i=1, 2, 3 or 4)-O and/or $L_{i2}$ (i=1, 2, 3 or 4)-O, the molecular weight of polyethylene glycol moiety connected with the drug molecule decreases, and thus the shielding effect for the drug molecule is reduced and the drug efficacy increases.

Several typical degradation manners are as follows: (a) wherein, g is equal to 0 or 1, degradable reactions only occur within U (i.e., only U contains degradable groups), and the eight-arm polyethylene glycol derivative can be degraded into two, three or four individual polyethylene glycol fragments; (b) wherein, g is equal to 0 or 1, degradable reactions only occur at the connection U-$E_i$ (i=1, 2, 3 or 4), and the eight-arm polyethylene glycol derivative can be degraded into four two-arm polyethylene glycol fragments; (c) wherein, g is equal to 0 or 1, degradable reactions only occur within $E_i$ (i=1, 2, 3 or 4), and the degradation manners include but are not limited to degradation into four two-arm polyethylene glycol fragments, degradation into eight linear polyethylene glycol fragments, and degradation into to one four-arm polyethylene glycol fragment together with four linear polyethylene glycol fragments; (d) wherein, g is equal to 0 or 1, degradable reactions only occur at positions including $E_i$-$L_{i1}$ (i=1, 2, 3 or 4), $E_i$-$L_{i2}$ (i=1, 2, 3 or 4), $L_{11}$, $L_{12}$, $L_{21}$, $L_{22}$, $L_{31}$, $L_{32}$, $L_{41}$, $L_{42}$, $L_{i1}$ (i=1, 2, 3 or 4)-O and $L_{i2}$ (i=1, 2, 3 or 4)-O, and the eight-arm polyethylene glycol derivative can be degraded into eight linear polyethylene glycol fragments, or be degraded into one four-arm polyethylene glycol fragment together with four linear polyethylene glycol fragments; (e) wherein, g is equal to 0 or 1, degradable reactions only occur at —$(Z_2)_q$—$(Z_1)_{q1}$—, wherein, the degradation position described by "occur at" also includes the connection between —$(Z_2)_q$—$(Z_1)_{q1}$— and its adjacent group towards the PEG side, and the eight-arm polyethylene glycol derivative can be degraded into an eight-arm polyethylene glycol structure together with individual residues of functional groups; (f) wherein, g is equal to 1, degradable reactions only occur at $L_0$, wherein, the degradation positions include inside of $L_0$, connection O-$L_0$ and connection $L_0$-G, and the eight-arm polyethylene glycol derivative can be degraded into an eight-arm polyethylene glycol structure together with several clusters of functional groups connected by G groups; (g) wherein, g is equal to 1, degradable reactions only occur within G, and the eight-arm polyethylene glycol derivative can be degraded into an eight-arm polyethylene glycol structure, and individual residues of functional groups and/or residues of functional group clusters.

The eight-arm polyethylene glycol derivative can involve one or one more degradation manners. When more than one degradation manners are concerned, gradient degradation can occur to more flexibly control the degradation kinetics of pegylated product; with respect to the pegylated drug, the pharmacokinetics in body can be controlled more flexibly and more finely, and the requirement for therapeutic effect of more comprehensive treatment can be met better.

According to whether the eight PEG chains can turn separate along with degradation, the degradation positions can be simply classified into octavalent center $CORE_8$ (O—)$_8$ and functional terminals. Wherein, when g is equal to 0, the eight-arm derivative has a non-branched divalent terminal —O$(Z_2)_q(Z_1)_{q1}$—; when g is equal to 1, the eight-arm derivative has a branched terminal —O-$L_0$-G-$((Z_2)_q(Z_1)_{q1}$-$)_k$. The degradation manners include but are not limited to the following embodiments:

(1) wherein, the eight-arm polyethylene glycol derivative has a stable octavalent center and stable terminals.

(2) wherein, the eight-arm polyethylene glycol derivative has a stable octavalent center and degradable terminals.

(3) wherein, the eight-arm polyethylene glycol derivative has a degradable octavalent center and stable terminals.

(4) wherein, the eight-arm polyethylene glycol derivative has a degradable octavalent center and degradable terminals.

All the eight-arm polyethylene glycol derivatives represented by the general formulas from (6) to (37) in the present invention have a stable octavalent center, wherein, the terminals can be stable or degradable. One preferable embodiment is that the eight-arm polyethylene glycol derivative has a stable octavalent center, including the above case (1) and case (2).

1.1.3. Branching Groups U, $E_i$ (i=1, 2, 3 or 4) and G

U can be a tetravalent group selected from the set $G^4$ consisting of tetravalent groups.

$E_1$, $E_2$, $E_3$ and $E_4$ can be each independently a trivalent group selected from the set $G^3$ consisting of trivalent groups. When an asterisk symbol "*" is used for marking $E_1$, $E_2$, $E_3$ and $E_4$, the marked terminus should be directed to the tetravalent core U.

If without particular instructions, as for a group G with the valence of k+1 (k is from 2 to 250), any one of its radical termini can be directed to the corresponding PEG chain.

When an asterisk mark is used, the marked radical terminus should be oriented towards the corresponding PEG moiety.

In the general formula (1), k represents the number of functional end-groups ($R_{01}$) contained in one PEG terminal, and the k values in one molecule are each independently an integer of 1 or an integer from 2 to 250. When k is equal to 1 and g is zero, G is absent;

when k is an integer from 2 to 250, g is 1 and G is present and exists as a linking group with the valence of k+1, wherein, $L_0$ can be present and absent. Herein, k can be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or an integer from 33 to 250. Correspondingly, the valence of G can be selected from 3 to 251, specifically selected from 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33 and integers from 34 to 251.

Wherein, k is preferably selected from 1 to 100; specifically, k is preferably 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or an integer from 33 to 100, more preferably 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or an integer from 33 to 64, and more preferably 1, 2, 3, 4, 5, 6, 7, 8, 9, 10, 11, 12, 13, 14, 15, 16, 17, 18, 19 or 20.

When all the k values of the eight PEG chains are greater than 2, those k values of the eight PEG chains can be each independently identical or not identical.

For a k-value from 2 to 250, the corresponding G can be a (k+1)-valent group selected from the set $G^{k+1}$ consisting of groups with the valence of k+1.

The stability of any (k+1)-valent group in the set $G^{k+1}$ is not particularly limited and can be stable in or be degradable. The conditions "to remain stable" and "to be degraded" are the same as above in the term-defining section.

$E_i$ (i=1, 2, 3 or 4) and trivalent G are each independently a trivalent group selected from the set $G^3$ consisting of trivalent groups, and can be each independently identical or not identical in one molecule.

U and tetravalent G are each independently a tetravalent group selected from the set $G^4$ consisting of tetravalent groups, and can be the same or different in one molecule.

As for k-values from 2 to 250, the corresponding (k+1)-valent groups in the set $G^{k+1}$ with set $G^3$ and set $G^4$ included, and preferable embodiments thereof include but are not limited to the groups described and exemplified in the documents CN104530413A, CN104530415A and CN104530417A.

Trivalent groups in the set $G^3$ contain one trivalent core. The trivalent core can be an atom $CM_3$, an unsaturated bond $CB_3$ or a cyclic structure $CC_3$. The trivalent atom core $CM_3$, trivalent unsaturated-bond core $CB_3$, trivalent cyclic core $CC_3$ and preferable embodiments of the three kinds of trivalent cores include but are not limited to the groups described and listed in the documents CN104530413A, CN104530415A and CN104530417A. Take CN104530417A for example, corresponding to paragraphs from [0211] to [0284].

Wherein, the trivalent atom core ($CM_3$) is not particularly limited as long as it can provide three covalent single bonds individually. Examples of $CM_3$ include a trivalent nitrogen-atom core, a trivalent carbon-atom core

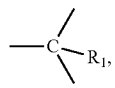

a trivalent silicon-atom core

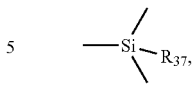

a trivalent phosphorus-atom core (such as

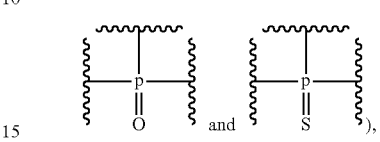

etc. The trivalent core atom can connect with no other atoms or groups, such as a trivalent nitrogen atom core

or can also connect with another atom or group, e.g., a trivalent carbon atom core, a trivalent silicon atom core, a trivalent phosphorous atom core, etc.

Wherein, $R_{37}$ is the substituent of a trivalent silicon-branching center, selected from hydrocarbyl groups, preferably a $C_{1-20}$ hydrocarbyl group, more preferably a $C_{1-20}$ alkyl group, and most preferably a methyl group.

Wherein, $R_1$ is a hydrogen atom or a substituent bound to a carbon atom.

When as a group substituent, $R_1$ is not particularly limited, but preferably a group substituent that can remain stable under anionic polymerization conditions.

When as a group substituent, the carbon-atom number of $R_1$ is not particularly limited, preferably from 1 to 20, and more preferably from 1 to 10.

When as a group substituent, $R_1$ can contain heteroatoms or not.

When as a group substituent, the structure of $R_1$ is not particularly limited, including but not limited to a linear structure, a branched structure which bearing one or more pendant groups and a ring-containing structure. Wherein, the ring of the ring-containing structure is not particularly limited, preferably an aliphatic ring, an aromatic ring, a sugar ring or a condensed ring as above-described.

$R_1$ is a hydrogen atom or a group selected from the group consisting of $C_{1-20}$ hydrocarbyl groups, substituted $C_{1-20}$ hydrocarbyl groups and the like. Wherein, the atom or group substituent of $R_1$ is not particularly limited. Examples of substituents of $R_1$ include but are not limited to all the above-described atom substituents and group substituents in the term-defining section, selected from the group consisting of halogen atoms, hydrocarbyl substituents and heteroatom-containing substituents.

$R_1$ is preferably a hydrogen atom or a group selected from the group consisting of a $C_{1-20}$ alkyl group, an arylalkyl group, a $C_{1-20}$ open-chain heterohydrocarbyl group, a heteroarylhydrocarbyl group, a substituted $C_{1-20}$ alkyl group, a substituted arylhydrocarbyl group, a substituted $C_{1-20}$ open-chain heterohydrocarbyl group, a substituted heteroarylhydrocarbyl group and the like.

Specific examples of $R_1$ can be a hydrogen atom or a group selected from, but not limited to, a methyl group, an ethyl group, a 1-propyl group (or an n-propyl group), an isopropyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a benzyl group, a substituted $C_{1-20}$ alkyl group, a substituted arylhydrocarbyl group, a substituted $C_{1-20}$ open-chain heterohydrocarbyl group, a substituted heteroarylhydrocarbyl group and the like. Wherein, the butyl group includes but is not limited to an n-butyl group and a t-butyl group. The octyl group includes but is not limited to an n-octyl group and a 2-ethylhexyl group. Wherein, the atom or group substituent can be a halogen atom, a hydrocarbyl substituent or a heteroatom-containing substituent, and preferably a fluorine atom, a chlorine atom, a bromine atom, an iodine atom, a $C_{1-6}$ alkyl group, an alkoxy group or a nitro group.

$R_1$ is preferably a hydrogen atom, a methyl group, an ethyl group, an n-propyl group, an isopropyl group, a butyl group, a pentyl group, a hexyl group, a heptyl group, an octyl group, a nonyl group, a decyl group, a $C_{1-10}$ halogenated hydrocarbyl group (or a $C_{1-10}$ halohydrocarbyl group), a halogenated acetyl group or an alkoxy-substituted $C_{1-10}$ aliphatic hydrocarbyl group. Wherein, the halogen atom is F, Cl, Br or I.

$R_1$ is most preferably a hydrogen atom, a methyl group or an ethyl group.

Wherein, the trivalent unsaturated-bond core $CB_3$ is not particularly limited, as long as it can provide three covalent single bonds individually. The bond-membering atoms of the unsaturated bond can be two or two more, preferably two or three, and more preferably two. For example,

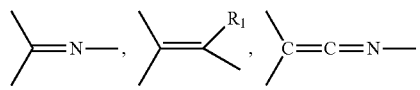

and the like.

Wherein, the trivalent cyclic core $CC_3$ is not particularly limited, as long as it can protrude three covalent single bonds individually. The ring-membering atoms to form a covalent single bond radical are not particularly limited, including but not limited to N, C, Si, P, etc. The cyclic structure can be but not limited to an aliphatic ring, an aromatic ring, a sugar ring or a condensed ring. The cyclic structure can be a monocyclic ring, such as a trivalent ring deriving from cyclohexane, a furanose ring, a pyranose ring, a benzene ring, pyridine, triazole, triazacyclononane or the like, or be a polycyclic ring, such as a ring deriving from fluorene, carbazole, adamantane or the like. The cyclic structure can come from natural sources, such as from a trivalent monocyclic ring of a cyclic monosaccharide. The cyclic structure can also be a synthesized trivalent ring formed via chemical reactions, such as a cyclopeptide, a lactone, a lactam, a lactide (a cyclic diester of hydroxycarboxylic acids), etc. The covalent single bonds can protrude directly from a ring-membering atom, or via an unsaturated bond. It also allows three covalent single bonds to protrude from three ring-membering atoms respectively such as

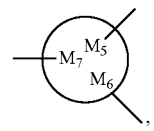

or two of the three covalent single bonds to come from a common ring-membering atom together such as

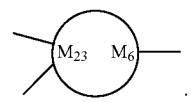

Wherein, $M_5$, $M_6$, $M_7$ and $M_{23}$ are ring-membering atoms, i.e. constituting the ring skeleton. $M_5$, $M_6$, $M_7$ and $M_{23}$ are each independently a carbon atom or a heteroatom, and they can be the same or different in one molecule. $M_5$, $M_6$, $M_7$ and $M_{23}$ are each independently preferably a carbon atom, a nitrogen atom, a phosphorus atom or a silicon atom. The number of ring-membering atoms of a ring containing $M_5$, $M_6$, $M_7$ or $M_{23}$ is not particularly limited, preferably from 3 to 50, more preferably from 3 to 32, more preferably from 3 to 18, and more preferably from 5 to 18.

$M_{23}$ is a carbon atom, a nitrogen atom, a phosphorus atom or a silicon atom of the ring skeleton which protrudes two single bonds. When as a nitrogen atom, the ring-membering nitrogen atom is in the form of a quaternary ammonium cation.

The ring containing $M_5$, $M_6$ and $M_7$, and the ring containing $M_{23}$ and $M_6$ are not particularly limited, including but not limited to

and the like. The number of ring-membering atoms is not particularly limited, preferably from 3 to 50, more preferably 3 to 32, and more preferably 3 to 18.

Wherein, the aliphatic ring

is an alicyclic ring or an aliphatic-derived heteroring of any type, and the ring-membering atoms are each independently a carbon atom or a heteroatom; wherein, the heteroatom is not particularly limited, including but not limited to a nitrogen atom, an oxygen atom, a sulfur atom, a phosphorus atom, a silicon atom, a boron atom and the like. The hydrogen linked to a ring-membering atom can be substituted by any heteroatom or group substituent, or not be substituted. The heteroatom or group substituent is not particularly limited, including but not limited to all the heteroatom and group substituents above-described in the term-defining section, and can be selected from a halogen atom, a hydrocarbyl substituent and a heteroatom-containing substituent. Generally speaking, the alicyclic ring and the aliphatic-derived heteroring include but are not limited to cyclic structures selected from the group consisting of a monocyclic ring, a polycyclic ring, a spiro-ring, a bridged ring, a condensed ring, a carbon ring, a heteroring, an aliphatic-derived heteroring, a heteromonocyclic ring, a heteropolycyclic ring, a hetero-spiroring, a hetero-bridged ring, a hetero-aliphatic ring and the combination of any two or more ring types of the foregoing.

Wherein, the aromatic ring

is an aromatic all-carbon ring (or an aryl ring) or an aromatic-derived heteroring, and the ring-membering atoms are each independently a carbon atom or a heteroatom; the heteroatom is not particularly limited, and can be but not limited to a nitrogen atom, a phosphorus atom, a silicon atom, a boron atom or the like. The hydrogen atom linked to the arylring-membering atoms can be substituted with any heteroatom or group substituent, or not be substituted. The heteroatom or group substituent is not particularly limited, including but not limited to all the heteroatom and group substituents above-described in the term-defining section, and can be selected from halogen atoms, hydrocarbyl substituents and heteroatom-containing substituents. The heteroatom substituent is preferably a halogen atom, and the group substituent is preferably a group that can favor inductive effect, conjugation effect, or both inductive and conjugation effects of electrons of unsaturated bonds. Generally speaking, the aryl ring and the aromatic-derived heteroring include but are not limited to cyclic structures selected from the group consisting of a monocyclic ring, a polycyclic ring, a condensed ring, a condensed aryl ring, a condensed heteroring, an aryl-condensed heteroring, an aryloheteroring, a benzoheteroring, a heterocondensed heteroring, a carbon ring, a heteroring, an aromatic-derived heteroring, a heteromonocyclic ring, a heteropolycyclic ring, a hetero-condensed ring, a heteroaromatic ring and the combination of any two or two more ring types of the foregoing. The aromatic ring is preferably derived from one cyclic structure selected from the group consisting of benzene, pyridine, pyridazine, pyrimidine, pyrazine, 1,3,5-triazine, tetrazine (three isomers of 1,2,3,4-, 1,2,4,5- and 1,2,3,5-), indene, indane, indole, isoindole, purine, naphthalene, dihydroanthracene, xanthene, thioxanthene, dihydrophenanthrene, 10,11-dihydro-5H-dibenzo[a,d]cycloheptane, dibenzocycloheptene, 5-dibenzosuberenone, quinoline, isoquinoline, fluorene, carbazole, iminodibenzyl, acenaphthene (or 1,2-dihydroacena-phthylene), dibenzocyclooctyne, aza-dibenzocyclooctyne, the like, the substituted form of any aforesaid cyclic structure and the heterosubstituted for of any aforesaid cyclic structure.

Wherein, the sugar ring

is the skeleton of a saccharide or a saccharide derivative which contains a cyclic monosaccharide skeleton. The saccharide or the saccharide derivative can be derived from natural or unnatural monosaccharides. The structure of the cyclic monosaccharide can be any form selected from the group consisting of isomers, enantiomers, optical isomers, conformational isomers, rotamers and the combination of any two or two more of the foregoing. For example, a pyranose ring can be of boat conformation, or be of chair conformation.

is selected from

(the skeleton of a cyclic monosaccharide or the derivative thereof),

(the skeleton of an oligosaccharide or the derivative thereof) and

(the skeleton of a polysaccharide or the derivative thereof). Wherein,

and their preferable embodiments include but are not limited to those described and listed in the documents CN104530413A, CN104530415A and CN104530417A. Take CN104530417A as an example, corresponding to paragraphs from [0231] to [0234].

With respect to the skeleton of a cyclic monosaccharide or a cyclic monosaccharide derivative, its carbon-atom number can be 3, 4, 5, 6 or 7, wherein, the structure can be an isomer, an enantiomer, an optical isomer, a conformational isomer, a rotamer or the combination of any two or two more of the foregoing. It is preferably the skeleton of a monosaccharide or a monosaccharide derivative which contains a $C_6$ cyclic monosaccharide skeleton, wherein, examples of the monosaccharide include but are not limited to glucose, allose, altrose, mannose, gulose, idose, galactose, talose, psicose, fructose, sorbose, tagatose and inositol. The cyclic structure is preferably a five-membered ring or a six-membered ring.

With respect to the skeleton of an oligosaccharide or an oligosaccharide derivative, the combination manners between the cyclic monosaccharide skeletons include but are not limited to linear, branched, hyperbranched, dendritic, comb-like and cyclic manners. The number of the monosaccharide units is from 2 to 10. Take the cyclic manner for example, the monosaccharide units can be combined into a cyclodextrin selected from α-cyclodextrin, β-cyclodextrin and γ-cyclodextrin or a cyclodextrin derivative.

With respect to the skeleton of a polysaccharide or a polysaccharide derivative, the combination manners between the cyclic monosaccharide skeletons include but are not limited to linear, branched, hyperbranched, dendritic, comb-like and cyclic manners. The number of the monosaccharide units is more than 10. For example, the D-glucopyranose units can be linked in sequence via α-1,4-glycosidic bonds to form a linear combination, and the linear structure can further be interconnected end-to-end to form a cyclic combination. For another example, when at least one D-glucopyranose unit is bound together with its adjacent glucopyranose units via at least two glycosidic bonds selected from an α-1,2-glycosidic bond, an α-1,3 glycosidic bond, an α-1,4-glycosidic bond and an α-1,6-glycosidic bond, a branched or hyperbranched combination can be achieved. When all the glucose units are repeatedly bound in a regular manner together via more than three specific glycosidic bonds, a comb-like combination can be obtained. Specifically, for example, the polysaccharide or the polysaccharide derivative can come from starch, chitin, cellulose or glucan.

Wherein, the condensed ring

is a ring containing at least one chemical bond formed by condensation reaction, wherein, the chemical bond can be selected from an amide bond, an ester bond, an imide bond, an anhydride bond and the like. Specific examples include a lactone, a lactide (a cyclic diester of hydroxycarboxylic acids), a lactam, a cycloimide, a cycloanhydride, a cyclopeptide and the like.

The trivalent cyclic core structure $CC_3$ is preferably derived from but not limited to a furanose ring, a pyranose ring, benzene, tetrahydrofuran, pyrrolidine, thiazolidine, cyclohexane, cyclohexene, tetrahydropyran, piperidine, 1,4-dioxane, pyridine, pyridazine, pyrimidine, pyrazine, 1,3,5-triazine, 1,4,7-triazacyclononane, cyclotripeptides, indene, indane, indole, isoindole, purine, naphthalene, dihydroanthracene, xanthene, thioxanthene, dihydrophenanthrene, 10,11-dihydro-5H-dibenzo[a,d]cycloheptane, dibenzocycloheptene, 5-dibenzosuberenone, quinoline, isoquinoline, fluorene, carbazole, iminodibenzyl, acenaphthene (or 1,2-dihydroacena-phthylene), dibenzocyclooctyne, aza-dibenzocyclooctyne, the like, the substituted form of any aforesaid cyclic structure or the heterosubstituted form of any aforesaid cyclic structure.

The Tetravalent Groups in the Set $G^4$ have Two Trivalent Core Structures or One Tetravalent Core Structure.

The trivalent core structure is defined as that in the above-described set $G^3$, no more repeated here.

The tetravalent core structure can be an atom $CM_4$, an unsaturated bond $CB_4$ or a cyclic structure $CC_4$. Wherein, $CM_4$, $CB_4$ and $CC_4$ and their preferable embodiments include but are not limited to those described and listed in the documents CN104530413A, CN104530415A and CN104530417A. Take CN104530417A as an example, corresponding to paragraphs from [0287] to [0291]. They also include but are not limited to

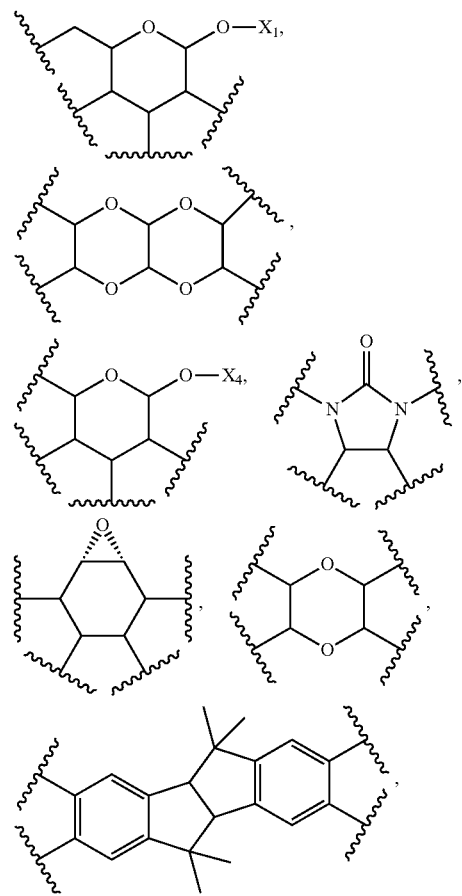

Wherein, $X_1$ and $X_4$ Each Independently Connects to an Oxy Group, and are Each Independently a Hydrogen Atom, a Hydroxyl Protecting Group or a Group $LG_4$.

When $X_1$ and $X_4$ are contained in $CORE_8(O—)_8$, they are preferably non-hydrogen atoms.

When as a hydroxyl protecting group, $X_1$ and $X_4$ are selected from hydroxyl protecting groups as recited for $PG_4$. A protected hydroxyl group is denoted as $OPG_4$. The type of the hydroxyl protecting group is not particularly limited.

Wherein, the carbon-atom number of $LG_4$ is not particularly limited, preferably from 1 to 20, and more preferably from 1 to 10.

The structure of $LG_4$ is not particularly limited, can be, but not limited to, a linear type, a branched type bearing pendant groups or a ring-containing type. Wherein, the ring is not particularly limited, preferably an aliphatic ring, an aromatic ring, a sugar ring or a condensed ring as above-described.

$LG_4$ can contain heteroatoms, or do not contain heteroatoms.

$LG_4$ can be a $C_{1-20}$ hydrocarbyl group, a $C_{1-20}$ heterohydrocarbyl group, a substituted $C_{1-20}$ hydrocarbyl group or a substituted heterohydrocarbyl group. Wherein, the heteroatom or group substituent of $LG_4$ is not particularly limited, including but not limited to all the above-described heteroatom and group substituents in the term-defining section, and can be a halogen atom, a hydrocarbyl substituent or a heteroatom-containing substituent.

$LG_4$ is preferably selected from the group consisting of a $C_{1-20}$ alkyl group, a $C_{2-20}$ unsaturated aliphatic hydrocarbyl group, an aryl group, an arylhydrocarbyl group, a $C_{1-20}$ heterohydrocarbyl group, a $C_{1-20}$ aliphatic hydrocarbyl-acyl group, a $C_{1-20}$ aliphatic-derived heterohydrocarbyl-acyl group, an aryl-acyl group, a heteroaryl-acyl group, a $C_{1-20}$ hydrocarbyloxy-acyl group, a $C_{1-20}$ hydrocarbylthio-acyl group, a $C_{1-20}$ hydrocarbylamino-acyl group, a $C_{1-20}$ heterohydrocarbyloxy-acyl group, a $C_{1-20}$ heterohydrocarbylthio-acyl group, a $C_{1-20}$ heterohydrocarbylamino-acyl group and substituted forms of any aforesaid group. Wherein, the acyl group of $LG_4$ is not particularly limited, and can be but not limited to one of all the above-described acyl groups in the term-defining section. For example, the acyl group of $LG_4$ can be selected from the group consisting of a carbonyl group, a sulfonyl group, a sulfinyl group, a phosphoryl group, a phosphiryl group, a phosphinyl group, a nitroxyl group, a nitrosyl group, a thiocarbonyl group, an imidoyl group, a thiophosphoryl group, a dithiophosphoryl group, a trithiophosphoryl group, a thiophosphiryl group, a dithiophosphiryl group, a thiophosphinyl group, a thiophosphono group, a dithiophosphono group, a thiophosphino group and the like. The acyl group of $LG_4$ is preferably a carbonyl group, a thiocarbonyl group, a sulfonyl group, a sulfinyl group or the like, and more preferably a carbonyl group, a thiocarbonyl group or a sulfonyl group.

$LG_4$ is more preferably selected from the group consisting of a $C_{1-20}$ alkyl group, a $C_{3-20}$ alkenylhydrocarbyl group, an aryl group, an arylalkyl group, a $C_{1-20}$ heteroalkyl group, a heteroaryl group, a heteroarylalkyl group, a $C_{1-20}$ alkylcarbonyl group, an arylcarbonyl group, an arylalkylcarbonyl group, a $C_{1-20}$ heteroalkylcarbonyl group, a heteroarylcarbonyl group, a heteroarylalkylcarbonyl group, a $C_{1-20}$ alkoxycarbonyl group (or an alkyloxycarbonyl group, alkyl-O—CO—), an aryloxycarbonyl group (or an aroxycarbonyl group, aryl-O—CO—), an arylalkoxycarbonyl group (or an arylalkyloxycarbonyl group, arylalkyl-O—CO—), a $C_{1-20}$ (alkylthio)carbonyl group (or an alkylthio-carbonyl group, alkyl-S—CO—), an (arylthio)carbonyl group (aryl-S—CO—), an (arylalkylthio)carbonyl group (arylalkyl-S—CO—), a $C_{1-20}$ alkylaminocarbonyl group (e.g., alkyl-NH—CO—, alkyl-N(alkyl)-CO—, etc), an arylaminocarbonyl group, an arylalkylaminocarbonyl group, a $C_{1-20}$ heteroalkoxycarbonyl group, a heteroaryloxycarbonyl group, a heteroarylalkoxycarbonyl group, a $C_{1-20}$ hetero(alkylthio) carbonyl group, a hetero(arylthio)carbonyl group, a hetero (arylalkylthio)carbonyl group, a $C_{1-20}$ heteroalkylaminocarbonyl group, a heteroarylaminocarbonyl group, a heteroarylalkylaminocarbonyl group, a $C_{1-20}$ alkyl-thiocarbonyl group (or an alkyl-thioxocarbonyl group, alkyl-CS—), an aryl-thiocarbonyl group (aryl-CS—), an arylalkyl-thiocarbonyl group (arylalkyl-CS—), a $C_{1-20}$ heteroalkyl-thiocarbonyl group, a heteroaryl-thiocarbonyl group, a heteroarylalkyl-thiocarbonyl group, a $C_{1-20}$ alkoxy-thiocarbonyl group (alkyl-O—CS—), an aryloxy-thiocarbonyl group (aryl-O—CS—), an arylalkoxy-thiocarbonyl group (arylalkyl-O—CS—), a $C_{1-20}$ (alkylthio)thiocarbonyl group (alkyl-S—CS—), an (arylthio)thiocarbonyl group (aryl-S—CS—), an (arylalkylthio)thiocarbonyl group (arylalkyl-S—CS—), a $C_{1-20}$ alkylaminothiocarbonyl group (e.g., alkyl-NH—CS—, alkyl-N(alkyl)-CS—, etc), an arylaminothiocarbonyl group (e.g., aryl-NH—CS—, etc), an arylalkylaminothiocarbonyl group, a $C_{1-20}$ heteroalkoxythiocarbonyl group, a heteroaryloxy-thiocarbonyl group, a heteroarylalkoxy-thiocarbonyl group, a $C_{1-20}$ hetero(alkylthio)thiocarbonyl group, a hetero(arylthio)thiocarbonyl group, a hetero(arylalkylthio)thiocarbonyl group, a $C_{1-20}$ heteroalkylaminothiocarbonyl group, a heteroarylaminothiocarbonyl group, a heteroarylalkylaminothiocarbonyl group and substituted forms of any aforesaid group.

$LG_4$ is more preferably selected from the group consisting of a $C_{1-20}$ alkyl group, a $C_{3-20}$ alkenylhydrocarbyl group, an aryl group, an arylalkyl group, a $C_{1-20}$ heteroalkyl group, a heteroaryl group, a heteroarylalkyl group and substituted forms of any aforesaid group.

Specifically, $LG_4$ can be but not limited to a methyl group, an ethyl group, an n-propyl group, an isopropyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, an allyl group, a trityl group, a benzyl group, a methylbenzyl group, a 1-ethoxyethyl group, a methoxyethoxymethyl group, a benzyloxymethyl group, a (methylthio)methyl group, a tetrahydropyranyl group, an acetyl group, a benzoyl group, a methoxy-acyl group, an ethoxy-acyl group, a t-butoxy-acyl group, a phenoxy-acyl group, a benzyloxy-acyl group, a (methylthio)acyl group (a methylthio-acyl group, a $CH_3S$-acyl group), an ethylthio-acyl group, a t-butylthio-acyl group, a phenylthio-acyl group, a benzylthio-acyl group, a methylamino-acyl group, an ethylamino-acyl group, a t-butylamino-acyl group, a benzylamino-acyl group, the like or the substituted form of any aforesaid group. Wherein, the butyl group includes but is not limited to an n-butyl group and a t-butyl group. The octyl group includes but is not limited to an n-octyl group and a 2-ethylhexyl group. Wherein, the atom or group substituent can be a halogen atom, a hydrocarbyl substituent or a heteroatom-containing substituent, and preferably a fluorine atom, a chlorine atom, a bromine atom, an iodine atom, an alkoxy group, an alkenyl group or a nitro group.

$LG_4$ is further preferably a methyl group, an ethyl group, an n-propyl group, an isopropyl group, a t-butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, an allyl group, a trityl group, a phenyl group, a benzyl group, a methylbenzyl group, a 1-ethoxyethyl group, a methoxyethoxymethyl group, a benzyloxymethyl group, a (methylthio)methyl group, a tetrahydropyranyl group, an acetyl group, a benzoyl group, a methoxycarbonyl group (or a methyloxycarbonyl group), an ethoxycarbonyl group (or an ethyloxycarbonyl group), a t-butoxycarbonyl group (or a t-butyloxycarbonyl group), a phenoxycarbonyl group (or a phenyloxycarbonyl group), a benzyloxycarbonyl group (or a benzoxycarbonyl group), a (methylthio)carbonyl group ($CH_3$—S—CO—), an (ethylthio)carbonyl group ($CH_3CH_2$—S—CO—), a (t-butylthio)carbonyl group, a (phenylthio)carbonyl group, a (benzylthio)carbonyl group, a methylaminocarbonyl group, an ethylaminocarbonyl group, a t-butylaminocarbonyl group, a benzylaminocarbonyl group, an (ethyl)thiocarbonyl group ($CH_3CH_2$—CS—), a (phenyl)thiocarbonyl group (Ph-CS—), a methoxy-thiocarbonyl group ($CH_3$—O—CS—), an ethoxy-thiocarbonyl group, a t-butoxy-thiocarbonyl group, a phenoxy-thiocarbonyl group, a benzyloxy-thiocarbonyl group, a (methylthio)thiocarbonyl group ($CH_3$—S—CS—), an (ethylthio)thiocarbonyl group ($CH_3CH_2$—S—CS—), a (t-butylthio)thiocarbonyl group, a (phenylthio) thiocarbonyl group, a (benzylthio)thiocarbonyl group, a (methylamino)thiocarbonyl group, an (ethylamino)thiocarbonyl group, a (t-butylamino)thiocarbonyl group, a (benzylamino)thiocarbonyl group, a $C_{1-10}$ halohydrocarbyl group, a trifluoroacetyl group, a halophenyl group (or a halogenated phenyl group), a halobenzyl group (or a halogenated benzyl group), a nitrobenzyl group, a p-methoxybenzyl group, a (trifluoromethyl)benzyl group, the like or the substituted form of any aforesaid group. Wherein, the atom or group substituent is preferably a fluorine atom, an alkoxy group or a nitro group.

$LG_4$ is more preferably a methyl group, an ethyl group, an n-propyl group, an isopropyl group, a t-butyl group, a pentyl group, a hexyl group, an allyl group, a trityl group, a phenyl group, a benzyl group, a 1-ethoxyethyl group, a 2-ethoxyethyl group, a methoxyethoxymethyl group, a benzyloxymethyl group, a (methylthio)methyl group, a tetrahydropyranyl group, a nitrobenzyl group, a p-methoxybenzyl group, a (trifluoromethyl)benzyl group, a t-butoxycarbonyl group, a phenoxycarbonyl group, a benzyloxycarbonyl group, an acetyl group, a trifluoroacetyl group or the like.

$LG_4$ is more preferably a methyl group, an ethyl group, an n-propyl group, an isopropyl group, a t-butyl group, a pentyl group, a hexyl group, an allyl group, a trityl group, a phenyl group, a benzyl group, a nitrobenzyl group, a p-methoxybenzyl group, a (trifluoromethyl)benzyl group or the like.

$LG_4$ is most preferably a methyl group, an ethyl group, an allyl group or a benzyl group.

Wherein, the tetravalent core-atom $CM_4$ is not particularly limited, as long as it can provide four covalent single bonds individually, such as a tetravalent carbon-atom core, a tetravalent silicon-atom core, a tetravalent phosphorus-atom core and the like.

Wherein, the core structure $CB_4$ of a tetravalent unsaturated bond type is not particularly limited, as long as it can provide four covalent single bonds individually. The bond-membering atoms of the unsaturated bond can be two or two more, preferably two or three, and more preferably two.

Wherein, the tetravalent cyclic core structure $CC_4$ is not particularly limited, as long as it can protrude four covalent single bonds individually. The ring-membering atoms that provide covalent bond radicals are not particularly limited, including but not limited to N, C, Si, P, etc. The cyclic structure can be but not limited to an aliphatic ring, an aromatic ring, a sugar ring or a condensed ring. The cyclic structure can come from natural sources, such as a sugar ring, or be formed via chemical reactions, etc. The covalent single bonds can protrude directly from a ring-membering atom, or from an unsaturated bond. Each covalent single bond protrudes individually from a ring-membering atom, or two covalent single bonds protrude from one common ring-membering atom together. A typical structure of $CC_4$ is that four covalent single bonds protrude from four ring-membering atoms respectively. The tetravalent cyclic structure $CC_4$ is preferably derived from but not limited to a furanose ring, a pyranose ring, cycleanine, a cyclic tetrapeptide, tetrahydrofuran, pyrrolidine, thiazolidine, cyclohexane, benzene, cyclohexene, tetrahydropyran, piperidine, 1,4-dioxane, pyridine, pyridazine, pyrimidine, pyrazine, indene, indane, indole, isoindole, purine, naphthalene, dihydroanthracene, xanthene, thioxanthene, dihydrophenanthrene, 10,11-5H-dihydro-dibenzo[a,d]cycloheptane, dibenzocycloheptene, 5-dibenzosuberenone, quinoline, isoquinoline, fluorene, carbazole, iminodibenzyl, tetramethyl tetrahydroindene, dipyridamole skeleton, the tetravalent skeleton of triethanedial dihydrate, the tetravalent six-membered ring of D-sorbitol skeleton with 2-hydroxyl group and 4-hydroxyl group being protected, the like, the substituted form of any aforesaid cyclic structure or the heterosubstituted form of any aforesaid cyclic structure.

A (k+1)-valent group in the set $G^{k+1}$ (k≥4) can contain one (k+1)-valent cyclic core structure $CC_{k+1}$, or contain two or two more lower-valent cyclic core structures with the valence of 3 to k, including but not limited to the groups described and listed in the documents CN104530413A, CN104530415A and CN104530417A. Take CN104530417A as an example, corresponding to paragraphs from [0292] to [0295]. For example:

When k is equal to 4 (k=4), in the set $G^5$, the cyclic core $CC_5$ is a cyclic core structure, wherein, five covalent single bonds protrude from five ring-membering atoms, respectively. $CC_5$ can be but not limited to a cyclic monosaccharide core structure, a cyclopeptide, a saturated carbon ring, an azacycloalkane or the like, such as a cyclic structure deriving from a pyranose ring, a cyclic structure deriving from a cyclopeptide or the like,

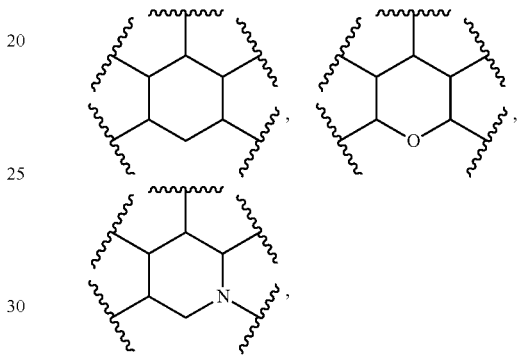

etc.

When k is greater than or equal to 5 (k≥5), in the set $G^{k+1}$ (k≥5), examples of the cyclic core structure $CC_{k+1}$ include but are not limited to a cyclopeptide, an azacycloalkane, a polymeric ring and the like.

A (k+1)-valent group in the set $G^k+1$ (k≥2), when containing a core structure with the valence of 3 to k+1, can contain or not contain non-core moieties beyond the (3 to k+1)-valent core structure.

When containing non-core moieties beyond the (3 to k+1)-valent core structure, the non-core moieties can contain carbon atom or not, also can contain heteroatoms or not. The non-core moieties beyond the (3 to k+1)-valent core structure can be a heteroatom-containing group or a hydrocarbylene group without heteroatoms. The heteroatoms include but are not limited to O, S, N, P, Si, F, Cl, Br, I, B and the like. Wherein, the heteroatom-number can be one, two or two more. The heteroatom can be present as an atom substituent or individually as a divalent linkage, such as —O— (an oxy group or an ether bond), —S— (a thioxy group or a thioether bond), —N($R_7$)— (a secondary amino group or a divalent t-amino group) or the like, or be present as a divalent substituent, such as —C(=O)—, —C(=S)—, —P(=O)—, —S(=O)$_2$—, —S(=O)— or the like, or participate in combining into some specific covalent bonds, such as —C(=O)—N($R_7$)—, —N($R_7$)—C(=O)—, —S—S—, —C(=O)—O—, —O—C(=O)—, —C(=O)—S—, —S—C(=O)—, —C(=S)—O—, —O—C(=S)—, —C(=S)—S—, —S—C(=S)—, —O—C(=O)—O—, —S—C(=O)—O—, —O—C(=S)—O—, —O—C(=O)—S—, —S—C(=S)—O—, —O—C(=S)—S—, —S—C(=O)—S—, —S—C(=S)—S—, —N($R_7$)—C(=O)—O—, —O—C(=O)—N($R_7$)—, —N($R_7$)—C(=S)—O—, —O—C(=S)—N($R_7$)—, —N($R_7$)—C —C(=O)—S—, —S—C(=O)—N($R_7$)—, —N($R_7$)—C(=S)—S—, —S—C(=S)—N($R_7$)—, —N($R_{19}$)—N($R_{18}$)—, —N($R_{19}$)—C(=O)—N($R_{18}$)—, —N($R_{19}$)—C(=S)—N($R_{18}$)—, —N($R_{15}$)—N($R_{19}$)—C(=O)—, —C(=O)—N($R_{19}$)—N($R_{18}$)—, —N($R_{18}$)—N($R_{19}$)—C(=S)—, —C(=S)—N($R_{19}$)—N($R_{18}$)—, —($R_{15}$)C=N—, —N=C($R_{15}$)—, —($R_{15}$)C=N—N($R_7$)—, —N($R_7$)—N=C($R_{15}$)—, —($R_{15}$)C=N—N($R_7$)—C(=O)—, —C(=O)—N($R_7$)—N=C($R_{15}$)—, —($R_{15}$)C=N—O—, —O—N=C($R_{15}$)—, —($R_{18}$)C=N—S—, —S—N=C($R_{15}$)—, —N=N—, —N($R_{18}$)—N($R_{19}$)—C(=O)—N=N—, —N=N—C(=O)—N($R_{19}$)—N($R_{18}$)—, —N($R_{18}$)—C(=O)—N($R_{19}$)—, —C(=N$R_7$)—N($R_{23}$)—, —N($R_{23}$)—C(=N$R_7$)—, —N($R_7$)—C(=NH$_2^+$)—, —C(=NH$_2^+$)—N($R_7$)—, —C(=N$R_7$)—O—, —O—C(=N$R_7$)—, —O—C(=NH$_2^+$)—, —C(=NH$_2^+$)—O—, —C(=N$R_7$)—S—, —S—C(=N$R_7$)—, —S—C(=NH$_2^+$)—, —C(=NH$_2^+$)—S—, —S(=O)$_2$—O—, —O—S(=O)$_2$—, —S(=O)—O—, —O—S(=O)—, —S(=O)$_2$—N($R_7$)—, —N($R_7$)—S(=O)$_2^-$, —S(=O)$_2$—N($R_{18}$)—N($R_{19}$)—, —N($R_{19}$)—N($R_{18}$)—S(=O)$_2$— or the like. The hydrocarbylene group without heteroatoms is not particularly limited, and preferably a $C_{1-10}$ hydrocarbylene group.

The non-core moiety beyond the core structure is preferably a $C_{1-6}$ alkylene group, an ether bond, a thioether bond, a secondary amino group, a divalent t-amino group, an amide bond, a carbamate bond, a thiocarbamate bond or a divalent linking group combined by a $C_{1-6}$ alkylene group and any aforesaid divalent linkage, and more preferably a $C_{1-6}$ alkylene group or an ether bond.

Wherein, $R_7$, $R_{18}$, $R_{19}$ and $R_{23}$ each independently connects to an amino group and are each independently a hydrogen atom, an amino protecting group or an $LG_5$ group. In one molecule, $R_7$, $R_{18}$, $R_{19}$ and $R_{23}$ can be each independently identical or not identical.

Wherein, the carbon-atom number of $LG_5$ is not particularly limited, preferably from 1 to 20, and more preferably from 1 to 10.

The structure of $LG_5$ is not particularly limited, including but not limited to a linear structure, a branched structure bearing pendant groups or a ring-containing structure. Wherein, the ring is not particularly limited, preferably an aliphatic ring, an aromatic ring, a sugar ring or a condensed ring as above-described.

$LG_5$ can contain heteroatoms, or do not contain heteroatoms.

$LG_5$ can be a $C_{1-20}$ hydrocarbyl group, a $C_{1-20}$ heterohydrocarbyl group, a substituted $C_{1-20}$ hydrocarbyl group or a substituted heterohydrocarbyl group. Wherein, the heteroatom or group substituent of $LG_5$ is not particularly limited, including but not limited to all the above-described heteroatom and group substituents in the term-defining section, and can be a halogen atom, a hydrocarbyl substituent or a heteroatom-containing substituent.

$LG_5$ is more preferably a $C_{1-20}$ alkyl group, a $C_{2-20}$ unsaturated aliphatic hydrocarbyl group, an aryl group, an arylhydrocarbyl group, a $C_{1-20}$ heterohydrocarbyl group, a $C_{1-20}$ aliphatic hydrocarbyl-acyl group, a $C_{1-20}$ aliphatic-derived heterohydrocarbyl-acyl group, an aryl-acyl group, a heteroaryl-acyl group, a $C_{1-20}$ hydrocarbyloxy-acyl group, a $C_{1-20}$ hydrocarbylthio-acyl group, a $C_{1-20}$ hydrocarbylamino-acyl group, a $C_{1-20}$ heterohydrocarbyloxy-acyl group, a $C_{1-20}$ heterohydrocarbylthio-acyl group, a $C_{1-20}$ heterohydrocarbylamino-acyl group, the like or the substituted form of any aforesaid group. Wherein, the acyl group within $LG_5$ is not particularly limited, including but not limited to all the above-described acyl groups in the term-defining section. For example, the acyl group within $LG_5$ can be a carbonyl group, a sulfonyl group, a sulfinyl group, a phosphoryl group, a phosphiryl group, a phosphinyl group, a nitroxyl group, a nitrosyl group, a thiocarbonyl group, an imidoyl group, a thiophosphoryl group, a dithiophosphoryl group, a trithiophosphoryl group, a thiophosphiryl group, a dithiophosphiryl group, a thiophosphinyl group, a thiophosphono group, a dithiophosphono group, a thiophosphino group or the like, preferably a carbonyl group, a thiocarbonyl group, a sulfonyl group, a sulfinyl group or the like, and more preferably a carbonyl group, a thiocarbonyl group or a sulfonyl group.

$LG_5$ is more preferably a $C_{1-20}$ alkyl group, a $C_{2-20}$ alkenyl group, a $C_{3-20}$ alkenylhydrocarbyl group, an aryl group, an arylalkyl group, a $C_{1-20}$ heteroalkyl group, a heteroaryl group, a heteroarylalkyl group, a $C_{1-20}$ alkylcarbonyl group, an arylcarbonyl group, an arylalkylcarbonyl group, a $C_{1-20}$ heteroalkylcarbonyl group, a heteroarylcarbonyl group, a heteroarylalkylcarbonyl group, a $C_{1-20}$ alkoxycarbonyl group, an aryloxycarbonyl group, an arylalkoxycarbonyl group, a $C_{1-20}$ (alkylthio)carbonyl group, an (arylthio)carbonyl group, an (arylalkylthio)carbonyl group, a $C_{1-20}$ alkylaminocarbonyl group, an arylaminocarbonyl group, an arylalkylaminocarbonyl group, a $C_{1-20}$ heteroalkoxycarbonyl group, a heteroaryloxycarbonyl group, a heteroarylalkoxycarbonyl group, a $C_{1-20}$ hetero(alkylthio)carbonyl group, a hetero(arylthio)carbonyl group, a hetero(arylalkylthio)carbonyl group, a $C_{1-20}$ heteroalkylaminocarbonyl group, a heteroarylaminocarbonyl group, a heteroarylalkylaminocarbonyl group, a $C_{1-20}$ (alkyl)thiocarbonyl group, an (aryl)thiocarbonyl group, an (arylalkyl)thiocarbonyl group, a $C_{1-20}$ hetero(alkyl)thiocarbonyl group, a hetero(aryl)thiocarbonyl group, a hetero(arylalkyl)thiocarbonyl group, a $C_{1-20}$ alkoxy-thiocarbonyl group, an aryloxy-thiocarbonyl group, an arylalkoxy-thiocarbonyl group, a $C_{1-20}$ (alkylthio)thiocarbonyl group, an (arylthio)thiocarbonyl group, an (arylalkylthio)thiocarbonyl group, a $C_{1-20}$ alkylaminothiocarbonyl group, an arylaminothiocarbonyl group, an arylalkylaminothiocarbonyl group, a $C_{1-20}$ heteroalkoxy-thiocarbonyl group, a heteroaryloxy-thiocarbonyl group, a heteroarylalkoxy-thiocarbonyl group, a $C_{1-20}$ hetero(alkylthio)thiocarbonyl group, a hetero(arylthio)thiocarbonyl group, a hetero(arylalkylthio)thiocarbonyl group, a $C_{1-20}$ heteroalkylaminothiocarbonyl group, a heteroarylaminothiocarbonyl group, a heteroarylalkylaminothiocarbonyl group, the like or the substituted form of any aforesaid group.

$LG_5$ is more preferably a C1-20 alkyl group, a $C_{2-20}$ alkenyl group, a $C_{3-20}$ alkenyl-hydrocarbyl group, an aryl group, an arylalkyl group, a $C_{1-20}$ heteroalkyl group, a heteroaryl group, a heteroarylalkyl group or the substituted form of any aforesaid group.

Specifically, $LG_5$ can be, but not limited to, a methyl group, an ethyl group, an n-propyl group, an isopropyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, an allyl group, a trityl group, a benzyl group, a methylbenzyl group, a 1,3,5-dioxo-azacyclohexyl group, a formyl group, an acetyl group, a benzoyl group, a methoxyacyl group, an ethoxy-acyl group, a t-butoxy-acyl group, a phenoxy-acyl group, a benzyloxy-acyl group, a 9-fluorenylmethoxycarbonyl group (a Fmoc group), a 2-(methylsulfonyl)ethylcarbonyl group, a 2-(p-toluenesulfonyl)ethoxycarbonyl group, a methylthio-acyl group, an ethylthio-acyl group, a t-butylthio-acyl group, a phenylthio-acyl group, a benzylthio-acyl group, a methylamino-acyl group, an ethylamino-acyl group, a t-butylamino-acyl group, a benzylamino-acyl group, the like or the substituted form of any aforesaid group. Wherein, the butyl group includes but is not limited to an n-butyl group and a t-butyl group. The octyl group includes but is not limited to an n-octyl group and a 2-ethylhexyl group. Wherein, the atom or group substituent can be a halogen atom, a hydrocarbyl substituent or a heteroatom-containing substituent, and preferably a fluorine atom, a chlorine atom, a bromine atom, an iodine atom, an alkoxy group, an alkenyl group or a nitro group.

$LG_5$ is further preferably a methyl group, an ethyl group, an n-propyl group, an isopropyl group, a t-butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, an allyl group, a trityl group, a phenyl group, a benzyl group, a methylbenzyl group, a 1,3,5-dioxo-azacyclohexyl group, a formyl group, an acetyl group, a benzoyl group, a methoxycarbonyl group, an ethoxycarbonyl group, a t-butoxycarbonyl group, a phenoxycarbonyl group, a benzyloxycarbonyl group, a 9-fluorenylmethoxycarbonyl group, a 2-(methylsulfonyl)ethylcarbonyl group, a 2-(p-toluenesulfonyl)ethyloxycarbonyl group, a (methylthio)carbonyl group, an (ethylthio)carbonyl group, a (t-butylthio)carbonyl group, a (phenylthio)carbonyl group, a (benzylthio)carbonyl group, a methylaminocarbonyl group, an ethylaminocarbonyl group, a t-butylaminocarbonyl group, a benzylaminocarbonyl group, an (ethyl)thiocarbonyl group, a (phenyl)thiocarbonyl group, a methoxy-thiocarbonyl group, an ethoxy-thiocarbonyl group, a t-butoxy-thiocarbonyl group, a phenoxy-thiocarbonyl group, a benzyloxy-thiocarbonyl group, a (methylthio)thiocarbonyl group, an (ethylthio)thiocarbonyl group, a (t-butylthio)thiocarbonyl group, a (phenylthio)thiocarbonyl group, a (benzylthio)thiocarbonyl group, a methylaminothiocarbonyl group, an ethylaminothiocarbonyl group, a t-butylaminothiocarbonyl group, a benzylaminothiocarbonyl group, a [2-(methylsulfonyl)ethoxy]carbonyl group, a $C_{1-10}$halohydrocarbyl group, a trifluoroacetyl group, a 2-iodoethoxycarbonyl group, a halophenyl group, a halobenzyl group, a nitrobenzyl group, a p-methoxybenzyl group, a (trifluoromethyl)benzyl group, the like or the substituted form of any aforesaid group. Wherein, the atom or group substituent is preferably a fluorine atom, an alkoxy group or a nitro group.

$LG_5$ is more preferably a methyl group, an ethyl group, an n-propyl group, an isopropyl group, a t-butyl group, a pentyl group, a hexyl group, an allyl group, a trityl group, a phenyl group, a benzyl group, a nitrobenzyl group, a p-methoxybenzyl group, a (trifluoromethyl)benzyl group, a 1,3,5-dioxo-azacyclohexyl group, a 9-fluorenylmethoxycarbonyl group, a 2-(methylsulfonyl)ethylcarbonyl group, a 2-(p-toluenesulfonyl)ethyloxycarbonyl group, a t-butoxycarbonyl group, a benzyloxycarbonyl group, a formyl group, an acetyl group, a trifluoroacetyl group or the like.

$LG_5$ is more preferably a methyl group, an ethyl group, an n-propyl group, an isopropyl group, a t-butyl group, a pentyl group, a hexyl group, an allyl group, a trityl group, a phenyl group, a benzyl group, a nitrobenzyl group, a p-methoxybenzyl group, a (trifluoromethyl)benzyl group or the like.

$LG_5$ is most preferably a methyl group, an ethyl group, an allyl group or a benzyl group.

$R_7$, $R_{18}$, $R_{19}$ and $R_{23}$ are each independently most preferably a hydrogen atom, a methyl group, an ethyl group or a benzyl group.

$R_{15}$ is linked to the carbon atom of structures containing a C=N bond, and can be a hydrogen atom, an atom substituent or a group substituent. Examples of structures containing a C=N bond include but are not limited to —C=N—, —C=N$^+$=N$^-$, —C=N—NH—, —C=N—NH—C(=O)— and the like. C=N is termed as an imine bond or an imino bond in the present invention.

When as an atom substituent, $R_{15}$ can be a halogen atom, and preferably a fluorine atom.

When as a group substituent, the carbon-atom number of $R_{15}$ is not particularly limited, preferably from 1 to 20, and more preferably from 1 to 10.

When as a group substituent, the structure of $R_{15}$ is not particularly limited, including but not limited to a linear structure, a branched structure bearing pendant groups or a ring-containing structure. The ring is not particularly limited, and preferably an aliphatic ring, an aromatic ring, a sugar ring or a condensed ring as above-described.

When as a group substituent, $R_{15}$ can contain or do not contain heteroatoms.

$R_{15}$ can be a hydrogen atom, a halogen atom, a $C_{1-20}$ hydrocarbyl group, a $C_{1-20}$ heterohydrocarbyl group, a substituted $C_{1-20}$ hydrocarbyl group or a substituted heterohydrocarbyl group. Wherein, the atom or group substituent of $R_{15}$ is not particularly limited, including but not limited to all the atom and group substituents described in the term-defining section, and can be a halogen atom, a hydrocarbyl substituent or a heteroatom-containing substituent.

$R_{15}$ is more preferably a hydrogen atom, a halogen atom, a $C_{1-20}$ alkyl group, a $C_{2-20}$ unsaturated aliphatic hydrocarbyl group, an aryl group, an arylhydrocarbyl group, a $C_{1-20}$ heterohydrocarbyl group, a $C_{1-20}$ hydrocarbyloxy-acyl group, a $C_{1-20}$ hydrocarbylthio-acyl group, a $C_{1-20}$ hydrocarbylamino-acyl group or the substituted form of any aforesaid group. Wherein, the acyl group within $R_{15}$ is not particularly limited, including but not limited to all the above-described acyl groups in the term-defining section. For examples, the acyl group within $R_{15}$ can be a carbonyl group, a sulfonyl group, a sulfinyl group, a phosphoryl group, a phosphiryl group, a phosphinyl group, a nitroxyl group, a nitrosyl group, a thiocarbonyl group, an imidoyl group, a thiophosphoryl group, a dithiophosphoryl group, a trithiophosphoryl group, a thiophosphiryl group, a dithiophosphiryl group, a thiophosphinyl group, a thiophosphono group, a dithiophosphono group, a thiophosphino group or the like, preferably a carbonyl group, a thiocarbonyl group, a sulfonyl group, a sulfinyl group or the like, and more preferably a carbonyl group or a thiocarbonyl group.

$R_{15}$ is more preferably a hydrogen atom, a halogen atom, a $C_{1-20}$ alkyl group, a $C_{2-20}$ alkenyl group, an aryl group, an arylhydrocarbyl group, a $C_{1-20}$ aliphatic-derived heterohydrocarbyl group, a heteroaryl group, a heteroarylhydrocarbyl group, a $C_{1-20}$ alkoxy-acyl group, an aryloxy-acyl group, a $C_{1-20}$ alkylthio-acyl group, an arylthio-acyl group, a $C_{1-20}$ alkylamino-acyl group, an arylamino-acyl group or the substituted form of any aforesaid group. Wherein, the atom or group substituent can be a halogen atom, a hydrocarbyl substituent or a heteroatom-containing substituent, and preferably a halogen atom, an alkenyl group or a nitro group.

$R_{15}$ is more preferably a hydrogen atom, a halogen atom, a $C_{1-20}$ alkyl group, a $C_{2-20}$ alkenyl group, an aryl group, an arylhydrocarbyl group, a $C_{1-20}$ aliphatic-derived heterohydrocarbyl group, a heteroaryl group, a heteroarylhydrocarbyl group, a $C_{1-20}$ alkoxycarbonyl group, an aryloxycarbonyl group, a C$_{1-20}$ (alkylthio)carbonyl group, an (arylthio) carbonyl group, a C$_{1-20}$ alkylaminocarbonyl group, an arylaminocarbonyl group, a C$_{1-20}$ alkoxy-thiocarbonyl group, an aryloxy-thiocarbonyl group, a C$_{1-20}$ (alkylthio) thiocarbonyl group, an (arylthio)thiocarbonyl group, a C$_{1-20}$ alkylaminothiocarbonyl group, an arylaminothiocarbonyl group or the substituted form of any aforesaid group. Wherein, the atom or group substituent can be a halogen atom, a hydrocarbyl substituent or a heteroatom-containing substituent, and preferably a fluorine atom, a chlorine atom, a bromine atom, an iodine atom, an alkenyl group or a nitro group.

Specifically, R$_{15}$ can be but not limited to a hydrogen atom, a fluorine atom, a chlorine atom, a bromine atom, an iodine atom, a methyl group, an ethyl group, an n-propyl group, an isopropyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, an allyl group, a propenyl group, an ethenyl group, a phenyl group, a methylphenyl group, a butylphenyl group, a benzyl group, a methoxycarbonyl group, an ethoxycarbonyl group, a phenoxycarbonyl group, a benzyloxycarbonyl group, a (methylthio)carbonyl group, an (ethylthio)carbonyl group, a (phenylthio)carbonyl group, a (benzylthio)carbonyl group, an ethylaminocarbonyl group, a benzylaminocarbonyl group, a methoxy-thiocarbonyl group, an ethoxy-thiocarbonyl group, a phenoxy-thiocarbonyl group, a benzyloxy-thiocarbonyl group, a (methylthio) thiocarbonyl group, an (ethylthio)thiocarbonyl group, a (phenylthio)thiocarbonyl group, a (benzylthio)thiocarbonyl group, an ethylaminothiocarbonyl group, a benzylaminothiocarbonyl group, a substituted C$_{1-20}$ alkyl group, a substituted C$_{2-20}$ alkenyl group, a substituted aryl group, a substituted arylhydrocarbyl group, a substituted C$_{1-20}$ aliphatic-derived heterohydrocarbyl group, a substituted heteroaryl group, a substituted heteroarylhydrocarbyl group, a substituted C$_{1-20}$ alkoxycarbonyl group, a substituted aryloxycarbonyl group, a substituted C$_{1-20}$ (alkylthio)carbonyl group, a substituted (arylthio)carbonyl group, a substituted C$_{1-20}$ alkylaminocarbonyl group, a substituted arylaminocarbonyl group, a substituted C$_{1-20}$ alkoxy-thiocarbonyl group, a substituted aryloxy-thiocarbonyl group, a substituted C$_{1-20}$ (alkylthio)thiocarbonyl group, a substituted (arylthio)thiocarbonyl group, a substituted C$_{1-20}$ alkylaminothiocarbonyl group, a substituted arylaminothiocarbonyl group or the like. Wherein, the butyl group includes but is not limited to an n-butyl group and a t-butyl group. The octyl group includes but is not limited to an n-octyl group and a 2-ethylhexyl group. Wherein, the atom or group substituent can be a halogen atom, a hydrocarbyl substituent or a heteroatom-containing substituent, and preferably a fluorine atom, a chlorine atom, a bromine atom, an iodine atom or a nitro group.

R$_{15}$ is further preferably a hydrogen atom, a fluorine atom, a methyl group, an ethyl group, an n-propyl group, an isopropyl group, a butyl group, a pentyl group, a hexyl group, a heptyl group, an octyl group, a nonyl group, a decyl group, an allyl group, a propenyl group, an ethenyl group, a phenyl group, a methylphenyl group, a butylphenyl group, a benzyl group, a C$_{1-10}$halohydrocarbyl group, a halophenyl group, a halobenzyl group, a nitrophenyl group, a methoxycarbonyl group, an ethoxycarbonyl group, a phenoxycarbonyl group, a benzyloxycarbonyl group, a (methylthio)carbonyl group, an (ethylthio)carbonyl group, a (phenylthio) carbonyl group, a (benzylthio)carbonyl group, an ethylaminocarbonyl group, a benzylaminocarbonyl group, a methoxy-thiocarbonyl group, an ethoxy-thiocarbonyl group, a phenoxy-thiocarbonyl group, a benzyloxy-thiocarbonyl group, a (methylthio)thiocarbonyl group, an (ethylthio)thiocarbonyl group, a (phenylthio)thiocarbonyl group, a (benzylthio)thiocarbonyl group, an ethylaminothiocarbonyl group, a benzylaminothiocarbonyl group, the like or the substituted form of any aforesaid group.

R$_{15}$ is most preferably a hydrogen atom, a fluorine atom or a methyl group.

Take trivalent groups (trivalent G with k=2, E$_1$, E$_2$, E$_3$, E$_4$ or the trivalent groups forming U) for example, examples of trivalent groups in which the non-core moiety beyond the trivalent core structure contains no heteroatoms, include but are not limited to the groups described and listed in the documents CN104530413A, CN104530415A and CN104530417A. Take CN104530417A as an example, corresponding to paragraphs from [0314] to [0315]. Examples also include but are not limited to the following structures:

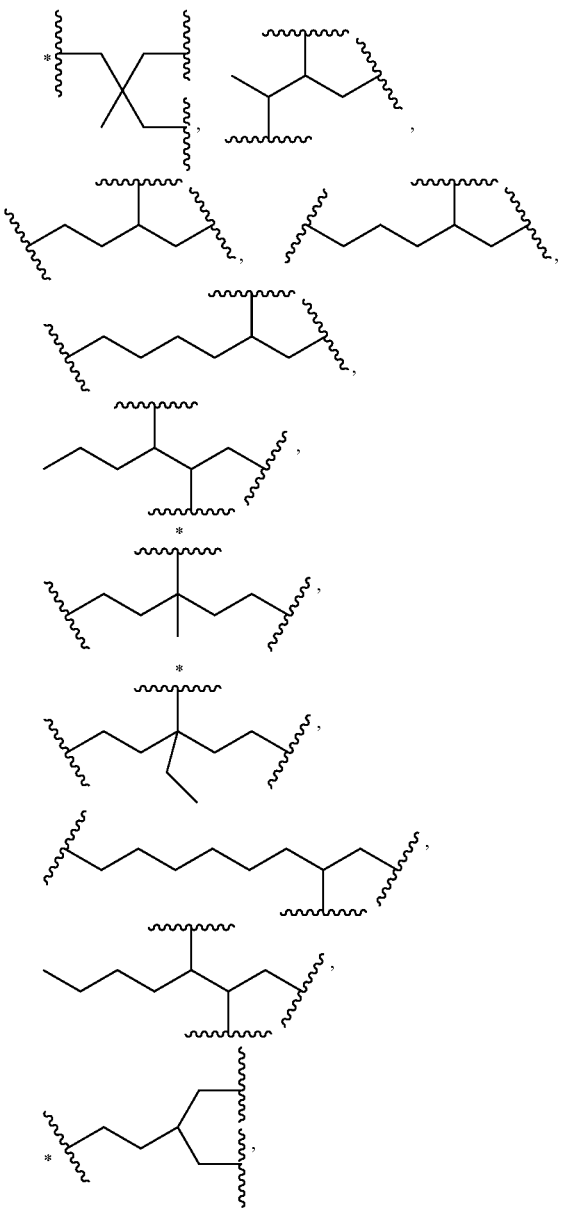

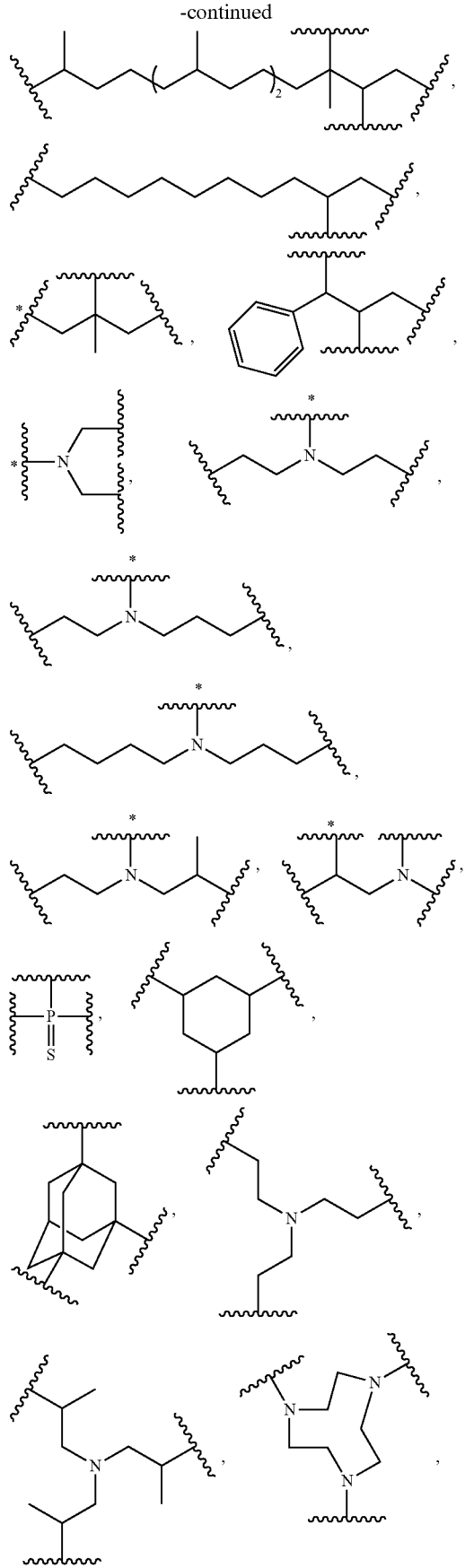
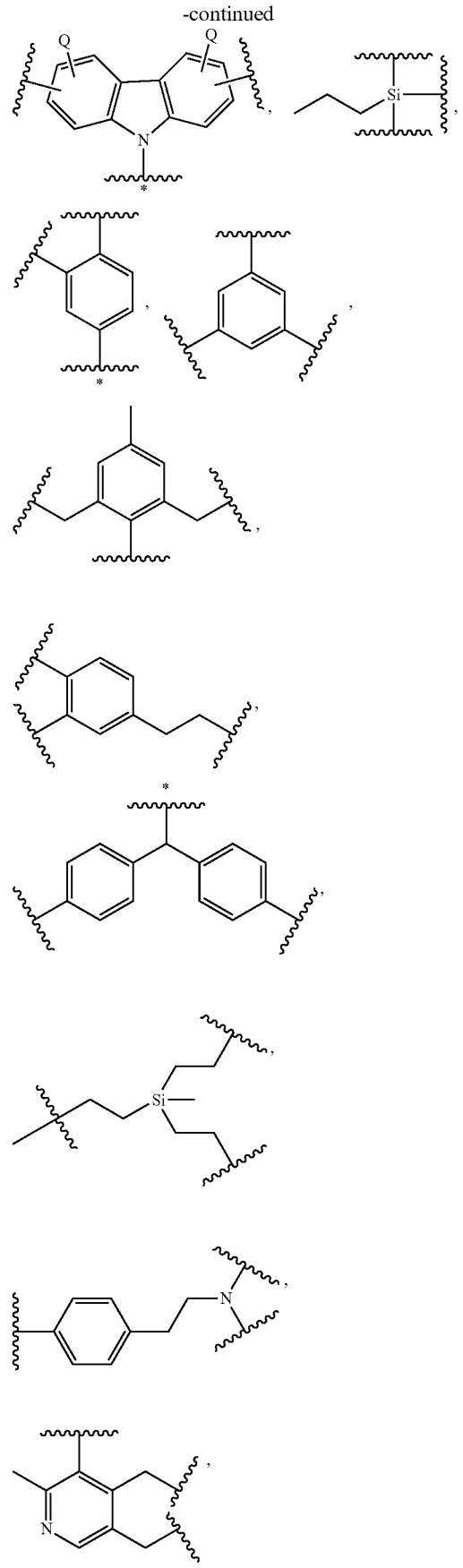

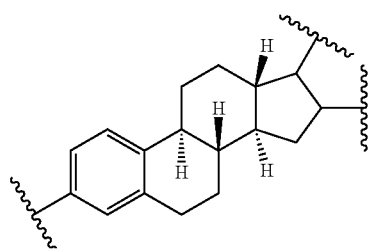
and the like.
Examples of trivalent groups in which the non-core moiety contains heteroatoms include but are not limited to the groups described and listed in the documents CN104530413A, CN104530415A and CN104530417A. Take CN104530417A as an example, corresponding to paragraphs from [0316] to [0320]. Examples also include but are not limited to the following structures:
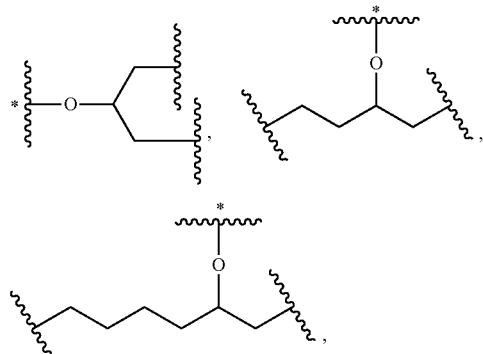
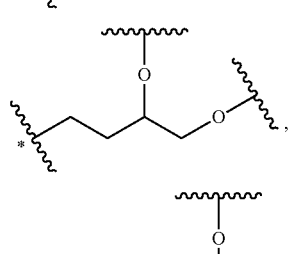
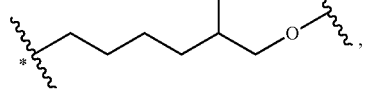
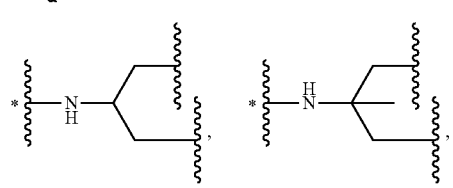
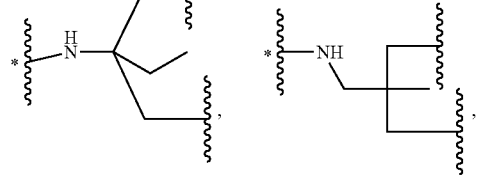
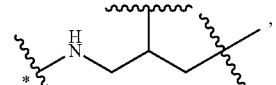
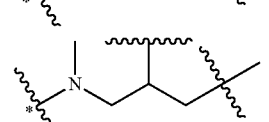
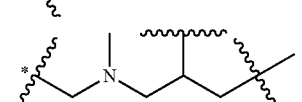
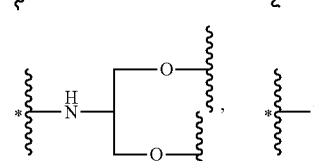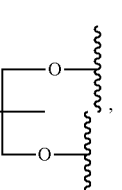
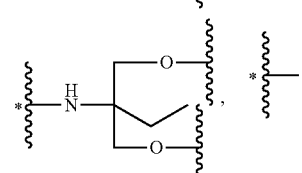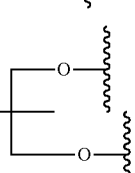
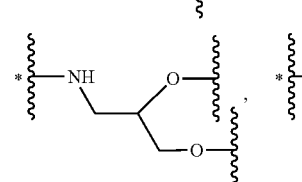
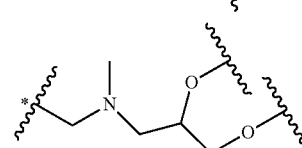
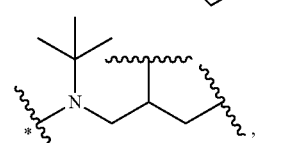
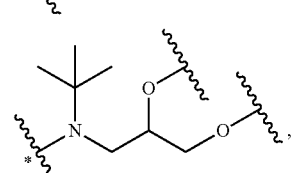
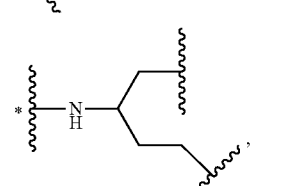
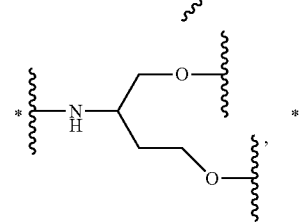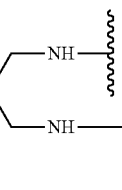

-continued
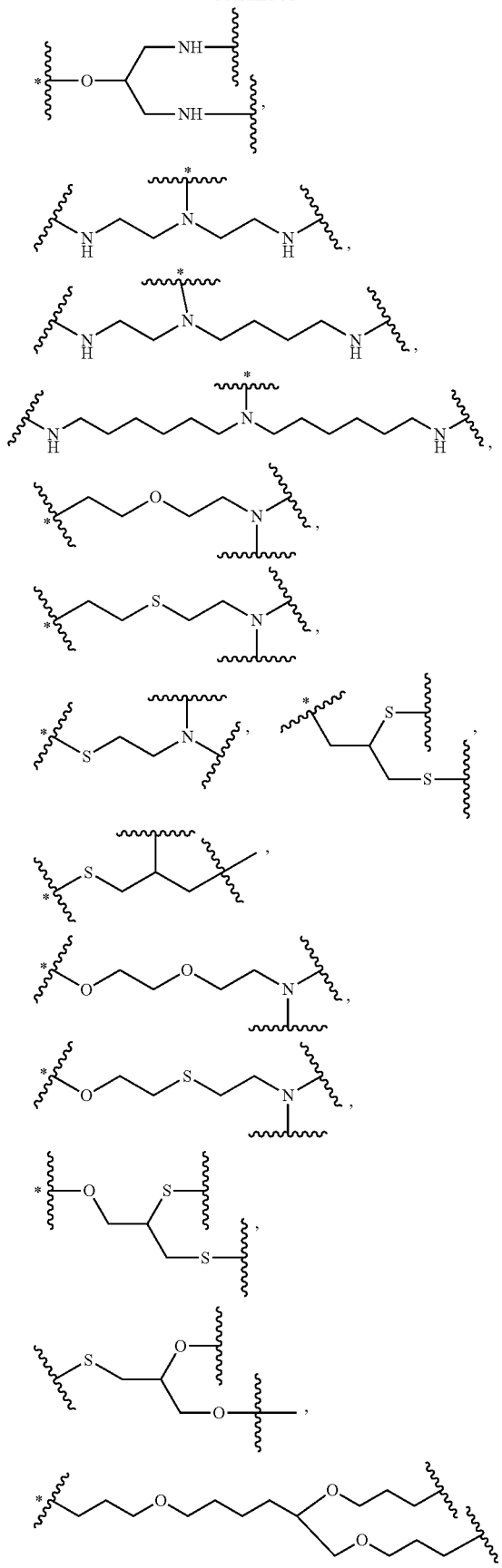
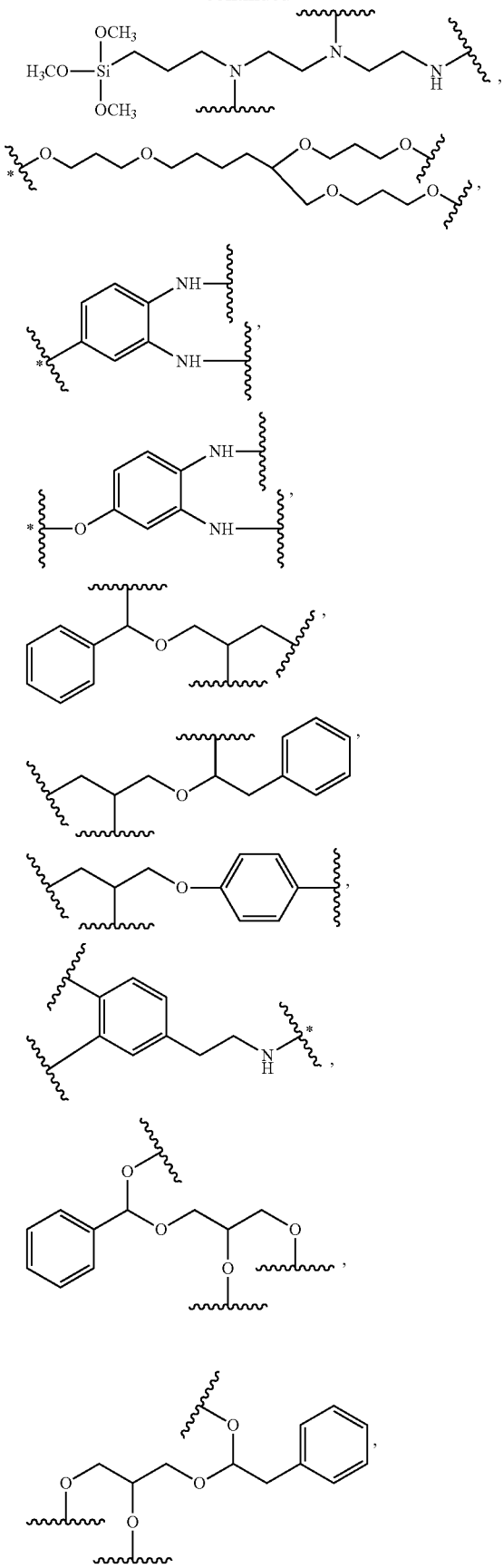

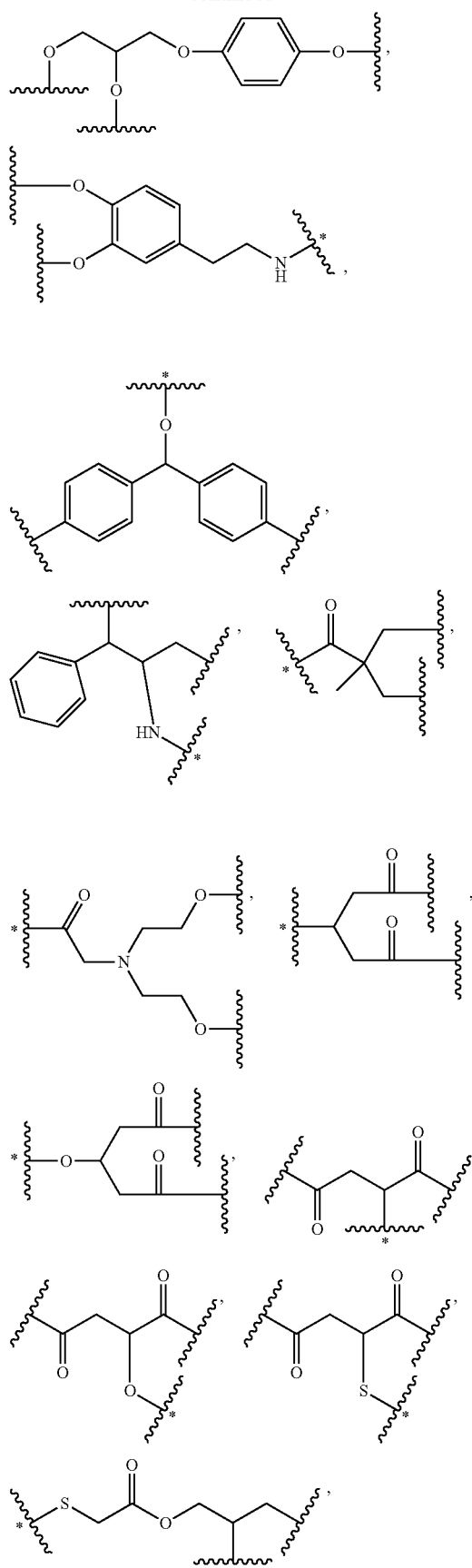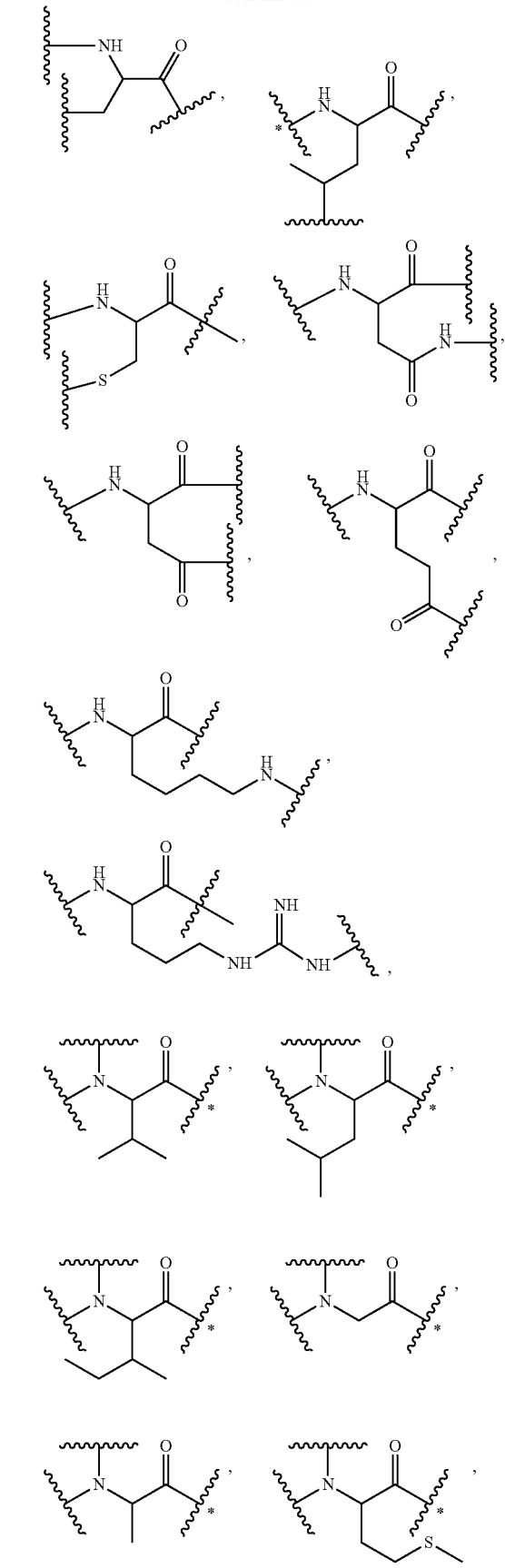

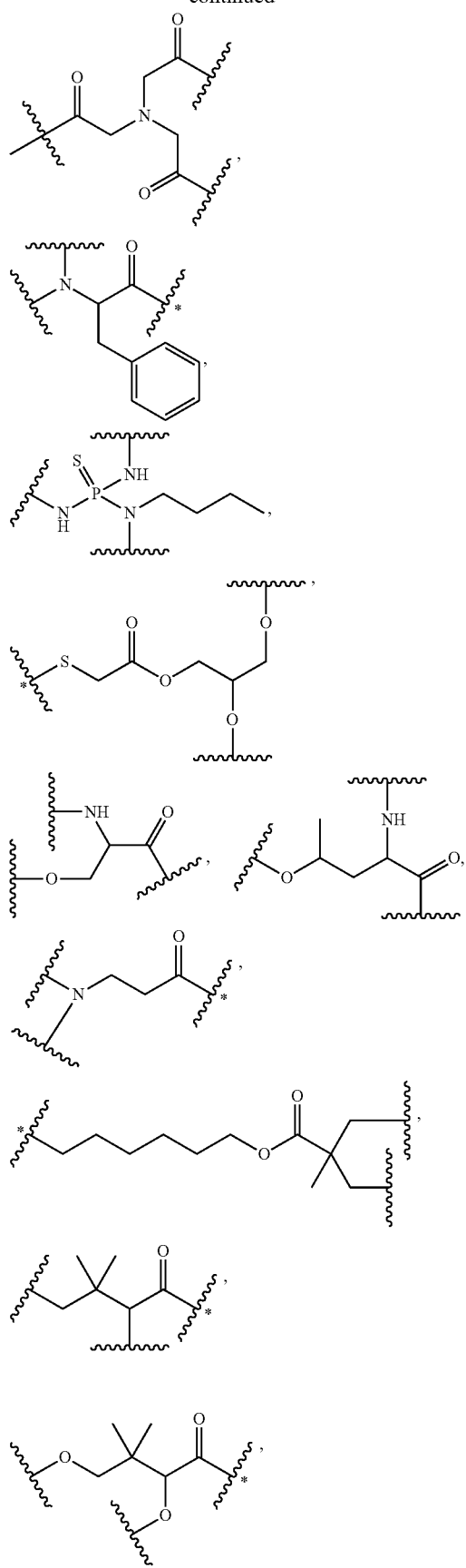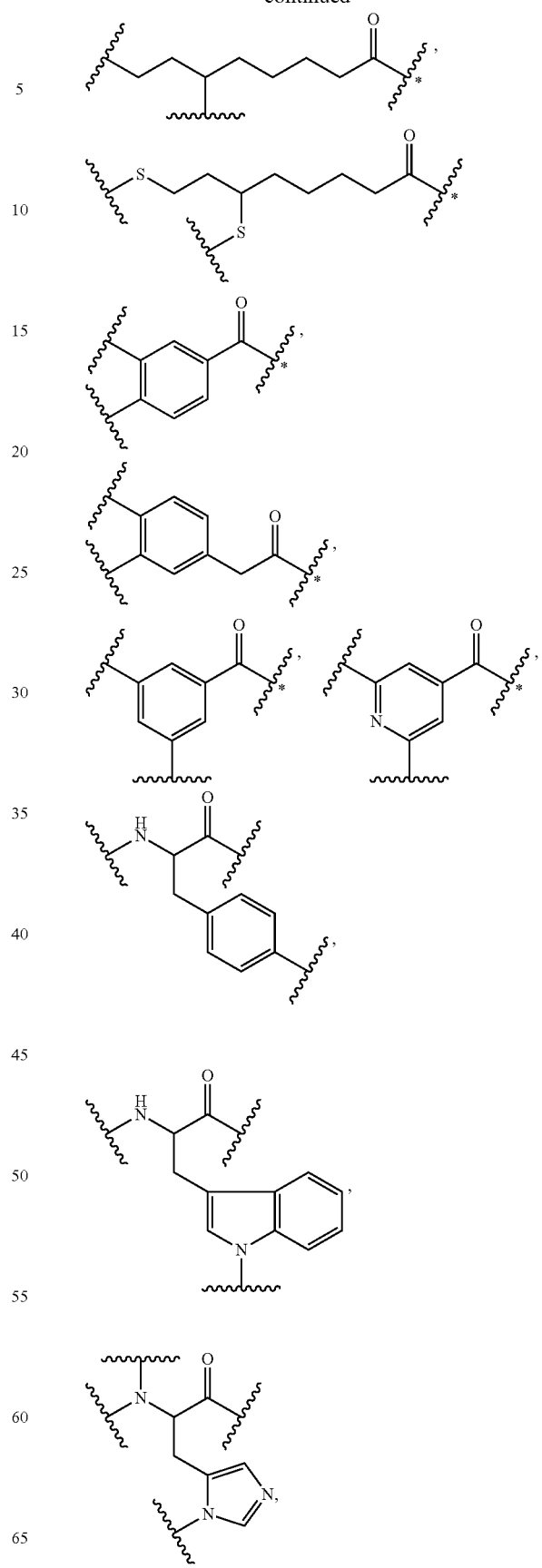

61
-continued
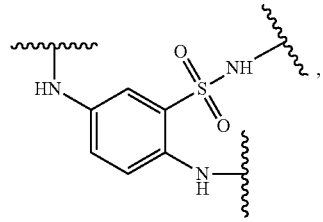
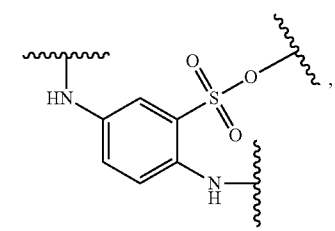
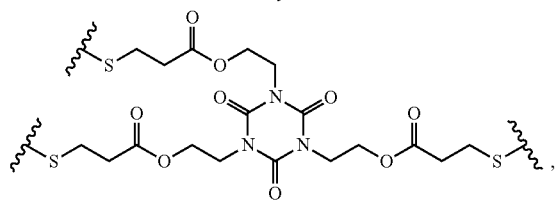
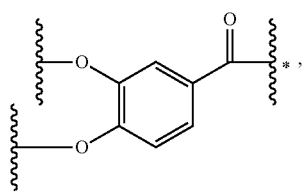
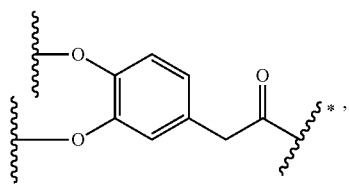
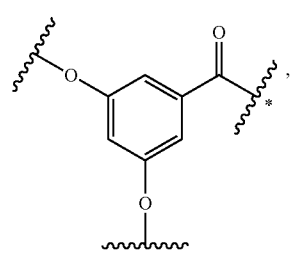
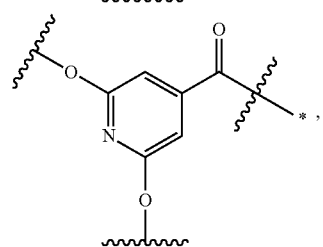
62
-continued
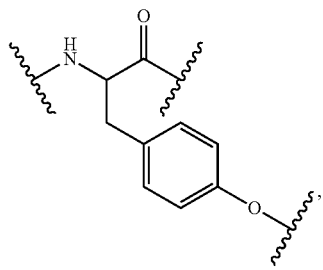
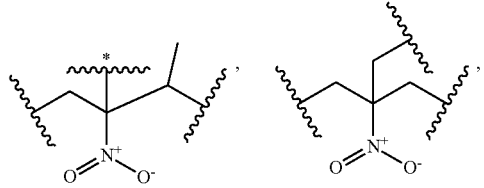
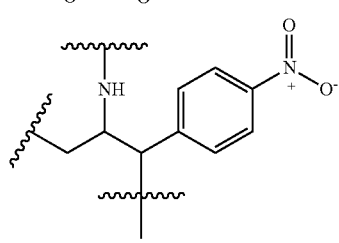
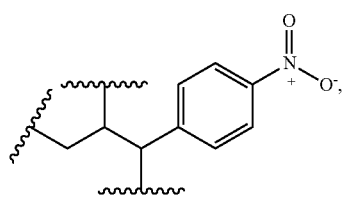
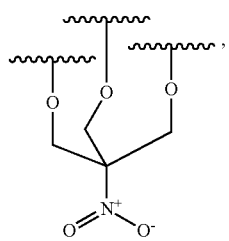
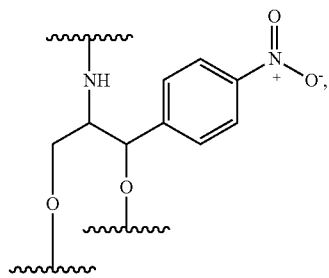
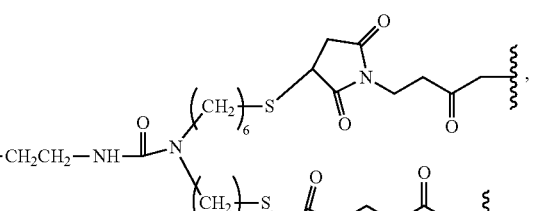

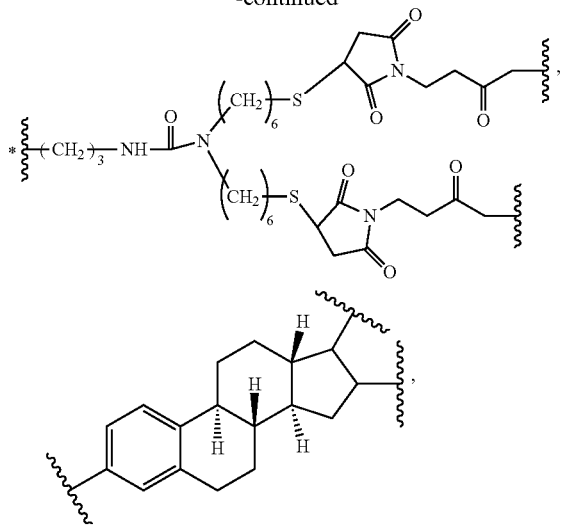

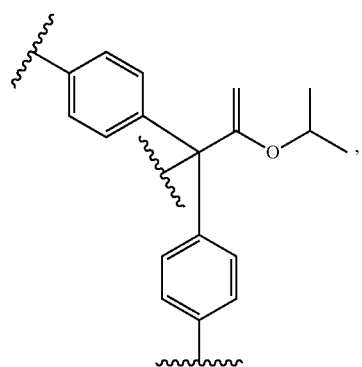

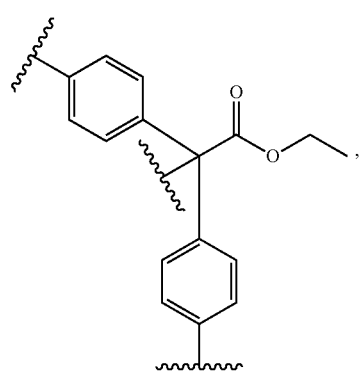

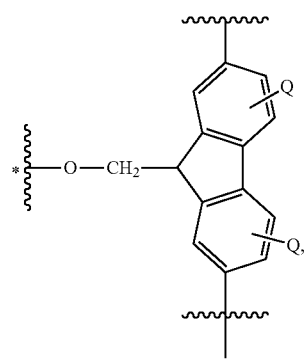

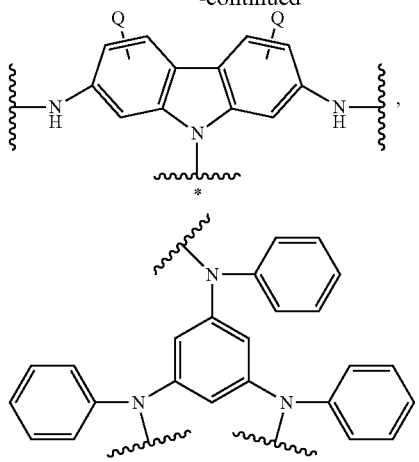

and the like. The above-listed examples are aimed to illustrate the characteristics of the trivalent groups in the set $G^3$ much better, and are not intended to limit the scope of the set $G^3$.

Wherein, Q is not particularly limited as long as it favors inductive effect, conjugation effect, or both inductive and conjugation effects of electrons of unsaturated bonds.

When Q is on the ring, the number of Q can be one or more. When the number of Q is more than one, the Q groups can have the same structure or be the combination of two or two more different structures.

Q can be an atom or a group substituent.

When as an atom, Q can be a hydrogen atom or a halogen atom, and preferably a hydrogen atom or a fluorine atom.

When as a group substituent, examples of Q include but are not limited to all the above-described group substituents in the term-defining section. Q can contain carbon atom or not.

One example of Q without carbon atom is a nitro group. When Q contains carbon atom, the carbon-atom number of Q is not particularly limited, preferably from 1 to 20, and more preferably from 1 to 10.

When as a group substituent, the structure of Q is not particularly limited, including but not limited to a linear structure, a branched structure bearing pendant groups or a ring-containing structure. Wherein, the ring is not particularly limited, and preferably an aliphatic ring, an aromatic ring, a sugar ring or a condensed ring as above-described.

Q can be a hydrogen atom, a halogen atom, a carbon-free substituent, a hydrocarbyl group, a heterohydrocarbyl group, a substituted hydrocarbyl group or a substituted heterohydrocarbyl group.

Q is preferably a hydrogen atom, a halogen atom, a nitro group, a nitro-containing substituent, an acyl-containing substituent, a $C_{1-20}$ haloalkyl group, a $C_{1-20}$ alkyl group, a $C_{2-20}$ alkenyl group, a $C_{3-20}$ open-chain alkenyl-hydrocarbyl group, a $C_{3-20}$ cycloalkenyl group, an aryl group, an arylhydrocarbyl group, a $C_{1-20}$ heteroalkyl group, a heteroaryl group, a heteroarylalkyl group, a $C_{1-20}$ alkoxy group, an aryloxy group, an arylhydrocarbyloxy group, a $C_{1-20}$ heteroalkoxy group, a heteroaryloxy group, a heteroarylhydrocarbyloxy group, a $C_{1-20}$ alkylthio group, an arylthio group, an arylhydrocarbylthio group, a $C_{1-20}$ heteroalkylthio group, a heteroarylthio group, a heteroarylhydrocarbylthio group, the like or the substituted form of any aforesaid group. Wherein, the atom or group substituents within Q are not particularly limited, including but not limited to all the above-described heteroatom and group substituents in the term-defining section, and can be selected from halogen atoms, hydrocarbyl substituents and heteroatom-containing substituents.

Q is more preferably a hydrogen atom, a halogen atom, a nitro group, a nitro-containing substituent, an acyl group, an ester-terminated substituent, a thioester-terminated substituent, an amide-terminated substituent, a $C_{1-20}$ haloalkyl group, a $C_{2-20}$ alkenyl group, a $C_{3-20}$ open-chain alkenyl-hydrocarbyl group, a $C_{3-20}$ cycloalkenyl group, an aryl group, an arylhydrocarbyl group, a $C_{1-20}$ heteroalkyl group, a heteroaryl group, a heteroarylalkyl group, a $C_{1-20}$ alkoxy group, an aryloxy group, an arylhydrocarbyloxy group, a $C_{1-20}$ heteroalkoxy group, a heteroaryloxy group, a heteroarylhydrocarbyloxy group, a $C_{1-20}$ alkylthio group, an arylthio group, an arylhydrocarbylthio group, a $C_{1-20}$ heteroalkylthio group, a heteroarylthio group, a heteroarylhydrocarbylthio group, the like or the substituted form of any aforesaid group. Wherein, the acyl group is not particularly limited, including but not limited to all the above-described acyl groups in the term-defining section. For example, the acyl group can be a carbonyl group, a sulfonyl group, a sulfinyl group, a phosphoryl group, a phosphiryl group, a phosphinyl group, a nitroxyl group, a nitrosyl group, a thiocarbonyl group, an imidoyl group, a thiophosphoryl group, a dithiophosphoryl group, a trithiophosphoryl group, a thiophosphiryl group, a dithiophosphiryl group, a thiophosphinyl group, a thiophosphono group, a dithiophosphono group, a thiophosphino group or the like. The acyl group is preferably a carbonyl group, a thiocarbonyl group, a sulfonyl group, a sulfinyl group or the like, and more preferably a carbonyl group, a thiocarbonyl group, a sulfinyl group or a sulfonyl group.

Q is more preferably a hydrogen atom, a halogen atom, a nitro group, a nitro-containing substituent, a $C_{1-20}$ carbonyl group, a $C_{1-20}$ (alkyl)thiocarbonyl group (alkyl-CS—), a $C_{1-20}$ sulfonyl group, a $C_{1-20}$ alkoxycarbonyl group, a $C_{1-20}$ (alkylthio)carbonyl group (alkyl-S—CO—), a $C_{1-20}$ alkylaminocarbonyl group, a $C_{1-20}$ (alkoxy)thiocarbonyl group, a $C_{1-20}$ (alkylthio)thiocarbonyl group (alkyl-S—CS—), a $C_{1-20}$ (alkylamino)thiocarbonyl group, a $C_{1-20}$ alkoxysulfonyl group (a $C_{1-20}$ alkylsulfonate group), a $C_{1-20}$ alkoxysulfinyl group (a $C_{1-20}$ alkylsulfinate group), an (aryl)thiocarbonyl group (aryl-CS—), an aryloxycarbonyl group, an (arylthio)carbonyl group, an arylaminocarbonyl group, an aryloxy-thiocarbonyl group, an (arylthio)thiocarbonyl group, an (arylamino)thiocarbonyl group, an aryloxy-sulfonyl group (an aryl-sulfonate group), an aryloxy-sulfinyl group (an arylsulfinate group), an (arylalkyl)thiocarbonyl group, an arylalkoxycarbonyl group, an (arylalkylthio)carbonyl group, an arylalkylaminocarbonyl group, an arylalkoxy-thiocarbonyl group, an (arylalkylthio)thiocarbonyl group, an (arylalkylamino)thiocarbonyl group, an arylalkoxy-sulfonyl group (an arylalkylsulfonate group), an arylalkoxy-sulfinyl group (an arylalkylsulfinate group), a $C_{1-20}$ alkyl group, a $C_{2-20}$ alkenyl group, a $C_{3-20}$ open-chain alkenyl-hydrocarbyl group, a $C_{3-20}$ cycloalkenyl group, an aryl group, an arylhydrocarbyl group, a $C_{1-20}$ heteroalkyl group, a heteroaryl group, a heteroarylalkyl group, a $C_{1-20}$ alkoxy group, an aryloxy group, an arylhydrocarbyloxy group, a $C_{1-20}$ heteroalkoxy group, a heteroaryloxy group, a heteroarylhydrocarbyloxy group, a $C_{1-20}$ alkylthio group, an arylthio group, an arylhydrocarbylthio group, a $C_{1-20}$ heteroalkylthio group, a heteroarylthio group, a heteroarylhydrocarbylthio group, a $C_{1-20}$ haloalkyl group, the like or the substituted form of any aforesaid group.

Q is more preferably a hydrogen atom, a halogen atom, a nitro group, a nitro-containing substituent, a $C_{1-10}$ carbonyl group, a $C_{1-10}$ (alkyl)thiocarbonyl group, a $C_{1-10}$ sulfonyl group, a $C_{1-10}$ alkoxycarbonyl group, a $C_{1-10}$ (alkylthio) carbonyl group, a $C_{1-10}$ alkylaminocarbonyl group, a $C_{1-10}$ alkoxy-thiocarbonyl group, a $C_{1-10}$ (alkylthio)thiocarbonyl group, a $C_{1-10}$ (alkylamino)thiocarbonyl group, a $C_{1-10}$ alkoxy-sulfonyl group (a $C_{1-10}$ alkylsulfonate group), a $C_{1-10}$ alkoxy-sulfinyl group (a $C_{1-10}$ alkylsulfinate group), an (aryl)thiocarbonyl group, an aryloxycarbonyl group, an (arylthio)carbonyl group, an arylaminocarbonyl group, an aryloxy-thiocarbonyl group, an (arylthio)thiocarbonyl group, an (arylamino)thiocarbonyl group, an aryloxy-sulfonyl group (an arylsulfonate group), an aryloxy-sulfinyl group (an arylsulfinate group), an (arylalkyl)thiocarbonyl group, an arylalkoxycarbonyl group, an (arylalkylthio)carbonyl group, an arylalkylaminocarbonyl group, an arylalkoxy-thiocarbonyl group, an (arylalkylthio)thiocarbonyl group, an (arylalkylamino)thiocarbonyl group, an arylalkoxy-sulfonyl group (an arylalkylsulfonate group), an arylalkoxy-sulfinyl group (an arylalkylsulfinate group), a $C_{1-20}$ alkyl group, a $C_{2-10}$ alkenyl group, a $C_{3-10}$ open-chain alkenyl-hydrocarbyl group, a $C_{3-10}$ cycloalkenyl group, an aryl group, an arylhydrocarbyl group, a $C_{1-10}$ heteroalkyl group, a heteroaryl group, a heteroarylalkyl group, a $C_{1-10}$ alkoxy group, an aryloxy group, an arylhydrocarbyloxy group, a $C_{1-10}$ heteroalkoxy group, a heteroaryloxy group, a heteroarylhydrocarbyloxy group, a $C_{1-10}$ alkylthio group, an arylthio group, an arylhydrocarbylthio group, a $C_{1-10}$ heteroalkylthio group, a heteroarylthio group, a heteroarylhydrocarbylthio group, a $C_{1-10}$ haloalkyl group, the like or the substituted form of any aforesaid group.

Specifically, Q can be a hydrogen atom, a fluorine atom, a chlorine atom, a bromine atom, an iodine atom, a nitro group, a nitrophenyl group, an acetyl group, a benzoyl group, a tosyl group, a mesyl group, a methoxycarbonyl group, an ethoxycarbonyl group, a t-butoxycarbonyl group, a phenoxycarbonyl group, a benzyloxycarbonyl group, a methylthio-carbonyl group, an ethylthio-carbonyl group, a (t-butylthio)carbonyl group, a (phenylthio)carbonyl group, a (benzylthio)carbonyl group, an ethylamino-carbonyl group, a t-butylaminocarbonyl group, a phenylaminocarbonyl group, a benzylaminocarbonyl group, a methoxy-thiocarbonyl group, an ethoxy-thiocarbonyl group, a t-butoxy-thiocarbonyl group, a phenoxy-thiocarbonyl group, a benzyloxy-thiocarbonyl group, a methylthio-thiocarbonyl group, an ethylthio-thiocarbonyl group, a (t-butylthio)thiocarbonyl group, a (phenylthio)thiocarbonyl group, a (benzylthio)thiocarbonyl group, an ethylamino-thiocarbonyl group, a t-butylaminothiocarbonyl group, a phenylaminothiocarbonyl group, a benzylaminothiocarbonyl group, a methyl group, an ethyl group, an n-propyl group, an isopropyl group, a butyl group, a pentyl group, a hexyl group, a heptyl group, a 2-ethylhexyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, an ethenyl group, a propenyl group, an allyl group, a propynyl group, a propargyl group, a cyclopropyl group, a cyclopropenyl group, a phenyl group, a benzyl group, a butylphenyl group, a p-methylphenyl group, a methoxy group (or a methyloxy group), an ethoxy group (or an ethyloxy group), a phenoxy group (or a phenyloxy group), a benzyloxy group (or a benzoxy group), a methylthio group, an ethylthio group, a phenylthio group, a benzylthio group, a $C_{1-20}$ haloalkyl group, the like or the substituted form of any aforesaid group. Wherein, the butyl group includes but is not limited to an n-butyl group and a t-butyl group. The octyl group includes but is not limited to an n-octyl group and a 2-ethylhexyl group. Wherein, the atom or group substituent can be a halogen atom, a hydrocarbyl substituent or a heteroatom-containing substituent, and can be preferably a halogen atom, an alkoxy group, an alkenyl group, an aryl group or a nitro group.

Q is preferably a hydrogen atom, a fluorine atom, a chlorine atom, a bromine atom, an iodine atom, a nitro group, a nitrophenyl group, an acetyl group, a benzoyl group, a tosyl group, a mesyl group, a methoxy-carbonyl group, an ethoxy-carbonyl group, a t-butoxycarbonyl group, a phenoxycarbonyl group, a benzyloxycarbonyl group, a methylthio-carbonyl group, an ethylthio-carbonyl group, a (t-butylthio)carbonyl group, a (phenylthio)carbonyl group, a (benzylthio)carbonyl group, an ethylamino-carbonyl group, a t-butylaminocarbonyl group, a phenylaminocarbonyl group, a benzylaminocarbonyl group, a methyl group, an ethyl group, an n-propyl group, an isopropyl group, a butyl group, a pentyl group, a hexyl group, a heptyl group, an octyl group, a nonyl group, a decyl group, an ethenyl group (also termed as a vinyl group), a propenyl group, an allyl group, a propynyl group, a propargyl group, a cyclopropyl group, a cyclopropenyl group, a phenyl group, a benzyl group, a butylphenyl group, a p-methylphenyl group, a methoxy group, an ethoxy group, a phenoxy group, a benzyloxy group, a methylthio group, an ethylthio group, a phenylthio group, a benzylthio group, a trifluoromethyl group, a 2,2,2-trifluoroethyl group, the like or the substituted form of any aforesaid group. Wherein, the atom or group substituent is preferably a fluorine atom, an alkoxy group, an alkenyl group, an aryl group or a nitro group.

Q is more preferably a hydrogen atom, a fluorine atom, a methyl group, a trifluoromethyl group, a methoxy group, a methoxycarbonyl group, a tosyl group, a mesyl group or the like.

Q is more preferably a hydrogen atom, a fluorine atom, a methyl group, a trifluoromethyl group, a methoxy group, a methoxycarbonyl group or the like.

Take tetravalent groups (tetravalent G with k equal to 3 or U) for example, examples of tetravalent groups in which the non-core moiety beyond the tetravalent core structure contains no heteroatoms, include but are not limited to the groups described and listed in the documents CN104530413A, CN104530415A and CN104530417A; take CN104530417A as an example, corresponding to paragraphs from [0321] to [0323]. Examples of tetravalent groups in which the non-core moiety contains heteroatoms include but are not limited to the groups described and listed in the documents CN104530413A, CN104530415A and CN104530417A; take CN104530417A as an example, corresponding to paragraphs from [0324] to [0325].

When k is greater than or equal to 3 (k≥3), that is when the valence of G is higher than or equal to 4, (k+1)-valent groups (groups with valence of k+1) in the set $G^{k+}$ can contain a corresponding (k+1)-valent cyclic core structure $CC_{k+1}$, or can be combined directly by lower-valent groups with the valence from 3 to k in quantities of 2 to k−1, or can be combined indirectly via one or more divalent spacer groups denoted as $L_{10}$. For example, when k is equal to 3, a tetravalent group can be combined by two trivalent groups, and a pentavalent group can be combined by three trivalent groups, or be combined by one trivalent group and one tetravalent group.

When two or two more spacer groups $L_{10}$ are present, the $L_{10}$ spacer groups can be the same or different.

$L_{10}$ is not particularly limited. $L_{10}$ can contain carbon atom or not; $L_{10}$ can contain heteroatoms or not; $L_{10}$ can be a divalent group of a single atom or a divalent group formed by two or two more atoms.

$L_{10}$ can be a single-atom divalent group, such as —O— or —S—, or be a secondary amino group or a divalent t-amino group.

$L_{10}$ can also be a hydrocarbylene group that contains no heteroatoms (i.e. heteroatom-free), and the carbon-atom number is preferably from 1 to 20. Specifically, $L_{10}$ is preferably a $C_{1-20}$ alkylene group, a $C_{1-20}$ divalent alkenyl group, a $C_{1-20}$ divalent alkenyl-hydrocarbyl group, a $C_{1-20}$ divalent alkynyl group, a $C_{1-20}$ divalent alkynyl-hydrocarbyl group, a $C_{1-20}$ divalent cycloalkyl group, a $C_{1-20}$ divalent cycloalkyl-hydrocarbyl group, a phenylene group, a divalent condensed aryl group or a divalent arylhydrocarbyl group.

$L_{10}$ can also be any one heteroatom-containing divalent linking group selected from the group consisting of —N($R_7$)—, —C(=O)—, —C(=S), —C(=NH)—, —C(=O)—N($R_7$)—, —N($R_7$)—C(=O)—, —S—S—, —C(=O)—O—, —O—C(=O)—, —C(=O)—S—, —S—C(=O)—, —C(=S)—O—, —O—C(=S)—, —C(=S)—S—, —S—C(=S)—, —O—C(=O)—O—, —S—C(=O)—O—, —O—C(=S)—O—, —O—C(=O)—S—, —S—C(=S)—O—, —O—C(=S)—S—, —S—C(=O)—S—, —S—C(=S)—S—, —N($R_7$)—C(=O)—O—, —O—C(=O)—N($R_7$)—, —N($R_7$)—C(=S)—O—, —O—C(=S)—N($R_7$)—, —N($R_7$)—C(=O)—S—, —S—C(=O)—N($R_7$)—, —N($R_7$)—C(=S)—S—, —S—C(=S)—N($R_7$)—, —N($R_{19}$)—N($R_{18}$)—, —N($R_{19}$)—C(=O)—N($R_{18}$)—, —N($R_{19}$)—C(=S)—N($R_{18}$)—, —N($R_{18}$)—N($R_{19}$)—C(=O)—, —C(=O)—N($R_{19}$)—N($R_{18}$)—, —N($R_{18}$)—N($R_{19}$)—C(=S)—, —C(=S)—N($R_{19}$)—N($R_{18}$)—, —($R_{15}$)C=N—, —N=C($R_{15}$)—, —($R_{15}$)C=N—N($R_7$)—, —N($R_7$)—N=C($R_{15}$)—, —($R_{18}$)C=N—N($R_7$)—C(=O)—, —C(=O)—N($R_7$)—N=C($R_{15}$)—, —($R_{18}$)C=N—O—, —O—N=C($R_{15}$)—, —($R_{15}$)C=N—S—, —S—N=C($R_{15}$)—, —N=N—, —N($R_{18}$)—N($R_{19}$)—C(=O)—N=N—, —N=N—C(=O)—N($R_{19}$)—N($R_{18}$)—, —N($R_{18}$)—C(=O)—N($R_{19}$)—, —C(=N$R_7$)—N($R_{23}$)—, —N($R_{23}$)—C(=N$R_7$)—, —N($R_7$)—C(=NH$_2^+$)—, —C(=NH$_2^+$)—N($R_7$)—, —C(=N$R_7$)—O—, —O—C(=N$R_7$)—, —O—C(=NH$_2^+$)—, —C(=NH$_2^+$)—O—, —C(=N$R_7$)—S—, —S—C(=N$R_7$)—, —S—C(=NH$_2^+$)—, —C(=NH$_2^+$)—S—, —S(=O)$_2$—O—, —O—S(=O)$_2$—, —S(=O)—O—, —O—S(=O)—, —S(=O)$_2$—N($R_7$)—, —N($R_7$)—S(=O)$_2$—, —S(=O)$_2$—N($R_{18}$)—N($R_{19}$)—, —N($R_{19}$)—N($R_{18}$)—S(=O)$_2$—, —CH$_2$—O—, —O—CH$_2$—, —CH$_2$CH$_2$—O—, —O—CH$_2$CH$_2$—, —O—CH$_2$CH$_2$—O—, —O—$R_{29}$—, —$R_{29}$—O—, —O—$R_{29}$—O—, the like and substituted forms of any aforesaid heteroatom-containing divalent linkage. Wherein, the definitions of $R_7$, $R_{18}$, $R_{19}$, $R_{23}$ and $R_{15}$ are the same as above. Wherein, $R_{29}$ is a $C_{3-20}$ alkylene group, its structure is not particularly limited, and can be a linear-chain type, a branched-chain type or a ring-containing type; the carbon-atom number of $R_{29}$ is preferably $C_{3-12}$; the structure of $R_{29}$ is preferably a linear-chain type.

$L_{10}$ is more preferably an oxy group, a thioxy group, a secondary amino group or a divalent t-amino group to form a stable connection. When $L_{10}$ exists within the initiator OctaIN, $L_{10}$ is preferably an oxy group, a thioxy group or a divalent t-amino group.

$L_{10}$ is most preferably an oxy group such as an ether bond formed by the condensation between two alcoholic hydroxyl groups.

$L_{10}$ can also be a monodisperse multi-form of —$CH_2CH_2$—O—, —O—$CH_2CH_2$—, —O—$R_{29}$— or —$R_{29}$—O—, wherein, the repeat-unit number can be from 2 to 20, and preferably from 2 to 10. However, these $L_{10}$ types do not appear in the octavalent group $CORE_8(O—)_8$.

Take tetravalent groups for example (e.g., the G group with k=3), tetravalent groups in the set $G^4$ can be based on a tetravalent core structure, and can also be the combination of any two trivalent groups in the set $G^3$. The combination can be in a direct manner, e.g., tetravalent groups derived from erythritol can be regarded as a direct combination of two trivalent groups. For another example, tetravalent groups which are formed by two amino acid or amino acid derivative skeletons via direct connections. The combination can also be in an indirect manner via one or one more divalent spacer groups $L_{10}$. When a tetravalent group in the set $G^4$ contains two or two more spacer groups $L_{10}$, the $L_{10}$ groups can be the same or different. Tetravalent groups formed by removing hydroxyl groups or hydrogen atoms of hydroxyl groups of tetraols belong to this manner, wherein, the tetraols can be formed by the condensation of two molecules of common triols.

The tetravalent groups in the set $G^4$ include but are not limited to the groups described and listed in the documents CN104530413A, CN104530415A and CN104530417A; take CN104530417A as an example, corresponding to paragraphs from [0321] to [0325] and paragraphs from [0334] to [0339].

The tetravalent G can be any one tetravalent group selected from the above-described set $G^4$. Examples of tetravalent G also include but are not limited to the following tetravalent structures:

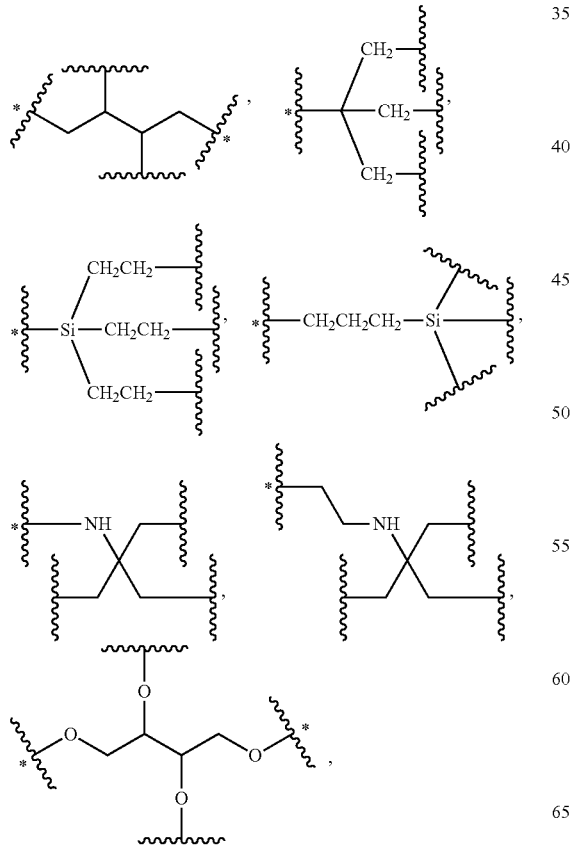

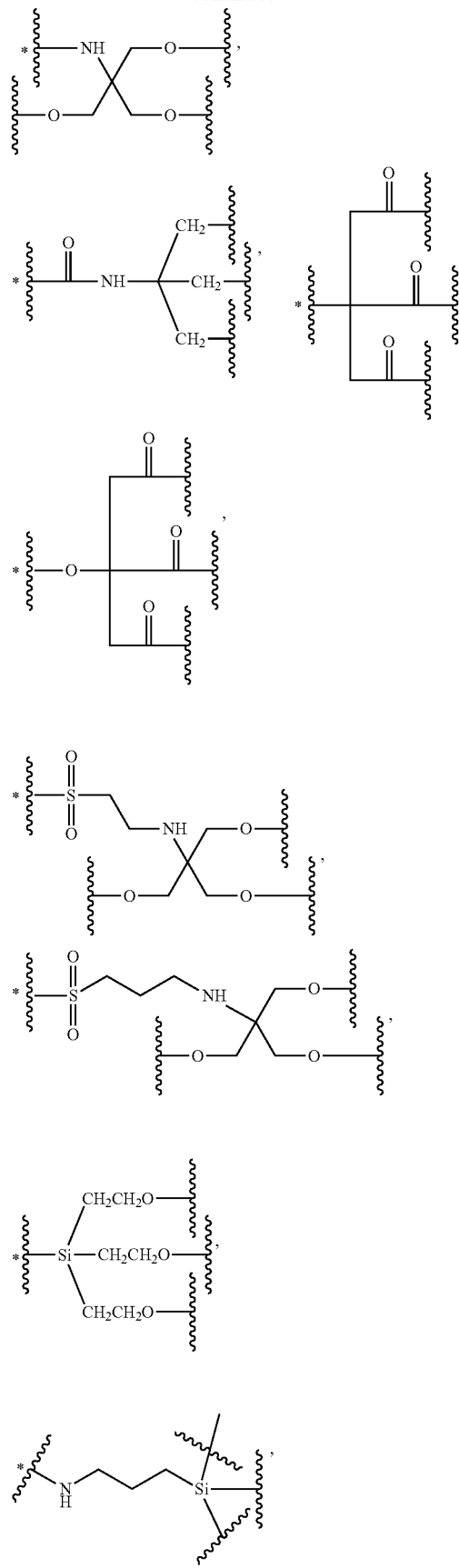

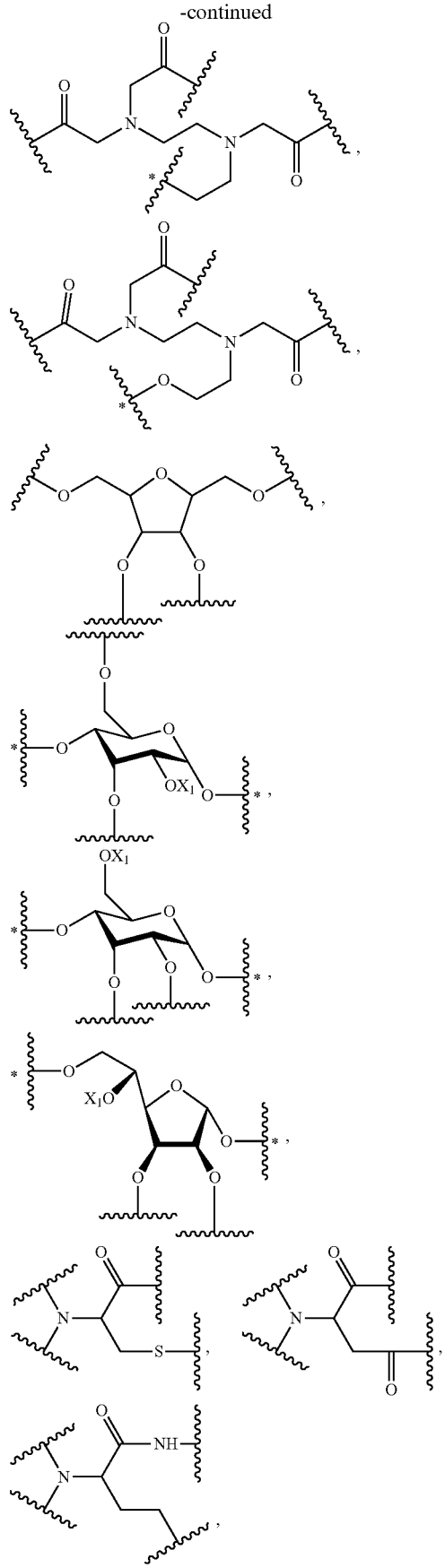
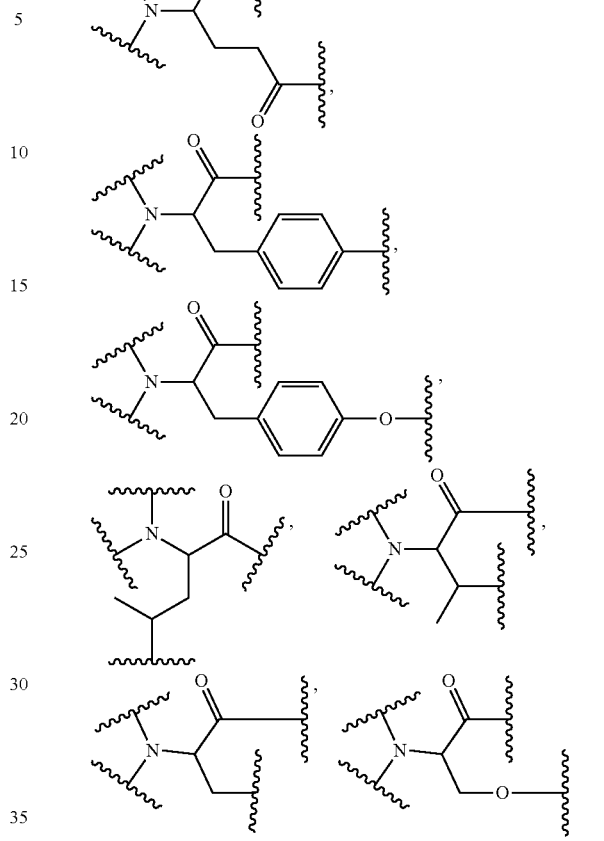
and the like. Wherein, the definition of $X_1$ is the same as above.
When k is equal to 4 (k=4), examples of pentavalent groups include but are not limited to the groups described and listed in the documents CN104530413A, CN104530415A and CN104530417A; take CN104530417A as an example, corresponding to paragraph [0341]. Examples of pentavalent groups also include but are not limited to the following structures:
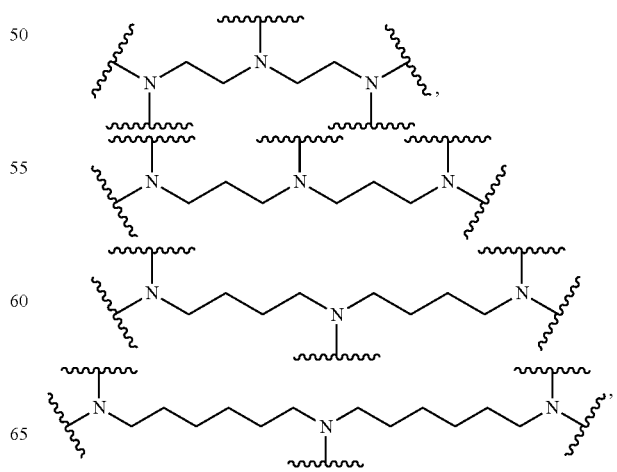

-continued
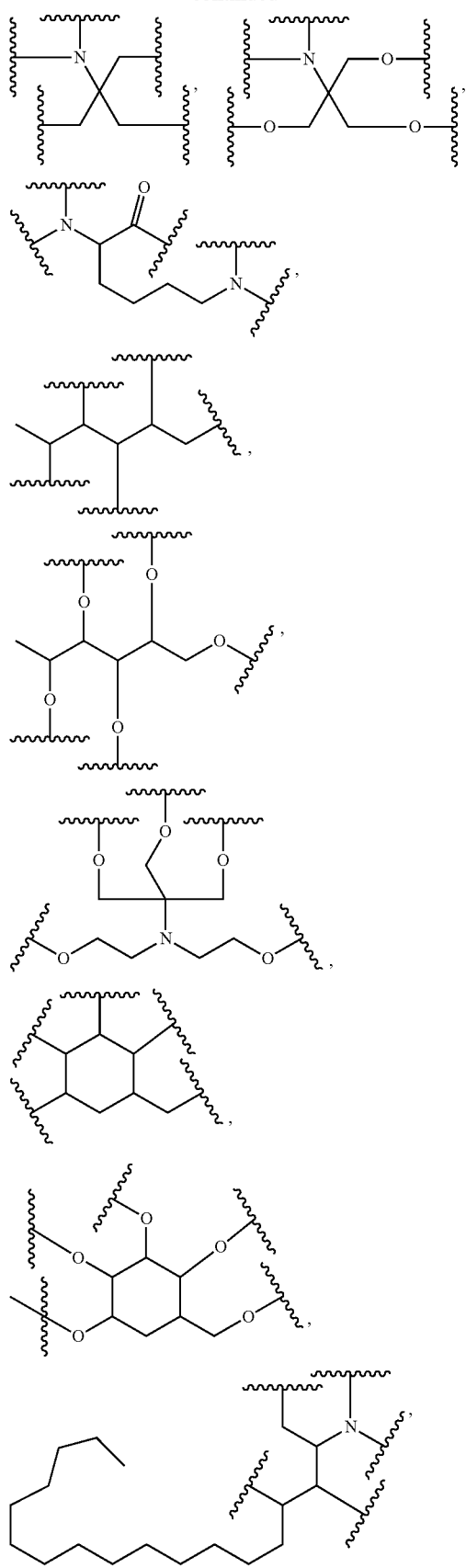
-continued
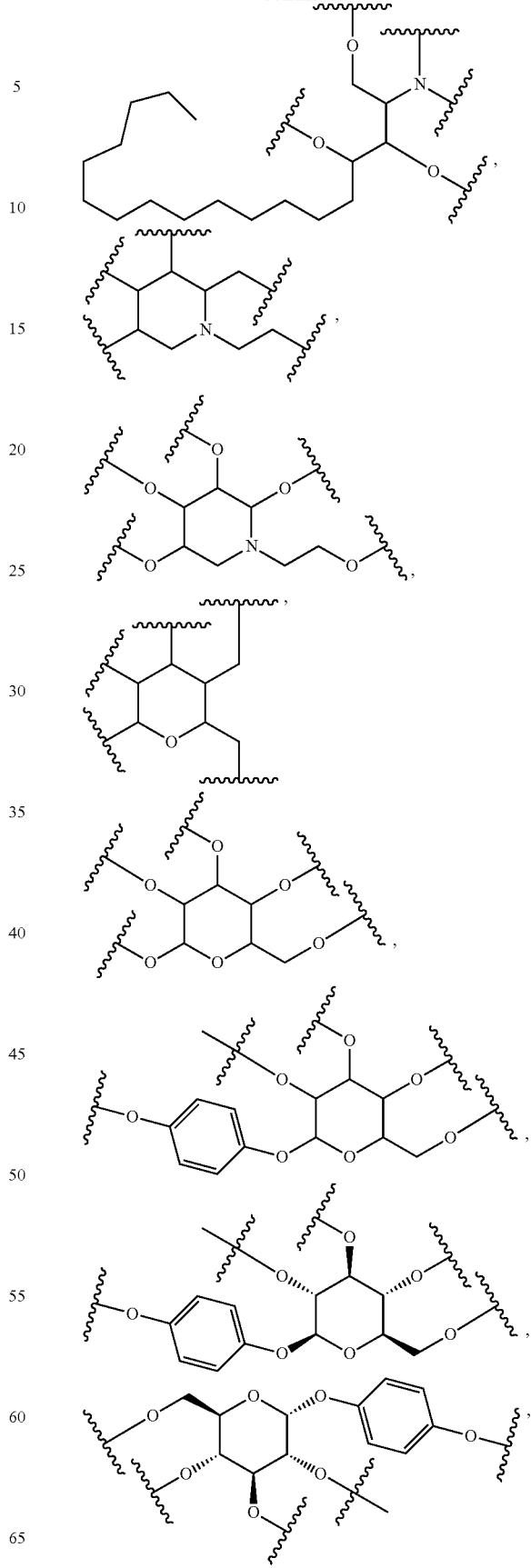

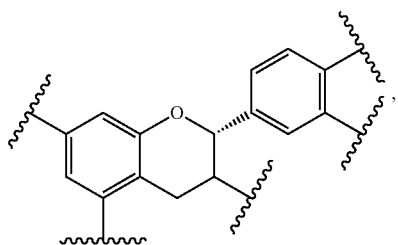

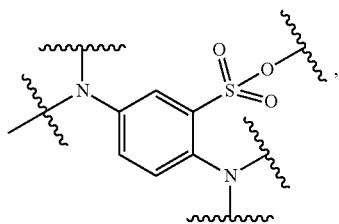

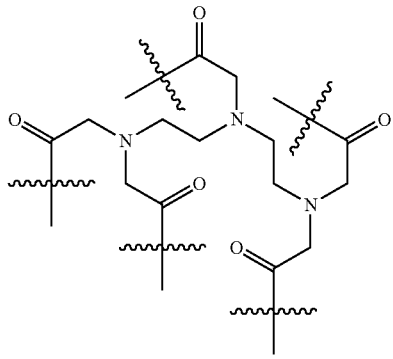

and the like. Wherein, the isomeric structures of

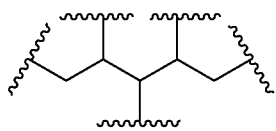 [SMILES: *CC(*)C(*)C(*)C*]

include but are not limited to pentavalent carbon skeletons of D-ribose, D-arabinose, D-xylose and D-lyxose. Pentavalent groups also include but are not limited to pentavalent skeleton structures of six-membered cyclic monosaccharides such as glucose, allose, altrose, mannose, gulose, idose, galactose, talose, psicose, fructose, sorbose, tagatose and the like.

Examples of hexavalent groups corresponding to k=5, heptavalent groups corresponding to k=6 and octavalent groups corresponding to k=7, include but are not limited to the groups described and listed in the documents CN104530413A, CN104530415A and CN104530417A; take CN104530417A as an example, corresponding to paragraphs from [0342] to [0347]. Wherein, hexavalent groups also include but are not limited to

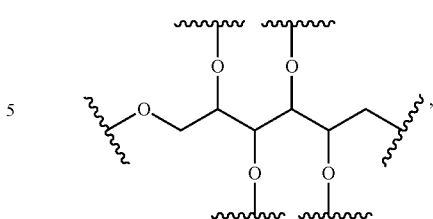

hexavalent skeletons derived from inositol, sorbitol, mannitol, D-glucamine, 1-mercapto-sorbitol, N-methyl-D-glucamine, tris(2,3-dichloropropyl)phosphate ester and D-sorbitol-3-phosphate ester after removing six hydrogen atoms of hydroxyl groups, amino groups or/and mercapto groups, and hexavalent skeletons derived from D-allose, D-altrose, D-glucose, D-mannose, D-gulose, D-idose, D-galactose, D-talose and D-psicose.

When k is greater than or equal to 4 (k≥4), the valence of G is greater than or equal to 5 (≥5). As for (k+1)-valent groups in the set $G^{k+1}$ which can be formed via a direct combination of lower-valent (from 3- to k-valent) groups in quantities of 3 to k−1, or can be combined indirectly via one or more divalent spacer groups $L_{10}$, wherein, the combination manner of the lower-valent (from 3- to k-valent) groups is not particularly limited. Examples of G(k≥4) groups include but are not limited to the groups described and listed in the documents CN104530413A, CN104530415A and CN104530417A; take CN104530417A as an example, corresponding to paragraphs from [0348] to [0407]. The combination manners include but are not limited to a comb-like manner, a dendritic manner, a branched manner, a hyperbranched manner, a cyclic manner and the like. With respect to a group combined by several lower-valent groups in a comb-like, dendritic, branched or hyperbranched manner, the lower-valent groups in one molecule can be identical or not identical, and preferably that the lower-valent groups in one molecule are identical.

For (k+1)-valent groups in the set $G^{k+1}$ (k≥4) formed by combing lower-valent groups in a comb-like manner, a dendritic manner, a branched manner, a hyperbranched manner or a cyclic manner, the number of the lower-valent groups is from 3 to 150, preferably from 3 to 100, and more preferably from 3 to 50. The dendritic combinations have a generation from 2 to 6 in terms of generation number, preferably from 2 to 5, and more preferably 2, 3 or 4.

1.1.4 Examples of $E_i$ and U

The structure of U is not particularly limited, and can be but not limited to a branched structure or a ring-containing structure. The degradability of U is not particularly limited, either stable or degradable. The structures of $E_1$, $E_2$, $E_3$ and $E_4$ are not particularly limited, and are each independently but not limited to a branched structure, a ring-containing structure or the like. Preferably, $E_1$, $E_2$, $E_3$ and $E_4$ are of the same structure type, each containing a trivalent atom core, or each containing a trivalent unsaturated bond core, or each containing a trivalent cyclic core. The structures of $E_1$, $E_2$, $E_3$ and $E_4$ can be the same or different. The stability of $E_1$, $E_2$, $E_3$ and $E_4$ are not particularly limited, each independently either stable or degradable; preferably, $E_1$, $E_2$, $E_3$ and $E_4$ have the same stability, that is $E_1$, $E_2$, $E_3$ and $E_4$ are all stable or are all degradable.

U is a tetravalent group $U_0$ or contains a tetravalent group $U_0$. The structure of $E_i$ (i=1, 2, 3, 4) are each independently a trivalent group $E_0$ or contains a trivalent group $E_0$. $E_i$ (i=1, 2, 3, 4) can be the same or different, and preferably $E_1$, $E_2$, $E_3$ and $E_4$ have the same structure. The CORE group formed by $U_0$ and $E_0$ can be combined via a direct manner or indirectly via $L_{10}$ spacers. When $U=U_0$ and $E=E_0$, the spacer group $L_{10}$ is not in need. The definition of $L_{10}$ is the same as above.

$E_0$ contains a trivalent core structure selected from an atom core $CM_3$, an unsaturated bond core $CB_3$ and a cyclic core $CC_3$. The preferable structures of the trivalent cyclic structure $CC_3$ are the same as above-described. Specifically, $E_0$ preferably contains a trivalent core selected from

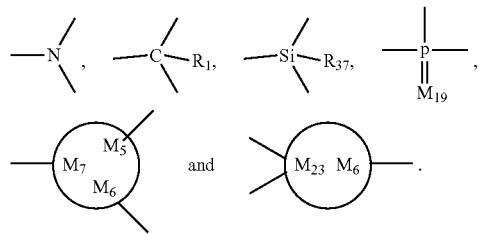

Wherein, the definitions of $R_1$, $R_{37}$, $M_5$, $M_6$, $M_7$, $M_{23}$ and rings containing $M_5$, $M_6$, $M_7$ or $M_{23}$ are the same as above. $M_{19}$ is an oxygen atom or a sulfur atom.

Examples of $E_0$ include but are not limited to above-described trivalent groups and the trivalent groups listed and preferably disclosed in paragraphs from [0732] to [0736] of the document CN104530417A.

$E_0$ preferably contains one of the following structures:

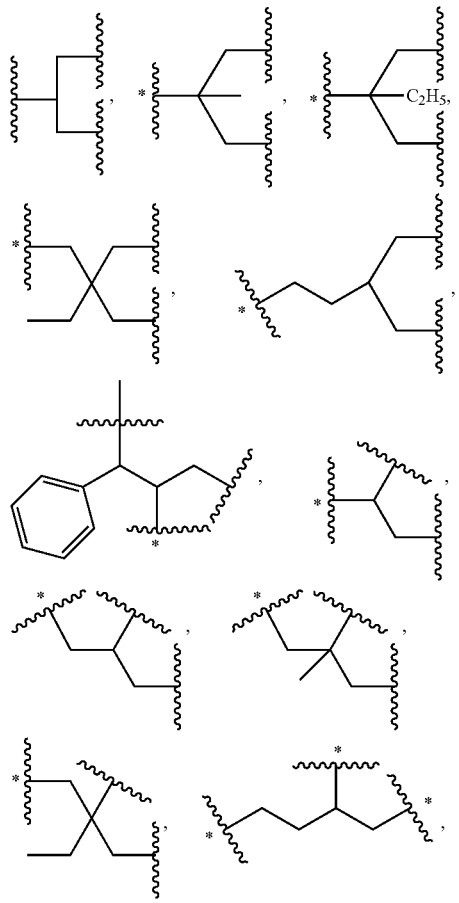

-continued

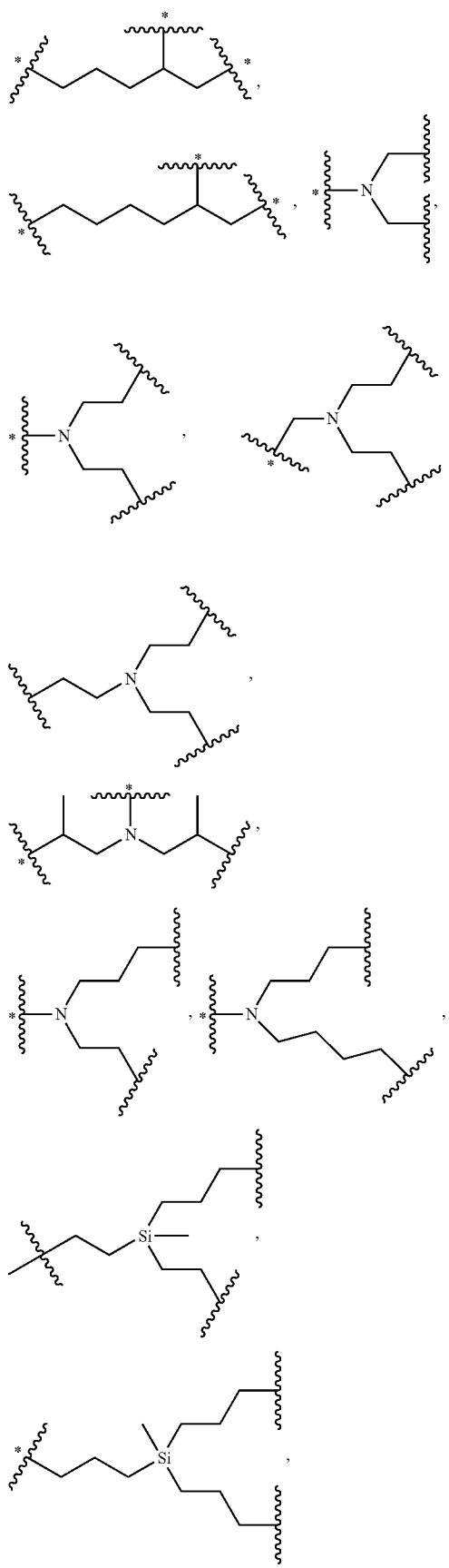

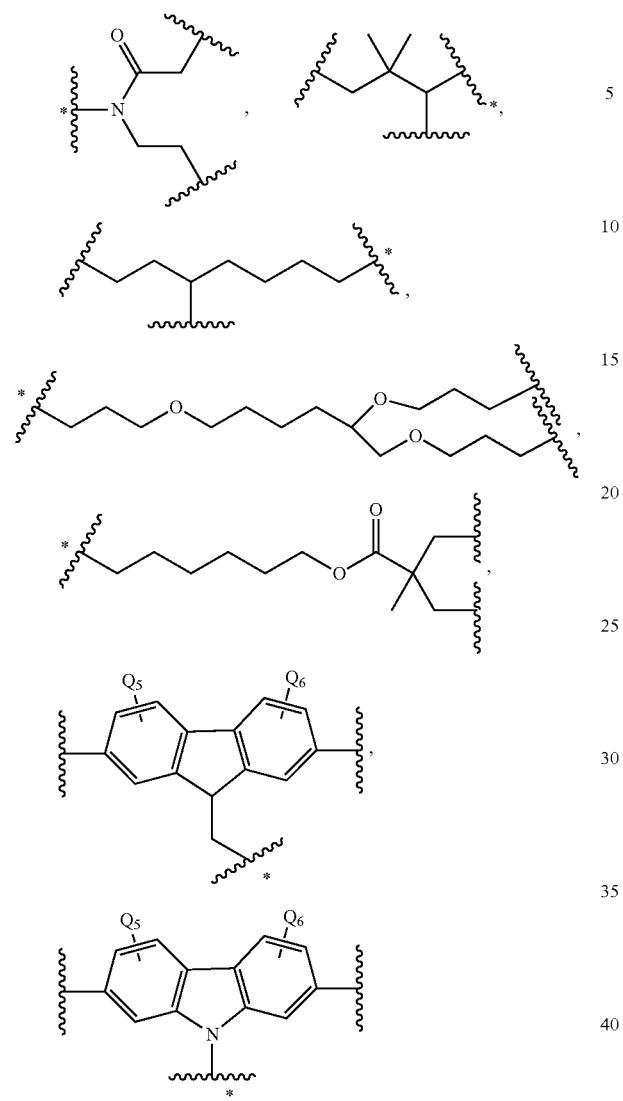

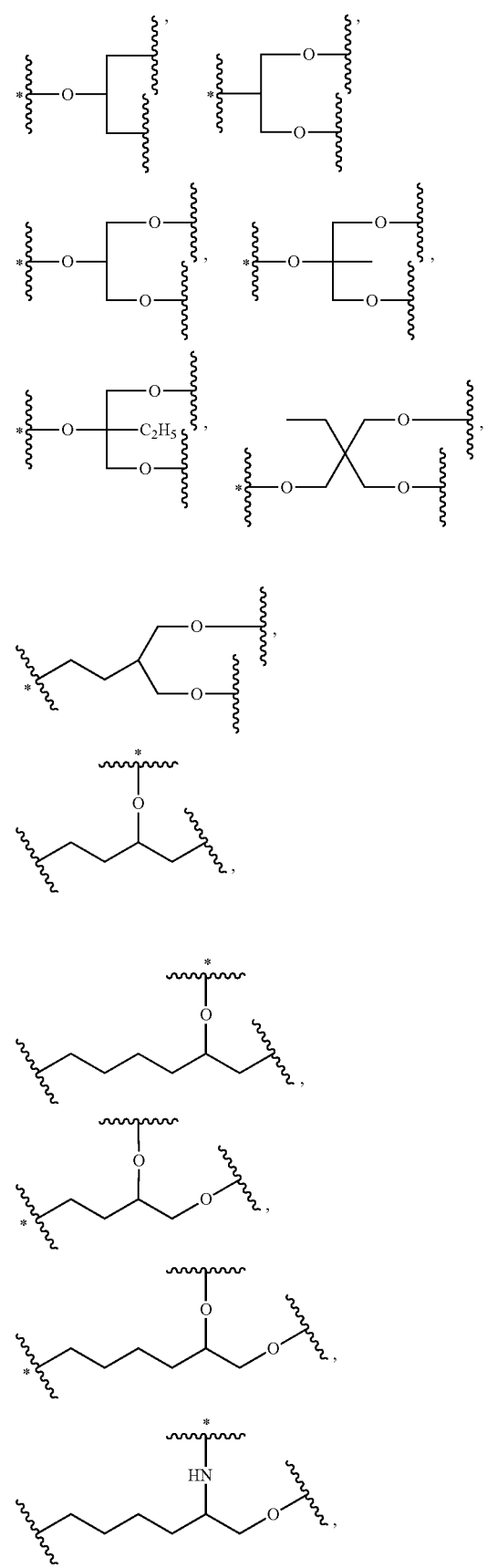

and the like.

$E_0$ further preferably contains the end-capped form of any above-said structure end-capped with one, two or three identical or different divalent linking groups, wherein, the divalent linking groups are selected from an oxy group, a thioxy group, a secondary amino group, a divalent t-amino group and a carbonyl group; when participating in constituting an initiator molecule for living anionic polymerization, $E_0$ is further preferably free of a carbonyl group and a secondary amino group. Wherein, $Q_5$ can be a hydrogen atom, an atom substituent or a group substituent, not particularly limited, but preferably a hydrogen atom, a methyl group, an ethyl group or a propyl group. When $Q_5$ is located at the ring, the number of $Q_5$ can be one or more. When the number of $Q_5$ is greater than one, the $Q_5$ groups can have the same structure, or be the combination of two or two more different structures. The $Q_5$-membered ring can be but not limited to a ring derived from fluorine, carbazole, norbornene or a 7-oxa-bicyclo[2.2.1]hept-5-en-2-yl group. For example, $E_0$ can be any one structure selected from the following structures:

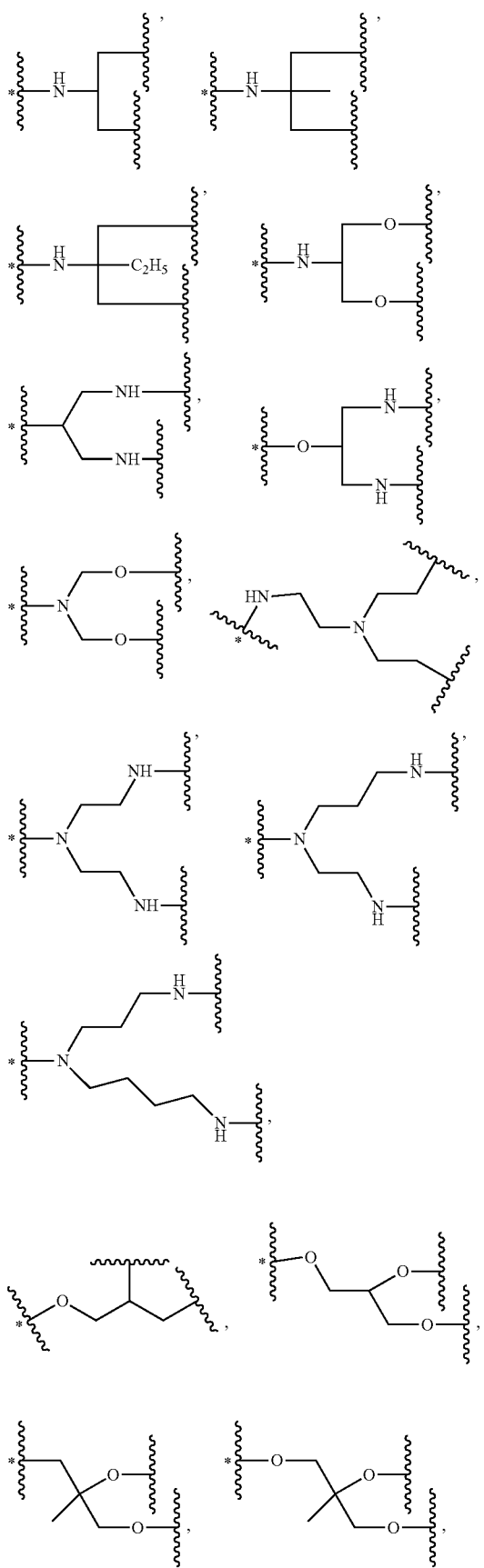
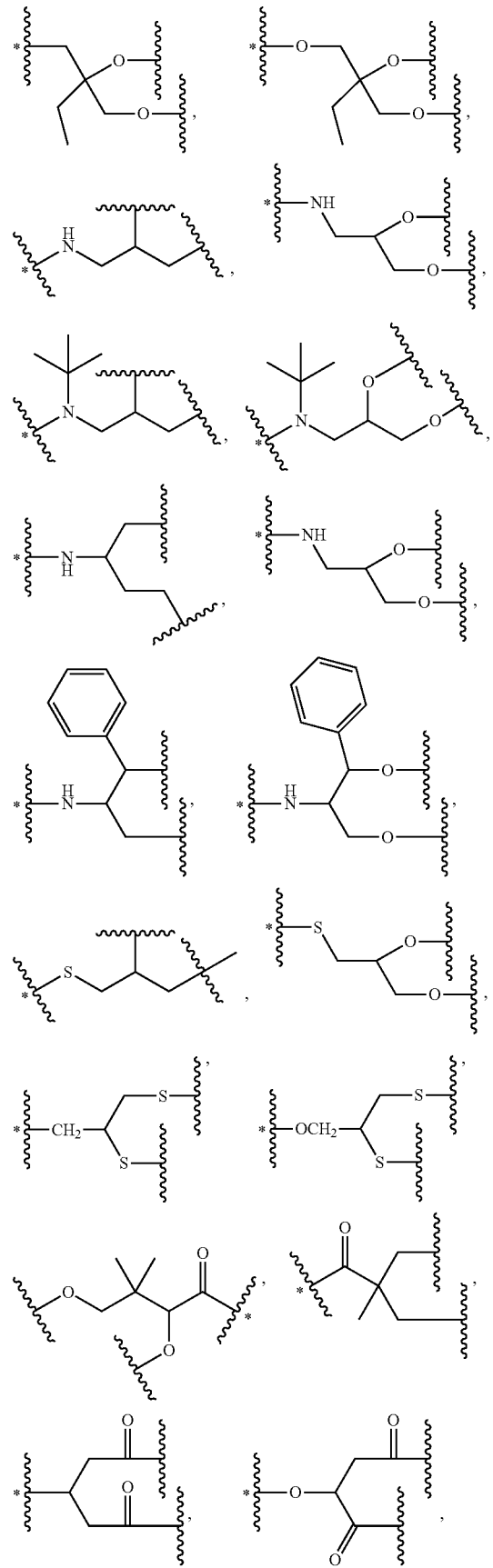

-continued

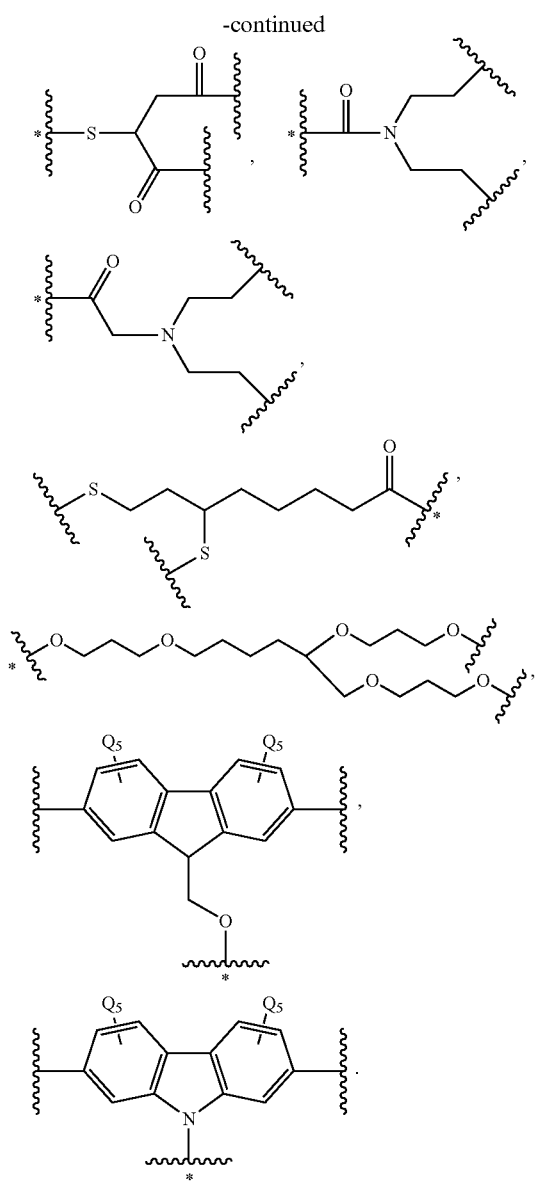

and the like. When contained in an initiator molecule for living anionic polymerization, $E_0$ is further preferably free of a carbonyl group and a secondary amino group. The definition of $Q_5$ is the same as above.

$E_0$ can also be a trivalent amino acid or amino acid derivative skeleton structure, but does not participate in constructing the initiator molecule for living anionic polymerization; wherein, the amino acids can be of $_L$-type or of $_D$-type. For example, $E_i$ (i=1, 2, 3, 4) can be derived from, but not limited to, the following amino acids and amino acid derivatives: hydroxyl- or sulfur-containing amino acids including serine, threonine, cysteine, tyrosine, hydroxyproline and derivatives thereof, acidic amino acids including aspartic acid, glutamic acid, asparagine, glutamine and derivatives thereof, and basic amino acids including lysine, arginine, citrulline, histidine, tryptophan and derivatives thereof.

$U_0$ contains any one tetravalent core structure selected from an atom core $CM_4$, an unsaturated bond core $CB_4$ and a cyclic core $CC_4$, or contains two trivalent core structures.

The preferable embodiments of the tetravalent cyclic structure $CC_4$ are the same as above-described. Specifically, $U_0$ preferably contains a tetravalent core structure selected from

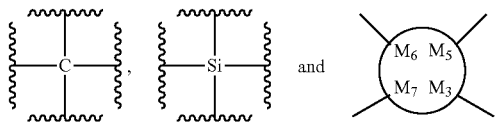

or contains a tetravalent structure formed by two trivalent core structures via a direct combination or an indirect combination. Wherein, the definition of $M_3$ is the same as $M_5$, $M_6$ and $M_7$; in one molecule, $M_5$, $M_6$, $M_7$ and $M_3$ can be each independently the same or different; two of $M_5$, $M_6$, $M_7$ and $M_3$ can be a common atom, such as

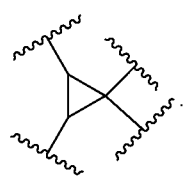 [SMILES: *C1C(*)C1(*)*]

$U_0$ can be but is not limited to one of the above-described tetravalent groups.

Examples of $U_0$ also include but are not limited to the following tetravalent groups:

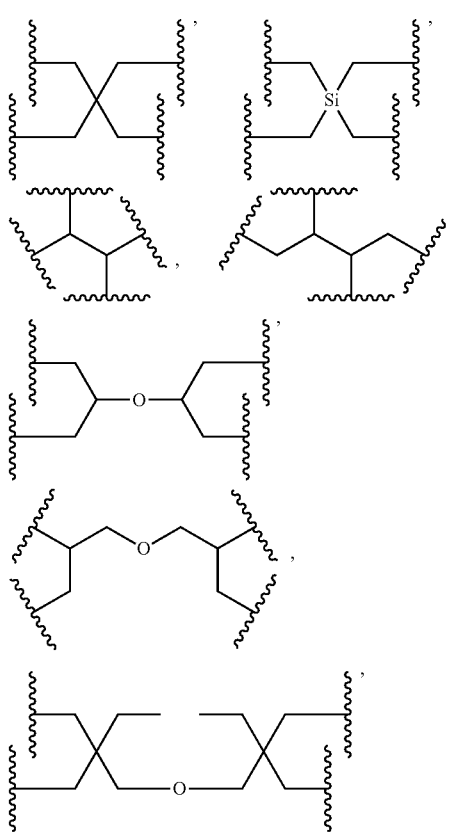

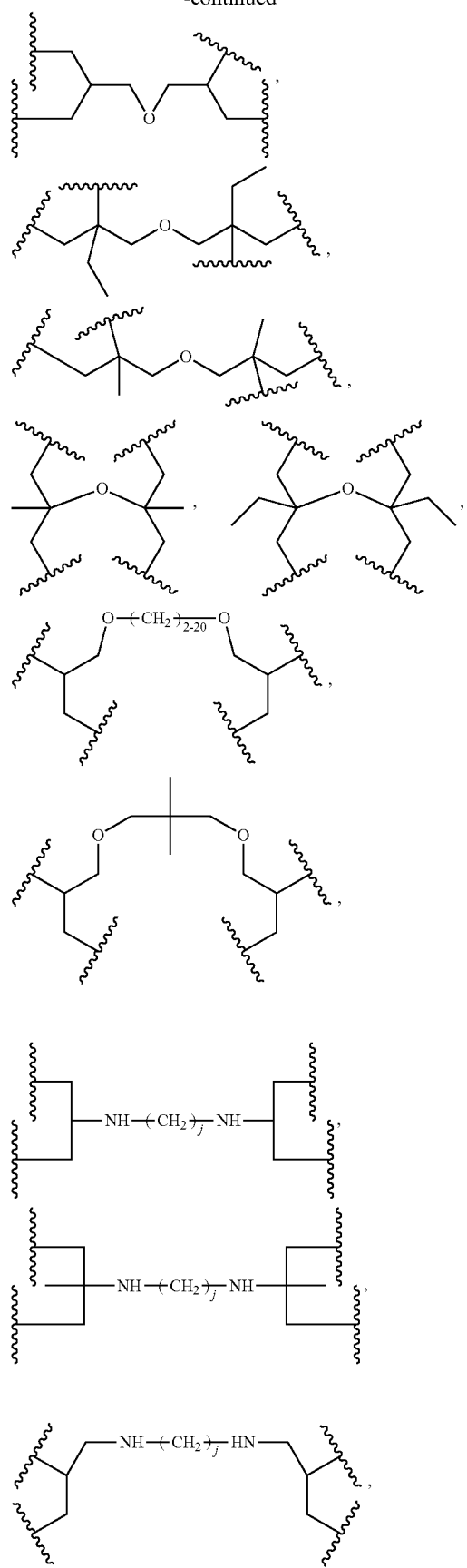
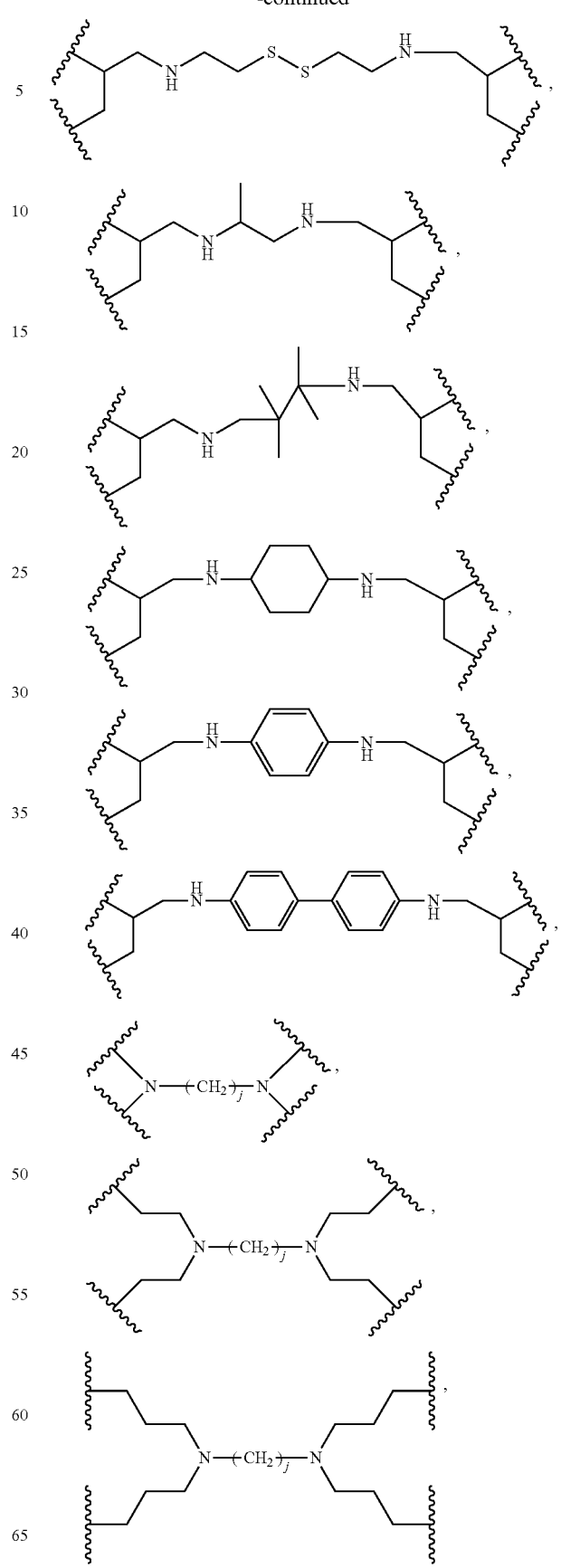

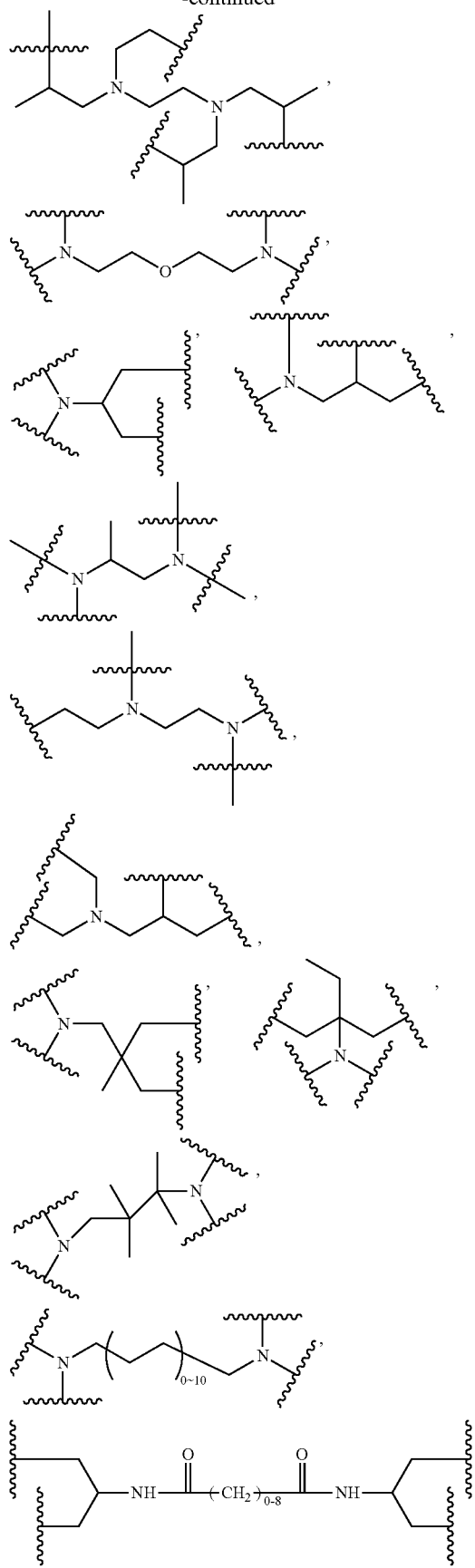
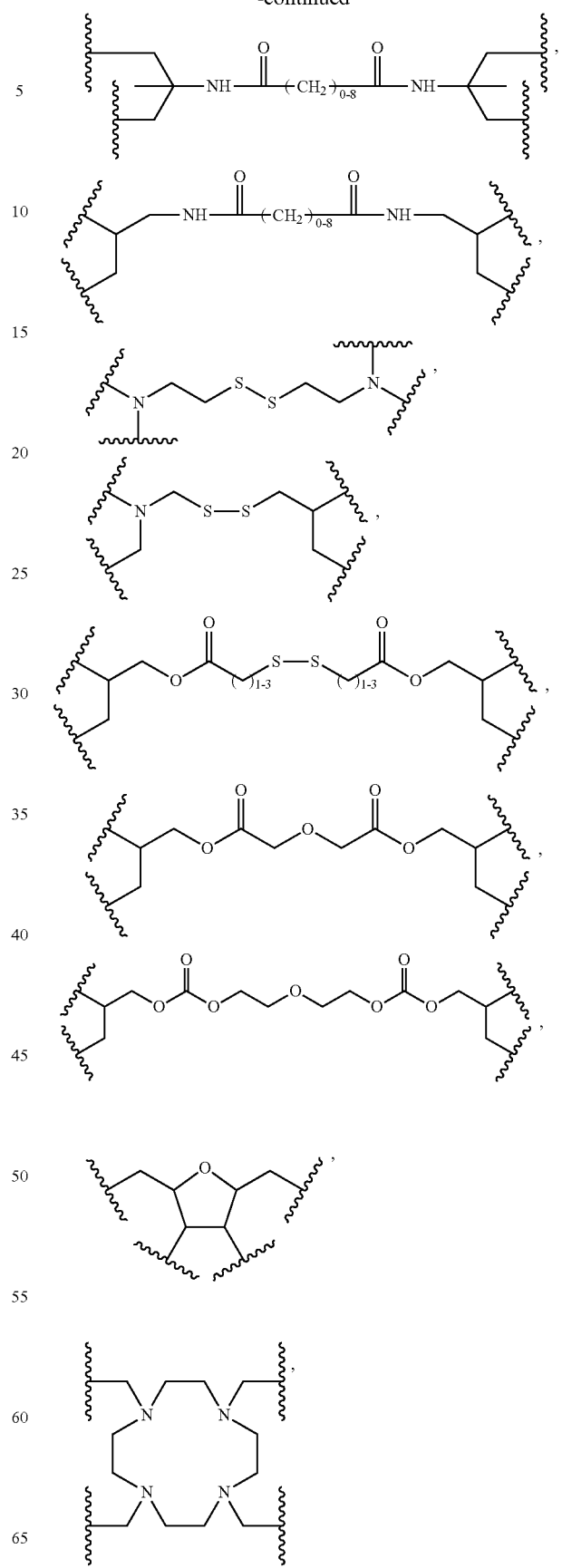

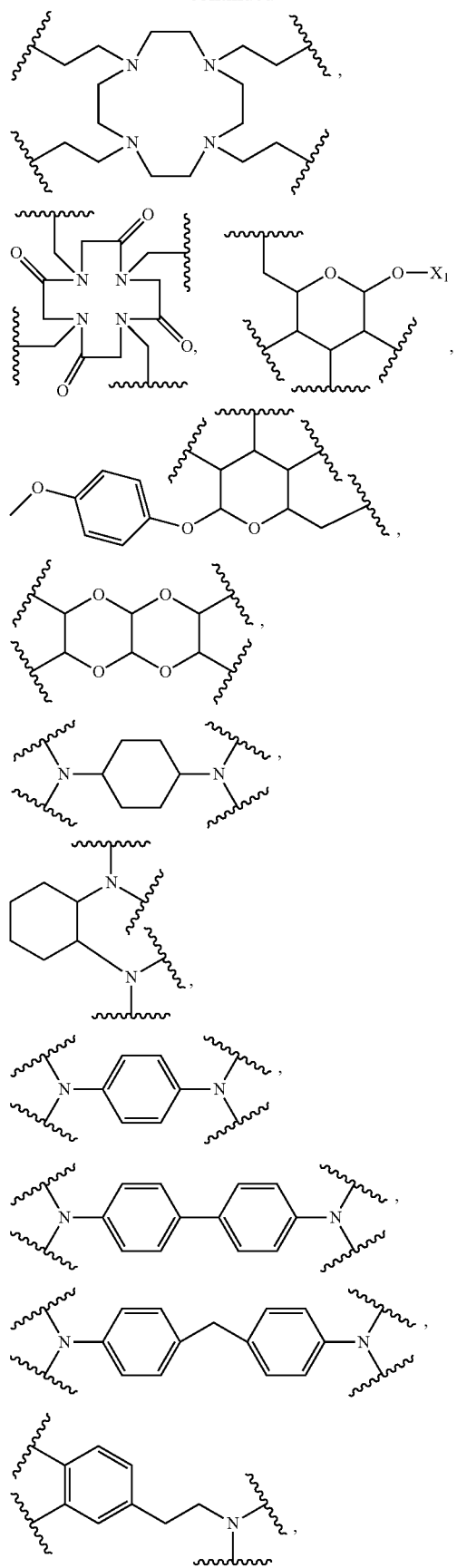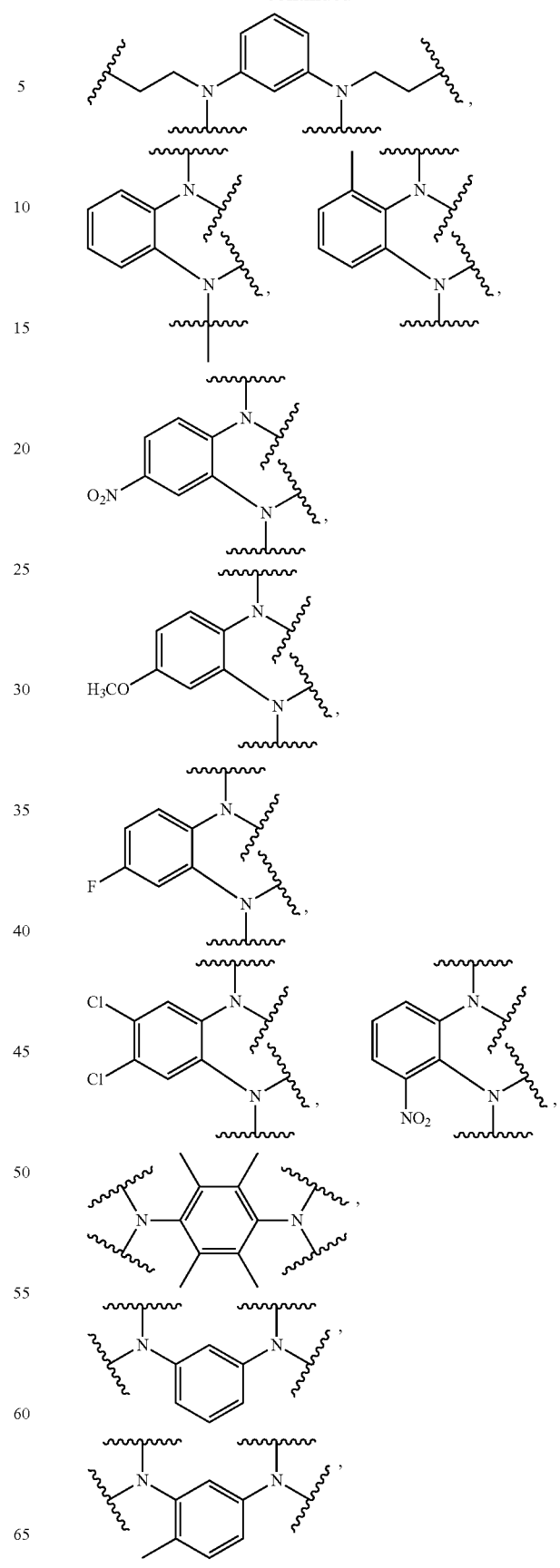

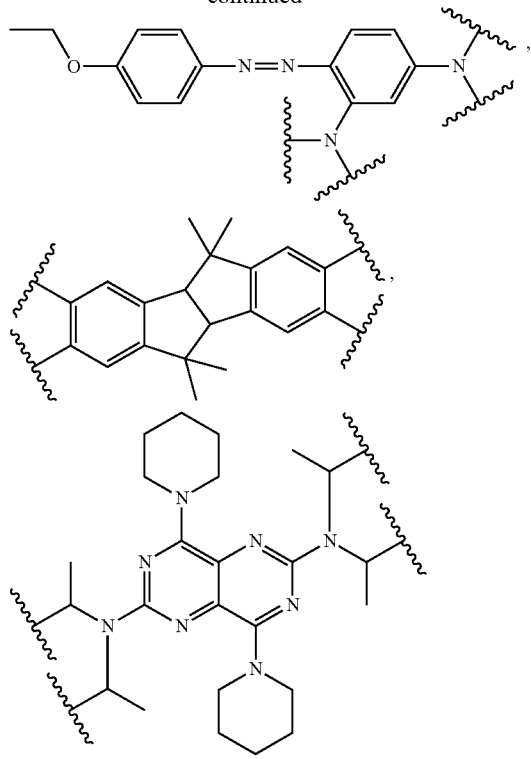

and the like; wherein, j is an integer from 2 to 20, preferably an even number from 2 to 12, more preferably 2, 4, 6 or 12, and most preferably 2. When a structure has isomers, $U_0$ can refer to any form of the isomers. For example, isomers of

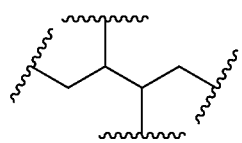 [SMILES: *CC(*)C(*)C*]

include but are not limited to the tetravalent carbon-skeletons of D-erythrose and D-threose. When constituting an initiator molecule for living anionic polymerization, $U_0$ is further preferably free of a carbonyl group, a secondary amino group and a nitro group.

Examples of $U_0$ also include but are not limited to the following tetravalent groups:

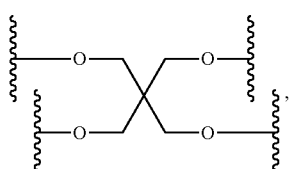

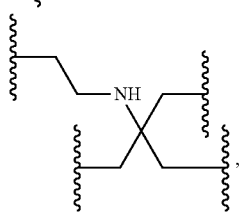

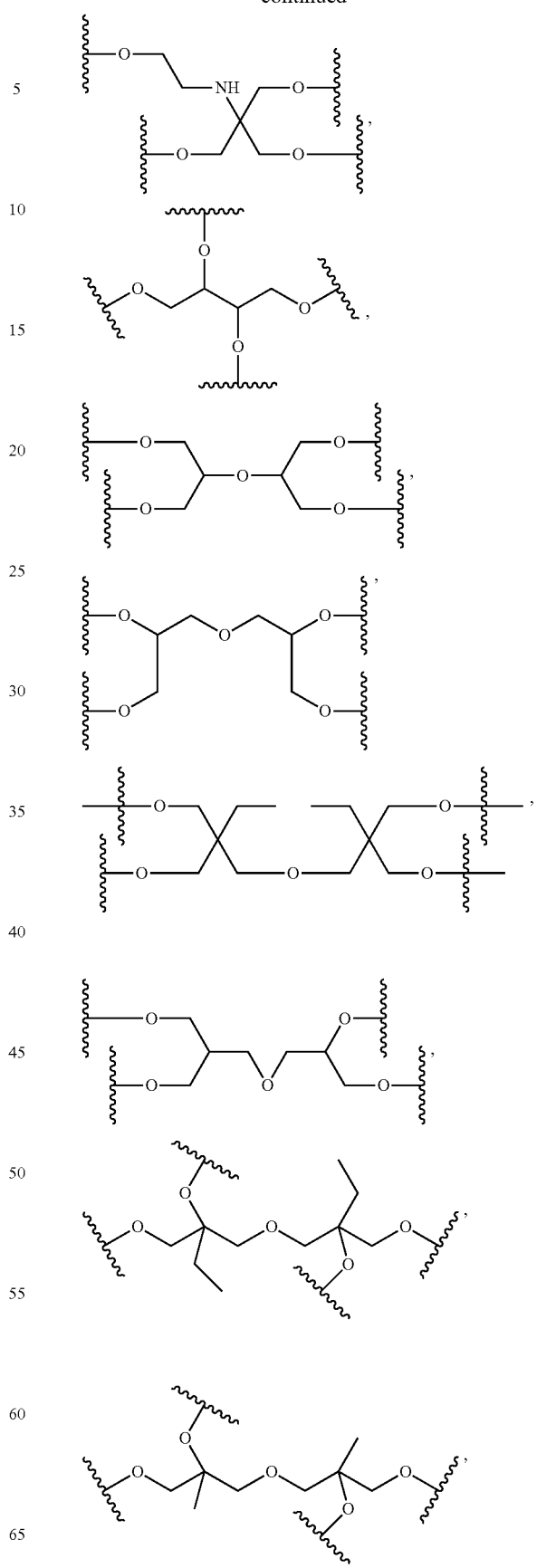

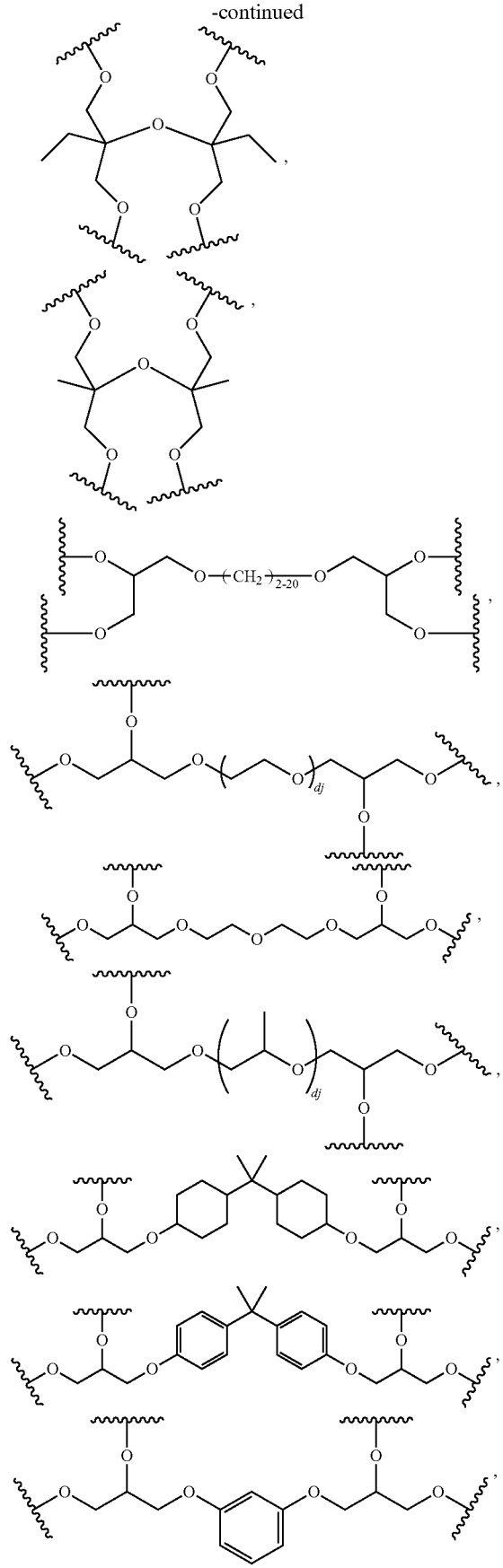
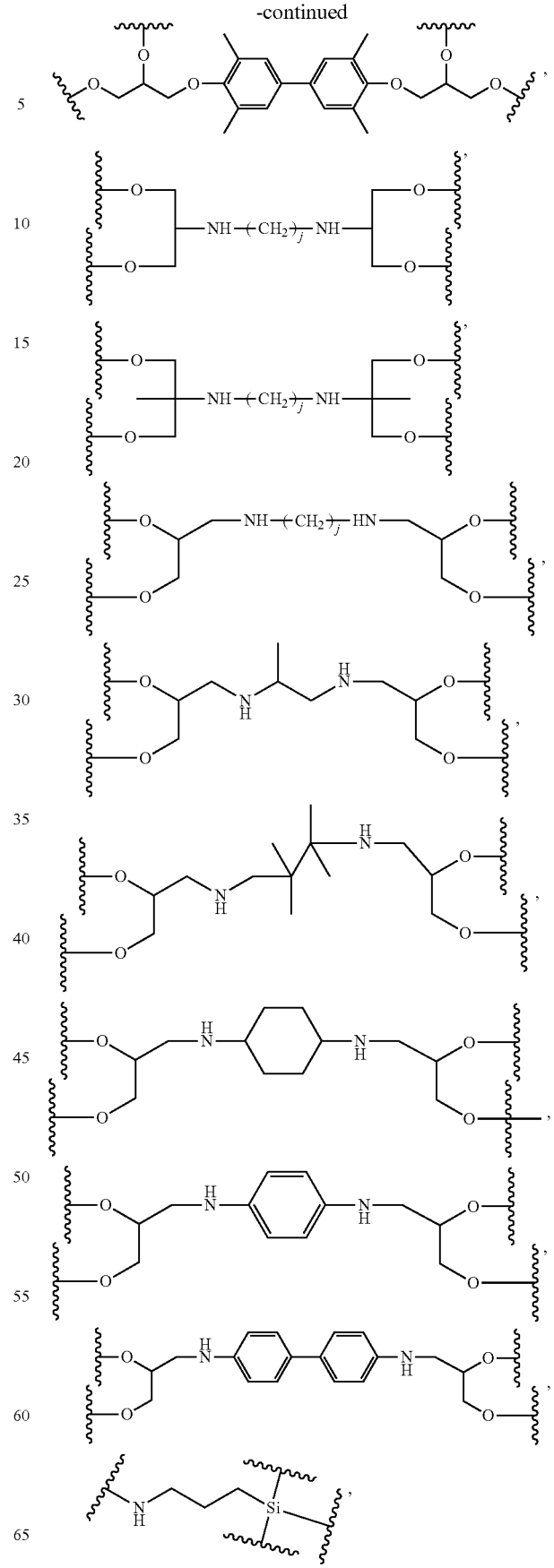

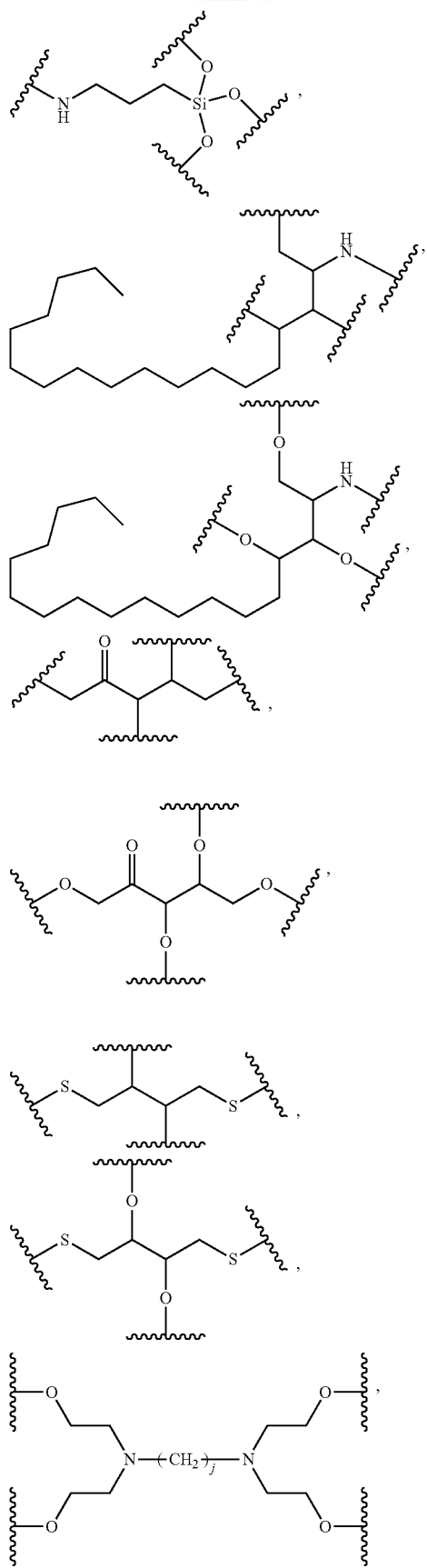
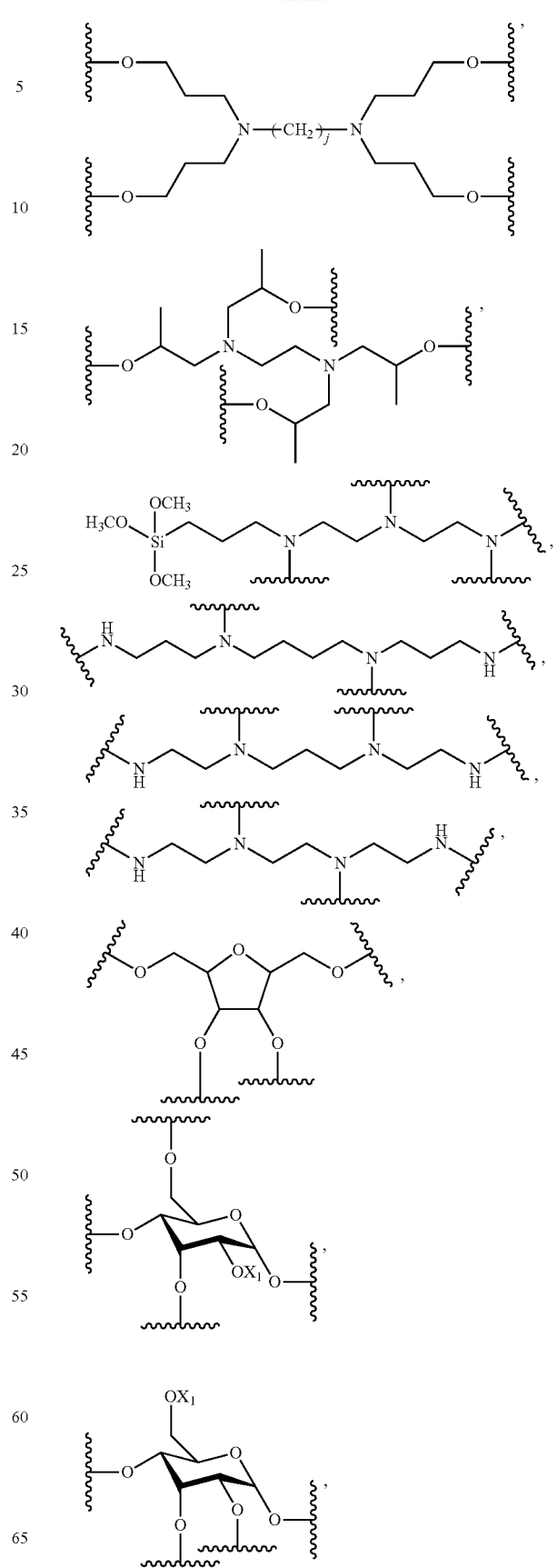

97
-continued
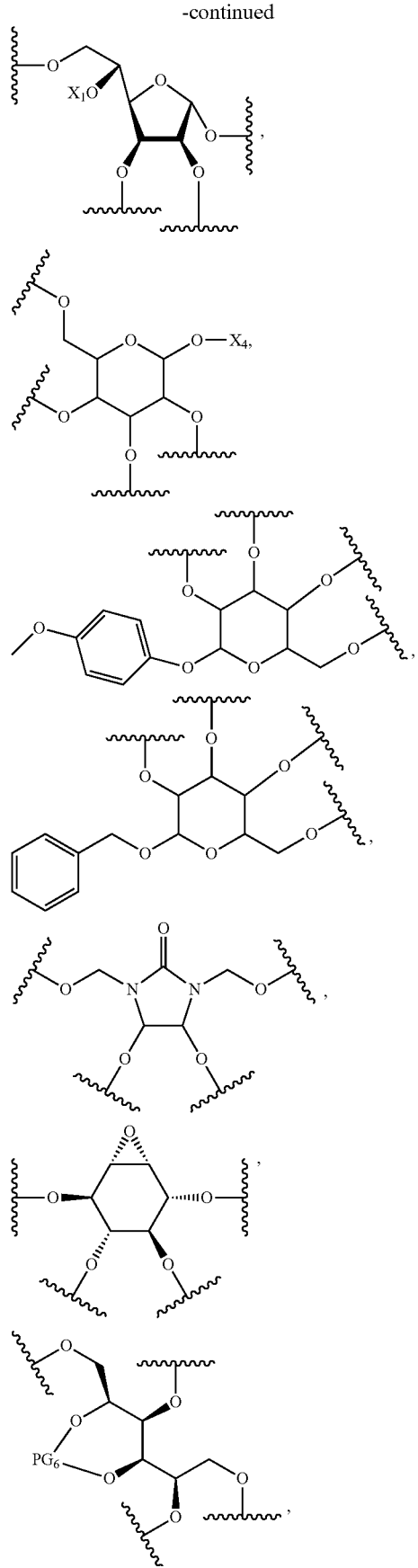
98
-continued
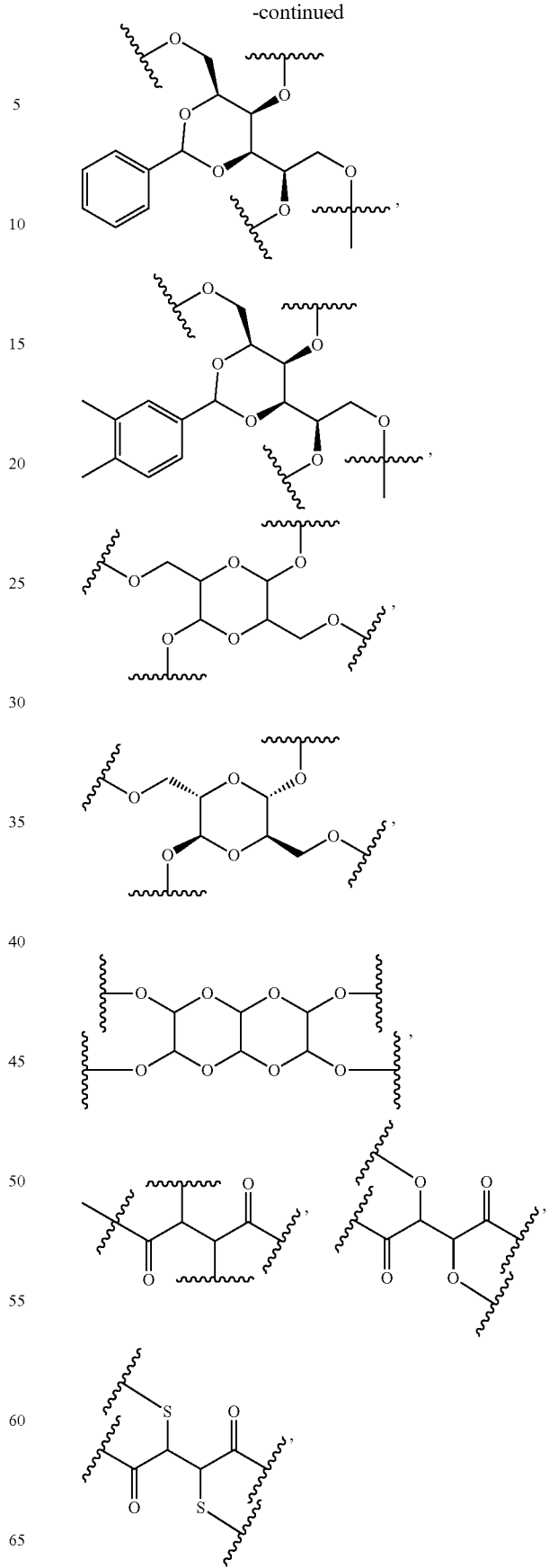

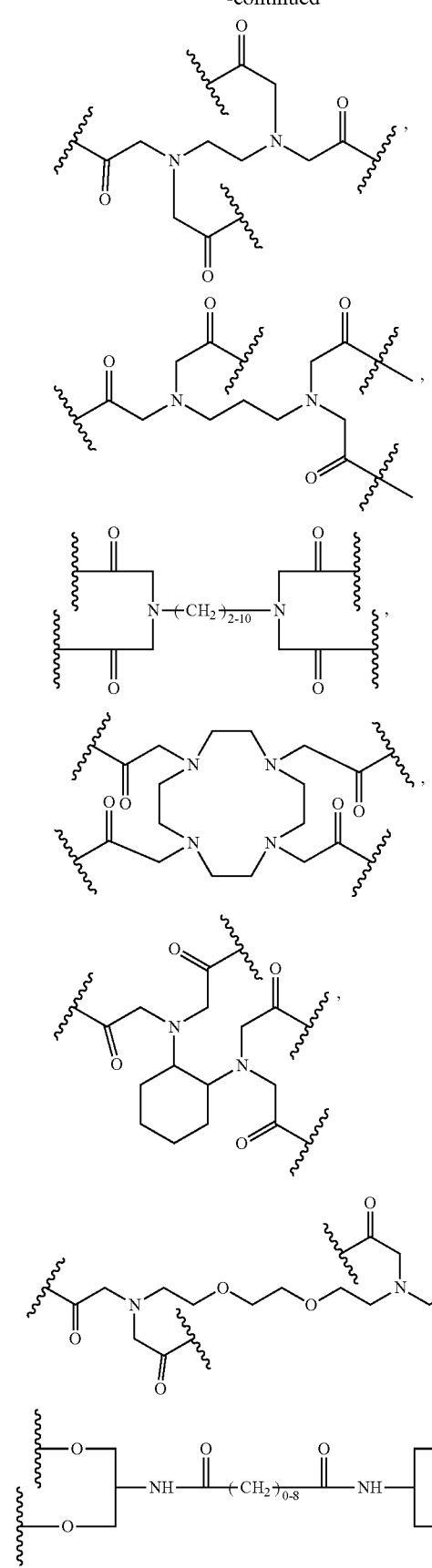
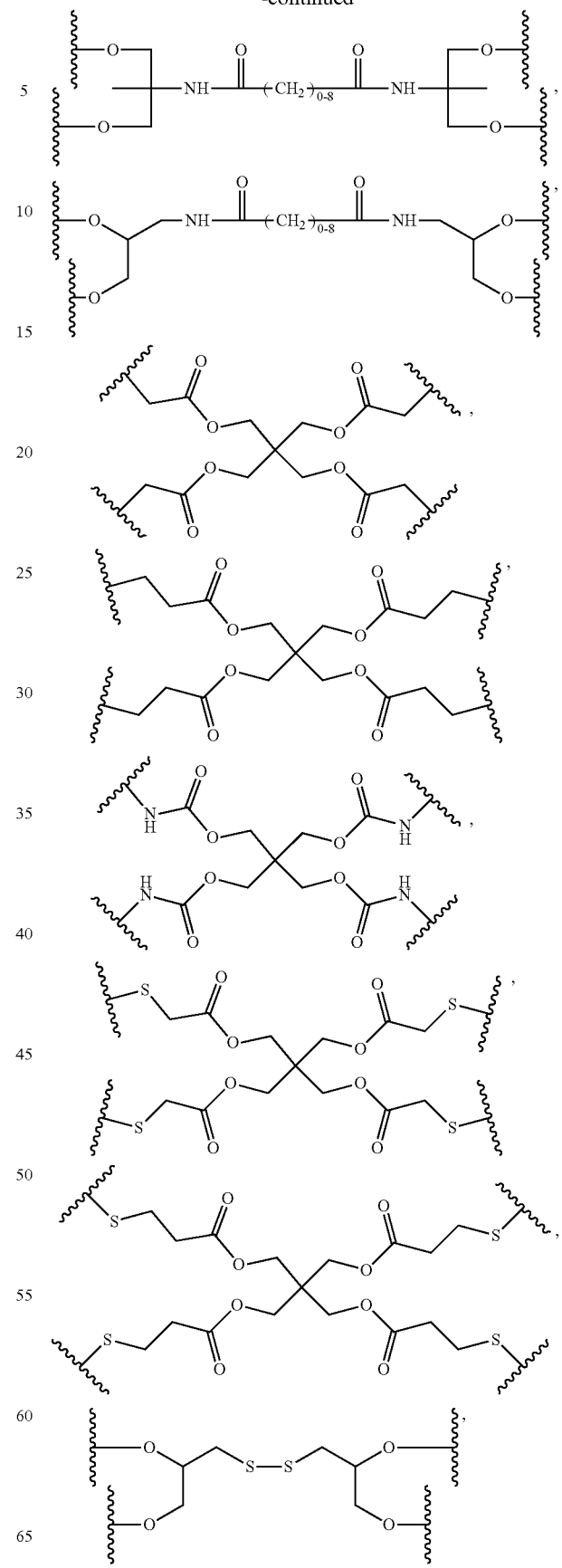

-continued

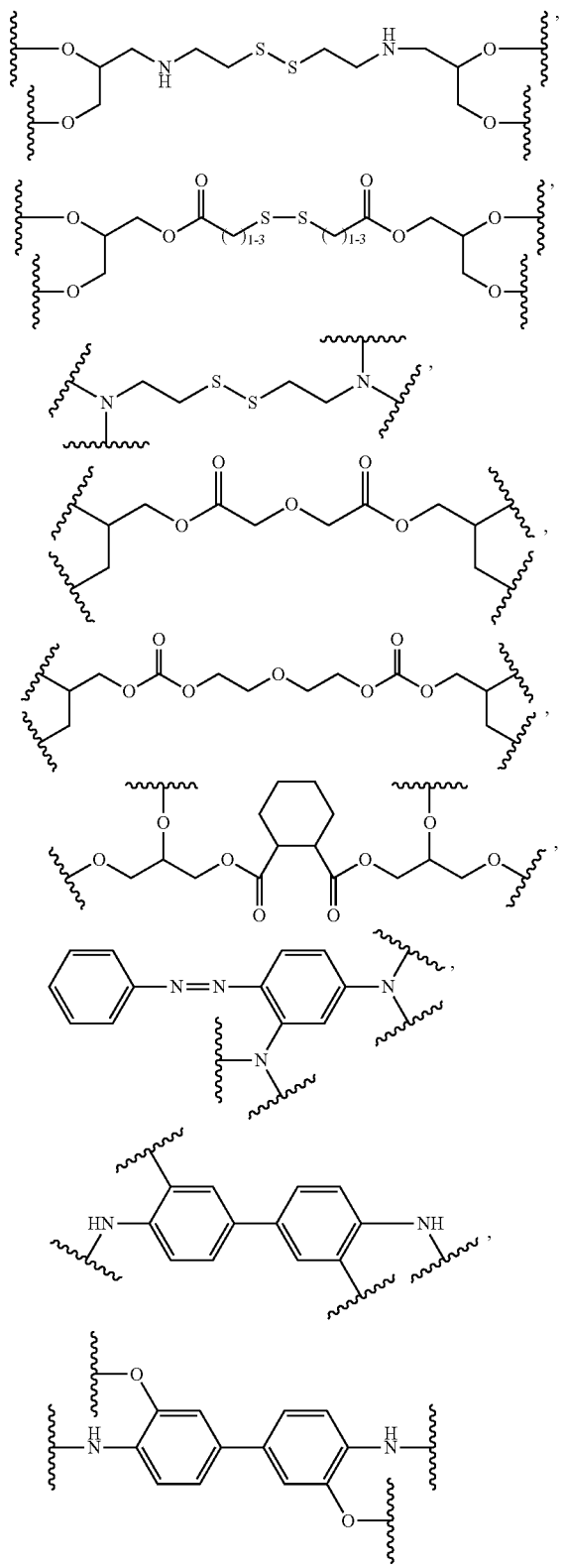

and the like. When constituting an initiator molecule for living anionic polymerization, $U_0$ is further preferably free of a carbonyl group, a secondary amino group and a nitro group. Wherein, the definition of j is the same as above. Wherein, dj represents the repeat-unit number of the oxy- alkylene unit, corresponding to a monodisperse or polydisperse structure, preferably corresponding to a monodisperse structure; the oxyalkylene is preferably oxyethylene; dj is preferably a value from 1 to 70; more preferably from 1 to 16, more preferably from 1 to 9, more preferably 1, 2, 3, 4, 5 or 6, more preferably 1 or 2, and most preferably 1.

Wherein, the definitions of $X_1$ and $X_4$ are the same as above, and no more repeated here.

Wherein, $PG_6$ is a dihydroxyl protecting group, and forms an acetal structure in a five- or six-membered ring together with two oxygen atoms. $PG_6$ can be a methylene group or a substituted methylene group. The group substituent of $PG_6$ can be a hydrocarbyl substituent or a heteroatom-containing substituent, and examples of $PG_6$ include but are not limited to the following groups: a methylene group, a 1-methylmethylene group, a 1,1-dimethylmethylene group, a 1,1-cyclopentylene group, a 1,1-cyclohexylene group, a 1-phenylmethylene group, a 3,4-dimethylphenylmethylene group and the like.

Specifically, $U_0$ is preferably one of the following structures:

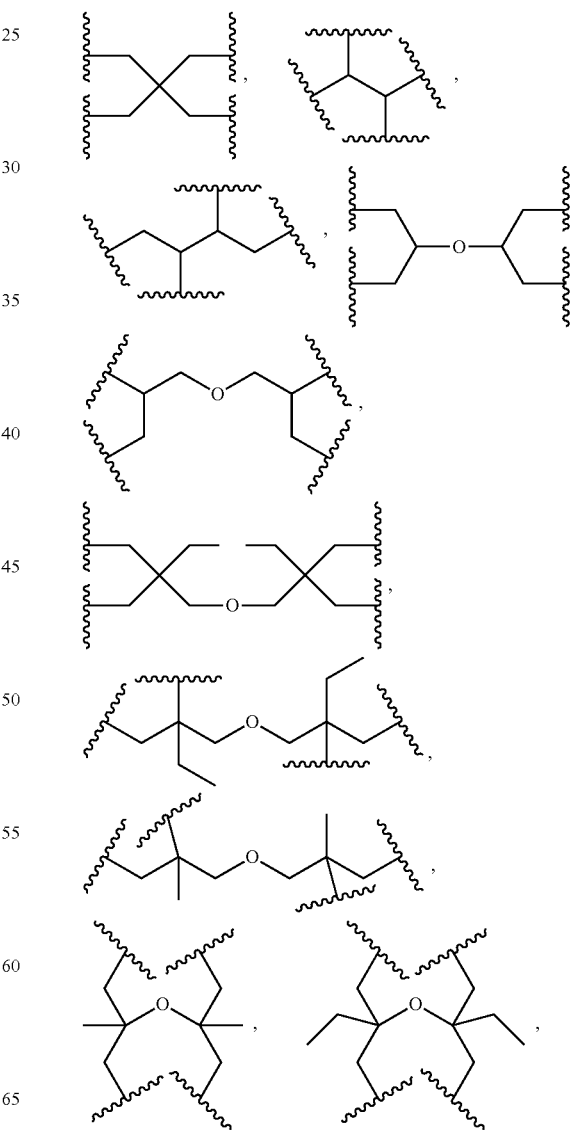

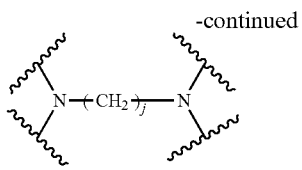

and the like, or can be a tetravalent structure formed by a bifunctional small molecule compound and two identical and suitable $E_i$ groups via a direct or indirect combination, wherein, the bifunctional small molecule compound can be but not limited to a compound with two hydroxyl groups (a diol), a compound with two amino groups (a diamine), a compound with two thiol groups (a dithiol), a compound with two carboxyl groups (a dicarboxylic acid), a compound with two isocyanato groups (a diisocyanate), a compound with two sulfonate groups (a disulfonate), a compound with two halide groups (a dihalide), a compound with two azido groups (a diazide), a compound with two acylhalide groups (a diacyl halide), a compound with two hydrazide groups (a dihydrazide), a compound with two aldehyde groups (a dialdehyde), a compound with two dichloroformate groups, a compound with two maleimido groups (a dimaleimide), a compound with two succinimidyl active ester groups (a disuccinimidyl active diester), a compound with two cyano groups (a dicyanide), a compound with two alkynyl groups (a dialkyne), a compound with two alkenyl groups (a dialkene), a compound with two aldoxime groups (a dialdoxime) and the like. Wherein, the definition of j is the same as above. The bifunctional small molecule compound is preferably a bifunctionalized derivative of an alkane or an aromatic hydrocarbon, preferably a bifunctionalized form of an alkane, benzene, biphenyl, an alkyl-substituted benzene or an alkyl-substituted biphenyl, and more preferably a bifunctionalized form of a $C_{2-20}$ alkane; the diamine is preferably derived from a $C_{2-20}$ hydrocarbon group, and is more preferably $H_2N(CH_2)_jNH_2$; the diol can be a diol derived from a $C_{2-20}$ hydrocarbon group or an oligomer or polymer of small molecule diols, preferably a diol monomer. When the diol is the oligomer or polymer of a small molecule diol, it is preferably an oligomer or polymer of ethanediol (that is ethylene glycol), and can be polydisperse or monodisperse, preferably monodisperse. With respect to the oligomer or polymer of ethanediol, for a monodisperse structure, the EO-unit number $j_2$ can be from 2 to 70, preferably from 2 to 50, more preferably from 2 to 32, more preferably from 2 to 16, more preferably from 2 to 6, and more preferably 2, 3 or 4. The spacer groups used for indirect combinations are preferably above-described $L_{10}$ groups, and the number of $L_{10}$ can be one or more. When two or two more $L_{10}$ spacer groups exist, the $L_{10}$ groups can be the same or different.

U is further preferably a structure formed by terminating any above-said $U_0$ structure with four identical or different divalent linking groups, wherein, the divalent linking groups are selected from an oxy group, a thioxy group, a secondary amino group, a divalent t-amino group and a carbonyl group; U is further preferably a structure formed by terminating any above-said $U_0$ structure with four identical or different divalent linking groups selected from an oxy group, a thioxy group and a divalent t-amino group. Examples of U formed by being terminated with oxy groups are as follows:

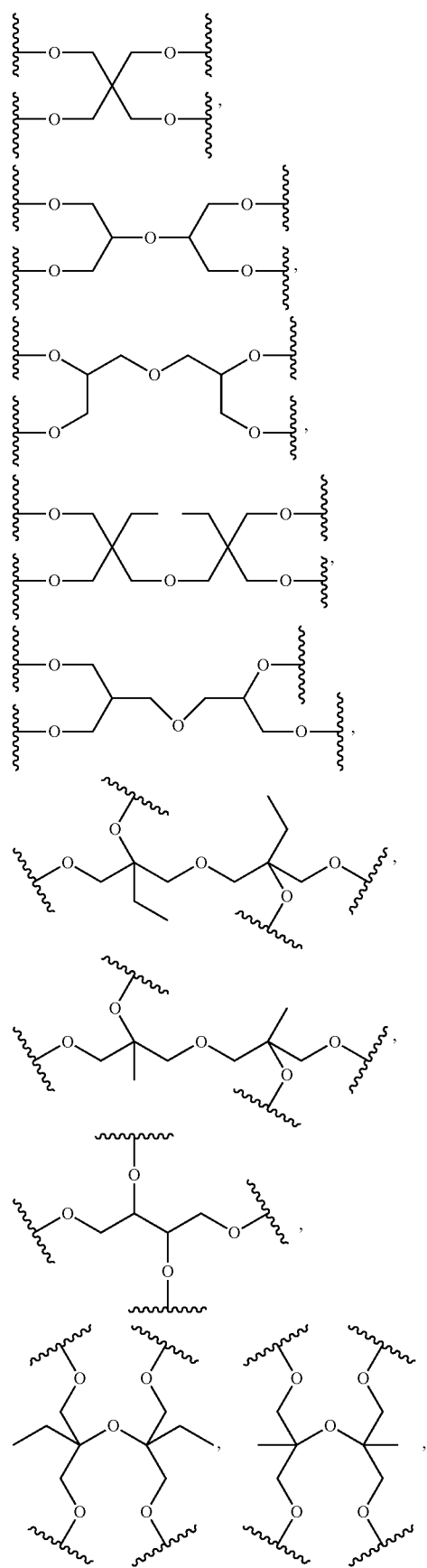

-continued

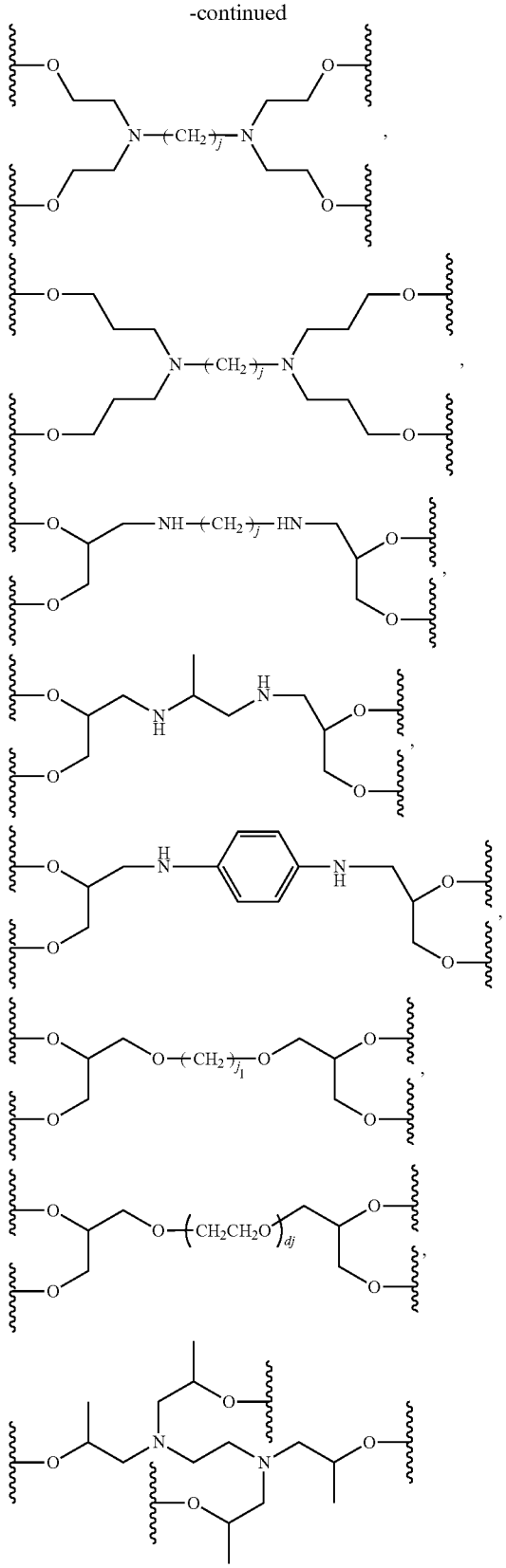

and the like; wherein, the definitions of j and dj are the same as above. Wherein, $j_1$ is an integer from 2 to 20, preferably from 2 to 12, more preferably 2 to 6, and most preferably 2.

Examples of U formed by being terminated with mercapto groups are as follows:

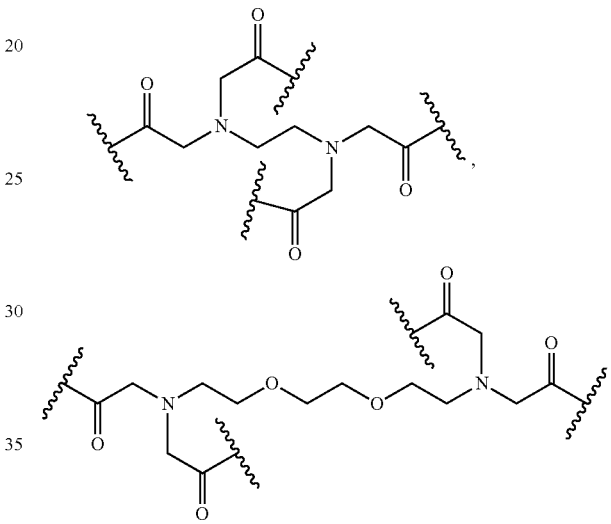

and the like.

Examples of U formed b being terminated with carbonyl groups are as follows:

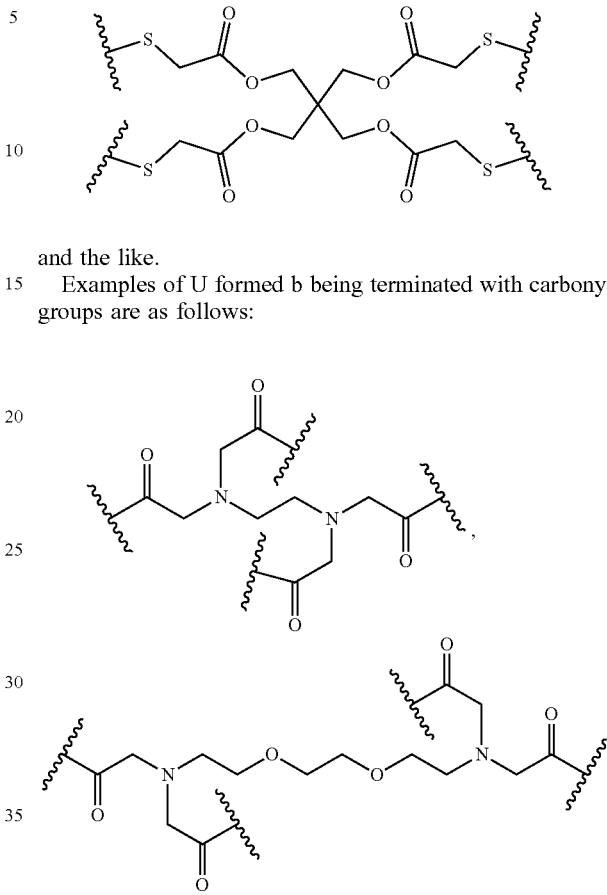

and the like.

U can also be a structure formed by terminating any above-said $U_0$ structure with four identical divalent skeletons of amino acids or amino acid derivatives; the skeletons of amino acids or amino acid derivatives are preferably derived from neutral amino acids or ω-amino acids; the neutral amino acids include but are not limited to glycine, alanine, valine, leucine, isoleucine, phenylalanine, proline, sarcosine, β-alanine and the like. The ω-amino acid is preferably $H_2N(CH_2)_{j_1}COOH$, wherein, the definition of $j_1$ is the same as above.

1.1.5. Examples of the Combination of U and E

In the general formula (1), the octavalent group CORE

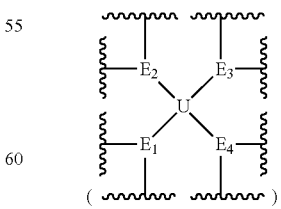

can be directly combined by one above-described tetravalent group $U_0$ and four above-described trivalent groups $E_0$, or be indirectly combined via optionally suitable stable or degradable divalent spacer groups. The divalent spacer groups include but are not limited to stable divalent linkages and degradable divalent linkages described and listed in the documents CN104530413A, CN104530415A and CN104530417A; take CN104530417A as an example, corresponding to paragraphs from [0613] to [0725]. The divalent spacer groups are preferably selected from $L_{10}$ groups. When as a moiety of initiator molecules for living anionic polymerization, the octaol initiator $CORE_8(OH)_8$ does not contain groups that are unstable under anionic polymerization conditions. When as a moiety of initiator molecules for living anionic polymerization, the covalent bonds linking U and $E_i$ (i=1, 2, 3, 4) in $CORE_8$ are preferably an oxy group, a thioxy group or a divalent t-amino group.

According to different combinations of the branching center of U and branching centers of $E_i$, the branching centers within the octavalent central group $CORE_8$ can be selected from but not limited to the following structures: a tetravalent carbon-atom center, a tetravalent silicon-atom center, a trivalent carbon-atom center, a trivalent nitrogen-atom center, a trivalent silicon-atom center without active hydrogen atom (a trivalent active-hydrogen-free silicon-atom center), the trivalent cyclic core structure $CC_3$, the tetravalent cyclic core structure $CC_4$, and trivalent groups formed by substituting the hydrogen atom of the above-said branching centers with a monovalent end-group having no active hydrogen atom, wherein, the monovalent end-group can be selected from the group consisting of a hydrocarbyl group, an alkoxy group, an alkylthio group, a dialkylamino group, a trihydrocarbylsilyl group and the like. The octavalent central group $CORE_8$ preferably contains one tetravalent core structure and four trivalent core structures, or contains six trivalent core structures. The preferable structures of the trivalent cyclic core structure $CC_3$ and the tetravalent cyclic core structure $CC_4$ are the same as above-described. The branching centers within $CORE_8$ are further preferably selected from the group consisting of a tetravalent carbon-atom center, a trivalent carbon-atom center, a trivalent nitrogen-atom center, a trivalent silicon-atom center without active hydrogen atom, a trivalent fluorene core, a trivalent carbazole core, a trivalent saturated six-membered carbon ring, a trivalent phenyl group, a trivalent naphthyl group, a trivalent azaphenyl group (e.g., pyridine, pyrazine, pyrimidine, etc.), a trivalent five-membered oxa-ring, a trivalent quinolyl group, a tetravalent five-membered oxa-ring, a tetravalent D-furanose ring, a tetravalent D-pyranose ring, a tetravalent saturated six-membered dioxa-ring (e.g., the ring skeleton of glyceraldehyde dimer), a tetravalent skeleton of triethanedial dihydrate, a tetravalent six-membered ring of D-sorbitol skeleton with 2- and 4-hydroxyl groups being protected and the like.

According to different combinations of heteroatom-containing linking groups, the species of heteroatom-containing linking groups in $CORE_8$ can be one or more, and the quantity of each species is not particularly limited, preferably including but not limited to suitable combinations of heteroatom-containing linking groups selected from the following structures: an oxy group, a thioxy group, a trivalent t-amino group, a divalent t-amino group, a secondary amino group, a divalent silyl group without active hydrogen atom and a trivalent silyl group without active hydrogen atom. In $CORE_8$, monovalent end-groups containing heteroatom but no active hydrogen atom, such as an alkoxy group, an alkylthio group, a dialkylamino group, a trihydrocarbylsilyl group or the like, can be present, and herein $CORE_8(O-)_8$ is stable.

According to the difference in degradability, $CORE_8$ $(O-)_8$ can only include stable linking groups, or contain one or more degradable linking groups.

One preferable embodiment of $CORE_8$ is that $CORE_8$ contains no $O(CH_2CH_2O)_{j3}$ segment (neither monodisperse segments nor polydisperse segments). Wherein, $j_3$ is preferably greater than or equal to 10 ($j_3 \geq 10$), further preferably greater than or equal to 3 ($j_3 \geq 3$), and further preferably greater than or equal to 2 ($j_3 \geq 2$). When the EO-unit number is less than $j_3$, such a moiety is preferably monodisperse.

Specifically, for example, the octavalent group CORE can be combined by a group selected from

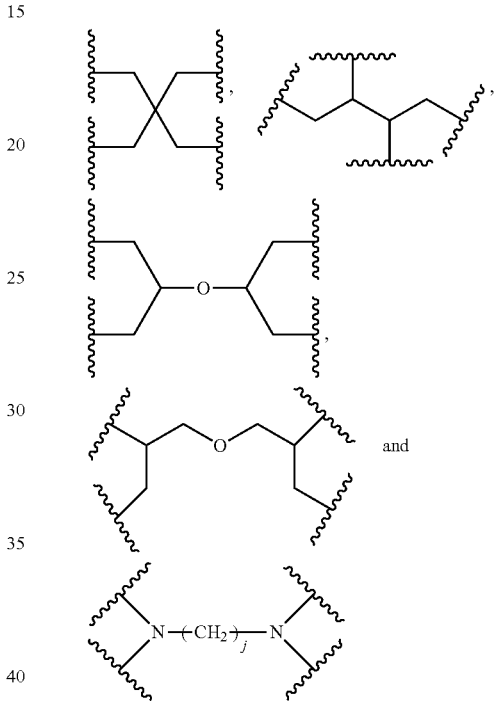

group selected from

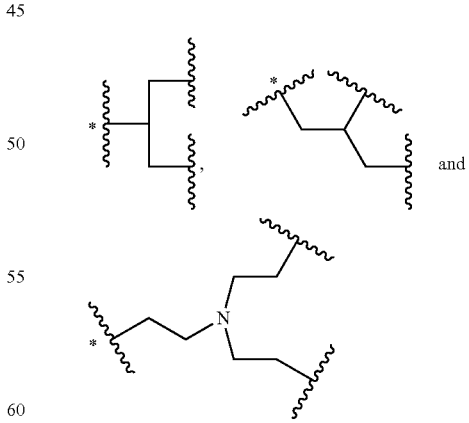

via stable or degradable divalent linking groups. Examples of CORE formed via linking groups selected from an oxy group, a thioxy group, an amino group, an ester bond, an amide bond and a urethane bond include but are not limited to the following octavalent structures:

109
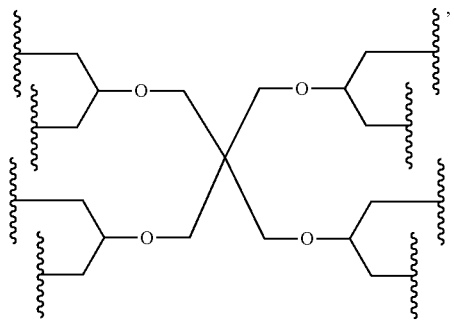
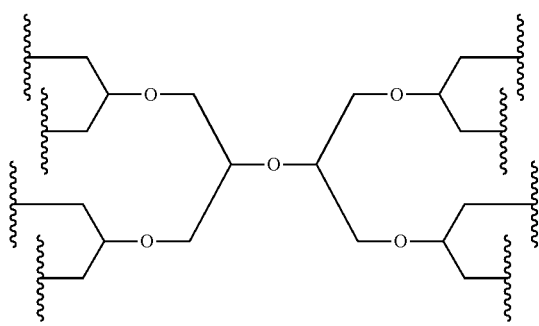
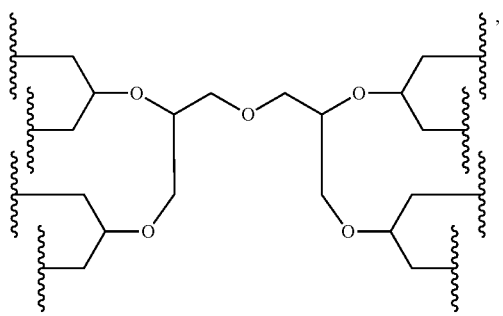
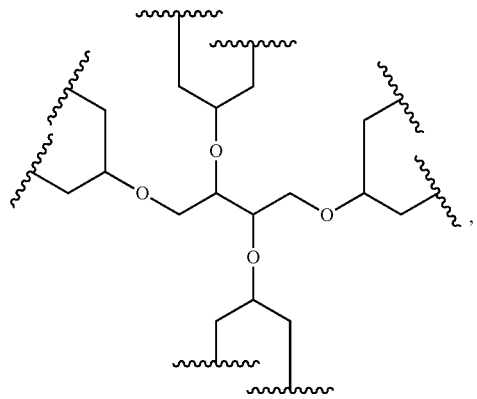
110
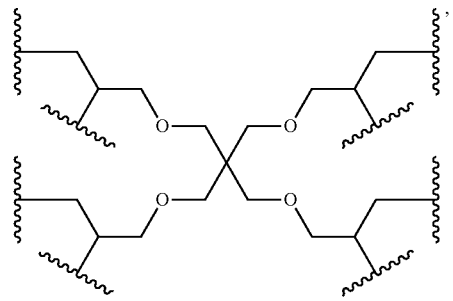
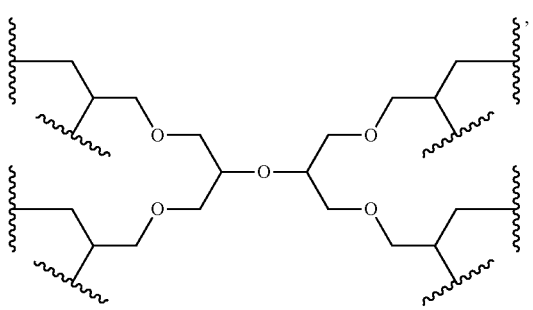
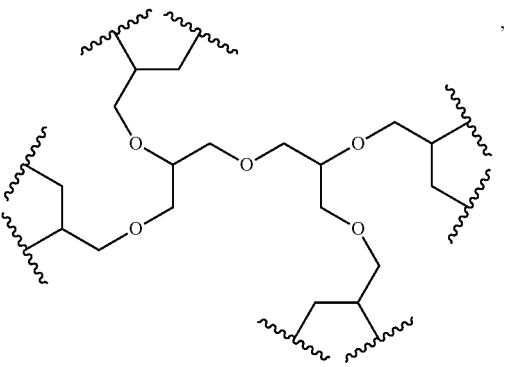
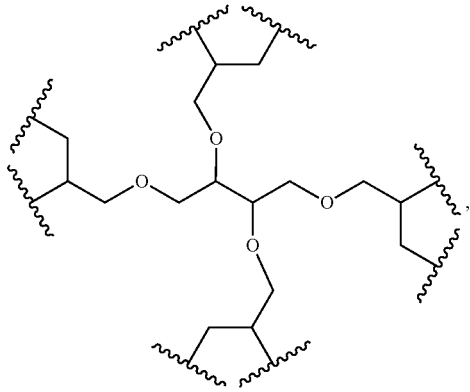

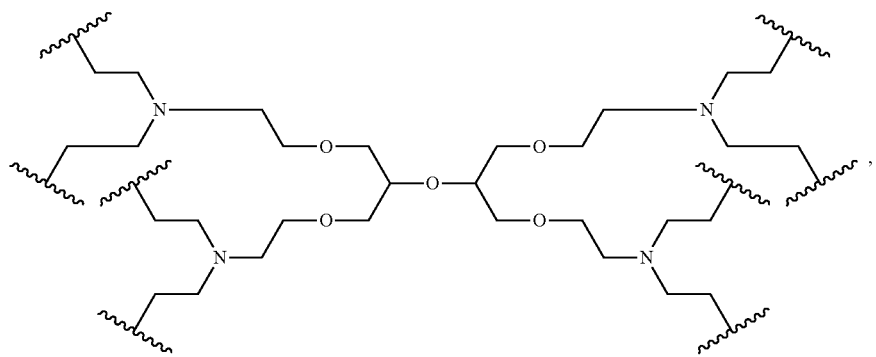,
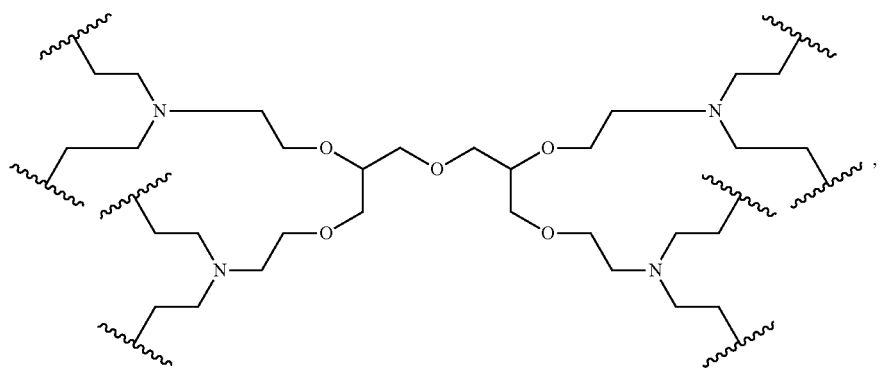,
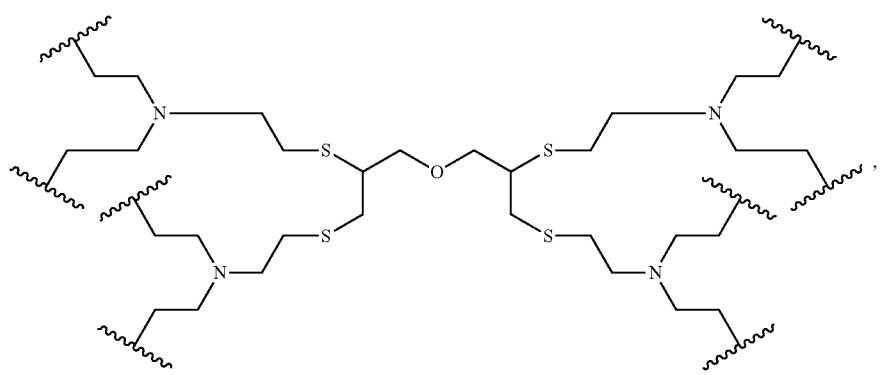,
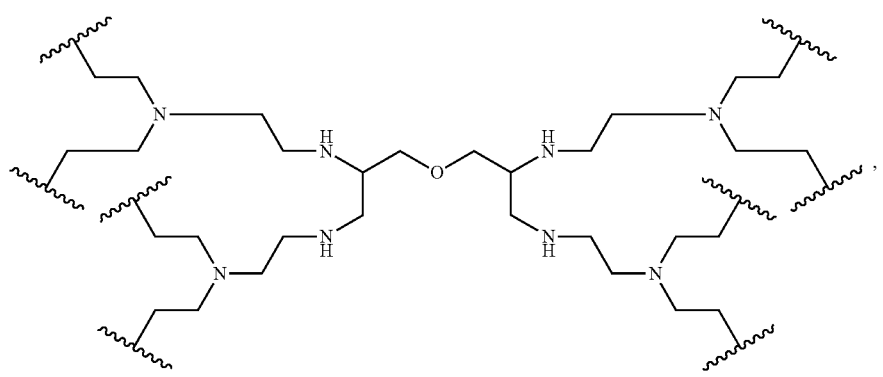,

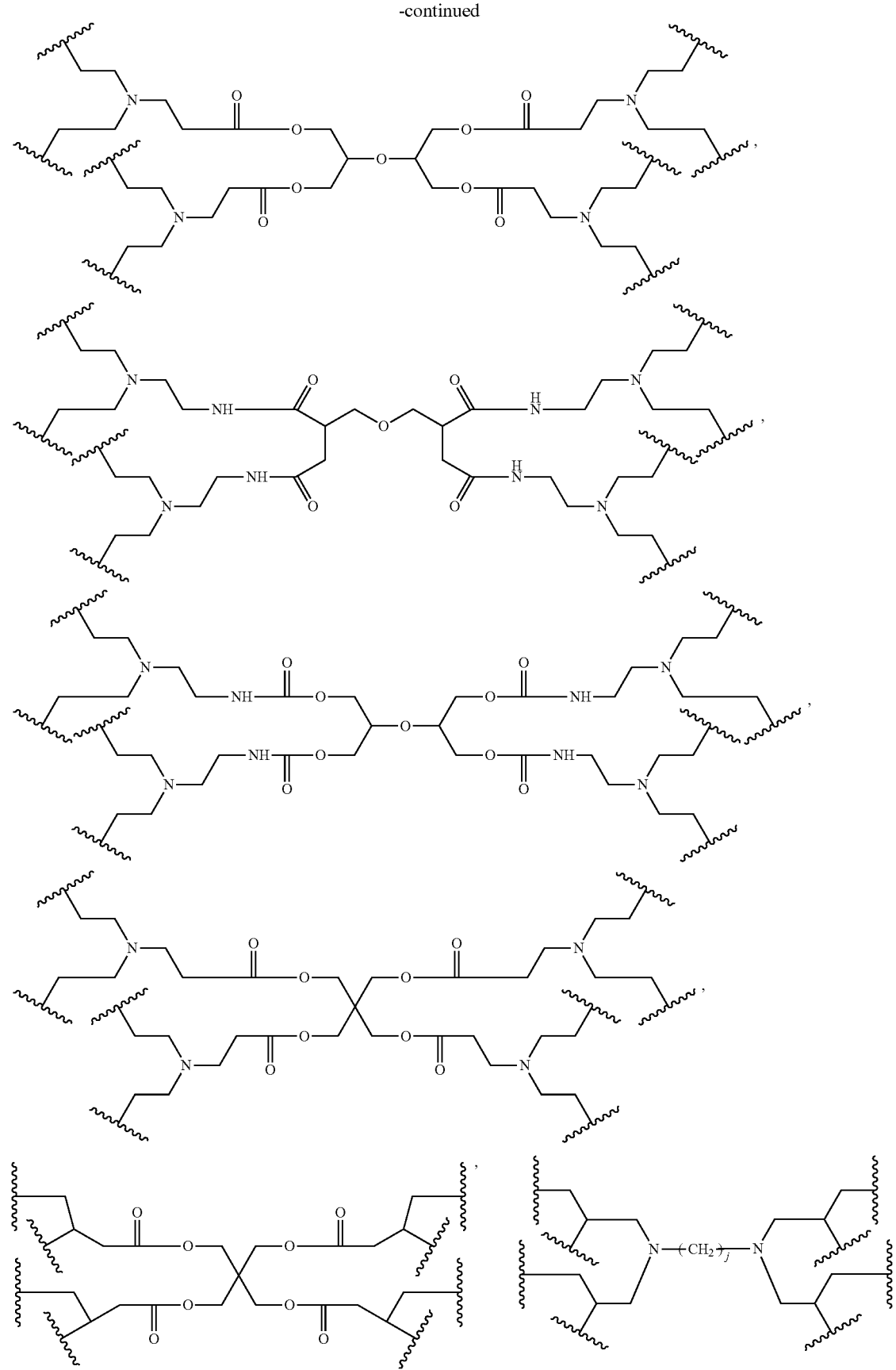

and the like. For example, U and $E_i$ (i=1, 2, 3, 4) can also be combined via some special heteroatom-containing linking groups selected from the group consisting of a urea bond, a carbonate bond, a thioester bond, an acetal linkage, a thioacetal linkage, an oxime bond, a dithioester bond, a trithioester bond and the like. Examples of the octavalent group CORE also include but are not limited to the following groups:

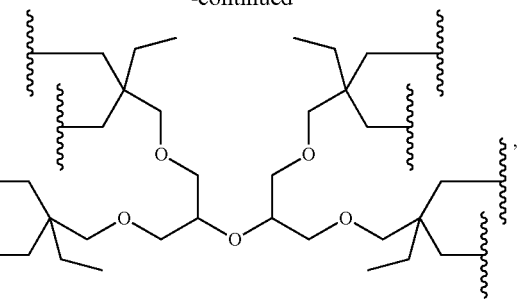

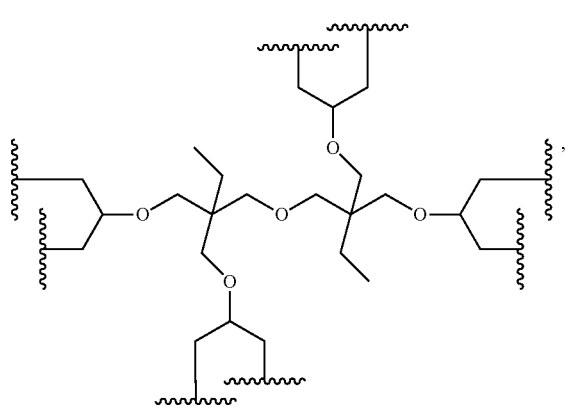

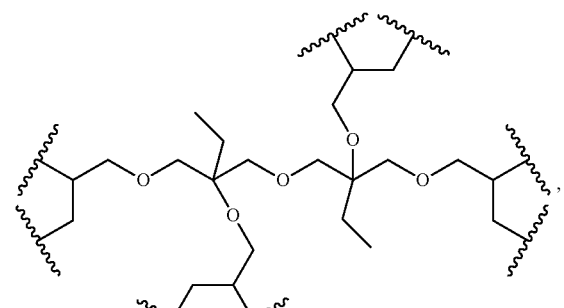

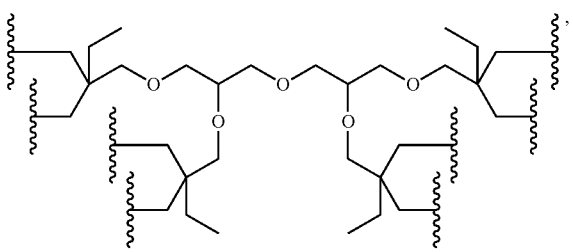

For example, the octavalent group CORE can also e combined by U and trivalent amino acid skeletons, herein, such a structure does not participate in constituting an initiator molecule for living anionic polymerization; examples of CORE formed by using lysine skeletons, aspartic acid skeletons or glutamic acid skeletons are as follows:

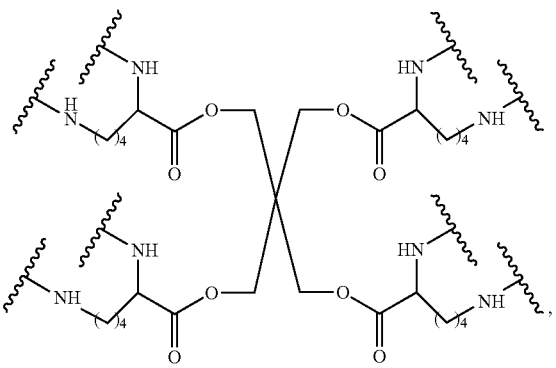
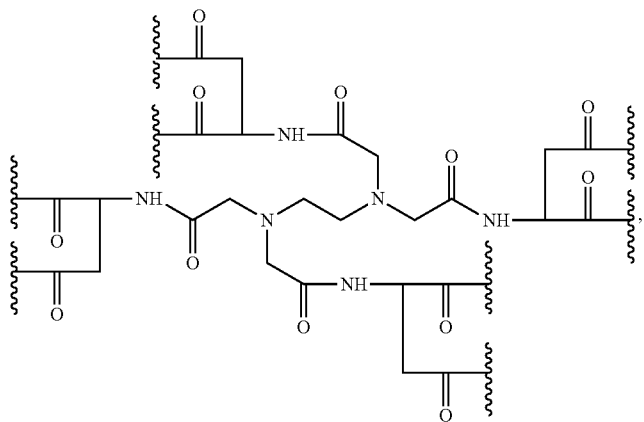
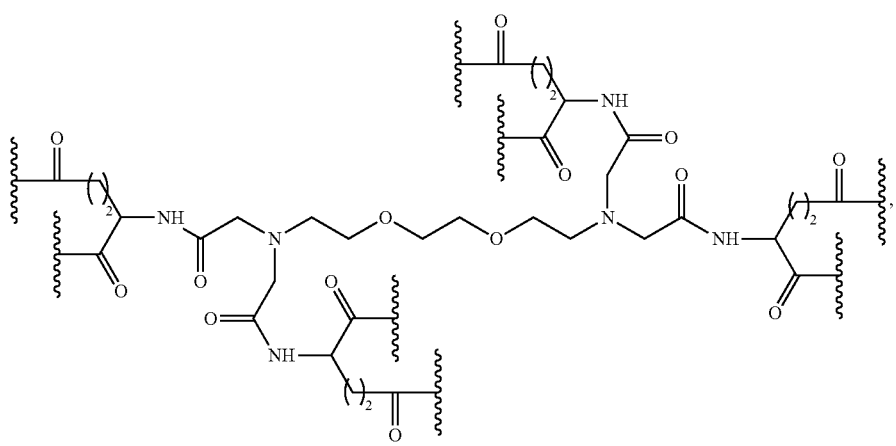
etc.
For example, the octavalent group CORE can also be combined by any above-said $U_0$ group and any above-said $E_0$ groups via suitable divalent amino acid skeletons. One example of the octavalent group is

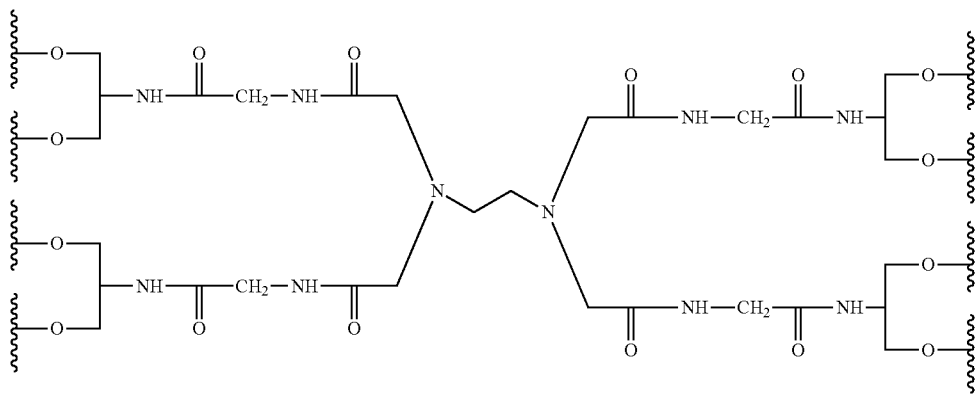 [SMILES: *OCC(CO*)NC(=O)CNC(=O)CN(CCN(CC(=O)NCC(=O)NC(CO*)CO*)CC(=O)NCC(=O)NC(CO*)CO*)CC(=O)NCC(=O)NC(CO*)CO*]

which is combined by

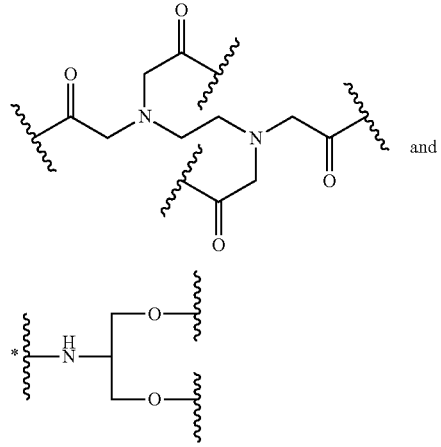

via glycine skeletons.

One preferable embodiment for the octavalent group $CORE_8(O—)_8$ is that $L_{11}$, $L_{12}$, $L_{21}$, $L_{22}$, $L_{31}$, $L_{32}$, $L_{41}$ and $L_{42}$ are all absent (wherein, $CORE=CORE_8$); further preferable embodiments are the following combinations of U and $E_t(E_1=E_2=E_3=E_4)$ in Group A and Group B. Typical examples can refer to the general formulas (6) to (35).

Group A: wherein, U is one of the following structures:

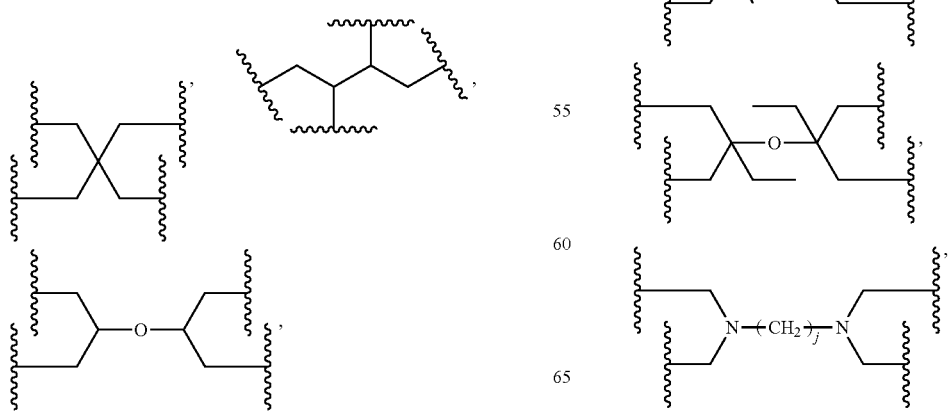

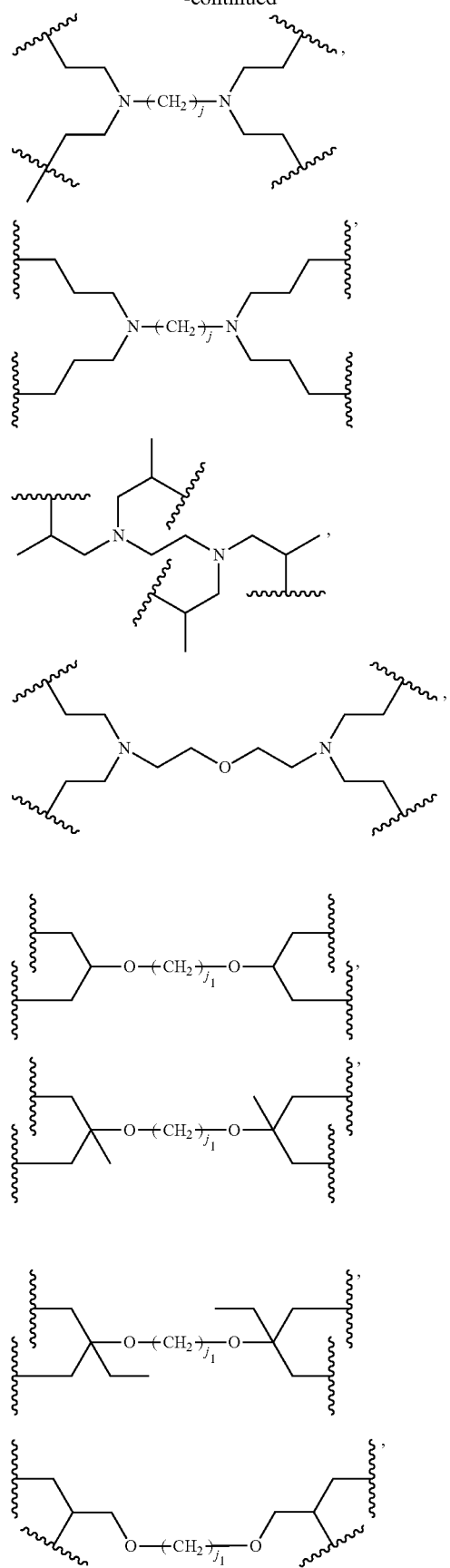
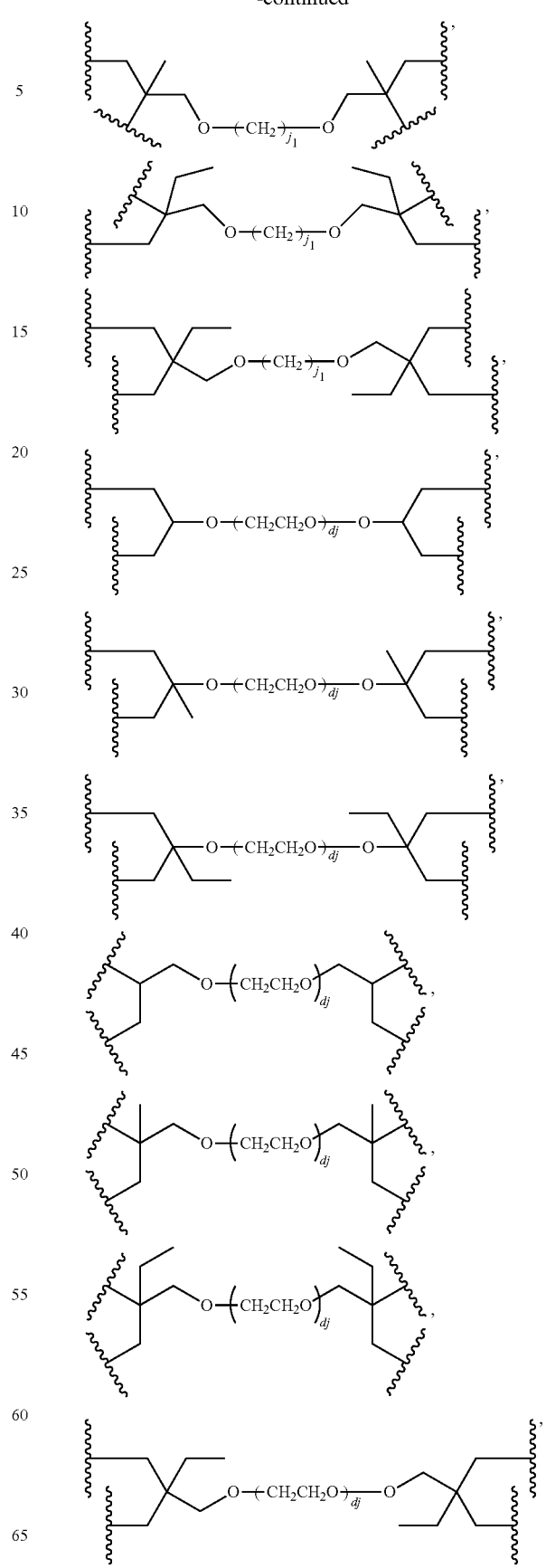

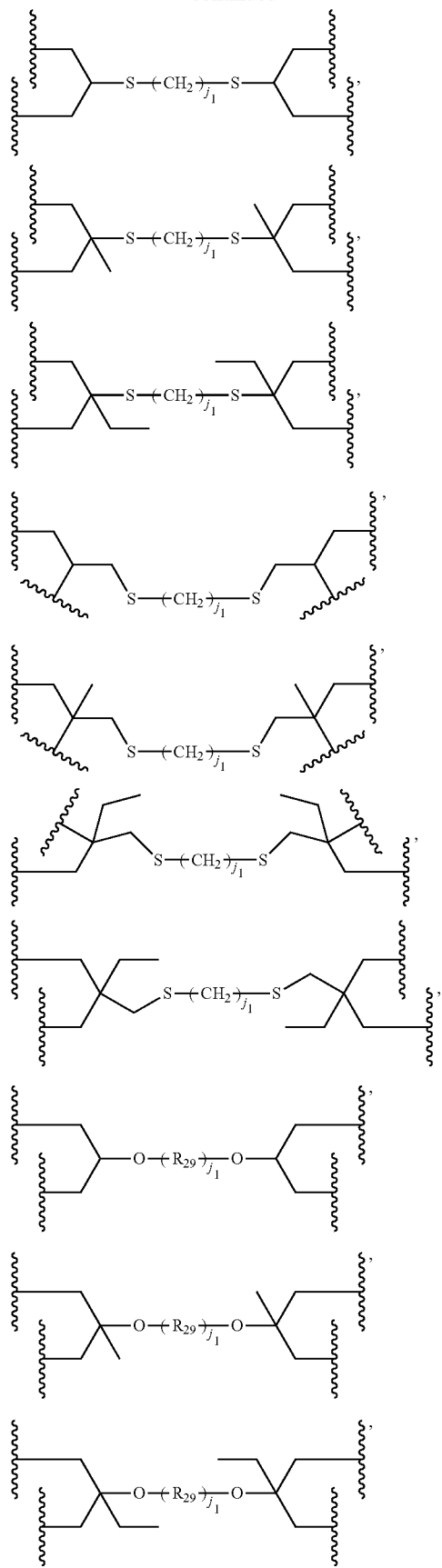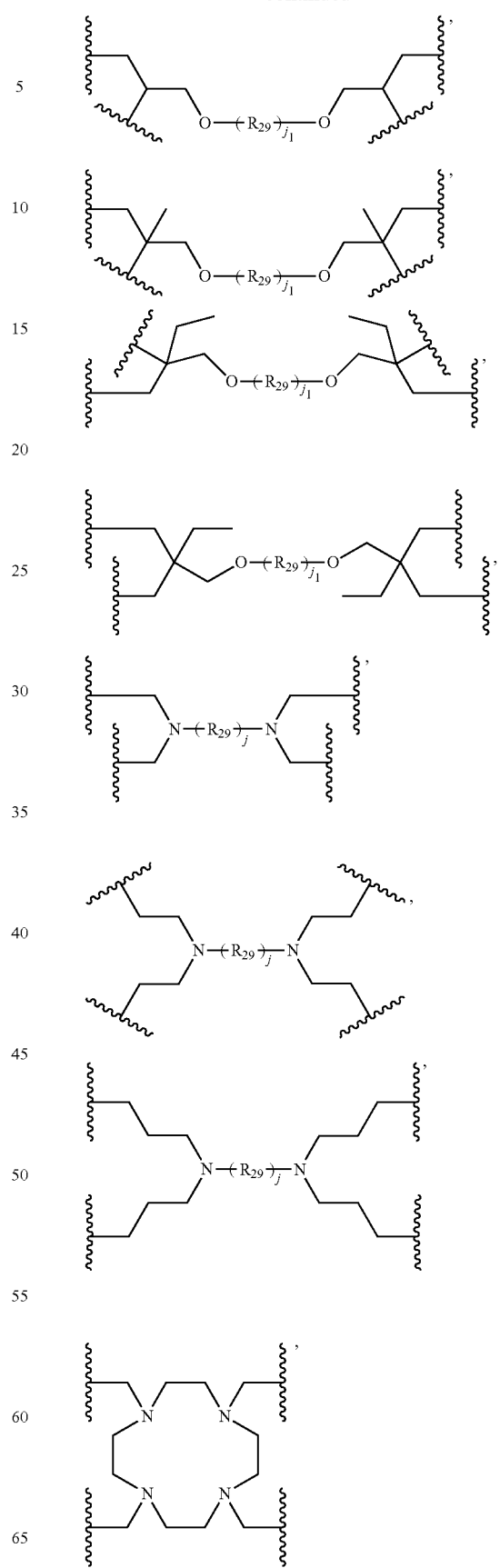

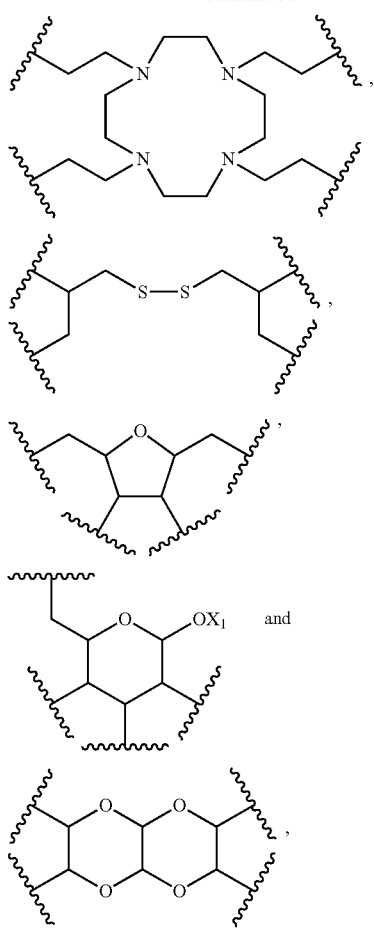
and $E_i(E_1=E_2=E_3=E_4)$ is one of the following structures:
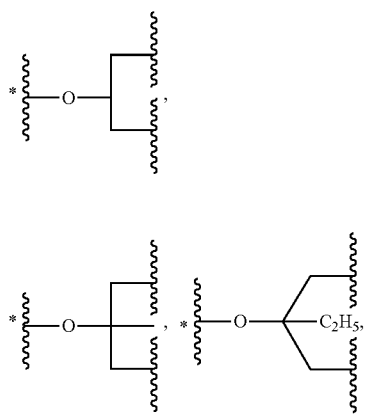
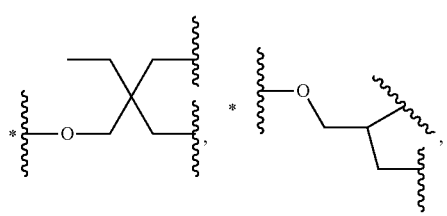
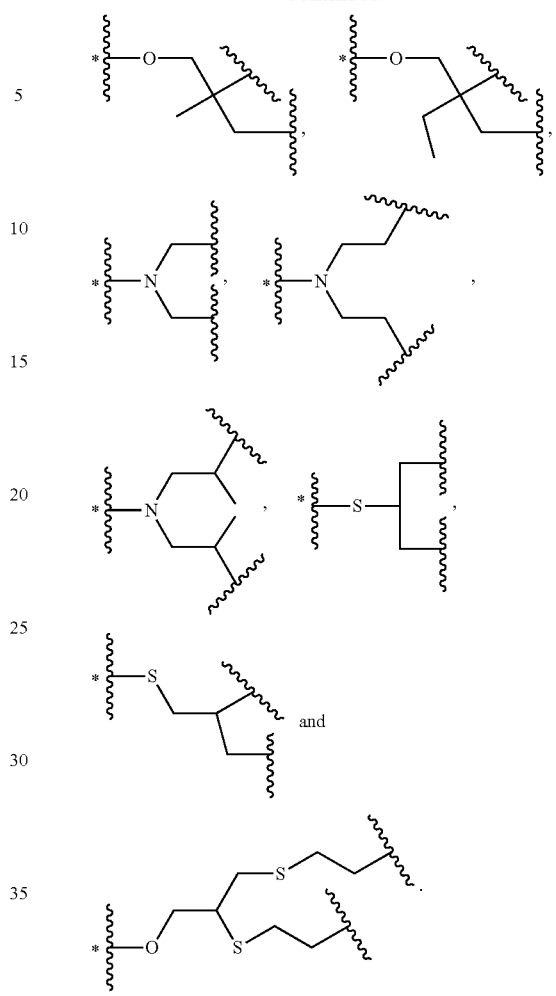
Group B: U is
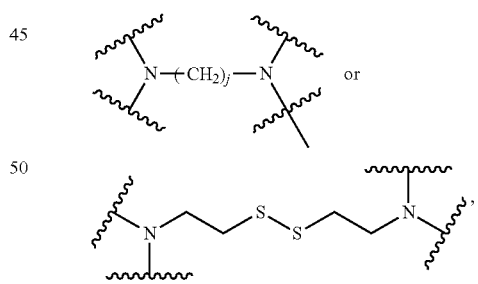
and $E_i(E_1=E_2=E_3=E_4)$ is one of the following structures:
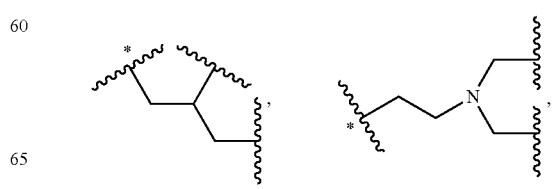

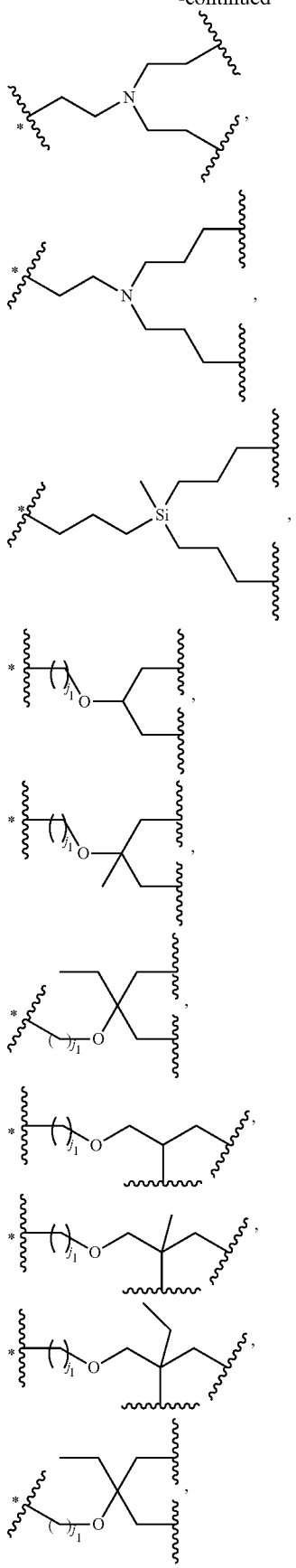

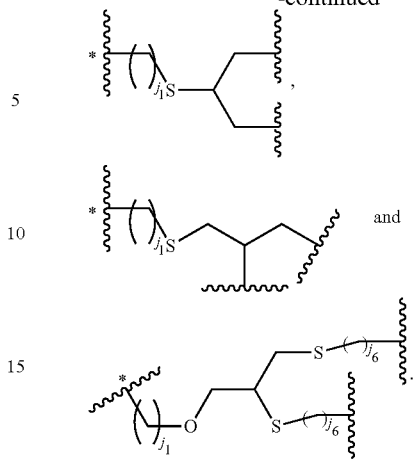

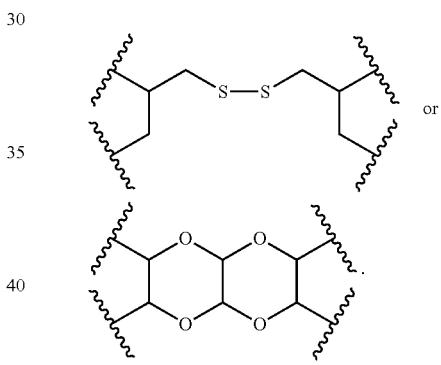

Wherein, the definitions of j, $j_1$, dj and $R_{29}$ are the same as above. The definition of integer $j_5$ is the same as $j_1$; in one molecule, $j_5$ and $j_1$ are each independently and can be the same or different.

The octaol $CORE_8(OH)_8$ containing a $CORE_8$ group from Group A or Group B can be used as an initiator for living anionic polymerization. When $CORE_8(O\text{—})_8$ is required to be stable, U is not

1.1.6 Functional Groups (F)

1.1.6.1 the Definition of $R_{01}$, the Functional End-Group

In the general formula (1), $R_{01}$ is a functional end-group capable of interreacting with a bio-related substance. The interreactions between $R_{01}$ and the bio-related substance include but are not limited to formation of covalent bonds, formation of hydrogen bonding, fluorescent response and targeting effect.

$R_{01}$ can be a functional group capable of generating a covalent bond, a dynamic covalent bond, dihydrogen-bonding, multiple hydrogen bonding, therapeutic targeting binding or photoreactive response.

$R_{01}$ is selected from a reactive group, a variant form of a reactive group, a therapeutic targeting functional group and a fluorescent functional group.

Wherein, the reactive group is active and capable of bonding with a bio-related substance to form a chemical linkage, mainly referring to the reaction involving formation of a covalent bond; when forming a non-covalent linkage, complexion can be achieved via dihydrogen-bonding or multiple hydrogen-bonding. The covalent bond can be but not limited to a stable covalent bond, a degradable covalent bond and a dynamic covalent bond.

The variant form of a reactive group can be but not limited to a precursor of a reactive group, an active form as the precursor of a reactive group, a substituted active form, a protected form, a deprotected form and the like.

The precursor of a reactive group refers to a structure that can be converted into said reactive group after at least one process selected from oxidation, reduction, hydration, dehydration, electronic rearrangement, structural rearrangement, salt complex and decomplexation, ionization, protonation, deprotonation, etc. The precursor can be active or non-active.

The variant form of a reactive group refers to an active form (still a reactive group) of a specific reactive group after said reactive group undergoing at least one process selected from oxidation, reduction, hydration, dehydration, electronic rearrangement, structural rearrangement, salt complexation and decomplexation, ionization, protonation, deprotonation, being substituted, deprotection and the like, or refers to a non-active form of the specific reactive group after said reactive group being protected.

As long as a functional group can generate fluorescence, or can generate fluorescence under stimulation of microenvironment in vivo (such as fluorescein diacetate), or can generate fluorescence under clinical stimulation (such as light stimulation, thermal stimulation, etc.), it falls into the scope of fluorescent functional groups. The dynamic covalent bonds include but are not limited to the dynamic covalent bonds disclosed in the documents "Top Curr Chem (2012) 322: 1-32", "Top Curr Chem (2012) 322: 291-314", "Angew. Chem. Int. Ed. 2002, 41, 898-952", "J. Am. Chem. Soc. 2015, 137, 14248-14251", "RSC Adv., 2015, 5, 67011-67030", "ACS Macro Lett., 2016, 5 (1), 78-82", "Synlett 2016; 27(02): 177-180", "Angew. Chem. Int. Ed. 2015, 54, 15739-15743", "Angew. Chem. Int. Ed. 2015, 54, 8980-8983", "Chem. Commun., 2015, 51, 16338-16341", "Molecular Cell, 2015, 59, 716-717", the like and cited references in the aforesaid documents.

$R_{01}$ includes but is not limited to functional groups selected from Groups A to H and variant forms thereof, wherein, $R_{01}$ or the variant form of $R_{01}$ is a reactive group.

Group A: active ester groups including but not limited to a succinimidyl ester group (e.g., A1 or A6), a p-nitrophenyl ester group (e.g., A2 or A7), an o-nitrophenyl ester group (e.g., A11 or A12), a benzotriazole ester group (e.g., A5 or A10), a 1,3,5-trichlorophenyl ester group (e.g., A3 or A8), A12 and A13 (e.g., a fluorophenyl ester group, a 1,3,5-trifluorophenyl ester group and a pentafluorophenyl ester group) and an imidazole ester group (e.g., A4 or A9), and analogs of active ester groups A16 to A18 (e.g., a 2-thioxothiazolidin-3-yl-formate group, a 2-thioxothiazolidin-3-yl-carbonyl group, a 2-thioxopyrrolidin-1-yl-carbonyl group, a 2-thioxopyrrolidin-1-yl-formate group, a 2-thioxobenzothiazol-3-yl-formate group, a 3-oxo-thioxoisoindolin-N-formate group and the like.), etc.

Group B: a sulfonate group, a sulfinate group, a sulfonyl group, a sulfoxide group, a 1,3-disulfonyl-2-propylcarbonylphenyl group, a (2-sulfonylmethyl)acryl group and the like;

Group C: a hydroxylamino group, a mercapto group (also termed as a thiol group), an amino group (a primary amino group such as C4, or a secondary amino group such as C5 and C15), a halogen atom, a haloacetylamino group (e.g., an iodoacetylamino group), a tetramethylpiperidinyloxy group, a dioxapiperidinyloxy group (a 3,5-dioxa-1-cyclohexylamino-N-oxy group), an ammonia salt group (an amine salt group), a hydrazino group, a disulfide group (the residue of a dithiol, e.g., a linear pyridyldithio group, a lipoyl group as a cyclodisulfide group which is a disulfide-containing cyclic group, etc.), C17 (e.g., an ester group, a thioester group or a thiocarboxylate group), C18 (a carbonate group, a thiocarbonate group, a dithiocarbonate group, a trithioester group or a trithiocarbonate group), a xanthate group, a perthiocarbonate group, a dithiobis(thionoformate) group, an O-carbonylhydroxylamino group (an O-hydroxylaminocarbonyl group, —C(=O)ONH$_2$), an amido group (e.g., a carbonylamino group of —CONH$_2$ containing an —NH$_2$ terminus), an imide group, a hydrazino-carbonyl group (an acylhydrazino group, —CONHNH$_2$), a sulfonylhydrazino group, a hydrazone group, an imino group, an enamine group, an alkynylamino group, a protected hydroxyl group or a protected mercapto group (a carbamate group, a thiocarbamate group or a dithiocarbamate group), a protected amino group (a carbamate group, a thiocarbamate group or a dithiocarbamate group) and the like;

Group D: a carboxyl group, a sulfonic acid group, a sulfenic acid group, a hydroxamic acid group, a thiohydroxamic acid group, a xanthogenic acid group, an acylhalide group (a haloacyl group), a chlorosulfonyl group, an aldehyde group, a glyoxal group, an acetal group, a hemiacetal group, a hydrated aldehyde group, a ketone group, a ketal group, a hemiketal group, a hydrated ketone group, an orthoacid group, an orthoester group, a cyanate group, a thiocyanate group, an isocyanato group, an isothiocyanato group, an ester group (a carboxylate group), an oxycarbonyl halide group, a dihydrooxazole group (an oxazoline group D13, an isooxazoline group), a thioaldehyde group, a thione group (a thioketone group), a thioacetal group, a thione hydrate group, a thioketal group or a dithioketal group, a thiohemiketal group, a thioester group (with a —S—(C=O)— bond, e.g., D26), a thiocarboxylate group (e.g., a thioate group with a —O—(C=S)— bond, e.g., D27), a dithioester group (a dithiocarboxylate group, e.g., D18), a thiohemiacetal group (including a hemithioacetal group), a monothiohydrate group, a dithiohydrate group, a thiol hydrate group, a thiocarboxylic acid group (a monothiocarboxylic acid group (e.g., D16 with the oxygen atom of carbonyl group to be replaced or D15 with the oxygen atom of hydroxyl group to be replaced), a dithiocarboxylic acid group (e.g., D17), a guanidino group (a guanidyl group) and the protonated form thereof, an amidino group (e.g, —C(=NH)NH$_2$) and the protonated form thereof, an anhydride group, a squaric acid group, a squarate group, a semi-squaric acid group, a semi-squarate group, an N-carbamoyl-3-imidazole group or an N-carbamoyl-3-methylimidazolium iodide group, an imidic acid group, an imidic ester group, a nitrone group, an oxime group or an oximino group, a urea group, a thiourea group, a pseudourea group and the like;

Group E: a maleimido group, an acrylate group, an N-acrylamide group, a methacrylate group, an N-methacrylamide group, a protected maleimido group (e.g., E4), a maleamic acid group, a 1,2,4-triazoline-3,5-dione group, an azo group (e.g., a linear azo compound, E7 with a cyclic structure and the like), a cycloalkenyl group (e.g., a cyclooctenyl group, a norbornenyl group, a 7-oxabicyclo [2.2.1]hept-5-en-2-yl group, a dicycloheptadienyl group (or a 2,5-norbornadienyl group), a 7-oxa-dicycloheptadienyl group and the like), etc; wherein, W$_3$ in E13 is a leaving group which can be but not limited to a halogen atom, a PhS— group or the like;

Group F: an epoxy group (a glycidyloxy group), an alkenyl group (including an ethenyl group, a propenyl group and the like), an alkenyl-hydrocarbyl group (e.g., an allyl group), an alkynyl group (a propynyl group), an alkynyl-hydrocarbyl group (e.g., a propargyl group) and the like;

Group G:

Group Ga: a cycloalkynyl group or a heterosubstituted cycloalkynyl group (e.g., G1, G2, G3, G4, G7, G8, G9 and G10), a conjugated dienyl group (e.g., a linear butadienyl group and a cyclopentadienyl group), a heterosubstituted conjugated dienyl group with a skeleton-membering heteroatom (e.g., a furyl group with a ring-membering heteroatom), a 1,2,4,5-tetrazinyl group and the like;

Group Gb: an azido group, a nitrile oxide group (a cyano oxide group, —C≡N$^+$O$^-$), a cyano group, an isocyano group, an aldoxime group, a diazo group, a diazonium group, an azoxy group, a nitrilimine group, an N-aldimine oxide group, a tetrazole group, a 4-acetyl-2-methoxy-5-nitrophenoxy group (e.g., G31) and its diazo form (e.g., G32) and the like; and other functional groups which can undergo 1,3-dipolar cycloaddition reactions are also incorporated into the present invention;

Group H: a hydroxyl group (including but not limited to an alcoholic hydroxyl group, a phenolic hydroxyl group, an enolic hydroxyl group, the hydroxyl group of a hemiacetal and the like), a protected hydroxyl group, a siloxy group, a protected dihydroxyl group, a trihydroxysilyl group, a protected trihydroxysilyl group and the like;

Functional groups related to click reactions reported and cited by the document "Adv. Funct. Mater., 2014, 24, 2572-2590" are incorporated into the present invention by reference. CN is a precursor of its oxidized form C—NO, —NH$_2$ is the precursor of ammonium ion —NH$_3^+$ and amine salt (—NH$_2$HCl), —COOH is the precursor of its sodium salt —COONa and anionic form —COO$^-$, G25 and G26 are precursors for each other, G5 and G6 are precursors of G2 and G3 respectively, G31 is the precursor of G32, etc. The protected forms include but are not limited to a protected hydroxyl group (e.g., H2), a protected dihydroxyl group (e.g., H3), a protected trihydroxyl group (e.g., H5), a protected orthocarbonic acid (e.g., D8), a protected mercapto group (e.g., C2), a protected amino group (e.g., C6 and C16), a protected carboxyl group (e.g., D11), a protected aldehyde group (e.g., D7), a protected maleimido group (e.g., E$_4$), a protected alkynyl group (e.g., F4) and the like. Functional groups selected from A13, A14 and E9-E12 also include substituted forms thereof. —NH(C=NH$_2^+$)NH$_2$ is the protonated form of a guanidino group. A functional group can belong to two subGroups simultaneously; for example, the o-pyridyl disulfide group in C13 also belongs to the protected form of mercapto group. C9 is not only a protected amino group but also a protected dihydroxyl group (H3). Esters (carboxylates), thioesters, thiocarboxylates (e.g., thioates, dithioesters) in C17, as well as carbonates and thiocarbonates in C18 can also be regarded as protected hydroxyl groups or protected mercapto groups.

The Applications of the Above-Described Functional Groups (Including Variant Forms Thereof), for Example, Include but are not Limited to:

Functional groups in Group A can undergo amino-modification (reactions with an amino group) and form an amide bond or a urethane bond (a carbamate group).

A sulfonate group and a sulfinate group in Group B can be used for alkylation, and functional groups containing a sulfonyl group or a sulfoxide group can be used for modification with a mercapto group or a disulfide bond.

Group C: Some groups also frequently occur in bio-related substances as a reactive site to be modified, such as a mercapto group, an amino group, a disulfide bond and the like. Group C mainly refers to functional groups that have similar reactivity (e.g., a hydroxylamino group, a hydrazino group), protected forms, salt forms and the like. Leaving groups which are liable to leave such as a halogen atom and the like are also included. What's more, an iodoacetylamino group of C10 can also undergo thio-modification (reactions with a thiol group). C13 and C14 can also both belong to protected mercapto group C3. Typical examples of C14 include lipoic acid.

Group D: Some functional groups or deprotected forms thereof can interreact with a hydroxyl group or a functional group selected from Group C. For example, an unprotected functional group such as D1-D6, D9, D10, D12, D13, D14-D16, D19, D20, D21, D22, D23, D25 or D29 or a deprotected form of D7, D8, D11, D18, D24 or D26-D28, is capable of reacting with a suitable group selected from the group consisting of an amino group, a mercapto group, a hydroxyl group and a halide. A functional group in Group D can also react with another functional group in Group D, e.g., D25 can react with D1, and D13 can react with D1 or D4. Wherein, a guanidino group is capable of reacting with the two carbonyl groups of tanshinone IIa to form dihydrogen-bonding.

Functional groups in Group E contain an α,β-unsaturated bond, and thus can undergo 1,2-addition reactions, such as reactions with an amino group and a mercapto group in Group C and reactions with a hydroxyl group in Group H. E$_{13}$ can also undergo a substitution reaction with two mercapto groups.

Regarding functional groups in group F, several mostly common structures are similar in production method, and can be obtained via a substitution reaction with the corresponding halide. For instance, an epoxy group can undergo reactions including but not limited to a ring-opening reaction to obtain an unprotected dihydroxyl group, a ring-opening addition reaction with an amino group, etc. An alkenyl group in F2 can undergo an addition reaction. The alkynyl group F3 and deprotected form F4 are commonly used as a functional group for click reactions.

Functional groups in group G can undergo click reactions, and can be classified into two types: Group Ga and Group Gb. A cycloalkynyl group or precursor thereof, a conjugated dienyl group and a 1,2,4,5-tetrazinyl group from Group Ga can undergo a cycloaddition reaction or a Diels-Alder addition reaction. Functional groups from Group Gb, such as an allyl group, a propargyl group, an allenyl group and the like, can undergo a 1,3-dipolar cycloaddition reaction. In addition, G31 can be converted into a reactive group as represented by G32 with the treatment of hydrozine, and G32 can further react with a carboxyl group to generate an ester bond.

Functional groups in Group H including a hydroxyl group, a dihydroxyl group, a trihydroxyl group and protected form of any aforesaid type, are important starting groups for functionalization in the present invention (e.g., a hydroxyl group at the terminal end of a PEG chain). A functional group that contains a hydroxyl group or a deprotonated hydroxyl group is a necessary moiety of the initiator center in order to initiate the polymerization of ethylene oxide in the present invention. Hydroxyl groups in Group H can also occur in bio-related substances as a reactive site to be modified. Additionally, functional groups H6 and H7 can be converted into an enolic hydroxyl form under light irradiation and further undergo an addition reaction with a functional group such as an α,β-unsaturated bond in Group E.

$R_{01}$ can also do not undergo bonding reaction with bio-related substances, and herein the functional group $R_{01}$ should have special functions (meaning active). Functional group $R_{01}$ of this type includes but is not limited to a targeting moiety, a fluorescent group and substituted forms of these special functional moieties. The substituted forms of these special functional moieties should still bear corresponding special function and can correspondingly fall into the scope of targeting groups or fluorescent groups. $R_{01}$ of this type (not for bonding reactions) includes but is not limited to functional groups selected from Groups I and J and derivatives thereof:

Group I: Targeting groups and pharmaceutically acceptable salts thereof, such as folic acid and derivatives thereof, cholesterol and derivatives thereof, biotins and derivatives thereof and functional derivatives of any aforesaid targeting group. Examples of derivatives of biotin include D-desthiobiotin, 2-iminobiotin and the like.

Group J: Fluorescent groups, such as the residue of phthalocyanine coordination compound, a fluorescein group, a rhodamine group, an anthracenyl group, a pyrenyl group, a coumarin group, a fluorescent yellow 3G group, a carbazole group, an imidazole group, an indole group, a galleinmonohydrate group, the like, and functional derivatives of any aforesaid fluorescent group. Wherein, derivatives of rhodamine include but are not limited to tetramethylrhodamine, tetraethyl rhodamine (rhodamine B, RB200), rhodamine 3G, rhodamine 6G (rhodamine 590), 5-carboxy-X-rhodamine, 6-carboxy-X-rhodamine, sulfonylrhodamine B, sulfonylrhodamine G, sulfonylrhodamine 101, rhodamine X (R101), rhodamine 101, rhodamine 110, rhodamine 123, rhodamine 700, rhodamine 800 and the like, as well as derivatives of rhodamine disclosed in the reference "Progress in Chemistry, 2010, 22 (10): 1929-1939" and cited references therein.

In the present invention, $—(Z_1)_{q1}—R_{01}$ can be regarded as a whole functional moiety. Wherein, functional groups such as an active ester group, an amino group, an aldehyde group, a carboxyl group, a haloacyl group, an anhydride group, a cyano group, an alkynyl group, a hydroxyl group and the like include but are not limited to the groups disclosed and recited in the documents CN104530413A, CN104530415A and CN104530417A; take CN104530417A as an example, inclusively but not limited, corresponding to paragraphs from [0423] to [0432]. For example, When $R_{01}$ is an active ester group, $—(Z_1)_{q1}—R_{01}$ can be but not limited to an active ester of one type selected from the group consisting of carbonate, acetate, propionate, butyrate, pentanoate (e.g., valerate), hexanoate, heptanoate, octanoate, nonanoate (e.g., pelargonate), decanoate (e.g., caprate), oxalate, malonate, methylmalonate, ethylmalonate, butylmalonate, succinate, 2-methylsuccinate ester, 2,2-dimethylsuccinate, 2-ethyl-2-methylsuccinate, 2,3-dimethylsuccinate, glutarate, 2-methylglutarate, 3-methylglutarate, 2,2-dimethylglutarate, 2,3-dimethylglutarate, 3,3-dimethylglutarate, adipate, pimelate, suberate, azelate, sebacate, maleate, fumarate, an amino acid ester, a polypeptide ester, a poly(amino acid) ester and the like;

When $R_{01}$ is an amino group, $—(Z_1)_{q1}—R_{01}$ can be a primary amino residue formed by removing a non-amino hydrogen atom of a primary amine, or be a secondary amino residue formed by removing a hydrogen atom of the amino group of a primary amine, or be a secondary residue formed by removing a non-amino hydrogen atom of a secondary amine, wherein, the primary amine includes but is not limited to methylamine, ethylamine, propylamine, butylamine, pentylamine, hexylamine, heptylamine, octylamine, cyclohexylamine, aniline and the like, and the secondary amine includes but is not limited to dimethylamine, diethylamine, dipropylamine, dibutylamine, diamylamine, dihexylamine, diheptyl amine, dioctylamine, dicyclohexylamine, N-methylaniline, N-ethylaniline, N-propylaniline, N-isopropylaniline, N-butylaniline, N-cyclohexylaniline, azetidine, pyrrolidine, piperidine and the like. $—(Z_1)_{q1}—R_{01}$ can also be a residue group formed by removing the hydroxyl group of the C-carboxyl group or a pendant carboxyl group from an amino acid, an amino acid derivative, an ω-amino acid (e.g., β-alanine, γ-piperidic acid, δ-norvaline, ε-norleucine and the like), a polypeptide or a polypeptide derivative, wherein, and the resulting $R_{01}$ is an N-amino group or a pendant amino group.

When $R_{01}$ is an aldehyde group, $—(Z_1)_{q1}—R_{01}$ can be the monovalent functional residue group formed by removing a non-aldehyde hydrogen atom of an aldehyde or by removing an aldehyde hydrogen atom of formaldehyde, wherein, the aldehyde can be but not limited to formaldehyde, acetaldehyde, propionaldehyde, butanal (also butyraldehyde), petanal (also pentanaldehyde, e.g., valeraldehyde), hexanal, heptanal, octanal (also octanaldehyde), nonanal, decanal, crotonaldehyde, acraldehyde (or acrolein, propenal), methacrolein, 2-ethylacraldehyde (or 2-ethylacrolein, 2-ethylpropenal), chloroacetaldehyde, iodoacetaldehyde, dichloroacetaldehyde, benzaldehyde, phenylacetaldehyde, tolualdehyde (also methylbenzaldehyde), cinnamaldehyde (or cinnamic aldehyde), nitrocinnamaldehyde, bromobenzaldehyde, chlorobenzaldehyde or the like. When two or two more structural forms such as isomers exist, any structural form can be selected. For example, butyraldehyde includes but is not limited to n-butyraldehyde, isobutyraldehyde, 2-methylpropanal and 2,2-dimethyl-acetaldehyde.

When $R_{01}$ is a carboxyl group, $—(Z_1)_{q1}—R_{01}$ can be the monovalent functional residue group formed by removing a non-carboxyl hydrogen atom of a monocarboxylic acid, or by removing a hydroxyl group of a dicarboxylic acid. The monocarboxylic acid includes but is not limited to formic acid, acetic acid, propionic acid, butanoic acid (butyric acid), pentanoic acid (e.g., valeric acid), hexanoic acid, heptanoic acid, octanoic acid, nonanoic acid, decanoic acid, lauric acid, myristic acid, palmitic acid, stearic acid, oleic acid, eicosanoic acid, heneicosanoic acid, docosanoic acid, isobutyric acid, 3-methylbutyric acid, acrylic acid, methacrylic acid, citric acid, vinylacetic acid, tiglic acid, 6-heptenoic acid, itaconic acid, citronellic acid, monochloroacetic acid, dichloroacetic acid, monofluoroacetic acid, difluoroacetic acid, benzoic acid, methylbenzoic acid, fluorobenzoic acid, ethoxybenzoic acid, methoxybenzoic acid, ethylbenzoic acid, vinylbenzoic acid, propylbenzoic acid, 2-isopropylbenzoic acid, 2-butylbenzoic acid, 2-isobutylbenzoic acid, N-carbamoylmaleamic acid, N-phenylmaleamic acid, maleamic acid, arachidonic acid, tetracosanoic acid, tetracosenoic acid (or nervonic acid), glycolic acid, lactic acid, isonicotinic acid, ascorbic acid, gentisic acid, gluconic acid, alduronic acid, sorbic acid, N-(ω-aminocarboxylic acid) and the like. The dicarboxylic acid includes but is not limited to oxalic acid, malonic acid (propanedioic acid), methylmalonic acid, ethylmalonic acid, butylmalonic acid, succinic acid, 2-methylsuccinic acid, 2,2-dimethylsuccinic acid, 2-ethyl-2-methylsuccinic acid, 2,3-dimethylsuccinic acid, glutaric acid, 2-methylglutaric acid, 3-methylglutaric acid, 2,2-dimethylglutaric acid, 2,3-dimethylglutaric acid, 3,3-dimethylglutaric acid, adipic acid, pimelic acid, suberic acid, azelaic acid, sebacic acid, maleic acid, fumaric acid, oxaloacetic acid, dimethylmalonic acid, isopropylmalonic acid, benzylmalonic acid, 1,1-epoxy-dicarboxylic acid (or 1,1-cyclopropanedicarboxylic acid), 1,1-cyclobutanedicarboxylic acid, dibutylmalonic acid, ethyl(1-methylpropyl)malonic acid, ethyl(1-methylbutyl)malonic acid, ethyl (isopentyl)malonic acid, phenylmalonic acid, 2-oxoglutaric acid, 3-oxoglutaric acid, 5-norbornene-endo-2,3-dicarboxylic acid, 1,4-cyclohexanedicarboxylic acid, 1,3-cyclohexanedicarboxylic acid, 1,2-cyclohexanedicarboxylic acid, pyrrolidine-3,4-dicarboxylic acid, camphoric acid, chlorendic acid, dibenzyl-2-oxoimidazolidine-4,5-dicarboxylic acid, 5-methyl-1,3-benzenedicarboxylic acid (5-methylisophthalic acid), phthalic acid, 4-methyl-1,2-benzenedicarboxylic acid, 4-chlorophthalic acid, 3,4-pyridinedicarboxylic acid, 2,3-pyridinedicarboxylic acid, 2,4-pyridinedicarboxylic acid, 3,5-pyridinedicarboxylic acid, 2,6-pyridinedicarboxylic acid, 2,4-dimethyl-H-pyrrole-3,5-dicarboxylic acid, 5-methylpyridine-2,3-dicarboxylic acid, 5-ethylpyridine-2,3-dicarboxylic acid, 5-methoxymethyl-2,3-pyridinedicarboxylic acid, pyridazine-4,5-dicarboxylic acid (4,5-pyridazinedicarboxylic acid), 2,3-pyrazinedicarboxylic acid (pyrazine-2,3-dicarboxylic acid), 5-methylpyrazine-2,3-dicarboxylic acid, 4,5-imidazoledicarboxylic acid, 2-propyl-1H-imidazoledicarboxylic acid, biphenyldicarboxylic acid, 4,4'-stilbenedicarboxylic acid, 2,7-naphthalenedicarboxylic acid, 4,4'-oxybisbenzoic acid (4-(4-carboxyphenoxy)benzoic acid), 2,2'-bipyridine-5,5'-dicarboxylic acid, 2,2'-bipyridine-3,3'-dicarboxylic acid, 4-pyrone-2,6-dicarboxylic acid (chelidonic acid), 1,2-phenylenedioxydiacetic acid, thiophene-2,3-dicarboxylic acid (2-thiazolylisocyanate), thiophene-2,5-dicarboxylic acid, 2,5-dicarboxylic acid-3,4-ethylene dioxythiophene, 1,3-acetonedicarboxylic acid (3-ketoglutaric acid), itaconic acid (methylenesuccinic acid), 2-methyl-2-butenedioic acid (citraconic acid and mesaconic acid), 1,3-butadiene-1,4-dicarboxylic acid, butynedioic acid, norbornene-2,3-dicarboxylic acid (bicyclo[2.2.1]hept-5-ene-2,3-dicarboxylic acid), bicyclo[2.2.1]hept-2-ene-2,3-dicarboxylic acid, diglycolic acid, dithiodiglycolic acid, malic acid, tartaric acid, 2,3-dimercaptosuccinic acid, 2,3-dibromosuccinic acid, mefenpyr, 4,4'-dichlorodiphenic acid, 4,4'-dibromodiphenic acid, glucaric acid, saccharic acid, pamoic acid, 2-bromosuccinic acid, 2-mercaptosuccinic acid, 1,3-adamantanedicarboxylic acid, 2,6-dimethyl-1,4-dihydro-3,5-pyridinedicarboxylic acid, mesoxalic acid, ethoxymethylenemalonic acid, 3,3'-dithiodipropionic acid, 5-exo-methyl-2-norbornene-5,6-endo-cis-dicarboxylicacid, acetylmalonic acid and the like. The above structures include their various isomeric forms such as cis-type, trans-type, $_D$-type, L-type and the like; for example, malic acid includes $_D$-type and $_L$-type. —$(Z_1)_{q1}$—$R_{01}$ can also be a residue group formed by removing an N-amino group or a pendant amino group from an amino acid, an amino acid derivative, a polypeptide or a polypeptide derivative, wherein, $R_{01}$ is a C-carboxyl group or a pendant carboxyl group.

When $R_{01}$ is a haloacyl group (or an acyl halide group), the halogen atom therein can be a fluorine atom, a chlorine atom, a bromine atom or an iodine atom, and preferably a chlorine atom or a bromine atom. Wherein, —$(Z_1)_{q1}$—$R_{01}$ can be a monovalent residue group obtained by removing a hydrogen atom of an acyl halide or be the combination of a diacyl group and a halogen atom. The acyl halide can be but not limited to acetyl chloride, acetyl bromide, chloroacetyl chloride, dichloroacetyl chloride, propionyl chloride, propionyl bromide, butanoyl chloride (butyryl chloride), 3-cyclopentylpropionyl chloride, 2-chloropropionyl chloride, 3-chloropropionyl chloride, t-butylacetyl chloride, pentanoyl chloride (e.g., valeroyl chloride, isovaleryl chloride), hexanoyl chloride, heptanoyl chloride, octanoyl chloride, nonanoyl chloride, decanoyl chloride, lauroyl chloride, myristoyl chloride, palmitoyl chloride, stearoyl chloride, oleoyl chloride, behenoyl chloride, cyclopentanecarbonyl chloride, methoxyacetyl chloride, acetoxyacetyl chloride or the like. The diacyl group can be but not limited to an oxalyl group, a malonyl group, a methylmalonyl group, an ethylmalonyl group, a butylmalonyl group, a succinyl group, a 2-methylsuccinyl group, a 2,2-dimethylsuccinyl group, a 2-ethyl-2-methylsuccinyl group, a 2,3-dimethylsuccinyl group, a glutaryl group, a 2-methylglutaryl group, a 3-methylglutaryl group, a 2,2-dimethylglutaryl group, a 2,3-dimethylglutaryl group, a 3,3-methylglutaryl group, an adipoyl group, a pimeloyl group, an octanedioyl group, an azelaoyl group, a decanedioyl group, a maleoyl group, a fumaroyl group or the like. Herein, the diacyl group of a dicarboxylic acid refers to the residue after removing two hydroxyl groups.

When $R_{01}$ is an anhydride group, it can be an open-chain anhydride or an intramolecular anhydride. For example, —$(Z_1)_{q1}$—$R_{01}$ can be the monovalent functional residue formed by removing a hydrogen atom of an anhydride, wherein, the anhydride can be but not limited to acetic anhydride, propionic anhydride, butyric anhydride, pentanoic anhydride (e.g., valeric anhydride), hexanoic anhydride, heptanoic anhydride, octanoic anhydride, nonanoic anhydride, decanoic anhydride, lauric anhydride, myristic anhydride, palmitic anhydride, stearic anhydride, behenic anhydride, crotonic anhydride, methacrylic anhydride, oleic anhydride, linoleic anhydride, chloroacetic anhydride, iodoacetic anhydride, dichloroacetic anhydride, succinic anhydride, methylsuccinic anhydride, 2,2-dimethylsuccinic anhydride, itaconic anhydride, maleic anhydride, glutaric anhydride, diglycolic anhydride, benzoic anhydride, phenylsuccinic anhydride, phenylmaleic anhydride, homophthalic anhydride, isatoic anhydride, phthalic anhydride or the like. The intramolecular anhydride can also include but not limited to anhydrides deriving from butanedioic anhydride, 2,2-dimethylsuccinic anhydride, cyclopentane-1,1-diacetic anhydride, 1,1-cyclohexane diacetic anhydride, 2-methylenesuccinic anhydride (or itaconic anhydride), glutaric anhydride, caronic anhydride, cyclobutane-1,2-dicarboxylic anhydride, hexahydrophthalic anhydride, methylhexahydrophthalic anhydride, 1,2,3,6-tetrahydrophthalic anhydride, 1,2,5,6-tetrahydrophthalic anhydride, 3-methyltetrahydrophthalic anhydride, methyltetrahydrophthalic anhydride, citraconic anhydride, 2,3-dimethylmaleic anhydride, 2,3-dichloromaleic anhydride, 3,4,5,6-tetrahydrophthalic anhydride, 3-methylphthalic anhydride, 4-t-butylphthalic anhydride, 1,8-naphthalic anhydride, 2,2'-diphenyldicarboxylic anhydride, 4-fluorophthalic anhydride, 3-fluorophthalic anhydride, 4-bromophthalic anhydride, 4-chlorophthalic anhydride, 3,6-dichlorophthalic anhydride, 3-nitrophthalic anhydride, 4-nitrophthalic anhydride, 4-bromo-1,8-naphthalic anhydride, 4,5-dichloro-1,8-naphthalic anhydride, 4-nitro-1,8-naphthalic anhydride, norbornene-dicarboxylic anhydride, methyl nadic anhydride (methylnorbornene-2,3-dicarboxylic anhydride), norcantharidin (7-oxabicyclo[2.2.1]heptane-2,3-dicarboxylic anhydride), 2,3-pyridinedicarboxylic anhydride, 2,3-pyrazinedicarboxylic anhydride, benzothioxanthenedicarboxylic anhydride and the like.

When $R_{01}$ is an intramolecular imide group, —$(Z_1)_{q1}$—$R_{01}$ can be but not limited to any corresponding imide form of the above-described intramolecular anhydrides, such as a succinimide corresponding to a succinic anhydride, a maleimide corresponding to a maleic anhydride, phthalimide corresponding to phthalic anhydride and the like, no more repeated here. Saccharin, also termed as o-sulfobenzimide, is also included.

When $R_{01}$ is a maleimido group, $-(Z_1)_{q1}-R_{01}$ can be the residue group deriving from the following compounds or groups, including but not limited to 3,4,5,6-tetrahydrophthalimide, a maleimidoacetyl group, a 3-maleimidopropionyl group, a 4-maleimidobutanoyl group, a 5-maleimidopentanoyl group (e.g., a 5-maleimidovaleryl group), a 6-maleimidohexanoyl group, a 3-maleimidobenzoyl group, a 4-maleimidobenzoyl group, a 4-(N-maleimidomethyl)cyclohexyl-1-formyl group, a 4-(4-maleimidophenyl)butanoyl group, a 11-maleimidoundecanoyl group, N-(2-aminoethyl)maleimide, N-(4-aminophenyl)maleimide, a 2-maleimidoethyl group and the like.

When $R_{01}$ is an alkynyl group, $-(Z_1)_{q1}-R_{01}$ can be but not limited to an ethynyl group, a propynyl group, a propargyl group, a cycloalkynyl group, the like and a hydrocarbyl-substituted form of any aforesaid group.

When $R_{01}$ is a cyano group, $-(Z_1)_{q1}-R_{01}$ can be the monovalent functional residue group formed by removing a hydrogen atom from one of the following cyano-containing cyanides including but not limited to formonitrile, acetonitrile, butyronitrile, pentanonitrile (e.g., valeronitrile), hexanenitrile, heptanenitrile, octanenitrile, nonanenitrile (also nonanonitrile), decanenitrile, undecyl nitrile, allyl nitrile, acrylonitrile, crotononitrile, methacrylonitrile, dichloroacetonitrile, fluoroacetonitrile, benzenonitrile, benzyl nitrile, methylbenzyl nitrile, chlorobenzonitrile, methylbenzonitrile and the like.

When $R_{01}$ is a hydroxyl group, $-(Z_1)_{q1}-R_{01}$ can be the monovalent functional residue group formed by removing a non-hydroxyl hydrogen atom from one of the following mono-ols, including but not limited to methanol, ethanol, propanol, butanol, pentanol, hexanol, heptanol, octanol, nonanol, decanol, undecyl alcohol, lauryl alcohol (or dodecanol), tridecanol (or tridecyl alcohol), tetradecanol (or tetradecyl alcohol), pentadecanol (pentadecyl alcohol), hexadecanol (or hexadecyl alcohol), heptadecanol (or heptadecyl alcohol), octadecanol (or octadecyl alcohol), oleyl alcohol, benzyl alcohol, cumyl alcohol, phenol, cresol, stilboestol, propofol, cumylphenol, naphthol, cyclopentanol, cyclohexanol and the like.

When $R_{01}$ is a cholesterol moiety or the derivative thereof, $-(Z_1)_{q1}-R_{01}$ includes but is not limited to the residue groups of cholesterol, cholesterol derivatives, cholesterol succinate and the like after being connected at the terminal ends of PEG chains.

When $R_{01}$ is a biotin moiety or the derivative thereof, $-(Z_1)_{q1}-R_{01}$ can be selected from the residue groups of biotin-containing compounds after being bound to the terminal ends of PEG chains, wherein, the biotin-containing compounds include but are not limited to biotin N-hydroxysuccinimide ester (or biotin N-succinimidyl ester, or N-succinimidyl biotinate), succinimidyl 3-[3-[2-(biotinamido)ethyl]amino-3-oxopropyl]dithio]propionate, sulfosuccinimidyl 3-[[2-(biotinamido)ethyl]dithio]propionate, N-(3-azidopropyl)biotinamide, N-biotinyl-3,6-dioxaoctane-1,8-diamine, N-biotinyl-3,6,9-trioxaundecanediamine, biotinyl-6-aminoquinoline, N-(6-[biotinamido]hexyl)-3'-(2'-pyridyldithio)propionamide, 15-[D-(+)-biotinylamino]-4,7,10,13-tetraoxapentadecanoic acid, 3-(4-(N-biotinoyl-6-aminocaproyloxy)phenyl)propionic acid, N-Fmoc-N'-biotinyl-$_L$-lysine, D-biotin hydrazide, biotin-Asp-Glu-Val-Asp-aldehyde and the like.

When $R_{01}$ is a fluorescein moiety or the derivative thereof, $-(Z_1)_{q1}-R_{01}$ can be selected from the residue groups of fluorescein-containing compounds after being bound to the terminal ends of PEG chains, wherein, the fluorescein-containing compounds include but are not limited to 5-carboxyfluorescein succinimidyl ester, 6-carboxyfluorescein succinimidyl ester, 5-aminofluorescein, 6-aminofluorescein, 5-(aminomethyl)fluorescein hydrochloride, 6-(4,6-dichlorotriazin-2-yl]amino)fluorescein hydrochloride, 5'-fluorescein phosphoramidite, fluorescein-5-maleimide, fluorescein-6-maleimide, 5-carboxyfluorescein, 6-carboxylfluorescein, 2,7-bis(2-carboxyethyl)-5-carboxyfluorescein, 2,7-bis(2-carboxyethyl)-6-carboxyfluorescein, 5-(4,6-dichlorotriazinyl)aminofluorescein, CI 45350 and the like.

When $R_{01}$ is a rhodamine moiety or the derivative thereof, $-(Z_1)_{q1}-R_{01}$ can be selected from the residue groups of rhodamine-containing compounds after being bound to the terminal ends of PEG chains, wherein, the rhodamine-containing compounds include but are not limited to tetramethylrhodamine, rhodamine B (RB200), rhodamine 3G, rhodamine 6G (rhodamine 590), 5-carboxy-X-rhodamine, 6-carboxy-X-rhodamine, sulfonylrhodamine B, sulfonylrhodamine G, sulfonylrhodamine 101, rhodamine X (R101), rhodamine 101, rhodamine 110, rhodamine 123, rhodamine 700, rhodamine 800, 5-carboxytetramethylrhodamine, 6-carboxytetramethylrhodamine, 5-carboxytetramethylrhodamine succinimidyl ester, 6-carboxytetramethylrhodamine succinimidyl ester, 5-carboxyrhodamine 6G succinimidyl ester, 6-carboxyrhodamine 6G succinimidyl ester, tetramethylrhodamine-5-maleimide, tetramethylrhodamine-6-maleimide, 6-carboxy-X-rhodamine succinimidyl ester, tetramethylrhodamine-5-isothiocyanate, tetramethylrhodamine-6-isothiocyanate, tetramethylrhodamine B-5-isothiocyanate, tetramethylrhodamine B-6-isothiocyanate, chlororhodamine 101, sulforhodamine B and the like.

When $R_{01}$ is an anthracene moiety or the derivative thereof, $-(Z_1)_{q1}-R_{01}$ can be selected from the residue groups of anthryl-containing compounds after being bound to the terminal ends of PEG chains, wherein, the anthryl-containing compounds include but are not limited to 9-anthracenemethanol, 1-aminoanthracene, 2-aminoanthracene (2-anthracenamine), 9-anthraldehyde (anthracene-9-carboxaldehyde), 10-methyl-9-anthraldehyde, 9-anthroic acid, 9-anthracenylmethyl acrylate, 9-anthracenylmethyl methacrylate, 9-anthraldehyde oxime, 9-anthraceneacrolein and the like.

When $R_{01}$ is a pyrene moiety or the derivative thereof, $-(Z_1)_{q1}-R_{01}$ can be selected from the residue groups of pyrenyl-containing compounds after being bound to the terminal ends of PEG chains, wherein, the pyrenyl-containing compounds include but are not limited to 1-pyrenemethanol, 7,8,9,10-tetrahydrogenbenzo[a]pyren-7-ol, 1-pyrenebutyric acid N-hydroxysuccinimide ester, 1-pyrenecarboxaldehyde, 1-pyrenebutyrate (or 1-pyrenebutyric acid, or 1-pyrenebutanoic acid), 1-pyrenecarboxylic acid, 1-pyreneacetic acid, 10-(1-pyrene)decanoic acid, 1-pyrenedodecanoic acid, Fmoc-3-(1-pyrenyl)-L-alanine, Boc-3-(1-pyrenyl)-D-alanine, Boc-3-(1-pyrenyl)-L-alanine, 1-aminopyrene, 1,3-diaminopyrene, 1,8-diaminopyrene, 1,6-diaminopyrene, 1-pyrenylmethylamine, N-(1-pyrenyl)maleimide and the like.

When $R_{01}$ is a carbazole moiety or the derivative thereof, $-(Z_1)_{q1}-R_{01}$ can be selected from the residue groups of carbazole-containing compounds after being bound to the terminal ends of PEG chains, wherein, the carbazole-containing compounds include but are not limited to carbazole, carbazole-9-ethanol, 2-hydroxycarbazole, 2-(9H-carbazolyl)ethylboronic acid pinacol ester, 2-(9H-carbazolyl)ethylboronic acid diethanolamine ester, N-aminocarbazole, 9-(4-aminophenyl)carbazole, carbazole-9-acetic acid and the like.

When $R_{01}$ is an imidazole moiety or the derivative thereof, $-(Z_1)_{q1}-R_{01}$ can be selected from the residue groups of imidazole-containing compounds after being bound to the terminal ends of PEG chains, wherein, the imidazole-containing compounds include but are not limited to 4-(hydroxymethyl)imidazole, 4-(hydroxyethyl)imidazole, 1-(2-hydroxyethyl)imidazole, 1-methyl-2-(hydroxymethyl)imidazole, 1-(2-hydroxypropyl)imidazole, 1-(2-hydroxyethyl)-2-methylimidazole, 4-hydroxymethyl-5-methyl-2-phenylimidazole, 1-hydroxyethyl-3-methylimidazole, 1-hydroxyethyl-3-methylimidazolium chloride, 4-hydroxymethyl-5-methylimidazole, 4-bromo-1H-imidazole, 2-bromo-1H-imidazole, 1-methyl-2-bromo-1H-imidazole (2-bromo-1-methyl-1H-imidazole), 5-chloro-1-methylimidazole, 2-aminoimidazole, 4-aminoimidazole, 1-(3-aminopropyl)imidazole, 1-methylimidazole-4-carboxylic acid, imidazole-4-carboxaldehyde (4-formylimidazole), 1-formylimidazole, 2-formylimidazole, 4-(imidazol-1-yl)benzaldehyde, 1-methyl-2-imidazolecarboxaldehyde, 2-butyl-1H-imidazole-4-carboxaldehyde, 5-methyl-4-imidazolecarboxaldehyde, 2-ethyl-4-formylimidazole, 2-ethyl-4-methyl-5-imidazolecarboxaldehyde, 1-benzyl-1H-imidazole-5-carboxaldehyde, 2-ethyl-4-formylimidazole, 5-amino-1H-imidazole-4-carbonitrile, histidine and the like.

When $R_{01}$ is an indole moiety or the derivative thereof, $-(Z_1)_{q1}-R_{01}$ can be selected from the residue groups of indole-containing compounds after being bound to the terminal ends of PEG chains, wherein, the indole-containing compounds include but are not limited to 4-hydroxyindole, 5-hydroxyindole, 6-hydroxyindole, 7-hydroxyindole, 5-hydroxy-2-methylindole, 4-hydroxy-2-methylindole, 3-(2-methylaminoethyl)indole, 2-(2-aminoethyl)indole, 3-(2-aminoethyl)-6-methoxyindole, 4-aminoindole, 5-aminoindole, 6-aminoindole, 7-aminoindole, 4-methyl-5-aminoindole, 3-bromoindole, 4-bromoindole, 5-bromoindole, 6-bromoindole, 7-bromoindole, 5-bromo-1-methyl-1H-indole, 3-(2-aminoethyl)indol-5-ol, 5-hydroxyindole-2-carboxylic acid, 6-hydroxyindole-2-carboxylic acid, 7-hydroxyindole-2-carboxylic acid, 5-bromoindole-2-carboxylic acid, 6-bromoindole-2-carboxylic acid, 7-bromoindole-2-carboxylic acid, 5-bromoindole-3-carboxylic acid, 6-bromoindole-3-carboxylic acid, 4-bromoindole-3-carbaldehyde, 6-bromoindole-3-carbaldehyde, 5-bromo-1H-indole-3-ethanol and the like.

1.1.6.2 Specific Structures of Functional End-Groups ($R_{01}$)

Specifically, $R_{01}$ can be selected from the group consisting of functional groups from Groups A to J, variant forms of functional groups from Groups A to H and functional derivatives of functional groups from Groups I to J.

GROUP A:

A1

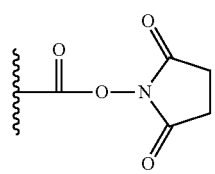

A2

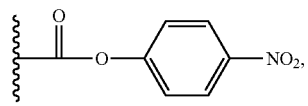

A3

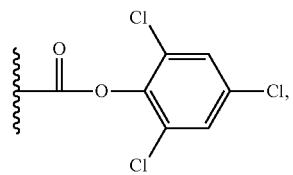

A4

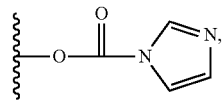

A5

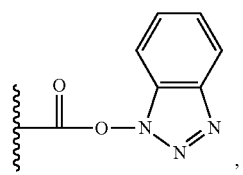

A6

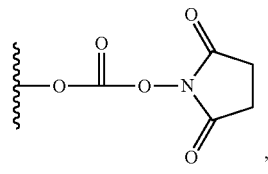

A7

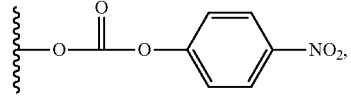

A8

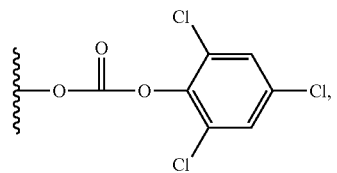

A9

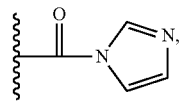

A10

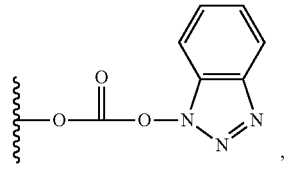

A11

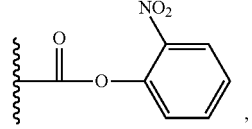

A12

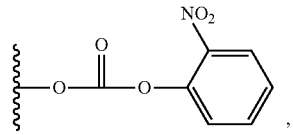

-continued
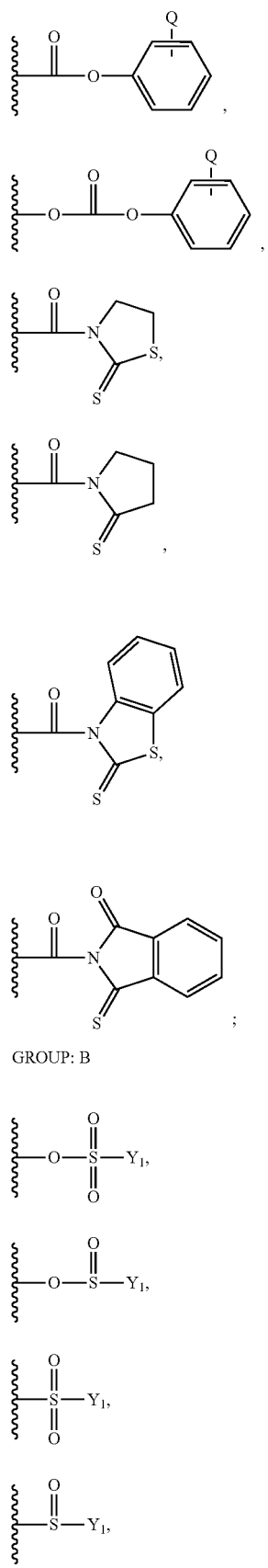
GROUP: B
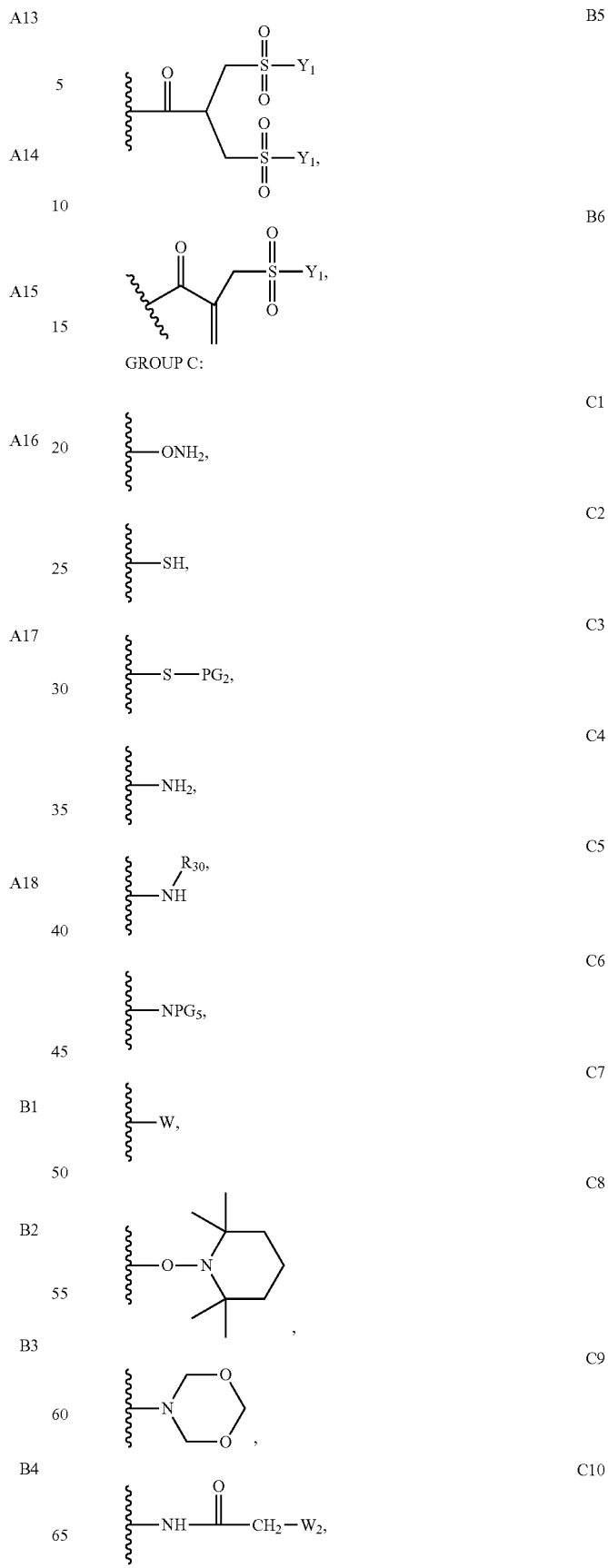
GROUP C:

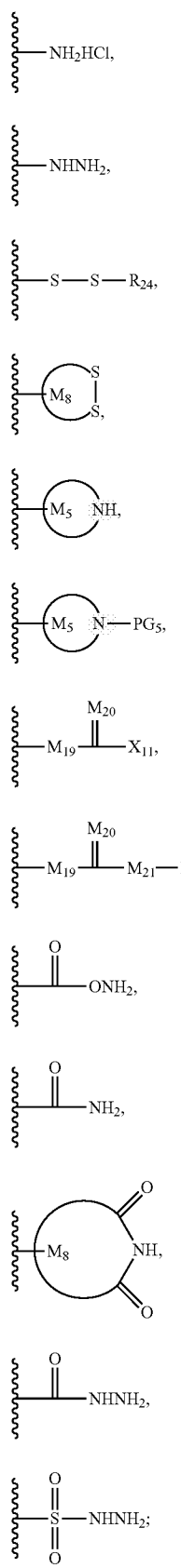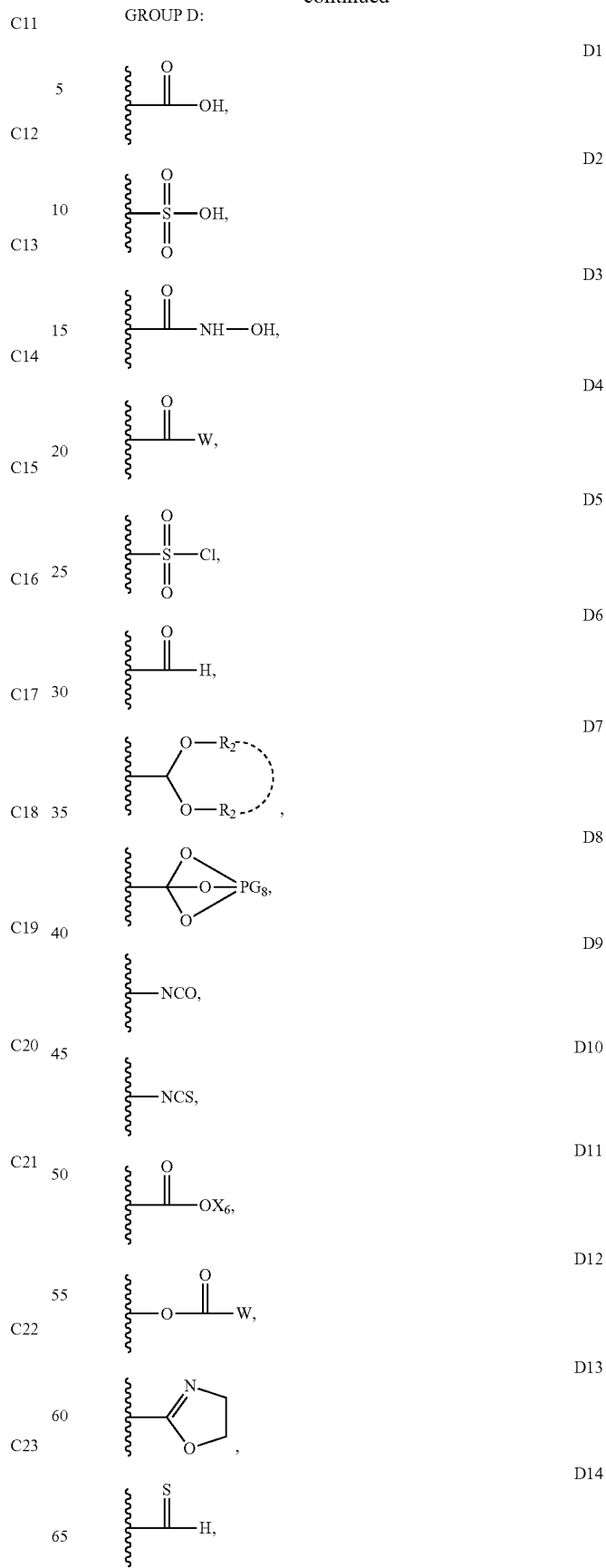

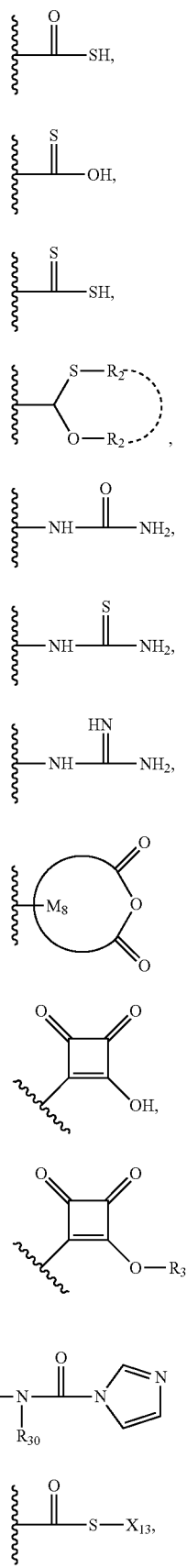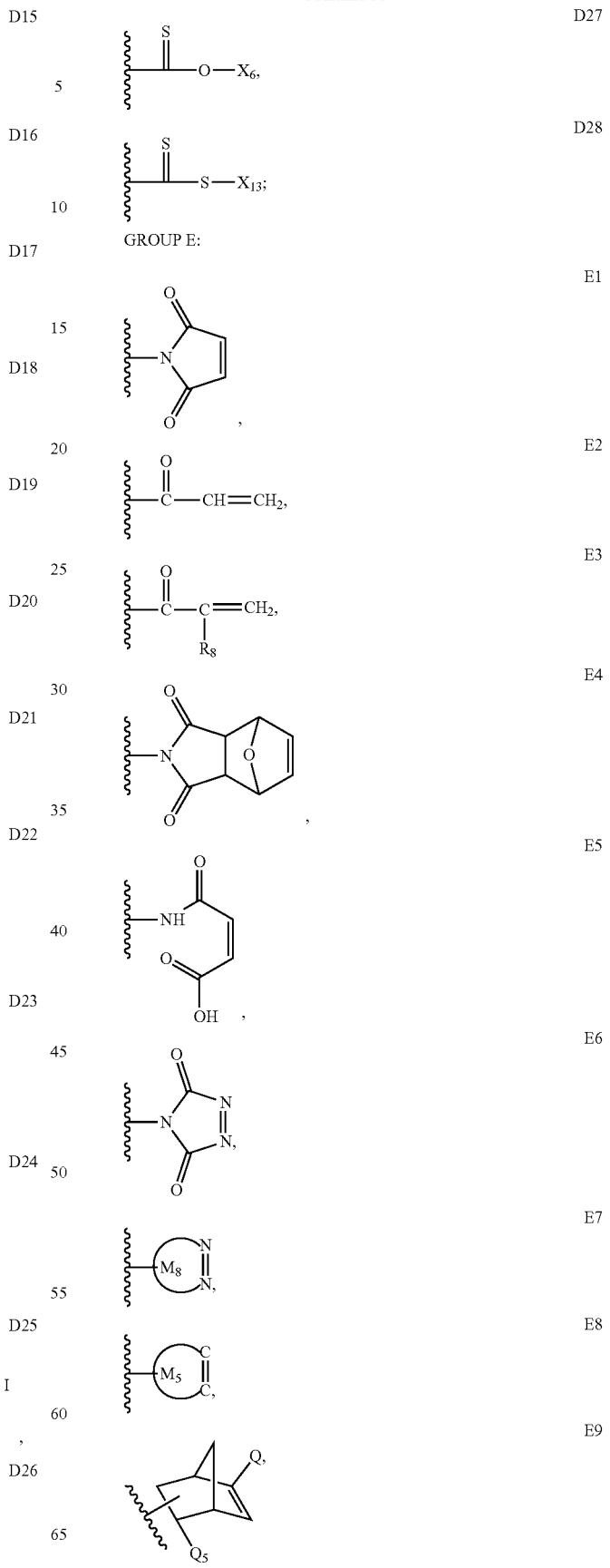

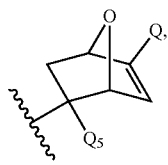
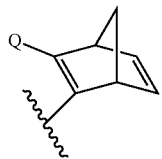
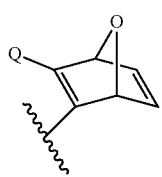
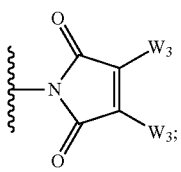
GROUP F:
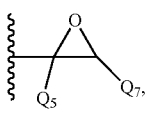
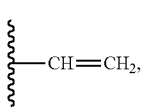
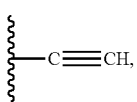
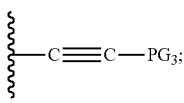
GROUP G:
GROUP Ga:
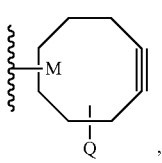
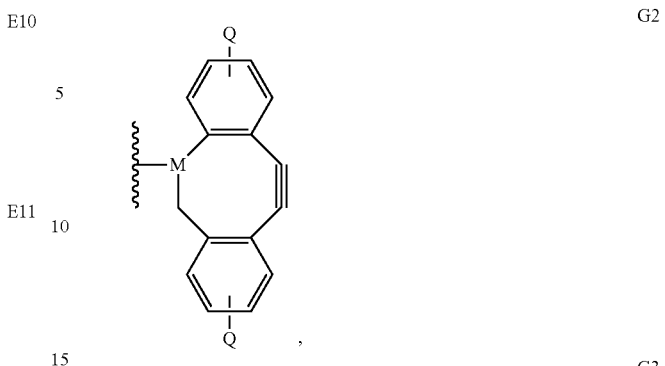
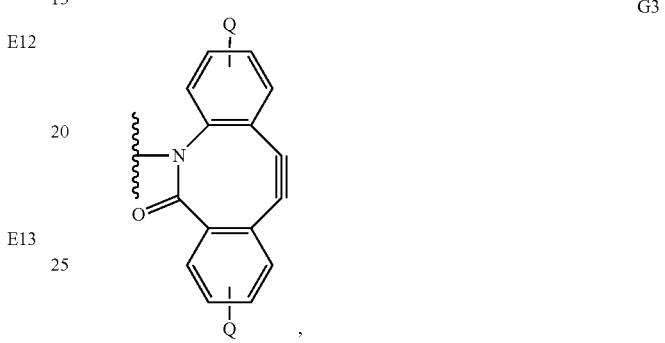
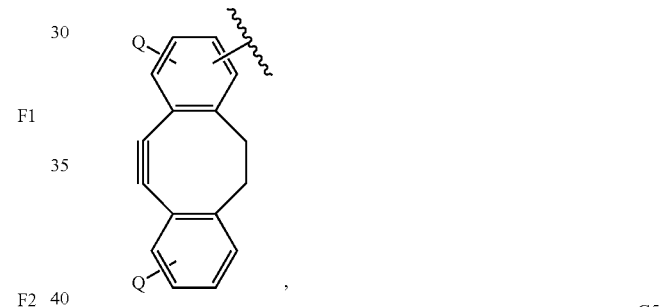
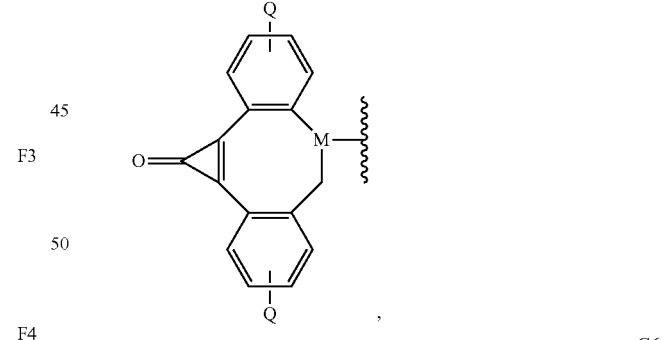
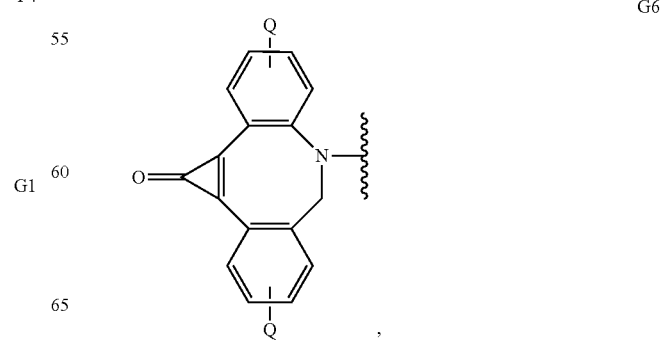

-continued
G7
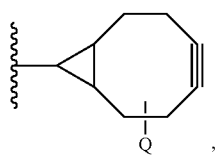
G8
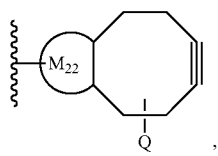
G9
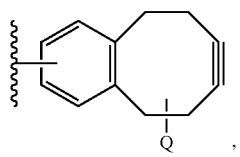
G10
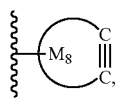
G11
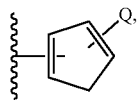
G12
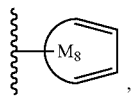
G13
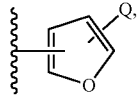
G14
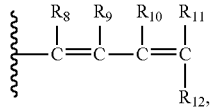
G15
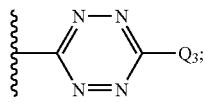
Group Gb:
G21
G22
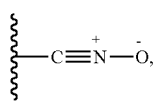
G23
-continued
G24
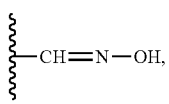
G25
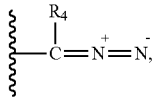
G26
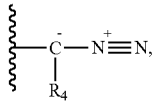
G27
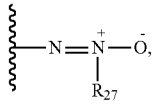
G28
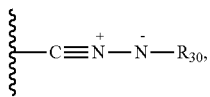
G29
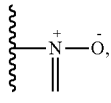
G30
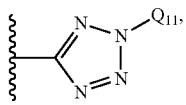
G31
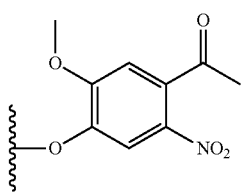
G32
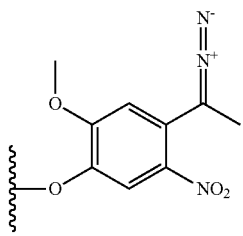
Group H:
H1
H2
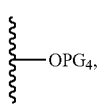
H3
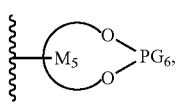

151
-continued
H4
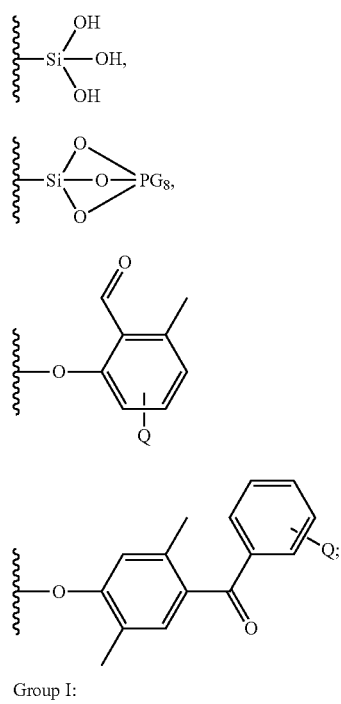
H5
H6
H7
Group I:
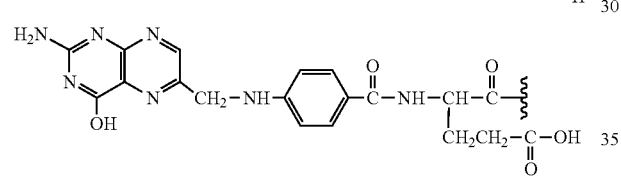
I1
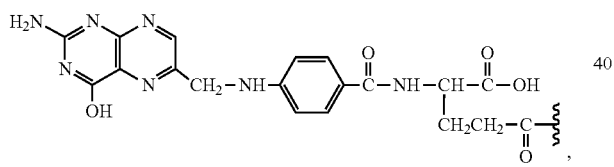
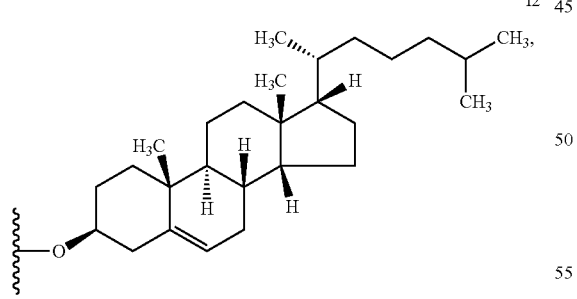
I2
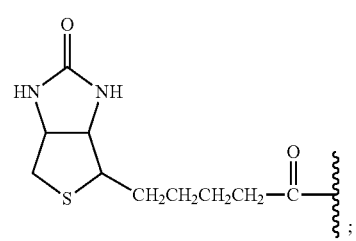
I3
152
-continued
Group J:
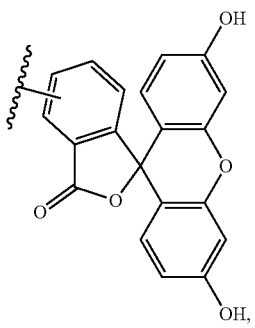
J1
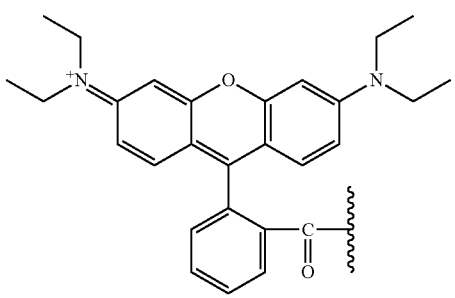
J2
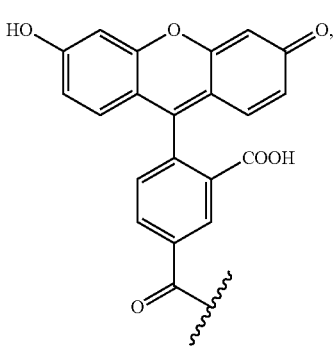
J3
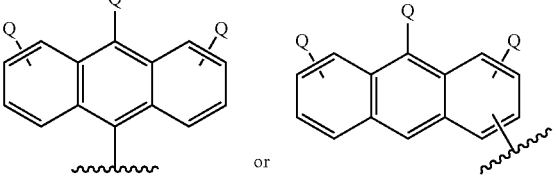
J4
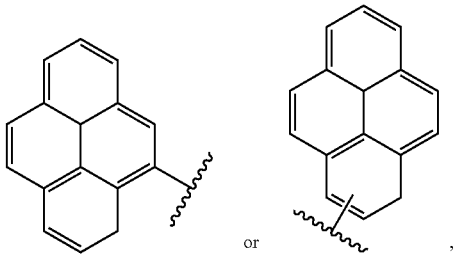
J5

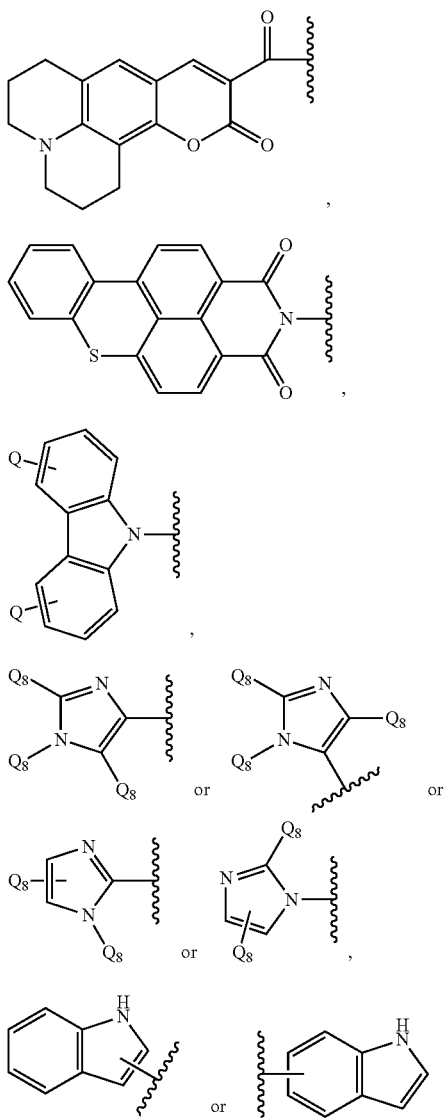

and the like.

Wherein, $X_6$ is a terminal group connected to the oxygen atom of an ester group, and can be a hydroxyl protecting group or a group $LG_4$.

Wherein, the definitions of $LG_4$, Q, $Q_5$, $PG_6$, $M_5$ and $M_5$-membered rings are the same as above, no more repeated here.

Wherein, $Y_1$ is a leaving group that connects to a sulfonyl group, a sulfinyl group, an oxysulfonyl group (a sulfonate group) or an oxysulfinyl group (a sulfinate group). $Y_1$ is not particularly limited. $Y_1$ is preferably a $C_{1-10}$ hydrocarbyl group or a fluorinated $C_{1-10}$ hydrocarbyl group. $Y_1$ is more preferably a $C_{1-10}$ alkyl group, a $C_{2-10}$ alkenyl group, a phenyl group, the like or the substituted form of any aforesaid group. Wherein, the atom or group substituent can be a halogen atom, an alkenyl group, an alkoxy group or a nitro group. Specifically, for example, $Y_1$ can be but not limited to a methyl group, an ethyl group, an n-propyl group, an isopropyl group, a butyl group, a pentyl group, a hexyl group, a heptyl group, an octyl group, a nonyl group, a decyl group, an ethenyl group, a phenyl group, a benzyl group, a p-methylphenyl group, a 4-(trifluoromethoxy)phenyl group, a trifluoromethyl group, a 2,2,2-trifluoroethyl group or the like. Wherein, the butyl group includes but is not limited to an n-butyl group and a t-butyl group. The octyl group includes but is not limited to an n-octyl group and a 2-ethylhexyl group. $Y_1$ is preferably a methyl group, a methylphenyl group, a 2,2,2-trifluoroethyl group, a trifluoromethyl group, an ethenyl group or the like.

Wherein, W is F, Cl, Br or I, and preferably Br or Cl.
Wherein, $W_2$ is F, Cl, Br or I, and preferably I.
Wherein, $W_3$ is a leaving group, and can be but not limited to F, Cl, Br, I or PhS—, and preferably Br or Cl.
Wherein,

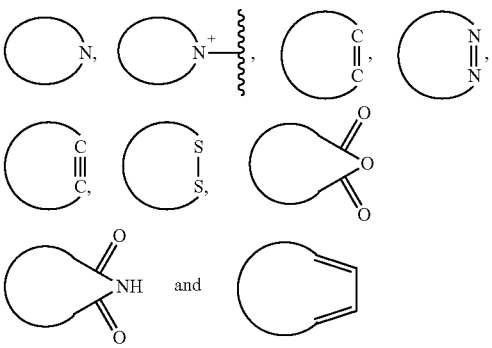

are cyclic structures, also denoted as ring structures, in which the ring skeleton contains a nitrogen atom, a nitrogen cation, a carbon-carbon double bond, an azo bond, a carbon-carbon triple bond, a disulfide bond, an anhydride moiety, an imide moiety and a dienylene moiety, respectively, and the cyclic structures include but are not limited to a carbon ring, a heteroring, a benzoheteroring, a substituted carbon ring, a substituted heteroring, a substituted benzoheteroring and the like.

Wherein, M is a carbon atom or a heteroatom of the ring skeleton, i.e. a ring-membering atom, including but not limited to a carbon atom, a nitrogen atom, a phosphorus atom or a silicon atom.

Wherein, $M_8$ is a carbon atom or a heteroatom of the ring skeleton. $M_8$ is preferably a carbon atom, a nitrogen atom, a phosphorus atom or a silicon atom. The number of ring-membering atoms of $M_8$-membered rings is not particularly limited, preferably from 4 to 50, more preferably from 4 to 32, more preferably from 5 to 32, more preferably from 5 to 18, and most preferably from 5 to 8. $M_8$ can be a carbon atom or a heteroatom of a 4- to 50-membered ring skeleton, preferably a carbon atom, a nitrogen atom, a phosphorus atom or a silicon atom of a 4- to 32-membered ring skeleton, more preferably a carbon atom, a nitrogen atom, a phosphorus atom or a silicon atom of a 5- to 32-membered ring skeleton, more preferably a carbon atom, a nitrogen atom, a phosphorus atom or a silicon atom of a 5- to 18-membered ring skeleton, and most preferably a carbon atom, a nitrogen atom, a phosphorus atom or a silicon atom of a 5- to 8-membered ring skeleton.

Wherein, $M_{22}$ is a carbon atom or a heteroatom of an alicyclic ring or an aliphatic-derived heteroring, wherein, $M_{22}$ can be a carbon atom, a nitrogen atom, a phosphorus atom or a silicon atom; the number of ring-membering atoms of $M_{22}$-membered rings is 4, 5, 6, 7 or 8, and preferably 4, 5 or 6.

Wherein, $PG_8$ is a protecting group for orthocarbonic acid and orthosilicic acid, wherein, the functional group D8 is the protected form of orthoacid, and the functional group H5 is the protected form of orthosilicic acid. $PG_8$ can be an individual trivalent end-group such as

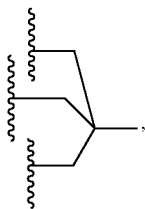 [SMILES: *CC(C)(C*)C*]

taking D8 for example, corresponding to

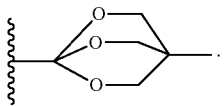

$PG_8$ can also be the combination of two or three individual end-groups, e.g., corresponding to

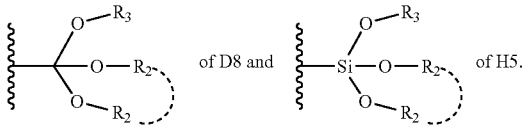

Wherein, $R_2$ is a terminal group (a monovalent group) or a divalent linking group that connects with an oxygen atom or a sulfur atom in structures such as acetal, ketal, hemiacetal, hemiketal, orthoester, thioacetal, thioketal, thiohemiacetal, thiohemiketal, thioorthoester, orthosilicate and the like, e.g., D7, D18, D8 and H5.

$R_2$ is a Hydrogen Atom, a Divalent Group $R_{21}$ or a Monovalent Group $R_3$.

Wherein, $R_{21}$ is a divalent linking group and participates in forming a ring (a ring-membering linking group).

The carbon-atom number of $R_{21}$ is not particularly limited, preferably from 1 to 20, and more preferably from 1 to 10.

The structure of $R_{21}$ is not particularly limited, including but not limited to a linear structure, a branched structure bearing pendant groups or a ring-containing structure. Wherein, the ring is not particularly limited, and preferably an aliphatic ring, an aromatic ring, a sugar ring or a condensed ring.

$R_{21}$ can contain or not contain heteroatoms.

$R_{21}$ is a $C_{1-20}$ hydrocarbylene group, a divalent $C_{1-20}$ heterohydrocarbyl group, a substituted $C_{1-20}$ hydrocarbylene group, a substituted divalent $C_{1-20}$ heterohydrocarbyl group, or a divalent linking group combined by any two or three aforesaid groups. Wherein, the atom or group substituent is not particularly limited, including but not limited to all the above-described atom and group substituents in the term-defining section, and can be a halogen atom, a hydrocarbyl substituent or a heteroatom-containing substituent.

$R_{21}$ is preferably a $C_{1-20}$ open-chain alkylene group, a $C_{2-20}$ open-chain alkenylene group, a $C_{3-20}$ cycloalkylene group, a $C_{3-20}$ cycloalkenylene group, an arylene group, an arylhydrocarbylene group, a divalent $C_{1-20}$ aliphatic-derived heteroalkyl group, a divalent $C_{2-20}$ aliphatic-derived heteroalkenyl group, a divalent heteroaryl group, a divalent heteroarylhydrocarbyl group, a substituted alkylene group, a substituted $C_{2-20}$ open-chain alkenylene group, a substituted $C_{3-20}$ cycloalkylene group, a substituted $C_{3-20}$ cycloalkenylene group, a substituted arylene group, a substituted arylhydrocarbylene group, a substituted divalent $C_{1-20}$ aliphatic-derived heteroalkyl group, a substituted divalent $C_{2-20}$ aliphatic-derived heteroalkenyl group, a substituted divalent heteroaryl group, a substituted divalent heteroarylhydrocarbyl group, or a divalent linking group combined by any two or three aforesaid groups. Wherein, the atom or group substituent is preferably a halogen atom, an alkoxy group or a nitro group.

$R_{21}$ is more preferably a divalent linking group selected from the group consisting of a $C_{2-10}$ open-chain alkylene group, a $C_{3-10}$ open-chain alkenylene group, a $C_{3-10}$ cycloalkylene group, a $C_{3-10}$ cycloalkenylene group, an arylene group, an arylhydrocarbylene group, a divalent C10 aliphatic-derived heteroalkyl group, a divalent $C_{2-10}$ aliphatic-derived heteroalkenyl group, a divalent heteroaryl group, a divalent heteroarylhydrocarbyl group, a substituted alkylene group, a substituted $C_{2-10}$ open-chain alkenylene group, a substituted $C_{3-10}$ cycloalkylene group, a substituted $C_{3-10}$ cycloalkenylene group, a substituted arylene group, a substituted arylalkylene group, a substituted divalent $C_{1-10}$ aliphatic-derived heteroalkyl group, a substituted divalent $C_{2-10}$ aliphatic-derived heteroalkenyl group, a substituted divalent heteroaryl group, a substituted divalent heteroarylhydrocarbyl group, a divalent linking group combined by any two aforesaid groups and a divalent linking group combined by any three aforesaid groups.

Specifically, $R_{21}$ can be a methylene group, an ethylene group, a propylene group, a butylene group, a pentylene group, a hexylene group, a heptylene group, an octylene group, a nonylene group, a decylene group, a 1,2-phenylene group, a benzylene group, a $C_{1-20}$ oxa-alkylene group, a $C_{1-20}$ thia-alkylene group, a $C_{1-20}$ aza-alkylene group, an aza-arylhydrocarbylene group, the substituted form of any aforesaid group or the combination of any two or two more identical or different aforesaid groups or/and substituted forms. Wherein, the atom or group substituent can be a halogen atom, a hydrocarbyl substituent or a heteroatom-containing substituent, and preferably a halogen atom, an alkoxy group or a nitro group.

$R_{21}$ is more preferably a 1,2-ethylene group or a 1,3-propylene group.

Wherein, $R_3$ is a terminal group connecting to an oxy group (—O—) or a thioxy group (—S—).

The carbon-atom number of $R_3$ is not particularly limited, preferably from 1 to 20, and more preferably from 1 to 10.

The structure of $R_3$ is not particularly limited, including but not limited to a linear structure, a branched structure bearing pendant groups or a ring-containing structure. The ring is not particularly limited, and preferably an aliphatic ring, an aromatic ring, a sugar ring or a condensed ring.

$R_3$ can contain heteroatoms or do not contain heteroatoms.

$R_3$ can be a $C_{1-20}$ hydrocarbyl group, a $C_{1-20}$ heterohydrocarbyl group, a $C_{1-20}$ substituted hydrocarbyl group or a $C_{1-20}$ substituted heterohydrocarbyl group. The heteroatom or group substituent within $R_3$ is not particularly limited, including but not limited to all the above-described heteroatoms and group substituents in the term-defining section, and can be preferably a halogen atom, a hydrocarbyl substituent or a heteroatom-containing substituent.

$R_3$ is preferably a $C_{1-20}$ alkyl group, a $C_{3-20}$ alkenyl-hydrocarbyl group, an aryl group, an arylhydrocarbyl group, a $C_{1-20}$ aliphatic-derived heterohydrocarbyl group, a heteroaryl group, a heteroarylhydrocarbyl group, a substituted $C_{1-20}$ alkyl group, a substituted $C_{3-20}$ alkenyl-hydrocarbyl group, a substituted aryl group, a substituted arylhydrocarbyl group, a substituted $C_{1-20}$ aliphatic-derived heterohydrocarbyl group, a substituted heteroaryl group or a substituted heteroarylhydrocarbyl group. Wherein, the atom or group substituent can be a halogen atom, a hydrocarbyl substituent or a heteroatom-containing substituent.

$R_3$ is preferably a $C_{1-20}$ linear alkyl group, a $C_{1-20}$ branched alkyl group, a $C_{3-20}$ cycloalkyl group, an aryl group, an arylhydrocarbyl group, a $C_{1-20}$ aliphatic-derived heterohydrocarbyl group, a heteroaryl group, a heteroarylhydrocarbyl group, a substituted $C_{1-20}$ linear alkyl group, a substituted $C_{1-20}$ branched alkyl group, a substituted $C_{3-20}$ cycloalkyl group, a substituted aryl group, a substituted arylhydrocarbyl group, a substituted $C_{1-20}$ aliphatic-derived heterohydrocarbyl group, a substituted heteroaryl group or a substituted heteroarylhydrocarbyl group. Wherein, the atom or group substituent can be a halogen atom, a hydrocarbyl substituent or a heteroatom-containing substituent, and can be preferably a halogen atom, an alkoxy group, a hydrocarbyl group, an aryl group or a nitro group.

$R_3$ is more preferably a $C_{1-10}$ linear alkyl group, a $C_{1-10}$ branched alkyl group, a $C_{3-10}$ cycloalkyl group, an aryl group, an arylhydrocarbyl group, a $C_{1-10}$ aliphatic-derived heterohydrocarbyl group, a heteroaryl group, a heteroarylhydrocarbyl group, a substituted $C_{1-10}$ linear alkyl group, a substituted $C_{1-10}$ branched alkyl group, a substituted $C_{3-10}$ cycloalkyl group, a substituted aryl group, a substituted arylhydrocarbyl group, a substituted $C_{1-10}$ aliphatic-derived heterohydrocarbyl group, a substituted heteroaryl group or a substituted heteroarylhydrocarbyl group. Wherein, the atom or group substituent can be a halogen atom, a hydrocarbyl substituent or a heteroatom-containing substituent, and can be preferably a fluorine atom, a chlorine atom, a bromine atom, an iodine atom, a hydrocarbyl group, an aryl group or a nitro group, and more preferably a halogen atom, an alkoxy group or a nitro group.

Specifically, $R_3$ can be a methyl group, an ethyl group, an n-propyl group, an isopropyl group, a butyl group, a pentyl group, a hexyl group, a heptyl group, an octyl group, a nonyl group, a decyl group, a benzyl group, an allyl group, the like or the substituted form of any aforesaid group. Wherein, the butyl group includes but is not limited to an n-butyl group and a t-butyl group. The octyl group includes but is not limited to an n-octyl group and a 2-ethylhexyl group. Wherein, the atom or group substituent can be a halogen atom, a hydrocarbyl substituent or a heteroatom-containing substituent, and can be preferably a fluorine atom, a chlorine atom, a bromine atom, an iodine atom, a hydrocarbyl group, an aryl group or a nitro group, and more preferably a halogen atom, an alkoxy group or a nitro group.

$R_3$ is most preferably a methyl group, an ethyl group or a benzyl group.

Wherein, $R_4$ is a hydrogen atom, an atom substituent or a group substituent linked to the carbon atom of —$(R_4)C=N^+=N^-$ (G25) or —$(R_4)C^-—N^+\equiv N$ (G26).

When as an atom substituent, $R_4$ can be a halogen atom, and preferably a fluorine atom.

When as a group substituent, the carbon-atom number of $R_4$ is not particularly limited, preferably from 1 to 20, and more preferably from 1 to 10.

When as a group substituent, the structure of $R_4$ is not particularly limited, including but not limited to a linear structure, a branched structure bearing pendant groups or a ring-containing structure. Wherein, the ring is not particularly limited, and preferably an aliphatic ring, an aromatic ring, a sugar ring or a condensed ring.

When as a group substituent, $R_4$ can contain heteroatoms, or not.

$R_4$ can be a hydrogen atom, a halogen atom, a $C_{1-20}$ hydrocarbyl group, a $C_{1-20}$ heterohydrocarbyl group, a substituted $C_{1-20}$ hydrocarbyl group or a substituted heterohydrocarbyl group. Wherein, the atom or group substituent of $R_4$ is not particularly limited, including but not limited to all the above-described atom and group substituents in the term-defining section, and can be a halogen atom, a hydrocarbyl substituent or a heteroatom-containing substituent.

$R_4$ is more preferably a hydrogen atom, a halogen atom, a $C_{1-20}$ alkyl group, a $C_{2-20}$ unsaturated aliphatic hydrocarbyl group, an aryl group, an arylhydrocarbyl group, a $C_{1-20}$ heterohydrocarbyl group, a $C_{1-20}$ hydrocarbyloxy-acyl group, a $C_{1-20}$ hydrocarbylthio-acyl group, a $C_{1-20}$ hydrocarbylamino-acyl group or the substituted form of any aforesaid group. Wherein, the acyl group within $R_4$ is not particularly limited, including but not limited to all the acyl types described in the term-defining section, and more preferably a carbonyl group or a thiocarbonyl group.

$R_4$ is more preferably a hydrogen atom, a halogen atom, a $C_{1-20}$ alkyl group, a $C_{2-20}$ alkenyl group, an aryl group, an arylhydrocarbyl group, a $C_{1-20}$ aliphatic-derived heterohydrocarbyl group, a heteroaryl group, a heteroarylhydrocarbyl group, a $C_{1-20}$ alkoxy-acyl group, an aryloxy-acyl group, a $C_{1-20}$ (alkylthio)acyl group, an (arylthio)acyl group, a $C_{1-20}$ alkylamino-acyl group, an arylamino-acyl group or the substituted form of any aforesaid group.

$R_4$ is more preferably a hydrogen atom, a halogen atom, a $C_{1-20}$ alkyl group, a $C_{2-20}$ alkenyl group, an aryl group, an arylhydrocarbyl group, a $C_{1-20}$ aliphatic-derived heterohydrocarbyl group, a heteroaryl group, a heteroarylhydrocarbyl group, a $C_{1-20}$ alkoxycarbonyl group, an aryloxycarbonyl group, a $C_{1-20}$ (alkylthio)carbonyl group, an (arylthio)carbonyl group, a $C_{1-20}$ alkylaminocarbonyl group, an arylaminocarbonyl group, a $C_{1-20}$ alkoxy-thiocarbonyl group, an aryloxy-thiocarbonyl group, a $C_{1-20}$ (alkylthio)thiocarbonyl group, an (arylthio)thiocarbonyl group, a $C_{1-20}$ alkylaminothiocarbonyl group, an arylaminothiocarbonyl group or the substituted form of any aforesaid group.

Specifically, $R_4$ can be but not limited to a hydrogen atom, a fluorine atom, a chlorine atom, a bromine atom, an iodine atom, a methyl group, an ethyl group, an n-propyl group, an isopropyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, an allyl group, a propenyl group, an ethenyl group, a phenyl group, a methylphenyl group, a butylphenyl group, a benzyl group, a methoxycarbonyl group, an ethoxycarbonyl group, a phenoxycarbonyl group, a benzyloxycarbonyl group, a (methylthio)carbonyl group, an (ethylthio)carbonyl group, a (phenylthio)carbonyl group, a (benzylthio)carbonyl group, an ethylaminocarbonyl group, a benzylaminocarbonyl group, a methoxy-thiocarbonyl group, an ethoxy-thiocarbonyl group, a phenoxy-thiocarbonyl group, a benzyloxy-thiocarbonyl group, a (methylthio)thiocarbonyl group, an (ethylthio)thiocarbonyl group, a (phenylthio)thiocarbonyl group, a (benzylthio)thiocarbonyl group, an ethylaminothiocarbonyl group, a benzylaminothiocarbonyl group, a substituted $C_{1-20}$ alkyl group, a substituted $C_{2-20}$ alkenyl group, a substituted aryl group, a substituted arylhydrocarbyl group, a substituted $C_{1-20}$ aliphatic-derived heterohydrocarbyl group, a substituted heteroaryl group, a substituted heteroarylhydrocarbyl group, a substituted $C_{1-20}$ alkoxycarbonyl group, a substituted aryloxycarbonyl group, a substituted $C_{1-20}$ (alkylthio)carbonyl group, a substituted (arylthio)carbonyl group, a substituted $C_{1-20}$ alkylaminocarbonyl group, a substituted arylaminocarbonyl group, a substituted $C_{1-20}$ alkoxy-thiocarbonyl group, a substituted aryloxy-thiocarbonyl group, a substituted $C_{1-20}$ (alkylthio)thiocarbonyl group, a substituted (arylthio)thiocarbonyl group, a substituted $C_{1-20}$ alkylaminothiocarbonyl group, a substituted arylaminothiocarbonyl group or the like. Wherein, the butyl group includes but is not limited to an n-butyl group and a t-butyl group. The octyl group includes but is not limited to an n-octyl group and a 2-ethylhexyl group. Wherein, the atom or group substituent can be a halogen atom, a hydrocarbyl substituent or a heteroatom-containing substituent, and can be preferably a fluorine atom, a chlorine atom, a bromine atom, an iodine atom, an alkenyl group or a nitro group.

$R_4$ is further preferably a hydrogen atom, a methyl group, an ethyl group, an n-propyl group, an isopropyl group, a butyl group, a pentyl group, a hexyl group, a heptyl group, an octyl group, a nonyl group, a decyl group, an allyl group, a propenyl group, an ethenyl group, a phenyl group, a methylphenyl group, a butylphenyl group, a benzyl group, a methoxycarbonyl group, an ethoxycarbonyl group, a phenoxycarbonyl group, a benzyloxycarbonyl group, a (methylthio)carbonyl group, an (ethylthio)carbonyl group, a (phenylthio)carbonyl group, a (benzylthio)carbonyl group, an ethylaminocarbonyl group, a benzylaminocarbonyl group, a methoxy-thiocarbonyl group, an ethoxy-thiocarbonyl group, a phenoxy-thiocarbonyl group, a benzyloxy-thiocarbonyl group, a (methylthio)thiocarbonyl group, an (ethylthio)thiocarbonyl group, a (phenylthio)thiocarbonyl group, a (benzylthio)thiocarbonyl group, an ethylaminothiocarbonyl group, a benzylaminothiocarbonyl group, a $C_{1-10}$ halohydrocarbyl group, a halophenyl group, a halobenzyl group, a nitrophenyl group, the like or the substituted form of any aforesaid group.

$R_4$ is preferably a hydrogen atom, a methyl group, an ethyl group, an n-propyl group, an isopropyl group, a butyl group, a pentyl group, a hexyl group, a heptyl group, an octyl group, a nonyl group, a decyl group, an allyl group, a propenyl group, an ethenyl group, a phenyl group, a methylphenyl group, a butylphenyl group or a benzyl group.

$R_4$ is most preferably a hydrogen atom, a methyl group or a benzyl group.

Wherein, $R_8$, $R_9$, $R_{10}$, $R_{11}$ and $R_{12}$ are each independently a hydrogen atom, an atom substituent or a group substituent of carbon-carbon double bonds (—C=C—). In one molecule, $R_8$, $R_9$, $R_{10}$, $R_{11}$ and $R_{12}$ can be identical or not identical.

When as an atom substituent, $R_8$, $R_9$, $R_{10}$, $R_{11}$ and $R_{12}$ each independently can be a halogen atom selected from F, Cl, Br and I, and each independently preferably a fluorine atom.

When as a group substituent, the carbon-atom number of $R_8$, $R_9$, $R_{10}$, $R_{11}$ and $R_{12}$ are not particularly limited, each independently preferably from 1 to 20, and more preferably from 1 to 10.

When as a group substituent, the structure of $R_8$, $R_9$, $R_{10}$, $R_{11}$ and $R_{12}$ are not particularly limited, each independently can be but not limited to a linear structure, a branched structure bearing pendant groups or a ring-containing structure. The ring is not particularly limited, and preferably an aliphatic ring, an aromatic ring, a sugar ring or a condensed ring.

When as a group substituent, $R_8$, $R_9$, $R_{10}$, $R_{11}$ and $R_{12}$ each independently can contain heteroatoms or not.

$R_8$, $R_9$, $R_{10}$, $R_{11}$ and $R_{12}$ each independently can be a hydrogen atom, a halogen atom, a $C_{1-20}$ hydrocarbyl group, a $C_{1-20}$ heterohydrocarbyl group, a substituted $C_{1-20}$ hydrocarbyl group or a substituted heterohydrocarbyl group. Wherein, the atom or group substituents are not particularly limited, including but not limited to all the above-described atom and group substituents in the term-defining section, and can be a halogen atom, a hydrocarbyl substituent or a heteroatom-containing substituent.

$R_8$, $R_9$, $R_{10}$, $R_{11}$ and $R_{12}$ are each independently more preferably a hydrogen atom, a halogen atom, a $C_{1-20}$ alkyl group, a $C_{2-20}$ unsaturated aliphatic hydrocarbyl group, an aryl group, an arylhydrocarbyl group, a $C_{1-20}$ heterohydrocarbyl group, a $C_{1-20}$ hydrocarbyloxy-acyl group, a $C_{1-20}$ hydrocarbylthio-acyl group, a $C_{1-20}$ hydrocarbylamino-acyl group or the substituted form of any aforesaid group. Wherein, the acyl group is not particularly limited, including but not limited to all the above-described acyl groups in the term-defining section.

$R_8$, $R_9$, $R_{10}$, $R_{11}$ and $R_{12}$ are each independently more preferably a hydrogen atom, a halogen atom, a $C_{1-20}$ alkyl group, a $C_{2-20}$ alkenyl group, an aryl group, an arylhydrocarbyl group, a $C_{1-20}$ aliphatic-derived heterohydrocarbyl group, a heteroaryl group, a heteroarylhydrocarbyl group, a $C_{1-20}$ alkoxy-acyl group, an aryloxy-acyl group, a $C_{1-20}$ alkylthio-acyl group, an arylthio-acyl group, a $C_{1-20}$ alkylamino-acyl group, an arylamino-acyl group or the substituted form of any aforesaid group. The atom or group substituent can be a halogen atom, a hydrocarbyl substituent or a heteroatom-containing substituent, and can be preferably a halogen atom, an alkenyl group or a nitro group.

$R_8$, $R_9$, $R_{10}$, $R_{11}$ and $R_{12}$ are each independently more preferably a hydrogen atom, a halogen atom, a $C_{1-20}$ alkyl group, a $C_{2-20}$ alkenyl group, an aryl group, an arylhydrocarbyl group, a $C_{1-20}$ aliphatic-derived heterohydrocarbyl group, a heteroaryl group, a heteroarylhydrocarbyl group, a $C_{1-20}$ alkoxycarbonyl group, an aryloxycarbonyl group, a $C_{1-20}$ (alkylthio)carbonyl group, an (arylthio)carbonyl group, a $C_{1-20}$ alkylaminocarbonyl group, an arylaminocarbonyl group, a $C_{1-20}$ alkoxy-thiocarbonyl group, an aryloxy-thiocarbonyl group, a $C_{1-20}$ (alkylthio)thiocarbonyl group, an (arylthio)thiocarbonyl group, a $C_{1-20}$ alkylaminothiocarbonyl group, an arylaminothiocarbonyl group or the substituted form of any aforesaid group. The acyl group is more preferably a carbonyl group or a thiocarbonyl group. Wherein, the atom or group substituent can be a halogen atom, a hydrocarbyl substituent or a heteroatom-containing substituent, and can be preferably a fluorine atom, a chlorine atom, a bromine atom, an iodine atom, an alkenyl group or a nitro group.

Specifically, $R_8$, $R_9$, $R_{10}$, $R_{11}$ and $R_{12}$ each independently can be but not limited to a hydrogen atom, a fluorine atom, a chlorine atom, a bromine atom, an iodine atom, a methyl group, an ethyl group, an n-propyl group, an isopropyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, an allyl group, a propenyl group, an ethenyl group, a phenyl group, a methylphenyl group, a butylphenyl group, a benzyl group, a methoxycarbonyl group, an ethoxycarbonyl group, a phenoxycarbonyl group, a benzyloxycarbonyl group, a (methylthio)carbonyl group, an (ethylthio)carbonyl group, a (phenylthio)carbonyl group, a (benzylthio)carbonyl group, an ethylaminocarbonyl group, a benzylaminocarbonyl group, a methoxy-thiocarbonyl group, an ethoxy-thiocarbonyl group, a phenoxy-thiocarbonyl group, a benzyloxy-thiocarbonyl group, a (methylthio)thiocarbonyl group, an (ethylthio)thiocarbonyl group, a (phenylthio)thiocarbonyl group, a (benzylthio)thiocarbonyl group, an ethylaminothiocarbonyl group, a benzylaminothiocarbonyl group, a substituted $C_{1-20}$ alkyl group, a substituted $C_{2-20}$ alkenyl group, a substituted aryl group, a substituted arylhydrocarbyl group, a substituted $C_{1-20}$ aliphatic-derived heterohydrocarbyl group, a substituted heteroaryl group, a substituted heteroarylhydrocarbyl group, a substituted $C_{1-20}$ alkoxycarbonyl group, a substituted aryloxycarbonyl group, a substituted $C_{1-20}$ (alkylthio)carbonyl group, a substituted (arylthio)carbonyl group, a substituted $C_{1-20}$ alkylaminocarbonyl group, a substituted arylaminocarbonyl group, a substituted $C_{1-20}$ alkoxy-thiocarbonyl group, a substituted aryloxy-thiocarbonyl group, a substituted $C_{1-20}$ (alkylthio)thiocarbonyl group, a substituted (arylthio)thiocarbonyl group, a substituted $C_{1-20}$ alkylaminothiocarbonyl group, a substituted arylaminothiocarbonyl group or the like. Wherein, the butyl group includes but is not limited to an n-butyl group and a t-butyl group. The octyl group includes but is not limited to an n-octyl group and a 2-ethylhexyl group. Wherein, the atom or group substituent can be a halogen atom, a hydrocarbyl substituent or a heteroatom-containing substituent, and preferably a halogen atom, an alkenyl group or a nitro group.

$R_8$, $R_9$, $R_{10}$, $R_{11}$ and $R_{12}$ are each independently further preferably a hydrogen atom, a methyl group, an ethyl group, an n-propyl group, an isopropyl group, a butyl group, a pentyl group, a hexyl group, a heptyl group, an octyl group, a nonyl group, a decyl group, an allyl group, a propenyl group, an ethenyl group, a phenyl group, a methylphenyl group, a butylphenyl group, a benzyl group, a methoxycarbonyl group, an ethoxycarbonyl group, a phenoxycarbonyl group, a benzyloxycarbonyl group, a (methylthio)carbonyl group, an (ethylthio)carbonyl group, a (phenylthio)carbonyl group, a (benzylthio)carbonyl group, an ethylaminocarbonyl group, a benzylaminocarbonyl group, a methoxy-thiocarbonyl group, an ethoxy-thiocarbonyl group, a phenoxy-thiocarbonyl group, a benzyloxy-thiocarbonyl group, a (methylthio)thiocarbonyl group, an (ethylthio)thiocarbonyl group, a (phenylthio)thiocarbonyl group, a (benzylthio)thiocarbonyl group, an ethylaminothiocarbonyl group, a benzylaminothiocarbonyl group, a $C_{1-10}$ halohydrocarbyl group, a halophenyl group, a halobenzyl group, a nitrophenyl group, the like or the substituted form of any aforesaid group. Wherein, the atom or group substituent can be a halogen atom, a hydrocarbyl substituent or a heteroatom-containing substituent, and can be preferably a fluorine atom, a chlorine atom, a bromine atom, an iodine atom, an alkenyl group or a nitro group.

$R_8$, $R_9$, $R_{10}$, $R_{11}$ and $R_{12}$ are each independently more preferably a hydrogen atom, a fluorine atom or a methyl group.

In the functional group $E_3$, $R_8$ is most preferably a methyl group.

Wherein, $R_{24}$ is a terminal monovalent group connecting to a disulfide bond, and preferably a $C_{1-20}$ alkyl group, an aryl group, an arylhydrocarbyl group, a heterosubstituted phenyl group with one or more ring-membering heteroatoms or the like, such as a 2-pyridyl group. Herein, the heterosubstituted phenyl group also allows presence or absence of heteroatom substituents.

Wherein, $R_{27}$ is a substituent connecting to an azo group, and preferably a phenyl group, a substituted phenyl group or a heterosubstituted phenyl group with one or more ring-membering heteroatoms. Herein, the heterosubstituted phenyl group also allows presence or absence of heteroatom substituents.

Wherein, $R_{30}$ is a hydrocarbyl group, and preferably a $C_{1-20}$ alkyl group, a benzyl group, or a substituted benzyl group in which the benzene ring is substituted with one or more $C_{1-20}$ hydrocarbyl groups.

Wherein, $M_{19}$, $M_{20}$ and $M_{21}$ are each independently an oxygen atom or a sulfur atom, and in one molecule they can be the same or different.

Wherein, $X_{11}$ is a terminal group connecting to a carbonyl group or a thiocarbonyl group, preferably a $C_{1-20}$ alkyl group, and more preferably a methyl group, an ethyl group, an isopropyl group or a t-butyl group.

Wherein, $X_{12}$ is a terminal group connecting to a carbonate group or a thiocarbonate group, and can be selected from hydrocarbyl groups with or without a phenyl ring, preferably a $C_{1-20}$ hydrocarbyl group, and more preferably a $C_{1-20}$ alkyl group, a phenylhydrocarbyl group or a hydrocarbyl-substituted phenyl group.

Wherein, $X_{13}$ is a terminal monovalent group connecting to a thioxy group, and can be selected from a mercapto protecting group and a group $LG_2$.

When as a mercapto protecting group, $X_{13}$ can be any of the mercapto protecting groups recited for $PG_2$.

Wherein, the carbon-atom number of $LG_2$ is not particularly limited, preferably from 1 to 20, and more preferably from 1 to 10.

The structure of $LG_2$ is not particularly limited, including but not limited to a linear structure, a branched structure bearing pendant groups or a ring-containing structure. Wherein, the ring is not particularly limited, and preferably an aliphatic ring, an aromatic ring, a sugar ring or a condensed ring.

$LG_2$ can contain heteroatoms, or do not contain heteroatoms.

$LG_2$ can be a $C_{1-20}$ hydrocarbyl group, a $C_{1-20}$ heterohydrocarbyl group, a substituted $C_{1-20}$ hydrocarbyl group or a substituted heterohydrocarbyl group. Wherein, the heteroatom or group substituent within $LG_2$ is not particularly limited, including but not limited to all the above-described heteroatom and group substituents in the term-defining section, and can be a halogen atom, a hydrocarbyl substituent or a heteroatom-containing substituent.

$LG_2$ is more preferably a $C_{1-20}$ alkyl group, a $C_{2-20}$ unsaturated aliphatic hydrocarbyl group, an aryl group, an arylhydrocarbyl group, a $C_{1-20}$ heterohydrocarbyl group, a $C_{1-20}$ alkylthio group, a $C_{1-20}$ aliphatic-derived heterohydrocarbylthio group, an arylthio group, an arylhydrocarbylthio group, a $C_{1-20}$ aliphatic hydrocarbyl-acyl group, a $C_{1-20}$ aliphatic-derived heterohydrocarbyl-acyl group, an aryl-acyl group, a heteroaryl-acyl group, a $C_{1-20}$ hydrocarbyloxy-acyl group, a $C_{1-20}$ hydrocarbylthio-acyl group, a $C_{1-20}$ hydrocarbylamino-acyl group, a $C_{1-20}$ heterohydrocarbyloxy-acyl group, a $C_{1-20}$ heterohydrocarbylthio-acyl group, a $C_{1-20}$ heterohydrocarbylamino-acyl group or the substituted form of any aforesaid group. Wherein, the acyl group within $LG_2$ is not particularly limited, including but not limited to all the above-described acyl groups in the term-defining section. For examples, the acyl group within $LG_2$ can be a carbonyl group, a sulfonyl group, a sulfinyl group, a phosphoryl group, a phosphiryl group, a phosphinyl group, a nitroxyl group, a nitrosyl group, a thiocarbonyl group, an imidoyl group, a thiophosphoryl group, a dithiophosphoryl group, a trithiophosphoryl group, a thiophosphiryl group, a dithiophosphiryl group, a thiophosphinyl group, a thiophosphono group, a dithiophosphono group, a thiophosphino group or the like, preferably a carbonyl group, a thiocarbonyl group, a sulfonyl group or a sulfinyl group, and more preferably a carbonyl group, a thiocarbonyl group or a sulfonyl group.

$LG_2$ is more preferably a $C_{1-20}$ alkyl group, an aryl group, an arylalkyl group, a $C_{1-20}$ heteroalkyl group, a heteroaryl group, a heteroarylalkyl group, a $C_{1-20}$ alkylthio group, an arylthio group, an arylalkylthio group, a $C_{1-20}$ heteroalkylthio group, a heteroarylthio group, a heteroarylalkylthio group, a $C_{1-20}$ alkylcarbonyl group, an arylcarbonyl group, an arylalkylcarbonyl group, a $C_{1-20}$ heteroalkylcarbonyl group, a heteroarylcarbonyl group, a heteroarylalkylcarbonyl group, a $C_{1-20}$ alkoxycarbonyl group, an aryloxycarbonyl group, an arylalkoxycarbonyl group, a $C_{1-20}$ (alkylthio)carbonyl group, an (arylthio)carbonyl group, an (arylalkylthio)carbonyl group, a $C_{1-20}$ alkylaminocarbonyl group, an arylaminocarbonyl group, an arylalkylaminocarbonyl group, a $C_{1-20}$ heteroalkoxycarbonyl group, a heteroaryloxycarbonyl group, a heteroarylalkoxycarbonyl group, a $C_{1-20}$ hetero(alkylthio)carbonyl group, a hetero(arylthio)carbonyl group, a hetero(arylalkylthio)carbonyl group, a $C_{1-20}$ heteroalkylaminocarbonyl group, a heteroarylaminocarbonyl group, a heteroarylalkylaminocarbonyl group, a $C_{1-20}$ alkyl-thiocarbonyl group, an aryl-thiocarbonyl group, an arylalkyl-thiocarbonyl group, a $C_{1-20}$ heteroalkyl-thiocarbonyl group, a heteroaryl-thiocarbonyl group, a heteroarylalkyl-thiocarbonyl group, a $C_{1-20}$ alkoxy-thiocarbonyl group, an aryloxy-thiocarbonyl group, an arylalkoxy-thiocarbonyl group, a $C_{1-20}$ (alkylthio)thiocarbonyl group, an (arylthio)thiocarbonyl group, an (arylalkylthio)thiocarbonyl group, a $C_{1-20}$ alkylaminothiocarbonyl group, an arylaminothiocarbonyl group, an arylalkylaminothiocarbonyl group, a $C_{1-20}$ heteroalkoxy-thiocarbonyl group, a heteroaryloxy-thiocarbonyl group, a heteroarylalkoxy-thiocarbonyl group, a $C_{1-20}$ hetero(alkylthio)thiocarbonyl group, a hetero(arylthio)thiocarbonyl group, a hetero(arylalkylthio)thiocarbonyl group, a $C_{1-20}$ heteroalkylaminothiocarbonyl group, a heteroarylaminothiocarbonyl group, a heteroarylalkylaminothiocarbonyl group or the substituted form of any aforesaid group.

$LG_2$ is more preferably a $C_{1-20}$ alkyl group, an aryl group, an arylalkyl group, a $C_{1-20}$ heteroalkyl group, a heteroaryl group and a heteroarylalkyl group, a $C_{1-20}$ alkylthio group, an arylthio group, an arylalkylthio group, a $C_{1-20}$ heteroalkylthio group, a heteroarylthio group, a heteroarylalkylthio group or the substituted form of any aforesaid group.

Specifically, $LG_2$ can be but not limited to a methyl group, an ethyl group, an n-propyl group, an isopropyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, an allyl group, a trityl group, a phenyl group, a benzyl group, a methylbenzyl group, a nitrobenzyl group, a t-butylthio group, a benzylthio group, a 2-pyridylthio group, an ethyl-acyl group, a benzoyl group, a methoxy-acyl group, an ethoxy-acyl group, a t-butoxy-acyl group, a phenoxy-acyl group, a benzyloxy-acyl group, a methylthio-acyl group, an ethylthio-acyl group, a t-butylthio-acyl group, a phenylthio-acyl group, a benzylthio-acyl group, a 2-pyridyl-acyl group (e.g., a 2-pyridylcarbonyl group), a methylamino-acyl group, an ethylamino-acyl group, a t-butylamino-acyl group, a benzylamino-acyl group, the like or the substituted form of any aforesaid group. Wherein, the butyl group includes but is not limited to an n-butyl group and a t-butyl group. The octyl group includes but is not limited to an n-octyl group and a 2-ethylhexyl group. Wherein, the atom or group substituent can be a halogen atom, a hydrocarbyl substituent or a heteroatom-containing substituent, and can be preferably a fluorine atom, a chlorine atom, a bromine atom, an iodine atom or a nitro group.

$LG_2$ is further preferably a methyl group, an ethyl group, an n-propyl group, an isopropyl group, a t-butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, an allyl group, a trityl group, a phenyl group, a benzyl group, a methylbenzyl group, a t-butylthio group, a benzylthio group, a 2-pyridylthio group, an acetyl group, a benzoyl group, a methoxycarbonyl group, an ethoxycarbonyl group, a t-butoxycarbonyl group, a phenoxycarbonyl group, a benzyloxycarbonyl group, a (methylthio)carbonyl group, an (ethylthio)carbonyl group, a (t-butylthio)carbonyl group, a (phenylthio)carbonyl group, a (benzylthio)carbonyl group, a 2-pyridylcarbonyl group, a methylaminocarbonyl group, an ethylaminocarbonyl group, a t-butylaminocarbonyl group, a benzylaminocarbonyl group, an ethyl-thiocarbonyl group, a phenyl-thiocarbonyl group, a methoxy-thiocarbonyl group, an ethoxy-thiocarbonyl group, a t-butoxy-thiocarbonyl group, a phenoxy-thiocarbonyl group, a benzyloxy-thiocarbonyl group, a (methylthio)thiocarbonyl group, an (ethylthio)thiocarbonyl group, a (t-butylthio)thiocarbonyl group, a (phenylthio)thiocarbonyl group, a (benzylthio)thiocarbonyl group, a methylaminothiocarbonyl group, an ethylaminothiocarbonyl group, a t-butylaminothiocarbonyl group, a benzylaminothiocarbonyl group, a $C_{1-10}$ halohydrocarbyl group, a trifluoroacetyl group, a halophenyl group, a halobenzyl group, a nitrophenyl group, a nitrobenzyl group, the like or the substituted form of any aforesaid group. Wherein, the atom or group substituent is preferably a fluorine atom, an alkoxy group or a nitro group.

$LG_2$ is more preferably a t-butyl group, a trityl group, a phenyl group, a benzyl group, a methylbenzyl group, a t-butylthio group, a benzylthio group, a 2-pyridylthio group, a 2-pyridylcarbonyl group, a t-butoxycarbonyl group, a phenoxycarbonyl group, a benzyloxycarbonyl group, a t-butoxy-thiocarbonyl group, a phenoxy-thiocarbonyl group, a benzyloxy-thiocarbonyl group, a (t-butylthio)thiocarbonyl group, a (phenylthio)thiocarbonyl group, a (benzylthio)thiocarbonyl group, a trifluoroacetyl group or the like.

$LG_2$ is more preferably a t-butyl group, a trityl group, a phenyl group, a benzyl group, a methylbenzyl group, a t-butylthio group, a benzylthio group, a 2-pyridylthio group or the like.

$LG_2$ is most preferably a methyl group, an ethyl group, an allyl group or a benzyl group.

Wherein, $Q_3$ is a hydrogen atom or a substituent that can favor inductive effect, conjugation effect, or both inductive and conjugation effects of electrons of unsaturated bonds.

$Q_3$ can be but not limited to any of all the above-described atom and group substituents in the term-defining section, as long as it can favor inductive effect or/and conjugation effect.

$Q_3$ can contain carbon atom or not. When containing no carbon atom, for example, $Q_3$ can be a nitro group. When $Q_3$ contains carbon atom, the carbon-atom number is not particularly limited, preferably from 1 to 20, and more preferably from 1 to 10.

The structure of $Q_3$ is not particularly limited, including but not limited to a linear structure, a branched structure bearing pendant groups or a ring-containing structure. Wherein, the ring is not particularly limited, and preferably an aliphatic ring, an aromatic ring, a sugar ring or a condensed ring.

$Q_3$ can be a hydrogen atom, a halogen atom, a carbon-free substituent, a hydrocarbyl group, a heterohydrocarbyl group, a substituted hydrocarbyl group or a substituted heterohydrocarbyl group. Wherein, the heteroatom or group substituent within $Q_3$ is not particularly limited, including but not limited to all the above-described heteroatom and group substituents in the term-defining section, and can be a halogen atom, a hydrocarbyl substituent or a heteroatom-containing substituent.

$Q_3$ is more preferably a hydrogen atom, a halogen atom, a $C_{1-20}$ alkyl group, a $C_{2-20}$ alkenyl group, a $C_{3-20}$ open-chain alkenyl-hydrocarbyl group, a $C_{3-20}$ cycloalkenyl group, an aryl group, an arylhydrocarbyl group, a $C_{1-20}$ heteroalkyl group, a heteroaryl group, a heteroarylalkyl group, a $C_{1-20}$ alkoxy group, an aryloxy group, an arylhydrocarbyloxy group, a $C_{1-20}$ heteroalkoxy group, a heteroaryloxy group, a heteroarylhydrocarbyloxy group, a $C_{1-20}$ heteroalkylthio group, a heteroarylthio group, a heteroarylhydrocarbylthio group, a $C_{1-20}$ haloalkyl group, the like or the substituted form of any aforesaid group.

$Q_3$ is more preferably a hydrogen atom, a halogen atom, a $C_{1-10}$ haloalkyl group, a $C_{1-10}$alkyl group, a $C_{2-10}$ alkenyl group, a $C_3$-10 open-chain alkenyl-hydrocarbyl group, a $C_{3-10}$ cycloalkenyl group, an aryl group, an arylhydrocarbyl group, a $C_{1-10}$ heteroalkyl group, a heteroaryl group, a heteroarylalkyl group, a $C_{1-10}$ alkoxy group, an aryloxy group, an arylhydrocarbyloxy group, a $C_{1-10}$ heteroalkoxy group, a heteroaryloxy group, a heteroarylhydrocarbyloxy group, the like or the substituted form of any aforesaid group.

Specifically, $Q_3$ can be a hydrogen atom, a fluorine atom, a chlorine atom, a bromine atom, an iodine atom, a methyl group, an ethyl group, an n-propyl group, an isopropyl group, a butyl group, a pentyl group, a hexyl group, a heptyl group, an octyl group (e.g., a 2-ethylhexyl group), a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, an ethenyl group, a propenyl group, an allyl group, a propynyl group, a propargyl group, a cyclopropyl group, a cyclopropenyl group, a phenyl group, a benzyl group, a butylphenyl group, a p-methylphenyl group, a nitrophenyl group, a p-methoxyphenyl group, an azaphenyl group, a methoxy group, an ethoxy group, a phenoxy group, a benzyloxy group, a methylthio group, an ethylthio group, a phenylthio group, a benzylthio group, a $C_{1-20}$ haloalkyl group, the like or the substituted form of any aforesaid group. Wherein, the butyl group includes but is not limited to an n-butyl group and a t-butyl group. The octyl group includes but is not limited to an n-octyl group and a 2-ethylhexyl group. Wherein, the atom or group substituent can be a halogen atom, a hydrocarbyl substituent or a heteroatom-containing substituent, and can be preferably a halogen atom, an alkoxy group, an alkenyl group or a nitro group.

$Q_3$ is preferably a hydrogen atom, a fluorine atom, a chlorine atom, a bromine atom, an iodine atom, a methyl group, an ethyl group, an n-propyl group, an isopropyl group, a butyl group, a pentyl group, a hexyl group, a heptyl group, an octyl group, a nonyl group, a decyl group, an ethenyl group, a propenyl group, an allyl group, a propynyl group, a propargyl group, a cyclopropyl group, a cyclopropenyl group, a phenyl group, a benzyl group, a butylphenyl group, a p-methylphenyl group, a p-nitrophenyl group, an o-nitrophenyl group, a p-methoxyphenyl group, an azaphenyl group, a methoxy group, an ethoxy group, a phenoxy group, a benzyloxy group, a methylthio group, an ethylthio group, a phenylthio group, a benzylthio group, a trifluoromethyl group, a 2,2,2-trifluoroethyl group, the like or the substituted form of any aforesaid group. Wherein, the atom or group substituent is preferably a fluorine atom, an alkoxy group, an alkenyl group or a nitro group. The azaphenyl group is preferably a pyridyl group, a pyrimidinyl group, a pyrazinyl group, a 1,3,5-triazinyl group.

$Q_3$ is more preferably a hydrogen atom, a methyl group, a trifluoromethyl group, a phenyl group, a p-nitro phenyl group, an o-nitro phenyl group, a pyridyl group or the substituted form thereof, a diazaphenyl group or the substituted form thereof, a triazaphenyl group or the substituted form thereof, or the like.

$Q_3$ is more preferably a hydrogen atom, a methyl group, a phenyl group, a pyridyl group, a diazaphenyl group or a triazaphenyl group.

$Q_3$ is more preferably a hydrogen atom, a methyl group, a phenyl group or a pyridyl group.

$Q_3$ is most preferably a hydrogen atom, a phenyl group or a pyridyl group.

Wherein, $Q_6$ is a hydrogen atom or a methyl group. $Q_7$ is a hydrogen atom, a methyl group, a phenyl group or a substituted phenyl group, wherein, one example of the substituted phenyl group is a p-methoxyphenyl group. In one molecule, $Q_6$ and $Q_7$ can be identical or different from each other.

Wherein, $Q_8$ is an atom or a group substituent of an imidazole group, not particularly limited, and preferably a hydrogen atom, a methyl group, an ethyl group, a propyl group, a butyl group or a phenyl group. $Q_8$ can be one or more in quantities. When the number is more than one, the $Q_8$ groups can have the same structure, or be the combination of two or two more different structures.

Wherein, $Q_{11}$ is a group substituent of the nitrogen atom of a tetrazole group, and preferably a phenyl group, a substituted phenyl group or an azaphenyl group.

Wherein, $PG_2$ is a mercapto protecting group, and the protected mercapto group is represented as $SPG_2$.

Wherein, $PG_3$ is an alkynyl protecting group, and the protected alkynyl group is represented as $C\equiv CPG_3$.

Wherein, $PG_4$ is a hydroxyl protecting group, and the protected hydroxyl group is represented as $OPG_4$.

Wherein, $PG_5$ is an amino protecting group, and the protected amino group is represented as $NPG_5$.

$PG_2$, $SPG_2$, $PG_3$, $PG_4$, $OPG_4$, $PG_5$ and $NPG_5$ include but are not limited to the structures described and listed in the documents CN104530413A, CN104530415A and CN104530417A; take CN104530417A as an example, corresponding to paragraphs from [0520] to [0530].

In summary, $SPG_2$ as a mercapto protecting group is preferably a sulfide (or a thioether), a disulfide, a silyl thioether, a thiocarboxylate (a thioester, a thioate, or —S—CS—), etc. Specifically, $SPG_2$ is preferably a t-butyl thioether, a triphenylmethyl thioether, a substituted triphenylmethyl thioether, a t-butyldimethylsilyl thioether, a triisopropylsilyl thioether, a benzyl thioether, a substituted benzyl thioether, a p-nitrobenzyl thioether, an o-nitrobenzyl thioether, an acetyl thioester, a benzoyl thioester, a trifluoroacetyl thioester, a t-butyl disulfide, a substituted phenyl disulfide, a 2-pyridyl disulfide or the like.

$PG_3$ as an alkynyl protecting group is preferably a silyl group. Examples of $PG_3$ include but are not limited to the following structures: a trimethylsilyl group, a triethylsilyl group, a t-butyldimethylsilyl group, a dimethyl(1,1,2-trimethylpropyl)silyl group, a dimethyl[1,1-dimethyl-3-(tetrahydro-pyran-2H-2-yloxy)propyl]silyl group, a biphenyldimethylsilyl group, a triisopropylsilyl group, a biphenyldiisopropylsilyl group, a t-butyldiphenylsilyl group, a 2-(2-hydroxyl) propylsilyl group and the like.

$PG_4$ can be a protecting group for an alcoholic hydroxyl group or a phenolic hydroxyl. $OPG_4$ is preferably an ether, a silyl ether, an ester, a carbonate, a sulfonate or the like. Specifically, $OPG_4$ is preferably a methyl ether, a 1-ethoxyethyl ether, a t-butyl ether, an allyl ether, a benzyl ether, a p-methoxybenzyl ether, an o-nitrobenzyl ether, a p-nitrobenzyl ether, a 2-trifluoromethylbenzyl ether, a methoxymethyl ether, a 2-methoxyethoxymethyl ether, a benzyloxymethyl ether, a p-methoxybenzyloxymethyl ether, a (methylthio) methyl ether, a tetrahydropyranyl ether, a trimethylsilyl ether, a triethylsilyl ether, a triisopropylsilyl ether, a t-butyldimethylsilyl ether, an acetate, a chloroacetate, a trifluoroacetate, a carbonate or the like, and preferably a 1-ethoxyethyl ether, a benzyl ether, a p-methoxybenzyl ether, an o-nitrobenzyl ether, a p-nitrobenzyl ether, a 2-trifluoromethylbenzyl ether, an ethyl vinyl ether, a benzyloxymethyl ether, a p-methoxybenzyloxymethyl ether or a tetrahydropyranyl ether.

$PG_5$ is an amino protecting group, and can protect a primary amine, a secondary amine, a hydrazine or the like. $NPG_5$ as the protected form is preferably a carbamate, an amide, an imide, an N-alkyl amine, an N-aryl amine, an imine, an enamine, an imidazole, a pyrrole, an indole or the like. Specifically, $NPG_5$ is preferably a formamide, an acetamide, a trifluoroacetamide, a t-butyl carbamate, a 2-iodoethyl carbamate, a benzyl carbamate, a 9-fluorenylmethyl carbamate, a 2-trimethylsilylethyl carbamate, a 2-methylsulfonylethyl carbamate, a 2-(p-toluenesulfonyl)ethyl carbamate, a phthalimide, a diphenylmethyleneamine, a 1,3,5-dioxazine, a methylamine, a triphenylmethylamine, a t-butylamine, an allylamine, a benzylamine, a 4-methoxybenzylamine, a benzylimine or the like.

1.1.6.3. Examples of $R_{01}$-containing functional groups —$(Z_1)_{q1}$—$R_{01}$ Examples of —$(Z_2)_q$—$(Z_1)_{q1}$—$R_{01}$, as denoted by —$(Z_2)_q$—$(Z_1)_{q1}$—$R_{01}$, include but are not limited to the structures described and listed in the documents CN104530413A, CN104530415A and CN104530417A; take CN104530417A as an example, corresponding to paragraphs from [0531] to Examples of —$(Z_2)_q$—$(Z_1)_{q1}$—$R_{01}$ also include but are not limited to structures selected from the following functional Groups A to J:

Group A:

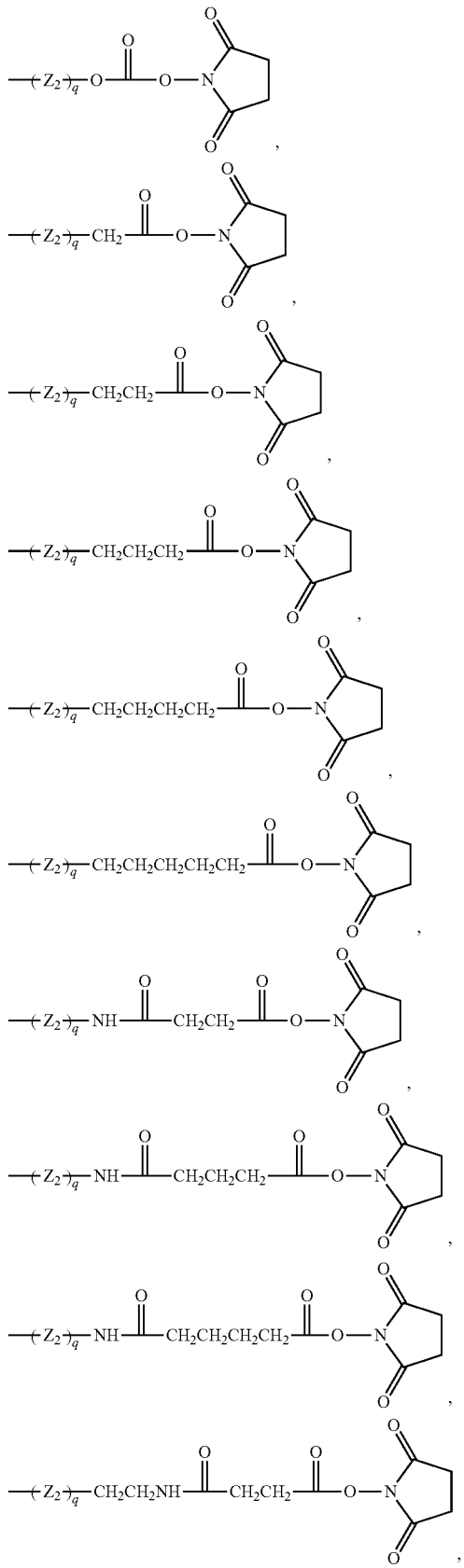

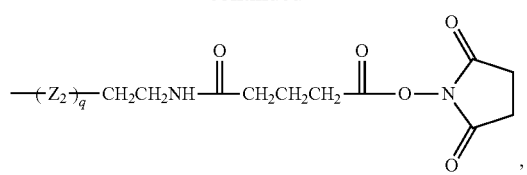
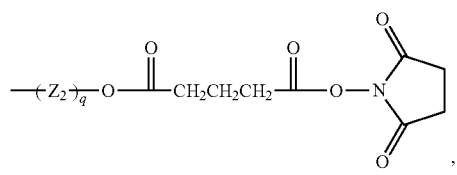
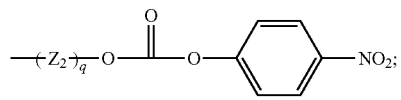
Group B:
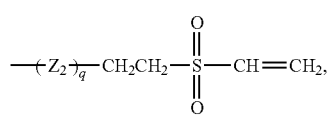
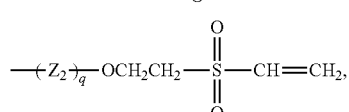
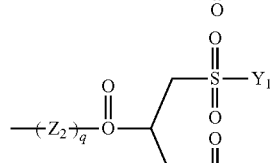
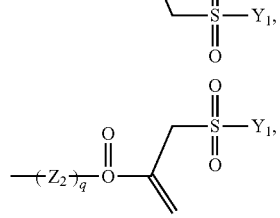
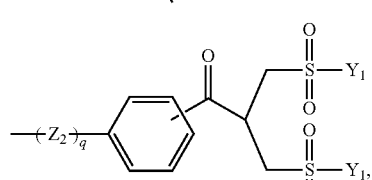
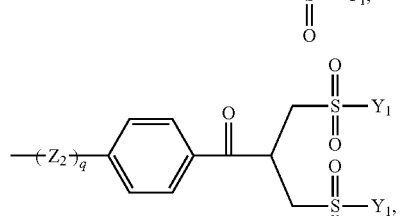
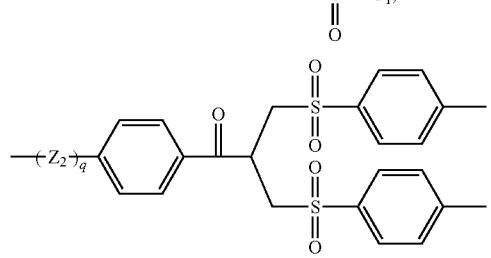
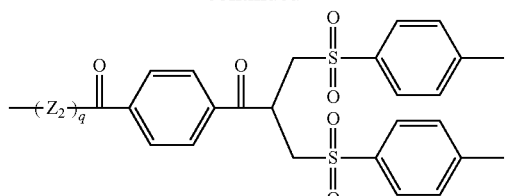
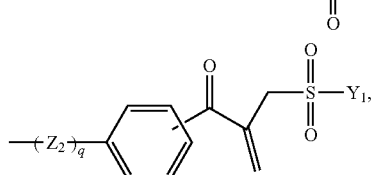
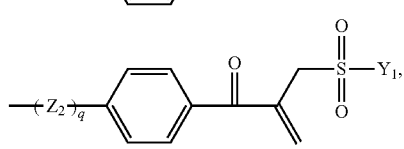
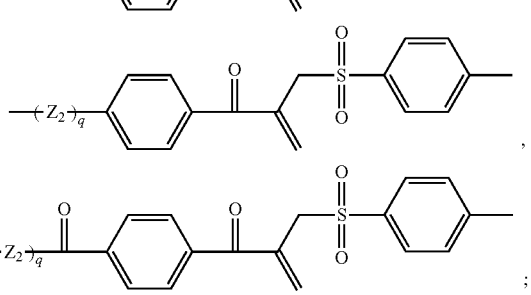
;
Group C:
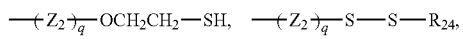
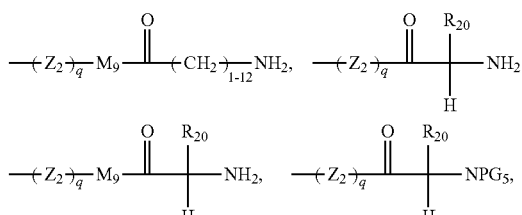
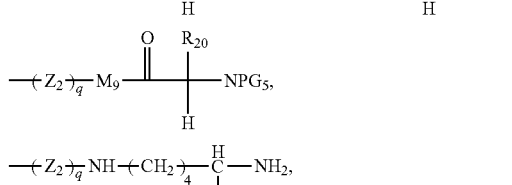
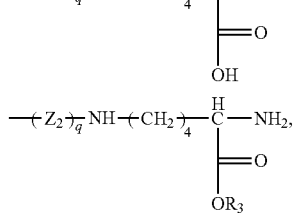
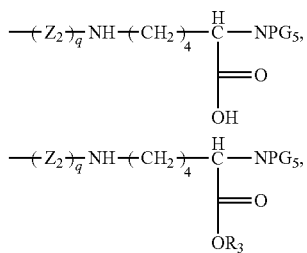

-continued $-\!\!+\!\!Z_2\!\!\cdot\!\!_q\!\!-\!\!M_9\!-\!\!\overset{O}{\overset{\|}{C}}\!-\!\!CH_2\!-\!\!\overset{H}{\underset{\underset{OH}{\overset{\|}{C}=O}}{C}}\!-\!\!NH_2,$ $-\!\!+\!\!Z_2\!\!\cdot\!\!_q\!\!-\!\!M_9\!-\!\!\overset{O}{\overset{\|}{C}}\!-\!\!CH_2\!-\!\!\overset{H}{\underset{\underset{OR_3}{\overset{\|}{C}=O}}{C}}\!-\!\!NH_2,$ $-\!\!+\!\!Z_2\!\!\cdot\!\!_q\!\!-\!\!M_9\!-\!\!\overset{O}{\overset{\|}{C}}\!-\!\!CH_2\!-\!\!\overset{H}{\underset{\underset{OH}{\overset{\|}{C}=O}}{C}}\!-\!\!NPG_5,$ $-\!\!+\!\!Z_2\!\!\cdot\!\!_q\!\!-\!\!M_9\!-\!\!\overset{O}{\overset{\|}{C}}\!-\!\!CH_2\!-\!\!\overset{H}{\underset{\underset{OR_3}{\overset{\|}{C}=O}}{C}}\!-\!\!NPG_5,$ $-\!\!+\!\!Z_2\!\!\cdot\!\!_q\!\!-\!\!M_9\!-\!\!\overset{O}{\overset{\|}{C}}\!-\!\!(CH_2)_2\!-\!\!\overset{H}{\underset{\underset{OH}{\overset{\|}{C}=O}}{C}}\!-\!\!NH_2,$ $-\!\!+\!\!Z_2\!\!\cdot\!\!_q\!\!-\!\!M_9\!-\!\!\overset{O}{\overset{\|}{C}}\!-\!\!(CH_2)_2\!-\!\!\overset{H}{\underset{\underset{OR_3}{\overset{\|}{C}=O}}{C}}\!-\!\!NH_2,$ $-\!\!+\!\!Z_2\!\!\cdot\!\!_q\!\!-\!\!M_9\!-\!\!\overset{O}{\overset{\|}{C}}\!-\!\!(CH_2)_2\!-\!\!\overset{H}{\underset{\underset{OH}{\overset{\|}{C}=O}}{C}}\!-\!\!NPG_5,$ $-\!\!+\!\!Z_2\!\!\cdot\!\!_q\!\!-\!\!M_9\!-\!\!\overset{O}{\overset{\|}{C}}\!-\!\!(CH_2)_2\!-\!\!\overset{H}{\underset{\underset{OR_3}{\overset{\|}{C}=O}}{C}}\!-\!\!NPG_5,$ $-\!\!+\!\!Z_2\!\!\cdot\!\!_q\!\!-\!\!\overset{R_{30}}{\underset{}{N}}H\!\!-\!\!\overset{}{\underset{}{}}\!,\quad -\!\!+\!\!Z_2\!\!\cdot\!\!_q\!\!-\!\!NH\!\!-\!\!\overset{}{\underset{}{}}\!,\quad -\!\!+\!\!Z_2\!\!\cdot\!\!_q\!\!-\!\!NH\!\!-\!\!\overset{}{\underset{}{}}\!,$ $-\!\!+\!\!Z_2\!\!\cdot\!\!_q\!\!-\!\!NH\!\!-\!\!\overset{}{\underset{}{}}\!,\quad -\!\!+\!\!Z_2\!\!\cdot\!\!_q\!\!-\!\!NH\!\!-\!\!\overset{}{\underset{}{}}\!,$ $-\!\!+\!\!Z_2\!\!\cdot\!\!_q\!\!-\!\!NH\!\!-\!\!\text{Ph},\quad -\!\!+\!\!Z_2\!\!\cdot\!\!_q\!\!-\!\!NH\!\!-\!\!\text{C}_6\text{H}_4\text{CH}_3,$ $-\!\!+\!\!Z_2\!\!\cdot\!\!_q\!\!-\!\!M_{19}\!\!\overset{M_{20}}{\overset{\|}{=}}\!\!X_{11},\quad -\!\!+\!\!Z_2\!\!\cdot\!\!_q\!\!-\!\!M_{19}\!\!\overset{M_{20}}{\overset{\|}{=}}\!\!CH_3,$ $-\!\!+\!\!Z_2\!\!\cdot\!\!_q\!\!-\!\!O\!-\!\!\overset{O}{\overset{\|}{C}}\!-\!\!X_{11},\quad -\!\!+\!\!Z_2\!\!\cdot\!\!_q\!\!-\!\!O\!-\!\!\overset{S}{\overset{\|}{C}}\!-\!\!X_{11},$ -continued $-\!\!+\!\!Z_2\!\!\cdot\!\!_q\!\!-\!\!S\!-\!\!\overset{S}{\overset{\|}{C}}\!-\!\!X_{11},\quad -\!\!+\!\!Z_2\!\!\cdot\!\!_q\!\!-\!\!M_{19}\!\!\overset{M_{20}}{\overset{\|}{=}}\!\!M_{21}\!-\!\!X_{12},$ $-\!\!+\!\!Z_2\!\!\cdot\!\!_q\!\!-\!\!M_{19}\!\!\overset{M_{20}}{\overset{\|}{=}}\!\!M_{21}\!\!\diagup,\quad -\!\!+\!\!Z_2\!\!\cdot\!\!_q\!\!-\!\!O\!-\!\!\overset{O}{\overset{\|}{C}}\!-\!\!O\!-\!\!X_{12},$ $-\!\!+\!\!Z_2\!\!\cdot\!\!_q\!\!-\!\!S\!-\!\!\overset{O}{\overset{\|}{C}}\!-\!\!O\!-\!\!X_{12},\quad -\!\!+\!\!Z_2\!\!\cdot\!\!_q\!\!-\!\!O\!-\!\!\overset{S}{\overset{\|}{C}}\!-\!\!O\!-\!\!X_{12},$ $-\!\!+\!\!Z_2\!\!\cdot\!\!_q\!\!-\!\!O\!-\!\!\overset{O}{\overset{\|}{C}}\!-\!\!S\!-\!\!X_{12},\quad -\!\!+\!\!Z_2\!\!\cdot\!\!_q\!\!-\!\!S\!-\!\!\overset{S}{\overset{\|}{C}}\!-\!\!O\!-\!\!X_{12},$ $-\!\!+\!\!Z_2\!\!\cdot\!\!_q\!\!-\!\!S\!-\!\!\overset{O}{\overset{\|}{C}}\!-\!\!S\!-\!\!X_{12},$ $-\!\!+\!\!Z_2\!\!\cdot\!\!_q\!\!-\!\!O\!-\!\!\overset{S}{\overset{\|}{C}}\!-\!\!S\!-\!\!X_{12},\quad -\!\!+\!\!Z_2\!\!\cdot\!\!_q\!\!-\!\!S\!-\!\!\overset{S}{\overset{\|}{C}}\!-\!\!S\!-\!\!X_{12},$

[glutarimide with $M_8$], [succinimide],

[maleimide], [phthalimide],

[norbornene-dicarboximide variants (4 structures)], $-\!\!+\!\!Z_2\!\!\cdot\!\!_q\!\!-\!\!NH\!-\!\!\overset{O}{\overset{\|}{C}}\!-\!\!CH_2\!-\!\!I,$ $-\!\!+\!\!Z_2\!\!\cdot\!\!_q\!\!-\!\!CH_2CH_2NH\!-\!\!\overset{O}{\overset{\|}{C}}\!-\!\!CH_2\!-\!\!I,$ $-\!\!+\!\!Z_2\!\!\cdot\!\!_q\!\!-\!\!OCH_2CH_2NH\!-\!\!\overset{O}{\overset{\|}{C}}\!-\!\!CH_2\!-\!\!I,$ $-\!\!+\!\!Z_2\!\!\cdot\!\!_q\!\!-\!\!CH_2CH_2NH_2\!\cdot\!HCl,$ $-\!\!+\!\!Z_2\!\!\cdot\!\!_q\!\!-\!\!OCH_2CH_2NH_2\!\cdot\!HCl,\quad -\!\!+\!\!Z_2\!\!\cdot\!\!_q\!\!-\!\!\overset{O}{\overset{\|}{C}}\!-\!\!ONH_2,$ $-\!\!+\!\!Z_2\!\!\cdot\!\!_q\!\!-\!\!\overset{O}{\overset{\|}{C}}\!-\!\!NH_2,\quad -\!\!+\!\!Z_2\!\!\cdot\!\!_q\!\!-\!\!\overset{O}{\overset{\|}{C}}\!-\!\!NHNH_2,$ $-\!\!+\!\!Z_2\!\!\cdot\!\!_q\!\!-\!\!\overset{O}{\underset{O}{\overset{\|}{S}}}\!-\!\!NHNH_2;$ Group D:

$-\!\!+\!\!Z_2\!\!\cdot\!\!_q\!\!-\!\!OCH_2\!-\!\!COOH,\quad -\!\!+\!\!Z_2\!\!\cdot\!\!_q\!\!-\!\!OCH_2CH_2\!-\!\!COOH,$

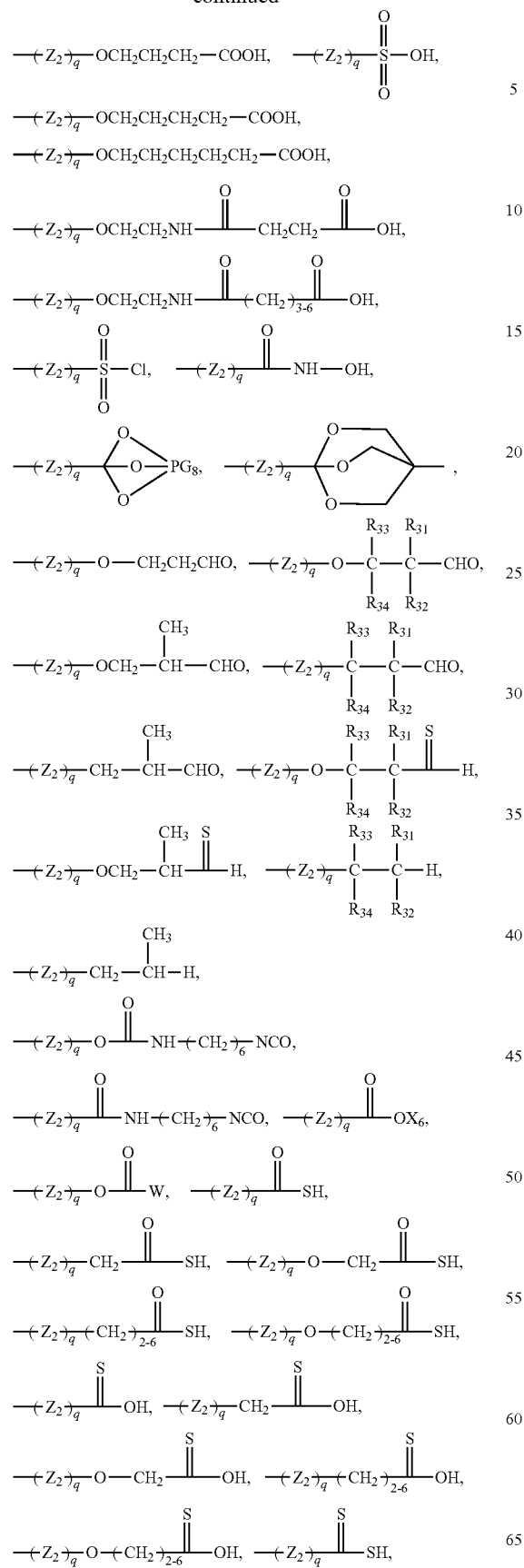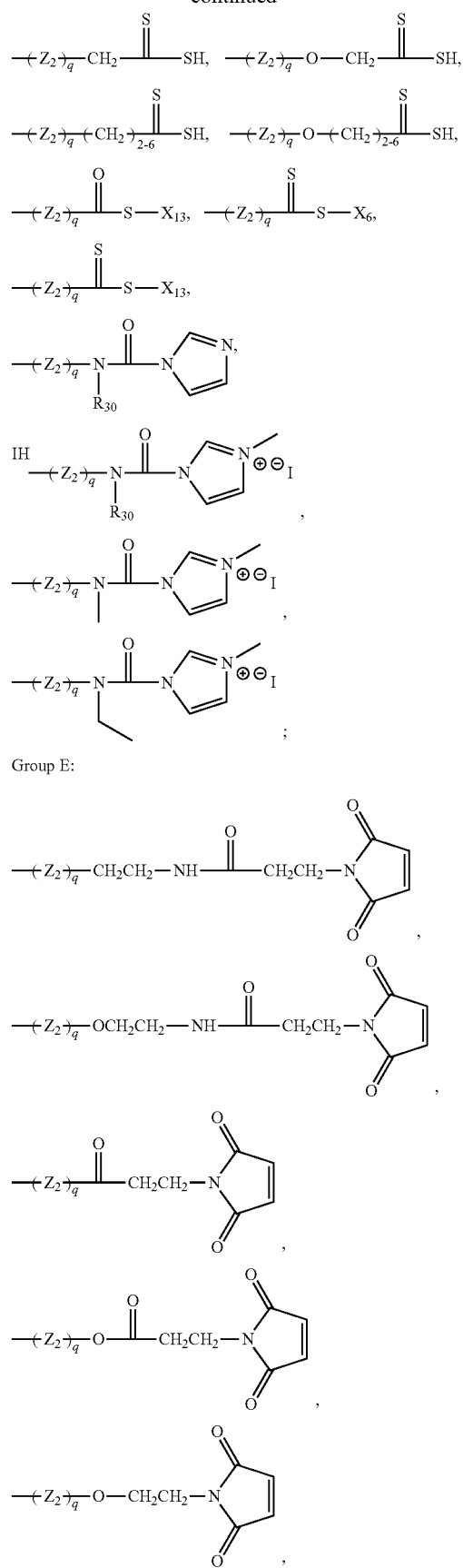

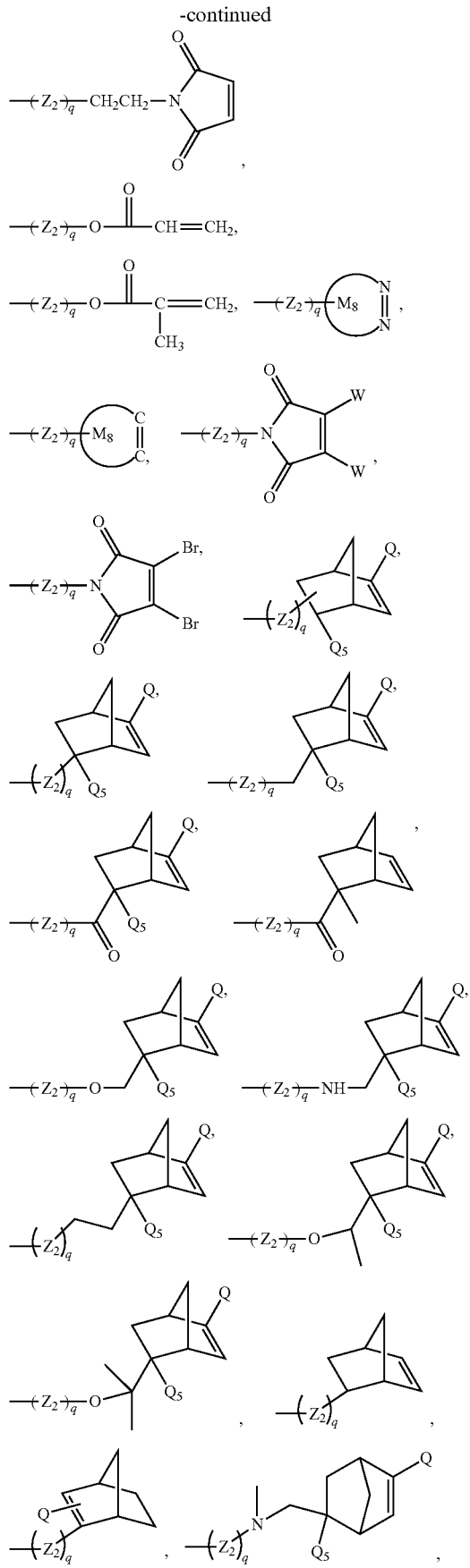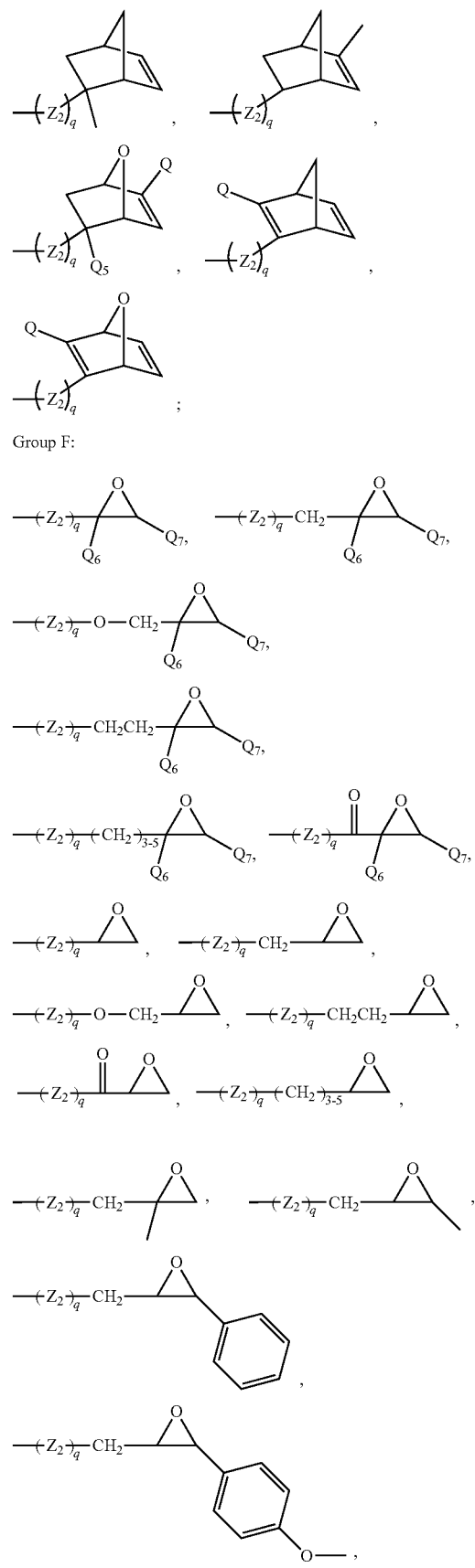
Group F:

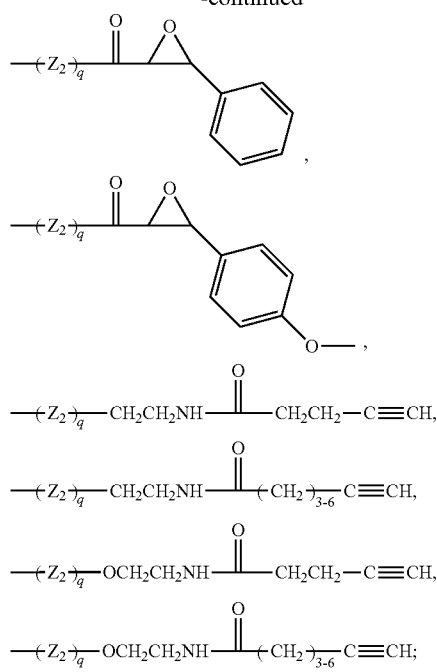
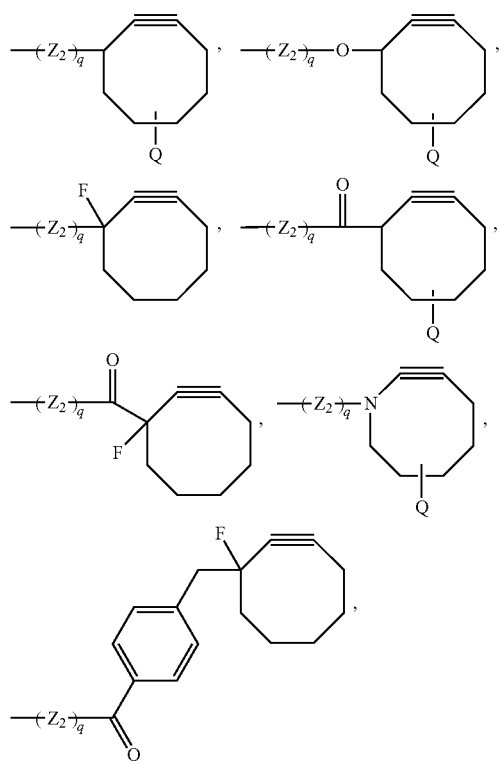
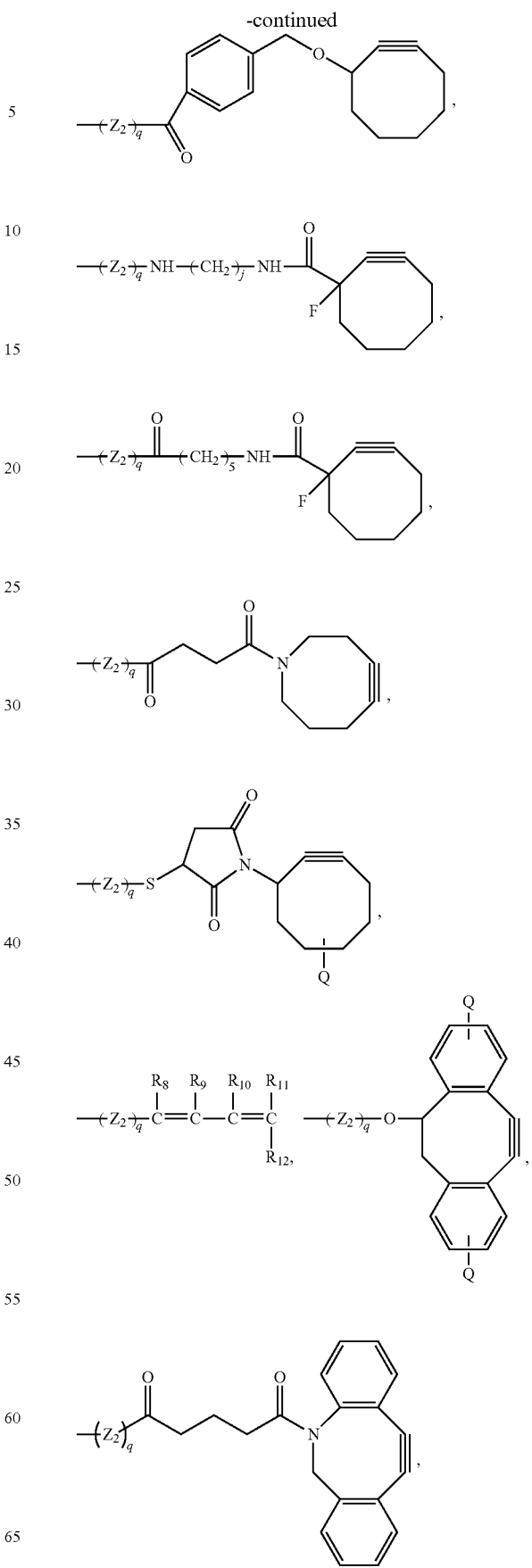

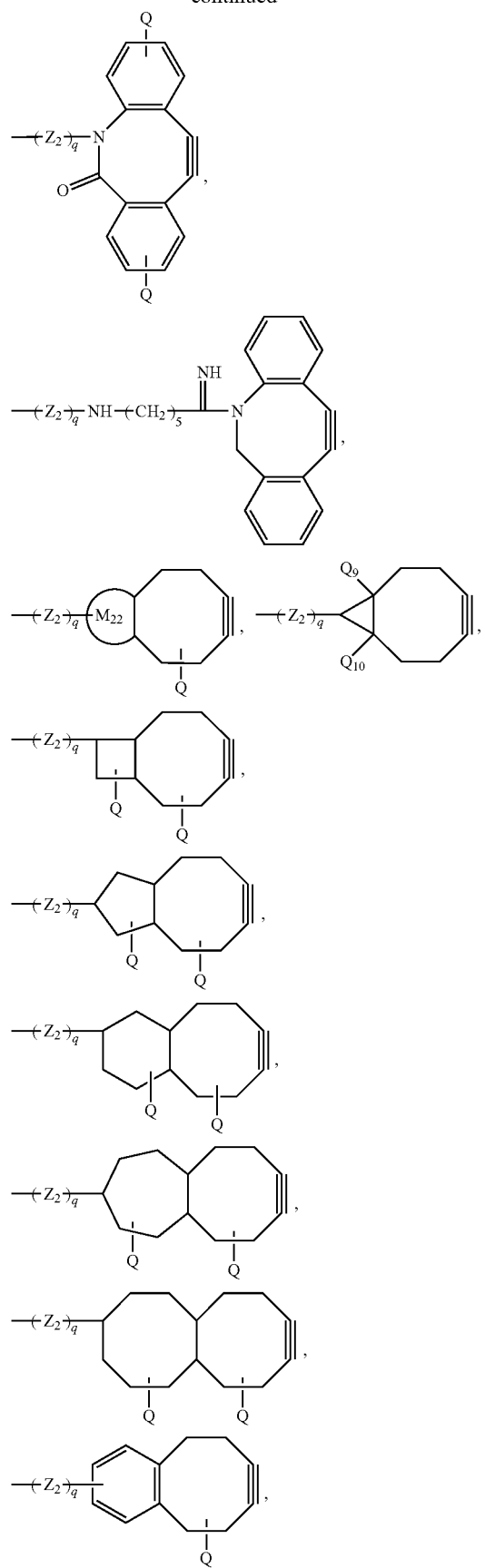
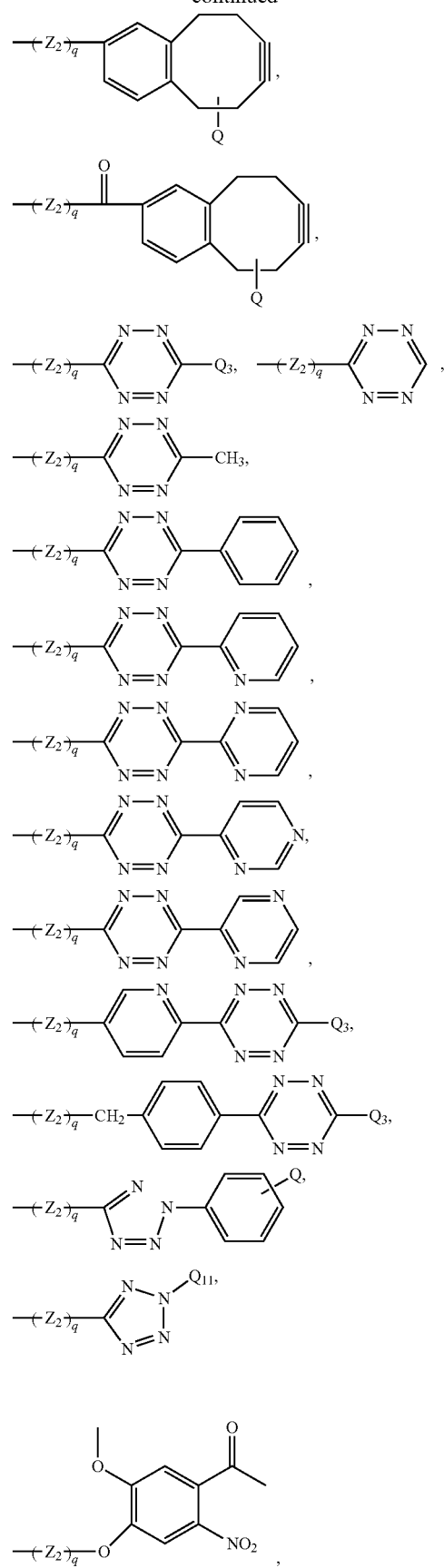

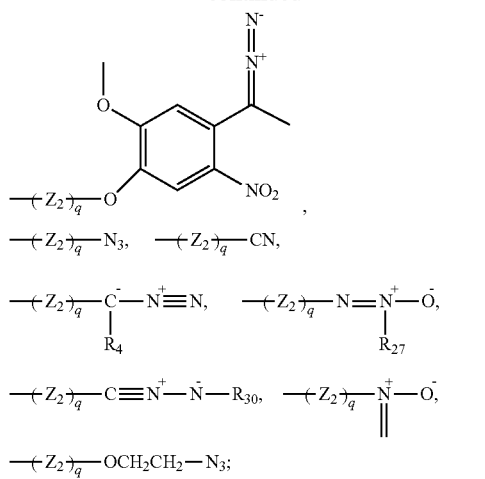
Group H:
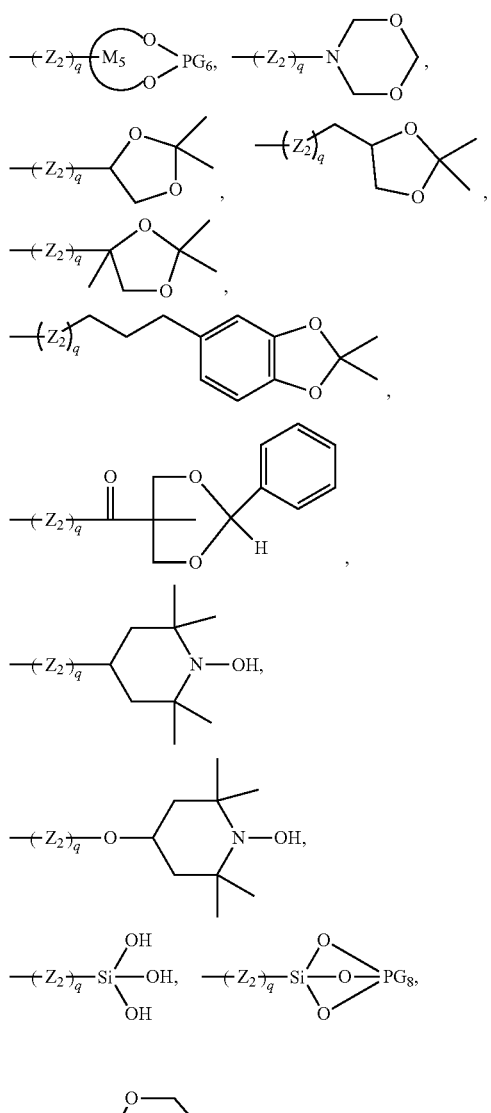
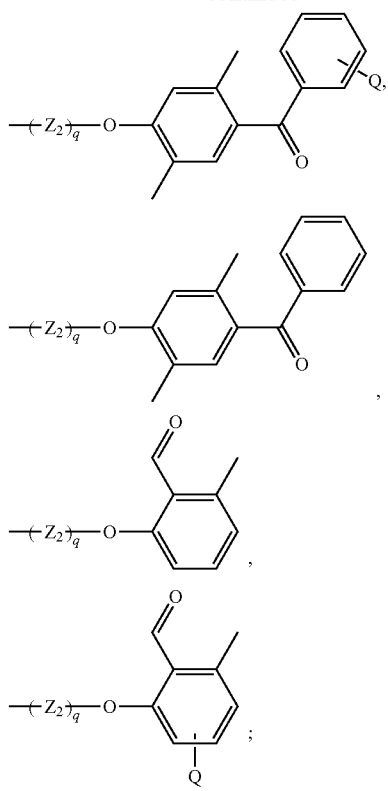
Group I:
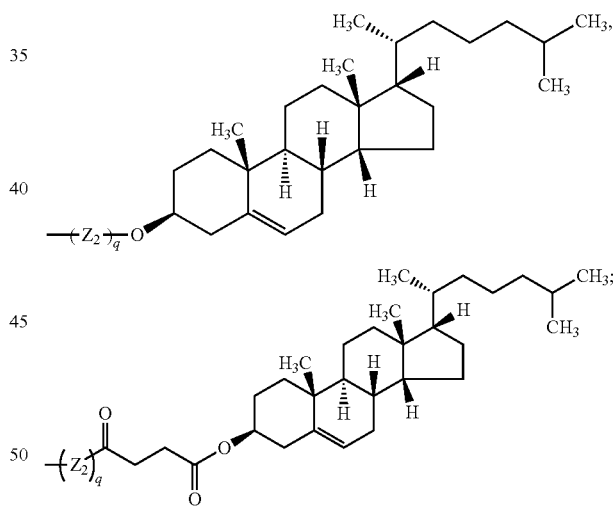
Group J:
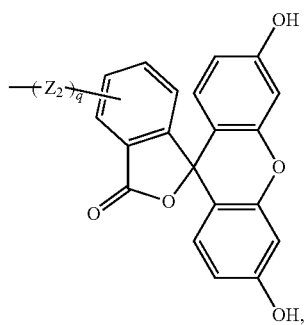

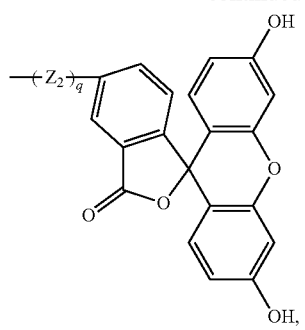
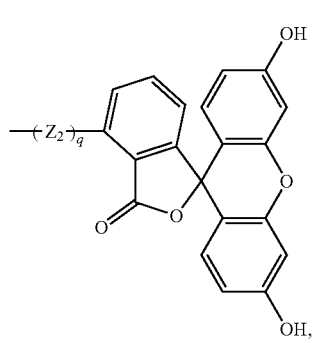
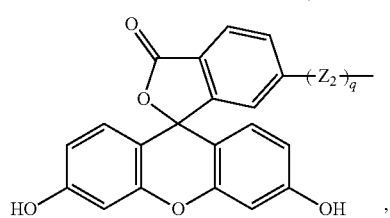
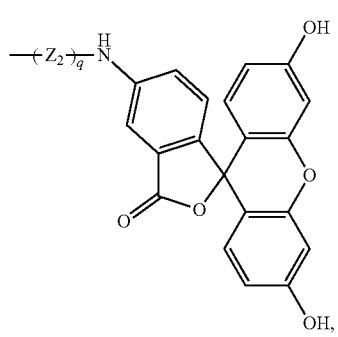
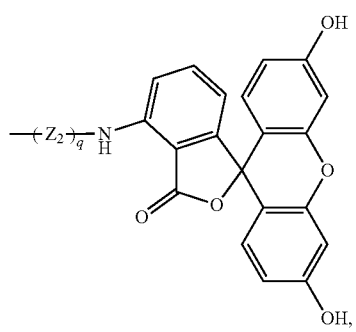
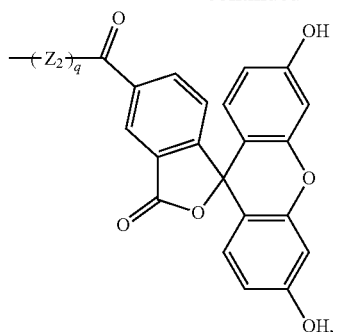
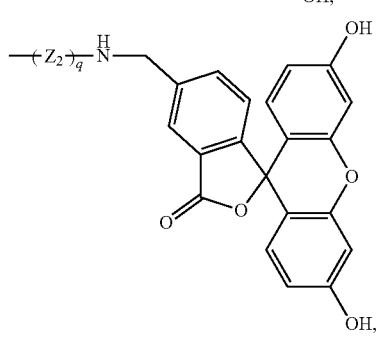
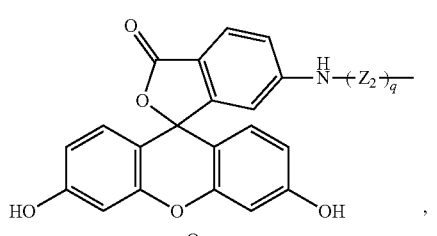
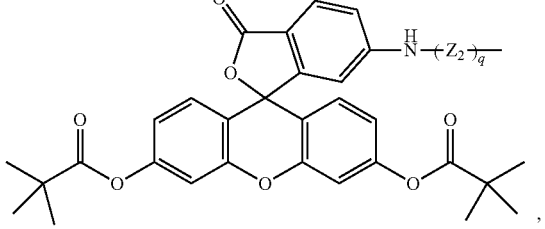
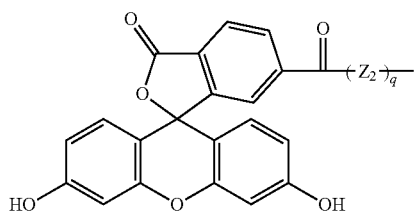
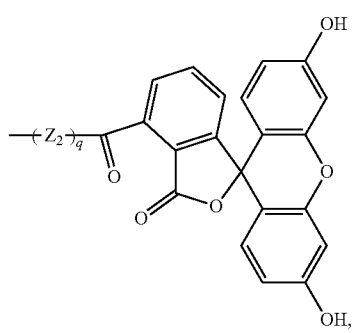

-continued
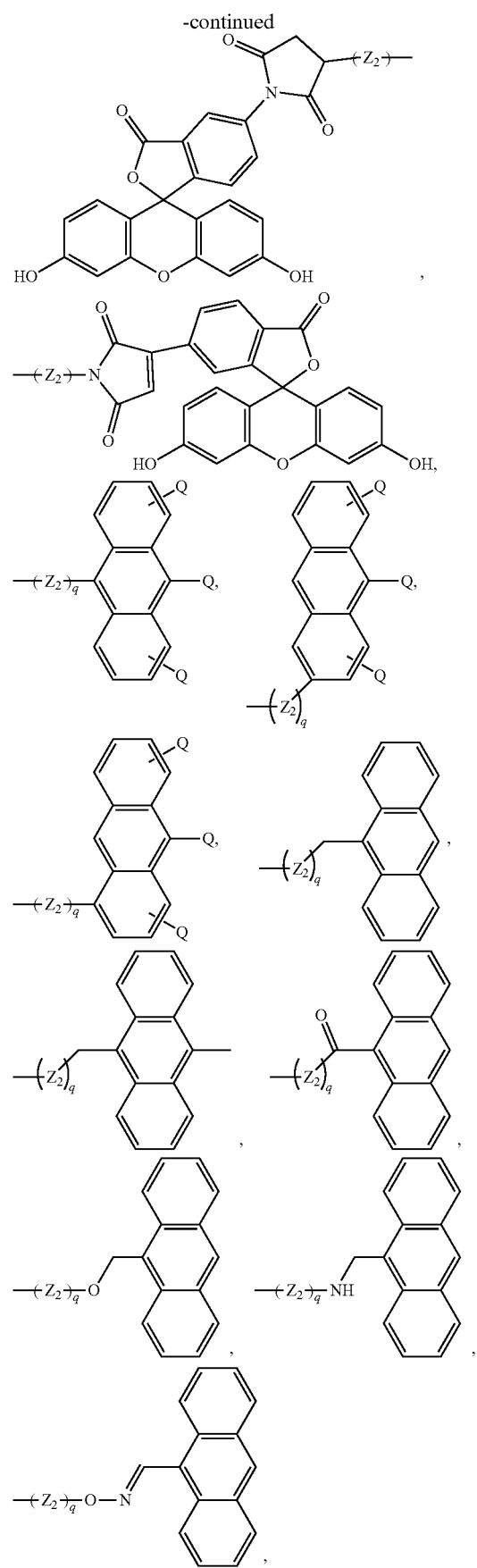
-continued
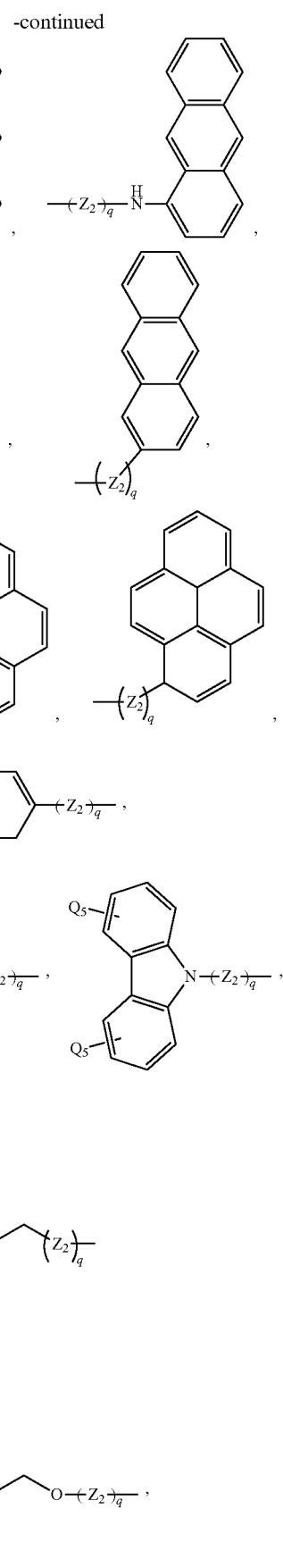

187
-continued
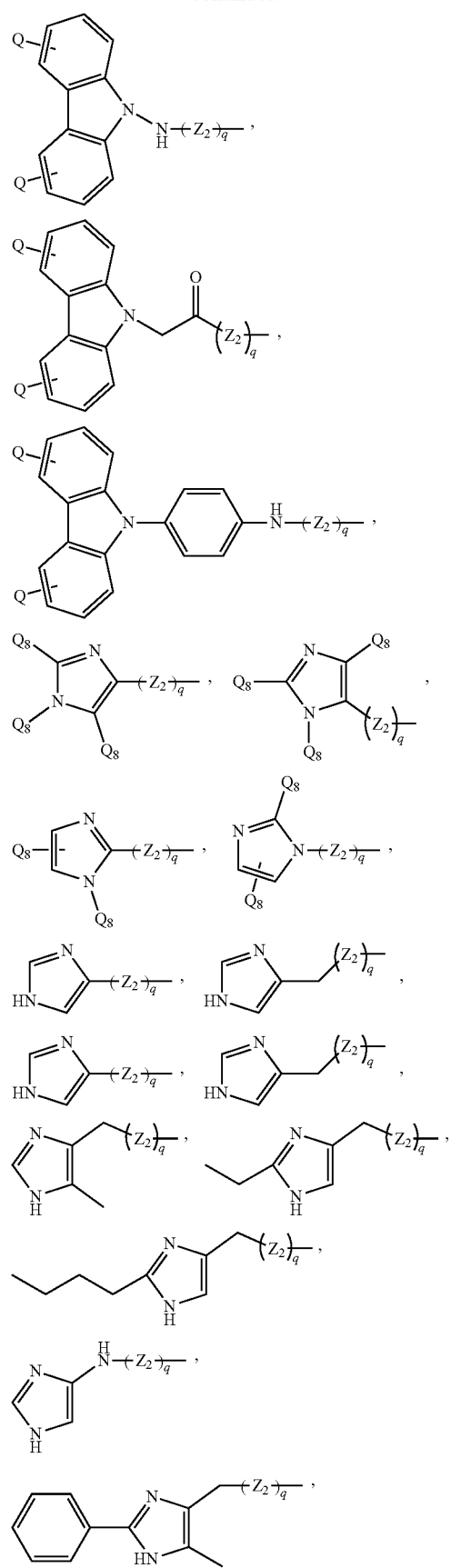
188
-continued
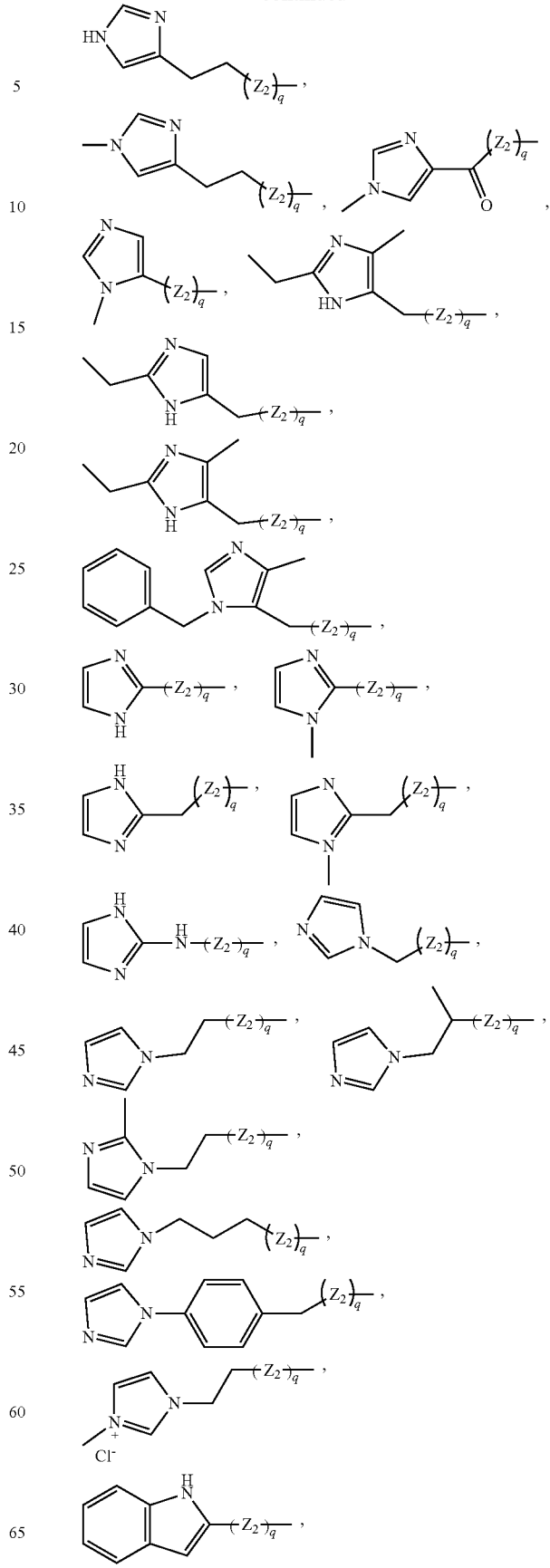

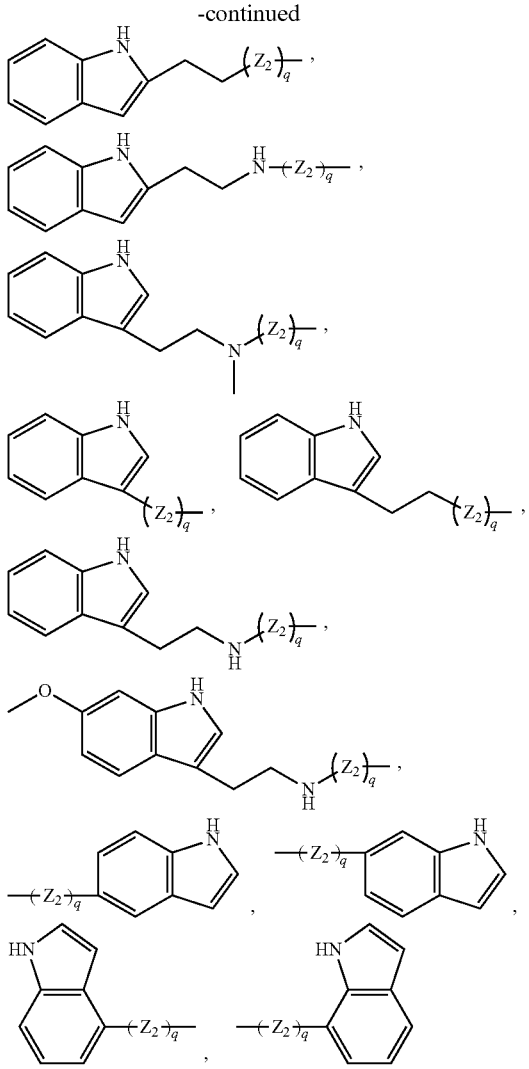

and the like.

With respect to above-said functional groups from Groups A to J:

Wherein, q is 0 or 1.

Wherein, $Z_2$ is a divalent linking group that can be stable or degradable, and is defined in detail hereinafter.

Wherein, —$(Z_2)_q$— is most preferably, but not limited to, absent or an ethylene group.

Wherein, the definitions of j, $Y_1$, $R_3$, $R_4$, $R_8$, $R_9$, $R_{10}$, $R_{11}$, $R_{12}$, $R_{24}$, $R_{27}$, $R_{30}$, $X_6$, $X_{11}$, $X_{12}$, $X_{13}$, $M_{19}$, $M_{20}$, $M_{21}$, $M_{22}$, Q, $Q_3$, $Q_5$, $Q_6$, $Q_7$, $Q_8$, $Q_{11}$, $PG_5$, $PG_6$, $PG_8$, W, $M_8$, $M_8$-membered rings, $M_8$ and $M_8$-membered rings are the same as above, no more repeated here.

Wherein, $Q_9$ and $Q_{10}$ are each independently a hydrogen atom, a $C_{1-20}$ alkyl group, a $C_{6-20}$ aryl group, a $C_{6-20}$ arylhydrocarbyl group, a heterosubstituted $C_{6-20}$ aryl group with a ring-membering heteroatom or a heterosubstituted $C_{6-20}$ arylhydrocarbyl group with a ring-membering heteroatom. In one molecule, $Q_9$ and $Q_{10}$ can be the same or different from each other. $Q_9$ and $Q_{10}$ are each independently preferably a hydrogen atom, a $C_{1-6}$ alkyl group, a phenyl group, a heterosubstituted phenyl group with a ring-membering heteroatom or a substituted phenyl group.

Wherein, $M_9$ is O, S or $NX_{10}$.

Wherein, $X_{10}$ is a hydrogen atom or a $C_{1-20}$ hydrocarbyl group.

The structure of $X_{10}$ is not particularly limited, and can be but not limited to a linear structure, a branched structure or a ring-containing structure.

The species of $X_{10}$ is not particularly limited, and can be but not limited to a linear alkyl group, a branched alkyl group, a cycloalkyl group, an aryl group, an arylalkyl group, a substituted cycloalkyl group, a substituted aryl group, a substituted arylalkyl group or the like.

$X_{10}$ is preferably a hydrogen atom, a methyl group, an ethyl group, a propyl group, an isopropyl group, a butyl group, a t-butyl group, a pentyl group, a hexyl group, a heptyl group, a 2-ethyl hexyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a $C_{3-20}$ cycloalkyl group, an aryl group, a phenyl group, an arylhydrocarbyl group, an arylalkyl group, a benzyl group, a butylphenyl group, a substituted $C_{3-20}$ cycloalkyl group, a substituted aryl group, a substituted $C_{7-20}$ arylhydrocarbyl group, a substituted $C_{7-20}$ arylalkyl group or the like. $X_{10}$ is more preferably a methyl group, an ethyl group, a propyl group, an isopropyl group, a butyl group, a t-butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a benzyl group, a butylphenyl group or the like.

$X_{10}$ is more preferably a hydrogen atom or a hydrocarbyl group containing 1 to 10 carbon atoms. Examples of $X_{10}$ include but are not limited to a hydrogen atom, a methyl group, an ethyl group, a propyl group, an isopropyl group, a butyl group, a t-butyl group, a pentyl group, a hexyl group, a heptyl group, an octyl group, a nonyl group, a decyl group, a benzyl group, a butylphenyl group and the like.

$X_{10}$ is more preferably a hydrogen atom or a hydrocarbyl group containing 1 to 5 carbon atoms, and $X_{10}$ can be but not limited to a hydrogen atom, a methyl group, an ethyl group, a propyl group, an isopropyl group, a butyl group, a t-butyl group, a pentyl group or the like.

$X_{10}$ is more preferably a hydrogen atom or a methyl group.

Wherein, $R_{20}$ is a pendant group, a protected pendant group or a substituted pendant group of an amino acid or an amino acid derivative.

The amino acid as the source of $R_{20}$ can be itself or its derivative, and the amino acid can be of $L$-type or $D$-type.

For example, $R_{20}$ can be but not limited to a pendant group, a protected pendant group or a substituted pendant group of an amino acid or an amino acid derivative derived from any of the following amino acids and derivatives thereof of any Group:

Neutral amino acids and their derivatives: glycine, alanine, valine, leucine, isoleucine, phenylalanine, proline and sarcosine;

Hydroxyl-containing or mercapto-containing amino acids and their derivatives: serine, threonine, cysteine, methionine, tyrosine and hydroxyproline;

Acidic amino acids and their derivatives: aspartic acid, glutamic acid, asparagine and glutamine;

Basic amino acids and their derivatives: lysine, arginine, citrulline, histidine and tryptophan.

Wherein, $R_{31}$, $R_{32}$, $R_{33}$ and $R_{34}$ are each independently a hydrogen atom or a $C_{1-6}$ hydrocarbyl group. In one molecule, they can be the same or different. $R_{31}$, $R_{32}$, $R_{33}$ and $R_{34}$ are each independently preferably a hydrogen atom or a methyl group.

With respect to $Z_1$ in the above examples, taking —$(Z_2)_q$—$CH_2$—$NH_2$ and —$(Z_2)_q$—$(CH_2)_2$—$NH_2$ for example, both belonging to C4, herein, $R_{01}$ is $NH_2$ and $q_1$ is equal to 1 ($q_1$=1), while the former $Z_1$ is a methylene group, and the latter $Z_1$ is an ethylene group.

The connection between $Z_2$ and $Z_1$ is not particularly limited in the present invention. The terminus of $Z_1$ directly connecting with $Z_2$ can be a heteroatom (such as —O—, —S—, —NH— or the like), a substituted heteroatom (i.e. a heteroatom which is substituted, such as —N($X_{10}$)—, —S(=O)—, —S(=O)$_2$—, —P(=O)— or the like), —$CH_2$—, —CH($X_{10}$)—, —$CR_{22}$—, a carbonyl group, a thiocarbonyl group, —C(=$NR_7$)—, etc. Wherein, the definition of $X_{10}$ is the same as above, no more repeat here. Wherein, $R_{22}$ is a divalent linking group to form a ring substituent, wherein, the number of ring-membering atoms is preferably from 3 to 8, and the ring substituent is preferably a $C_{3-8}$ ring, and more preferably a $C_{3-8}$ saturated ring. Take embodiments when both $g_1$ and $g_2$ are equal to zero ($g_1$=$g_2$=0) and the $R_{01}$ groups are identical for example, with respect to pairs of $F_1$ and $F_2$ including the pair of a succinimidyl propionate group and a succinimidyl acetate group (corresponding to two functional A1 groups having the same $R_{01}$ of a succinimidyl group, and —$(Z_2)_q$—$(Z_1)_{q1}$— being a 1,2-ethylene group and a methylene group, respectively), the pair of a propionaldehyde group and a butyraldehyde group (corresponding to two functional D5 groups having the same $R_{01}$ of CHO, and —$(Z_2)_q$—$(Z_1)_{q1}$— being a 1,2-ethylene group and a 1,3-propylene group, respectively), and the pair of an acetic acid group and a propionic acid group (corresponding to two functional D4 groups having the same $R_{01}$ of COOH, and —$(Z_2)_q$—$(Z_1)_{q1}$— being a methylene group and a 1, 2-ethylene group, respectively), herein, one embodiment is that q is 0, $q_1$ is 1, $Z_2$ is absent and two ($Z_1$)s are different, and another embodiment is that q is 1, $q_1$ is 0, $Z_1$ is absent, and two ($Z_2$)s are different.

1.1.7. Divalent Linking Groups

In the general formula (1), $L_{11}$, $L_{12}$, $L_{21}$, $L_{22}$, $L_{31}$, $L_{32}$, $L_{41}$, $L_{42}$, $L_0$ (g=1), $Z_1$ and $Z_2$ are each independently a divalent group and can be each independently the same or different in one molecule.

A preferable embodiment is that $L_{11}$, $L_{12}$, $L_{21}$, $L_{22}$, $L_{31}$, $L_{32}$, $L_{41}$ and $L_{42}$ are exactly the same, denoted as L.

A preferable embodiment is that $L_{11}$, $L_{12}$, $L_{21}$, $L_{22}$, $L_{31}$, $L_{32}$, $L_{41}$ and $L_{42}$ are all absent.

A preferable embodiment is that $L_{11}$, $L_{12}$, $L_{21}$, $L_{22}$, $L_{31}$, $L_{32}$, $L_{41}$ and $L_{42}$ are all present, and are exactly the same.

The structures of $L_{11}$, $L_{12}$, $L_{21}$, $L_{22}$, $L_{31}$, $L_{32}$, $L_{41}$, $L_{42}$, $L_0$ (g=1), $Z_1$ and $Z_2$ are not particularly limited, and each independently can be but not limited to a linear structure, a branched structure or a ring-containing structure.

The non-hydrogen atom number of $L_{11}$, $L_{12}$, $L_{21}$, $L_{22}$, $L_{31}$, $L_{32}$, $L_{41}$, $L_{42}$, $L_0$ (g=1), $Z_1$ and $Z_2$ are not particularly limited, each independently preferably from 1 to 50, more preferably from 1 to 20, and more preferably from 1 to 10. The non-hydrogen atom is a carbon atom or a heteroatom. The heteroatom can be but not limited to O, S, N, P, Si, B or the like. When the non-hydrogen atom number is 1, it can be a carbon atom or a heteroatom. When the non-hydrogen atom number is greater than 1, the species of the non-hydrogen atoms are not particularly limited, and can be of merely one species, or be the combination of two or two more species; when the non-hydrogen atom number is greater than 1, combinations of the non-hydrogen atoms can be the combination of carbon atoms with carbon atoms, the combination of carbon atoms with heteroatoms, or the combination of heteroatoms with heteroatoms.

Preferably, the non-hydrogen atom number of $L_{11}$, $L_{12}$, $L_{21}$, $L_{22}$, $L_{31}$, $L_{32}$, $L_{41}$, $L_{42}$, $L_0$ (g=1), $Z_1$ and $Z_2$ are each independently preferably from 1 to 50, wherein, the non-hydrogen atoms can be C, O, S, N, P, Si, B or the like; when the non-hydrogen atom number is greater than 1, the species number of non-hydrogen atoms can be one, two, or two more; the non-hydrogen atoms can be the combination of carbon atoms with carbon atoms, the combination of carbon atoms with heteroatoms, or the combination of heteroatoms with heteroatoms.

The stability of $L_{11}$, $L_{12}$, $L_{21}$, $L_{22}$, $L_{31}$, $L_{32}$, $L_{41}$, $L_{42}$, $L_0$ (g=1), $Z_1$ and $Z_2$ are not particularly limited, wherein, any aforesaid divalent linking group or any joint divalent linking group formed by one aforesaid group together with its adjacent heterosubstituted group can be either a stable linking group denoted as STAG (i.e. a linking group which can remain stable, or a linking group which can keep covalently linking with the adjacent groups along the backbone, not side groups or pendent groups, under a certain condition) or a degradable linking group denoted as DEGG (i.e. a linking group which can be degraded, or a linking group which can be degraded into at least two separate individual submoieties). With respect to the preferable embodiments, any divalent linking group selected from $L_0$, $L_0$ (g=1) and $(Z_2)_q$—$(Z_1)_q$, and any joint divalent linking groups formed by one aforesaid group together with its adjacent heterosubstituted group can be each independently either a stable linking group denoted as STAG or a degradable linking group denoted as DEGG.

1.1.8. Description for Stable and Degradable Groups

In the present invention, a stable linking group denoted as STAG or a degradable linking group denoted as DEGG, can exist within any of the above-described divalent linking groups including $L_{11}$, $L_{12}$, $L_{21}$, $L_{22}$, $L_{31}$, $L_{32}$, $L_{41}$, $L_{42}$, $L_0$ (g=1), $Z_1$ and $Z_2$, or within the divalent linking group formed by any divalent linking group together with its adjacent heterosubstituted group, or within any of the multivalent groups including U, $E_i$ (i=1, 2, 3 or 4) and G, or within the divalent linking group formed by a multivalent group and its adjacent group.

1.1.8.1. Stable Divalent Linking Groups (Stable Divalent Linkages): STAG

The condition "to be stable" or "to remain stable" is not particularly limited, including but not limited to conditions such as light illumination, heat, low temperature, an enzymatic condition, an oxidation-reduction condition, an acidic condition, a basic condition, a physiological condition, a simulated physiological environment in vitro and the like, preferably conditions such as light illumination, heat, an enzymatic condition, an oxidation-reduction condition, an acidic condition, a basic condition, etc.

The structural type of STAG is not particularly limited. STAG can be but not limited to an alkylene group, a divalent heteroalkyl group, a carbon-carbon double bond, a carbon-carbon triple bond, a divalent dienyl group, a divalent cycloalkyl group, a divalent cycloalkenyl group, a divalent cycloalkenylhydrocarbyl group, a divalent cycloalkynyl group, an arylene group, an aliphatic-derived heteroring linkage, a heterophenylene group (with one or more heteroatoms as ring-membering atom), an aryloheteroring linkage, a heterocondensed heteroring linkage, a substituted alkylene group, a substituted heteroalkylene group (or a substituted divalent heteroalkyl group), a substituted double bond (e.g., an amino-substituted double bond such as —($R_8$)C=C(N$R_7R_{39}$)—), a substituted divalent dienyl group, a substituted divalent cycloalkyl group, a substituted divalent cycloalkenyl group, a substituted divalent cycloalkenylhydrocarbyl group, a substituted divalent cycloalkynyl group, a substituted arylene group, a substituted aliphatic-derived heterorring linkage, a substituted heterophenylene group, a substituted aryloheteroring linkage, a substituted heterocondensed heteroring linkage, an ether bond, a thioether bond, a urea bond, a thiourea bond, a carbamate bond, a thiocarbamate bond, a linkage containing a —P(=O)— moiety, a linkage containing a —P(=S)— moiety, a divalent active-hydrogen-free silyl group, a boron-containing divalent linking group, a secondary amino bond, a tertiary amino bond, a carbonyl group, a thiocarbonyl group, a —S(=O)$_2$— linkage (a sulfuryl group), a —S(=O)— linkage, a 1,1-ring linkage such as -$M_{17}(R_{22})$—, an amide bond, a thioamide bond, a sulfonamide bond, an enamino group, a triazole linkage, a 4,5-dihydroisoxazole linkage,

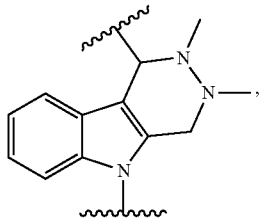 [SMILES: *C1c2c(n(*)c3ccccc23)CN(C)N1C]

the skeleton of an amino acid or an amino acid derivative, the like or a stable divalent linking group combined by any two or two more linkages of the foregoing (e.g., —S—CH$_2$C(=O)N($R_7$)—).

Specifically, examples of STAG include but are not limited to the structures described and listed in the documents CN104530413A, CN104530415A and CN104530417A; take CN104530417A as an example, corresponding to paragraphs from [0627] to [0704]. The combination manners of any two or two more stable divalent linking groups into STAG linkages are not particularly limited, including but not limited to the combination manners described and listed in paragraph [0704] of the document CN104530417A.

For example in brief, a STAG linkage can be but not limited to any of the following structures, or the combination of any two or two more of the following structures:
-$L_7$-, —($R_5$)$_{r1}$—C($R_8$)=C($R_9$)—($R_6$)$_{r2}$—, —($R_5$)$_{r1}$—C≡C—($R_6$)$_{r2}$—, ($R_5$)$_{r1}$—C($R_8$)=C($R_9$)—C($R_{10}$)=C($R_{11}$)—($R_6$)$_{r2}$—, —($R_5$)$_{r1}$—O—($R_6$)$_{r2}$—, —($R_5$)$_{r1}$—S—($R_6$)$_{r2}$—, —($R_5$)$_{r1}$—N($R_{18}$)—C(=O)—N($R_{19}$)—($R_6$)$_{r2}$—, —($R_5$)$_{r1}$—N($R_{18}$)—C(=S)—N($R_{19}$)—($R_6$)$_{r2}$—, ($R_5$)$_{r1}$—N($R_7$)—C(=O)—O—($R_6$)$_{r2}$—, —($R_5$)$_{r1}$—O—C(=O)—N($R_7$)—($R_6$)$_{r2}$—, —($R_5$)$_{r1}$—N($R_7$)—C(=S)—O—($R_6$)$_{r2}$—, —($R_5$)$_{r1}$—O—C(=S)—N($R_7$)—($R_6$)$_{r2}$—, —($R_5$)$_{r1}$—N($R_7$)—C(=O)—S—($R_6$)$_{r2}$—, —($R_5$)$_{r1}$—S—C(=O)—N($R_7$)—($R_6$)$_{r2}$—, —($R_5$)$_{r1}$—N($R_7$)—C(=S)—S—($R_6$)$_{r2}$—, —($R_5$)$_{r1}$—S—C(=S)—N($R_7$)—($R_6$)$_{r2}$—, —($R_5$)$_{r1}$—N($R_7$)—C(=O)—($R_6$)$_{r2}$—, —($R_5$)$_{r1}$—C(=S)—($R_6$)$_{r2}$—, —($R_5$)$_{r1}$—P(=O)—($R_6$)$_{r2}$—, —($R_5$)$_{r1}$—($R_{38}$)P(=O)—($R_6$)$_{r2}$—, —($R_5$)$_{r1}$—($R_{38}$)OP(=O)—($R_6$)$_{r2}$—, —($R_5$)$_{r1}$—P(=S)—($R_6$)$_{r2}$—, —($R_5$)$_{r1}$—($R_{38}$)P(=S)—($R_6$)$_{r2}$—, —($R_5$)$_{r1}$—($R_{38}$)OP(=S)—($R_6$)$_{r2}$—, —($R_5$)$_{r1}$—C(=O)N($R_7$)—($R_6$)$_{r2}$, —($R_5$)$_{r1}$—N($R_7$)C(=O)—($R_6$)$_{r2}$—, —($R_5$)$_{r1}$—CH$_2$N($R_7$)CH$_2$—($R_6$)$_{r2}$—, —($R_5$)$_{r1}$—NHCH$_2$—($R_6$)$_{r2}$—, —($R_5$)$_{r1}$—CH$_2$NH($R_6$)$_{r2}$—, —($R_5$)$_{r1}$—N($R_7$)C(=O)CH$_2$—S—($R_6$)$_{r2}$—, —($R_5$)$_{r1}$—S—CH$_2$C(=O)N($R_7$)—($R_6$)$_{r2}$—, —($R_5$)$_{r1}$—S(=O)$_2$—($R_6$)$_{r2}$—, —($R_5$)$_{r1}$—S(=O)—($R_6$)$_{r2}$—, —($R_5$)$_{r1}$—($R_8$)C=C(N$R_7R_{39}$)—($R_6$)$_{r2}$—, —($R_5$)$_{r1}$—(N$R_7R_{39}$)C=C($R_8$)—($R_6$)$_{r2}$—, —($R_5$)$_{r1}$-$M_{17}(R_{22})$—($R_6$)$_{r2}$—,

the skeleton of an ω-amino acid, and a divalent linking group deriving from an amino acid skeleton or an amino acid derivative skeleton. The preferable embodiments of the ω-amino acid are the same as above-described.

Wherein, r1 and r2 are each independently 0 or 1 and typically r1 is 0. Wherein, the definitions of $R_7$, $R_{18}$, $R_{19}$, $R_8$, $R_9$, $R_{10}$, $R_{11}$, $M_5$, $M_6$, $M_5$-membered rings and $M_6$-membered rings are the same as above, no more repeated here.

Wherein, $R_{39}$ is a hydrogen atom or a group substituent connecting to a nitrogen atom, preferably a hydrogen atom or a $C_{1-20}$ hydrocarbyl group, and further preferably a hydrogen atom, a methyl group, an ethyl group, an n-propyl group, an isopropyl group, an n-butyl group or a benzyl group. In —N$R_7R_{39}$, $R_7$ and $R_{39}$ can be the same or different from each other. N$R_7R_{39}$ is preferably NH$_2$, NH$R_{39}$ or N($R_{39}$)$_2$.

Wherein, typical examples of STAG include but are not limited to: wherein, $R_7$, $R_{18}$ and $R_{19}$ are each independently a hydrogen atom, a methyl group, an ethyl group, an n-propyl group, an isopropyl group, an n-butyl group, a t-butyl group, a pentyl group, a hexyl group, an allyl group, a triphenylmethyl group (a trityl group), a phenyl group, a benzyl group, a nitrophenyl group, a p-methoxyphenyl group or a (trifluoromethyl)benzyl group; $R_8$, $R_9$, $R_{10}$ and $R_{11}$ are each independently a hydrogen atom or a methyl group.

Wherein, $L_7$ is a stable hydrocarbylene group or a stable substituted hydrocarbylene group. Wherein, the heteroatom or group substituent is not particularly limited, including but not limited to all the above-described heteroatoms and group substituents in the term-defining section, and can be a halogen atom, a hydrocarbyl substituent or a heteroatom-containing substituent. The structure of $L_7$ is not particularly limited, including but not limited to a linear structure, a branched structure or a ring-containing structure. The carbon-atom number of $L_7$ is not particularly limited, preferably from 1 to 20, and more preferably from 1 to 10. $L_7$ is preferably a stable $C_{1-20}$ hydrocarbylene group or a stable substituted $C_{1-20}$ hydrocarbylene group. The conditions "to be stable" are consistent with those in the term-defining section. $L_7$ is more preferably a $C_{1-20}$ hydrocarbylene group or a substituted $C_{1-20}$ hydrocarbylene group which can remain stable under the condition of light illumination, heat, low temperature, an enzymatic condition, an oxidation-reduction condition, an acidic condition, a basic condition or the like. Besides the divalent linking groups listed in the document CN104530417A, corresponding to paragraphs from [0633] to [0657] and including a ring-containing hydrocarbylene group, a methylene group and a substituted methylene group, examples of $L_7$ also include but are not limited to a phenyl-substituted methylene group (—CH(Ph)-), a benzyl-substituted methylene group (—CH(Bn)-) and the like.

Embodiments of —N($R_7$)— include but are not limited to that $R_7$ is a methyl group, an ethyl group, an isopropyl group, a cyclopropyl group, a cyclopropylmethyl group, a phenyl group or a benzyl group.

Wherein, $R_5$ and $R_6$ can remain stable, and are each independently a hydrocarbylene group or a substituted hydrocarbylene group. In one molecule, $R_5$ and $R_6$ can be the same or different from each other. The conditions "to be stable" are the same as the above-described conditions in the term-defining section. The structure of $R_5$ and $R_6$ are not particularly limited, each independently including but not limited to a linear structure, a branched structure or a ring-containing structure. The carbon-atom number of $R_5$ and $R_6$ are not particularly limited, each independently preferably from 1 to 20, and more preferably from 1 to 10. $R_5$ and $R_6$ are each independently a stable $C_{1-20}$ hydrocarbylene group or a stable substituted $C_{1-20}$ hydrocarbylene group. $R_5$ and $R_6$ are each independently more preferably a linear alkylene group, a branched alkylene group, a cycloalkylene group, a phenylene group, a condensed arylene group, an arylalkylene group, or the substituted form of any aforesaid hydrocarbylene group with a substituent selected from the group consisting of a $C_{1-6}$ alkyl group, a phenyl group, a benzyl group, a methylphenyl group or a butylphenyl group.

$R_5$ and $R_6$ each independently preferably have 1 to 10 carbon atoms.

Specifically, for example, $R_5$ and $R_6$ can each independently be but not limited to a methylene group, a 1,1-ethylene group, a 1,2-ethylene group, a 1,3-propylene group, a 1,2-propylene group, an isopropylene group, a butylene group, a pentylene group, a hexylene group, a heptylene group, an octylene group, a nonylene group, a decylene group, an undecylene group, a dodecylene group, a tridecylene group, a tetradecylene group, a pentadecylene group, a hexadecylene group, a heptadecylene group, an octadecylene group, a nonadecylene group, an eicosylene group, a cyclopropylene group, a cyclohexylene group, a cyclooctylene group, a cyclodecylene group, a 1,4-phenylene group, a 1,2-phenylene group, a 1,3-phenylene group, a benzylene group, a substituted form of any aforesaid group, or the combination of any two or two more hydrocarbylene groups or/and substituted hydrocarbylene groups of the foregoing. Wherein, the substituent can be a $C_{1-6}$ alkyl group, a phenyl group, a benzyl group, a methylphenyl group or a butylphenyl group. Wherein, the pentylene group includes but is not limited to a 1,5-pentylene group and a 3,3-pentylene group. Wherein, the heptylene group includes but is not limited to a 1,7-heptylene group and a 1,1-diisopropylmethylene group.

$R_5$ and $R_6$ are each independently more preferably a methylene group, a 1,2-ethylene group, a 1,3-propylene group, a 1,2-propylene group, an isopropylene group, a butylene group, a pentylene group, a hexylene group, a 1,7-heptylene group, a 1,1-diisopropylmethylene group, an octylene group, a cyclopropylene group, a 1,4-phenylene group, a 1,2-phenylene group, a 1,3-phenylene group, a benzylene group, a 1-benzylmethylene group, a 1-phenylmethylene group or the like.

$R_5$ and $R_6$ are each independently most preferably a methylene group, a 1,2-ethylene group, a 1,3-propylene group, a 1,4-butylene group, a 1,5-pentylene group or a 1,6-hexylene group.

-$M_{17}(R_{22})$— is a divalent 1,1-cyclic linking group, and the ring-membering atom number is preferably from 3 to 8 (i.e. 3, 4, 5, 6, 7 or 8).

Wherein, $M_{17}$ is a carbon atom or heteroatom of the ring skeleton (i.e. a ring-membering atom), preferably a carbon atom, a phosphorus atom or a silicon atom of the ring.

Wherein, $R_{22}$ is a divalent linking group, and participates in forming a ring (i.e. a ring-membering divalent linking group).

The carbon-atom number of $R_{22}$ is not particularly limited, preferably from 1 to 20, and more preferably from 1 to 10.

The structure of $R_{22}$ is not particularly limited, including but not limited to a linear structure, a branched structure bearing pendent groups or a ring-containing structure. Wherein, the ring is not particularly limited, and can be preferably an aliphatic ring, an aromatic ring, a sugar ring or a condensed ring.

$R_{22}$ can contain heteroatoms, or not.

$R_{22}$ can be a $C_{1-20}$ hydrocarbylene group, a $C_{1-20}$ divalent heterohydrocarbyl group, a substituted $C_{1-20}$ hydrocarbylene group, a substituted $C_{1-20}$ divalent heterohydrocarbyl group, or a divalent linking group combined by any two or three linking groups of the foregoing. Wherein, the atom or group substituent is not particularly limited, including but not limited to all the above-described atom and group substituents in the term-defining section, and can be a halogen atom, a hydrocarbyl substituent or a heteroatom-containing substituent.

$R_{22}$ is more preferably a $C_{1-20}$ open-chain alkylene group, a $C_{2-20}$ open-chain alkenylene group, a $C_{3-20}$ cycloalkylene group, a $C_{3-20}$ cycloalkenylene group, an arylhydrocarbylene group, a $C_{1-20}$ divalent aliphatic-derived heteroalkyl group, a $C_{2-20}$ divalent aliphatic-derived heteroalkenyl group, a divalent heteroarylhydrocarbyl group, a substituted alkylene group, a substituted $C_{2-20}$ open-chain alkenylene group, a substituted $C_{3-20}$ cycloalkylene group, a substituted $C_{3-20}$ cycloalkenylene group, a substituted arylalkylene group, a substituted $C_{1-20}$ divalent aliphatic-derived heteroalkyl group, a substituted $C_{2-20}$ divalent aliphatic-derived heteroalkenyl group, a substituted divalent heteroarylhydrocarbyl group, or a divalent linking group combined by any two or three linking groups of the foregoing. Wherein, the heteroatom is not particularly limited, and preferably O, S, N, P or Si.

$R_{22}$ is more preferably a $C_{1-10}$ open-chain alkylene group, a $C_{2-10}$ open-chain alkenylene group, a $C_{3-10}$ cycloalkylene group, a $C_{3-10}$ cycloalkenylene group, an arylhydrocarbylene group, a $C_{1-10}$ divalent aliphatic-derived heteroalkyl group, a $C_{2-10}$ divalent aliphatic-derived heteroalkenyl group, a divalent heteroarylhydrocarbyl group, a substituted alkylene group, a substituted $C_{2-10}$ open-chain alkenylene group, a substituted $C_{3-10}$ cycloalkylene group, a substituted $C_{3-10}$ cycloalkenylene group, a substituted arylalkylene group, a substituted $C_{1-10}$ divalent aliphatic-derived heteroalkyl group, a substituted $C_{2-10}$ divalent aliphatic-derived heteroalkenyl group, a substituted divalent heteroarylhydrocarbyl group, or a divalent linking group combined by any two or three linking groups of the foregoing.

Specifically, $R_{22}$ can be a linking group selected from the group consisting of a methylene group, an ethylene group, a propylene group, a butylene group, a pentylene group, a hexylene group, a heptylene group, an octylene group, a nonylene group, a decylene group, a $C_{1-20}$ divalent oxa-alkyl group, a $C_{1-20}$ divalent thia-alkyl group, a $C_{1-20}$ divalent aza-alkyl group, a divalent aza-aryl group, the substituted form of any aforesaid linking group, and the combination of any two or more identical or different linking groups or/and substituted linking groups of the foregoing. Wherein, the atom or group substituent can be a halogen atom, a hydrocarbyl substituent or a heteroatom-containing substituent, and preferably a halogen atom, an alkoxy group or a nitro group.

$R_{22}$ is preferably a 1,2-ethylene group, a 1,2-vinylene group (an ethenylene group) or a 1,3-propylene group.

Wherein, for example, when $R_{22}$ is a 1,2-ethylene group, -$M_{17}(R_{22})$— corresponds to

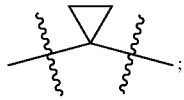 [SMILES: *C1(*)CC1]

when $R_{22}$ is an ethenylene group, -$M_{17}(R_{22})$— corresponds to

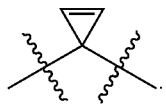

Wherein, $R_{38}$ is a hydrocarbyl group, preferably a $C_{1-20}$ hydrocarbyl group, more preferably a $C_{1-20}$ alkyl group, and more preferably a methyl group, an ethyl group, a propyl group, a butyl group, a pentyl group or a hexyl group.

Examples of the combination of any two or two more linkages include —$CH_2O$—, —$OCH_2$—, —$CH_2CH_2O$—, —$OCH_2CH_2$—, —$OCH_2CH_2O$—, —$(CH_2)_{30}$—, —$O(CH_2)_3$— and the like. For example, $L_0$ can contain an oligopeptide or polypeptide segment of multiple amino acids that are linked together end-to-end via N-terminus and C-terminus, wherein, the amino acids can be the same or different, but polypeptide fragments which can be enzymatically degraded should be excluded. In addition, $L_0$ can also contain a linkage selected from -$(L_7O)_{nj}$—, —$(OL_7)_{nj}$-, —$(R_{29}O)_{nj}$—, —$(OR_{29})_{nj}$—, —$(CH_2CH_2O)_{nj}$—, —$(OCH_2CH_2)_{nj}$— and the like. Wherein, the definitions of $L_7$ and $R_{29}$ are the same as above. Wherein, nj is an integer representing the repeat-unit number of a monodisperse structure, selected from 2 to 20, and preferably from 2 to 10. In the present invention, the heteroatom-containing repeat units other than —$CH_2CH_2O$— are not included in $CORE_8$ (O—)$_8$.

1.1.8.2. Degradable Divalent Linking Group (Degradable Divalent Linkage): DEGG

The condition "to be degradable" or "to degrade" or "to be degraded" is not particularly limited, including but not limited to conditions such as light illumination, heat, low temperature, an enzymatic condition, an oxidation-reduction condition, an acidic condition, a basic condition, a physiological condition, a simulated physiological environment in vitro and the like, preferably conditions such as light illumination, heat, an enzymatic condition, an oxidation-reduction condition, an acidic condition, a basic condition, etc.

The divalent linking group formed by the combination of a DEGG linkage and any one STAG linkage is still a degradable linking group. A degradable divalent linking group bearing an aryl ring to can also be combined by an aryl ring and a degradable divalent linking group.

The structural type of DEGG linkage is not particularly limited, and DEGG should contain at least one degradable divalent linkage selected from the group including, but not limited to, a disulfide bond, a vinylether bond, an ester bond (also referred to as an ester linkage), a thioester bond (also referred to as a thioester linkage), a thiocarboxylate bond (e.g., a thioate bond or a monothioester bond), a dithioester bond, a carbonate bond, a thiocarbonate bond, a dithiocarbonate bond, a trithiocarbonate bond, a carbamate bond, a thiocarbamate bond, a dithiocarbamate bond, an acetal linkage, a cycloacetal linkage, a mercaptal linkage, an azaacetal linkage, an azacycloacetal linkage, an azathiaacetal linkage, a dithioacetal linkage, a hemiacetal linkage, a thiohemiacetal linkage, an azahemiacetal linkage, a ketal linkage, a thioketal linkage, an azaketal linkage, an azacycloketal linkage, an azathiaketal linkage, an imine bond (e.g., —CH═N—), a hydrazone bond, an acylhydrazone bond, an oxime bond (e.g., —C(alkyl)═N—O—, or an iminoxy linkage, or an iminooxy linkage, or an oxyimino linkage, or an oximino bond, e.g., —O—N═CH—), a thiooxime bond (e.g., —C(alkyl)═N—S—), a semicarbazone bond, a thiosemicarbazone bond, a hydrazino bond, an acylhydrazino bond, a thiocarbonyl-hydrazino bond (—C(═S)—NH—NH—), an azocarbonyl-hydrazino linkage (e.g., —N═N—C(═O)—NH—NH—), an azo-thiocarbonyl-hydrazino linkage (e.g., —N═N—C(═S)—NH—NH—), a hydrazino formate linkage, a hydrazino thioformate linkage, a carbohydrazide bond, a thiocarbohydrazide bond, an azo bond, an isourea bond, an isothiourea bond, an allophanate linkage, a thioallophanate linkage, a guanidino linkage, an amidino linkage, an aminoguanidino linkage, an aminoamidino linkage, an iminocarbonyl-oxy linkage (e.g., —C(═NH)—O—), an iminocarbonyl-thioxy linkage (e.g., —C(═NH)—S—), a sulfonate linkage, a sulfinate linkage, a sulfonylhydrazino linkage, a sulfonylureido linkage, a maleimide linkage, an orthoester linkage, a benzyloxycarbonyl linkage, a phosphate linkage, a phosphirate linkage, a phosphinate linkage, a phosphonate linkage, a phosphosilicate linkage, a silicate linkage, an amide bond, a thioamide bond, a sulfonamide bond, a polyamide linkage, a phosphamide linkage, a phosphiramide linkage, a phosphinamide linkage, a phosphonamide linkage, a pyrophosphamide linkage, a cyclophosphamide linkage, an ifosfamide linkage, a thiophosphamide linkage, an aconityl linkage, a benzyloxycarbonyl linkage, a peptide bond, a polypeptide fragment, the skeletons of a nucleotide and derivatives thereof, the skeletons of a deoxynucleotide and derivatives thereof, and the divalent linking groups containing any two or two more divalent degradable linkages of the foregoing.

Herein, the carbamate group, the thiocarbamate group, the amide group, the phosphamide group and the like, can exist as a stable linking group or as a degradable linking group, depending on the use environment.

Specifically, examples of DEGG include but are not limited to the structures described and listed in the documents CN104530413A, CN104530415A and CN104530417A; take CN104530417A as an example, corresponding to paragraphs from [0705] to [0725]. Briefly, typical structures of DEGG can be but are not limited to any of the following structures, or the divalent linking groups containing any two or two more following structures:
—$(R_5)_{r1}$—S—S—$(R_6)_{r2}$—, —$(R_5)_{r1}$—C($R_8$)═C($R_9$)—O—$(R_6)_{r2}$—, —$(R_5)_{r1}$—O—C($R_9$)═C($R_8$)—$(R_6)_{r2}$—, —$(R_5)_{r1}$—C(═O)—O—$(R_6)_{r2}$—, —$(R_5)_{r1}$—O—C(═O)—$(R_6)_{r2}$—, —$(R_5)_{r1}$—C(═O)—S—$(R_6)_{r2}$—, —$(R_5)_{r1}$—S—C(═O)—$(R_6)_{r2}$—, —$(R_5)_{r1}$—C(S)—$(R_6)_{r2}$—, —$(R_5)_{r1}$—O—C(═S)—$(R_6)_{r2}$—, —$(R_5)_{r1}$—C(═S)—S—$(R_6)_{r2}$—, —$(R_5)_{r1}$—S—C(═S)—$(R_6)_{r2}$—, —$(R_5)_{r1}$—C(═O)—O—$(R_6)_{r2}$—, —$(R_5)_{r1}$—S—C(O)—O—$(R_6)_{r2}$—, —$(R_5)_{r1}$—O—C(═S)—$(R_6)_{2}$—, —$(R_5)_{r1}$—O—C(═O)—S—$(R_6)_{r2}$—, —$(R_5)_{r1}$—S—C(═S)—O—$(R_6)_{r2}$—, —$(R_5)_{r1}$—O—C(═S)—S—$(R_6)_{r2}$—, —$(R_5)_{r1}$—S—C(═O)—S—$(R_6)_{r2}$—, —$(R_5)_{r1}$—S—C(═S)—S—$(R_6)_{r2}$—, —$(R_5)_{r1}$—N($R_7$)—C(═O)—O($R_6)_{r2}$, —$(R_5)_{r1}$—O—C(═O)—N($R_7$)—$(R_6)_{r2}$—, —$(R_5)_{r1}$—N($R_7$)—C —(=S)—O—(R$_6$)$_{r2}$—, —(R$_5$)$_{r1}$—O—C(=S)—N(R$_7$)—(R$_6$)$_{r2}$—, —(R$_5$)$_{r1}$—N(R$_7$)—C(=O)—S—(R$_6$)$_{r2}$—, —(R$_5$)$_{r1}$—S—C(=O)N(R$_7$)—(R$_6$)$_{r2}$—, —(R$_5$)$_{r1}$—N(R$_7$)C(S)—S—(R$_6$)$_{r2}$—, —(R$_5$)$_{r1}$—S—C(=S)—N(R$_7$)—(R$_6$)$_{r2}$—, —(R$_5$)$_{r1}$—CH(OR$_3$)—O—(R$_6$)$_{r2}$—, —(R$_5$)$_{r1}$—O—CH(OR$_3$)—(R$_6$)$_{r2}$—, —(R$_5$)$_{r1}$—CH(OR$_3$)—S—(R$_6$)$_{r2}$—, —(R$_5$)$_{r1}$—S—CH(OR$_3$)—(R$_6$)$_{r2}$—, —(R$_5$)$_{r1}$—CH(SR$_3$)—O—(R$_6$)$_{r2}$—, —(R$_5$)$_{r1}$—O—CH(SR$_3$)—(R$_6$)$_{r2}$—, —(R$_5$)$_{r1}$—CH(SR$_3$)—S—(R$_6$)$_{r2}$—, —(R$_5$)$_{r1}$—S—CH(SR$_3$)—(R$_6$)$_{r2}$—, —(R$_5$)$_{r1}$—CH(OR$_3$)—N(R$_7$)—(R$_6$)$_{r2}$—, —(R$_5$)$_{r1}$—N(R$_7$)—CH(OR$_3$)—(R$_6$)$_{r2}$—, —(R$_5$)$_{r1}$—CH(NR$_{18}$R$_{19}$)—O—(R$_6$)$_{r2}$—, —(R$_5$)$_{r1}$—O—CH(NR$_{18}$R$_{19}$)—(R$_6$)$_{r2}$—, —(R$_5$)$_{r1}$—CH(NR$_{18}$R$_{19}$)—N(R$_7$)—(R$_6$)$_{r2}$—, —(R$_5$)$_{r1}$—N(R$_7$)—CH(NR$_{18}$R$_{19}$)—(R$_6$)$_{r2}$—, —(R$_5$)$_{r1}$—(R$_{18}$R$_{19}$N)C(SR$_3$)(R$_6$)$_{r2}$—, —(R$_5$)$_{r1}$—CH(SR$_3$)—N(R$_7$)—(R$_6$)$_{r2}$—, —(R$_5$)$_{r1}$—N(R$_7$)—CH(SR$_3$)—(R$_6$)$_{r2}$—, —(R$_5$)$_{r1}$—CH(NR$_{18}$R$_{19}$)—S—(R$_6$)$_{r2}$—, —(R$_5$)$_{r1}$—S—CH(NR$_{18}$R$_{19}$)—(R$_6$)$_{r2}$—, —(R$_5$)$_{r1}$—CH(OH)—O—(R$_6$)$_2$—, —(R$_5$)$_{r1}$—O—CH(OH)—(R$_6$)$_{r2}$—, —(R$_5$)$_{r1}$—CH(OH)—S—(R$_6$)$_{r2}$—, —(R$_5$)$_{r1}$—S—CH(OH)—(R$_6$)$_{r2}$—, —(R$_5$)$_{r1}$—CH(OH)—N(R$_7$)—(R$_6$)$_{r2}$—, —(R$_5$)$_{r1}$—N(R$_7$)—CH(OH)—(R$_6$)$_{r2}$—, —(R$_5$)$_{r1}$—CR$_{13}$(OR$_3$)—O—(R$_6$)$_{r2}$—, —(R$_5$)$_{r1}$—O—CR$_{13}$(OR$_3$)—(R$_6$)$_{r2}$—, —(R$_5$)$_{r1}$—CR$_{13}$(OR$_3$)—S—(R$_6$)$_{r2}$—, —(R$_5$)$_{r1}$—S—CR$_{13}$(OR$_3$)—(R$_6$)$_{r2}$—, —(R$_5$)$_{r1}$—CR$_{13}$(SR$_3$)—O—(R$_6$)$_{r2}$—, —(R$_5$)$_{r1}$—O—CR$_{13}$(SR$_3$)—(R$_6$)$_{r2}$—, —(R$_5$)$_{r1}$—CR$_{13}$(SR$_3$)—S—(R$_6$)$_{r2}$—, —(R$_5$)$_{r1}$—S—CR$_3$(SR$_3$)—(R$_6$)$_{r2}$—, —(R$_5$)$_{r1}$—CR$_{13}$(OR$_3$)—N(R$_7$)—(R$_6$)$_{r2}$—, —(R$_5$)$_{r1}$—N(R$_7$)—CR$_{14}$(OR$_3$)—(R$_6$)$_{r2}$—, —(R$_5$)$_{r1}$—CR$_{14}$(NR$_8$R$_9$)—O—(R$_6$)$_{r2}$—, —(R$_5$)$_{r1}$—O—CR$_{13}$(NR$_{18}$R$_{19}$)—(R$_6$)$_{r2}$—, —(R$_5$)$_{r1}$—CR$_{13}$(NR$_{18}$R$_{19}$)—N(R$_7$)—(R$_6$)$_{r2}$—, —(R$_5$)$_{r1}$—N(R$_7$)—CR$_{13}$(NR$_{18}$R$_{19}$)—(R$_6$)$_{r2}$—, —(R$_5$)$_{r1}$—CR$_{13}$(SR$_3$)—N(R$_7$)—(R$_6$)$_{r2}$, —(R$_5$)$_{r1}$—N(R$_7$)—CR$_{13}$(SR$_3$)—(R$_6$)$_{r2}$—, —(R$_5$)$_{r1}$—CR$_{13}$(NR$_{18}$R$_{19}$)—S—(R$_6$)$_{r2}$—, —(R$_5$)$_{r1}$—S—CR$_{13}$(NR$_{18}$R$_{19}$)—(R$_6$)$_{r2}$—, —(R$_5$)$_{r1}$—CR$_{13}$(OH)—O—(R$_6$)$_{r2}$—, —(R$_5$)$_{r1}$—O—CR$_{13}$(OH)—(R$_6$)$_{r2}$—, —(R$_5$)$_{r1}$—CR$_{13}$(OH)—S—(R$_6$)$_{r2}$—, —(R$_5$)$_{r1}$—S—CR$_{13}$(OH)—(R$_6$)$_{r2}$—, —(R$_5$)$_{r1}$—CR$_{13}$(OH)—N(R$_7$)—(R$_6$)$_{r2}$—, —(R$_5$)$_{r1}$—N(R$_7$)—CR$_{13}$(OH)—(R$_6$)$_{r2}$—, —(R$_5$)$_{r1}$—(R$_{15}$)C=N—(R$_6$)$_{r2}$—, —(R$_5$)$_{r1}$—N=C(R$_{15}$)—(R$_6$)$_{r2}$—, —(R$_5$)$_{r1}$—(R$_{15}$)C=N—N(R$_7$)—(R$_6$)$_{r2}$—, —(R$_5$)$_{r1}$—N(R$_7$)—N=C(R$_5$)—(R$_6$)$_{r2}$—, —(R$_5$)$_{r1}$—(R$_{15}$)C=N—N(R$_7$)—C(=O)—(R$_6$)$_{r2}$—, —(R$_5$)$_{r1}$—C(=O)—N(R$_7$)—N=C(R$_{15}$)—(R$_6$)$_{r2}$—, —(R$_5$)$_{r1}$—(R$_{15}$)C=N—O—(R$_6$)$_{r2}$—, —(R$_5$)$_{r1}$—O—N=C(R$_{15}$)—(R$_6$)$_{r2}$—, —(R$_5$)$_{r2}$—(R$_{15}$)C=N—S—(R$_6$)$_{r2}$—, —(R$_5$)$_{r1}$—S—N=C(R$_{15}$)—(R$_6$)$_{r2}$—, —(R$_5$)$_{r1}$—N(R$_7$)—C(=O)—N(R$_1$)—N=C—(R$_6$)$_{r2}$—, —(R$_5$)$_{r1}$—C=N—N(R$_{18}$)—C(=O)—N(R$_7$)—(R$_6$)$_{r2}$—, —(R$_5$)$_{r1}$—N(R$_7$)C(=S)—N(R$_{18}$)—N=C—(R$_6$)$_{r2}$—, —(R$_5$)$_{r1}$—C=N—N(R$_{18}$)—C(=S)—N(R$_7$)—(R$_6$)$_{r2}$—, —(R$_5$)$_{r1}$—N(R$_7$)—N(R$_{18}$)—(R$_6$)$_{r2}$—, (R$_5$)$_{r1}$—N(R$_7$)—N(R$_{18}$)—C(=O)—(R$_6$)$_{r2}$—, —(R$_5$)$_{r1}$—C(=O)—N(R$_{18}$)—N(R$_7$)—(R$_6$)$_{r2}$—, (R$_5$)$_{r1}$—N(R$_7$) N(R$_{18}$)—C(=S)—(R$_6$)$_{r2}$—, —(R$_5$)$_{r1}$—C(=S)—N(R$_{18}$)—N(R$_7$)—(R$_6$)$_{r2}$—, —(R$_5$)$_{r1}$—N(R$_7$)—N(R$_{18}$)—C(=O)—N=N—(R$_6$)$_{r2}$—, —(R$_5$)$_{r1}$—N=N—C(=O)N(R$_{18}$)—N(R$_7$)—(R$_6$)$_{r2}$—, —(R$_5$)$_{r1}$—N(R$_7$)—N(R$_{18}$)—C(=S)—N=N—(R$_6$)$_{r2}$—, —(R$_5$)$_{r1}$—N=N—C(=S)—N(R$_{18}$)—N(R$_7$)—(R$_6$)$_{r1}$—, —(R$_5$)$_{r1}$—N(R$_{18}$)—N(R$_7$)—C(=O)—O—(R$_6$)$_{r2}$—, —(R$_5$)$_{r1}$—O—C(=O)—N(R$_7$)—N(R$_{18}$)—(R$_6$)$_{r2}$—, —(R$_5$)$_{r1}$—N(R$_{18}$)—N(R$_7$)—C(=S)—O—(R$_6$)$_{r2}$—, —(R$_5$)$_{r1}$—O—C(=S)—N(R$_7$)—N(R$_{18}$)—(R$_6$)$_{r2}$—, —(R$_5$)$_{r1}$—N(R$_{18}$)—N(R$_7$)—C(=O)—S—(R$_6$)$_{r2}$—, —(R$_5$)$_{r1}$—S—C(=O)—N(R$_7$)—N(R$_{18}$)—(R$_6$)$_{r2}$—, —(R$_5$)$_{r1}$—N(R$_{18}$)—N(R$_7$)—C(=S)—S—(R$_6$)$_{r2}$—, —(R$_5$)$_{r1}$—S—C(=S)—N(R$_7$)—N(R$_{18}$)—(R$_6$)$_{r2}$—, —(R$_5$)$_{r1}$—N(R$_7$)—N(R$_{18}$)—C(=O)—N(R$_{19}$)—N(R$_{23}$)—(R$_6$)$_{r2}$—, —(R$_5$)$_{r1}$—N(R$_7$)—N(R$_{18}$)—C(=S)—N(R$_{19}$)—N(R$_{23}$)—(R$_6$)$_{r2}$—, —(R$_5$)$_{r1}$—N=N—(R$_6$)$_{r2}$—, —(R$_5$)$_{r1}$—O—C(=NR$_{18}$)—N(R$_7$)—(R$_6$)$_{r2}$—, —(R$_5$)$_{r1}$—N(R$_7$)—C(=NR$_{18}$)—O—(R$_6$)$_{r2}$—, —(R$_5$)$_{r1}$—O—C(=NH$_2^+$)—N(R$_7$)—(R$_6$)$_{r2}$—, —(R$_5$)$_{r1}$—N(R$_7$)—C(=NH$_2^+$)—O—(R$_6$)$_{r2}$—, —(R$_5$)$_{r1}$—N(R$_7$)—C(=NR$_{18}$)—S—(R$_6$)$_{r2}$—, —(R$_5$)$_{r1}$—S—C(=NR$_{18}$)—N(R$_7$)—(R$_6$)$_{r2}$—, —(R$_5$)$_{r1}$—N(R$_7$)—C(=NH$_2^+$)—S—(R$_6$)$_{r2}$—, —(R$_5$)$_{r1}$—S—C(=NH$_2^+$)—N(R$_7$)—(R$_6$)$_{r2}$—, —(R$_5$)$_{r1}$—N(R$_{18}$)—C(=O)—N(R$_7$)—C(=O)—O—(R$_6$)$_{r2}$—, —(R$_5$)$_{r1}$—O—C(=O)—N(R$_7$)—C(=O)—N(R$_{18}$)—(R$_6$)$_{r2}$—, —(R$_5$)$_{r1}$—N(R$_{18}$)—C(=S)—N(R$_7$)—C(=O)—O—(R$_6$)$_{r2}$—, —(R$_5$)$_{r1}$—O—C(=O)—N(R$_7$)—C(=S)—N(R$_{18}$)—(R$_6$)$_{r2}$—, —(R$_5$)$_{r1}$—N(R$_{18}$)—C(=NR$_7$)—N(R$_{19}$)—(R$_6$)$_{r2}$—, —(R$_5$)$_{r1}$—N(R$_{18}$)—C(=NH$_2^+$)—N(R$_{19}$)—(R$_6$)$_{r2}$—, —(R$_5$)$_{r1}$—C(=NR$_7$)—N(R$_{19}$)—(R$_6$)$_{r2}$—, —(R$_5$)$_{r1}$—N(R$_{18}$)—C(=NH$_2^+$)—(R$_6$)$_{r2}$—, —(R$_5$)$_{r1}$—C(=NH$_2^+$)—N(R$_{18}$)—(R$_6$)$_{r2}$—, —(R$_5$)$_{r1}$—N(R$_{23}$)—N(R$_{18}$)—C(=NR$_7$)—N(R$_{19}$)—(R$_6$)$_{r2}$—, —(R$_5$)$_{r1}$—N(R$_{19}$)—C(=NR$_7$)—N(R$_{18}$)—N(R$_{23}$)—(R$_6$)$_{r2}$—, —(R$_5$)$_{r1}$—N(R$_7$)—N(R$_{18}$)—C(=NH$_2^+$)—N(R$_{19}$)—(R$_6$)$_{r2}$—, —(R$_5$)$_{r1}$—N(R$_{19}$)—C(=NH$_2^+$)—N(R$_{18}$)—N(R$_7$)—(R$_6$)$_{r2}$—, —(R$_5$)$_{r1}$—C(=NR$_7$)—N(R$_{18}$)—N(R$_{19}$)—(R$_6$)$_{r2}$—, —(R$_5$)$_{r1}$—N(R$_{19}$)—N(R$_{18}$)—C(=NR$_7$)—(R$_6$)$_{r2}$—, —(R$_5$)$_{r1}$—N(R$_{19}$)—N(R$_{18}$)—C(=NH$_2^+$)—, —(R$_5$)$_{r1}$—C(=NH$_2^+$)—N(R$_{18}$)—N(R$_{19}$)—(R$_6$)$_{r2}$—, —(R$_5$)$_{r1}$—C(=NR$_7$)—O—(R$_6$)$_{r2}$—, —(R$_5$)$_{r1}$—O—C(=NR$_7$)—(R$_6$)$_{r2}$—, —(R$_5$)$_{r1}$—O—C(=NH$_2^+$)—(R$_6$)$_{r2}$—, —(R$_5$)$_{r1}$—C(=NH$_2^+$)—O—(R$_6$)$_{r2}$—, —(R$_5$)$_{r1}$—C(=NR$_7$)—S—(R$_6$)$_{r2}$—, —(R$_5$)$_{r1}$—S—C(=NR$_7$)—(R$_6$)$_{r2}$—, —(R$_5$)$_{r1}$—S—C(=NH$_2^+$)—(R$_6$)$_{r2}$—, —(R$_5$)$_{r1}$—C(=NH$_2^+$)—S—(R$_6$)$_{r2}$—, —(R$_5$)$_{r1}$—S(=O)$_2$—O—(R$_6$)$_{r2}$—, —(R$_5$)$_{r1}$—O—S(=O)$_2$—(R$_6$)$_{r2}$—, —(R$_5$)$_{r1}$—S(=O)—O—(R$_6$)$_{r2}$—, —(R$_5$)$_{r1}$—O—S(=O)—(R$_6$)$_{r2}$—, —(R$_5$)$_{r1}$—S(=O)$_2$—N(R$_7$)—(R$_6$)$_{r2}$—, —(R$_5$)$_{r1}$—N(R$_7$)—S(=O)$_2$—(R$_6$)$_{r2}$—, —(R$_5$)$_{r1}$—N(R$_{19}$)—S(=O)$_2$—N(R$_{18}$)—(R$_6$)$_{r2}$—, —(R$_5$)$_{r1}$—S(=O)$_2$—N(R$_{18}$)—N(R$_{19}$)—(R$_6$)$_{r2}$—, —(R$_5$)$_{r1}$—N(R$_{19}$)—N(R$_{18}$)—S(=O)$_2$—(R$_6$)$_{r2}$—, —(R$_5$)$_{r1}$—S(=O)$_2$—N(R$_{18}$)—C(=O)—N(R$_7$)—(R$_6$)$_{r2}$—(R$_6$)$_{r2}$—, —(R$_5$)$_{r1}$—N(R$_7$)—C(=O)—N(R$_{18}$)—S(=O)$_2$—(R$_6$)$_{r2}$—, —(R$_5$)$_{r1}$—N(R$_7$)—(CH$_2$)$_{r3}$—O—C(=O)—, —(R$_5$)$_{r1}$—N(R$_7$)—(CH$_2$)$_{r3}$—O—C(=O)—(R$_6$)$_{r2}$—, —(R$_5$)$_{r1}$—O—Si(R$_{41}$R$_{42}$)—O—(R$_6$)$_{r2}$—, an orthoester linkage, a phosphate linkage, a phosphirate linkage, a phosphinate linkage, a phosphonate linkage, a phosphosilicate linkage, a silicate linkage, an amide bond, a thioamide bond, a sulfonamide bond, a polyamide linkage, a phosphamide linkage, a phosphiramide linkage, a phosphinamide linkage, a phosphonamide linkage, a pyrophosphamide linkage, a cyclophosphamide linkage, an ifosfamide linkage, a thiophosphamide linkage, an aconityl linkage, a benzyloxycarbonyl linkage, a peptide bond, a polypeptide fragment, divalent linkages deriving from a nucleotide and derivatives thereof, divalent linkages deriving from a deoxynucleotide and derivatives thereof,

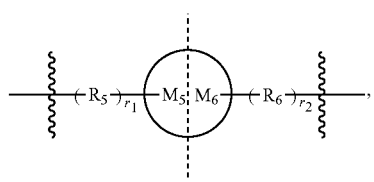

-continued

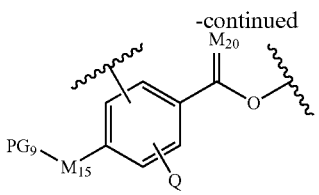

and the like; wherein, the definitions of $R_3$, $R_5$, $R_6$, $R_7$, $R_{18}$, $R_{19}$, $R_{23}$, $R_8$, $R_9$, $R_{13}$, $R_{15}$, $M_{19}$, $M_{20}$, $M_5$, $M_6$, $M_5$-membered rings and $M_6$-membered rings are the same as above, no more repeated here. Wherein, $R_{41}$ and $R_{42}$ are each independently a $C_{1-20}$ alkyl group, a phenyl group, a benzyl group, a $C_{1-20}$ alkyl-substituted phenyl group, a $C_{1-20}$ alkyl-substituted benzyl group or a $C_{1-20}$ alkoxy group, preferably a $C_{1-6}$ alkyl group, a phenyl group, a benzyl group, a $C_{1-6}$ alkyl-substituted phenyl group, a $C_{1-6}$ alkyl-substituted benzyl group or a $C_{1-6}$ alkoxy group, and more preferably a $C_{1-6}$ alkyl group, a phenyl group or a benzyl group; $R_{41}$ and $R_{42}$ attached to a common silicon atom are the same or different. In addition, linking groups such as

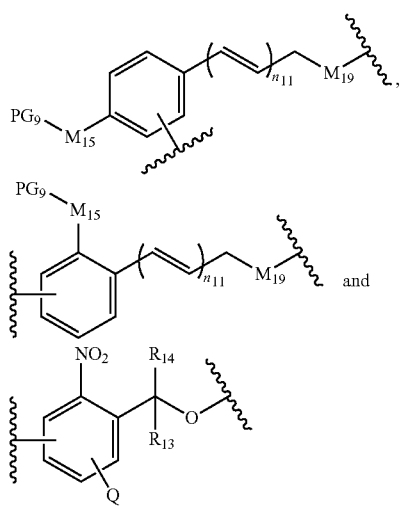

can remain stable under some physiological conditions, and can also be degraded under a special condition of light illumination. Common ester bonds can be degraded under acidic or basic conditions, however, ester groups such as that in the benzyloxycarbonyl group

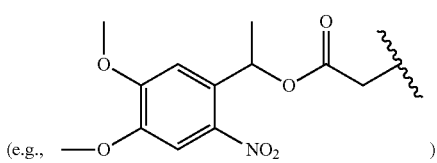 [SMILES: *CC(=O)OC(C)c1cc(OC)c(OC)cc1[N+](=O)[O-]]

can also be degraded under a special condition of light illumination ("Journal of Polymer Science: Part A: Polymer Chemistry, 2008, 46, 6896-6906").

Wherein, r1 and r2 are each independently 0 or 1.

Wherein, r3 is 2, 3, 4, 5 or 6.

Wherein, $M_{15}$ is a heteroatom selected from an oxygen atom, a sulfur atom and a nitrogen atom; $PG_9$ is the protecting group for $M_{15}$; when $M_{15}$ is an oxygen atom, $PG_9$ corresponds to a hydroxyl protecting group denoted as $PG_4$; when $M_{15}$ is a sulfur atom, $PG_9$ corresponds to a mercapto protecting group denoted as $PG_2$; when $M_{15}$ is a nitrogen atom, $PG_9$ corresponds to an amino protecting group denoted as $PG_5$.

Wherein, $n_{11}$ is the number of carbon-carbon double bonds, and can be 0 or an integer from 1 to 10.

Wherein,

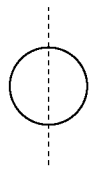

is a cyclic structure that can be degraded into at least two individual fragments. For example, a lactide ring, a cyclopeptide ring and the like.

Wherein, $R_{13}$ and $R_{14}$ are each independently a hydrogen atom, a heteroatom or a group substituent linked to a secondary or tertiary carbon atom.

The heteroatom and group substituent of $R_{13}$ and $R_{14}$ are not particularly limited.

The carbon-atom number of $R_{13}$ and $R_{14}$ is not particularly limited. For aliphatic hydrocarbyl groups and aliphatic-derived heterohydrocarbyl groups, the carbon-atom number is preferably from 1 to 20, and more preferably 1 to 10. With respect to aryl groups, arylhydrocarbyl group, heteroaryl groups, heteroarylhydrocarbyl groups and condensed heterocyclohydrocarbyl groups, the carbon-atom number is not particularly limited.

$R_{13}$ and $R_{14}$ each independently can be but not limited to a hydrogen atom, a halogen atom, a $C_{1-20}$ hydrocarbyl group, a $C_{1-20}$ heterohydrocarbyl group, a substituted $C_{1-20}$ hydrocarbyl group, a substituted $C_{1-20}$ heterohydrocarbyl group or the like.

Wherein, the atom or group substituent is not particularly limited, including but not limited to all the above-described atom and group substituents in the term-defining section, and can be a halogen atom, a hydrocarbyl substituent or a heteroatom-containing substituent.

$R_{13}$ and $R_{14}$ are each independently preferably a hydrogen atom, a halogen atom, a $C_{1-20}$ alkyl group, a $C_{3-20}$ unsaturated hydrocarbyl group, a $C_{1-20}$ linear aliphatic hydrocarbyl group, a $C_{3-20}$ branched aliphatic hydrocarbyl group, a $C_{3-20}$ alicyclic hydrocarbyl group, an aryl group, an arylhydrocarbyl group, a $C_{1-20}$ open-chain heterohydrocarbyl group, a $C_{3-20}$ aliphatic-derived heterocyclohydrocarbyl group, a heteroaryl group, a heteroarylhydrocarbyl group, a condensed heterocyclohydrocarbyl group, a $C_{1-20}$ hydrocarbyloxy group, a $C_{1-20}$ hydrocarbylthio group, a $C_{1-20}$ hydrocarbylamino group, a $C_{1-20}$ aliphatic hydrocarbyl-acyl group, an aryl-acyl group, an arylhydrocarbyl-acyl group, a $C_{1-20}$ aliphatic-derived heterohydrocarbyl-acyl group, a heteroaryl-acyl group, a heteroarylhydrocarbyl-acyl group, a $C_{1-20}$ hydrocarbyloxy-acyl group, a $C_{1-20}$ hydrocarbylthio-acyl group, a $C_{1-20}$ hydrocarbylamino-acyl group, a $C_{1-20}$ hydrocarbyl-acyloxy group, a $C_{1-20}$ hydrocarbyl-acylthio group, a $C_{1-20}$ hydrocarbyl-acylamino group, the like or the substituted form of any aforesaid group. Wherein, the atom or group substituent is preferably a fluorine atom, a chlorine atom, a bromine atom, an iodine atom, a $C_{1-6}$ alkyl group, a $C_{1-6}$ alkenyl group, an aryl group, an alkoxy group or a nitro group.

Wherein, the acyl group is not particularly limited, including but not limited to all the above-described acyl groups in the term-defining section. The acyl group is preferably a carbonyl group, a sulfonyl group, a sulfinyl group, a phosphoryl group, a phosphiryl group, a phosphinyl group, a phosphinyl group, a nitroxyl group, a nitrosyl group, a thiocarbonyl group, an imidoyl group, a thiophosphoryl group, a dithiophosphoryl group, a trithiophosphoryl group, a thiophosphiryl group, a dithiophosphiryl group, a thiophosphinyl group, a thiophosphono group, a dithiophosphono group, a thiophosphino group or the like, and more preferably a carbonyl group, a thiocarbonyl group, a sulfonyl group or a sulfinyl group.

$R_{13}$ and $R_{14}$ are each independently preferably a hydrogen atom, a halogen atom, a $C_{1-20}$ alkyl group, a $C_{2-20}$ alkenyl group, a $C_{2-20}$ alkynyl group, a $C_4$-20 dienyl group, a $C_{3-20}$ alkenyl-hydrocarbyl group, a $C_{3-20}$ alkynyl-hydrocarbyl group, a $C_5$-20 dienyl-hydrocarbyl group, a $C_{1-20}$ linear aliphatic hydrocarbyl group, a $C_{3-20}$ branched aliphatic hydrocarbyl group, a $C_{3-20}$ cycloalkyl group, a $C_{3-20}$ cycloalkenyl group, a $C_{3-20}$ cycloalkynyl group, a $C_{5-20}$ cyclodienyl-hydrocarbyl group, a phenyl group, a condensed cyclohydrocarbyl group, an arylhydrocarbyl group, a $C_{1-20}$ open-chain heterohydrocarbyl group, a $C_{3-20}$ aliphatic-derived heterocyclohydrocarbyl group, a heteroaryl group, a heteroarylhydrocarbyl group, an aryl-condensed heterocyclic hydrocarbyl group, a heterocondensed heterocyclic hydrocarbyl group, a $C_{1-20}$ alkoxy group, a $C_{2-20}$ alkenyloxy group, a $C_{2-20}$ alkynyloxy group, an aryloxy group, an arylhydrocarbyloxy group, a $C_{1-20}$ alkylthio group, a $C_{2-20}$ alkenylthio group, a $C_{2-20}$ alkynylthio group, an arylthio group, a $C_{1-20}$ alkylamino group, a $C_{2-20}$ alkenylamino group, a $C_{1-20}$ alkyl-acyl group, a $C_{2-20}$ alkenyl-acyl group, a $C_{2-20}$ alkynyl-acyl group, an aryl-acyl group, an arylhydrocarbyl-acyl group, a $C_{1-20}$ aliphatic-derived heterohydrocarbyl-acyl group, a heteroaryl-acyl group, a heteroarylhydrocarbyl-acyl group, a $C_{1-20}$ alkoxy-acyl group, an aryloxy-acyl group, a $C_{1-20}$ alkylthio-acyl group, an arylthio-acyl group, a $C_{1-20}$ alkylamino-acyl group, a $C_{1-20}$ alkyl-acyloxy group, an aryl-acyloxy group, a $C_{1-20}$ alkyl-acylthio group, an aryl-acylthio group, a $C_{1-20}$ alkyl-acylamino group, the like or the substituted form of any aforesaid group.

Specifically, $R_{13}$ and $R_{14}$ can be each independently a hydrogen atom, a fluorine atom, a chlorine atom, a bromine atom, an iodine atom, a methyl group, an ethyl group, an n-propyl group, an isopropyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a cyclopropyl group, a cyclohexyl group, a phenyl group, a benzyl group, a butylphenyl group, a p-methylphenyl group, an ethenyl group, a propenyl group, an allyl group, a propynyl group, a propargyl group, a methoxy group, an ethoxy group, a phenoxy group, a benzyloxy group, a methylthio group, an ethylthio group, a phenylthio group, a benzylthio group, a methylamino group, an ethylamino group, a benzylamino group, an acetyl group, a benzoyl group, a methoxy-acyl group, an ethoxy-acyl group, a phenoxy-acyl group, a benzyloxy-acyl group, a methylthio-acyl group, an ethylthio-acyl group, a phenylthio-acyl group, a benzylthio-acyl group, a methylamino-acyl group, an ethylamino-acyl group, a phenylamino-acyl group, a benzylamino-acyl group, an ethyl-acyloxy group, a phenyl-acyloxy group, an ethyl-acylthio group, a phenyl-acylthio group, an ethyl-acylamino group, a phenyl-acylamino group, a $C_{1-20}$ haloalkyl group, the like or the substituted form of any aforesaid group. Wherein, the butyl group includes but is not limited to an n-butyl group and a t-butyl group. The octyl group includes but is not limited to an n-octyl group and a 2-ethylhexyl group. The acyl group can be any one of the above-described acyl groups. Wherein, the atom or group substituent can be a halogen atom, a hydrocarbyl substituent or a heteroatom-containing substituent, and can be preferably a halogen atom, a $C_{1-6}$ alkyl group, an alkoxy group, a $C_{1-6}$ alkenyl group or a nitro group.

$R_{13}$ and $R_{14}$ are each independently more preferably a hydrogen atom, a fluorine atom, a chlorine atom, a bromine atom, an iodine atom, a methyl group, an ethyl group, an n-propyl group, an isopropyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a cyclopropyl group, a cyclohexyl group, a phenyl group, a benzyl group, a butylphenyl group, a p-methylphenyl group, a vinylphenyl group, an ethenyl group, a propenyl group, an allyl group, a propynyl group, a propargyl group, a nitrophenyl group, a p-methoxyphenyl group, a methoxy group, an ethoxy group, a phenoxy group, a benzyloxy group, a methylthio group, an ethylthio group, a phenylthio group, a benzylthio group, a methylamino group, an ethylamino group, a benzylamino group, an acetyl group, a benzoyl group, a methoxycarbonyl group, an ethoxycarbonyl group, a phenoxycarbonyl group, a benzyloxycarbonyl group, a (methylthio)carbonyl group, an (ethylthio)carbonyl group, a (phenylthio)carbonyl group, a (benzylthio)carbonyl group, a methylaminocarbonyl group, an ethylaminocarbonyl group, a phenylaminocarbonyl group, a benzylaminocarbonyl group, a methoxysulfonyl group, an ethoxysulfonyl group, a phenoxysulfonyl group, a benzyloxysulfonyl group, an acetyloxy group, a benzoyloxy group, an acetylthio group, a benzoylthio group, an acetylamino group, a benzoylamino group, an ethyl-thiocarbonyl group, a phenyl-thiocarbonyl group, a methoxy-thiocarbonyl group, an ethoxy-thiocarbonyl group, a phenoxy-thiocarbonyl group, a benzyloxy-thiocarbonyl group, a (methylthio)thiocarbonyl group, an (ethylthio)thiocarbonyl group, a (phenylthio)thiocarbonyl group, a (benzylthio)thiocarbonyl group, a methylaminothiocarbonyl group, an ethylaminothiocarbonyl group, a phenylaminothiocarbonyl group, a benzylaminothiocarbonyl group, an ethyl-thiocarbonyloxy group, a phenyl-thiocarbonyloxy group, an ethyl-thiocarbonylthio group, a phenyl-thiocarbonylthio group, an ethyl-thiocarbonylamino group, a phenyl-thiocarbonylamino group, a trifluoromethyl group, a 2,2,2-trifluoroethyl group, the like or the substituted form of any aforesaid group. Wherein, the butyl group includes but is not limited to an n-butyl group and a t-butyl group. The octyl group includes but is not limited to an n-octyl group and a 2-ethylhexyl group.

$R_{13}$ and $R_{14}$ are each independently more preferably a hydrogen atom, a fluorine atom, a methyl group, an ethyl group, an n-propyl group, an isopropyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a cyclopropyl group, a cyclohexyl group, a phenyl group, a benzyl group, a butylphenyl group, a p-methylphenyl group, a vinylphenyl group, an ethenyl group, a propenyl group, an allyl group, a nitrophenyl group, a p-methoxyphenyl group, a methoxy group, an ethoxy group, a phenoxy group, a benzyloxy group, a methylthio group, an ethylthio group, a phenylthio group, a benzylthio group, a methylamino group, an ethylamino group, a benzylamino group, a trifluoromethyl group, a 2,2,2-trifluoroethyl group, the like or the substituted form of any aforesaid group. Wherein, the atom or group substituent is preferably a fluorine atom, a $C_{1-6}$ alkyl group, an alkoxy group, a $C_{1-6}$ alkenyl group or a nitro group.

$R_{13}$ and $R_{14}$ are each independently more preferably a hydrogen atom, a fluorine atom, a methyl group, an ethyl group, an n-propyl group, an isopropyl group, a butyl group, a phenyl group, a benzyl group, a butylphenyl group, a p-methylphenyl group, a trifluoromethyl group, a 2,2,2-trifluoroethyl group, the like or the substituted form of any aforesaid group.

$R_{13}$ and $R_{14}$ are each independently most preferably a hydrogen atom or a methyl group.

Further preferable embodiments of the DEGG linkage include structures from the aforesaid groups which also satisfy the following conditions: r1 and r2 are equal to 0 (r1=r2=0), $R_7$, $R_{18}$, $R_{19}$ and $R_{23}$ are identical ($R_7=R_{18}=R_{19}=R_{23}$) and preferably a hydrogen atom or a methyl group, $R_8$, $R_9$, $R_{13}$, $R_{14}$ and $R_1$ are a hydrogen atom ($R_8=R_9=R_{13}=R_{14}=R_{15}=H$), and $R_3$ is preferably a methyl group, an ethyl group or a benzyl group.

Embodiments of DEGG also include the combination of any above-said degradable divalent linking group and any suitable stable divalent linking group.

1.1.8.3. Degradable Multivalent Groups

A degradable trivalent, tetravalent or higher-valent group contains at least one degradable divalent linking group DEGG.

The degradable trivalent groups include but are not limited to the combination of a stable trivalent group containing a trivalent atom core structure together with a degradable divalent linking group, the combination of a trivalent aryl ring together with a degradable divalent linking group, the combination of a degradable trivalent cyclic structure together with a stable divalent linking group, the combination of a degradable trivalent cyclic structure together with a degradable divalent linking group, the trivalent form of any above-said degradable divalent linking groups and the like. Wherein, the degradable trivalent cyclic structure refers to a trivalent cyclic structure that can be degraded into at least two individual fragments. The typical example can be a trivalent closed cyclic structure formed by two or two more degradable groups that are connected in sequence, such as a cyclopeptide, and a cyclic structure formed via two or two more ester bonds in sequence. Examples of degradable multivalent groups include but are not limited to the structures described and listed in the documents CN104530413A, CN104530415A and CN104530417A; take CN104530417A as an example, corresponding to paragraphs from [0726] to [0731].

1.1.9. End-Branching Group G and Examples Thereof

The structure of G groups are not particularly limited, each independently can be but not limited to a branched type, a ring-containing type, a comb-like type, a dendritic type, a hyperbranched type or the like. G can be degradable or stable.

The $L_0$ group is a divalent linking group that connects a PEG chain with corresponding end-branching group G, and can be independently present or absent. $L_0$ can be stable or degradable, and can be any above-described STAG linkage or DEGG linkage.

The end-branching groups G of an eight-arm polyethylene glycol derivative have the same structural type, e.g., they can all be of the same tribranched type, of the same tetrabranched type, of the same comb-like type, of the same dendritic type, of the same hyperbranched type, or of the same ring-containing type (a cyclic type). When having the same structural type (in terms of geometry), the chemical structures of the eight PEG-chain terminals are allowed not to be exactly the same. For instance, with respect to a comb-like branching type, different chemical structures can have different valences due to the difference in the repeat-unit number. With respect to structures of a hyperbranched type, the number of the branching units does not need to be strictly the same, and also the branching units are allowed to be randomly combined. Therefore, in one molecule, when the PEG chain terminals are of a comb-like type or of a hyperbranched type, the corresponding k values can be different. However, with respect to a dendritic type or a cyclic type, chemical structures should be exactly the same, while the corresponding k values should be exactly equal. In addition, the present invention also discloses dendritic and cyclic structures which have the same structural type but different k values, for example, with respect to subsequent functionalization to the eight terminal hydroxyl groups of a third-generation dendritic structure

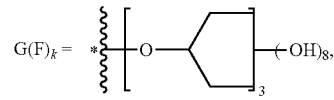

the functionalization ratio is preferably equal to or close to 100%; other cases in which the functionalization ratio is greater than 0 but less than 100% are also disclosed.

Examples of G also include but are not limited to the above-said (k+1)-valent groups, wherein, k is from 2 to 250 (k=2 to 250). Preferable structures of G include but are not limited to the structures described and listed in the documents CN104530413A, CN104530415A and CN104530417A; take CN104530417A as an example, corresponding to paragraphs from [0824] to [0825].

When k (the terminal-reactive-site number, i.e. the number of functional end-group $R_{01}$) is equal to 2, the corresponding G is a trivalent group, and examples of G include but are not limited to trivalent groups in the above-said set $G^3$ and all $E_i$ (i=1, 2, 3 or 4) groups. Herein, $L_0$-G preferably contains any of the following structures: any one of the above-described $E_0$ groups, any one of the above-described preferable examples of $E_0$,

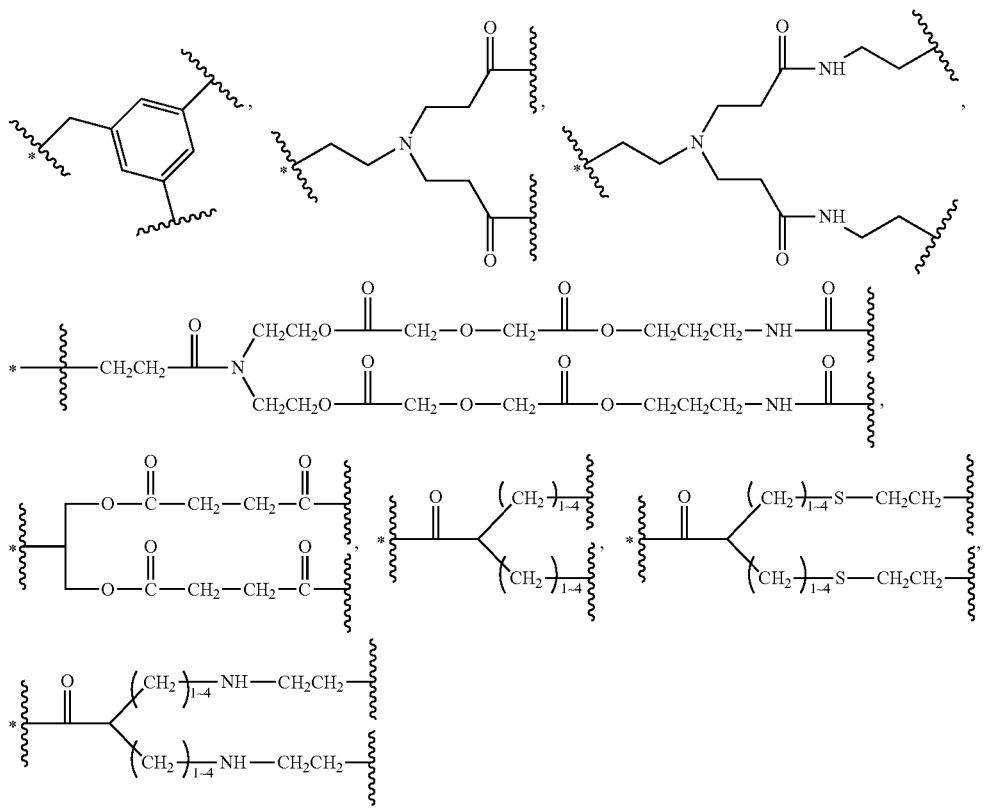

and the like.

When the terminal-reactive-site number k is equal to 3, the corresponding G is a tetravalent group, and examples of G include but are not limited to tetravalent groups in the above-said set $G^4$. A tetravalent G preferably contains a tetravalent core structure selected from an atom $CM_4$, an unsaturated bond $CB_4$ and a cyclic structure $CC_4$, or contains two trivalent core structures. $L_0$-G further preferably contains any one of the following structures:

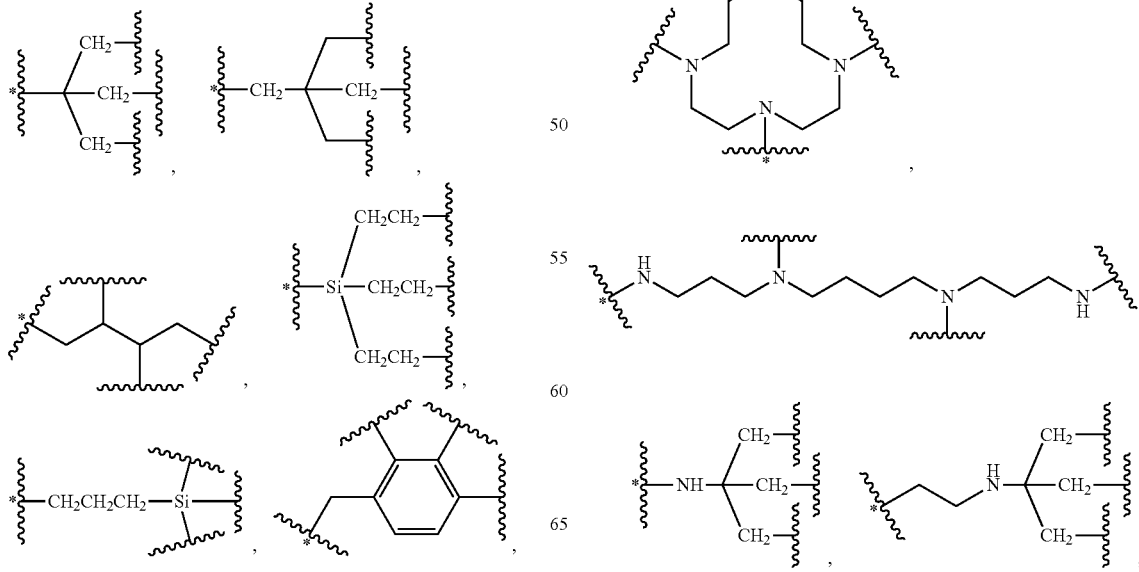

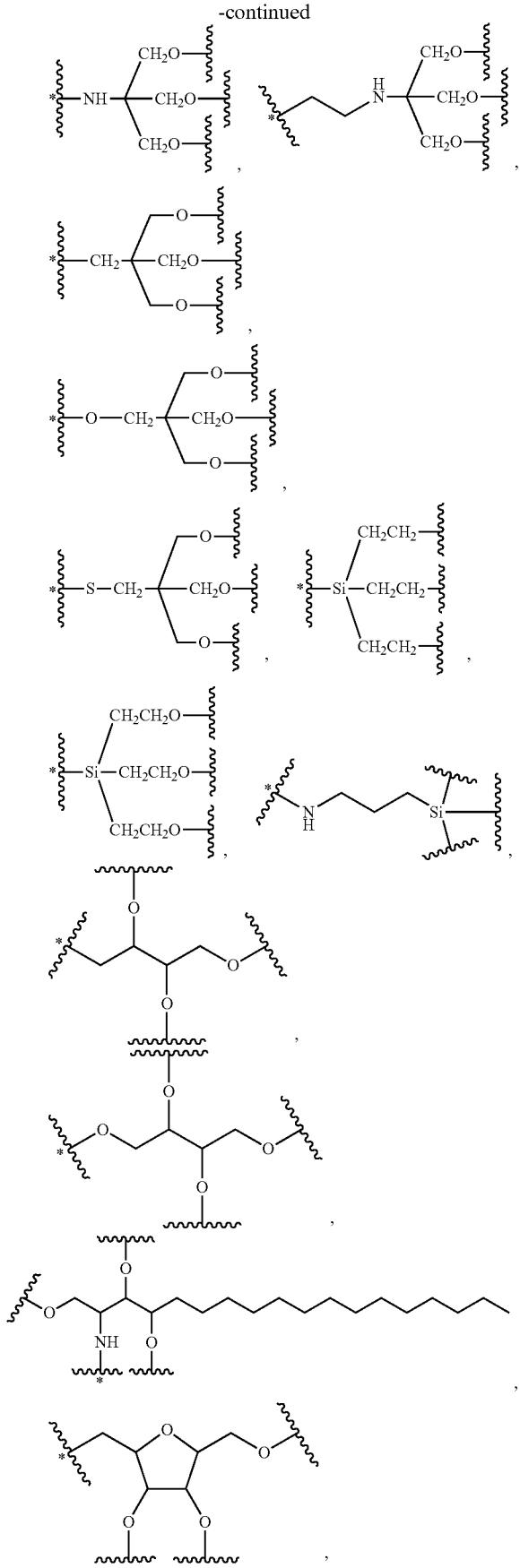
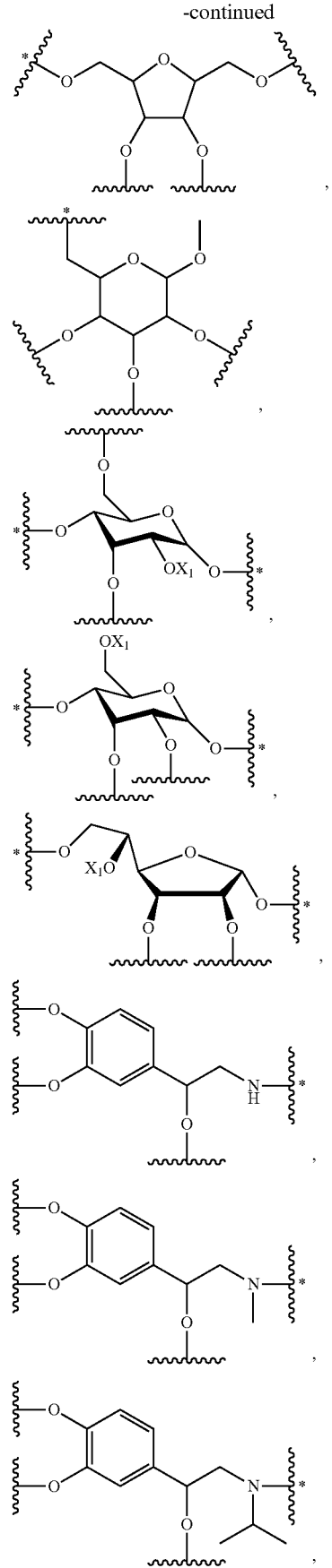

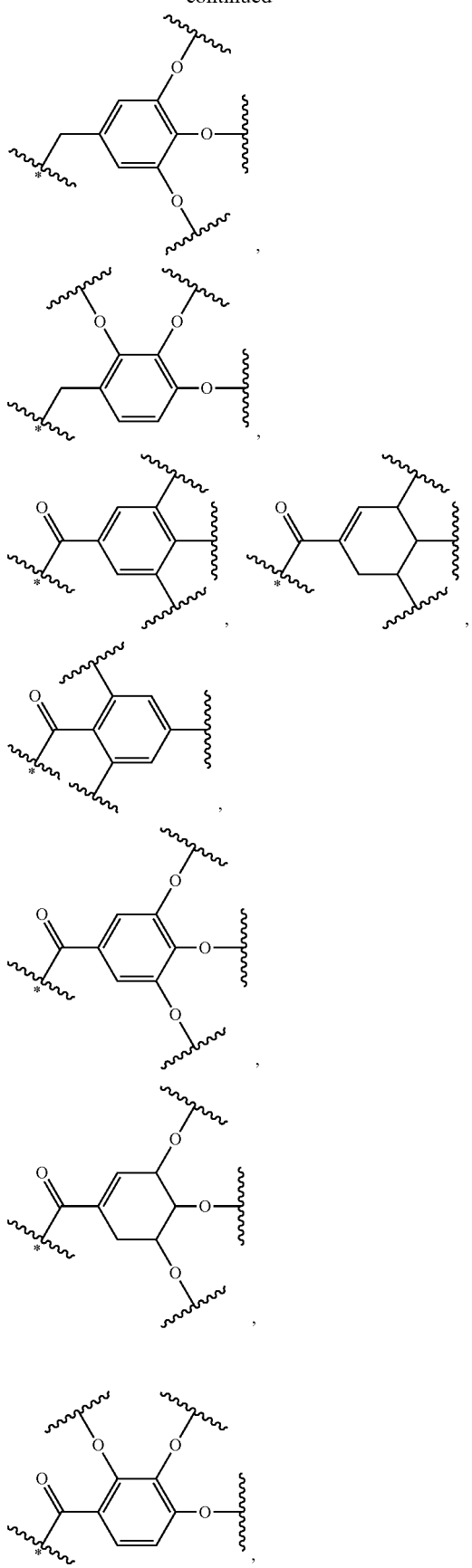
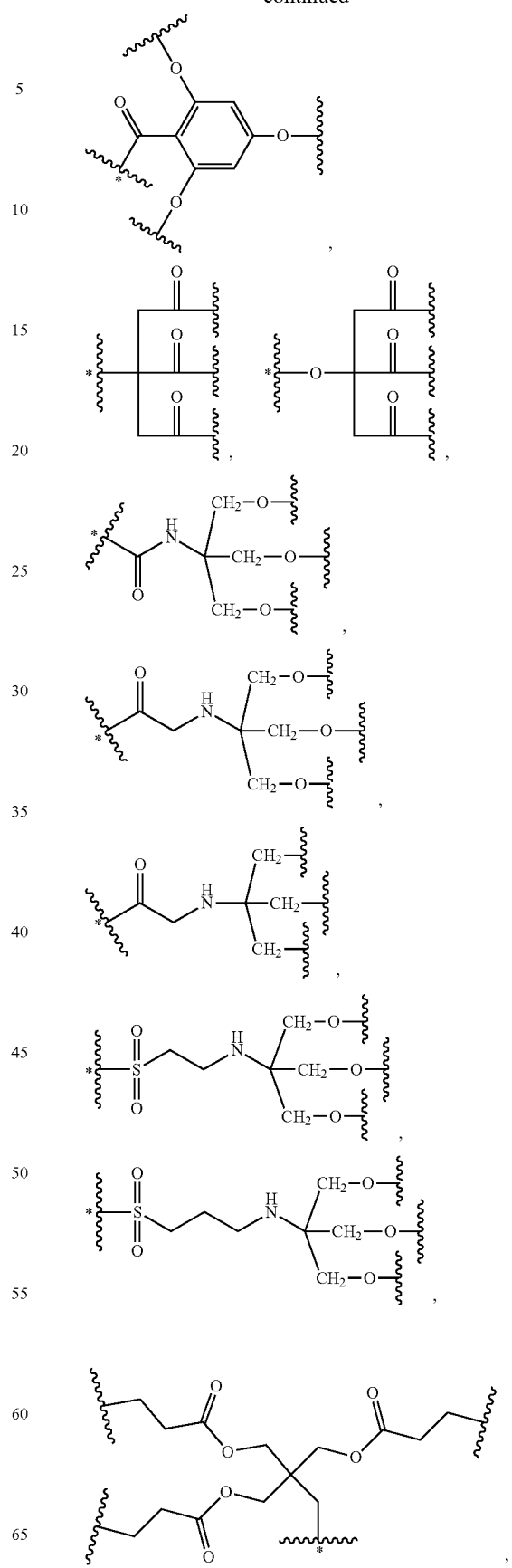

-continued

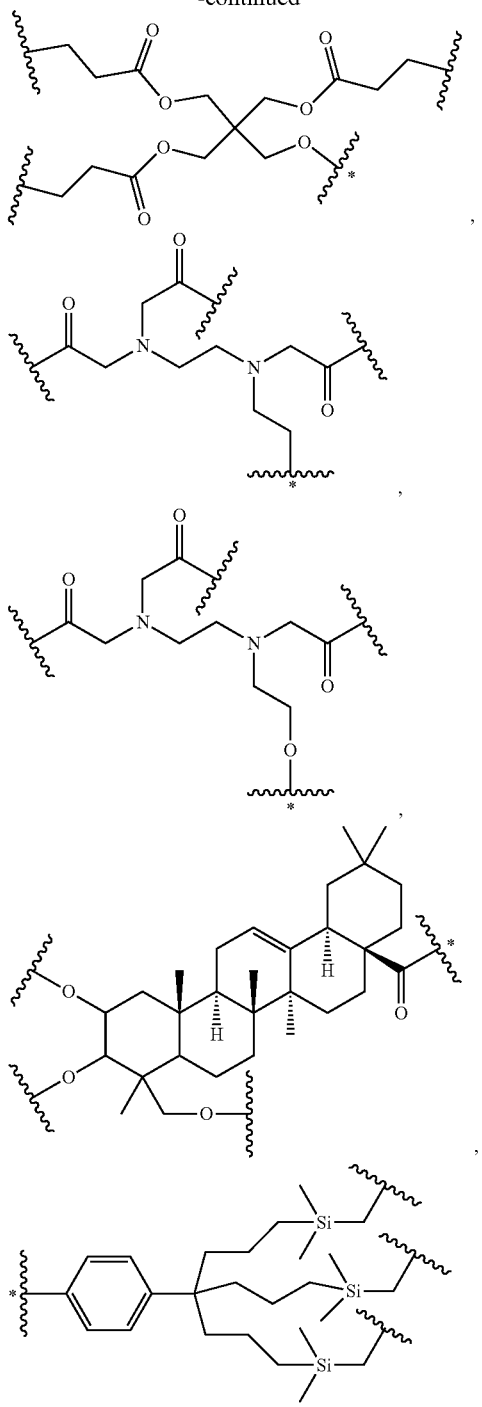

and the like.

When the terminal-reactive-site number k is equal to or greater than 3 (k≥3), that is, the valence of G is equal to or higher than 4 (≥4), then (k+1)-valent G groups include but are not limited to (k+1)-valent groups (groups with a valence of k+1) in the above-said set $G^{k+1}$. A (k+1)-valent G can contain one (k+1)-valent core structure, or be directly combined by lower-valent groups with a valence from 3 to k in quantities of 2 to k−1, or be combined indirectly via one or more divalent spacer groups denoted as $L_{10}$. The lower-valent groups of 3- to k-valence can be identical or not identical in structure, and can also be identical or different in valence. For example, two different trivalent groups can be combined into a structure shown as

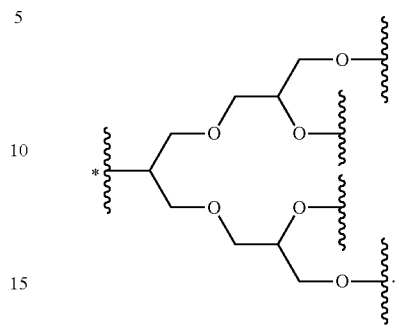

With respect to a (k+1)-valent core structure in which k is equal to or greater than 4 (k≥4), when a (k+1)-valent core is contained, the (k+1)-valent core structure is preferably a cyclic structure. When two or two more spacer groups denoted as $L_{10}$ are contained, these $L_{10}$ groups can be identical or not identical. The definition of $L_{10}$ is the same as the above.

As for (k+1)-valent G groups (k≥24) formed via a direct or indirect combination, the combination manners include but are not limited to a comb-like manner, a dendritic manner, a branched manner, a hyperbranched manner, a cyclic manner, etc. For example, with respect to groups formed by multiple lower-valent groups in a comb-like, dendritic or hyperbranched manner, the multiple lower-valent groups can be identical or different, and are preferred to be identical.

Dendritic structures combined in a dendritic manner can also be denoted as DENR ($U_{denr}$, NONE, d) or DENR ($U_{denr}$, $L_{10}$, d). Wherein, $U_{denr}$ represents the multivalent repeat unit; NONE represents direct connection between multivalent repeat units; $L_{10}$ serves as a divalent linking group for multivalent repeat units to be indirectly combined; d represents the generation number of dendritic combination, preferably from 2 to 6, more preferably from 2 to 5, and most preferably 2, 3 or 4. The structural unit of multivalent G via a dendritic combination is preferably trivalent or tetravalent.

Examples of dendritic combination include

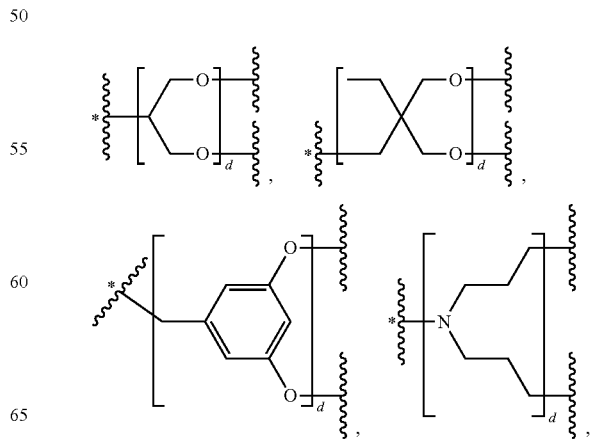

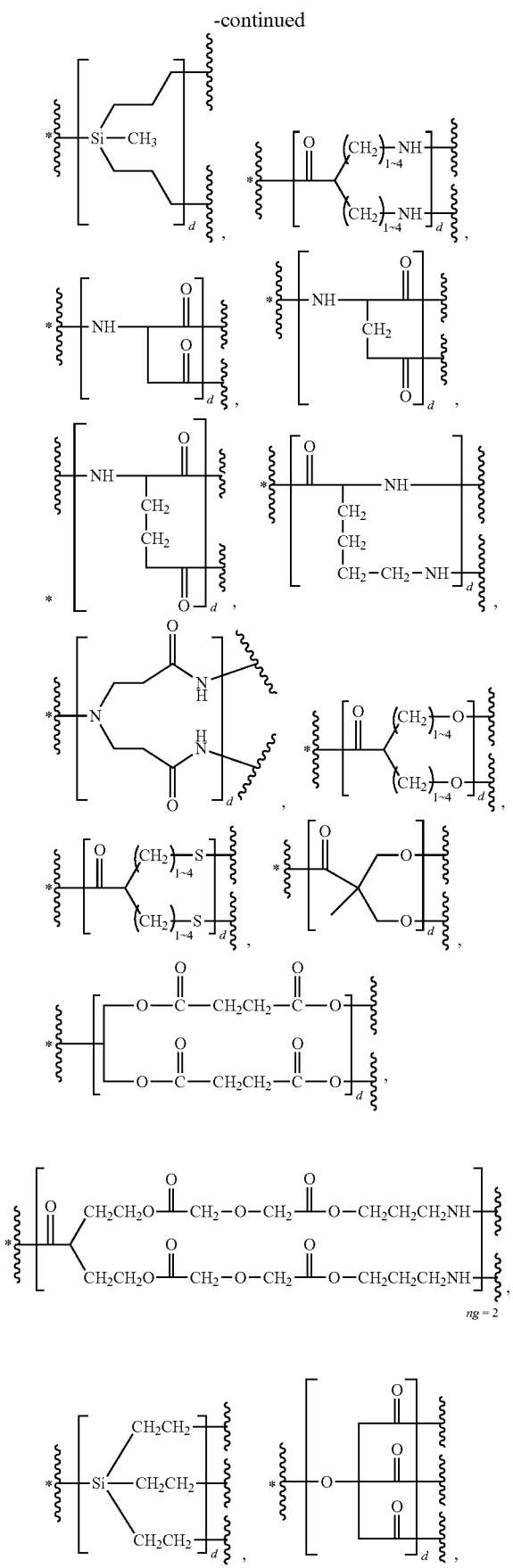

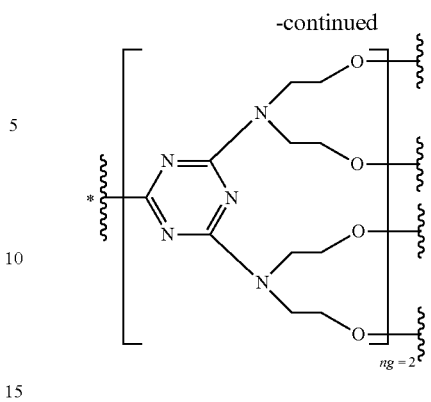

and the like. Wherein, ng represents the generation number of dendritic combination.

Wherein, the structural unit of multivalent G via a branched or hyperbranched combination is preferably any of the above-said trivalent or tetravalent G groups. Preferable structural units include but are not limited to those for the above-described dendritic combination, and also include

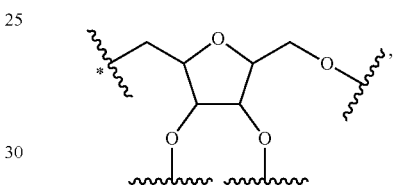

etc. The branched and hyperbranched combinations are different from the above dendritic combination in that they are a hybrid combination of the multivalent structural units and lower-valent forms thereof. Regarding the lower-valent forms of a multivalent structural unit, for example, the lower-valent forms of

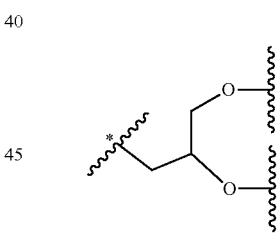

include

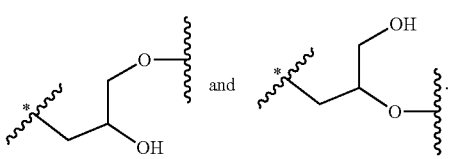

Wherein, the structural unit of multivalent G via a comb-like combination is preferably a trivalent, tetravalent or pentavalent above-said G group. The structural unit is preferably selected from the repeat units disclosed in paragraphs from [0824] to [0825] of the document CN104530417A and paragraphs from [1130] and [1143] of the document CN104530413A. The structural units of multivalent G via a comb-like combination include but are not limited to glycerol, pentaerythritol, substituted epoxypropane, the combination of substituted epoxypropane with carbon dioxide, acrylate and derivatives thereof, methacrylate and derivatives thereof, acetal-containing structural units (such as (1→6)β-D glucopyranoside), hydroxyl- or mercapto-containing amino acids and derivatives thereof, acidic amino acids and derivatives thereof, basic amino acids and derivatives thereof and the like. G can also be an acetalated-dextran structure formed by D-glucopyranose units that are linked end to end via any of the following glucosidic bonds: β-1,6-glucosidic bond, α-1,6-glucosidic bond, β-1,4-glucosidic bond, α-1,4-glucosidic bond, β-1,3-glycosidic bond, α-1,3-glycosidic bond and the like, or be an oxidized form of the above-said acetalated-dextran. The repeat unit of a comb-like combination can also be a suitable triol, a suitable tetraol, an open-chain pentitol or an open-chain hexitol, and the corresponding reagents are preferably in a form in which all hydroxyl groups except for the ether-bond hydroxyl groups are protected. Examples of above alcohols include glycerol, trihydroxyethylethane and trihydroxyethylpropane.

Wherein, the multivalent G group via a cyclic combination is preferably the residue of a cyclopeptide or a cyclopeptide derivative, the residue of a monosaccharide or a monosaccharide derivative, the residue of a polysaccharides or a polysaccharide derivative (e.g., a functionalized derivative of cyclodextrin), the skeleton of 1,4,7-tri-t-butoxycarbonyl-1,4,7,10-tetraazacyclododecane, the skeleton of 2-hydroxymethylpiperidine-3,4,5-triol, the skeleton of 6-amino-4-(hydroxymethyl)-4-cyclohexyl-[4H,5H]-1,2,3-triol or the like.

For example, when the terminal-reactive-site number k is equal to 4 (k=4), then G is a pentavalent group, including but not limited to the pentavalent groups in the above-described set $G^5$; the pentavalent G groups can contain merely one pentavalent core structure, a combination of one tetravalent together with one trivalent core structure, or a combination of three trivalent core structures. $L_0$-G preferably contains any of the following structures:

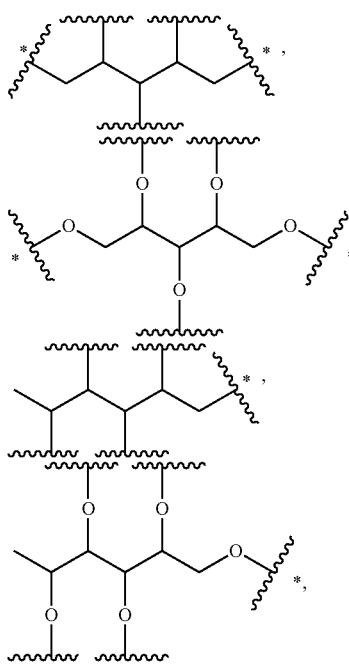

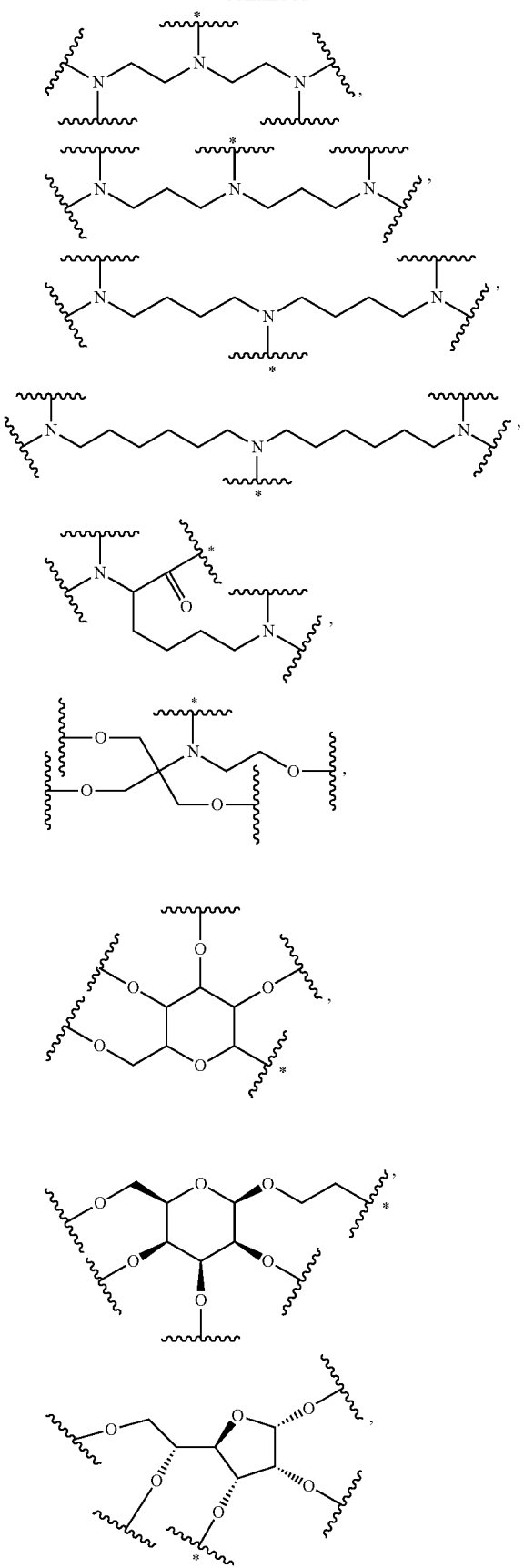

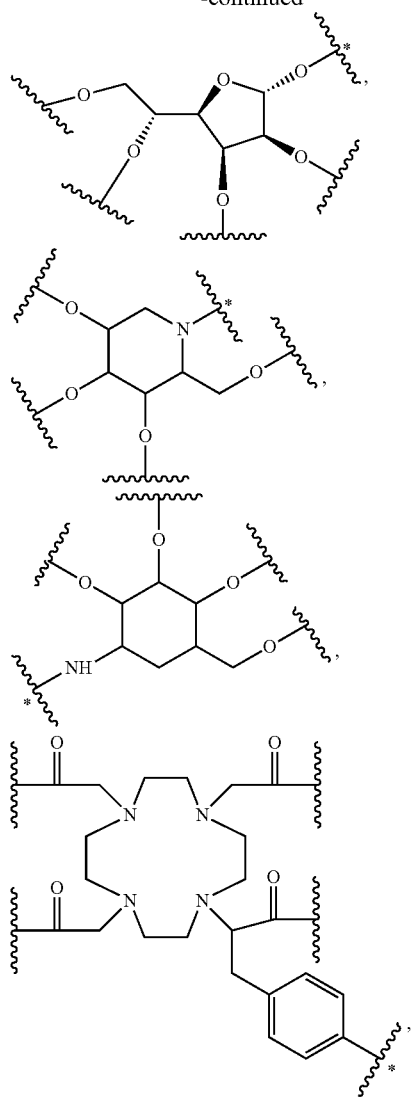

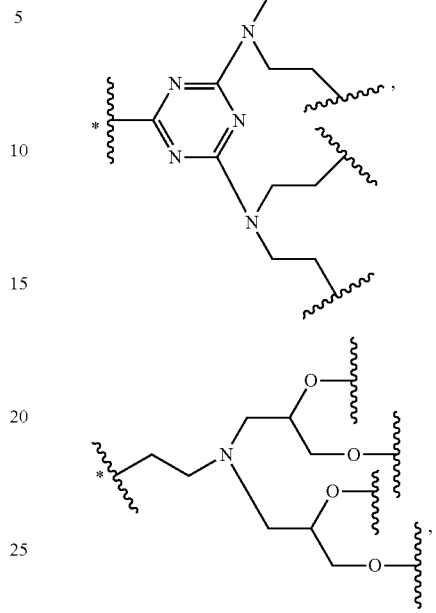

the dendritic structures directly or indirectly combined by three trivalent G groups via a direct or indirect combination, the comb-like structures formed by three trivalent G groups via a direct or indirect combination and the like. Wherein, examples of the dendritic structures formed by three trivalent G groups via a direct or indirect combination include above-said structures in which the generation number d is equal to 2 (d=2). The comb-like structures formed by three trivalent G groups via a direct combination include but are not limited to a skeleton of trilysine, a skeleton of trimer of glutamic acid, a skeleton of trimer of aspartic acid, a skeleton of triglycerol and the like, such as

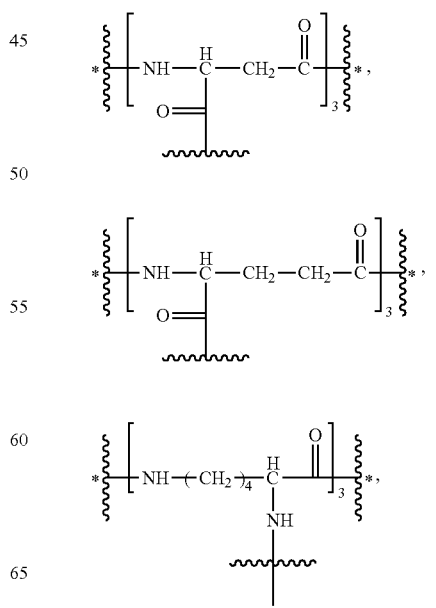

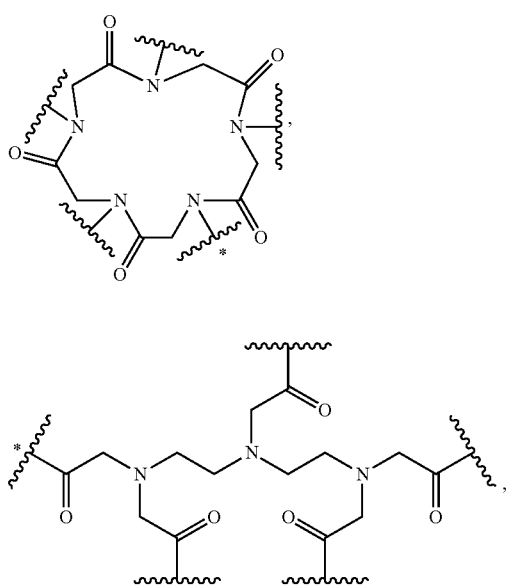

-continued

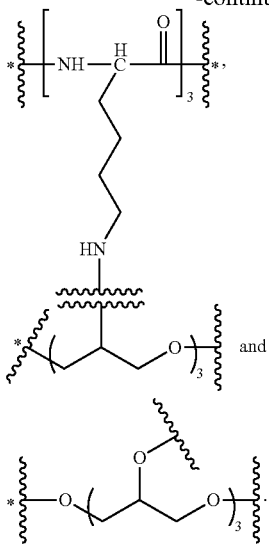
and

-continued

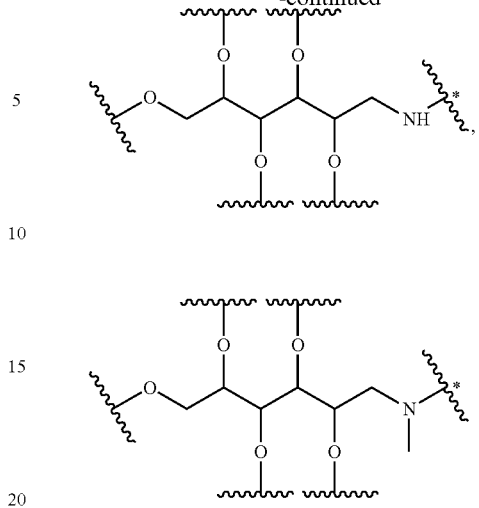

One typical example of the comb-like structures formed by three trivalent groups via an indirect combination is the combination of three lysines by using amino acid spacers such as glycine, alanine or the like.

For example, when the terminal-reactive-site number k is equal to 5 (k=5), then G is a hexavalent group, including but not limited to the hexavalent groups in the above-described set $G^6$. The hexavalent G groups can contain merely one hexavalent core structure, a combination of one pentavalent core structure and one trivalent core structure, a combination of two tetravalent core structures, a combination of one tetravalent core structure and two trivalent core structures or a combination of four trivalent core structures. $L_0$-G preferably contains any of the following structures: the comb-like structures directly or indirectly combined by four trivalent G groups (e.g., tetraglycerol, tetralysine, tetramer of aspartic acid, tetramer of glutamic acid and the like),

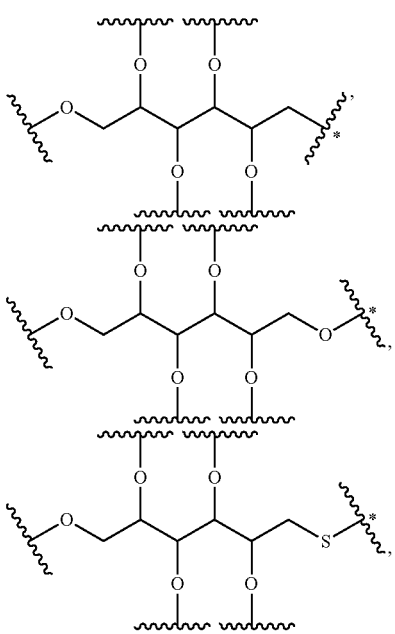

and the like.

1.2. The invention also discloses an eight-arm polyethylene glycol derivative, and the structure is shown by the general formula (3).

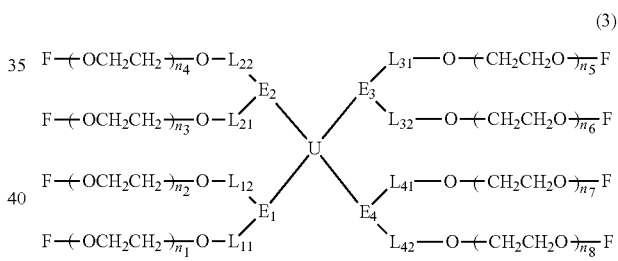

(3)

Wherein, the definitions of U, $E_1$, $E_2$, $E_3$, $E_4$, $L_{11}$, $L_{12}$, $L_{21}$, $L_{22}$, $L_{31}$, $L_{32}$, $L_{41}$, $L_{42}$, $n_1$, $n_2$, $n_3$, $n_4$, $n_5$, $n_6$, $n_7$, $n_8$ and F are the same as those in the general formula (1), and no more repeated here, corresponding to the case of g=0 in the general formula (1). Wherein, each polyethylene glycol chain terminal only connects with one functional group.

The eight-arm polyethylene glycol derivative is either stable or degradable; in one molecule, U, $E_1$, $E_2$, $E_3$, $E_4$, $L_{11}$, $L_{12}$, $L_{21}$, $L_{22}$, $L_{31}$, $L_{32}$, $L_{41}$, $L_{42}$ and $(Z_2)_q$—$(Z_1)_{q1}$ can be each independently either stable or degradable, and the joint linking group formed by any aforesaid group with its adjacent group can be each independently either stable or degradable.

Preferably that $n_1 \approx n_2 \approx n_3 \approx n_4 \approx n_5 \approx n_6 \approx n_7 \approx n_8$ or $n_1 = n_2 = n_3 = n_4 = n_5 = n_6 = n_7 = n_8$.

1.3. The invention also discloses an eight-arm polyethylene glycol derivative, and the structure is shown by the general formula (4).

(4)

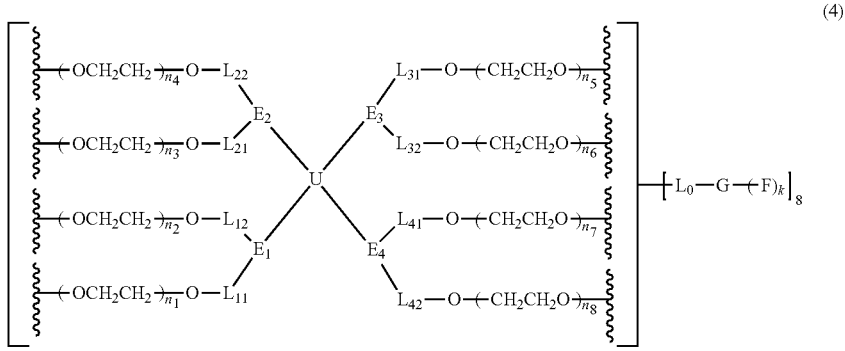

Wherein, the definitions of U, $E_1$, $E_2$, $E_3$, $E_4$, $L_{11}$, $L_{12}$, $L_{21}$, $L_{22}$, $L_{31}$, $L_{32}$, $L_{41}$, $L_{42}$, $L_0$, G, $n_1$, $n_2$, $n_3$, $n_4$, $n_5$, $n_6$, $n_7$, $n_8$, k and F are the same as those in the general formula (1), and no more repeated here, corresponding to the case of g=1 in the general formula (1).

The eight-arm polyethylene glycol derivative is either stable or degradable; in one molecule, U, $E_1$, $E_2$, $E_3$, $E_4$, $L_{11}$, $L_{12}$, $L_{21}$, $L_{22}$, $L_{31}$, $L_{32}$, $L_{41}$, $L_{42}$, $L_0$, G and $(Z_2)_q$—$(Z_1)_{q1}$ can be each independently either stable or degradable, and the joint linking group formed by any aforesaid group with its adjacent group can be each independently either stable or degradable.

Preferably that $n_1 \approx n_2 \approx n_3 \approx n_4 \approx n_5 \approx n_6 \approx n_7 \approx n_8$ or $n_1 = n_2 = n_3 = n_4 = n_5 = n_6 = n_7 = n_8$.

1.4. The invention also discloses an eight-arm polyethylene glycol derivative, and the structure is shown by the general formula (5).

(5)

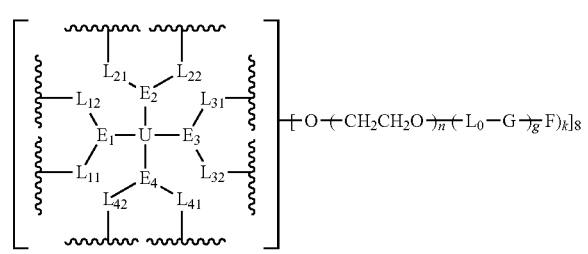

Wherein, the definitions of U, $E_1$, $E_2$, $E_3$, $E_4$, $L_{11}$, $L_{12}$, $L_{21}$, $L_{22}$, $L_{31}$, $L_{32}$, $L_{41}$, $L_{42}$ and F are the same as those in the general formula (1), and no more repeated here, corresponding to the case of $n_1 \approx n_2 \approx n_3 \approx n_4 \approx n_5 \approx n_6 \approx n_7 \approx n_8$ or $n_1 = n_2 = n_3 = n_4 = n_5 = n_6 = n_7 = n_8$ in the general formula (1). The definition of n is the same as $n_1$, $n_2$, $n_3$, $n_4$, $n_5$, $n_6$, $n_7$ and $n_8$, corresponding to the case where the eight PEG chains are gained in the same manner.

The eight-arm polyethylene glycol derivative is either stable or degradable; in one molecule, U, $E_1$, $E_2$, $E_3$, $E_4$, $L_{11}$, $L_{12}$, $L_{21}$, $L_{22}$, $L_{31}$, $L_{32}$, $L_{41}$, $L_{42}$ and $(Z_2)_q$—$(Z_1)_{q1}$ can be each independently either stable or degradable, and the joint linking group formed by any aforesaid group with its adjacent group can be each independently either stable or degradable.

1.5. The invention also discloses eight-arm polyethylene glycol derivatives containing the following combinations of U and $E_i$ (i=1, 2, 3, 4).

1.5.1 The invention also discloses an eight-arm polyethylene glycol derivative, corresponding to the case of U=C$(CH_2O—)_4$, $E_i$ (i=1, 2, 3, 4)=

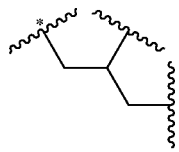 [SMILES: *CC(*)C*]

and without $L_{11}$, $L_{12}$, $L_{21}$, $L_{22}$, $L_{31}$, $L_{32}$, $L_{41}$ and $L_{42}$ in the general formula (1), and the structure is represented by the general formula (6) or (7).

(6)

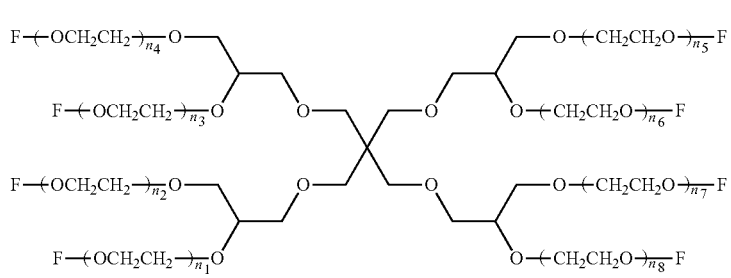

-continued

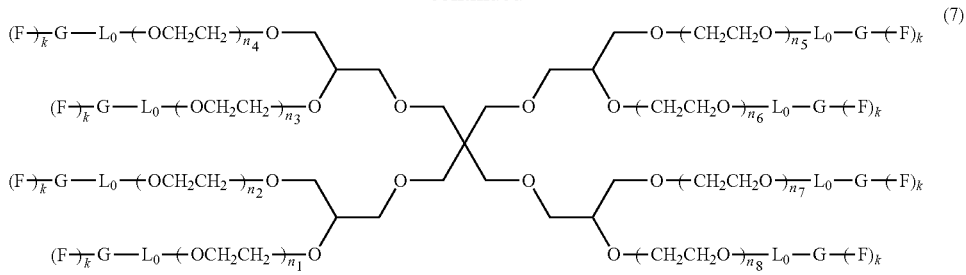
(7)

Wherein, the structure of F is represented by $-(Z_2)_q-(Z_1)_{q1}-R_{01}$; the definitions of $n_1$, $n_2$, $n_3$, $n_4$, $n_5$, $n_6$, $n_7$, $n_8$, F, $L_0$, G, q, $q_1$, $Z_1$, $Z_2$ and $R_{01}$ are the same as those in the general formula (1), and no more repeated here.

Preferably that $n_1 \approx n_2 \approx n_3 \approx n_4 \approx n_5 \approx n_6 \approx n_7 \approx n_8$ or $n_1 = n_2 = n_3 = n_4 = n_5 = n_6 = n_7 = n_8$.

The eight-arm polyethylene glycol derivative can be either stable or degradable. In one molecule of the general formula (6), $(Z_2)_q-(Z_1)_{q1}$ and the joint linking group formed by $(Z_2)_q-(Z_1)_{q1}$ with its adjacent group can be each independently either stable or degradable. In one molecule of the general formula (7), $L_0$, G, $(Z_2)_q-(Z_1)_{q1}$ can be each independently either stable or degradable, and the joint linking group formed by $(Z_2)_q-(Z_1)_{q1}$ with its adjacent group can be each independently either stable or degradable.

1.5.2 The invention also discloses an eight-arm polyethylene glycol derivative, corresponding to the case of $U=C(CH_2O-)_4$, $E_i$ (i=1, 2, 3, 4)=

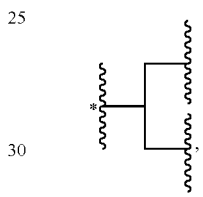

and without $L_{11}$, $L_{12}$, $L_{21}$, $L_{22}$, $L_{31}$, $L_{32}$, $L_{41}$ and $L_{42}$ in the general formula (1), and the structure is represented by the general formula (8) or (9).

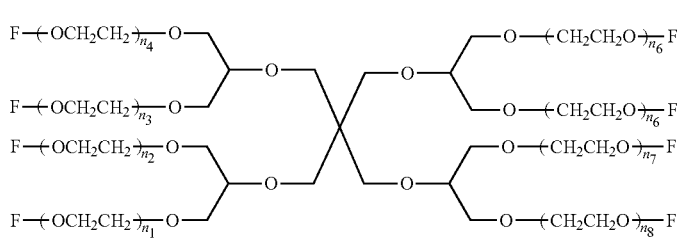
(8)

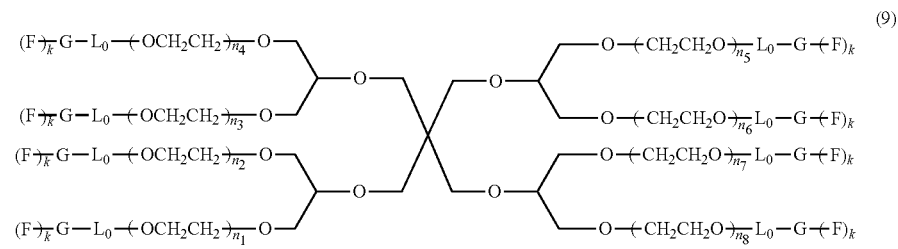
(9)

Wherein, the structure of F is represented by $-(Z_2)_q-(Z_1)_{q1}-R_{01}$; the definitions of $n_1$, $n_2$, $n_3$, $n_4$, $n_5$, $n_6$, $n_7$, $n_8$, F, $L_0$, G, q, $q_1$, $Z_1$, $Z_2$ and $R_{01}$ are the same as those in the general formula (1), and no more repeated here.

Herein, it is preferably that $n_1 \approx n_2 \approx n_3 \approx n_4 \approx n_5 \approx n_6 \approx n_7 \approx n_8$ or $n_1 = n_2 = n_3 = n_4 = n_5 = n_6 = n_7 = n_8$.

The eight-arm polyethylene glycol derivative can be either stable or degradable. In one molecule of the general formula (8), $(Z_2)_q-(Z_1)_{q1}$ and the joint linking group formed by $(Z_2)_q-(Z_1)_{q1}$ with its adjacent group can be each independently either stable or degradable. In one molecule of the general formula (9), $L_0$, G, $(Z_2)_q-(Z_1)_{q1}$ can be each independently either stable or degradable, and the joint linking group formed by any aforesaid group with its adjacent group can be each independently either stable or degradable.

1.5.3 The invention also discloses an eight-arm polyethylene glycol derivative, corresponding to the case of

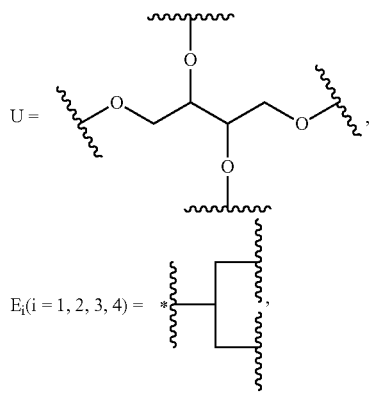

and without $L_{11}$, $L_{12}$, $L_{21}$, $L_{22}$, $L_{31}$, $L_{32}$, $L_{41}$ and $L_{42}$ in the general formula (1), and the structure is represented by the general formula (10) or (11).

Wherein, the structure of F is represented by $-(Z_2)_q-(Z_1)_{q1}-R_{01}$; the definitions of $n_1$, $n_2$, $n_3$, $n_4$, $n_5$, $n_6$, $n_7$, $n_8$, F, $L_0$, G, q, $q_1$, $Z_1$, $Z_2$ and $R_{01}$ are the same as those in the general formula (1), and no more repeated here.

Preferably that $n_1 \approx n_2 \approx n_3 \approx n_4 \approx n_5 \approx n_6 \approx n_7 \approx n_8$ or $n_1 = n_2 = n_3 = n_4 = n_5 = n_6 = n_7 = n_8$.

The eight-arm polyethylene glycol derivative can be either stable or degradable. In one molecule of the general formula (10), $(Z_2)_q-(Z_1)_{q1}$ and the joint linking group formed by $(Z_2)_q-(Z_1)_{q1}$ with its adjacent group can be each independently either stable or degradable. In one molecule of the general formula (11), $L_0$, G, $(Z_2)_q-(Z_1)_{q1}$ can be each independently either stable or degradable, and the joint linking group formed by any aforesaid group with its adjacent group can be each independently either stable or degradable.

1.5.4 The invention also discloses an eight-arm polyethylene glycol derivative, corresponding to the case of

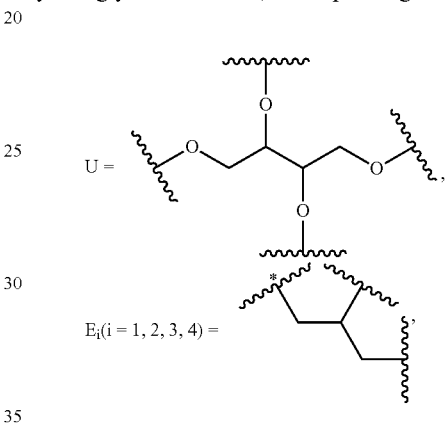

and without $L_{11}$, $L_{12}$, $L_{21}$, $L_{22}$, $L_{31}$, $L_{32}$, $L_{41}$ and $L_{42}$ in the general formula (1), and the structure is represented by the general formula (12) or (13).

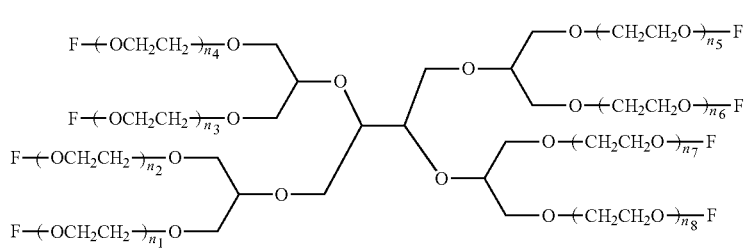

(10)

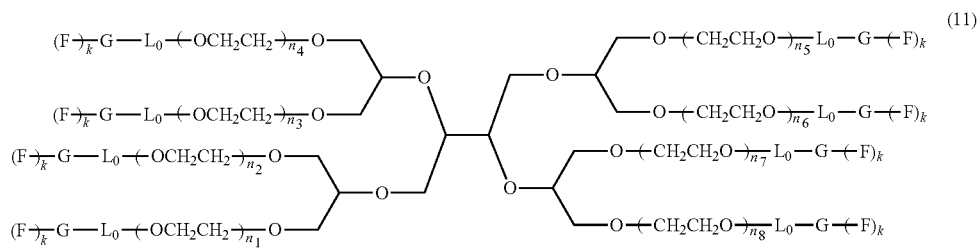

(11)

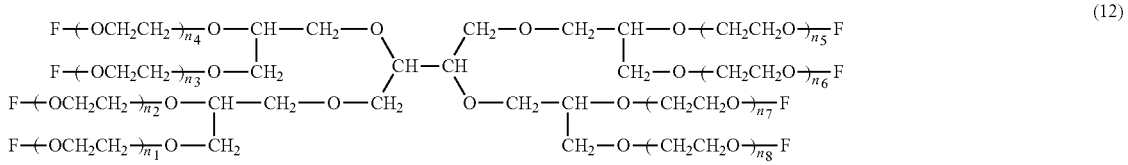

(12)

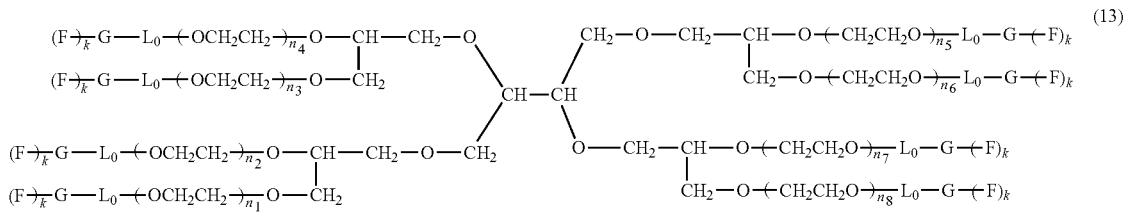

(13)

Wherein, the structure of F is represented by —$(Z_2)_q$—$(Z_1)_{q1}$—$R_{01}$; the definitions of $n_1$, $n_2$, $n_3$, $n_4$, $n_5$, $n_6$, $n_7$, $n_8$, F, $L_0$, G, q, $q_1$, $Z_1$, $Z_2$ and $R_{01}$ are the same as those in the general formula (1), and no more repeated here.

Preferably that $n_1 \approx n_2 \approx n_3 \approx n_4 \approx n_5 \approx n_6 \approx n_7 \approx n_8$ or $n_1 = n_2 = n_3 = n_4 = n_5 = n_6 = n_7 = n_8$.

The eight-arm polyethylene glycol derivative can be either stable or degradable. In one molecule of the general formula (12), $(Z_2)_q$—$(Z_1)_{q1}$ and the joint linking group formed by $(Z_2)_q$—$(Z_1)_{q1}$ with its adjacent group can be each independently either stable or degradable. In one molecule of the general formula (13), $L_0$, G, $(Z_2)_q$—$(Z_1)_{q1}$ can be each independently either stable or degradable, and the joint linking group formed by any aforesaid group with its adjacent group can be each independently either stable or degradable.

1.5.5 The invention also discloses an eight-arm polyethylene glycol derivative, corresponding to the case of

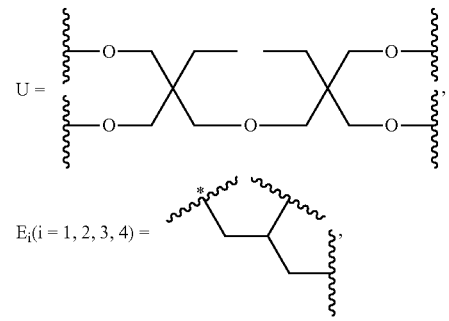

and without $L_{11}$, $L_{12}$, $L_{21}$, $L_{22}$, $L_{31}$, $L_{32}$, $L_{41}$ and $L_{42}$ in the general formula (1), and the structure is represented by the general formula (14 or (15).

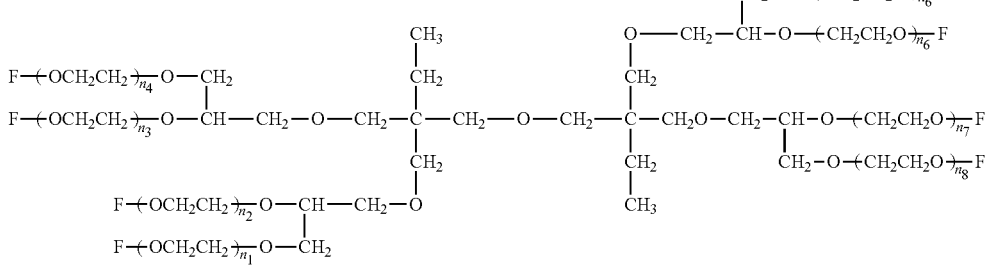

(14)

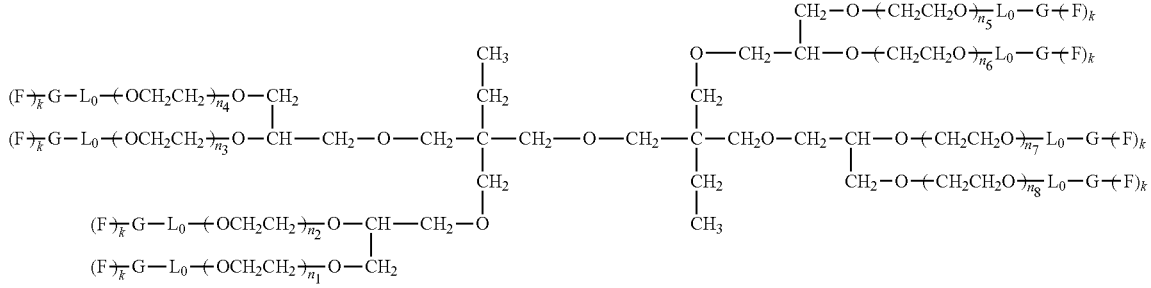

(15)

Wherein, the structure of F is represented by —$(Z_2)_q$—$(Z_1)_{q1}$—$R_{O1}$; the definitions of $n_1$, $n_2$, $n_3$, $n_4$, $n_5$, $n_6$, $n_7$, $n_8$, F, $L_0$, G, q, $q_1$, $Z_1$, $Z_2$ and $R_{O1}$ are the same as those in the general formula (1), and no more repeated here.

Preferably that $n_1 \approx n_2 \approx n_3 \approx n_4 \approx n_5 \approx n_6 \approx n_7 \approx n_8$ or $n_1 = n_2 = n_3 = n_4 = n_5 = n_6 = n_7 = n_8$.

The eight-arm polyethylene glycol derivative can be either stable or degradable. In one molecule of the general formula (14), $(Z_2)_q$—$(Z_1)_{q1}$ and the joint linking group formed by $(Z_2)_q$—$(Z_1)_{q1}$ with its adjacent group can be each independently either stable or degradable. In one molecule of the general formula (15), $L_0$, G, $(Z_2)_q$—$(Z_1)_{q1}$ can be each independently either stable or degradable, and the joint linking group formed by any aforesaid group with its adjacent group can be each independently either stable or degradable.

1.5.6 The invention also discloses an eight-arm polyethylene glycol derivative, corresponding to the case of

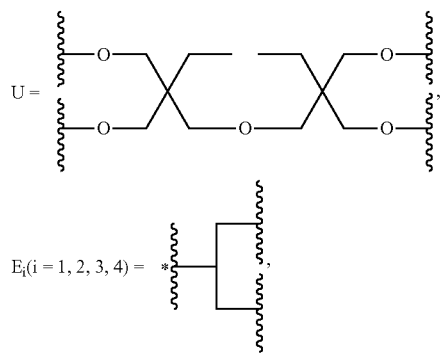

and without $L_{11}$, $L_{12}$, $L_{21}$, $L_{22}$, $L_{31}$, $L_{32}$, $L_{41}$ and $L_{42}$ in the general formula (1), and the structure is represented by the general formula (16) or (17).

Wherein, the structure of F is represented by —$(Z_2)_q$—$(Z_1)_{q1}$—$R_1$; the definitions of $n_1$, $n_2$, $n_3$, $n_4$, $n_5$, $n_6$, $n_7$, $n_8$, F, $L_0$, G, q, $q_1$, $Z_1$, $Z_2$ and $R_{O1}$ are the same as those in the general formula (1), and no more repeated here.

Preferably that $n_1 \approx n_2 \approx n_3 \approx n_4 \approx n_5 \approx n_6 \approx n_7 \approx n_8$ or $n_1 = n_2 = n_3 = n_4 = n_5 = n_6 = n_7 = n_8$.

The eight-arm polyethylene glycol derivative can be either stable or degradable. In one molecule of the general formula (16), $(Z_2)_q$—$(Z_1)_{q1}$ and the joint linking group formed by $(Z_2)_q$—$(Z_1)_{q1}$ with its adjacent group can be each independently either stable or degradable. In one molecule of the general formula (17), $L_0$, G, $(Z_2)_q$—$(Z_1)_{q1}$ can be each independently either stable or degradable, and the joint linking group formed by any aforesaid group with its adjacent group can be each independently either stable or degradable.

1.5.7 The invention also discloses an eight-arm polyethylene glycol derivative, corresponding to the case of

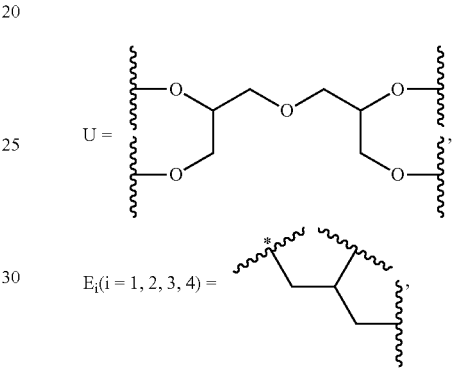

and without $L_{11}$, $L_{12}$, $L_{21}$, $L_{22}$, $L_{31}$, $L_{32}$, $L_{41}$ and $L_{42}$ in the general formula (1), and the structure is represented by the general formula (18) or (19).

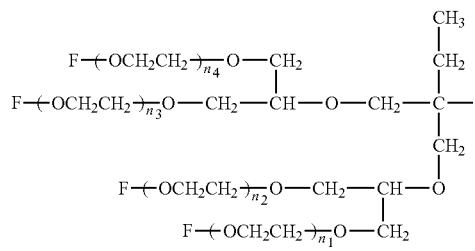

(16)

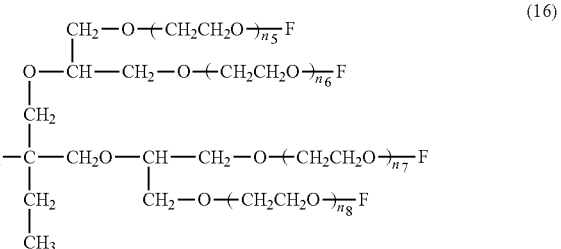

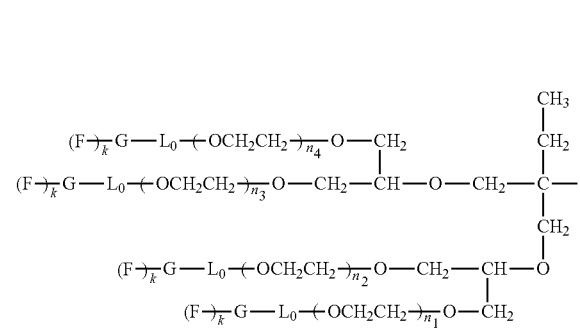

(17)

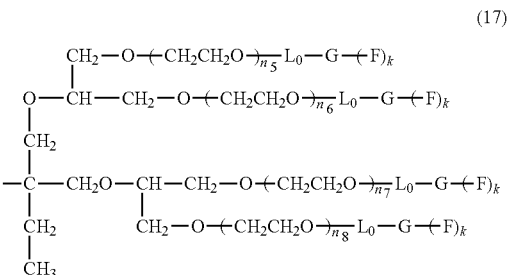

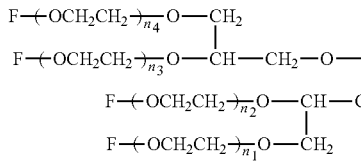 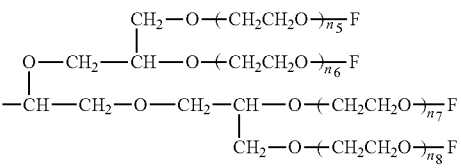

(18)

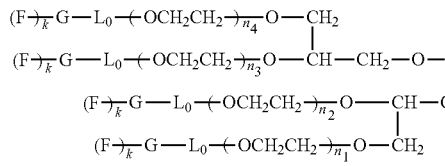 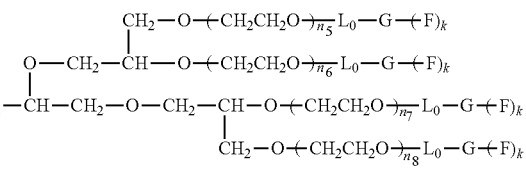

(19)

Wherein, the structure of F is represented by $-(Z_2)_q-(Z_1)_{q1}-R_{01}$; the definitions of $n_1$, $n_2$, $n_3$, $n_4$, $n_5$, $n_6$, $n_7$, $n_8$, F, $L_0$, G, q, $q_1$, $Z_1$, $Z_2$ and $R_{01}$ are the same as those in the general formula (1), and no more repeated here.

Preferably that $n_1 \approx n_2 \approx n_3 \approx n_4 \approx n_5 \approx n_6 \approx n_7 \approx n_8$ or $n_1 = n_2 = n_3 = n_4 = n_5 = n_6 = n_7 = n_8$.

The eight-arm polyethylene glycol derivative can be either stable or degradable. In one molecule of the general formula (18), $(Z_2)_q-(Z_1)_{q1}$ and the joint linking group formed by $(Z_2)_q-(Z_1)_{q1}$ with its adjacent group can be each independently either stable or degradable. In one molecule of the general formula (19), $L_0$, G, $(Z_2)_q-(Z_i)_{q1}$ can be each independently either stable or degradable, and the joint linking group formed by any aforesaid group with its adjacent group can be each independently either stable or degradable.

1.5.8 The invention also discloses an eight-arm polyethylene glycol derivative, corresponding to the case of without $L_{11}$, $L_{12}$, $L_{21}$, $L_{22}$, $L_{31}$, $L_{32}$, $L_{41}$ and $L_{42}$ in the general formula (1), and the structure is represented by the general formula (20) or (21).

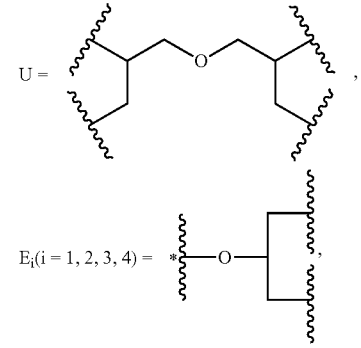

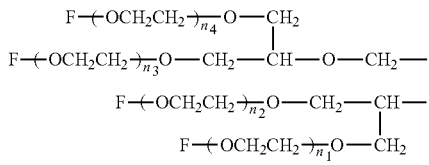 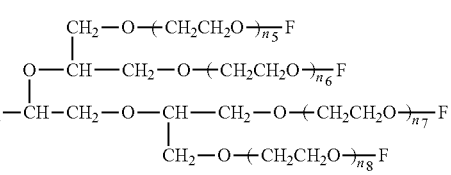

(20)

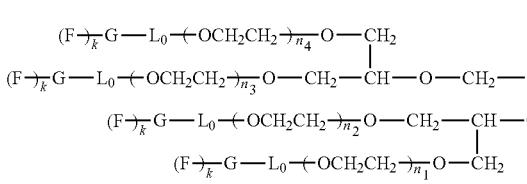 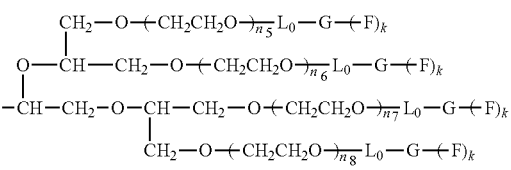

(21)

Wherein, the structure of F is represented by —$(Z_2)_q$—$(Z_1)_{q1}$—$R_{O1}$; the definitions of $n_1$, $n_2$, $n_3$, $n_4$, $n_5$, $n_6$, $n_7$, $n_8$, F, $L_0$, G, q, $q_1$, $Z_1$, $Z_2$ and $R_{O1}$ are the same as those in the general formula (1), and no more repeated here.

Preferably that $n_1 \approx n_2 \approx n_3 \approx n_4 \approx n_5 \approx n_6 \approx n_7 \approx n_8$ or $n_1 = n_2 = n_3 = n_4 = n_5 = n_6 = n_7 = n_8$.

The eight-arm polyethylene glycol derivative can be either stable or degradable. In one molecule of the general formula (20), $(Z_2)_q$—$(Z_1)_{q1}$ and the joint linking group formed by $(Z_2)_q$—$(Z_1)_{q1}$ with its adjacent group can be each independently either stable or degradable. In one molecule of the general formula (21), $L_0$, G, $(Z_2)_q$—$(Z_1)_{q1}$ can be each independently either stable or degradable, and the joint linking group formed by any aforesaid group with its adjacent group can be each independently either stable or degradable.

1.5.9 The invention also discloses an eight-arm polyethylene glycol derivative, corresponding to the case of

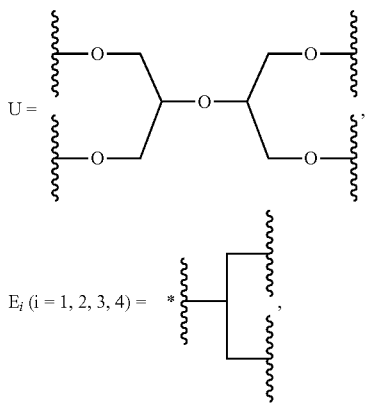

and without $L_{11}$, $L_{12}$, $L_{21}$, $L_{22}$, $L_{31}$, $L_{32}$, $L_{41}$ and $L_{42}$ in the general formula (1), and the structure is represented by the general formula (22) or (23).

Wherein, the structure of F is represented by —$(Z_2)_q$—$(Z_1)_{q1}$—$R_{O1}$; the definitions of $n_1$, $n_2$, $n_3$, $n_4$, $n_5$, $n_6$, $n_7$, $n_8$, F, $L_0$, G, q, $q_1$, $Z_1$, $Z_2$ and $R_{O1}$ are the same as those in the general formula (1), and no more repeated here.

Preferably that $n_1 \approx n_2 \approx n_3 \approx n_4 \approx n_5 \approx n_6 \approx n_7 \approx n_8$ or $n_1 = n_2 = n_3 = n_4 = n_5 = n_6 = n_7 = n_8$.

The eight-arm polyethylene glycol derivative can be either stable or degradable. In one molecule of the general formula (22), $(Z_2)_q$—$(Z_1)_{q1}$ and the joint linking group formed by $(Z_2)_q$—$(Z_1)_{q1}$ with its adjacent group can be each independently either stable or degradable. In one molecule of the general formula (23), $L_0$, G, $(Z_2)_q$—$(Z_1)_{q1}$ can be each independently either stable or degradable, and the joint linking group formed by any aforesaid group with its adjacent group can be each independently either stable or degradable.

1.5.10 The invention so discloses an eight-arm polyethylene glycol derivative, corresponding to the case of

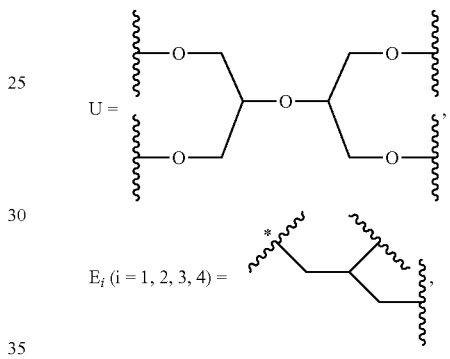

and without $L_{11}$, $L_{12}$, $L_{21}$, $L_{22}$, $L_{31}$, $L_{32}$, $L_{41}$ and $L_{42}$ in the general formula (1), and the structure is represented by the general formula (24) or (25)

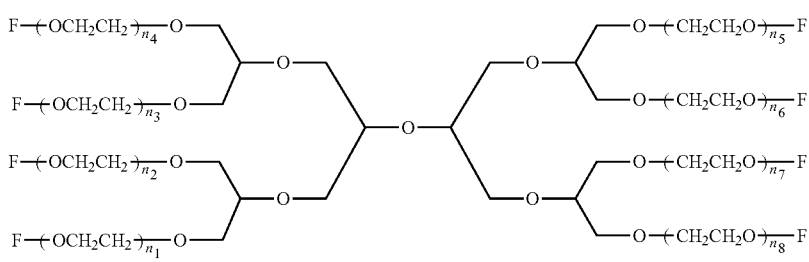

(22)

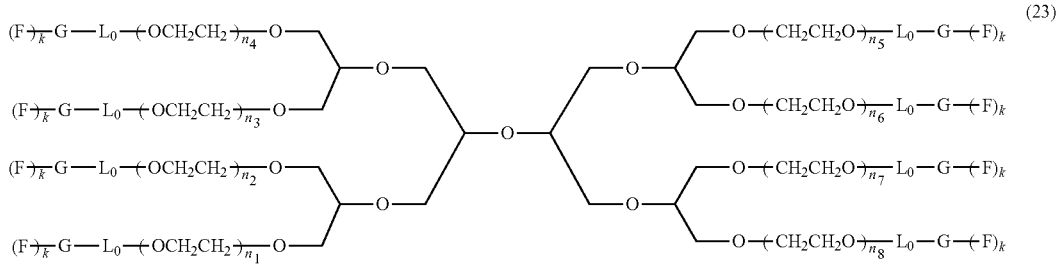

(23)

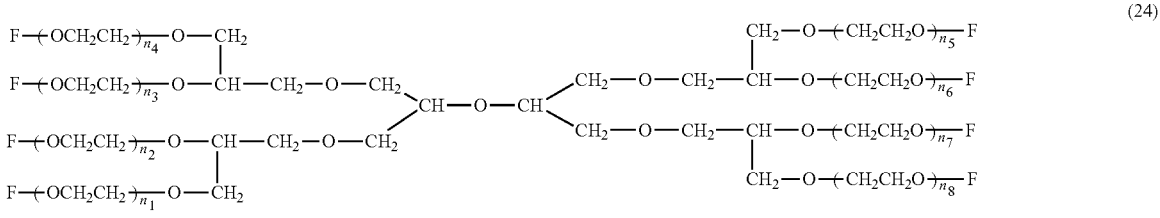

(24)

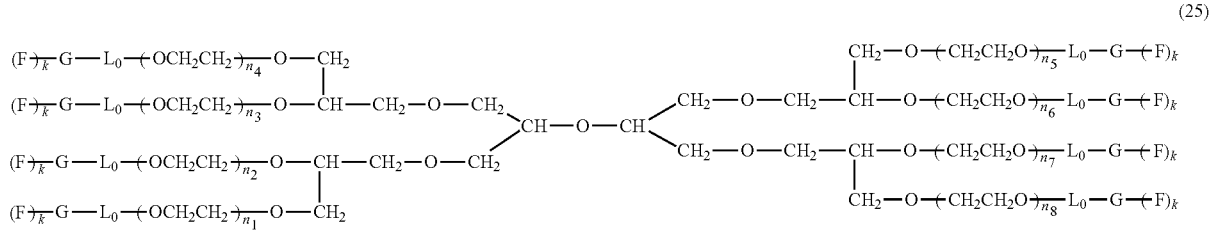

(25)

Wherein, the structure of F is represented by $-(Z_2)_q-(Z_1)_{q1}-R_{01}$; the definitions of $n_1$, $n_2$, $n_3$, $n_4$, $n_5$, $n_6$, $n_7$, $n_8$, F, $L_0$, G, q, $q_1$, $Z_1$, $Z_2$ and $R_{01}$ are the same as those in the general formula (1), and no more repeated here.

Preferably that $n_1 \approx n_2 \approx n_3 \approx n_4 \approx n_5 \approx n_6 \approx n_7 \approx n_8$ or $n_1 = n_2 = n_3 = n_4 = n_5 = n_6 = n_7 = n_8$.

The eight-arm polyethylene glycol derivative can be either stable or degradable. In one molecule of the general formula (24), $(Z_2)_q-(Z_1)_{q1}$ and the joint linking group formed by $(Z_2)_q-(Z_1)_{q1}$ with its adjacent group can be each independently either stable or degradable. In one molecule of the general formula (25), $L_0$, G, $(Z_2)_q-(Z_1)_{q1}$ can be each independently either stable or degradable, and the joint linking group formed by any aforesaid group with its adjacent group can be each independently either stable or degradable.

1.5.11 The invention also discloses an eight-arm polyethylene glycol derivative, corresponding to the case of

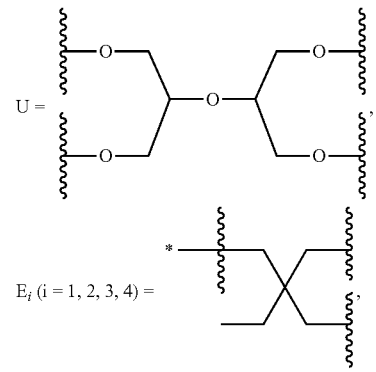

and without $L_{11}$, $L_{12}$, $L_{21}$, $L_{22}$, $L_{31}$, $L_{32}$, $L_{41}$ and $L_{42}$ in the general formula (1), and the structure is represented by the general formula (26) or (27).

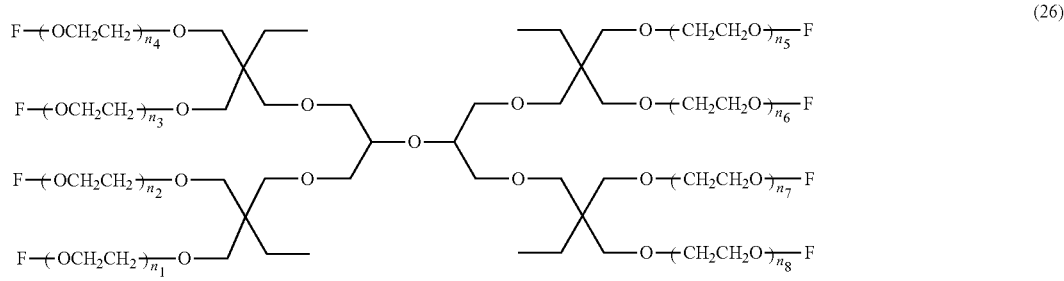

(26)

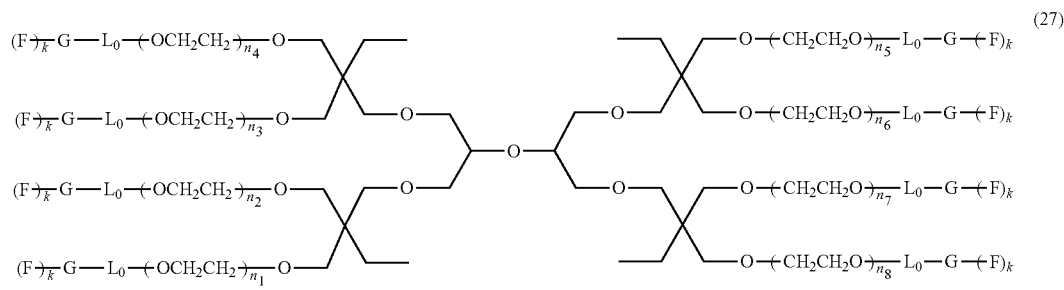

(27)

Wherein, the structure of F is represented by $-(Z_2)_q-(Z_1)_{q1}-R_{O1}$; the definitions of $n_1$, $n_2$, $n_3$, $n_4$, $n_5$, $n_6$, $n_7$, $n_8$, F, $L_0$, G, q, $q_1$, $Z_1$, $Z_2$ and $R_{O1}$ are the same as those in the general formula (1), and no more repeated here.

Preferably that $n_1 \approx n_2 \approx n_3 \approx n_4 \approx n_5 \approx n_6 \approx n_7 \approx n_8$ or $n_1 = n_2 = n_3 = n_4 = n_5 = n_6 = n_7 = n_8$.

The eight-arm polyethylene glycol derivative can be either stable or degradable. In one molecule of the general formula (26), $(Z_2)_q-(Z_1)_{q1}$ and the joint linking group formed by $(Z_2)_q-(Z_1)_{q1}$ with its adjacent group can be each independently either stable or degradable. In one molecule of the general formula (27), $L_0$, G, $(Z_2)_q-(Z_1)_{q1}$ can be each independently either stable or degradable, and the joint linking group formed by any aforesaid group with its adjacent group can be each independently either stable or degradable.

1.5.12 The invention also discloses an eight-arm polyethylene glycol derivative, corresponding to the case of

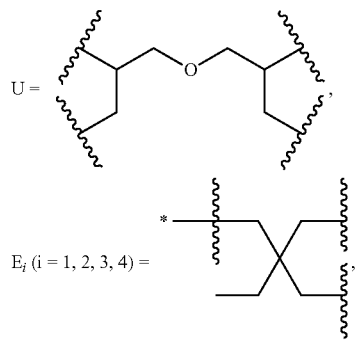

and without $L_{11}$, $L_{12}$, $L_{21}$, $L_{22}$, $L_{31}$, $L_{32}$, $L_{41}$ and $L_{42}$ in the general formula (1), and the structure is represented by the general formula (28) or (29).

Wherein, the structure of F is represented by $-(Z_2)_q-(Z_1)_{q1}-R_{O1}$; the definitions of $n_1$, $n_2$, $n_3$, $n_4$, $n_5$, $n_6$, $n_7$, $n_8$, F, $L_0$, G, q, $q_1$, $Z_1$, $Z_2$ and $R_{O1}$ are the same as those in the general formula (1), and no more repeated here.

Preferably that $n_1 \approx n_2 \approx n_3 \approx n_4 \approx n_5 \approx n_6 \approx n_7 \approx n_8$ or $n_1 = n_2 = n_3 = n_4 = n_5 = n_6 = n_7 = n_8$.

The eight-arm polyethylene glycol derivative can be either stable or degradable. In one molecule of the general formula (28), $(Z_2)_q-(Z_1)_{q1}$ and the joint linking group formed by $(Z_2)_q-(Z_1)_{q1}$ with its adjacent group can be each independently either stable or degradable. In one molecule of the general formula (29), $L_0$, G, $(Z_2)_q-(Z_1)_{q1}$ can be each independently either stable or degradable, and the joint linking group formed by any aforesaid group with its adjacent group can be each independently either stable or degradable.

1.5.13 The invention also discloses an eight-arm polyethylene glycol derivative, corresponding to the case where U is

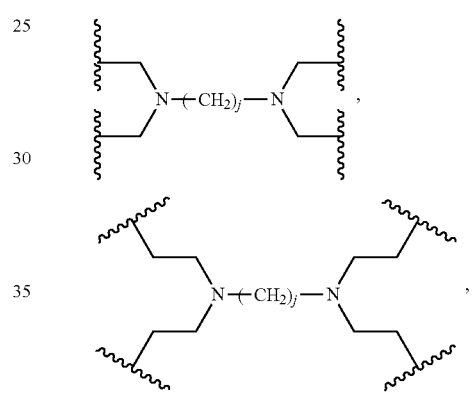

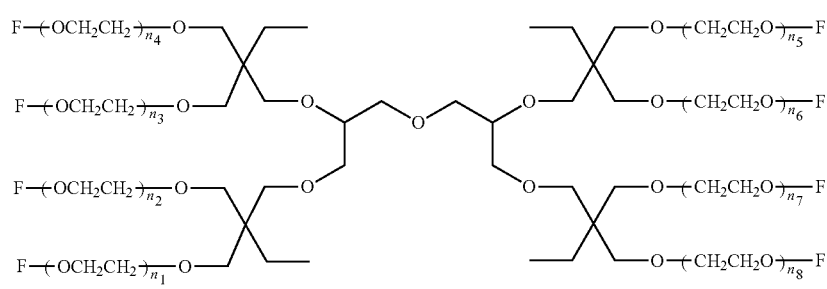

(28)

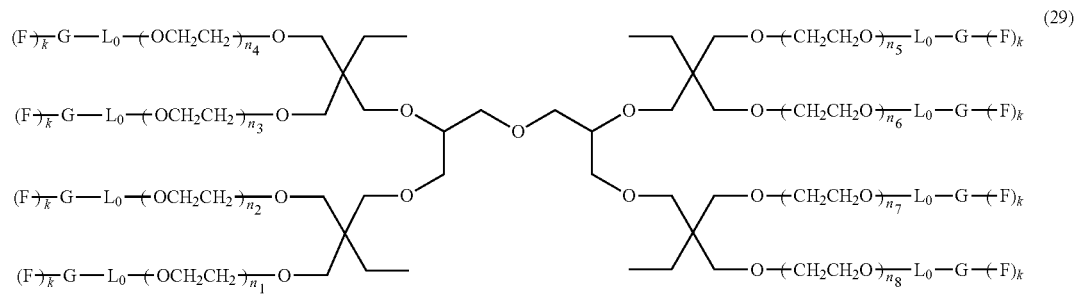

(29)

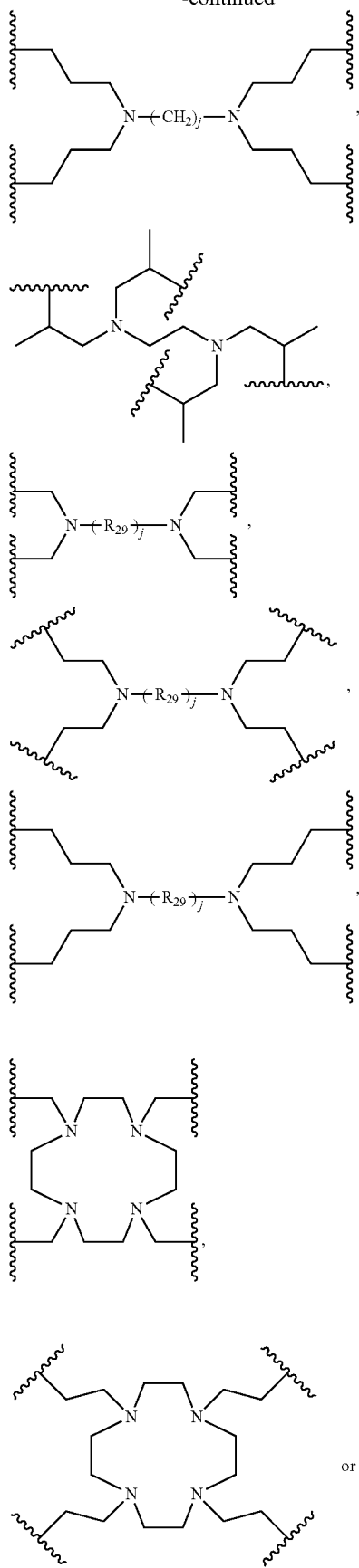

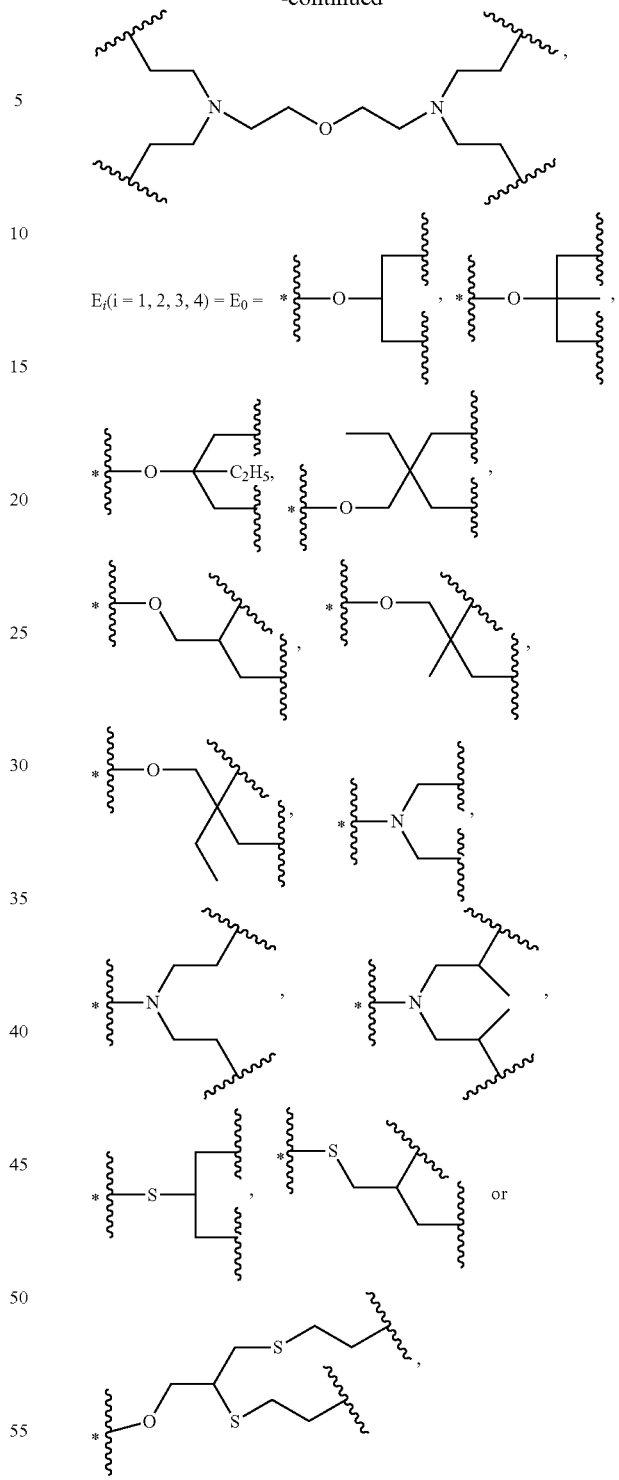

and $L_{11}$, $L_{12}$, $L_{21}$, $L_{22}$, $L_{31}$, $L_{32}$, $L_{41}$ and $L_{42}$ are all absent in the general formula (1). The definitions of j and $R_{29}$ are the same as above.

Preferably that $n_1 \approx n_2 \approx n_3 \approx n_4 \approx n_5 \approx n_6 \approx n_7 \approx n_8$ or $n_1 = n_2 = n_3 = n_4 = n_5 = n_6 = n_7 = n_8$.

When g is equal to 0 (g=0), the definitions of $n_1$, $n_2$, $n_3$, $n_4$, $n_5$, $n_6$, $n_7$, $n_8$, F, q, $q_1$, $Z_1$, $Z_2$ and $R_{01}$ are the same as those in the general formula (1); in one molecule, $(Z_2)_q$—$(Z)_{q1}$ and the joint linking group formed by $(Z_2)_q$—$(Z_1)_{q1}$ with its adjacent group can be each independently either stable or degradable.

When g is equal to 1 (g=1), the definitions of $n_1$, $n_2$, $n_3$, $n_4$, $n_5$, $n_6$, $n_7$, $n_8$, F, $L_0$, G, q, $q_1$, $Z_1$, $Z_2$ and $R_{01}$ are the same as those in the general formula (1); in one molecule, $L_0$, G, $(Z_2)_q$—$(Z_i)_{q1}$ can be each independently either stable or degradable, and the joint linking group formed by any aforesaid group with its adjacent group can be each independently either stable or degradable.

U is preferably any of the following structures:

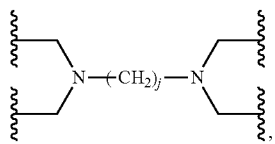

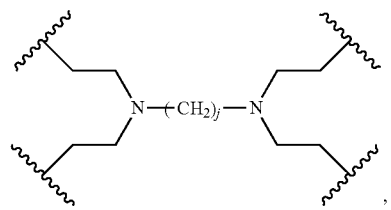

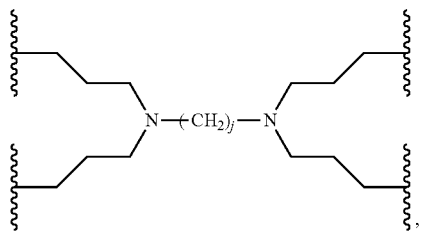

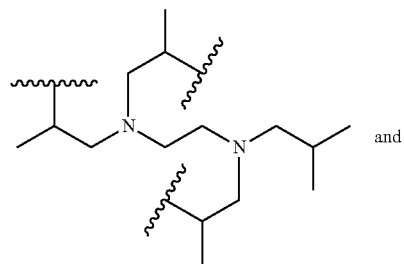

and

-continued

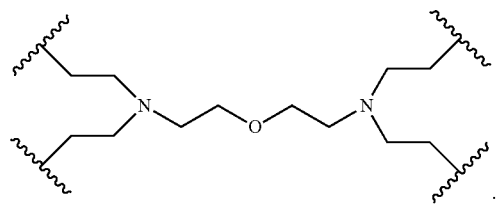

For example, when U is

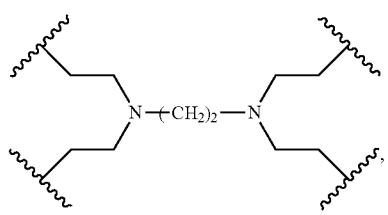

$E_i$ (i=1, 2, 3, 4)—O— are

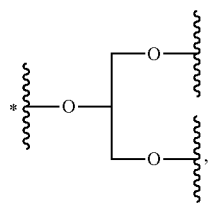

and $L_{11}$, $L_{12}$, $L_{21}$, $L_{22}$, $L_{31}$, $L_{32}$, $L_{41}$ and $L_4$ are all absent, the structures with g=0 and g=1 correspond to formula (30) and formula (31), respectively.

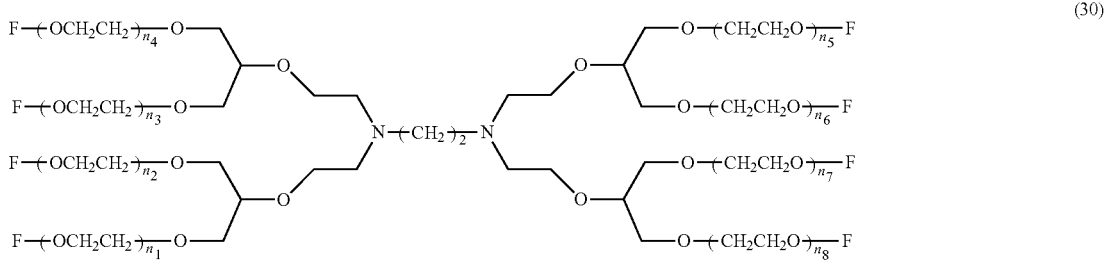

(30)

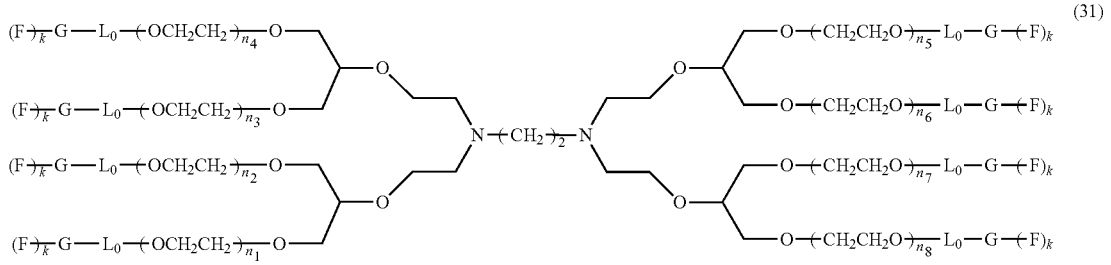
(31)

1.5.14 The invention also discloses an eight-arm polyethylene glycol derivative, corresponding to the case where U as a tetravalent central group is constituted by an alkanediol and two identical trivalent groups selected from the group consisting of

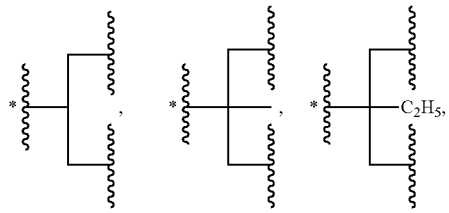

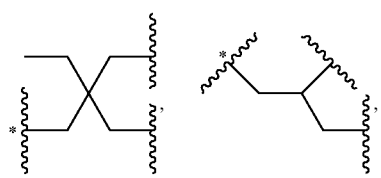

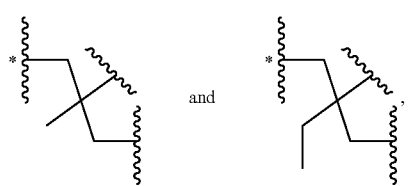

$E_i$ (i=1, 2, 3, 4) are a trivalent group selected from

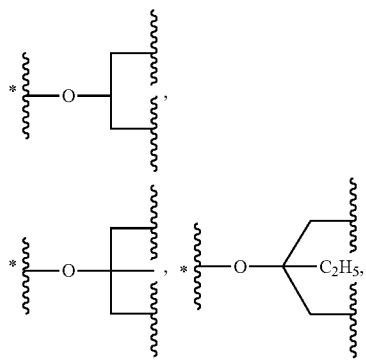

-continued

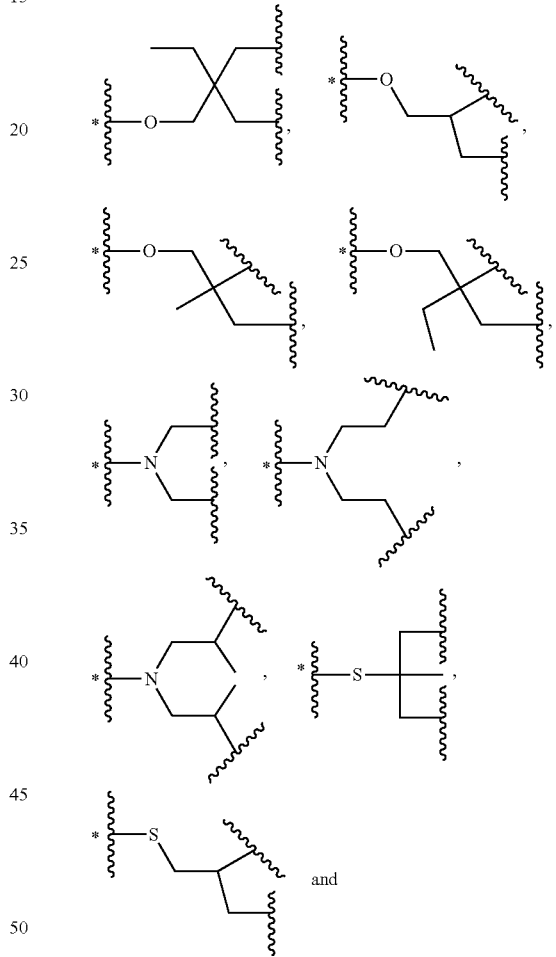

and $L_{11}$, $L_{12}$, $L_{21}$, $L_{22}$, $L_{31}$, $L_{32}$, $L_{41}$ and $L_{42}$ are all absent. The alkanediol is preferably a $C_{2-20}$ alkanediol, more preferably —O(CH$_2$)$_{j1}$O— or —O(R$_{29}$)$_{j1}$O—, wherein, $j_1$ is an integer from 2 to 20, preferably from 2 to 12, more preferably from 2 to 6, and most preferably 2. Wherein, the definition of $R_{29}$ is the same as above.

Herein, it is preferably that $n_1 \approx n_2 \approx n_3 \approx n_4 \approx n_5 \approx n_6 \approx n_7 \approx n_8$ or $n_1 = n_2 = n_3 = n_4 = n_5 = n_6 = n_7 = n_8$.

When g is equal to 0 (g=0), the definitions of $n_1$, $n_2$, $n_3$, $n_4$, $n_5$, $n_6$, $n_7$, $n_8$, F, q, $q_1$, $Z_1$, $Z_2$ and $R_{01}$ are the same as those in the general formula (1); in one molecule, $(Z_2)_q$—$(Z_1)_{q1}$ and the joint linking group formed by $(Z_2)_q$—$(Z_1)_{q1}$ with its adjacent group can be each independently either stable or degradable.

When g is equal to 1 (g=1), the definitions of $n_1$, $n_2$, $n_3$, $n_4$, $n_5$, $n_6$, $n_7$, $n_8$, F, $L_0$, G, q, $q_1$, $Z_1$, $Z_2$ and $R_{01}$ are the same as those in the general formula (1); in one molecule, $L_0$, G, $(Z_2)_q$—$(Z)_{q1}$ can be each independently either stable or degradable, and the joint linking group formed by any aforesaid group with its adjacent group can be each independently either stable or degradable.

For example, when U is formed by —O(CH$_2$CH$_2$)$_2$O— and two

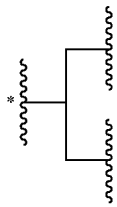

groups, $E_i$ (i=1, 2, 3, 4)—O— are

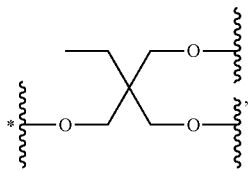 [SMILES: *OCC(CC)(CO*)CO*]

and $L_{11}$, $L_{12}$, $L_{21}$, $L_{22}$, $L_{31}$, $L_{32}$, $L_{41}$ and $L_4$ are all absent, the structures with g=0 and g=1 correspond to formula (32) and formula (33), respectively.

1.5.15 The invention also discloses an eight-arm polyethylene glycol derivative, corresponding to the case where U as a tetravalent-center structure is constituted by —O(CH$_2$CH$_2$O)$_{dj}$— and two identical trivalent groups selected from the group consisting of

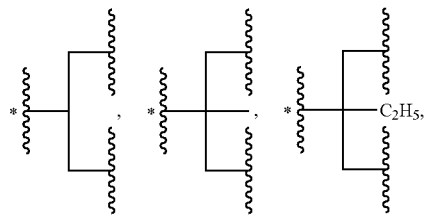

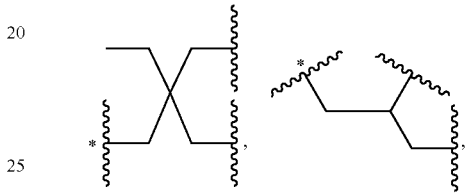

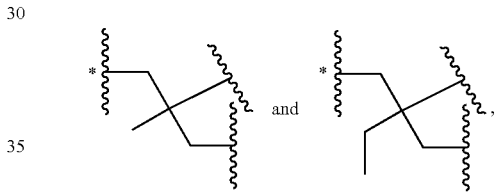

$E_i$ (i=1, 2, 3, 4) are a trivalent group selected from the group consisting of

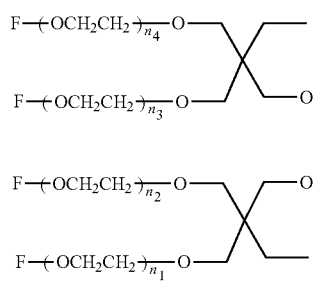

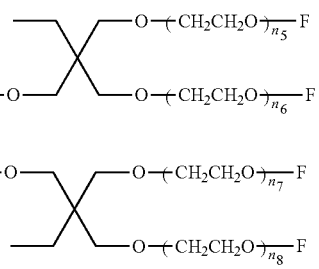

(32)

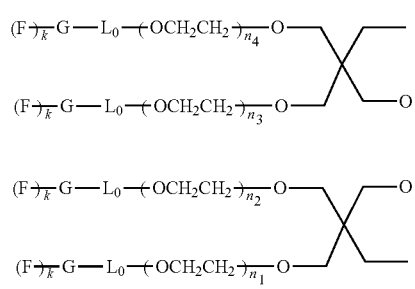

(33)

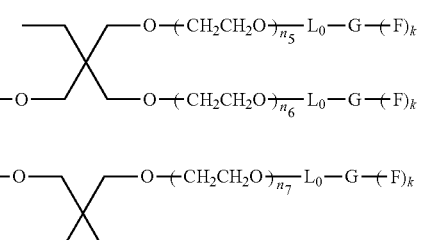

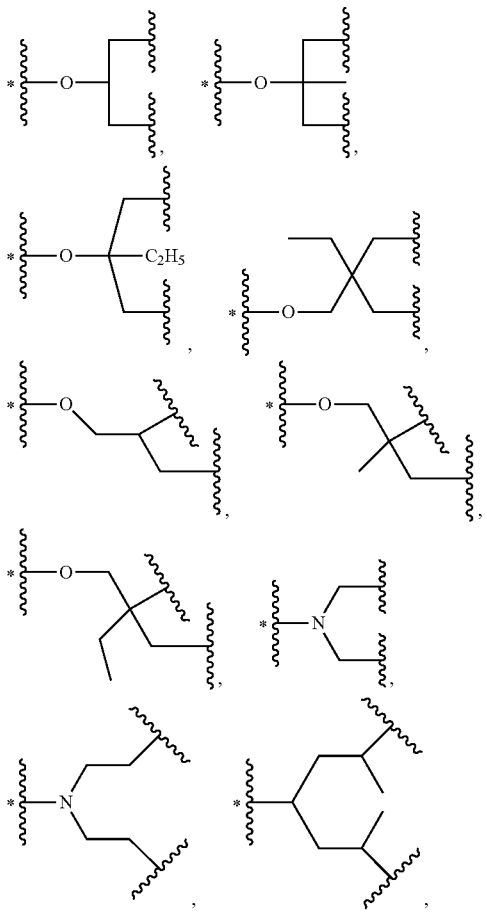

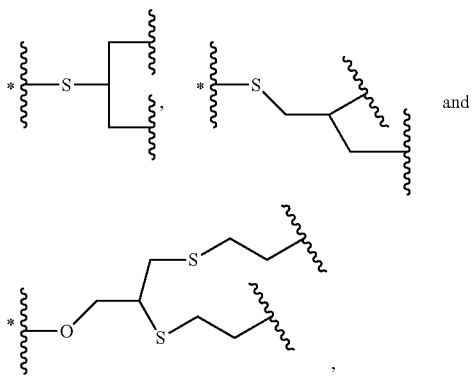

and $L_{11}$, $L_{12}$, $L_{21}$, $L_{22}$, $L_{31}$, $L_{32}$, $L_{41}$ and $L_{42}$ are all absent. Wherein, dj is the EO-unit number from 1 to 70, and corresponds to a monodisperse structure; dj is preferably from 1 to 16, more preferably from 1 to 9, more preferably 1, 2, 3, 4, 5 or 6, more preferably 1 or 2, and most preferably 1.

It is preferably that $n_1 \approx n_2 \approx n_3 \approx n_4 \approx n_5 \approx n_6 \approx n_7 \approx n_8$ or $n_1 = n_2 = n_3 = n_4 = n_5 = n_6 = n_7 = n_8$.

When g is equal to 0 (g=0), the definitions of $n_1$, $n_2$, $n_3$, $n_4$, $n_5$, $n_6$, $n_7$, $n_8$, F, q, $q_1$, $Z_1$, $Z_2$ and $R_{01}$ are the same as those in the general formula (1); in one molecule, $(Z_2)_q$—$(Z_1)_{q1}$ and the joint linking group formed by $(Z_2)_q$—$(Z_1)_{q1}$ with its adjacent group can be each independently either stable or degradable.

When g is equal to 1 (g=1), the definitions of $n_1$, $n_2$, $n_3$, $n_4$, $n_5$, $n_6$, $n_7$, $n_8$, F, $L_0$, G, q, $q_1$, $Z_1$, $Z_2$ and $R_{01}$ are the same as those in the general formula (1); in one molecule, $L_0$, G, $(Z_2)_q$—$(Z_1)_{q1}$ can be each independently either stable or degradable, and the joint linking group formed by any aforesaid group with its adjacent group can be each independently either stable or degradable.

For example, when U is formed by —O(CH$_2$CH$_2$O)$_2$— and two

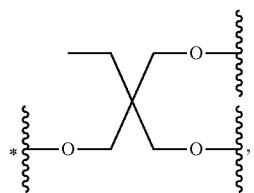 [SMILES: *OCC(CC)(CO*)CO*]

groups, $E_i$ (i=1, 2, 3, 4)—O— are

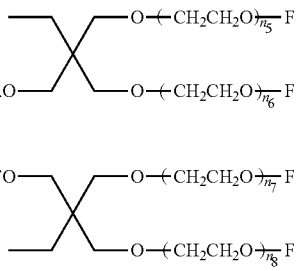

and $L_{11}$, $L_{12}$, $L_{21}$, $L_{22}$, $L_{31}$, $L_{32}$, $L_{41}$ and $L_4$ are all absents, structures with g=0 and g=1 correspond to formula (34) and formula (35), respectively.

(34)

F—(OCH$_2$CH$_2$)$_{n_4}$—O— ... —O—(CH$_2$CH$_2$O)$_{n_5}$—F
F—(OCH$_2$CH$_2$)$_{n_3}$—O— ... —O—(CH$_2$CH$_2$O)$_{n_6}$—F
F—(OCH$_2$CH$_2$)$_{n_2}$—O— ... —O—(CH$_2$CH$_2$O)$_{n_7}$—F
F—(OCH$_2$CH$_2$)$_{n_1}$—O— ... —O—(CH$_2$CH$_2$O)$_{n_8}$—F (35)

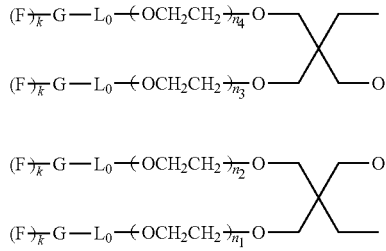 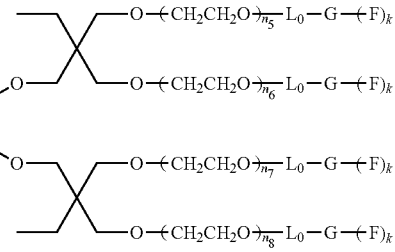

1.5.16 The invention also discloses an eight-arm polyethylene glycol derivative, corresponding to the case where U as a tetravalent residue of a hydrocarbyl-based primary diamine (a hydrocarbon-based primary diamine, a primary hydrocarbondiamine, also termed as hydrocarbon-bis(primary amine), i.e. a hydrocarbon substituted by two primary amino groups),

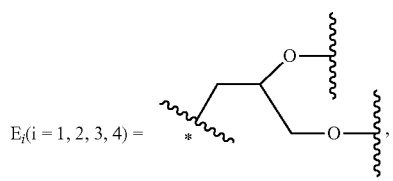 [SMILES: *CC(CO*)O*]

and $L_{11}$, $L_{12}$, $L_{21}$, $L_{22}$, $L_{31}$, $L_{32}$, $L_{41}$ and $L_{42}$ are all absent. Wherein, the definition of j is the same as above. Wherein, the primary hydrocarbondiamine is preferably an alkyl-based primary diamine (an alkane-based primary diamine, a primary alkanediamine), more preferably $NH_2(CH_2)_jNH_2$ or $NH_2(R_{29})_jNH_2$, corresponding to

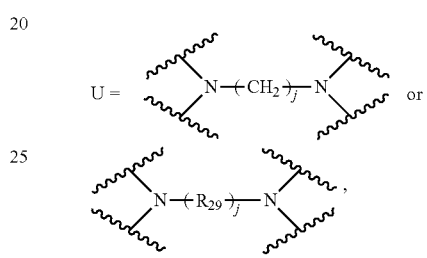

respectively. Wherein, the definitions of j and $R_{29}$ are the same as above. For example, taking $NH_2(CH_2)_jNH_2$ for instance, the eight-arm polyethylene glycol derivative can be represented by formula (36) or formula (37).

(36)

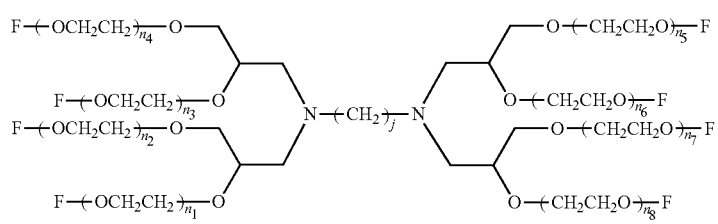

(37)

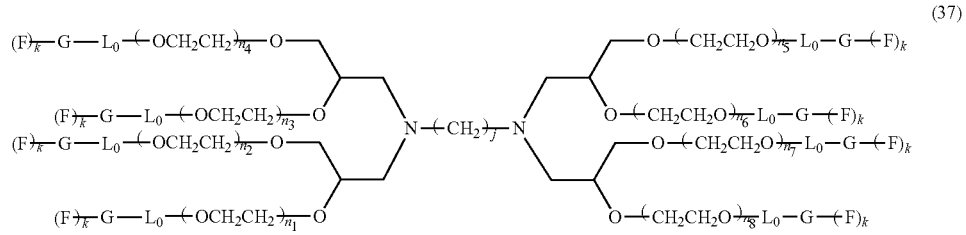

When g is equal to 0 (g=0), the definitions of $n_1$, $n_2$, $n_3$, $n_4$, $n_5$, $n_6$, $n_7$, $n_8$, F, q, $q_1$, 1, 2 and $R_{01}$ are the same as those in the general formula (1); in one molecule, $(Z_2)_q$—$(Z_1)_{q1}$ and the joint linking group formed by $(Z_2)_q$—$(Z_1)_{q1}$ with its adjacent group can be each independently either stable or degradable.

When g is equal to 1 (g=1), the definitions of $n_1$, $n_2$, $n_3$, $n_4$, $n_5$, $n_6$, $n_7$, $n_8$, F, $L_0$, G, q, $q_1$, $Z_1$, $Z_2$ and $R_{01}$ are the same as those in the general formula (1); in one molecule, $L_0$, G, $(Z_2)_q$—$(Z_1)_{q1}$ can be each independently either stable or degradable, and the joint linking group formed by any aforesaid group with its adjacent group can be each independently either stable or degradable.

2. The invention also discloses a modified bio-related substance of an eight-arm polyethylene glycol derivative (also referred to as a derivative of an eight-arm polyethylene glycol derivative which has been modified with a bio-related substance, an eight-arm-PEG-modified bio-related substance, or a bio-related substance modified with an eight-arm polyethylene glycol, or a bio-related substance modified by an eight-arm polyethylene glycol derivative). The structure of the modified bio-related substance of an eight-arm polyethylene glycol derivative is represented by the general formula (2):

wherein, D is different from $E_{01}$. Wherein, D represents the residue of a bio-related substance after reacting with an eight-arm polyethylene glycol derivative; L is the linking group formed after the reaction between the functional group of the eight-arm polyethylene glycol derivative and the bio-related substance; $E_{01}$ is selected from $R_{01}$, protected $R_{01}$, deprotected $R_{01}$ and end-capped $R_{01}$; the number of D grafted at one PEG chain terminal is denoted as $k_D$, wherein, $0 \leq k_D \leq k$; the $k_D$ values of different PEG chains in one molecule are each independently equal or not equal, and the total number of D in one molecule is at least 1, and preferably at least 8.

When g is equal to 1, G-(EF)$_k$ can be represented by

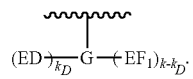

$(ED)_{k_D}$—G—$(EF_1)_{k-k_D}$.

Wherein, the definitions of U, $E_1$, $E_2$, $E_3$, $E_4$, $L_{11}$, $L_{12}$, $L_{21}$, $L_{22}$, $L_{31}$, $L_{32}$, $L_{41}$, $L_{42}$, $L_0$, G, $n_1$, $n_2$, $n_3$, $n_4$, $n_5$, $n_6$, $n_7$, (2)

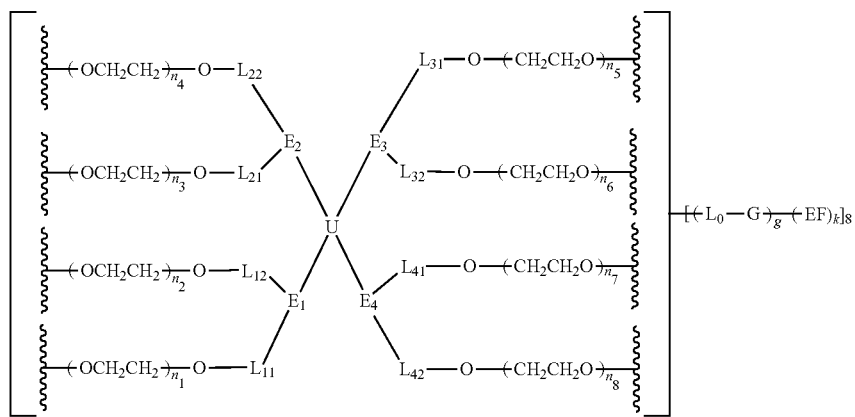

Wherein, g is 0 or 1; EF is represented as ED (with a structure of

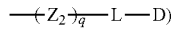

—$(Z_2)_q$—L—D)

or $EF_1$ (with a structure of

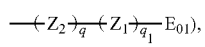

—$(Z_2)_q$—$(Z_1)_{q_1}$—$E_{01}$), $n_8$, g, k, $Z_1$, $Z_2$, q, $q_1$ and $R_{01}$ are the same as those in the general formula (1), and no more repeated here.

The modified bio-related substance of an eight-arm polyethylene glycol derivative can be either stable or degradable; in one molecule, U, $E_1$, $E_2$, $E_3$, $E_4$, $L_{11}$, $L_{12}$, $L_{21}$, $L_{22}$, $L_{31}$, $L_{32}$, $L_{41}$, $L_{42}$, $L_0$, G, $(Z_2)_q$—$(Z)_{q1}$ and $(Z_2)_q$-L can be each independently either stable or degradable, and the joint linking group formed by any aforesaid group with its adjacent group can be each independently either stable or degradable.

When all of $E_1$, $E_2$, $E_3$ and $E_4$ are identical and denoted as $U_c$, the general formula (2) can be represented by formula (2a).

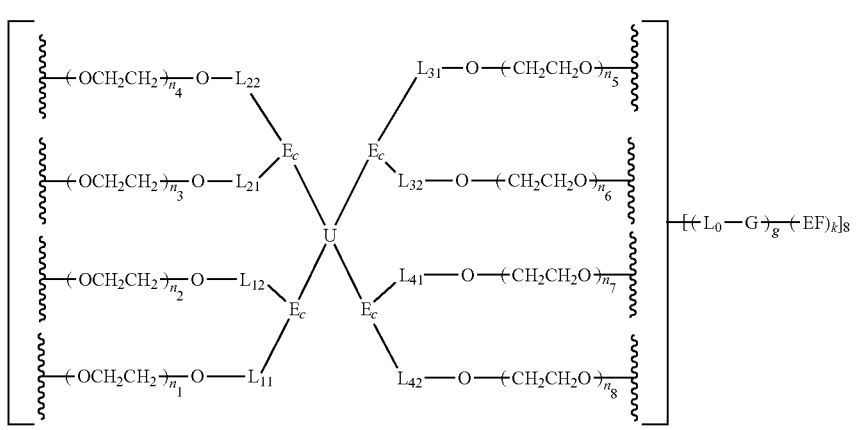
(2a)
When all of $L_{11}$, $L_{12}$, $L_{21}$, $L_{22}$, $L_{31}$, $L_{32}$, $L_{41}$ and $L_{42}$ are identical and denoted as $L_0$, the general formula (2) can be represented by formula (2b).
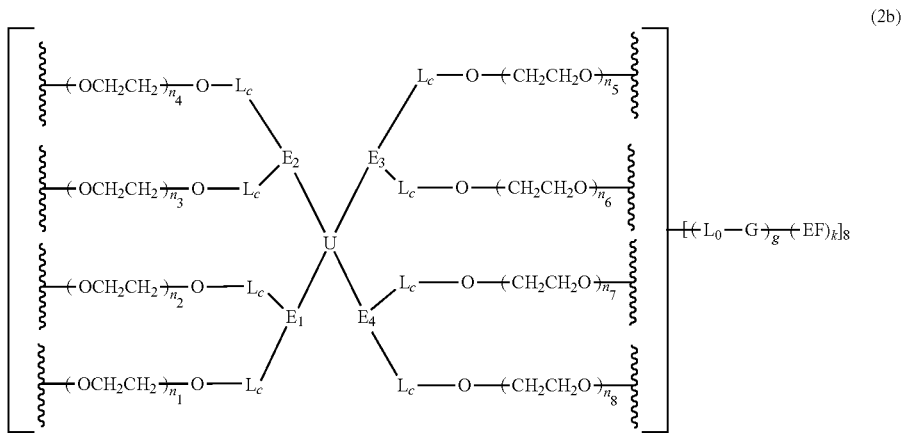
(2b)
When all of $E_1$, $E_2$, $E_3$ and $E_4$ are identical, and all of $L_{11}$, $L_{12}$, $L_{21}$, $L_{22}$, $L_{31}$, $L_{32}$, $L_{41}$ and $L_{42}$ are also identical, the general formula (2) can be represented by formula (2c).
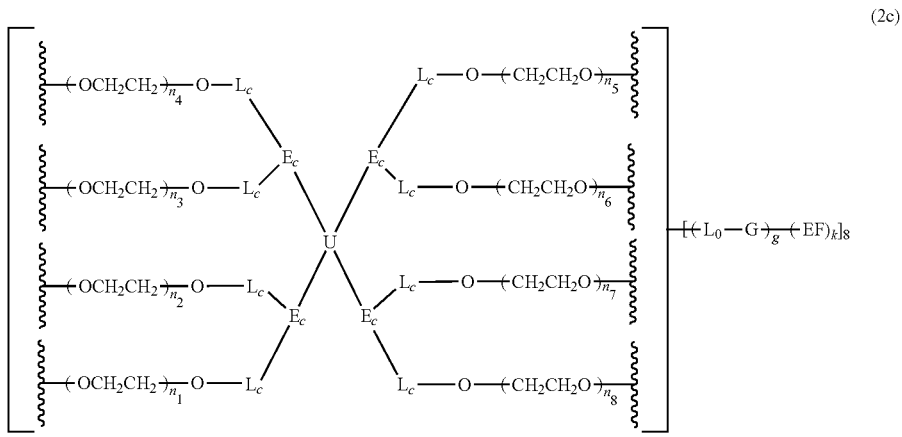
(2c)

In one molecule, $k_D$ values of the eight PEG chain terminals preferably satisfy $0 \leq k_D \leq k$, that is each PEG chain connects with at least one D. One ideal case is that $k_D$ values of the eight PEG chain terminals all satisfy $k_D = k$, that is all the terminal reactive sites respectively connects to one D, and the fractional content of D (in terms of number) reaches 100%.

The D groups as residues of a bio-related substance are derived from the same bio-related substance, but can be residue groups formed from different reactive sites after reacting with the functional end-group $R_{01}$, especially when the bio-related substance has multiple identical reactive groups.

In a single molecule, D content (the fraction of the number of D relative to the number of reactive sites) is not particularly limited, and can be greater than about 75% or less than about 75%. The D content of molecules in the eight-arm polyethylene glycol macroscopic substance can be identical or not identical, for example, it can be equal to 100%, be between 65% and 90%, or be between 75 and 94%. The higher the D content is (that is the higher drug loading is), then the easier to be increased the efficacy of the bio-related substance is, the higher the product homogeneity is and the better the product performance becomes. When the bio-related substance has multiple reactive sites, the same bio-related substance molecule can react with the same $R_{01}$ group but lead to identical or different D residues, and preferably lead to identical D residues, herein, the performance of the product becomes more uniform and more stable. In a single molecule, the D content is preferably greater than about 75%, more preferably greater than about 80%, more preferably greater than about 85%, more preferably greater than about 90%, more preferably greater than about 94%, and most preferably equal to 100%. With respect to a macroscopic substance, the average content of D (the average D content per eight-arm polyethylene glycol derivative molecule) can be greater than about 75% or less than about 75%, preferably greater than about 75%, more preferably greater than about 80%, more preferably greater than about 85%, more preferably greater than about 90%, more preferably greater than about 94%, and most preferably equal to 100%.

Wherein, $k_D$ is the number of reactive sites that actually react with the bio-related substance among the terminal functional groups of one PEG chain terminal of a single molecule; with respect to a macroscopic substance, $k_D$ corresponds to a mean value, that is the average number of reactive sites per PEG chain terminal per functional eight-arm polyethylene glycol molecule, wherein, the mean value can be an integer or a non-integer value; wherein, in a single molecule, the $k_D$ integers are each independently 0, 1 or an integer from 2 to 250. The present invention also includes the embodiments in which one bio-related substance molecule binds to two or more molecules of the eight-arm polyethylene glycol derivative, but preferably that one bio-related substance molecule only reacts with one terminal functional group, that is one bio-related substance molecule only connects to one eight-arm polyethylene glycol derivative molecule, wherein, the quality of product is more controllable. In other words, $k_D$ also represents the number of bio-related substance molecules bound to one PEG chain terminal (for a macroscopic substance, $k_D$ corresponds to a mean value, that is the average number of bio-related substance molecules attached to per PEG chain terminal per functional eight-arm polyethylene glycol molecule). The terminal functional groups of the eight-arm polyethylene glycol derivative can, in whole or in part, participate in the modification to the bio-related substance, and preferably that the terminal functional groups in whole participate in the modification to the bio-related substance. In the modified bio-related substance of the eight-arm polyethylene glycol derivative, the remaining terminal functional groups not bound to a bio-related substance can retain the pre-reaction structural form, be in a protected form, be in a deprotected form, or be end-capped with a non-bio-related substance.

L can be a covalent linkage or a non-covalent linkage, preferably a covalent linkage; L can also be a dihydrogen bond or a multiple hydrogen bond. Since allowed to react with different reactive sites from the same bio-related substance, the eight PEG chain terminals in one molecule can correspond to different L linkages, preferably that the eight PEG chain terminals in one molecule form the same L linkage. Any L group in one molecule can be each independently either stable or degradable, and the joint linking group formed by any L group with its adjacent heterosubstituted group can be each independently either stable or degradable. Correspondingly, any $(Z_2)_q$-L in one molecule can be each independently either stable or degradable and the joint linking group formed by any $(Z_2)_q$-L group with its adjacent heterosubstituted group can be each independently either stable or degradable. It is preferably that the L groups at the eight PEG chain terminals have the same stability, i.e. L groups are all stable or all degradable, wherein, $(Z_2)_q$-L groups at the eight PEG chain terminals also have the same stability.

According to the difference in degradable sites and the difference in the stability (also referred to as degradability) of the modified bio-related substance of an eight-arm polyethylene glycol derivative, embodiments include but are not limited to the following Groups:

(1) wherein, g is equal to 0, the octavalent center $CORE_8$ (O—)$_8$ is stable, and the —O—$(Z_2)_q$-L-groups are stable;

(2) wherein, g is equal to 0, the octavalent center $CORE_8$ (O—)$_8$ is stable, and the —O—$(Z_2)_q$-L-groups are degradable;

(3) wherein, g is equal to 0, the octavalent center $CORE_8$ (O—)$_8$ is degradable, and the —O—$(Z_2)_q$-L- groups are degradable;

(4) wherein, g is equal to 1, the octavalent center $CORE_8$ (O—)$_8$ is stable, the positions at —O-$L_0$-G- are stable (not including the connection between G and $Z_2$), and the positions at —$(Z_2)_q$-L- are stable (including the connection between G and $Z_2$);

(5) wherein, g is equal to 1, the octavalent center $CORE_8$ (O—)$_8$ is stable, the positions at —O-$L_0$-G- are degradable (not including the connection between G and $Z_2$), and the positions at —$(Z_2)_q$-L- are stable (including the connection between G and $Z_2$);

(6) wherein, g is equal to 1, the octavalent center $CORE_8$ (O—)$_8$ is stable, the positions at —O-$L_0$-G- are stable (not including the connection between G and $Z_2$), and the positions at —$(Z_2)_q$-L- are degradable (including the connection between G and $Z_2$);

(7) wherein, g is equal to 1, the octavalent center $CORE_8$ (O—)$_8$ is degradable, the positions at —O-$L_0$-G- are stable (not including the connection between G and $Z_2$), and the positions at —$(Z_2)_q$-L- are stable (including the connection between G and $Z_2$);

(8) wherein, g is equal to 1, the octavalent center $CORE_8$ (O—)$_8$ is degradable, and the positions at —O-$L_0$-G- are degradable (not including the connection between G and $Z_2$), and the positions at —$(Z_2)_q$-L- are stable (including the connection between G and $Z_2$);

(9) wherein, g is equal to 1, the octavalent center $CORE_8$ (O—)$_8$ is degradable, the positions at —O-$L_0$-G- are stable (not including the connection between G and $Z_2$), and the positions at $-(Z_2)_q$-L- are degradable (including the connection between G and $Z_2$);

(10) wherein, g is equal to 1, the octavalent center $CORE_8(O-)_8$ is stable, the positions at $-O-L_0-G-$ are degradable (not including the connection between G and $Z_2$), and the positions at $-(Z_2)_q$-L- are degradable (including the connection between G and $Z_2$);

(11) wherein, g is equal to 1, the octavalent center $CORE_8(O-)_8$ is degradable, the positions at $-O-L_0-G-$ are degradable (not including the connection between G and $Z_2$), and the positions at $-(Z_2)_q$-L- are degradable (including the connection between G and $Z_2$);

(12) wherein, g is equal to 0, the octavalent center $CORE_8(O-)_8$ is stable, the $-O-(Z_2)_q-$ groups are stable, and the L groups are degradable;

(13) wherein, g is equal to 1, the octavalent center $CORE_8(O-)_8$ is stable, the $-O-L_0-G-[(Z_2)_q-]_k$ groups are stable, and the L groups are degradable;

(14) wherein, g is equal to 0, the octavalent center $CORE_8(O-)_8$ is stable, the $-O-(Z_2)_q-$ groups are stable, and the L-D groups are degradable;

(15) wherein, g is equal to 1, the octavalent center $CORE_8(O-)_8$ is stable, the $-O-L_0-G-[(Z_2)_q-]_k$ groups are stable, and the L-D groups are degradable.

Different combinations according to the number and position of degradable sites have been described hereinbefore, and no more repeated here. Wherein, embodiments (1), (4), (12) and (13) correspond to a stable eight-arm polyethylene glycol moiety; embodiments (3), (5) and (7) to (11) correspond to a degradable eight-arm polyethylene glycol moiety; in the embodiments (2) and (6), any one of $(Z_2)_q-$ (including the connection between $Z_2$ and terminal O atom or G group of PEG) and L is degradable, and the structure can correspond to a stable eight-arm polyethylene glycol moiety together with degradable L groups, or correspond to a degradable eight-arm polyethylene glycol moiety together with stable L groups. One preferable embodiment of the above-described combinations is that the octavalent center $CORE_8(O-)_8$ is stable, including the embodiments (1), (2), (4), (5), (6), (10), (12), (13), (14) and (15). Wherein, with respect to the embodiments (1) and (4), the PEG moiety is undegradable, and its connection with the bio-related substance is also stable, herein, the bio-related substance to be modified with a polyethylene glycol moiety can be a pre-modified bio-related substance; when the bio-related substance is a drug moiety, if the connection between the drug moiety and the PEG moiety contains no additional spacer which generates a degradable linkage, the bio-related substance and the PEG moiety can be metabolized as a whole, and can bring the benefits including accelerating solubilization, increasing interaction rate between the drug moiety and the lesion site or target tissue, enhancing therapeutic efficacy, etc. Wherein, with respect to the embodiments (14) and (15), the reaction between D and $(Z_1)_{q1}-R_{01}$ can result in a degradable L or a stable L. When D is undegradable, L can be degradable, such as Example S56; when D is degradable such as the modified bio-related substance in Examples S45-S48, wherein, a degradable ester group exists between the drug moiety and the spacer group, then L is preferably stable, or preferably a degradable group with higher stability (such as a urethane bond which has higher stability than an ester group).

The general formula (2) preferably has a structure represented by formula (41).

In this case, the eight PEG chains are generated in the same manner, so their lengths are completely identical or substantially identical (close), and the modified bio-related substance of an eight-arm polyethylene glycol derivative is more homogeneous in composition, much better in controllability, more stable in performance, and more suitable for industrial applications and large-scale production. With respect to the PEG chain lengths, an embodiment can be the case of $n_1=n_2=n_3=n_4=n_5=n_6=n_7=n_8=n$ corresponding to monodisperse PEG chains, or the case of $n_1 \approx n_2 \approx n_3 \approx n_4 \approx n_5 \approx n_6 \approx n_7 \approx n_8 \approx n$ corresponding to polydisperse PEG chains.

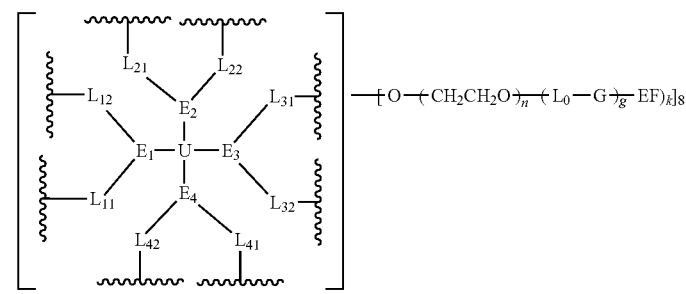

(41)

In the above formula (41), when g is equal to 0, then $EF_1$ is preferably

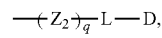

herein, the D content is 100%, and the structure can be represented by formula (42).

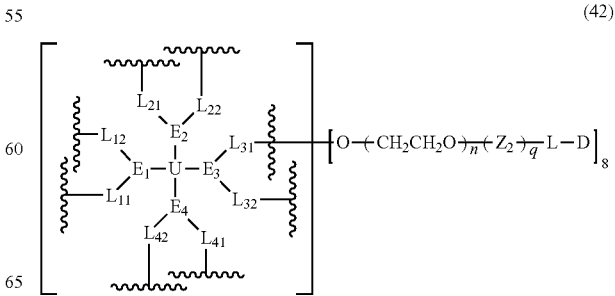

(42)

In the above formula (41), when g is equal to 1, the D content is preferably greater than 75% or less than 75%, preferably greater than 80%, more preferably greater than 85%, more preferably greater than 90%, more preferably greater than 94%, and most preferably equal to 100%. Wherein, when g is equal to 1 and the D content is 100%, the structure can be represented by formula (43).

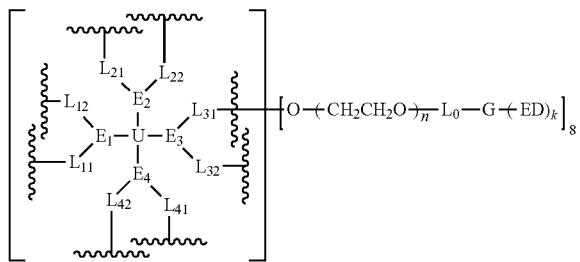

(43)

2.1. The Bio-Related Substance

In the general formula (2), the bio-related substance can be a bio-related substance (itself), a modified bio-related substance or a composite bio-related substance. Wherein, the composite bio-related substance is a chemical conjugate of two or two more species of bio-related substances.

The bio-related substance can come from natural sources or be artificially synthesized. The sources of the bio-related substance are not particularly limited, including but not limited to natural extracts and derivatives thereof, degraded products of natural extracts, products of recombinant DNA technology (molecularly cloned products), products via chemical synthesis (chemically synthesized products), and so on. The hydrophilicity-hydrophobicity property of the bio-related substance is not particularly limited. The bio-related substance can be hydrophilic or water-soluble, and can also be hydrophobic or liposoluble. The charge property of the bio-related substance is not particularly limited.

The bio-related substance can be the bio-related substance itself, a dimer or multimer thereof, a subunit or fragment thereof, etc.

The bio-related substance can be the bio-related substance itself, can be a related form selected from the group consisting of precursors, active forms (or activated forms), derivatives, isomers, mutants, analogs, mimetics, polymorphs, pharmaceutically acceptable salts, fusion proteins, chemically modified substances, genetic recombinant substances and the like, and can also be a corresponding related form selected from the group consisting of agonists, activating agents, activators, inhibitors, antagonists, modulators, receptors, ligands, aptamers, antibodies and antibody fragments, enzymes (e.g., kinases, hydrolases, lyases, oxidoreductases, isomerases, transferases, deaminases, deiminases, convertases, synthetases and the like), substrates for enzymes (e.g., the substrate for coagulation cascade proteases and the like) and the like. The derivatives include but are not limited to derivatives of glycosides, nucleosides, amino acids and peptides. Both chemically modified products with newly introduced reactive groups, and modified products with additionally introduced functional groups, reactive groups, amino acids or amino acid derivatives, polypeptides or the like, belong to the chemically modified forms of the bio-related substance. The bio-related substances can also bear given molecules, tags or delivery carriers prior to or after binding the eight-arm polyethylene glycol derivative, wherein, modified bio-related substances or composite bio-related substances are formed. Wherein, the pharmaceutically acceptable salts can be either inorganic salts such as hydrochloride, or organic salts such as oxalate, malate, citrate and the like.

The derivation source of the bio-related substance is not particularly limited, including but not limited to human, rabbit, rat or mouse, goat, bovine, porcine, etc.

The application fields of the bio-related substance are not particularly limited, including but not limited to medicine, regenerative medicine, tissue engineering, stem cell engineering, biological engineering, genetic engineering, polymer engineering, surface engineering, nanoengineering, detection and diagnosis, chemical staining, fluorescent labeling, cosmetics, food, food supplements, nutrients, etc. Bio-related substances for the field of medicine include but are not limited to drugs, drug carriers, medical devices, and can be used for various aspects such as prevention and treatment of diseases, wound treatment, tissue repair and replacement, diagnostic imaging, etc. Examples of the biorelated substance also include dye molecules used for quantitative or semi-quantitative analysis, fluorocarbon molecules used for diagnostic imaging, blood substitutes and the like, antiparasitics such as primaquine and the like, and carriers such as chelating agents used for antidotes including ethylenediaminetetraacetic acid (EDTA), diethylene-triamine pentacetic acid (DTPA) and the like. When the bio-related substances are used as drugs, the therapeutic fields of the bio-related substances are not particularly limited, and examples include but are not limited to drugs for treating cancers, tumors, liver diseases, hepatitis, diabetes, gout, rheumatism, rheumatoid, Alzheimer's disease, cardiovascular disease and other diseases; examples of the bio-related substance also include anti-allergic drugs, anti-infective agents, antibiotics, antiviral agents, antifungal agents, vaccines, central nervous system depressants, central nervous system stimulants, psychotropic drugs, respiratory drugs, peripheral nervous system drugs, drugs acting on synaptic connections or effector connections, drugs acting on smooth muscle activities, histamine agents, antihistamine agents, blood drugs and drugs on hematopoietic system, gastrointestinal drugs, steroid agents, cell growth inhibitors, anthelmintics, antimalarial agents, antiprotozoal agents, antimicrobials, anti-inflammatory drugs, immunosuppressants, drugs or compounds for Alzheimer's disease, imaging agents, antidotes, anticonvulsants or antispasmodics or spasmolytics, muscle relaxants, antiphlogistic drugs, appetite suppressants, antimigraine agents, muscle contractants, antiemetics, bronchodilators, antithrombotic drugs, antihypertensive drugs, antiarrhythmic drugs, antioxicants, anti-asthmatic drugs, diuretics, lipid-regulating agents, antiandrogens, anti-parasitic drugs, anticoagulants, neoplastic agents, hypoglycaemic drugs, nutritional agents and supplements, growth supplements, antienteritis agents, vaccines, antibodies, diagnostic agents (including but not limited to contrast agents), contrasting agents, hypnotic agents (e.g., soporific drugs), sedatives, psychostimulants, tranquilizers, antiparkinson drugs, analgesics, anti-anxiety drugs, anti-myositis drugs, inhibitors for auditory diseases, etc. Wherein, typical examples of anticancer or anti-tumor drugs include but are not limited to drugs for treating breast cancer, ovarian cancer, cervical cancer, uterine cancer, endometrial cancer, gastrointestinal cancer, intestinal cancer, metastatic colorectal cancer, rectal cancer, colon cancer, colorectal cancer, gastric cancer (stomach cancer), squamous cell cancer (squamous cell carcinoma), laryngeal cancer, esophageal cancer (esophageal carcinoma), malignant tumor, lung cancer, small cell lung cancer, non-small cell lung cancer, liver cancer, thyroid cancer, kidney cancer, bile duct cancer (cholangiocarcinoma), brain cancer, skin cancer, pancreatic cancer, prostate cancer, bladder cancer, testicular cancer, nasopharyngeal cancer, head and neck cancer, gallbladder and bile duct cancer, retinal cancer, renal cell cancer, gallbladder cancer, multidrug resistance in cancer, melanoma, lymphoma, non-Hodgkin's lymphoma, adenoma, leukemia, chronic lymphocytic leukemia, multiple myeloma, brain tumor, Wilms' tumor (nephroblastoma), liposarcoma, endometrial sarcoma, rhabdomyosarcoma, neuroblastoma, and AIDS-related cancers (such as Kaposi's sarcoma) and other primary or secondary cancers, sarcomas and carcinosarcomas.

Applicable "drugs" in the present invention include medicaments, compounds, compositions or mixtures which can provide a physiological or pharmacological effect in vivo or in vitro, and often achieve an advantageous effect. The species of drugs are not particularly limited, including but not limited to medicaments, vaccines, antibodies, vitamins, food, food supplements, nutrients, dietary supplements and other agents that can provide a beneficial effect. The action region of the "drugs" where to provide a physiological or pharmacological effect in vivo is not particularly limited, and it can be a systemic or local effect. The activity of a "drug" is not particularly limited, and the drug can mainly be an active substance capable of interacting with other substances, or be an inert substance which does not undergo interactions. However, with respect to an inert medicament, it can be converted into an active form by in vivo actions or under specific stimulation.

The species of the bio-related substance are not particularly limited, including but not limited to the following substances: drugs, proteins, peptides, oligopeptides, protein mimetics, fragments and analogs of proteins, enzymes, antigens, antibodies and fragments thereof, receptors, small molecule drugs, nucleosides, nucleotides, oligonucleotides, antisense oligonucleotides, polynucleotides, nucleic acids, aptamers, polysaccharides, proteoglycans, glycoproteins, steroids, lipids, hormones, vitamins, vesicles, liposomes, phospholipids, glycolipids, dyes, fluorescent substances, targeting factors, cytokines, neurotransmitters, extracellular matrix substances, plant or animal extracts, viruses, vaccines, cells, micelles, etc.

The bio-related substances can be classified into the following Groups with some examples listed to illustrate the scope. One bio-related substance can occur in one or more Groups. Summarily as follows:

Examples of the bio-related substance in the general formula (2) include but are not limited to those described and listed in the documents CN104530413A, CN104530415A and CN104530417A; take CN104530413A for example, corresponding to paragraphs from [0813] to [0921] and paragraphs from [0971] to [1146].

(1) Proteins, peptides and related-substance thereof.

Examples of this Group are not particularly limited, including but not limited to hormones, serum proteins, cytokines and fragments thereof, peptides, enzymes and corresponding zymogens, immunoglobulins, monoclonal or polyclonal antibodies and fragments thereof, antigens, polyamino acids, vaccines and the like. The enzymes and corresponding zymogens also include but are not limited to neutral plasmin, thimetoligopeptidase, leukotriene A4 hydrolase, endothelin-converting enzymes, ste24 protease, mitochondrial intermediate peptidase, interstitial collagenase, collagenases, macrophage elastase, gelatinases, transmembrane peptidases, procollagen C-endopeptidase, procollagen N-endopeptidase, ADAM metalloproteases and ADAMT metalloproteases, myelin-associated metalloproteinases, enamelysin, tumor necrosis factor-α converting enzyme, insulin-degrading enzyme, nardilysin, mitochondrial processing peptidase, magnolysin, dactylysin-like metalloproteases, neutrophils collagenase, matrix metalloproteinases, membrane-type matrix metalloproteinases, SP2 endopeptidase, trypsin, calpain I, pancreatic elastase, pancreatic endopeptidases, erepsin, leukocyte elastases, chymotrypsins, trypsin-like proteases, granzymes, stratum corneum chymotrytic enzyme, acrosin, Kallikrein, alternative-complement-pathway c3/c5 convertase, mannan-binding lectin serine protease (mannose-associated serine protease), thrombin, cathepsin G, heparinase, serine proteases, hepatocyte growth factor activator, proprotein convertase subtilisin/kexin types, furin, proprotein convertases, prolyl peptidases, acylaminoacyl peptidase, peptidyl-glycaminase, signal peptidases, N-terminal nucleophile aminohydrolases (Ntn hydrolases), 20s proteasomes, γ-glutamyl transpeptidase, mitochondrial endopeptidases, endopeptidase mitochondrial Ia, htra2 peptidase, site-1 protease (S1P), asparagine endopeptidase, cathepsins, cathepsin D, cysteine cathepsins, calpains, ubiquitin isopeptidase T, caspases, glycosylphosphatidylinositol-protein transamidase, prohormone thiol protease, γ-glutamyl hydrolase, bleomycin hydrolase, pepsin, chymosin, gastricsin, memapsins, cyclosporin synthetase, canine urate oxidase and the like. Examples of the bio-related substance in this Group also include but are not limited to neurolysin, stromelysin, fibroblast activation proteins, human fibroblast activation proteins, matrilysin, complement components and factors, coagulation factors, renin, cancer procoagulant, prostate-specific antigen, protein C, u- and t-type plasminogen activators, cyclosporin, canine leptin polypeptides, immunosuppressive peptides (avian leukemia virus subgroup J), VEGF mimetic peptides (vascular endothelial growth factor mimetic peptides) and the like.

Examples of this Group also include but are not limited to dimers or multimers, subunits or fragments, precursors, activated forms, derivatives, isomers, mutants, analogs, mimetics, polymorphs, pharmaceutically acceptable salts, fusion proteins, chemically modified substances, genetic recombinant substances and the like of the aforesaid bio-related substances, and also include corresponding related substances such as agonists, activating agents, activators, inhibitors, antagonists, modulators, receptors, ligands, aptamers, antibodies and antibody fragments, enzymes (e.g., kinases, hydrolases, lyases, oxidoreductases, isomerases, transferases, deaminases, deiminases, convertases, synthetases and the like), substrates for enzymes and the like.

(2) Small Molecule Drugs

The species of small molecule drugs are not particularly limited, including but not limited to flavonoids, terpenoids, carotenoids, saponins, steroids, quinines, anthraquinones, fluoroquinones, coumarins, alkaloids, porphyrins, polyphenols, macrolides, monobactams, phenylpropanoids, anthracyclines, aminoglycosides, amino acids and derivatives thereof (natural and non-natural), etc. The therapeutic fields of small molecule drugs are not particularly limited. Small molecule drugs preferably include anticancer or antitumor drugs, antibiotics, antivirals, antifungals, other anticancer or antitumor drugs, other antibiotics, other antivirals, other antifungals and other small molecule drugs; small molecule drugs are preferably anticancer or antitumor drugs or antifungals.

Anticancer or antitumor drugs: including but not limited to taxanes, paclitaxel and derivatives thereof, docetaxel, camptothecin and derivatives thereof (including but not limited to 7-ethyl-10-hydroxycamptothecin, 9-nitrocamptothecin, 9-aminocamptothecin and the like), irinotecan, SN38, topotecan, topotecan hydrochloride, belotecan, exatecan, diflomotecan, rubitecan, karenitecin, chimmitecan, gimatecan, afeletecan, lurtotecan, cisplatin, oxaliplatin, hydroxycamptothecins (including but not limited to 10-hydroxycamptothecin and the like), vinblastine, vincristine, emetine, emetine hydrochloride, colchicine, pirarubicin, valrubicin, doxorubicin or doxorubicin hydrochloride, epirubicin, rubidomycin, daunomycin, mitomycin, aclacinomycin, idarubicin, bleomycin, peplomycin, mithramycin, rapamycin, bleomycin, streptozotocin, podophyllotoxin, actinomycin D (dactinomycin), maytansines, amikacin, mitoxantrone, tretinoin (vitamin A acid), vindesine, vinorelbine, gemcitabine, capecitabine, cladribine, pemetrexed disodium, tegafur, letrozole, anastrozole, fulvestrant, goserelin, triptorelin, leuprolide, buserelin, temozolomide, cyclophosphamide, ifosfamide, gefitinib, sunitinib, sunitinib malate, erlotinib, erlotinib hydrochloride, icotinib, lapatinib, lapatinib di-p-toluenesulfonate, sorafenib, imatinib, imatinib methanesulfonate, N-demethylated imatinib, neratinib, bosutinib, axitinib, vandetanib, saracatinib, canertinib, canertinib dihydrochloride, tandutinib, mubritinib, tenidap, dovitinib, lestaurtinib, octenidine, octenidine, bafetinib, tilisolol, pirtenidine, tienilic acid, tenilsetam, afatinib, brotianide, sunitinib methanesulfonate, tenilapine, antienite, teniloxazine, sorafenib tosylate, tenylidone, dasatinib, nilotinib, telatinib, sirolimus, everolimus, mercaptopurine, methotrexate, 5-fluorouracil, dacarbazine, hydroxyurea, vorinostat, ixabepilone, bortezomib, cytarabine, etoposide, azacytidine, teniposide, propranolol, procaine, tetracaine, lidocaine, bexarotene, carmustine (bis-chloroethylnitrosourea), chlorambucil, (methoxybenzyl)hydrazine, thiotepa, plitidepsin, ranimustine, genistein, bendamustine and the like;

Antibiotics, antivirals and antifungals: including but not limited to macrolides, defensins, colistimethate, polymyxins (e.g., polymyxin B), capreomycin, bacitracin, gramicidin, amphotericin B, aminoglycoside antibiotics, gentamicin, paramecin, tobramycin, kanamycin, neomycin, streptomycin, nystatin, echinocandins, carbenicillin, penicillin, penicillin-sensitive agents, penicillin G, penicillin V, penicillin-resistant agents (such as methicillin, oxacillin, cloxacillin, dicloxacillin, flucloxacillin, nafcillin and the like), penem, vancomycin, daptomycin, anthracyclines, chloramphenicol, erythromycin cydocarbonate, flavomycin, oleandomycin, troleandomycin, clarithromycin, davercin, erythromycin, dirithromycin, roxithromycin, azithromycin, flurithromycin, josamycin, spiramycin, medemycin, midecamycin, albomycin, miocamycin, rokitamycin, doxycycline, swinolide A, teicoplanin, rampolanin, mideplanin, colistin, flucytosine, miconazole, econazole, fluconazole, itraconazole, ketoconazole, voriconazole, clotrimazole, bifonazole, netilmicin, amikacin, caspofungin, micafungin, terbinafine, fluoroquinolone, lomefloxacin, norfloxacin, ciprofloxacin, enoxacin, ofloxacin, levofloxacin, trovafloxacin, alatrofloxacin, moxifloxacin, grepafloxacin, gatifloxacin, sparfloxacin, temafloxacin, pefloxacin, amifloxacin, fleroxacin, tosufloxacin, prulifloxacin, irloxacin, pazufloxacin, clinafloxacin, sitafloxacin, idarubicin, colitimethate, antiviral nucleoside drugs, ribavirin, antipseudomonal penicillins, ticarcillin, azlocillin, mezlocillin, piperacillin, Gram-negative microorganism active agents, ampicillin, hetacillin, galampicillin, amoxicillin, cephalosporins (such as cefpodoxime, cefprozil, ceftizoxime, ceftriaxone, cephalothin, cephapirin, cephalexin, cephradine, cefoxitin, cefamandole, cefazolin, cefaloridine, cefaclor, cefadroxil, cephaloglycin, cefuroxime, ceforanide, cefotaxime, cephacetrile, cefepime, cefixime, cefonicid, cefoperazone, cefotetan, cefmetazole, ceftazidime, loracarbef, latamoxef, ceftibuten, cephalosporin, cephaloridine II, ceftriaxone sodium and the like), monobactams, aztreonam, carbapenem, imipenem, meropenem, aceyl thiourea, albuterol sulfate, lidocaine, orciprenaline sulfate, beclomethasone, beclomethasone dipropionate, metaproterenol sulfate, triamcinolone acetamide, budesonide, budesonide acetonide, fluticasone, fluticasone propionate, ipratropium bromide, flunisolide, cromolyn sodium, ergotamine tartrate, pentamidine, pentamidine isethionate, chlorogenic acid and the like.

Other anticancer drugs, antitumor drugs, antibiotics, antivirals, antifungals and other small molecule drugs: including but not limited to cytochalasin B, aminomethylbenzoic acid, p-aminohippuric acid sodium, aminoglutethimide, aminolevulinic acid, aminosalicylic acid, pamidronic acid, amsacrine, anagrelide, anastrozole, levamisole, busulfan, cabergoline, leuplin, carboplatin, cilastatin sodium, disodium clodronate, amiodarone, ondansetron, deacetylation cyproterone acetate, megestrol acetate, testosterone, estramustine, exemestane, fluoxymesterone, diethylstilbestrol, fexofenadine, fludarabine, fludrocortisone, 16-methylepihydrocortisone, fluticasone, deferoxamine, flutamide, bicalutamide, thalidomide, L-DOPA, leucovorin, lisinopril, levothyroxine sodium, chlormethine (or mechlorethamine), medroxyprogesterone, metaraminol bitartrate, metoclopramide, mexiletine, mitotane, nicotine, nicotine tartrate, nilutamide, octreotide, pentostatin, pilcamycin, porfimer, prednisone, procarbazine, prochlorperazine, raltitrexed, streptozotocin, sirolimus, tacrolimus, tamoxifen, teniposide, tetrahydrocannabinol, thioguanine, thiotepa, dolasetron, granisetron, formoterol, formoterol fumarate, melphalan, midazolam, alprazolam, podophylotoxins, sumatriptan, lowmolecularweight heparin, amifostine, carmustine, lomustine, tyrphostin, antiosteoarthritis drugs (including, but not limited to aspirin, salicylic acid, phenylbutazone, indomethacin, naproxen, diclofenac, meloxicam, nabumetone, etodolac, sulindac acid, acemetacin, diacerein and the like), amdoxovir, cyanurin, aminoarone, aminocaproic acid, butanediol dimethanesulfonate, clodronic acid, disodium clodronate, dihydroxy-L-phenylalanine, lovothyroxine sodium, o,p-dichlorophenyl dichloroethane, aroylhydrazones, miokamycin, rokitamycin (ricamycin), maltoryzine, isorhamnetin, myricetin, dicyanomyricetin, catechin, epicatechin, phlorizin, acarbose, salmeterol, salmeterol xinafoate, naloxone, opioids (such as mu-opioid, kappa-opioid and the like), phenytoin, cinacalcet, diphenhydramine and so on.

The amino acids can be natural aminoacids or non-natural amino acids.

(3) Gene Related Substances

The gene-related substances are not particularly limited and can include as follows: nucleosides, nucleotides, oligonucleotides, polynucleotides, antisense oligonucleotides, nucleic acids, DNA, RNA, aptamers, related aptamers or ligands, etc.

(4) Vitamins.

Specific examples of vitamins include but are not limited to vitamin A (including but not limited to vitamin A, vitamin A acid, isotretinoin, retinene, 3-dehydroretinol, 13-cis-retinoic acid, all-trans-retinoic acid, α-carotene, β-carotene, γ-carotene, δ-carotene, cryptoxanthin, etretinate, eretin and the like), vitamin B (such as folic acid and the like), vitamin C, vitamin D, vitamin E, vitamin K, vitamin H, vitamin M, vitamin T, vitamin U, vitamin P, vitamin PP and the like.

(5) Saccharides

Saccharides are not particularly limited, and mainly include glycolipids, glycoproteins, glycogens and the like. Glycolipids are widely distributed in the organism, and mainly include glycosyl-acylglycerids and glycosphingolipids. Specific examples of glycolipids include ceramides, cerebrosides, sphingosines, gangliosides, glyceroglycolipids and the like. Glycoproteins, a kind of polyconjugates that contain oligosaccharide chains (glycans) covalently attached to polypeptide side-chains, are commonly secreted into body fluid or act as a component of membrane protein, specifically including but not limited to transferrins, serum ceruloplasmins, membrane-binding proteins, histocompatibility antigens, hormones, carriers, lectins, heptarin, antibodies and the like.

(6) Lipids

Lipids mainly include fatty acid esters and lipoids.

Typical fatty acid ester is fat, a kind of ester formed by fatty acid and glycerol. Fatty acid esters also include esters formed by non-glycerol alcohols and fatty acids, including but not limited to esters of coconut-oil fatty acid, polyglycerol esters of fatty acid, sucrose fatty acid esters, etc. Herein, fatty acids are not particularly limited, but preferably a fatty acid having 12 to 24 carbon atoms. The fatty acids can be a saturated fatty acid or an unsaturated fatty acid.

Lipoids include glycolipids, phospholipids and cholesteryl esters.

Glycolipids mainly include glycerol glycolipids, glycosphingolipids, sophorolipids, cerebrosides, ceramidetrihexosides, sphingosine-1-phosphate, rhamnolipids, di-rhamnolipids and the like.

Phospholipids can be derived from natural phospholipid substances, or from semisynthetic or synthetic phospholipid compounds.

Natural phospholipids include but are not limited to phosphatidic acids, lecithins (a kind of phosphatidylcholine, derived from egg yolk, soybean and the like, e.g., egg yolk lecithin, soybean lecithin and the like), cephalins (a kind of phosphatidylethanolamine, derived from brain, nerve, soybean and the like), lipositols (e.g., phosphatidylinositol), phosphatidylserines, sphingomyelins, lysophospholipids, lysolecithins, lysocephalins, lysophosphatidic acids, myelins, cardiolipins (diphosphatidylglycerols), heparins, low-molecular-weight heparins, other phospholipids derived from egg and soybean and the like.

Semisynthetic or synthetic phospholipid compounds include but are not limited to phosphatidic acid (PA), plasmalogen, phosphatidylglycerol (PG), phosphatidylcholine (PC), phosphatidylethanolamine (PE), phosphatidylserine (PS), phosphatidylinositol (PI), ceramides, ceramide-containing phospholipids (including but not limited to ceramide phosphatidylcholine, ceramide phosphatidylethanolamine, ceramide phosphatidylglycerol, ceramide phosphatidylserine, ceramide phosphatidylinositol, ceramide phosphatidylglycerol phosphate and the like), lysoglycerophospholipid isomers, hydrogenated natural phospholipids, O-amino-acid esters of phosphatidylglycerol and the like. The number of fatty chains in synthetic phospholipids can be one or two; if two fatty chains are present, they can be identical or different. Wherein, the fatty chains in synthetic phospholipids can be derived from saturated or unsaturated fatty acids. The species of fatty moieties are not particularly limited, including but not limited to butyric acid, tert-butyric acid, pentanoic acid (e.g., valeric acid), heptanoic acid, a 2-ethylhexanoic acid, octanoic acid (caprylic acid), decanoic acid (capric acid), lauric acid, myristic acid, palmitic acid, heptadecanoic acid, a stearic acid, isostearic acid, oleic acid, elaidic acid, linoleic acid, linolenic acid, arachidic acid, arachidonic acid, behenic acid, erucic acid, lignoceric acid, cerotic acid, octacosanic acid, melissic acid, dotriacontanoic acid and so on. For example, phosphatidic acids include but are not limited to dilauroyl phosphatidic acid, dimyristoyl phosphatidic acid, dipalmitoyl phosphatidic acid and the like; phosphatidylglycerols include but are not limited to dicaproylphosphatidylglycerol, dicaprylphosphatidylglycerol, didecanoylphosphatidylglycerol, dilauroylphosphatidylglycerol, dimyristoylphosphatidylglycerol, dipalmitoylphosphatidylglycerol, distearoylphosphatidylglycerol, dioleoylphosphatidylglycerol, etc.; phosphatidylcholines include but are not limited to dicaproylphosphatidylcholine, dicaprylphosphatidylcholine, didecanoylphosphatidylcholine, dilauroylphosphatidylcholine, dimyristoylphosphatidylcholine, dipalmitoylphosphatidylcholine, distearoylphosphatidylcholine, dioleoylphosphatidylcholine, hydrogenated soybean phosphatidylcholine, etc.; phosphatidylethanolamines include but are not limited to N-glutaryl-phosphatidylethanolamine, dilauroylphosphatidylethanolamine, dimyristoylphosphatidylethanolamine, dipalmitoylphosphatidylethanolamine, distearoylphosphatidylethanolamine, dioleoylphosphatidylethanolamine, dilinoleoylphosphatidylethanolamine, dierucoylphosphatidylethanolamine, etc.; phosphatidylinositols include but are not limited to dilauroylphosphatidylinositol, dimyristoylphosphatidylinositol, dipalmitoylphosphatidylinositol, distearoylphosphatidylinositol, dioleoylphosphatidylinositol, lysophosphatidylinositol, etc.; hydrogenated natural phospholipids include but are not limited to hydrogenated soybean lecithin and hydrogenated egg yolk lecithin, etc.; synthetic phospholipids which contain two different fatty moieties include but not limited to 1-palmitoyl-2-oleoyl phosphatidylethanolamine, 1-palmitoyl-2-linoleoyl phosphatidylcholine, 1-stearoyl-2-linoleoyl phosphatidylcholine, 1-stearoyl-2-oleoyl phosphatidylcholine, 1-stearoyl-2-arachidonoyl phosphatidylcholine, 1-palmitoyl-2-oleoyl phosphatidylcholine, 1-palmitoyl-2-stearoyl phosphatidylcholine and the like.

Cholesterols, steroids and the like include but are not limited to cholesterol, dihydrocholesterol, sitosterol, β-sitosterol, lanosterol, annasterol, avenasterol, brassicasterol, ergosterol, ergocalciferol, dihydroergocalciferol, ergostadienol, dihydroergostadienol, campesterol, chalinosterol, chinasterol, cholestanol, coprosterol, cycloartenol, dehydrocholesterol, desmosterol, dinosterol, epicholesterol, fucosterol, hexahydrolumisterin, hydroxycholesterol, lumisterin, parkeol, poriferasterol, fucasterol, sitostanol, stigmastanol, stigmasterol, weinbersterol, cryptosterol, cholesterin, bile acids (including but not limited to cholic acid, chenocholic acid, glycocholic acid, taurocholic acid, deoxycholic acid, lithocholic acid and the like), sex hormones, vitamin D, aldosterone, deoxycorticosterone, clobetasol, fludrocortisone, cortisone, hydrocortisone, prednisone, medrysone, meprednisone, alclometasone, beclomethasone, betamethasone, dexamethasone, diflorasone, flumethasone, triamcinolone, mometasone, desoximetasone, fluocinolone, flunisolide, paramethasone, halcinonide, amcinonide, desonide, prednisolone, methylprednisolone, clocortolone, flurandrenolone and the like.

(7) Neurotransmitters

Neurotransmitters can be classified into monoamines, peptides, amino acids, etc. Wherein, the monoamines include dopamine, norepinephrine, epinephrine, 5-hydroxytryptamine (also termed as serotonin, seronine or thrombocytin) and the like; the peptides include neurotensin, cholecystokinin, vasoactive intestinal peptide, vasopressin, endogenous opioid peptides, somatostatin, neuropeptide y, neuromedin U, etc.; other species include nucleotides, anandamide, sigma receptors (σ-receptors) and the like. Related drugs include but are not limited to diphenhydramine, bromodiphenhydramine, doxylamine, carbinoxamine, clemastine, dramamine (or dimenhydrinate), tripelennamine, pyrilamine, methapyrilene, thonzylamine, pheniramine, chlorpheniramine, dexchlorpheniramine, bromopheniramine, dexbromopheniramine, pyrrobutamine, triprolidine, promethazine, alimemazine, methdilazine, cyclizine, chlorcyclizine, diphenylpyraline, phenindamine, dimetindene, meclizine, buclizine, antazo, cyproheptadine, azatadine, terfenadine, fexofenadine, astemizole, cetirizine, azelastine, azatadine, loratadine, desloratadine and the like.

(8) Extracellular Matrix Substances

Extracellular matrix substances include but are not limited to the biomacromolecules of collagen (such as type I collagen, type II collagen and the like), hyaluronic acid, glycoproteins, proteoglycans, laminin, fibronectin, elastin, etc.;

(9) Dyes and Fluorescent Substances

Dyes include but are not limited to trypan blue, Coomassie Brilliant Blue, crystal violet, pyrogallol red, phenylamyl ketone, etc. Fluorescent substances can be used for chemical staining, immunofluorescent staining and the like, or be used for fluorescent labeling and tracing. Fluorescent substances include but are not limited to fluorescent proteins, rhodamines, phalloidin and derivatives thereof, cyanine dyes, indocyanine green, acridines, phycoerythrin, phycocyanin, methyl green, alizarin red, aniline blue, pyronin, fluoresceins, aggregation-induced emission dyes, near infrared fluorescent dyes, fluorescent carbonaceous nanodots, hematoxylin, eosin, neutral red, fuchsin, Alexa Fluor dyes, Oregon green dyes, BODIPY dyes, Cy3, Cy3.5, Cy5, Cy5.5, Cy7, Cy7.5, Hex, PerCP, DAPI, Hoechst dyes, Cascade blue, Astrazon dyes, SYTO dyes, stilbene dyes, naphthalimide dyes, coumarin dyes, pyrene dyes, phenanthridine dyes, porphyrin dyes, indole dyes, chromomycin A, ethidium bromide, purpurin and the like. All the fluorescent substances disclosed in the patent documents CN1969190A, CN101679849B and U.S. Ser. No. 14/526,901 (US20150119281A1) are incorporated into the present invention by reference. Rhodamine derivatives disclosed in the document "Progress in Chemistry, 2010, 22 (10): 1929-1939" and cited references therein are also incorporated into the present invention by reference. The coumarin dyes also include but not limited to 4,5,7-trihydroxyl coumarin. Functional groups in the general formula (1) from Group J also belong to this Group.

(10) Targeting Factors

Targeting factors are not particularly limited. They can have a single or multiple target sites (mono-target or multi-target). They can be an individual molecule or a conjugate of multiple molecules. The targeting factors can be themselves, molecules modified with targeting factors, conjugates of multiple molecules, self-assembled substances, nanoparticles, liposomes, vesicles, drugs, etc.

The target sites are not particularly limited, including but not limited to brain, lung, kidney, stomach, liver, pancreas, breast, prostate, thyroid, uterus, ovary, nasopharynx, esophagus, rectum, colon, small intestine, gall bladder, bladder, bone, glands, skin, blood vessel, lymph, joints, soft tissues and other sites.

The target tissues are not specifically limited, including but not limited to tumor tissue, inflammatory tissue, diseased tissue, etc.

Targeting factors include but are not limited to functional groups above-described in Group I.

Specific examples of targeting factors include but are not limited to: polypeptide ligands, small molecule ligands, other ligands that can be recognized by cell surface receptors and ligand variants, ligands targeting tumor-associated angiogenesis, disease cell cycle targeting ligands, ligands targeting tumor cell apoptosis, disease receptor targeting ligands, kinase inhibitors or protease inhibitors, PI3K/Akt/mTOR inhibitors, angiogenesis inhibitors, cytoskeletal signaling inhibitors, stem cells and Wnt-inhibitors, protease inhibitors, tyrosine kinase inhibitors, apoptosis inhibitors, MAPK inhibitors, cell cycle inhibitors, TGF-beta/Smad inhibitors, nerve signal inhibiting peptides, endocrine and hormone inhibitors, metabolic inhibitors, microbial inhibitors, epigenetic inhibitors, JAK/STAT inhibitors, DNA damage inhibitors, NF-κB inhibitors, GPCR & G protein inhibitors, transmembrane transport protein inhibitors, autophagy inhibitors, ubiquitin inhibitors, multitarget inhibitors, receptors, antibodies, targeting drugs, gene targeting molecules, viruses, vaccines, biomacromolecular targeting factors, vitamins and the like.

The target sites of targeting factors include but are not limited to CD3, CD11, CD20, CD22, CD25, CD30, CD33, CD41, CD44, CD52, CD6, CD3, CD11a, Her2, GpIIb/IIIa, RANKL, CTLA-4, CO17-1A, IL-1β, IL-12/23, IL6, IL13, IL-17, Blys, RSV, IgE-25, integrin-α4, respiratory syncytial virus F-protein, tumor necrosis factor α (TNFα), vascular endothelial growth factors, epidermal growth factor receptors (EGFR), FGR3, EGFL-7, interferon-α and the like.

Functional groups in the general formula (1) from Group I also belong to this Group.

(11) Other bio-related substances well known to those skilled in the art such as vesicles, liposomes, micelles, nanocarriers used for drug delivery, cells (e.g., myeloblasts), viruses (e.g., cyanovirins) and the like are also included in the present invention.

(12) Plant or Animal Extracts

Examples include but are not limited to *Tripterygium wilfordii* extracts, boxwood extracts, cantharidin extracts and derivatives thereof, flavone and flavonoid drugs, *salvia* extracts, *Silybum marianum* extracts (or silymarin extracts), glycyrrhetinic acid, scopoletin, *terrestris* extracts, pollen extracts, gingko extracts, cajan leaf extracts, honeysuckle extracts, schisandrae sphenantherae extracts, veratrum extracts, cinobufagin extracts, snake venom extracts, leech extracts and the like, and also include herbal extracts.

*Tripterygium wilfordii* extracts include but are not limited to triptolide, tripdiolide, triptonide, hypolide methyl ether, triptonide, tripchlorolide, triptriolide, wilforonide, wilfordine, wilforgine, wilforine, wilfortrine, wilforzine, tripterygic acid, hydroxyl wilfordic acid, tripterine, tripterygium glucosides, etc. Boxwood extracts include but are not limited to buxines, including but not limited to cyclovirobuxine, cycloprotobuxamine, cyclovirobuxine C, etc. Cantharidin extracts and derivatives thereof include but are not limited to cantharidin, norcantharidin, methylcantharidinimide, hydroxycantharidinimide, amino acid derivatives of norcantharidinimide, etc.; all the cantharidin derivatives disclosed in the literature "Yuan Lihong, The synthesis of norcantharidin derivatives [D], Zhongshan University, 2005." and cited references therein are also incorporated into the present invention by reference. Flavone and flavonoid drugs include but are not limited to puerarin, hydroxyisoflavone, scutellarein, skullcapflavone II, baicalein, baicalin, 4',5,7-trihydroxylflavone, 3',4',7-hydroxylisoflavone, emodin anthrone, emodin, 5,7,4'-trihydroxylflavone, 3,5,7-trihydroxylflavone, 4',6,7-trihydroxylisoflavone, genistein, 4',5,7-trihydroxyisoflavone 7-glucoside, etc. *Salvia* extracts, such as tanshinone and derivatives thereof, include but are not limited to tanshinone IIa, tanshinone IIb, tanshinone I, cryptotanshinone, danshenxinkun A, danshenxinkun B, danshenxinkun C, etc; Water-soluble *salvia* extracts and salts thereof include but are not limited to tanshinol, protocatechuic aldehyde, rosemary acid, lithospermic acid, salvianolic acids A, B, C, D, E, F and G, etc. *Silybum marianum* extracts include but are not limited to silibinin, silychristin, silydianin, etc. Pollen extracts can be derived from cell-wall-broken pine pollen or from cell-wall-unbroken pine pollen. Gingko extracts include but are not limited to flavones, ginkgolides, etc. Veratrum extracts include but are not limited to resveratrol, cyclopamine, etc. Snake venom extracts include such as thrombin, defibrase, etc. Leech extracts include such as hirudin, etc.

(13) In addition, all the bio-related substances disclosed in the patent document CN102316902A and cited references therein are also incorporated into the present invention by reference, including central nervous system depressants, central nervous system stimulants, psychotropic drugs, respiratory drugs, peripheral nervous system drugs, drugs acting on synaptic connections or effector connections, drugs acting on smooth muscle activities, histamine agents, anti-histamine agents, cardiovascular drugs, blood drugs and drugs on hematopoietic system, gastrointestinal drugs, steroid agents, cell growth inhibitors, antitumor agents, anti-infective agents, antibiotic agents, antifungal agents, anthelmintics, antimalarial agents, antiprotozoal agents, antimicrobial agents, anti-inflammatory drugs, immunosuppressants, cytokines, enzymes, iminosugars, ceramide analogues, brain hormones or neurotransmitters, neuropeptides and derivatives thereof, neurotrophic factors, antibodies or fragments thereof, drugs or compounds to treat Alzheimer's disease, nucleic acid-based compounds, imaging agents, antidotes (e.g., organophosphates) and the like. All the bio-related substances disclosed in the document "Biotech Drugs (Biological High-tech 863 Series)" which was published in 2001 and cited references therein are also incorporated into the present invention by reference, including recombinant hormone drugs, recombinant cytokine drugs, recombinant thrombolytic drugs, human blood substitutes, therapeutic antibodies, recombinant soluble receptors and adhesion molecule drugs, antisense oligonucleotide drugs, generic drugs, genetically engineered viral vaccines, genetically engineered bacterins, genetically engineered parasites vaccines and therapeutic vaccines. All the anticancer drugs listed in the literatures "Macromolecular Anticancer Therapeutics (Cancer Drug Discovery and Development)" (L. Harivardhan Reddy and Patrick Couvreur as authors, publicated in 2010) are also incorporated into the present invention by reference.

(14) Phloretin and 2,4,6-Trihydroxy-3,5-Dimethylacetophenone are Also Included.

With respect to composite bio-related substances, examples include conjugates of lipids with bio-related substances of other species, conjugates of fluorescent substances with bio-related substances of other species, conjugates of targeting factors with bio-related substances of other species, conjugates of sugars with bio-related substances of other species, and other conjugates of two or more species of suitable bio-related substances.

2.2. Linking Group L that Connects the Bio-Related Substance with the PEG Chain

The covalent linking group L is formed after the reaction between the terminal functional group of the eight-arm polyethylene glycol derivative and the reactive group of the bio-related substance, and the structure of L is related to the reactive groups of the bio-related substance and the terminal functional group of the polyethylene glycol derivative. Examples of L include but are not limited to those described and listed in the documents CN104530413A, CN104530415A and CN104530417A; take CN104530413A as an example, corresponding to paragraphs from [0922] to [0935] and the Example part.

Summarily as follows:

The reactive site of the bio-related substance is not particularly limited, and can come from natural reactive sites, or from activated groups or reactive groups additionally introduced via modification. Take drug molecules for example, common examples of natural reactive sites include an amino group, a mercapto group, a carboxyl group, a disulfide group, an N-amino group, a C-carboxyl group, a hydroxyl group (e.g., an alcoholic hydroxyl group, a phenolic hydroxyl group, and the like), a carbonyl group, a guanidino group and the like. The reactive sites of amino acids disclosed in the literatures "Journal of Controlled Release, 161 (2012): 461-472", "Expert Opin Drug Deliv, 2009, 6(1):1-16", "Pharm Sci Technol Today, 1998, 1(8): 352-6" and "Polymers, 2012, 4(1):561-89" are all incorporated into the present invention by reference. Non-natural reactive groups, especially reactive groups introduced via modification include but are not limited to $R_{01}$ groups in the above Groups A to H in terms of functional groups, e.g., an aldehyde group, an alkynyl group, an azido group, etc.

Examples of the reactive groups of the bio-related substance include but are not limited to the group consisting of an amino group, a mercapto group, a disulfide group, a carboxyl group, a hydroxyl group, a carbonyl group, an aldehyde group, an unsaturated bond and an introduced reactive group. For example, an amino-containing bio-related substance reacts with a polyethylene glycol derivative containing an active ester, an active formate, a sulfonate group, an aldehyde group, an α,β-unsaturated bond, a carboxyl group, an epoxy group, an isocyanato group, an isothiocyanato group or an anhydride group can obtain a pegylated conjugate bearing an amide bond, a urethane bond, an amino bond, an imide bond (which can further be reduced to a secondary amino bond), an amino bond, an amide bond, a hydroxyalkylamino bond, a urea bond, a thiourea bond or an imide linkage, respectively; a mercapto-containing bio-related substance reacts with a polyethylene glycol derivative containing an active ester, an active formate group, a sulfonate group, a mercapto group, a maleimido group, an aldehyde group, an α,β-unsaturated bond, a carboxyl group or an iodoacetamide group can obtain a pegylated conjugate bearing a thioester bond, a thiocarbonate bond, a thioether bond, a disulfide bond, a thioether bond, a thiohemiacetal linkage, a thioether bond, a thioester bond or a thioether bond, respectively; an unsaturated bond-containing bio-related substance reacts with a polyethylene glycol derivative containing a mercapto group can obtain a pegylated conjugate bearing a thioether bond; a carboxyl-containing bio-related substance reacts with a polyethylene glycol derivative containing a mercapto group or an amino group can obtain a pegylated conjugate bearing a thioester bond or an amide bond, respectively; a hydroxyl-containing bio-related substance reacts with a polyethylene glycol derivative containing a carboxyl group, an isocyanato group, an epoxy group or a chlorocarbonyloxy group can obtain a pegylated conjugate bearing an ester bond, a carbamate bond, an ether bond or a carbonate group, respectively; a bio-related substance containing a carbonyl group or an aldehyde group reacts with a polyethylene glycol derivative containing an amino group, a hydrazino group or an acylhydrazido group can obtain a pegylated conjugate bearing an imine bond, a hydrazone bond or an acylhydrazone, respectively; reactive groups containing an azido group, an alkynyl group, an alkenyl group, a mercapto group, a dienyl group, a maleimido group, a 1,2,4-triazoline-3,5-dione group, a dithioester group, a hydroxylamino group, an acylhydrazido group, an acrylate group, an allyloxy group, an isocyanato group, a tetrazole group or the like can undergo click reactions to form various linking groups including but not limited to a triazole linkage, an isoxazole linkage, a thioether bond and the like. The linking groups formed via click reactions described and cited in the literature "Adv. Funct. Mater., 2014, 24, 2572-2590" and cited references therein are also incorporated into the present invention by reference.

The structure of L is not particularly limited, and can be but is not limited to a linear type, a branched type or a ring-containing type.

The valence of L is not particularly limited, for example, L can be a divalent linking group, a trivalent group or a higher-valent covalent linking group, and L is preferably a divalent linking group. Herein, L is more generally a divalent linking group. One example of the trivalent linking group is the group formed by mercapto groups and an alkynyl group. Another example is the trivalent linking group

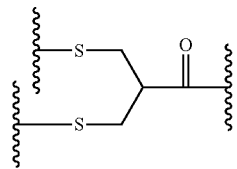 [SMILES: *SCC(CS*)C(*)=O]

formed via the reaction between the functional group B5 and a disulfide bond.

The stability of L is not particularly limited. L can be a stable linking group or a degradable linking group. The condition "to be stable" or "to be degradable" or "to degrade" is consistent with those in the term-defining section. L is preferably a stable linking group which can remain stable under the condition such as light illumination, heat, low temperature, an enzymatic condition, an oxidation-reduction condition, an acidic condition, a basic condition, a physiological condition or a simulated physiological environment in vitro, or preferably a degradable linking group which can be degraded under the condition such as light illumination, heat, low temperature, an enzymatic condition, an oxidation-reduction condition, an acidic condition, a basic condition, a physiological condition or a simulated physiological environment in vitro. L is more preferably a stable linking group which can remain stable under the condition such as light illumination, heat, low temperature, an enzymatic condition, an oxidation-reduction condition, an acidic condition or a basic condition, or preferably a degradable linking group which can be degraded under the condition such as light illumination, heat, low temperature, an enzymatic condition, an oxidation-reduction condition, an acidic condition or a basic condition.

When as a stable linking group, L can contain a linking group selected from the group including, but not limited to, an ether bond, a thioether bond, a urea bond, a thiourea bond, a carbamate bond, a thiocarbamate bond, a secondary amino bond, a tertiary amino bond, an amide bond, an imide bond, a thioamide bond, a sulfonamide bond, an enamino bond, a triazole linkage, an isoxazole linkage, the like and the combination thereof. For translation explanation, in the present invention, the term "linkage" can be referred to as a "bond", a divalent group, a tri- or higher-valent group and the like; for example, a urethane group as a divalent group and a urethane bond are equivalent.

When the position at L (L itself or the connections between L and its adjacent groups) is degradable, drug molecules can achieve depegylation to remove the coverage of polyethylene glycol moieties to exert drug efficacy to the greatest extent.

When as a degradable linking group, L can contain a degradable linking group selected from the group including, but not limited to, any of the above-described degradable linking groups; specifically including but not limited to a disulfide bond, a vinylether bond, an ester bond, a thioester bond, a thiocarboxylate bond (a thioate bond or a monothioester bond), a dithioester bond, a carbonate bond, a thiocarbonate bond, a dithiocarbonate bond, a trithiocarbonate bond, a carbamate bond, a thiocarbamate bond, a dithiocarbamate bond, an acetal linkage, a cycloacetal linkage, a mercaptal linkage, an azaacetal linkage, an azacycloacetal linkage, an azathiaacetal linkage, a dithioacetal linkage, a hemiacetal linkage, a thiohemiacetal linkage, an azahemiacetal linkage, a ketal linkage, a thioketal linkage, an azaketal linkage, an azacycloketal linkage, an azathiaketal linkage, an imine bond, a hydrazone bond, an acylhydrazone bond, an oxime bond (also an oximino bond), a thiooxime bond, a semicarbazone bond, a thiosemicarbazone bond, a hydrazino bond, an acylhydrazino bond, a thiocarbonylhydrazino bond, an azocarbonyl-hydrazino linkage, an azothiocarbonyl-hydrazino linkage, a hydrazino formate linkage, a hydrazino thioformate linkage, a carbohydrazide bond, a thiocarbohydrazide bond, an azo bond, an isourea bond, an isothiourea bond, an allophanate linkage, a thioallophanate linkage, a guanidino linkage, an amidino linkage, an aminoguanidino linkage, an aminoamidino linkage, an iminocarbonyl-oxy linkage, an iminocarbonyl-thioxy linkage, a sulfonate linkage, a sulfinate linkage, a sulfonamide bond, a sulfonylhydrazino linkage, a sulfonylureido linkage, a maleimide linkage, an orthoester linkage, a phosphate linkage, a phosphirate linkage, a phosphinate linkage, a phosphonate linkage, a phosphosilicate linkage, a silicate linkage, an amide bond, a thioamide bond, a phosphamide linkage, a phosphiramide linkage, a phosphinamide linkage, a phosphonamide linkage, a pyrophosphamide linkage, a cyclophosphamide linkage, an ifosfamide linkage, a thiophosphamide linkage, an aconityl linkage, a peptide bond and the like.

L is preferably a divalent linking group containing at least one linkage selected from the group consisting of a triazole linkage, a 4,5-dihydroisoxazole linkage, an ether bond, a thioether bond, an amide bond, an imide bond, an imine bond, a secondary amino bond, a tertiary amino bond, a urea bond, an ester bond, a thioester bond, a disulfide bond, a thiocarboxylate bond, a dithioester bond, a thiocarbonate bond, a sulfonate bond, a sulfonamide bond, a carbamate bond, a thiocarbamate bond, a dithiocarbamate bond, a thiohemiacetal linkage, a carbonate bond and the like.

Besides the above-said stable or degradable linking groups, L can also contain any of the aforesaid stable divalent linking groups STAG, and can also contain a combination of any two or two more stable divalent linking groups. For example, when modifying the hydroxyl group of a drug molecule, the drug molecule can be modified in advance with an amino acid molecule (e.g., most commonly glycine, diglycine or multiglycine) to convert the hydroxyl group into an amino group, and then the selection of functional groups for conducting the modification reaction is broader.

2.3. Reactions Between the Eight-Arm Polyethylene Glycol Derivative and the Bio-Related Substance The reactions include but are not limited to the reactions described and listed in the documents CN104530413A, CN104530415A and CN104530417A; take CN104530413A as an example, corresponding to paragraphs from [0936] to [0939].

The reaction types between the eight-arm polyethylene glycol derivative and the bio-related substance are not particularly limited, and can be site-specific modifications or non-specific modifications (also termed as random modifications). Examples of site-specific modification include, e.g., the site-specific reaction between the N-amino of methionine and an aldehyde group for the commercial product Neulasta®, the site-specific reactions between a mercapto group and a maleimido group, a vinylsulfone group, a 2-iodoacetamide group, an o-pyridyldisulfide group and the like, the site-specific reactions between an amino group and a cyanate group, an isocyanato group and an isothiocyanato group, etc. Examples of non-specific modifications include the reaction between an amino group and an active ester group, and non-specific modification reactions for preparing commercial products such as Adagen®, Oncaspar®, Pegasys® and Peg-intron®. The site-specific and non-specific modification methods disclosed in the literatures "Pharm Sci Technol Today, 1998, 1(8):352-6" and "Polymers, 2012, 4(1):561-89" are all incorporated into the present invention by reference.

When being modified, one bio-related substance molecule can connect with one or one more eight-arm polyethylene glycol molecules. With reference to the commercial products such as Adagen®, Oncaspar®, Pegasys®, Peg-intron® and Neulasta®, one polyethylene glycol molecule only reacts with one reactive site of a drug molecule; while in the commercial product Somavert®, one drug molecule can bind several polyethylene glycol molecules. In the present invention, it is preferably that one bio-related substance molecule only binds one eight-arm polyethylene glycol molecule.

When modifying a bio-related substance with two or more reactive sites, the eight-arm polyethylene glycol molecules can react with any one or more reactive sites of the bio-related substance if without particular instructions. Preferably, one bio-related substance molecule only reacts with one terminal functional group.

2.4. Modified Small Molecule Drug of an Eight-Arm Polyethylene Glycol Derivative This invention also discloses a modified small molecule drug of an eight-arm polyethylene glycol derivative, corresponding to the case where D is a residue of small molecule drug (SD) in the general formula (2). Preferable embodiments include the cases where D is a residue of small molecule drug (SD) in the general formulas (41), (42) and (43).

In one molecule, the SD residues are derived from the same small molecule drug, but can be resulting residue groups from different reactive sites of the small molecule drug.

The small molecule drug can be a bio-related substance with a molecular weight less than 1000 Da, or be selected from small-molecule mimetics and active fragments of a bio-related substance.

The small molecule drug can also be a derivative or a pharmaceutically acceptable salt of any small molecule drug. The derivative can be selected from molecularly modified derivatives, and can also be selected from, but not limited to, glycoside derivatives, nucleoside derivatives, amino acid derivatives and polypeptide derivatives.

The type of the small molecule drug is not particularly limited, and the small molecule drug can be an organic compound, an inorganic compound, an organometallic compound, an oligopeptide, a polypeptide, or another bio-related substance having a molecular weight less than 1000 Da. Specifically, examples of the small molecule drug not only include those in the above-described Group (2) in terms of bio-related substance, but also include, but are not limited to, the bio-related substances with a molecular weight less than 1000 Da and small-molecule mimetics or small-molecule active fragments (including mutants) of any bio-related substance in any above-described Group of Group (1) and Groups (3) to (14) in terms of bio-related substance.

The molecular weight of the small molecule drug is generally no more than 1000 Da, and can be selected from one of the following intervals: 0~300 Da, 300~350 Da, 350~400 Da, 400~450 Da, 450~500 Da, 500~550 Da, 550~600 Da, 600~650 Da, 650~700 Da, 700~750 Da, 750~800 Da, 800~850 Da, 850~900 Da, 900~950 Da or 950~1000 Da; wherein, each interval excludes the small value endpoint, but includes the large value endpoint.

The source of the small molecule drug is not particularly limited, and can be selected from, but not limited to, natural extracts and derivatives thereof, degraded products of natural extracts, products of recombinant DNA technology (molecularly cloned products), derivatives via molecular modification (chemically synthesized products), and so on.

The hydrophilicity-hydrophobicity property of the small molecule drug is not particularly limited. The small molecule drug can be hydrophilic or water-soluble, and can also be hydrophobic or liposoluble. The charge property of the small molecule drug is not particularly limited.

The small molecule drug can be the small molecule drug itself, a dimer or a multimer thereof, a subunit or a fragment thereof, etc.

The small molecule drug can be the small molecule drug itself, can also be a related form selected from the group consisting of precursors, active forms (or activated forms), derivatives, isomers, mutants, analogs, mimetics, polymorphs, pharmaceutically acceptable salts, fusion proteins, chemically modified substances, genetic recombinant substances and the like, and can also be a corresponding related form selected from the group consisting of agonists, activating agents, activators, inhibitors, antagonists, modulators, receptors, ligands, aptamers, antibodies and antibody fragments, etc. The small molecule drug can also bear given molecules, tags or delivery carriers prior to or after binding the polyethylene glycol moiety.

The application fields of the small molecule drug are not particularly limited, including but not limited to all the above-described therapeutic fields of the bio-related substance; examples of small molecule drugs for therapeutic application include but are not limited to anticancer drugs, antitumor drugs, drugs for treating liver diseases, drugs for treating hepatitis, drugs for treating diabetes, anti-infective agents, antibiotics, antiviral agents, antifungal agents, vaccines, respiratory drugs, anticonvulsants or antispasmodics or spasmolytics, muscle relaxants, antiphlogistic drugs, appetite suppressants, antimigraine agents, muscle contractants, antirheumatic agents, antimalarial agents, antiemetics, bronchodilators, antithrombotic drugs, antihypertensive drugs, cardiovascular drugs, antiarrhythmic drugs, antioxicants, anti-asthmatic drugs, diuretics, lipid-regulating agents, antiandrogens, anti-parasitic drugs, anticoagulants, neoplastic agents, hypoglycaemic drugs, nutritional agents and supplements, growth supplements, antienteritis agents, antibodies, diagnostic agents, contrast agents, contrasting agents and the like. The small molecule drug is preferably selected from anticancer or antitumor drugs, antibiotics, antiviral agents and antifungal agents. Typical examples of anticancer or antitumor drugs are the same as above-described.

Preferable examples of the small molecule drug include SN38, irinotecan, resveratrol, cantharidin and derivatives thereof, buxines, *Tripterygium wilfordii* extracts, flavone and flavonoid drugs, *salvia* extracts, *Silybum marianum* extracts, and derivatives or pharmaceutically acceptable salts of any above-said small molecule drug; the pharmaceutically acceptable salts can be either inorganic salts such as hydrochloride, or organic salts such as oxalate, malate, citrate and the like, preferably hydrochloride. The derivatives include derivatives via molecular modification (molecularly modified derivatives), and also include but are not limited to glycoside derivatives, nucleoside derivatives, amino acid derivatives and polypeptide derivatives. When the eight-arm polyethylene glycol derivative reacts with small molecule drugs through an alcoholic hydroxyl group or a phenolic hydroxyl group, the small molecule drug is preferably an amino acid derivative, or a derivative modified with an oligoethylene glycol fragment with 2 to 10 EO units (e.g., Examples S45, S46 and S47), more preferably an amino acid derivative, more preferably a glycine derivative or an alanine derivative, and most preferably a glycine derivative; in other words, L preferably contains an amino acid skeleton, more preferably contains a glycine or alanine skeleton, and most preferably contains an alanine skeleton (—C(=O)—CH$_2$—NH—); wherein, the reactive group of the amino acid derivative of the small molecule drug is converted into the corresponding amino group of the amino acid moiety. The SD residues of the small molecule drugs include but are not limited to the residue groups of small molecule drugs disclosed in paragraphs from [1078] to [1113] of the document CN104530413A.

3. Production Methods for the Eight-Arm Polyethylene Glycol Derivative 3.1. The present invention also discloses a production method for the eight-arm polyethylene glycol derivative, which, involves the synthesis of a polydisperse eight-arm polyethylene glycol (OctaPEG, CORE$_8$(PEG-OH)$_8$) in which the PEG chains are end-capped with eight hydroxyl groups respectively; the eight-arm polyethylene glycol is synthesized by using a coinitiator system comprising an octahydroxyl-containing small molecule initiator CORER (OH)$_8$ (denoted as OctaIN) and a base, wherein, the OctaIN has an octavalent group CORE

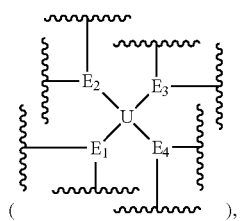

and then initiating the polymerization of ethylene oxide under an active anionic polymerization condition. Herein, $n_1 \approx n_2 \approx n_3 \approx n_4 \approx n_5 \approx n_6 \approx n_7 \approx n_8$.

This method is simple in route, easy to carry out and suitable for industrialization. By using the active anionic polymerization method to generate PEG chains, high-quality eight-arm polyethylene glycol which has precisely controlled molecular weight, narrow molecular weight distribution and little difference in molecular weight between different PEG chains can be achieved. Compared with the conventional method using tripentaerythritol or hexaglycerol as initiators, in virtue of the high symmetry in structure of the octahydroxyl-containing small molecule initiators, the control of the reaction process is facilitated, the molecular weight of the eight PEG chains becomes much closer and the quality of the product turns more uniform. Compared with a linear low-molecular-weight single PEG chain having the same molecular weight, such as about 2 kDa, the high-molecular-weight eight-arm structure corresponding to 16 kDa can possess a lower PDI by adjusting the molecular weight distribution. When the molecular weight of the objective eight-arm structure is high, such as 60 kDa, narrower distribution of molecular weight can be achieved by reducing the PDI value of single-chain reagents.

When the objective eight-arm polyethylene glycol derivative has a structure different from that of OctaPEG, the eight-arm polyethylene glycol derivative as represented by the general formula (1), (3), (4) or (5) can be obtained via end-functionalization to OctaPEG. The OctaPEG can be equivalent to the eight-arm polyethylene glycol derivative represented by the general formula (1), (3) or (5), wherein, g is equal to 0 and the terminal F is an ethylhydroxyl group. Herein, all the eight PEG chains are polydisperse, and the respective number average molecular weight ($M_n$) of the eight PEG chains are close to each other, wherein, the eight $M_n$ values are allowed to be in part or in whole equal. In order to distinguish from the monodisperse embodiment, "≈" is used here to represent the polydispersity property, wherein, all of $L_{11}$, $L_{12}$, $L_{21}$, $L_{22}$, $L_{31}$, $L_{32}$, $L_{41}$ and $L_{42}$ are absent or can also be regarded as an OCH$_2$CH$_2$ unit.

3.1.1. Octahydroxyl-Containing Small Molecule Initiator (OctaIN)

The octahydroxyl-containing small molecule initiator is not particularly limited as long as CORE$_8$ contains no groups that can cause interference to the active anionic polymerization. In general, try to avoid the groups, such as carbonyl-containing groups and a urethane bond, which may be attacked by oxygen anions. One preferable example of OctaIN is that the CORE$_8$ moiety other than the eight hydroxyl groups can contain heteroatom-containing linkages only selected from an oxy group (—O—), a thioxy group (—S—), a divalent tertiary amino group (—NR$_{35}$—), a trivalent tertiary amino group, a trivalent silyl group (>SiR$_{35}$—), a divalent silyl group (—R$_{35}$SiR$_{36}$—), the combination of any two thereof and the combination of any two more thereof, and more preferably can contain heteroatom-containing linkages only selected from an oxy group, a thioxy group, a trivalent tertiary amino group, a divalent tertiary amino group, a trivalent silyl group and optional combinations of the foregoing. Wherein, R$_{35}$ and R$_{36}$ are substituents present in the initiator center and can be stable under the condition of anionic polymerization; in one molecule, R$_{35}$ and R$_{36}$ are each independently, and can be the same or different. R$_{35}$ and R$_{36}$ each independently can contain heteroatoms or not. Heteroatom-free examples include a C$_{1-20}$ alkyl group, a phenyl group, a benzyl group, a C$_{1-20}$ alkyl-substituted phenyl group and a C$_{1-20}$ alkyl-substituted benzyl group, preferably a C$_{1-6}$ alkyl group, a phenyl group, a benzyl group, a C$_{1-6}$ alkyl-substituted phenyl group or a C$_{1-6}$ alkyl-substituted benzyl group, and more preferably a $C_{1-6}$ alkyl group, a phenyl group or a benzyl group. Heteroatom-containing examples can contain a stable divalent linking group such as an ether bond, a thioether bond and the like, or contain a degradable divalent linking group (such as a disulfide bond) which is stable under the condition of anionic polymerization, or contain a stable end-group such as an alkoxy group, a silyl group and the like. For example, $R_{35}$ and $R_{36}$ can be the combination of a methyl group and a phenyl group, or be the combination of an octyl group and a benzyl group. Among the above-described trivalent silyl groups, $R_{35}$ and $R_{36}$ are preferably the same. OctaIN can contain degradable acetal linkage or not. OctaIN is preferably a stable structure, wherein, OctaIN does not contain carbonyl-containing degradable linkages such as a urethane bond, an ester bond, a thioester bond, a thiocarbamate bond, a carbonate bond, a thiocarbonate bond or the like, and the sulfur atoms, when present, do not form a disulfide bond.

One preferable example of OctaIN is that OctaIN contains no $O(CH_2CH_2O)_{j_3}$ segment (neither monodisperse segments nor polydisperse segments). Wherein, $j_3$ is preferably greater than or equal to 10 ($j_3 \geq 10$), further preferably greater than or equal to 3 ($j_3 \geq 3$), and further preferably greater than or equal to 2 ($j_3 \geq 2$). For example, the structure represented by formula (IN-14) should be excluded.

According to the different combinations of heteroatom-containing linkages contained in OctaIN, preferable examples of OctaIN include but are not limited to the following Groups, and examples in each Group allow the presence of heteroatom-containing but active-hydrogen-free monovalent end-groups such as an alkoxy group, an alkylthio group, a dialkylamino group, a trihydrocarbyllsilyl group and the like. The number of species of heteroatom-containing linkages in OctaIN can be one or more, wherein, the quantity of each species is not particularly limited, and the heteroatom-containing linkages preferably can be selected from the group including but not limited to the following structures: an oxy group, a thioxy group, a disulfide bond, a trivalent t-amino group, a divalent t-amino group, a divalent active-hydrogen-free silyl group, a trivalent active-hydrogen-free silyl group and the like.

(1) One preferable Group of OctaIN, wherein, the heteroatom-containing linkage only exists as ether bonds.

The OctaIN for this Group can be obtained by using a tetraol as the starting reagent, then conducting an alkylation reaction or a dehydration-condensation reaction to generate four ether bonds which respectively connects to a monovalent group having two protected hydroxyl groups, and further carrying out deprotection to impart each ether bond with two unprotected hydroxyl groups respectively, such as

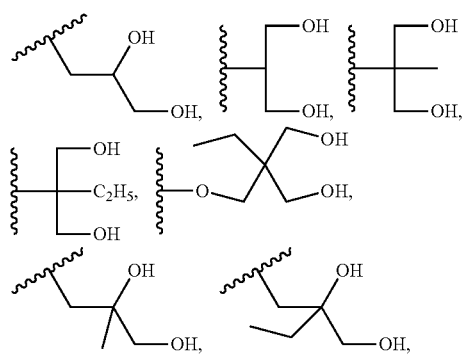

etc. The two protected hydroxyl groups in the monovalent group can be each independently protected by one hydroxyl protecting group $PG_4$, or be commonly protected by a dihydroxyl protecting group $PG_6$. The definitions of $PG_4$ and $PG_6$ are the same as above.

(a) The tetraol can be selected from commonly used small molecule tetraols, including but not limited to pentaerythritol, erythritol, L-threitol, DL-glyceraldehyde dimer, glyoxal hydrate trimer, 2,5-anhydro-D-glucitol, α-methyl-D-mannoside (α-methyl-D-mannopyranoside), 4-methoxyphenyl-α-D-mannopyranoside, benzyl-α-D-mannopyranoside, conduritol B epoxide, 2,4-O-(3,4-dimethylbenzylene)-D-sorbitol, 2,4-O-benzylidene-D-sorbitol (2,4-O-benzylidene-D-glucitol, 2,4-benzyliden-D-sorbit) and the like, and the tetraols are preferably hemiacetal-free and acetal-free structures including pentaerythritol, erythritol, L-threitol, 1,5-anhydro sorbitol, 2,5-anhydro sorbitol and 2,5-dehydro-D-glucitol. (b) The tetraol can also be an ether compound which is condensed by two identical or different triol molecules with the removal of one molecule of $H_2O$, and preferably an ether compound condensed by two identical triol molecules. Examples of the triol include but are not limited to glycerol, 2-hydroxymethyl-2-methyl-1,3-propanediol (also trimethylolethane), 1,1,1-trimethylolpropane, 2-hydroxymethyl-1,3-butanediol, 1,2,4-butanetriol, 1,2,3-butanetriol, 2-benzyloxy-1,3,4-butanetriol, 1,2,5-pentanetriol, 3-methyl-1,3,5-pentanetriol, 1,2,3-hexanetriol, 1,2,6-hexanetriol, 1,2,7-heptanetriol, 1,2,8-octanetriol, 1,2,9-nonanetriol, 1,2,10-decanetriol, 1,3,5-cyclohexanetriol, 1,3,5-benzenetrimethanol, 2-hydroxy-5-methyl-1,3-benzenedimethanol, pyrogallol, phloroglucinol, 1,2,4-benzenetriol, 2,4-dimethyl-1,3,5-benzenetriol and the like. The triol can be either isomer of cis- and trans-structures, such as 1,2,4-butanetriol can be (S)-1,2,4-butanetriol, (R)-1,2,4-butanetriol or the like. The triol can also be an ether compound formed by any aforesaid triol and a diol, such as polypropylene glycol 1,2,6-hexanetriol triether. The triol can also contain hydroxyl groups present in the form of hemiacetal, such as benzaldehyde glycerol acetal and phenylacetaldehyde glyceryl acetal. (c) The tetraol can be obtained via the ring-opening reaction of reagents containing two epoxy groups under a basic condition, wherein, the epoxy-containing reagents include but are not limited to ethylene glycol diglycidyl ether, 1,4-butanediol diglycidyl ether, 1,6-hexanediol diglycidyl ether, neopentyl glycol diglycidyl ether, diethylene glycol diglycidyl ether, oligoethylene glycol diglycidyl ether, oligopropylene glycol diglycidyl ether, 2,2'-((1-methylethylidene)bis(cyclohexane-4,1-diyloxymethylene))bisoxirane, resorcinol diglycidyl ether, bisphenol A diglycidyl ether, 3,3'5,5'-tetramethylbiphenyl diglycidyl ether (also 3,3',5,5'-tetramethyl-4,4'-diphenol diglycidyl ether), 9,9-bis[4-(2-glycidyloxyethyl)phenyl]fluorene (also 9,9-bis[4-(2,3-epoxypropoxy)phenyl]fluorene), etc. The reagents containing two epoxy groups can be obtained via an alkylation reaction between a diol and a reagent in which one terminal is an epoxy group and the other terminal is a halogen atom or a sulfonate group (e.g., epichlorohydrin, (R)-epichlorohydrin, 2-(chloromethyl)-2-methyloxirane, (3-chlorophenyl)oxirane, epifluorohydrin, epibromohydrin, 4-bromo-1,2-epoxybutane, 6-bromo-1,2-epoxyhexane and the like, preferably epichlorohydrin), or be obtained via a dehydration-condensation reaction between a diol and a reagent in which one terminal is an epoxy group and the other terminal is a hydroxyl group (e.g., glycidol), or be obtained via an alkylation reaction between a disulfonate or a dihalide and a reagent in which one terminal is an epoxy group and the other terminal is a hydroxyl group. The disulfonate or dihalide can be obtained by conducting functionalization to the hydroxyl groups of a diol, or be directly purchased. For example, 1,5-pentanediol dimethanesulfonate, diethylene glycol bis(p-toluenesulfonate) and bi-2-naphthyl di-p-toluenesulfonate can be obtained via modification to 1,5-pentanediol, diethylene glycol and binaphthol, respectively.

The diol and the diol used to synthesize a disulfonate or a dihalide are not particularly limited, and are preferably derived from a diol based on a $C_{1-20}$ hydrocarbon group (i.e. a $C_{1-20}$ hydrocarbondiol), or derived from an oligomer or polymer of small molecule diols. When as the oligomer or polymer of small molecule diols, the diol is preferably an oligomer or polymer of ethylene glycol, and the diol can be polydisperse or monodisperse, preferably monodisperse. When as the oligomer or polymer of ethylene glycol, the EO-unit number $j_2$ is the same as above-defined. The two hydroxyl groups of the diol are each independently an alcoholic hydroxyl group, a phenolic hydroxyl group, the hydroxyl group of a hemiacetal, an enolic hydroxyl group or the like, and preferably the two are both an alcoholic hydroxyl group. Examples of the diol include but are not limited to ethylene glycol, tetraethylene glycol, diethylene glycol, 1,2-dipheyl-1,2-ethanediol, 1,2-dicyclohexyl-1,2-ethanediol, 1-(2-naphthyl)-1,2-ethanediol (also 1-(2-naphthyl)ethane-1,2-diol), 1-phenyl-1,2-ethanediol, 1,2-di(1-naphthyl)-1,2-ethanediol (also 1,2-di(1-naphthyl)ethane-1, 2-diol), 1,1,2-triphenylethane-1,2-diol, 1,1,2,2-tetra-p-tolyl-1,2-ethanediol (also 1,1,2,2-tetrakis(4-methylphenyl)-1,2-ethanediol), 1,1,2,2-tetrakis(4-methoxyphenyl)-1,2-ethanediol, 1,2-diphenyl-1,2-di-p-tolyl-1,2-ethanediol (also 1,2-bis(4-methylphenyl)-1,2-diphenyl-1,2-ethanediol), 1,3-propanediol, 1,2-propanediol, 1-phenyl-1,3-propanediol, 2,2-dioctyl-1,3-propanediol, 2,2-diisobutyl-1,3-propanediol, 2,2-diisopentyl-1,3-propanediol, 2,2-di-n-butyl-1,3-propanediol, 2-phenyl-1,3-propanediol, 2-benzyloxy-1,3-propanediol, 2-butyl-1,3-propanediol, 2-butyl-2-ethyl-1,3-propanediol, 2-methyl-1,3-propanediol, 2-methyl-2-propyl-1,3-propanediol, 3-phenoxy-1,2-propanediol, 3-benzyloxy-1,2-propanediol, 2-phenyl-1,2-propanediol, 3-L-menthoxy-2-methylpropane-1,2-diol, 3-menthoxy-1,2-propanediol, 3-methoxy-1,2-propanediol, 3-ethoxy-1,2-propanediol, 3-(isooctadecyloxy)-1,2-propanediol, 3-octyloxy-1,2-propanediol, 1,4-butanediol, 1,2-butanediol, 1,3-butanediol, 2,3-butanediol, 2-methyl-1,4-butanediol, 2,3-dimethyl-2,3-butanediol, 2-butyne-1,4-diol, 1,5-pentanediol, 2-methyl-2, 4-pentanediol, 2,2-dimethyl-1,3-propanediol, 2,2,4-trimethyl-1,3-pentanediol, 3-methyl-1,5-pentanediol, 1,2-pentanediol, dipropylene glycol, triethylene glycol, 1,6-hexanediol, 1,5-hexanediol, 2-ethyl-1,3-hexanediol, 2,5-dimethyl-2,5-hexanediol, trimethyl-1,6-hexanediol, 2,5-hexanediol, 1,2-hexanediol, 2,5-dimethyl-3-hexyne-2,5-diol, 3-hexyne-2,5-diol (also 3-hexyn-2,5-diol), 5-norbornene-2,2-dimethanol, 5-norbornene-2,3-dimethanol, 1,3-cyclohexanediol, 1,4-cyclohexanediol, 1,2-cyclohexanediol, 1,10-decanediol, 1,2-decanediol, 2,4,7,9-tetramethyl-5-decyne-4,7-diol, 1,3-bis(2-hydroxyethoxy) benzene, hydroquinone bis(2-hydroxyethyl)ether, 1,4-benzenediol (also hydroquinone), 2,5-di-tert-butylhydroquinone, 2,3,5-trimethylhydroquinone, 2-methoxyhydroquinone, 2,5-bis(1,1,3,3-tetramethylbutyl) hydroquinone, 2-tert-octylhydroquinone (also 2-tert-octylbenzene-1,4-diol), t-butylhydroquinone, 2,5-bis(1,1-dimethylpropyl)hydroquinone, 2,5-diphenylhydroquinone, 2,5-diisooctylhydroquinone, 2-(hexadecan-2-yl)-5-methylbenzene-1,4-diol, 2,3-dimethoxy-5-methyl-1,4-hydroquinone, 2,6-dimethoxyhydroquinone, biphenyl-4,4'-diol, 2,2',6,6'-tetramethyl-4,4'-biphenol, 4-tert-butylcatechol, 1,2-benzenediol, 4-methylcatechol, 3,5-di-tert-butylcatechol, 4-butylcatechol, tert-butylcatechol, 3-methoxycatechol, 1,3-benzenediol, 3,5-dihydroxytoluene, 4-hexyl-1,3-benzenediol, 5-pentylresorcinol, 5-heptylresorcinol, 2-methylresorcinol, 4-ethylresorcinol, 4-propylresorcinol, 4-butylresorcinol, 4-isopropylresorcinol, 1,4-bis(hydroxymethyl)cyclohexane, 1,2-cyclohexanedimethanol, 5',5-diallyl-2,2'-biphenydiol, estradiol, 3,5-di-tert-butyl-4-hydroxylbenzyl alcohol, 3,6-dihydroxybenzonorbornane, 3-(dimethylamino)-1,2-propanediol, 3-(diethylamino)-1,2-propanediol, 3-piperidinyl-1,2-propanediol (also 3-piperidinopropane-1,2-diol), isosorbide and the like. The diol can be a cis- or trans-structure. Preferable examples are the above-said diols containing two alcoholic hydroxyl groups. Wherein, 3-dimethylamino-1,2-propanediol contains a dimethylamino group as a side group; the nitrogen atom in N-butyldiethanolamine acts as a divalent linking group, and therefore it is excluded.

With respect to the alkylation reaction for synthesizing OctaIN, another reagent besides the tetraol can be a derivative form of a triol in which one hydroxyl group is replaced with a sulfonate group or a halogen atom and the other two hydroxyl groups are protected. The halogen atom is preferably Br or Cl, most preferably Cl. Examples include

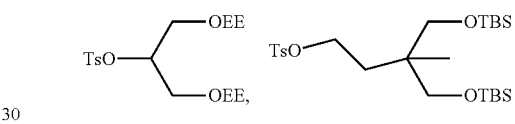

and methyl 2,3-O-isopropylidene-5-O-(p-tolylsulfonyl)-β-D-ribofuranoside, wherein, Ts is a p-toluenesulfonyl group (also referred to as a tosyl group, and OTs as a p-toluenesulfonate group), EE is a 1-ethoxyethyl group (OEE is a 1-ethoxyethoxy group to form a vinyl ethyl ether), and TBS is a t-butyldimethylsilyl group. The triol can be but is not limited to any of the above-said triols, such as 3-chloro-2-methyl-1,2-propanediol, 3-chloro-1,2-propanediol, 4-chloro-1,3-benzenediol, 3-(4-chlorophenoxy)-1,2-propanediol or the like.

With respect to the dehydration-condensation reaction for synthesizing OctaIN, another reagent besides the tetraol can be a derivative form of a triol in which two hydroxyl groups are protected and the other hydroxyl group is unprotected, such as

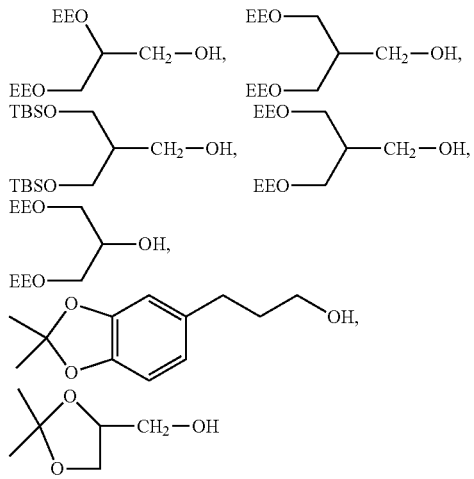

(also referred to as solketal). The triol can be but is not limited to any of the above-said triols.

OctaIN for this Group can be obtained by using a tetraol as the starting reagent, then conducting an alkylation reaction or dehydration-condensation reaction to generate four ether bonds which respectively connects to an epoxy group, and further carrying out a ring-opening reaction under a basic condition to form eight unprotected hydroxyl groups. Examples of the tetraols are the same as above. Another reagent besides the tetraol can be a compound in which one terminal is an epoxy group and the other terminal is a halogen atom or a sulfonate group. The halogen atom is not particularly limited, preferably Br or Cl, and most preferably Cl. The reagent used to synthesize OctaIN besides the tetraol can be a compound in which one terminal is an epoxy group and the other terminal is a hydroxyl group, such as pentaerythritol glycidyl ether and 4,4'-methylenebis(N,N-diglycidylaniline).

In addition, OctaIN for this Group can also be obtained by using a tetrasulfonate or a tetrahalide produced based on a tetraol as the starting reagent, and then carrying out an alkylation reaction with the above-said reagent which has two protected hydroxyl groups or one epoxy group and also one unprotected hydroxyl group. The production method for the tetrasulfonate and the tetrahalide by starting from the terminal hydroxyl groups of a tetraol can be found by reference to the methods for producing the B1- and C7-functionalized compounds in the following end-functionalization section, respectively.

Specific Examples of OctaIN for this Group Include the Following Structures:

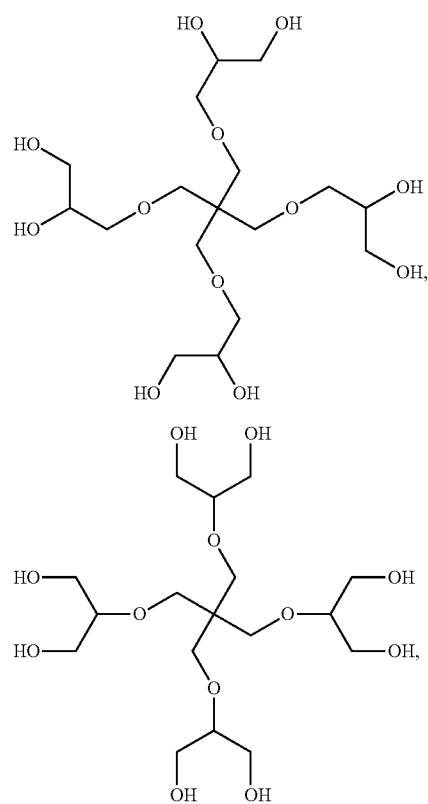

(IN-1)

(IN-2)

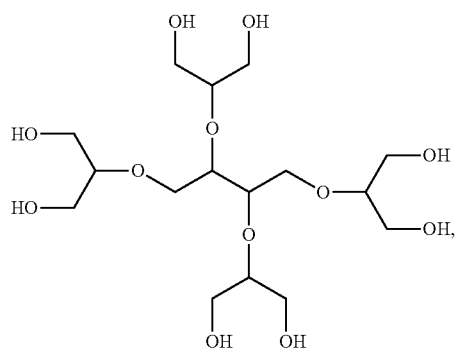

(IN-3)

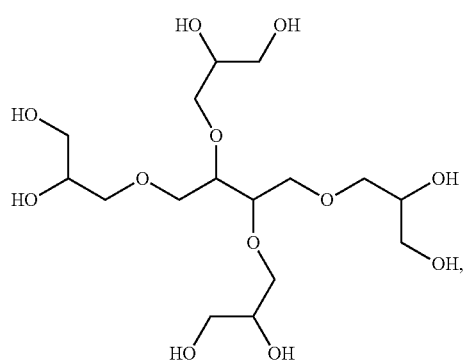

(IN-4)

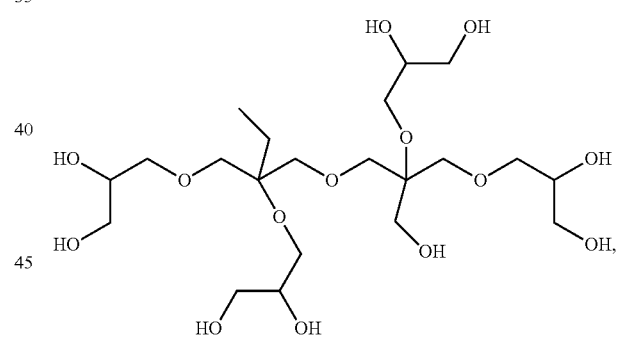

(IN-5)

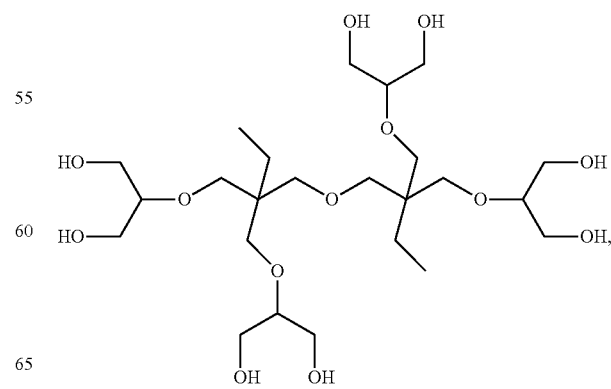

(IN-6)

(IN-7)

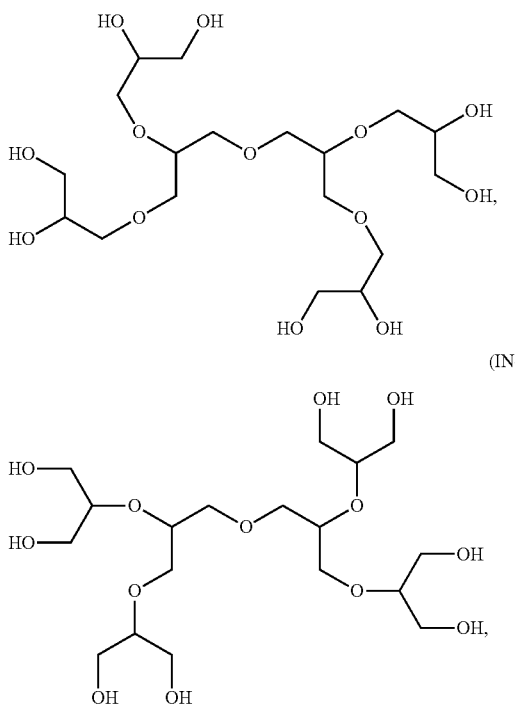

(IN-8)

(IN-9)

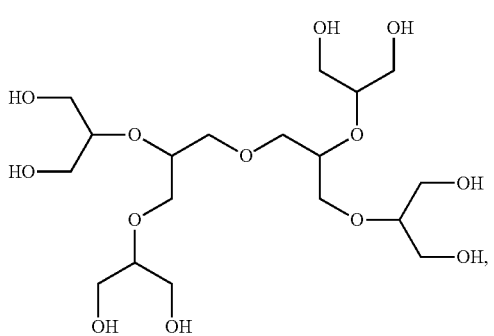

(IN-10)

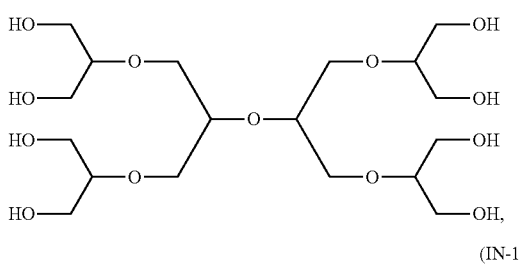

(IN-11)

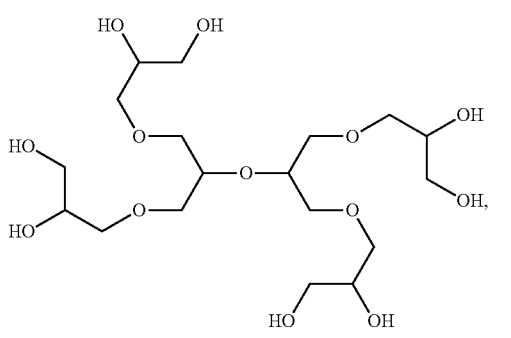

(IN-12)

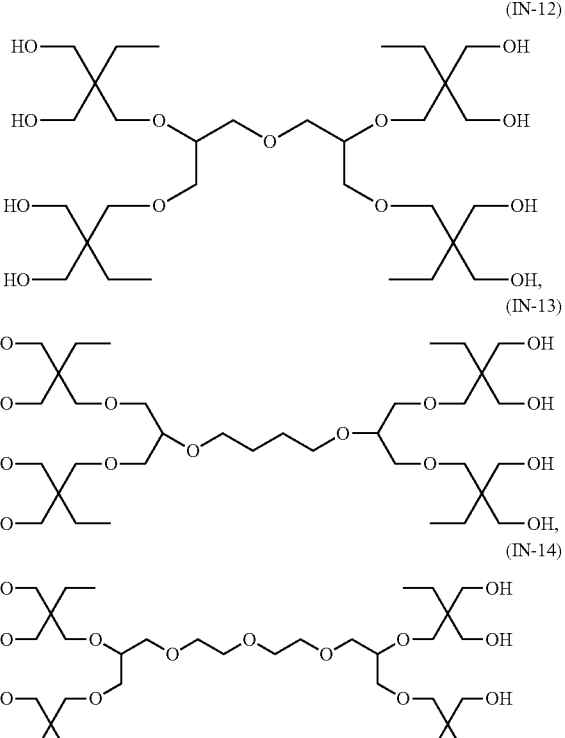

(IN-13)

(IN-14)

The above-listed OctaIN compounds can be used to prepare eight-arm polyethylene glycol derivatives as represented by the general formulas (6) and (7), the general formulas (8) and (9), the general formulas (10) and (11), the general formulas (12) and (13), the general formulas (14) and (15), the general formulas (16) and (17), the general formulas (18) and (19), the general formulas (20) and (21), the general formulas (22) and (23), the general formulas (24) and (25), the general formulas (26) and (27), the general formulas (28) and (29), the general formulas (32) and (33) and the general formulas (34) and (35). It should be noted that the above structural formulas are only to illustrate the connectivity of atoms and groups, but not intended to limit the chirality. For example, starting reagents for IN-3 include but are not limited to tetraols including erythritol and L-threitol.

One preferable embodiment of the regent for producing OctaIN is that the reagent does not contain the $O(CH_2CH_2O)_3$ fragment, neither monodisperse segments nor polydisperse segments. Wherein, the definition of β is the same as above, and the structure as represented by formula (IN-14) is excluded.

(2) One preferable Group of OctaIN, wherein, the heteroatom-containing linkage only exists as thioether bonds.

With reference to the first preferable Group, OctaIN for this Group can be obtained by using a tetrathiol in place of the tetraol as the starting reagent, then carrying out an alkylation reaction to generate four thioether bonds which respectively connects to a monovalent group having two protected hydroxyl groups, and then further carrying out deprotection to endow each thioether bond with two unprotected hydroxyl groups respectively. (a) The tetrathiol is preferably a hydrocarbontetrathiol, and more preferably an alkanetetrathiol. The terminal hydroxyls of a tetraol can be modified into mercapto groups to form a tetrathiol. For example, the production of 2,2-bis(mercaptomethyl)propane-1,3-dithiol from pentaerythritol can be found by reference to the methods for obtaining C2 functional groups via end-functionalization, or by reference to the reference "Chinese Journal Of Spectroscopy Laboratory, 2013, 30 (5), 2539-2542". (b) The tetrathiol can also be obtained by a click reaction between a diethynyl-containing compound and four molecules of thiols containing one unprotected or protected hydroxyl group. Examples of the diethynyl-containing compounds include but are not limited to 1,5-hexadiyne, 1,6-heptadiyne, 1,7-octadiyne, 1,8-nonadiyne, 1,9-decadiyne, 1,4-diethynylbenzene and the like. Another reagent besides the tetrathiol can be a derivative of a triol in which one hydroxyl group is replaced by a sulfonate group or a halogen atom and the other two hydroxyl groups are protected. What is different from the first preferable Group is that, the triol used for this Group to synthesize the sulfonate or halide is preferably a hydrocarbontriol, and more preferably an alkanetriol.

With reference to the first preferable Group, OctaIN for this Group can also be obtained by using a tetrathiol in place of the tetraol as the reagent, then conducting an alkylation reaction to generate four thioether bonds which respectively connects to an epoxy group, and further carrying out a ring-opening reaction under a basic condition to form eight unprotected hydroxyl groups. The production method for the tetrathiol is the same as above. Another reagent besides the tetrathiol can be a compound in which one terminal is an epoxy group and the other terminal is a halogen atom or a sulfonate group.

With reference to the first preferable Group, OctaIN for this Group can be obtained via an alkylation reaction between a tetrasulfonate or a tetrahalide and a reagent which has two protected hydroxyl groups or one epoxy group and also one unprotected mercapto group.

OctaIN for this Group can also be obtained by starting from a dithiol, first carrying out a reaction with a trifunctional small molecule which contains two unprotected or protected mercapto groups, and subsequently carrying out a reaction with another trifunctional small molecule which contains two unprotected or protected hydroxyl groups, wherein, the two alkylation reactions in sequence both lead to the formation of thioether bonds; one example of OctaIN is the compound as shown in IN-25. Examples of the dithiol include but are not limited to 1,2-ethanedithiol, 1,3-propanedithiol, 1,4-butanedithiol, 1,2-butanedithiol, 1,3-butanedithiol, 1,5-pentanedithiol, 1,6-hexanedithiol, 1,8-octanedithiol, 1,9-nonanedithiol, 1,10-decanedithiol, 2,3-butanedithiol, bis(2-mercaptoethyl) sulfide, 3,7-dithia-1,9-nonanedithiol, 3-mercapto-β,4-dimethyl-cyclohexaneethanethiol, 1,4-benzenedithiol, 1,2-benzenedithiol, 3,4-toluenedithiol, 1,5-naphthalenedithiol, 1,2,4,5-tetramethylbenzene-a,a'-dithiol, 4,4'-dimercaptodiphenyl sulfide and so on.

Examples of OctaIN for this Group are as follows:

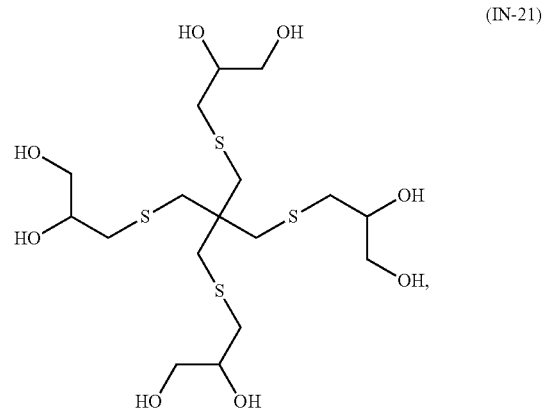

(IN-21)

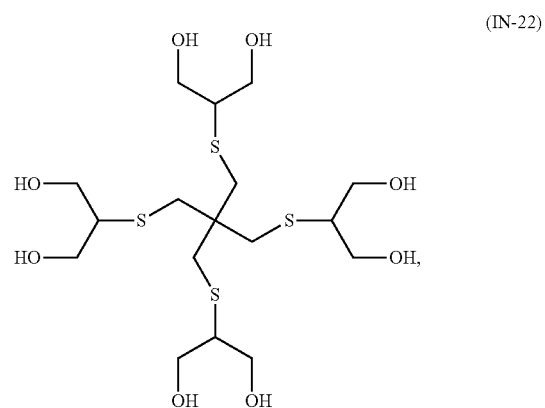

(IN-22)

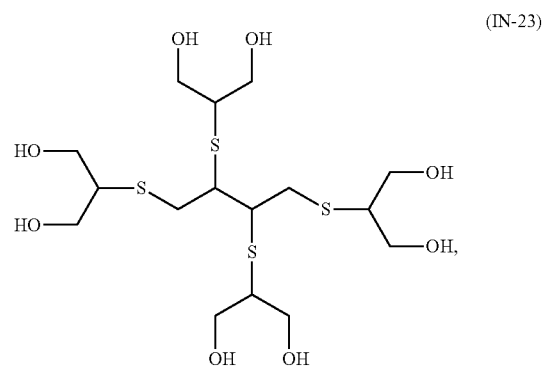

(IN-23)

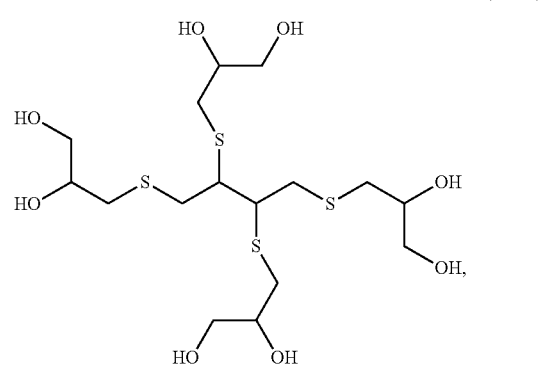

(IN-24)

289

-continued (IN-25)

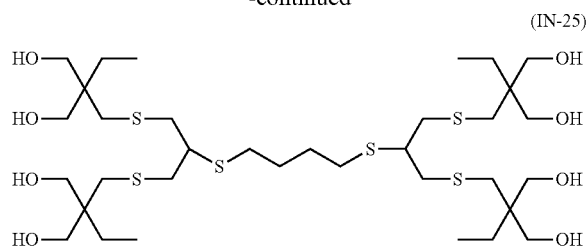

and the like.

(3) One preferable Group of OctaIN, wherein, the heteroatom-containing linkages only exist as nitrogen-atom-containing linkages selected from a divalent tertiary amino group, a trivalent tertiary amino group and the combination thereof.

Examples include

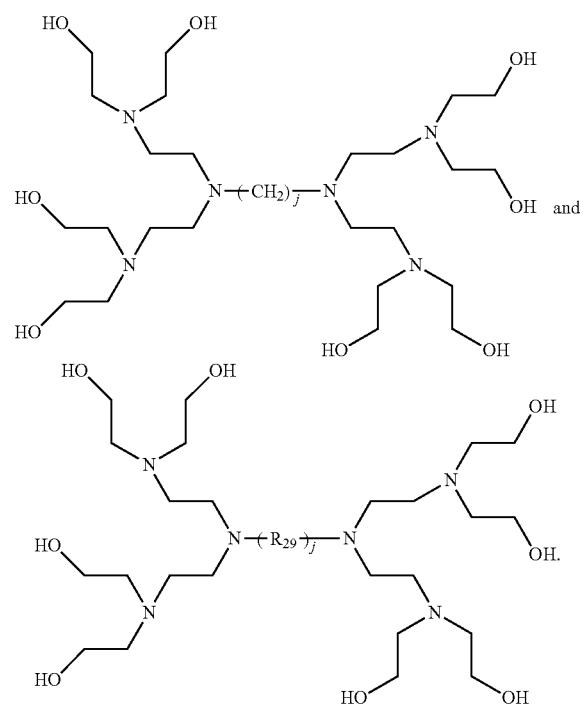

Wherein, the definitions of j and $R_{29}$ are the same as above. The production methods for OctaIN include but are not limited to the following manners:

A, OctaIN is obtained by an alkylation reaction between a tetrasulfonate or a tetrahalide and four molecules of secondary amines containing two protected hydroxyl groups, followed by deprotection of the hydroxyl groups. The secondary amine containing two protected hydroxyl groups is preferably an alkane-based secondary amine containing two protected hydroxyl groups, such as derivatives with two hydroxyl groups being protected of diethanolamine, bis(2-hydroxypropyl)amine, 3-methylamino-1,2-propanediol and 3-(t-butylamino)-1,2-propanediol.

The tetrasulfonate or tetrahalide can be obtained by starting from a tetraol containing two tertiary amino groups, and conducting chemical modification to convert the terminal hydroxyl group into a sulfonate group or a halogen atom. The tetraol containing two trivalent tertiary amino groups can be obtained by starting from a binary primary amine, conducting an alkylation reaction with four molecules of heterofunctional small molecules in which one terminal is a protected hydroxyl group and the other terminal is a sulfonate group or a halogen atom, and then carrying out deprotection to remove hydroxyl protecting groups. The binary primary amine is not particularly limited, preferably an alkanediamine, and more preferably $NH_2(CH_2)_jNH_2$, wherein, the definition of j is the same as above. Examples of the binary primary amine include 1,2-ethanediamine, 1,3-propanediamine, 1,2-propanediamine, 2-methyl-1,3-propanediamine, tetramethylpropanediamine 1,5-pentanediamine, 1,6-hexanediamine, 1,8-octanediamine, 1,2-cyclohexanediamine, 1,4-cyclohexanediamine, 5-amino-1,3,3-trimethylcyclohexanemethylamine, p-phenylenediamine (also 1,4-benzenediamine), o-phenylenediamine, m-phenylenediamine, 2,4,6-trimethyl-m-phenylenediamine, 2-methyl-1,4-benzenediamine, benzidine, 1,5-naphthalenediamine and N,N-bis(3-aminopropyl)methylamine.

The tetraol containing two tertiary amino groups can also be obtained by starting from a disulfonate or a dihalide, and conducting an alkylation reaction with two molecules of secondary amines containing two protected hydroxyl groups followed by removing the hydroxyl protecting groups.

Examples of the tetraol containing two tertiary amino groups include N,N,N',N'-tetrakis(2-hydroxyethyl)diamine, N,N,N',N'-tetrahydroxypropyldiamine, N,N,N',N'-tetrakis(2-hydroxypropyl)diamine and the like, preferably N,N,N',N'-tetrakis(2-hydroxyethyl)ethylenediamine, N,N,N',N'-tetrahydroxypropylethylenediamine and N,N,N',N'-tetrakis(2-hydroxypropyl)ethylenediamine. The chemical formula examples include $(HOCH_2CH_2)_2N(CH_2)_jN(CH_2CH_2OH)_2$ and $(HOCH_2CH_2CH_2)_2N(CH_2)_jN(CH_2CH_2CH_2OH)_2$.

The tetrasulfonate or tetrahalide can also be obtained by starting from a tetraol containing two tertiary amino groups, and conducting chemical modification to convert the terminal hydroxyl group into a sulfonate group or a halogen atom. The tetraol containing two tertiary amino groups can be obtained by starting from a binary secondary amine, conducting an alkylation reaction with two molecules of sulfonates or halides containing two protected hydroxyl groups, and then carrying out deprotection to remove hydroxyl protecting groups. The binary secondary amine is preferably an alkanediamine, such as N,N'-dimethylethylenediamine, N,N'-dimethyl-1,3-propanediamine, N,N'-diethylethylenediamine, N,N'-bis(1-methylpropyl)-1,4-phenylenediamine, N,N'-diphenyl-1,4-phenylenediamine, N,N'-bis(2-naphthyl)-p-phenylenediamine, N,N'-dibenzylethylenediamine and N,N'-diphenylbenzidine, specifically such as

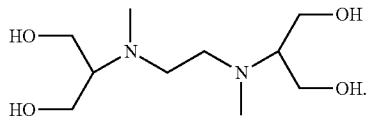 [SMILES: CN(CCN(C)C(CO)CO)C(CO)CO]

B, OctaIN can also be obtained by conducting an alkylation reaction between a quaternary secondary amine and four molecules of monoepoxy-containing halides, and then conducting a ring-opening reaction under a basic condition. One example of the quaternary secondary amine is 1,4,7,10-tetraazacyclododecane. Examples of the monoepoxy-containing halides include epichlorohydrin, (R)-epichlorohydrin, 2-(chloromethyl)-2-methyloxirane, (3-chlorophenyl)oxirane, epifluorohydrin, epibromohydrin, 4-bromo-1,2-epoxybutane, 6-bromo-1,2-epoxyhexane and the like; the epoxy-containing halide is preferably epichlorohydrin.

C, OctaIN can also be obtained by conducting a ring-opening addition reaction between a binary primary amine and four molecules of glycidol. Examples include as follows:

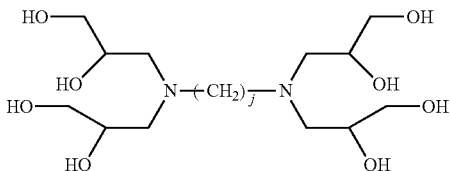

corresponding to the eight-arm polyethylene glycol derivative as represented by the general formulas (36) and (37) and

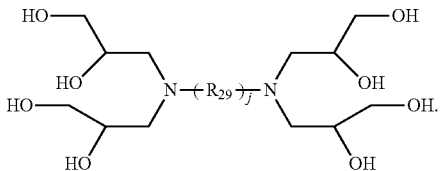

Wherein, the definitions of j and $R_{29}$ are the same as above.

(4) One preferable Group of OctaIN, wherein, the heteroatom-containing linkages contain at least one kind of active-hydrogen-free silyl group selected from a trivalent silyl group, a divalent silyl group or the combination thereof.

(5) One preferable Group of OctaIN, wherein, the heteroatom-containing linkages only exist as ether bonds and thioether bonds.

Applicable reagents include but are not limited to suitable combinations of diols, triols, tetraols, disulfonates, dihalides, sulfonates or halides containing two protected hydroxyl groups, dithiols, trithiols, tetrathiols, diols containing thioether bond (such as thiodiglycol), dithiols containing ether bond (such as bis(2-mercaptoethyl) ether), sulfonates or halides containing two protected mercapto groups, alcohols containing two protected mercapto groups, thiols containing two protected hydroxyl groups (e.g., the hydroxyl-protected form of 3-mercapto-1,2-propanediol) and the like, wherein, the combination of reagents comprises at least one compound containing an unprotected or protected mercapto group.

(6) One preferable Group of OctaIN, wherein, both oxy group and amino groups (selected from trivalent tertiary amino group, divalent tertiary amino group and the combination thereof) exist in the heteroatom-containing linkages.

Applicable reagents include but are not limited to suitable combinations of diols, triols, tetraols, disulfonates, dihalides, sulfonates or halides containing two protected hydroxyl groups, sulfonates or halides or amines containing one epoxy group, diols containing divalent tertiary amino group, triols containing trivalent tertiary amino group or divalent tertiary amino group, tetraols containing trivalent tertiary amino group or divalent tertiary amino group, binary primary amines, binary secondary amines, binary secondary amines containing ether bond, sulfonates or halides containing two protected primary amino groups, alcohols containing two protected primary amino groups, secondary amines containing two protected primary amino groups, alcohols containing two protected secondary amino groups, secondary amines containing two protected hydroxyl groups (e.g., 1,3,5-dioxazinane, bis(2-(benzyloxy)ethyl)amine and the like), monoepoxy-containing secondary amines (such as 4-epoxypropanoxycarbazole) and the like, wherein, the combination of reagents comprises at least one compound containing a primary amino group, a secondary amino group, a protected primary amino group or a protected secondary amino group. Examples of diols containing a divalent tertiary amino group include but are not limited to N-methyldiethanolamine, N-ethyldiethanolamine, N-n-propyldiethanolamine, N-isopropyldiethanolamine, N-n-butyldiethanolamine, N-t-butyldiethanolamine, N-o-tolylldiethanolamine, N-stearyldiethanolamine, 5-hydroxy-3-(2-hydroxyethyl)indole and the like.

(7) One preferable Group of OctaIN, wherein, the heteroatom-containing linkages only exist as trivalent silyl groups and ether bonds, wherein, the trivalent silyl group contains no active hydrogen atom.

(8) One preferable Group of OctaIN, wherein, the heteroatom-containing linkages only exist as divalent silyl groups and ether bonds, wherein, the divalent silyl group contains no active hydrogen atom.

(9) One preferable Group of OctaIN, wherein, both thioxy group and amino groups (selected from trivalent tertiary amino group, divalent tertiary amino group and the combination thereof) exist in the heteroatom-containing linkages.

(10) One preferable Group of OctaIN, wherein, the heteroatom-containing linkages only exist as trivalent silyl groups and thioether bonds, wherein, the trivalent silyl group contains no active hydrogen atom.

(11) One preferable Group of OctaIN, wherein, the heteroatom-containing linkages only exist as divalent silyl groups and thioether bonds, wherein, the divalent silyl group does not contain active hydrogen atom.

(12) One preferable Group of OctaIN, wherein, the heteroatom-containing linkages only exist as trivalent tertiary amino groups and ether bonds.

(13) One preferable Group of OctaIN, wherein, the heteroatom-containing linkages only exist as trivalent tertiary amino groups and thioether bonds.

(14) One preferable Group of OctaIN, wherein, two or two more species of heteroatoms exist in the heteroatom-containing linkages, selected from suitable combinations of ether bonds, thioether bonds, disulfide bonds, trivalent tertiary amino groups, divalent tertiary amino groups, divalent active-hydrogen-free silyl groups and trivalent active-hydrogen-free silyl groups. One example of the reagent containing two or more species of heteroatoms is cystamine.

(15) One preferable Group of OctaIN, preferably including those disulfide-free structures in Group (14).

The methods in Groups (3), (12) and (14) can be used to prepare eight-arm polyethylene glycol derivatives as illustrated in the Part 1.5.13, including but not limited to structures as represented by the general formulas (30) and (31).

3.1.2. Polymerization Process

Polymerization process of ethylene oxide includes the following two steps (A) and (B). Step (A): deprotonation of unprotected hydroxyl groups to form oxyanions; Step (B): polymerization of ethylene oxide. The reaction conditions and reaction parameters can be controlled with reference to those described and listed in the documents CN104530413A, CN104530415A and CN104530417A; take CN104530417A as an example, corresponding to paragraphs from [1321] to [1334].

In summary, these two steps can be carried out in a solvent or without any solvent. The solvent is not particularly limited, but is preferably an aprotic solvent, such as toluene, benzene, xylene, acetonitrile, ethyl acetate, tetrahydrofuran, chloroform, dichloromethane, dimethyl sulfoxide, dimethylformamide or dimethylacetamide. The solvent condition is normally preferably an aprotic solvent, preferably dimethyl sulfoxide, dimethylformamide, toluene or tetrahydrofuran. The oxyanions formed after deprotonating the unprotected hydroxyl group act as initiators to start the polymerization of ethylene oxide and to build a coinitiator system together with a base. The base used for deprotonation is not particularly limited, but is preferably sodium, potassium, sodium hydride, potassium hydride, sodium methoxide, potassium methoxide, naphthalene-lithium, n-butyllithium, t-butyllithium, potassium t-butanoate or diphenylmethyl potassium (DPMK), more preferably sodium, potassium or diphenylmethyl potassium, most preferably diphenylmethyl potassium. The resulting polymerized product after Step (B) is a mixture of alcohol and oxygen anion. When the polymerization is carried out to a certain extent, a hydroxyl-terminated intermediate having a given degree of polymerization can be obtained after the addition of proton source. Wherein, the proton source is not particularly limited as long as it can provide active hydrogen. Examples of the proton source include methanol, ethanol, water and acetic acid. The amount of ethylene oxide is determined by the designed molecular weight of the polyethylene glycol chain, and the ethylene oxide is added in a calculated amount according to $n_1$, $n_2$, $n_3$, $n_4$, $n_5$, $n_6$, $n_7$ and $n_8$.

3.1.3. Terminal Functionalization (Also Termed as End-Functionalization)

The process to modify a hydroxyl group or a non-objective functional group at the terminal ends of a polyethylene glycol chain into the objective functional group is termed as terminal functionalization or end-functionalization, including linear end-functionalization (also terminal linear-functionalization) and branched end-functionalization (also terminal branched-functionalization). Examples of the functional group include but are not limited to those listed in the above Groups A to J in terms of functional groups. The polyethylene glycol moieties after the polymerization of ethylene oxide are end-capped with a hydroxyl group, wherein, g is equal to zero and k is equal to 1 (g=0 and k=1), and the terminal can be considered as a terminal hydroxyethyl group.

In the general formulas (1), (3), (4) and (5), the end-functionalization process corresponding to g equal to zero is termed as linear end-functionalization, wherein, the corresponding G is absent, k is equal to 1, and the number of $R_{01}$ at the corresponding PEG-chain terminal is one; the end-functionalization process corresponding to g equal to 1 is termed as branched end-functionalization, wherein, the corresponding k is an integer from 2 to 250, the corresponding G is a (k+1)-valent branching group, and the number of $R_{01}$ at the corresponding PEG-chain terminal is k.

When k for F is equal to 1, the corresponding PEG-chain terminal is linearly end-functionalized; when k for F is greater than 1, the corresponding PEG-chain terminal is branchedly end-functionalized.

Specific methods for end-functionalization are described in detail hereinafter, and no more repeated here.

3.2. The present invention also discloses a production method for the eight-arm polyethylene glycol derivative, involving a coupling reaction between an octafunctional small molecule compound (OctaSM, wherein, OctaSM contains an octavalent group CORE), and eight molecules of a linear bifunctional PEG compound (biLPEG) to obtain an eight-arm polyethylene glycol derivative (OctafPEG).

3.2.1. Octafunctional Small Molecule Compound (OctaSM)

The degradability of OctaSM is not particularly limited, and can contain merely stable linking group (STAG), or contain one or more degradable linking groups (DEGG). Wherein, the species of degradable linking groups can be one or more in quantities.

OctaSM contains eight identical reactive groups which can be selected from suitable reactive groups of Groups A to H in the present invention.

OctaSM can be but is not limited to any octahydroxyl-containing small molecule initiator in the Part 3.1 hereinbefore.

(1) OctaSM can be obtained via a coupling reaction between a tetrafunctional small molecule compound (tetraSM) and four molecules of a heterofunctional small molecule compound (htriSM) which contains a trivalent core structure. The tetraSM can come from natural sources, be purchased, or be obtained via a coupling reaction between a bifunctional small molecule and two molecules of a heterofunctional small molecule compound (htriSM) which contains a trivalent core structure. The functional groups involved in the reaction can be selected from reactive groups of Groups A to H in the present invention.

The tetraSM containing four hydroxyl groups, besides examples listed in the polymerization method in Part 3.1 hereinbefore, also include but are not limited to 2-(2-hydroxyethylamino)-2-(hydroxymethyl)-1,3-propanediol, D-xylulose, N-(1,3-bis(hydroxymethyl)-2,5-dioxo-4-imidazolidinyl)-N,N'-bis(hydroxymethyl)-urea, 4,5-dihydroxy-1,3-bis(hydroxymethyl)-2-imidazolidinone, catechol violet, fenoterol, pentaerythritol tetrakis(3-(3,5-di-tert-butyl-4-hydroxyphenyl)propionate), dypyridamole, the tetraol product from diglycidyl 1,2-cyclohexanedicarboxylate after a ring-opening reaction and the like.

The tetraSM containing four mercapto groups, besides examples listed in the polymerization method in Part 3.1 hereinbefore, also include but are not limited to pentaerythritol tetrakis(2-mercaptoacetate) and pentaerythritol tetrakis (3-mercaptopropionate). The tetraSM can also be obtained by reducing the disulfide bonds of a small molecule containing two lipoyl groups, wherein, the reducing agent is preferably tris(2-carboxyethyl)phosphine (TCEP).

Examples of tetraSM also include but are not limited to ethylene glycol-bis-(2-aminoethylether)-N,N,N',N'-tetraacetic acid, ethylenediaminetetraacetic acid, 1,3-propylenediaminetertaacetic acid, 1,6-hexanediaminetetraacetic acid, 1,4,7,10-tetraazacyclododecane-N,N,N,N-tetraacetic acid, tetracyanoethylene, 7,7,8,8-tetracyanoquinodimethane and the like.

The bifunctional small molecule used to prepare tetraSM has two identical reactive groups, and can be a bifunctional small molecule compound selected from, but not limited to, the group consisting of a diol, a diamine, a dithiol, a dicarboxylic acid, a diisocyanate, a disulfonate, a disulfonic acid, a dihalide, a diazide, a diacyl halide, a compound with two chlorosulfonyl groups, a dihydrazide, a dialdehyde, a compound with two dichloroformate groups, a dimaleimide, a disuccinimidyl active diester, a dinitrile (a dicyanide), a dialkyne, a dialkene, a dialdoxime and the like. The bifunctional small molecule can contain any suitable divalent linking group STAG or DEGG incorporated in the present invention, wherein, the suitable divalent linking group can be selected from, but not limited to, the group consisting of an ether bond, a thioether bond, a divalent tertiary amino group, a secondary amino group, an amide bond, an alkenylene group, an alkynylene group, a carbamate group, a thiocarbamate group, an ester bond, a thiocarboxylate bond, a thioester bond, a carbonate group, a thiocarbonate group, a urea bond, a thiourea bond, a disulfide bond, an oxime bond, an imine bond, a hydrazone bond, an acylhydrazone bond and the like. Examples of the diol include but are not limited to those used in the polymerization method in Part 3.1, and also can include 2,6-bis[(2-hydroxyethyl)amino] toluene which contains a secondary amino group. Examples of the diamine include but are not limited to those used in the polymerization method in Part 3.1, and can also include but are not limited to a binary primary amine which contains two divalent secondary amino groups (such as triethylenetetramine, N,N'-bis(2-aminoethyl)-1,3-propanediamine and N,N'-bis(3-aminopropyl)-1,4-butanediamine), a binary primary amine which contains three divalent secondary amino groups (such as tetraethylenepentamine), a binary primary amine containing degradable linking group (such as 1,4-butanediol-bis(4-aminobenzoate), poly(1,4-butanediol) bis (4-aminobenzoate), poly(tetramethylene-3-methyltetramethylene ether)glycol, (tetramethylene-3-methyltetramethylene ether)glycol bis(4-aminobenzoate) and the like). Examples of the dithiol include but are not limited to those used in the polymerization method in Part 3.1, and also include but are not limited to ethylene glycol bis(mercaptoacetate). Examples of the dihalide include but are not limited to those used in the polymerization method in Part 3.1, and also include but are not limited to dihalides containing degradable linking groups such as 1,4-bis(bromoacetoxy)butane. Examples of the dialdehyde include but are not limited to glyoxal, propanedialdehyde (also malondialdehyde), succindialdehyde (also butanedial), glutaraldehyde (also pentanedial), 3-methylglutaraldehyde, 1,6-hexanedialdehyde (also adipodialdehyde), 2-(4-tolyl)malondialdehyde, 2-(4-methoxyphenyl)malondialdehyde, 2-(4-pyridyl)malondialdehyde, 2-benzoxazolylmalonaldehyde, 2-(2-pyridyl)malondialdehyde and 2-(2-quinoxalinyl)malondialdehyde. Examples of the disulfonic acid include but are not limited to 1,5-naphthalenedisulfonic acid. Examples of the disuccinate include but are not limited to 3,3'-dithioldipropionic acid bis(N-hydroxysuccinimide ester), disuccinimido oxalate and disuccinimidyl suberate. One example of the dihydrazide is dodecanedioic dihydrazide. Examples of the dicarboxylic acid include but are not limited to those in the part 1.1.6.1. The halogen atom of the diacyl halide is preferably a chlorine atom or a bromine atom; take acyl chloride for instance, examples include but are not limited to oxalyl chloride, malonyl chloride, succinyl chloride, glutaryl chloride, adipoyl chloride, fumaryl chloride, diethylene glycol bis-chloroformate, phthaloyl chloride, isophthaloyl chloride, terephthaloyl chloride and 3,6-endomethylene-1,2,3,6-tetrahydrophthalyl chloride. Examples of the disulfonyl chloride include but are not limited to 4,4'-bis(chlorosulphonyl)diphenyl ether and methylene bis-(chlorosulfate). Examples of the diisocyanate include but are not limited to 1,6-hexamethylene diisocyanate, 3,3'-dimethyl-4,4'-biphenylene diisocyanate, 4,4'-diphenylmethane diisocyanate, p-phenylene diisocyanate, tolylene-2,4-diisocyanate, 1,5-naphthalene diisocyanate, m-xylylene isocyanate, isophorone diisocyanate, 4,4'-diisocyanatodicyclohexylmethane and bis(2-isocyanatoethyl)-5-norbornene-2,3-dicarboxylate. Examples of the dimaleimide include but are not limited to 1,2-bis(maleimido)ethane, 1,3-bis(maleimido)propane, 1,4-bis(maleimido)butane, 1,5-bis(maleimido)pentane, 1,6-bis(maleimido)hexane, 1,7-bis(maleimido)heptane, 1,8-bis(maleimido)octane, 4,4'-bis(maleimido)-1,1'-biphenyl, N,N'-(1,3-phenylene)dimaleimide (also N,N'-1,3-phenylene bismaleimide), 1,1'-(methylenedi-4,1-phenylene)bismaleimide, N,N-(4-methyl-1,3-phenylene)bismaleimide, N,N'-(1,4-phenylene)dimaleimide, bis(3-ethyl-5-methyl-4-(N-maleimido)phenyl)methane and N,N'-(1,2-phenylene)dimaleimide. Examples of the dialkyne include but are not limited to those used in the polymerization method in Part 3.1, and also include but are not limited to diacetylene, 2,4-hexadiyne, 2,6-octadiyne, 3,5-octadiyne, 2,8-decadiyne, 4,6-decadiyne, 2,9-undecadiyne, 2,10-dodecadiyne and 3,9-dodecadiyne. Examples of the diazide include but are not limited to 2,6-bis[(4-azidophenyl)methylene]-4-methyl-cyclohexanone, 2,6-bis(4-azidobenzylidene)cyclohexanone and bis(3-[4-azidosalicylamido]ethyl)disulfide. Examples of the dinitrile include but are not limited to glutaronitrile, hexanedinitrile, 1,7-heptanedinitrile, 1,8-octanedinitrile, phthalonitrile, isophthalonitrile, terephthalonitrile, 4,5-bis(2-cyanoethylthio)-1,3-dithiol-2-one, 4,5-dicyanoimidazole, 3,3'-oxydipropionitrile, 2,6-pyridinedicarbonitrile, dithiocyanatomethane, 4,5-dicyano-1,3-dithiolen-2-one and 4,5-bis(2-cyanoethylthio)-1,3-dithiol-2-thione. One example of the dialdoxime is dimethylglyoxime.

The htriSM contains a heterofunctional group pair consisting of two different kinds of functional groups, wherein, one kind functional group is 1 in quantities, and the other kind functional group is 2 in quantities. The pairs of heterofunctional groups which can be present meanwhile include but are not limited to the group consisting of a hydroxyl group with a protected hydroxyl group, a hydroxyl group or a protected hydroxyl group with a non-hydroxyl reactive group belonging to Groups A to H in terms of functional groups (e.g., an amino group, a protected amino group, an amine salt group, an aldehyde group, an active ester group, a maleimido group, a carboxyl group, a protected carboxyl group, an alkynyl group, a protected alkynyl group, an azido group, an alkenyl group, an acrylic acid group, an acrylate group, a methacrylate group, an epoxy group, an isocyanato group, etc.), a hydroxyl group or a protected hydroxyl group with a functional group or derivative thereof belonging to Groups I to J in terms of functional groups (such as targeting group, a photosensitive group, etc.), an active ester group with a maleimido group, an active ester group with an aldehyde group, an active ester group with an azido group, an active ester group with an alkynyl group or a protected alkynyl group, an active ester group with an acrylate group, an active ester group with a methacrylate group, an active ester group with an acrylic acid group, a maleimido group with an azido group, a maleimido group with an alkynyl group or a protected alkynyl group, a maleimido group with an acrylate group, a maleimido group with a methacrylate group, a maleimido group with an acrylic acid group, a maleimido group with a carboxyl group, a maleimido group with an amino group or a protected amino group or an amine salt group, a maleimido group with an isocyanato group, a maleimido group with a protected mercapto group, an aldehyde group with an azido group, an aldehyde group with an acrylate group, an aldehyde group with a methacrylate group, an aldehyde group with an acrylic acid group, an aldehyde group with an epoxy group, an aldehyde group with a carboxyl group, an aldehyde group with an alkynyl group or a protected alkynyl group, an azido group with a mercapto group or a protected mercapto group, an azido group with an amino group or a protected amino group or an amine salt group, an azido group with an acrylate group, an azido group with a methacrylate group, an azido group with an acrylic acid group, an azido group with a carboxyl group, an acrylate group with an amino group or a protected amino group or an amine salt group, an acrylate group with an isocyanato group, an acrylate group with an epoxy group, an acrylate group with a methacrylate group, an acrylate group with a carboxyl group, a methacrylate group with a carboxyl group, a methacrylate group with an amino group or a protected amino group or an amine salt group, a methacrylate group with an isocyanato group, a methacrylate group with an epoxy group, an alkynyl group or a protected alkynyl group with an amino group or a protected amino group or an amine salt group, an alkynyl group or a protected alkynyl group with an isocyanato group, an alkynyl group or a protected alkynyl group with an acrylate group, an alkynyl group or a protected alkynyl group with a methacrylate group, an alkynyl group or a protected alkynyl group with acrylic acid group, an alkynyl group or a protected alkynyl group with an epoxy group, an alkynyl group or a protected alkynyl group with a carboxyl group, a protected alkynyl group with an azido group, an acrylic acid group with an isocyanato group, an acrylic acid group with an acrylate group, an acrylic acid group with an epoxy group, an acrylic acid group with a carboxyl group, a carboxyl group with a mercapto group or a protected mercapto group, a carboxyl group with an amino group or a protected amino group or an amine salt group, a carboxyl group with an isocyanato group, a carboxyl group with an epoxy group, an amino group or a protected amino group or an amine salt group with a mercapto group or a protected mercapto group, a targeting group with a non-hydroxyl reactive group, a photosensitive group with a non-hydroxyl reactive group and the like. Wherein, the examples of the active ester group include but are not limited to those disclosed in the present invention such as a succinimidyl active ester group (e.g., a succinimidyl carbonate group, etc.), a p-nitrophenyl active ester group, an o-nitrophenyl active ester group, a benzotriazole active ester group, a 1,3,5-trichlorobenzyl active ester group, a 1,3,5-fluorophenyl active ester group, a pentafluorophenyl active ester group, an imidazole active ester group, a 2-thioxothiazolidin-3-yl-carbonyl group, a 2-thioxopyrrolidin-1-yl-carbonyl group and the like. Wherein, the amino group can be a primary amino group or a secondary amino group, and the amine salt is preferably a hydrochlorinated form, such as $NH_2HCl$.

Examples of the htriSM include but are not limited to small molecule compounds which contain two unprotected or protected hydroxyl groups (e.g., triethanolamine p-toluenesulfonate, glycerol monomercaptoacetate, 2-chloro-3',4'-dihydroxyacetophenone and hydroxyl-protected forms of above-said htriSMs), contain two unprotected or protected mercapto groups (e.g., dimercapto-propanol and its mercapto-protected forms), contain two primary amino groups, contain two secondary amino groups, contain two protected primary amino groups or contain two protected secondary amino groups, wherein, the small molecule compounds include alcohols, thiols, primary amines, secondary amines, sulfonates, halides and the like. Examples of htriSM also include but are not limited to htriSMs used for the polymerization process of the present invention. Wherein, one example of alcohols containing two primary amino groups is 1,3-diamino-2-propanol.

The OctaSM which contains eight hydroxyl groups can also be obtained by conducting a reaction between a quaternary primary amine with four molecules of a compound containing two protected hydroxyl groups and one aldehyde group, reducing the primary amino groups into secondary amino groups, and then removing the hydroxyl protecting groups. The quaternary primary amine can be obtained by starting from a disulfonate or a dihalide, conducting an alkylation reaction with two molecules of secondary amines containing two protected primary amino groups, and then removing the amino protecting groups. Examples of the quaternary primary amine include $(NH_2CH_2CH_2)_2N(CH_2)_tN(CH_2CH_2NH_2)_2$, $(NH_2CH_2CH_2CH_2)_2N(CH_2)_tN(CH_2CH_2CH_2NH_2)_2$ and the like. Examples of the compound containing two protected hydroxyl groups and one aldehyde group include derivatives with two hydroxyl groups being protected of glyceraldehyde, 2,4-dihydroxybenzaldehyde, 3,4-dihydroxybenzaldehyde, 2,6-dihydroxybenzaldehyde and the like, and can include 2,3-O-isopropylidene-4-deoxy-L-threitol. Examples of the secondary amine containing two protected hydroxyl groups also include but are not limited to 1-(3,4-dihydroxy-phenyl)-2-methylamino-ethanone.

The OctaSM containing eight hydroxyl groups can also be obtained via conducting a reaction between a quaternary primary amine with four molecules of aldehydes containing one epoxy group, and then carrying out a ring-opening reaction. One example of the aldehyde containing one epoxy group is 2,3-epoxypropanal.

Examples of htriSM also include but are not limited to primary amines containing two hydroxyl groups, aldehydes containing two protected hydroxyl groups, aldehydes containing one epoxy group, primary amines containing one epoxy group, secondary amines containing two primary amino groups, sulfonic acids containing two hydroxyl groups, carboxylic acids containing two hydroxyl groups, azides containing two hydroxyl groups, and hydroxyl-protected forms of the above-said compounds. The primary amines containing two hydroxyl groups include but are not limited to 2-amino-1,3-propanediol, 2-amino-2-methyl-1,3-propanediol, N,N-bis(2-hydroxyethyl)ethylenediamine, 3-amino-1,2-propanediol, 2-amino-1-[4-(methylthio)phenyl]-1,3-propanediol, 2-amino-1-phenyl-1,3-propanediol, 2-(3,4-dihydroxylphenyl)ethylamine, 2-amino-1,3-benzenediol and the like. The secondary amines containing two primary amino groups include but are not limited to diethylenetriamine, N-(3-aminopropyl)-1,4-butanediamine, 3,3'-diaminodipropylamine, N-(2-aminoethyl)-1,3-propanediamine, 3,6-diaminocarbazole and the like. The sulfonic acids containing two hydroxyl groups include but are not limited to 6,7-dihydroxynaphthalene-2-sulfonic acid, 1,4-dihydroxyanthraquinone-2-sulfonic acid and the like. The carboxylic acids containing two hydroxyl groups include but are not limited to 2,3-dihydroxypropionic acid, 2,2-bis(hydroxymethyl)propionic acid, 2,4-dihydroxy-3,3-dimethylbutanoic acid, N,N-bis(hydroxyethyl)glycine, 2,3-dihydroxybenzoic acid, 2,4-dihydroxybenzoic acid, 2,5-dihydroxybenzoic acid, 2,6-dihydroxybenzoic acid, 3,4-dihydroxybenzoic acid, 3,5-dihydroxybenzoic acid, 3,4-dihydroxyphenylacetic acid, 3,5-dihydroxyphenylacetic acid, 3,4-dihydroxycinnamic acid, 2,6-dihydroxypyridine-4-carboxylic acid and 4,8-dihydroxyquinoline-2-carboxylic acid. The azides containing two hydroxyl groups include but are not limited to 3-azido-2,3-dideoxyl-1-O-(t-butyldimethylsilyl)-3-D-arabino-hexopyranose and azidohexyl 2,2-bis(hydroxymethyl)propionate. Wherein, with respect to protected forms of two hydroxyl groups, take dihydroxyl-protecting for example, e.g.,

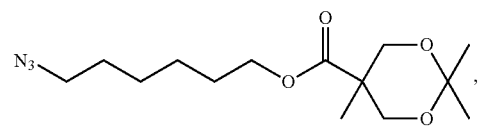

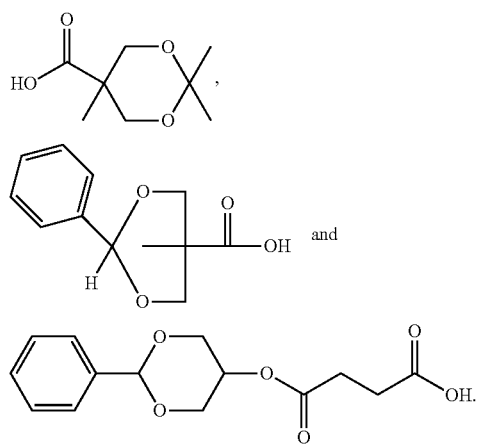

Examples of htriSM also include but are not limited to 3-allyloxy-1,2-propanediol, 5-norbornene-2,3-dicarboxylic acid, 3-(2-propynyloxy)propane-1,2-diol, 3-cyano-2,6-dihydroxy-4-methylpyridine, 1,3-dibromo-2-propanol, 2,3-dibromo-1-propanol, 1,4-dibromo-2-butanol, 1,4-diazido-2-butanol, 1,3-dichloro-2-propanol, 4,4'-dichlorobenzhydrol, 2-bromomalonaldehyde, 2-hydroxyhexanedial, 2-(4-chlorophenyl)malondialdehyde, 2-(5-carboxypyridin-2-yl)malondialdehyde, 7-amino-1,3-naphthalenedisulfonic acid, 4-chloro-1,2-diaminobenzene, 4-bromo-1,2-diaminobenzene, 6,8-dimercaptoctanoic acid, 4-chloro-1,3-benzenedithiol, 2,6-bis(p-azidobenzal)-4-carboxycyclohexanone, hydroxyl dicarboxylic acids which contain two carboxyl groups and one hydroxyl group (including but not limited to tartronic acid, L-malic acid, D-malic acid, 2-hydroxy-2-methylbutanedioic acid and 3-hydroxypentanedioic acid), amino dicarboxylic acids which contain two carboxyl groups and one amino group (including but not limited to 2-aminomalonic acid, diethyl 2-aminomalonate and 3-aminoglutaric acid), mercapto dicarboxylic acids which contain two carboxyl groups and one mercapto group (including but not limited to mercaptosuccinic acid), 4-chlorophthalic acid, 2-bromosuccinic acid, methylenesuccinic acid, 4-amino-2-(2-aminoethylamino)butyric acid, 4-amino-2-(2-aminoethylamino)butyric acid with two amino groups being protected, glycerol dimethacrylate, 2,2-bis(allyloxymethyl)-1-butanol,

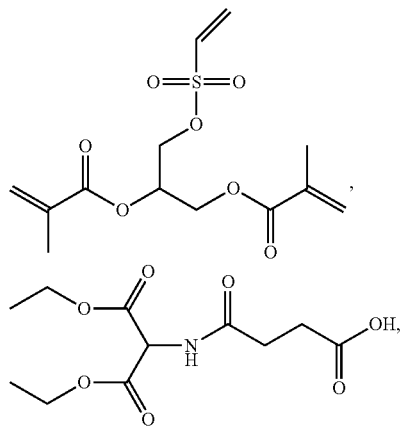

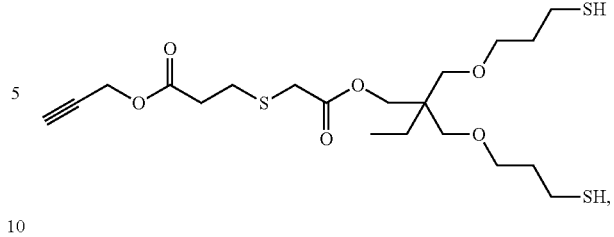

the like, and protected forms of any above-said htriSM with the two identical functional groups being protected.

Examples of htriSM also include but are not limited to lysine, lysine with two amino groups being protected, glutamic acid and aspartic acid.

Since the two hydrogen atoms of the primary amine can both be substituted to form a trivalent N-branching center, then heterofunctional small molecules containing a primary amino group and another reactive group can be used as htriSM. Examples include diglycolamine, 2-[(2-aminoethyl)thio]ethanol, 1-amino-2-propanol, 4-hydroxyphenylthylamine, mercaptoethylamine, N-methyl-1,3-propanediamine, N-ethyl-1,3-propanediamine and N-isopropyl-1,3-diaminopropane.

(2) The OctaSM can also be obtained via an alkylation reaction between a quaternary primary amine and eight molecules of heterofunctional sulfonates or halides.

(3) The OctaSM can also be obtained via a click reaction between a tetraalkyne and eight molecules of heterofunctional thiols.

(4) The OctaSM can also be obtained by a direct coupling reaction between two heterofunctional second-generation dendritic small molecules, or be obtained by coupling the heterofunctional 2nd-generation dendritic small molecules to the two terminals of a bifunctional small molecule (diSM), wherein, the heterofunctional dendritic small molecule contains four identical functional groups. The heterofunctional group pair of two different functional groups in the heterofunctional dendritic small molecule refers to the above description. The diSM preferably has identical functional groups.

3.2.2. Eight Linear Bifunctional PEG Derivatives (biLPEG)

One terminal of the biLPEG has a single functional group capable of reacting with OctSM to form divalent linking groups $L_{11}$, $L_{12}$, $L_{21}$, $L_{22}$, $L_{31}$, $L_{32}$, $L_{41}$ and $L_{42}$ respectively via a coupling reaction.

The structure of the other terminal of biLPEG can be the same as or different from the objective structure, while the functional group can also be the same as or different from the objective functional group. In the general formulas (1), (4) and (5), this terminal can lead to a PEG terminal hydroxyl group, a linearly functional group (containing only one functional group), or a branchedly functional group (containing two or more functional groups); in the general formula (3), this terminal can lead to a PEG terminal hydroxyl group or a linearly functional group. The functional groups grafted at this terminal can be selected from but not limited to all the functional groups from Groups A to J, also including precursors of any reactive group, variant forms as the precursors of reactive groups, substituted forms, protected forms, deprotected forms and the like. When comprising reactive groups, this terminal preferably comprises only one kind of reactive group. For example, when the terminal is end-capped by lysine, glutamic acid or aspartic acid, terminal carboxyl group and terminal amino group can exist meanwhile, but the compound can subsequently be selectively protected to achieve merely one kind of reactive group at the terminal. For another embodiment, the terminal can contain two or two more kinds of protected reactive groups, but only one kind of protected reactive group is deprotected to obtain a single kind of reactive group if the product is subsequently used for modifying bio-related substance. When the structure or/and functional group of the terminal are different from corresponding objectives, OctafPEG previously obtained via a coupling reaction can be end-functionalized to obtain the objective structure containing objective functional group. Suitable linear end-functionalization or branched end-functionalization can be carried out. When the terminal structure and the objective structure are both of a linear structure or both of a branched structure, and the differences between them only lie in the terminal function group, the objective functional group is preferably obtained just via deprotection.

The functional groups at the two terminals of biLPEG can be the same or different, and biLPEG is preferably a linear heterofunctional PEG derivative (biheteroLPEG) which contains two kinds of different functional groups. The pair of heterofunctional groups which can be present meanwhile are the same as above-defined.

The biLPEG can be polydisperse or monodisperse. When polydisperse, biLPEG corresponds to $n_1 \approx n_2 \approx n_3 \approx n_4 \approx n_5 \approx n_6 \approx n_7 \approx n_8$; when monodisperse, biLPEG corresponds to $n_1 = n_2 = n_3 = n_4 = n_5 = n_6 = n_7 = n_8$.

When biLPEG is polydisperse, the polydispersity index is not particularly limited, but is preferably less than 1.15, more preferably less than 1.10, more preferably less than 1.08, and more preferably less than 1.05. The lower the PDI is, the more uniform the molecular weight is and the narrower the molecular weight distribution is. When used for modifying drugs, the higher the quality of the modified product is and the better the industrial demand can be met.

When biLPEG is monodisperse, PDI is equal to 1, all of the eight PEG chains have fixed molecular weights which are identical, and an eight-arm polyethylene glycol derivative with a defined molecular structure (single component) can be obtained. When used for drug modification, modified products with a defined structure are available for more homogeneous and more controllable performance.

When using monodisperse reagents, the resulting product can have a more uniform molecular-weight distribution, however, the molecular weight is mostly limited by production methods with lengthy steps. The advantage of using polydisperse reagents is to provide a simple route and a larger range for molecule-weight adjustment.

When the linear-functional polyethylene glycol is a mixture comprising different molecular weights, a polymer in which $n_1$, $n_2$, $n_3$, $n_4$, $n_5$, $n_6$, $n_7$ and $n_8$ are each independently identical or not identical can be obtained.

The methods for producing monodisperse polyethylene glycol chains can employ techniques in the prior art, including but not limited to the following literatures including "J. Org. Chem. 2006, 71, 9884-9886" and cited references therein, "Angew. Chem. 2009, 121, 1274-1278" and cited references therein, "Expert Rev. Mol. Diagn. 2013, 13(4), 315-319" and cited references therein, "Angew. Chem. Int. Ed. 2014, 53, 6411-6413" and cited references therein, "Bioorganic & Medicinal Chemistry Letters, 2015, 25:38-42" and cited references therein, "Angew. Chem. Int. Ed., 2015, 54:3763-3767" and cited references therein, etc.

3.2.3. The Coupling Reactions

The types of coupling reactions involved in the present method are not particularly limited as long as two identical or different reactive groups can form a covalent linking group after reaction. The reaction conditions are related to the type of the resulting covalent linking group, and the techniques in the prior art can be used herein, including but are not limited to those described and listed in the documents CN104530413A, CN104530415A and CN104530417A; take CN104530417A as an example, corresponding to paragraphs from [1212] to [1280]. The coupling reactions also include but are not limited to all available reactions capable of forming a covalent linking group by using reactive functional groups from Groups A to H, and also include all the above-described reaction types. The valence of the covalent linking groups can be divalent or trivalent, and mainly divalent.

The coupling reaction can form stable or degradable groups.

In summary, for example, an amino group can react with an active ester, an active formate, a sulfonate ester, an aldehyde, an α,β-unsaturated compound, a carboxylic acid, an epoxide, an isocyanate, an isothiocyanate and an anhydride group to obtain a divalent linking group of an amide bond, a urethane bond, an amino bond, an imide bond (which can be further reduced to a secondary amino bond), an amino bond, an amide bond, a hydroxyalkylamino bond, a urea bond (a carbamide bond or a ureido bond), a thiourea bond and an imide linkage, respectively; a mercapto group can react with an active ester, an active formate, a sulfonate group, a mercapto group, a maleimido group, an aldehyde group, an α,β-unsaturated bond, a carboxyl group and an iodoacetamide group to obtain a divalent linking group of a thioester bond, a thiocarbonate bond, a thioether bond, a disulfide bond, a thioether bond, a thiohemiacetal linkage, a thioether bond, a thioester bond and a thioether bond, respectively; an unsaturated bond can react with a mercapto group to obtain a thioether group; a carboxyl group or an acyl halide can react with a mercapto group and an amino group to obtain a thioester bond and an amide bond, respectively; a hydroxyl group can react with a carboxyl group, an isocyanate, an epoxide or a chlorocarbonyloxy group to obtain a divalent linking group of an ester bond, a carbamate bond, an ether bond and a carbonate bond, respectively; a carbonyl group or an aldehyde group can react with an amino group, a hydrazine and a hydrazide to obtain a divalent linking group of an imine bond, a hydrazone bond and an acylhydrazone bond, respectively; a reactive group of an azido group, an alkynyl group, an alkenyl group, a mercapto group, a dienyl group, a maleimido group, a 1,2,4-triazoline-3,5-dione group, a dithioester group, a hydroxylamino group (a hydroxylamine), an acylhydrazino group (a hydrazide), an acrylate group, an allyloxy group, an isocyanato group (an isocyanate), a tetrazole group or the like can undergo click reactions to form various linking groups including but not limited to a triazole linkage, an isoxazole linkage, a thioether bond and the like. Click reactions and the resulting linking groups disclosed and cited in the literature "Adv. Funct. Mater., 2014, 24, 2572-2590" are all incorporated into the present invention by reference. Specifically, such as azide-alkyne cycloaddition reactions, Diels-Alder addition reactions, reactions with the formation of oximes or acylhydrazones, thiol-ene addition reactions, thiol-yne addition reactions, thiol-isocyanate reactions, 1,3-dipolar cycloaddition reactions and the like. Coupling reactions in the present invention also include but are not limited to cycloaddition reactions, Diels-Alder addition reactions, 1,3-dipolar cycloaddition reactions and the like which can be conducted by using functional groups in functional Group G. A primary amine can react with one molecule of sulfonate, halide, epoxide, or α,β-unsaturated compound to obtain a divalent secondary amino group, or react with two molecules of above-said reagents to form a trivalent t-amino group. Another example is the reaction between a functional group B5 or B6 and a disulfide bond to form a trivalent linking group.

Typical examples of the resulting divalent linking groups include an amide bond, a urethane bond, an ester bond, a secondary amino bond, a thioether bond, a triazole linkage and the like. When forming an amide bond (—CONH—) or an imide bond (—CON(—)$_2$), the reactions can be conducted, inclusively but not limited, through the following methods: (1) via the condensation reaction between an amino group and a carboxyl group; (2) via the reaction between an amino group and a carboxylic acid derivative; (3) via the amidation reaction of an amine substrate with an acyl halide, wherein, the acyl halide is preferably an acyl chloride. When forming a urethane bond (—OCONH—), the resulting divalent linking group can be obtained via the condensation reaction between a terminal amino group and a terminal active carbonate derivative, wherein, the active carbonate can be a derivative which is capable of reacting with an amino group to obtain a urethane bond, including but not limited to succinimidyl carbonate (SC), p-nitrophenol carbonate (p-NPC), 2,4,6-trichlorophenol carbonate, imidazole carbonate, N-hydroxybenzotriazole carbonate and the like, and preferably succinimidyl carbonate (SC), o-nitrophenol carbonate (o-NPC) and the like; a urethane bond can also be obtained via the reaction between a hydroxyl group and an isocyanate. When forming a thio- or dithio-carbamate bond, the reaction can be carried out between a terminal amino group and a terminal thio(oxycarbonyl) chloride (—O—C(═S)Cl, —S—C(═O)Cl or —S—C(═S)Cl), between a terminal hydroxyl or mercapto group and an isothiocyanate, or between a mercapto group and an isocyanate. When forming an ester bond (—OCO—), the resulting divalent linking group can be obtained via the condensation reaction between a terminal hydroxyl group and a terminal carboxyl group or an acyl halide, wherein, the acyl halide is preferably an acyl chloride. When forming a secondary amino bond (—CH$_2$NHCH$_2$—), the resulting divalent linking group can be obtained by the condensation reaction and subsequent reduction reaction of an aldehyde group and an amino group, and can also be obtained via the alkylation reaction of a primary amine with a sulfonate or a halide. When forming a thioether bond (>CHS—), the resulting divalent linking group can be obtained via the addition reaction between a terminal mercapto group and a maleimido group or another reactive group containing an unsaturated-bond ("Angew. Chem. Int. Ed., 2010, 49, 3415-3417"), or be obtained via the alkylation reaction between a terminal mercapto group and a sulfonate or a halide. When forming a triazole linkage, the resulting divalent linking group can be obtained via the click reaction between an alkynyl group and an azido group. When forming a 4,5-dihydroisoxazole linkage, the resulting divalent linking group can be obtained via the 1,3-dipolar cycloaddition reaction between a nitrile oxide and an alkynyl group.

Typical reactions to form a stable divalent linking group are alkylation reactions, including but not limited to alkylation reactions between a hydroxyl group, a mercapto group or an amino group and a sulfonate or a halide, corresponding to the formation of an ether bond, a thioether bond, a secondary amino bond or a tertiary amino bond, respectively.

Production methods in the present invention also allow small molecules containing two identical or different functional groups (biSM) as reagents, contributing to the linking groups between the tetraSM and htriSM moieties or the linking groups between the htriSM and biLPEG moieties. biSM are preferably heterofunctional biSM (biheteroSM). Typical examples include amino acids and derivatives thereof, preferably neutral amino acids and derivatives thereof, wherein, the neutral amino acids include glycine, alanine, 3-alanine and the like. Examples of biheteroSM also include but are not limited to 2-mercaptoethanol, N-(2-hydroxyethyl)ethylenediamine, 2-(2-aminoethoxy)ethanol, 2-((2-aminoethyl)thio)ethanol, 1-amino-2-propanol, 4-hydroxyphenylethylamine, 2-azidoethanol, 2-(2-(2-azidoethoxy)ethoxy)ethanol, hydroxycitronellal diethylacetal, hydroxycarboxylic acids, hydroxycarboxylic acids substituted with an arylalkyl group or an aryl group, N-hydroxymaleimide, N-(2-hydroxyethyl)maleimide, 3-hydroxybutyronitrile, 4-hydroxy-1-naphthalenesulfonic acid, 8-hydroxyquinoline-5-sulfonic acid, 2-(p-toluenesulfonyl)ethanol, 2-hydroxy-2-phenylethyl 4-methylbenzenesulfonate, 2-aminonaphthalene-1-sulfonic acid, 1-naphthylamine-8-sulfonic acid, 4-amino-1-naphthalenesulfonic acid, 5-amino-1-naphthalenesulfonic acid, 2-(methylsulfonyl) ethyl succinimidyl carbonate, 2-chloro-1-(p-toluenesulfonyl)ethane, N-succinimidyl 3-(2-pyridyldithio)propionate, 4-(toluenesulfonyl)acetonitrile, 2-(thien-2-yl)ethyl 4-methylbenzenesulfonate, mercaptoethylamine, mercaptoethylamine hydrochloride, mercaptoacetic acid, 2-mercaptopropionic acid, 2-aminoethanethiol, 2-azidoethanamine, O-(2-aminoethyl)-O'-(2-azidoethyl)pentaethylene glycol, 1-azido-2(2-(2-chloroethoxy)ethoxy)ethanol, 4-bromophenylsulfonyl chloride, 3-chloropropanesulfonyl chloride, 3-chloropropionyl chloride, 4-(chloromethyl)benzoyl chloride, 4-bromobutyryl chloride, iodoacetic acid, 3-chloropropyl isocyanate, 3-chloro-4-methylphenyl isocyanate, 3-bromophenyl isocyanate, 4-cyanophenyl isocyanate, 3-cyanophenyl isocyanate, 2-cyanophenyl isocyanate, Boc-piperazine-2-carboxylic acid, morpholine-3,4-dicarboxylic acid 4-tert-butyl ester, 2,4-morpholinedicarboxylic acid 4-(1,1-dimethylethyl) ester, N-benzylmaleamic acid, 4-carboxybenzenesulfonyl azide, 2-azido-2-methylpropionic acid, 4-azidobenzoic acid, N-succinimidyl 4-azido-2,3,5,6-tetrafluorobenzoate, Fmoc-4-azidobutyric acid, acrolein diethyl acetal, bromoacetaldehyde diethyl acetal, 3-bromopropionaldehyde dimethyl acetal; 2-bromobenzaldehyde diethyl acetal, 3-(2,2-diethoxy)propyne, (3,3-diethoxy-1-propynyl)trimethylsilane, succinimidyl maleimidoacetate, N-succinimidyl 3-maleimidopropionate, N-succinimidyl 6-maleimidohexanoate, N-(3-maleimidobenzoyloxy)succinamide, N-succinimidyl 4-(N-maleimidomethyl)cyclohexane-1-carboxylate, N-succinimidyl 4-(4-maleimidophenyl)butyrate, N-succinimidyl 11-(maleimido) undecanoate, N-succinimidyl 4-(maleimido)butanoate, 3-maleimidopropionic acid, 4-maleimidobenzoic acid, 6-maleimidocaproic acid, 11-maleamidoundecanoic acid, N-(2-aminoethyl)maleimide, N-(4-aminophenyl)maleimide, N-succinimidyl 4-pentynoate, propargyl chloroformate, 2-butyn-1-yl chloroformate, 3-butyn-1-yl chloroformate, 4-ethynylaniline, 2-ethynylaniline, 4-ethynylbenzaldehyde, 4-[(trimethylsilyl)ethynyl]benzaldehyde, 2-[(trimethylsilyl)ethynyl]benzaldehyde, 3-cyano-2-hydroxypyridine, 3-hdroxyenzonitrile, N-2-cyanoethylsuccinimide, cyanomethyl benzenesulfonate, cyanomethyl p-toluenesulfonate, 2-(chloromethyl)benzonitrile, 3-(chloromethyl)benzonitrile, 4-(chloromethyl)benzonitrile, 2-chloro-3-cyanopyridine, p-iodobenzonitrile, 4'-amino-4-cyanobiphenyl, 2-amino-5-methylbenzonitrile, 1-methyl-4-cyano-5-amino-1,2-pyrazole, 2-amino-5-trifluoromethylbenzonitrile, 2-amino-2- cyanoacetamide, cyanoacetic acid, p-cyanobenzoic acid, m-cyanobenzoic acid, o-cyanobenzoic acid, 1-cyano-1-cyclopropanecarboxylic acid, methyl 4-cyanobenzoate, 4-cyanobenzoyl chloride, 4-cyanobenzaldehyde, cyanoacetaldehyde diethylacetal, allyl cyanide, 5-norbornene-2-methanol, 5-norbornene-2-carboxamide, 5-norbornene-2-carbonitrile, 5-norbornene-2-methylamine, allyl chloride, propargyl chloroformate, allyl chloroformate, 2-hydroxyethyl methacrylate (HEMA), the like, and protected forms of any above-said compound with any one functional group being protected. Wherein, typical examples of hydroxycarboxylic acids include 2-hydroxycarboxylic acids and 3-hydroxycarboxylic acids. Examples of 2-hydroxycarboxylic acids include but are not limited to 2-hydroxypropionic acid, 2-hydroxybutyric acid, 2-hydroxypentanoic acid, 2-hydroxyhexanoic acid, 2-hydroxyheptanoic acid, 2-hydroxyoctanoic acid, 2-hydroxynonanoic acid, 2-hydroxydecanoic acid, 2-hydroxyundecanoic acid, 2-hydroxylauric acid, 2-hydroxymyristic acid, 2-hydroxypalmitic acid, 2-hydroxystearic acid, 2-hydroxyoleic acid, 2-hydroxyelaidic acid, 2-hydroxylinolenic acid, 2-hydroxyarachidic acid, 2-hydroxyarachidonic acid, 2-hydroxyundecanoic acid, 2-hydroxydocosanoic acid, 2-hydroxydocosenoic acid, 2-hydroxylignoceric acid, 2-hydroxytetracosenoic acid, 2-hydroxyhexacosanoic acid, 2-hydroxyoctacosanoic acid, 2-hydroxytriacontanoic acid and 2-hydroxydotriacontanoic acid, preferably $C_{3-20}$ 2-hydroxycarboxylic acids, more preferably $C_{3-10}$ 2-hydroxycarboxylic acids, and more preferably $C_{3-6}$ 2-hydroxycarboxylic acids. Wherein, 2-hydroxlcarboxylic acids substituted with an arylalkyl group or an aryl group include but are not limited to mandelic acid, 2,2-diphenyl-2-hydroxyacetic acid, 3-phenyl-2-hydroxypropionic acid and 2-phenyl-2-methyl-2-hydroxyacetic acid. Examples of 3-hydroxylcarboxylic acids include but are not limited to salicylic acid and 2-phenyl-3-hydroxypropionic acid. In addition, reagents of hydroxycarboxylic acids can also be in the form of salt or lactone.

3.3 The present invention also discloses a production method for the eight-arm polyethylene glycol derivative, involving an addition reaction between a tetrafunctional small molecule compound (tetraSM) and eight molecules of a linear bifunctional PEG compound (biLPEG) to obtain an eight-arm polyethylene glycol derivative (OctafPEG). The definition of biLPEG is the same as above. The tetraSM is preferably a small molecule compound containing four alkynyl groups (F3). Wherein, the end-group of biLPEG participating in the reaction with tetraSM is further preferably a mercapto group.

In this method, the click reaction between an alkynyl group and mercapto groups can be based on a tetrafunctional small molecule compound to obtain an eight-arm polyethylene glycol or an eight-arm polyethylene glycol derivative directly, which is a green and highly efficient reaction.

The biLPEG can be polydisperse or monodisperse. The biLPEG for this method is preferably a monodisperse reagent or a low-molecular-weight polydisperse reagent. When biLPEG is polydisperse, the number average molecular weight thereof is below 5 kDa, preferably below 3 kDa, and further preferably below 2 kDa. The lower the molecular weight is, the smaller steric hindrance the addition reaction has, and the easier to control the reaction is.

When the structure or/and functional group of the terminal of biLPEG which does not react with tetraSM are different from the objective structure or/and objective functional group, the OctafPEG previously obtained via an addition reaction can be end-functionalized to obtain the objective structure containing objective functional group. The end-functionalization is suitable linear end-functionalization or suitable branched end-functionalization. The objective product is preferably obtained just via deprotection.

With respect to the reaction between an alkynyl group and mercapto groups, the reaction conditions can refer to the techniques in the prior art, such as the following literatures including "Macromolecules, 2010, 43, 4937-4942" and cited references therein, "Angew. Chem. Int. Ed., 2010, 49, 3415-3417" and cited references therein, "Chem. Commun., 2011, 47, 11086-11088" and cited references therein, etc.

3.4. Method for End-Functionalization 3.4.1. Linear End-Functionalization for the Polyethylene Glycol Chain Terminal The method for linear end-functionalization is not particularly limited, but related to the type of the objective terminal functional group. The method can be a linear end-functionalization based on the terminal hydroxyl group of a polyethylene glycol chain, be the conversion of a reactive group into the objective functional group, or be the combination of the above-said two manners. All the techniques in the prior art can be used by reference, including but not limited to those described and listed in the documents CN104530413A, CN104530415A and CN104530417A; take CN104530417A as an example, corresponding to paragraphs from [0960] to [1205]. Parameters including reaction temperature, reaction time, feed amount, solvent conditions, reaction conditions (such as a strongly basic condition or an acidic condition), catalysts, deprotonation reagents, oxidizing agents, reducing agents, alkylating agents, halogenating agents, weakly acidic salts and the like as well as preferable embodiments of these parameters are well known to those skilled in the art, or can be obtained by optimization through limited experimentation, no more repeated here. Mainly, the reaction mechanism, reagents, reaction routes and other aspects of those involved reaction types (e.g., condensation reactions, ring-opening reactions, ring-closing condensation reactions, esterification reactions, oxidation reactions, addition reactions, substitution reactions, alkylation reactions, dehydrogenation reactions and the like) are described in brief, because the related details and preferable conditions are also well known to those skilled in the art, or can be obtained by limited experimentation.

3.4.1.1. Group A: End-Functionalization into $R_{01}$ Selected from Group A

The functional groups in Group A are mainly active ester groups or analogues of ester groups. Productions therefor include but are not limited to the following methods.

a: Active ester derivatives (A6-A10, A12 and A14) can be obtained through condensation reactions under a basic condition between terminal-hydroxyl-containing intermediates and corresponding carbonates (e.g., N,N'-disuccinimidyl carbonate, bis(p-nitrophenyl)carbonate, bis(o-nitrophenyl) carbonate, di(benzotriazol-1-yl)carbonate, etc.), haloformates (e.g., p-nitrophenyl chloroformate, o-nitrophenyl chloroformate, trichlorophenyl chloroformate and the like) and N,N'-carbonyldiimidazole. Substituted derivatives with substituents on the ring can also be obtained in a similar manner, for example, a 2-methylimidazole derivative can be obtained by reacting with 1,1'-carbonylbis(2-methylimidazole). The corresponding haloformates can be a chloride, a bromide or an iodide, preferably a chloride.

b: Active esters (A1-A5, A11 and A13) can also be obtained through a condensation reaction. The terminal hydroxyl group can be converted into a terminal carboxyl group through a one-step or multi-step reaction, and then reacts with corresponding alcohols (e.g., N-hydroxysuccinimide, p-nitrophenol, o-nitrophenol, trichlorophenol, 1-hydroxybenzotriazole and the like) to obtain corresponding active esters in the presence of condensing agents.

c: Analogs of active esters (A15-A18) can be obtained through condensation reactions between terminal carboxyl groups and corresponding amines (such as thiazolidine-2-thione, pyrrolidine-2-thione, benzo[d]thiazol-2(3H)-thione, 4-oxo-2-thiothiazolidine and the like) to obtain corresponding amides in the presence of condensing agents. Substituted derivatives with substituents on the ring can also be obtained in a similar manner, for example, active ester analogs can be obtained by reacting with 4-isopropyl-1,3-thiazolidine-2-thione, (R)-4-isopropylthiazolidine-2-thione, 4-phenylthiazoline-2-thione or the like.

The condensing agent is not particularly limited, but is preferably N,N'-dicyclohexylcarbodiimide (DCC), 1-ethyl-(3-dimethylaminopropyl)carbodiimide hydrochloride (EDC.HCl), 2-(7-azobenzotriazole-N,N,N',N'-tetramethyluronium hexafluorophosphate (HATU), (benzotriazol-1-yl)-N,N,N',N'-tetramethyluronium hexafluorophosphate (HBTU), and most preferably DCC. The solvent can be no solvent or an aprotic solvent. The base is usually an organic base, and preferably triethylamine or pyridine.

3.4.1.2. Group B: End-Functionalization into $R_{01}$ Selected from Group B

The sulfonate (B1) and sulfinate (B2) derivatives can be obtained through an esterification reaction under a basic condition between the terminal hydroxyl group and a sulfonyl chloride or a sulfinyl chloride that contains a leaving group $Y_1$. The definition of $Y_1$ is defined the same as above. The solvent can be no solvent or an aprotic solvent. The base can be an organic base or an inorganic base, preferably an organic base, and more preferably triethylamine or pyridine.

The sulfone (B3) and sulfoxide (B4) derivatives can be obtained through an oxidation reaction by using a sulfoxide intermediate or a thioether intermediate that contains a leaving group $Y_1$; wherein, $Y_1$ is defined the same as above. The oxidizing agent is not particularly limited as long as it is a compound or a combination of multiple compounds capable of increasing the valence of the substrate. The solvent can be no solvent or an aprotic solvent.

The sulfone (B3) derivative can be obtained via an addition reaction for deprotonation between the terminal hydroxyl group and a base, and a subsequent additional reaction with vinylsulfone.

The disulfone (B5) derivative and variant forms thereof (B6) can be obtained with the method disclosed in the literature "Advanced Drug Delivery Reviews, 2008, 60, 3-12".

3.4.1.3. Group C: End-Functionalization into $R_{01}$ Selected from Group C

The hydroxylamine compound (C1) can be obtained via the reaction under a strongly basic condition (e.g., diphenylmethyl potassium) between the terminal hydroxyl group and excess hydroxylamine hydrochloride.

The thiol derivative (C2) can be obtained via the reaction between the terminal hydroxyl group and a thiourea compound. The reaction can be carried out in a solvent or without any solvent. The solvent is not limited, preferably water, toluene, benzene, xylene, acetonitrile, ethyl acetate, diethyl ether, methyl tert-butyl ether, tetrahydrofuran, chloroform, dichloromethane, dimethyl sulfoxide, dimethylformamide or dimethylacetamide, and more preferably water, tetrahydrofuran, dichloromethane or acetonitrile.

The thiol derivative (C2) can also be obtained via the reaction between a sulfonate compound and a xanthate potassium compound followed by decomposition treatment with primary amine. This reaction can be carried out without any solvent or in a solvent, and the solvent is not limited, preferably an aprotic solvent.

The sulfide compound (C3) as a protected thiol can be obtained via the reaction between a thiol compound (C2) and a corresponding protective agent. The production method is not limited, including but not limited to the following manners: Manner (a), the sulfide having a thio-ether protective structure can be prepared via the reaction between a thiol compound and a corresponding alkylating agent under a basic condition, wherein, the corresponding alkylating agent contains a leaving group. The solvent can be no solvent or an aprotic solvent. Manner (b), the thioester compounds (C3 and C17) can be prepared via the reaction between a thiol compound and corresponding acyl halides under a basic condition. The solvent can be no solvent or an aprotic solvent.

The amine derivative (C4) can be synthesized in the following manner: by using base catalysis, the terminal hydroxyl group reacts with acrylonitrile or an analog of acrylonitrile through a coupling reaction in advance, and then the cyano group of the resulting compound is reduced by using palladium or nickel as a catalyst in a high-pressure reactor to obtain a corresponding amine compound. The reaction can be carried out in a solvent or without any solvent. The solvent is not particularly limited, but is preferably water, 1,4-dioxane or the combination thereof. The base can be an organic base or an inorganic base, preferably an inorganic base, and more preferably sodium hydroxide or potassium hydroxide.

The amine derivative (C4) can also be obtained via the reaction between a sulfonate compound (B1) and ammonia water.

The protected amine derivative (C5 and C6) can be prepared via the reaction between corresponding amine (C4) and corresponding protective agent. The production method is not limited, including but not limited to the following manners:

Manner a, the carbamate compound can be prepared via the reaction between an amine and a corresponding haloformate in the presence of a base. The solvent can be no solvent or an aprotic solvent. The base can be an organic base or an inorganic base, preferably an organic base, and more preferably triethylamine or pyridine.

Manner b, the amide compound can be prepared via the reaction between an amine and a corresponding acyl halide under a basic condition.

Manner c, the alkylamine compound can be prepared via the reaction between an amine and a corresponding alkylating agent under a basic condition, wherein, the corresponding alkylating agent contains a leaving group. The solvent can be no solvent or an aprotic solvent. The base can be an organic base or an inorganic base, preferably an organic base, and more preferably triethylamine, pyridine, sodium hydride, DPMK, potassium hydride or sodium alkoxide.

Manner d, the alkylamine compound can also be prepared by carrying out the reaction between an amine and a corresponding aldehyde or ketone to generate an imine compound and then the resulting imine (Schiff base) is reduced to corresponding alkylamine compound (C5) in the presence of a reducing agent. The aldehyde or ketone is not particularly limited. The solvent can be a protic solvent or an aprotic solvent, including toluene, benzene, xylene, acetonitrile, ethyl acetate, diethyl ether, methyl t-butyl ether, tetrahydrofuran, methanol, dimethylformamide or dimethylacetamide, and preferably tetrahydrofuran, methanol or ethyl acetate. The reducing agent is not particularly limited as long as it can reduce the resulting Schiff base formed by an amine and an aldehyde or ketone into an amino group, preferably sodium borohydride, sodium cyanoborohydride, lithium aluminum hydride, borane, diborane, diisobutylaluminum hydride, diisopinocampheylborane, lithium borohydride, zinc borohydride, borane-pyridine, borane-methyl sulfide, borane-tetrahydrofuran, the like or a combination thereof, and more preferably sodium cyanoborohydride.

The halide compound (C7), tetramethylpiperidinyloxy compound (C8) and dioxapiperidinyloxy compound (C9) can be prepared by carrying out the reaction between a sulfonate compound (B1) and corresponding halogenated salt, 2,2,6,6-tetramethylpiperidine-N-oxyl compound and 3,5-dioxo-1-cyclohexylamine, respectively. The bromide salt is not limited as long as free bromide ions exist in the solvent, preferably sodium bromide or potassium bromide.

The halide compound (C7) can also be obtained via the reaction between the terminal hydroxyl group and a halogenating agent. The halogenating agent is not particularly limited as long as it can convert the hydroxyl group to corresponding halogen atom, preferably dichlorosulfone, phosphorus trichloride, phosphorus tribromide, dibromosulfoxide, the like or a combination thereof. The solvent can be no solvent or an aprotic solvent.

The ester compound or thiocarboxylate compound (C17) can be obtained via the condensation reaction between the terminal hydroxyl group or mercapto group and a carboxyl group or an acyl halide, wherein, the acyl halide is preferably an acyl chloride.

The thioester compound (C17) can also be obtained via the reaction between a mercapto group and an active ester, referring to the literature "Journal of Controlled Release, 2014, 194: 301-309".

The carbonate or thiocarbonate compound (C18) can be obtained via the condensation reaction between the terminal hydroxyl group or mercapto group and an oxycarbonylchloride compound, such as ethyl chloroformate, ethyl chloroformate with one or two oxygen atoms being replaced by a sulfur atom, etc.

The trithiocarbonate derivative (C18) can also be prepared via the coupling reaction between a trithioester-containing small molecule compound (such as 3-(benzylthiothiocarbonylthio)propionate) and a functionalized polyethylene glycol bearing a suitable functional group.

The ester compound (D11) can be treated with ammonia water or hydrazine hydrate to obtain an amide compound (C20) or a hydrazide compound (C22), respectively.

The haloacetamide compound (C10) can be obtained by reacting haloacetic acid with a polyethylene glycol amine derivative (C4) in the presence of a condensing agent to form an amide bond.

The lipoic acid derivative (C14) can be obtained via the condensation reaction between lipoic acid and the corresponding alcohol (H1) or amine (C4).

3.4.1.4. Group D: End-Functionalization into $R_{01}$ Selected from Group D

The ester compound (D11) and the thiocarboxylate compound (D26, D27 and D28) can be obtained by deprotonating the terminal hydroxyl group and then carrying out a substitution reaction with an α-halogenated ester compound, e.g., ethyl chloroacetate or ethyl bromoacetate.

The thioester compound (D26) can also be obtained via the reaction between a corresponding ester (D11) and a thiol.

The ester compound (D11) can be hydrolyzed with a basic solution to obtain a carboxylic acid compound (D1).

The acyl halide compound (D4) can be obtained via the reaction between a carboxylic acid compound (D1) and a corresponding halogenating agent. The halogenating agent is not particularly limited as long as it can convert the hydroxyl group of carboxyl group to corresponding halogen atom, preferably thionyl chloride (also referred to as dichlorosulfoxide), phosphorus trichloride, phosphorus tribromide, dibromosulfoxide, the like or a combination thereof. The solvent can be no solvent or an aprotic solvent.

The anhydride derivative (D11) can be obtained via the reaction between a carboxylic acid derivative (D1) and an acyl halide, a small molecule anhydride or a mixture of small molecule anhydrides. The acyl halide, the small molecule anhydride and the mixture of small molecule anhydrides are not particularly limited as long as they can convert the carboxylic acid to corresponding anhydride, preferably a $C_{1-10}$ acyl chloride, a $C_{1-10}$ acyl bromide, a $C_{1-10}$ anhydride, the like or a combination thereof.

The sulfonic acid derivative (D2) can be obtained via the alkylation reaction between the haloalkylsulfonic acid (such as 2-bromoethylsulfonic acid) and the terminal hydroxyl group.

The acetaldehyde derivative (D6) can be obtained by directly oxidizing the terminal hydroxyl group. The oxidizing agent is not particularly limited, preferably PDC (pyridinium chlorochromate), PCC (pyridinium dichromate), "DCC+DMSO", "oxalyl chloride+DMSO", "sulfur trioxide pyridine+DMSO", "trifluoroacetic anhydride+DMSO" or $MnO_2$, and more preferably "DCC+DMSO". The reaction solvent is not particularly limited, but preferably an aprotic solvent. In addition, the salt with weak acidity which should be added to the reaction is not particularly limited, preferably pyridine trifluoroacetate, triethylamine trifluoroacetate, pyridine hydrochloride, triethylamine hydrochloride, pyridine sulfate, triethylamine sulfate or the like, and more preferably pyridine trifluoroacetate.

The propionaldehyde derivative and other aldehyde derivatives (D6) can be obtained by deprotonating the terminal hydroxyl group followed by the reaction with a halide to get a corresponding acetal intermediate (D7), and then the compound (D7) is hydrolyzed under an acidic condition to obtain corresponding aldehyde. The base used for deprotonation is not particularly limited, preferably sodium, potassium, sodium hydride, potassium hydride, sodium methoxide, potassium t-butoxide or diphenylmethyl potassium, and more preferably sodium hydride or diphenylmethyl potassium. The reaction solvent is not particularly limited, preferably an aprotic solvent. The deprotection of the acetal intermediate is carried out under an acidic condition, and the pH of the solution preferably ranges from 1 to 4. The acid is not particularly limited, preferably acetic acid, phosphoric acid, sulfuric acid, hydrochloric acid or nitric acid, and more preferably hydrochloric acid. The reaction solvent is not particularly limited as far as it can dissolve the reagents and the product, preferably water.

The aldehyde derivative (D6) can also be obtained by carrying out the coupling reaction with an acetal-containing small molecule reagent in advance, and then removing the acetal protection.

For example, after the amidation reaction between a polyethylene glycol amine and 2,2-diethoxyacetic acid, 3,3-diethoxypropionic acid, 4,4-diethoxybutyric acid, 5,5-diethoxypentanoic acid or the like and the subsequent removal of acetal protection, a corresponding aldehyde derivative such as $-C(=O)-(CH_2)_{0-3}CHO$ can be obtained.

The acetal derivative (D7) can also be obtained via the reaction between a polyethylene glycol aldehyde derivative (D6) and a corresponding alcohol via acid catalysis, and the resulting product is a protected PEG-aldehyde (D7). Wherein, the acid is not particularly limited and can be a protonic acid or a Lewis acid, preferably hydrochloric acid, sulfuric acid, trifluoroacetic acid, trifluoromethanesulfonic acid, p-toluenesulfonic acid, aluminum trichloride, tin chloride or the like. Wherein, the acid is preferably a protonic acid, and more preferably hydrochloric acid, sulfuric acid, trifluoroacetic acid, trifluoromethanesulfonic acid, phosphoric acid or nitric acid. The alcohol is not particularly limited and can be a monool, a diol or a multiol, preferably methanol, ethanol, propanol, butanol, pentanol, ethylene glycol, 1,3-propanediol, 1,4-butanediol or the like. The solvent can be no solvent or an aprotic solvent.

The isocyanate (D9) and thioisocyanate (D10) derivative can be obtained via the reaction between an alcohol derivative (H1) or an amine derivative (C4) and excess diisocyanate and dithioisocyanate, respectively. The diisocyanate and dithioisocyanate are not particularly limited, preferably a $C_{1-10}$ diisocyanate and a $C_{1-10}$ dithioisocyanate, respectively. The solvent can be no solvent or an aprotic solvent. The diisocyanate can be but not limited to 1,6-hexamethylene diisocyanate, dimethylbiphenylene diisocyanate, 4,4'-methylenebis(phenyl isocyanate), p-phenylene diisocyanate, tolylene-2,4-diisocyanate, 1,5-naphthalene diisocyanate, m-xylylene isocyanate, isophorone diisocyanate, 4,4'-diisocyanatodicyclohexylmethane or bis(2-isocyanatoethyl)-5-norbornene-2,3-dicarboxylate.

The oxycarbonylchloride derivative (D12) can be obtained via the reaction between the terminal hydroxyl group (H1) and triphosgene under a basic condition. The base is preferably an organic base, such as dimethylaminopyridine. The solvent is preferably an aprotic solvent, such as dichloromethane.

The squarate derivative (D24) can be obtained via the reaction between an amine derivative (C4) and squaryl diester.

3.4.1.5. Group E: End-Functionalization into $R_{01}$ Selected from Group E

The maleimide derivative (E1) can be obtained via the ring-opening reaction between an amine compound (C4) and maleic anhydride to get a maleic intermediate (E5), followed by a ring-closing condensation reaction by using acetic anhydride or sodium acetate as a catalyst. The reaction solvent is not particularly limited, preferably an aprotic solvent. In the ring-closing condensation reaction, the solvent is not limited, preferably an above-described aprotic solvent or acetic anhydride.

The maleimide derivative (E1) can also be obtained via the condensation reaction between an amine compound (C4) and a maleimido-containing (MAL-containing) acid or active ester. The MAL-containing acids include but are not limited to 3-maleimidopropionic acid, 4-maleimidobenzoic acid, 6-maleimidohexanoic acid, 11-(maleimido)undecanoic acid and the like. The MAL-containing active esters include but are not limited to N-succinimidyl maleimidoacetate, N-succinimidyl-3-maleimidopropinate, N-succinimidyl-6-maleimidohexanoate, 3-maleimidobenzoic acid N-hydroxysuccinimide ester, N-succinimidyl 4-(N-maleimidomethyl)cyclohexane-1-carboxylate, N-succinimidyl 4-(4-maleimidophenyl)butyrate, N-succinimidyl 11-(maleimido)undecanoate and N-(4-maleimidebutyryloxy)succinimide. Similarly, the diazamaleimide derivative (E6) can also be obtained via the condensation reaction between an amine compound (C4) and a corresponding acid or active ester.

The maleimide derivative (E1) can also be obtained via the condensation reaction between an active ester derivative (A1-A14) and a MAL-containing amine compound. The MAL-containing amines include but are not limited to N-(2-aminoethyl)maleimide and N-(4-aminophenyl)maleimide.

The $\alpha,\beta$-unsaturated esters (E2, E3) can be obtained by deprotonating the terminal hydroxyl group and then reacting with a corresponding halide. The deprotonating base is not particularly limited, preferably sodium, potassium, sodium hydride, potassium hydride, sodium methoxide, potassium t-butoxide or diphenylmethyl potassium, and more preferably sodium hydride or diphenylmethyl potassium. The reaction solvent is not limited, preferably an aprotic solvent. Examples of the halide include acryloyl chloride and methacryloyl chloride.

The maleamic acid derivative (E5) can also be obtained via the reaction between an amine derivative (C4) and a corresponding dicarboxylic acid to form an amide derivative in the presence of a condensing agent. The condensing agent is not particularly limited, preferably DCC, EDC.HCl, HATU or HBTU, and most preferably DCC. The solvent can be no solvent or an aprotic solvent. The base is usually an organic base, preferably triethylamine or pyridine.

The azo compound (E7), the unsaturated-double-bond-containing cyclic compound (E8) such as a cycloalkene compound, the norbornene derivatives (E9, E10), the 2,5-norbornadiene derivative (E11) and the 7-oxabicyclo[2.2.1]hept-5-ene derivative (E12) can be obtained via the condensation reactions between a corresponding ring-containing alcohol, carboxylic acid, amine, amide or methyl ester derivative and corresponding reactive groups, wherein, the resulting linking groups include but are not limited to an ester bond, an amide bond, a carbamate bond, a carbonate bond, a hydrazide bond and the like. Examples of reagents for E8 include cyclooct-4-enol, cyclooct-4-en-1-yl-methyl carbonate and cyclooct-4-enecarboxylic acid. Examples of reagents for E9 include but are not limited to 5-norbornenyl-2-methanol, 2-hydroxyethyl 5-norbornene-2-carboxylate, a,a-dimethylbicyclo[2.2.1]hept-5-ene-2-methanol, 5-norbonene-2-methanamine, 5-norbornene-2-carboxylic acid, 2-methyl-5-bicyclo[2.2.1]hepten-2-carboxylic acid, 1-(5-norbornen-2-yl)ethyl succinate, 5-norbornene-2-carboxamide, 2-norbornene-2-carboxamide, 2-methyl-5-norbornene-2-carboxamide, 5-norbornene-2-carbonitrile, 2-(5-norbornenyl)ethyldimethylchlorosilane, N-[4-(4-aminobenzyl)phenyl]-5-norbornene-2,3-dicarboximide, N-hydroxy-5-norbornene-2,3-dicarboximide, 5-norbornene-2,3-dicarboximide, 5-norbornene-2-carboxaldehyde, himic anhydride (also 5-norbornene-2,3-dicarboxylic anhydride), methyl nadic anhydride and N-methyl-N-2-propynyl-5-norbornene-2-methylamine.

3.4.1.6. Group F: End-Functionalization into $R_{01}$ Selected from Group F

Functionalized derivatives (F1, F2, F3 and F4) can be obtained by deprotonating the terminal hydroxyl group and then carrying out a substitution reaction with corresponding halides. The deprotonating base is not particularly limited, preferably sodium, potassium, sodium hydride, potassium hydride, sodium methoxide, potassium tert-butoxide or diphenylmethyl potassium, and more preferably sodium hydride or diphenylmethyl potassium. The reaction solvent is not particularly limited, preferably an aprotic solvent. The halide corresponding to the epoxide compound (F1) can be epichlorohydrin, 2-(chloromethyl)-2-methyloxirane, (3-chlorophenyl)oxirane, epifluorohydrin, epibromohydrin, 4-bromo-1,2-epoxybutane, 6-bromo-1,2-epoxyhexane or the like, preferably epichlorohydrin. The halide corresponding to the vinyl-containing compound (F2) can be, for example, 3-cholopropene or 3-bromopropene. The halide corresponding to the ethynyl-containing compound can be, for example, 3-bromopropyne. The halide corresponding to the protected ethyne compound can be, for example, 3-bromo-1-(trimethylsilyl)-1-propyne or 3-bromo-1-(tert-butyldimethylsilyl)-1-propyne.

3.4.1.7. Group G: End-Functionalization into $R_{01}$ Selected from Group G

The cyclic alkyne compounds (G1-G10), cyclodiene compounds (G11-G12) and furan derivative (G13) can be obtained via the condensation reactions between a corresponding ring-containing alcohol, carboxylic acid, amine, amide or methyl ester derivative and corresponding reactive groups, wherein, the resulting linking groups include but are not limited to an ester bond, an amide bond, a carbamate bond, a carbonate bond, a hydrazide bond and the like. Examples of reagents are as follows:

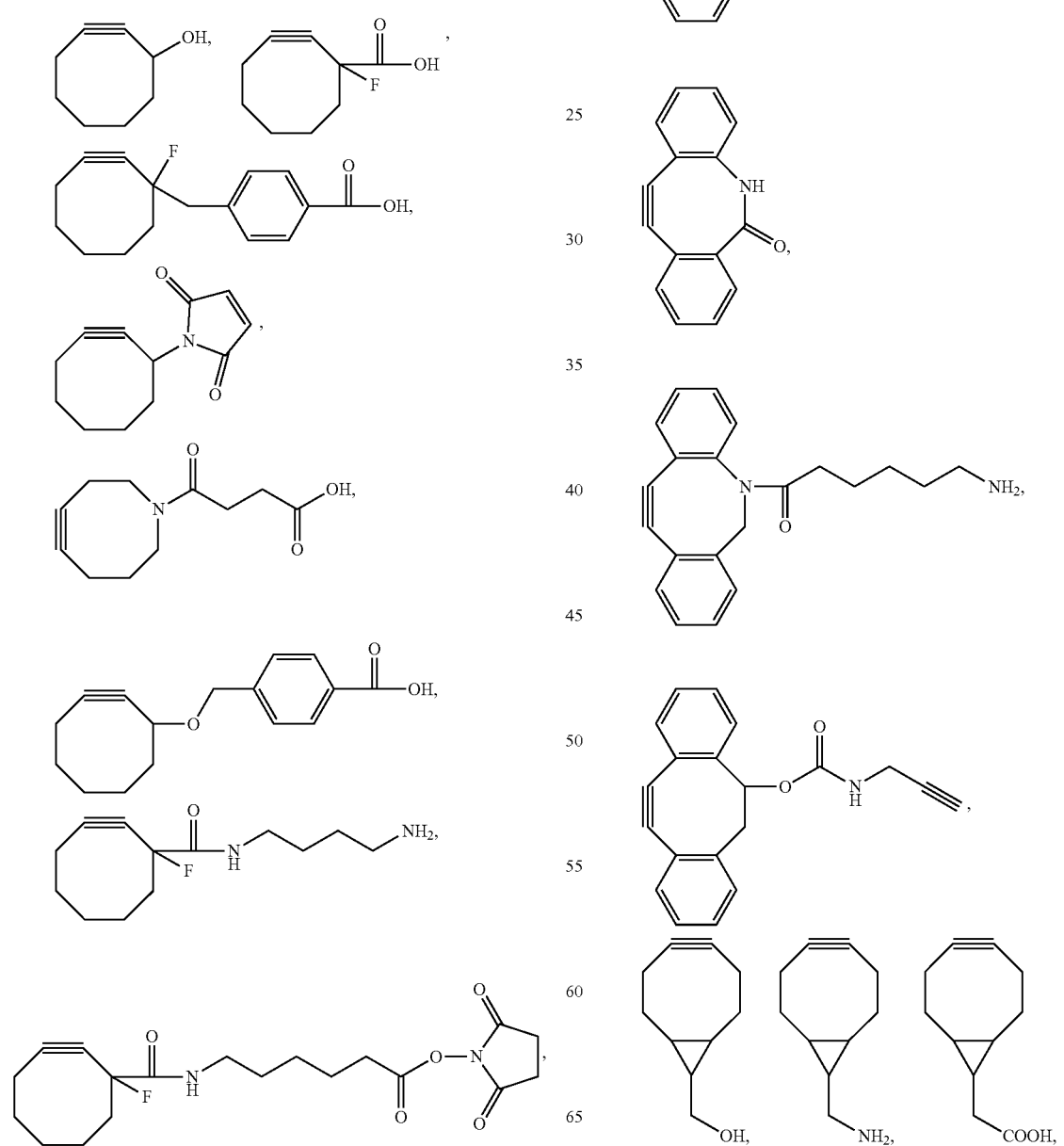

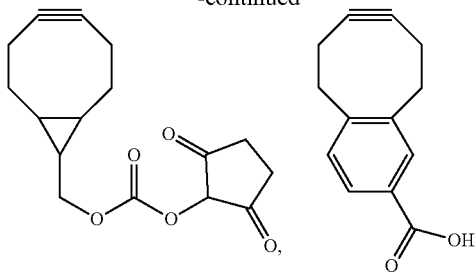

and the like.

The azide compound (G21) can be prepared by carrying out the reaction between a sulfonate compound (B1) and a corresponding azide salt. The azide salt is not limited as long as free azide ions can exist in the solvent, preferably sodium azide or potassium azide. The reaction solvent is not limited, preferably water, ethanol, acetonitrile, dimethyl sulfoxide, dimethylformamide or dimethylacetamide, and more preferably water and dimethylformamide.

The nitrile oxide (G22) can be obtained via the reaction between an aldehyde derivative (D6) and a hydroxylamine to form an oxime (G24) followed by an oxidation reaction. With respect to the reaction to form the oxime, the solvent can be no solvent or an aprotic solvent. In the oxidation process, the oxidizing agent is not particularly limited, preferably N-iodosuccinimide, N-chlorosuccinimide, N-bromosuccinimide, the like or a combination thereof. The solvent can be no solvent or an aprotic solvent.

The nitrile compound (G23) can be obtained via the addition reaction between the terminal hydroxyl group and an acrylonitrile under a basic condition. Alternatively, the nitrile compound can also be obtained in the following manner: by using palladium or nickel as a catalyst, an amine derivative (C4) is treated by ammonia in advance and by hydrogen subsequently under a high-pressure condition, and then is dehydrogenated at high temperature.

Compounds G31 and G32 can be prepared with the methods disclosed in the document PCT/US2013/046,989.

3.4.1.8. Group H: End-Functionalization into $R_{01}$ Selected from Group H

The resulting product obtained after the polymerization of ethylene oxide is a mixture of alcohols and oxygen anions, and can be protonated to obtain polyethylene glycol chains terminated with hydroxyl groups (H1).

The alcohol derivative terminated with the hydroxyl group (H1) can also be obtained by modifying a non-hydroxyl reactive group, e.g., the alcohol having a structure of —NH—CH(=O)CH$_2$CH$_2$OH can be formed via the reaction between ethylene carbonate and a secondary amine.

The alcohol derivative terminated with the hydroxyl group (H1) can also be obtained by treating an amine derivative (C4) with nitrite via a diazotization reaction followed by hydrolysis treatment under a low-temperature and acidic condition. Wherein, the acid is not particularly limited and can be a protonic acid or a Lewis acid, preferably a protonic acid, and more preferably hydrochloric acid, sulfuric acid, trifluoroacetic acid, trifluoromethanesulfonic acid, phosphoric acid or nitric acid. The low temperature is preferably about 0° C.

The protected hydroxyl group (H2) can be obtained via the reaction between the terminal hydroxyl group and a protective agent. Generally, the protective agent is not particularly limited, preferably a halosilane, a carboxylic acid, an acyl chloride, an anhydride, a halohydrocarbon, a sulfonyl chloride, an alkenyl ether, a carbonyl-containing compound or the like.

A. In general, the terminal hydroxyl group can react with a halosilane, an acyl chloride, an anhydride, a sulfonyl chloride or a halohydrocarbon under a neutral or basic condition to obtain a protected form (H2). The solvent can be no solvent or an aprotic solvent. The base can be an organic base or an inorganic base, preferably an organic base, and more preferably triethylamine or pyridine. The protected form OPG$_4$ with an ether structure is the same as above-defined.

B. The terminal hydroxyl group can react with a carboxylic acid in the presence of a base and a condensing agent to obtain the compound (H2). The reaction condition is similar to that for preparing the active ester with a $R_{01}$ group selected from Group A.

C. The terminal hydroxyl group can undergo an addition reaction with an alkenyl ether under an acidic condition to obtain the compound (H2). The alkenyl ether is not particularly limited, preferably ethyl vinyl ether or tetrahydropyran. Wherein, the acid is not particularly limited and can be a protonic acid or a Lewis acid. The solvent can be no solvent or an aprotic solvent.

D. The terminal hydroxyl group can react with t-butyldimethylchlorosilane, ethyl vinyl ether, dihydropyran, benzyl bromide or di-t-butyl dicarbonate to form a hydroxyl group protected by a silyl group, an ethoxyethyl group, a dihydropyryl group, a benzyl group or a Boc group, respectively.

The protected terminal dihydroxyl group (H3) can be obtained through methods including but not limited to the methods disclosed in the literatures "Macromol. Biosci. 2011, 11, 1570-1578" and "J. Am. Chem. Soc., Vol. 123, No. 25, 2001, 5908-5917".

The photoreactive groups (H6) and (H7) which can be converted to an enolic hydroxyl group can be prepared with the methods disclosed in the literature U.S. Ser. No. 14/021,040.

3.4.1.9. Group I: End-Functionalization into $R_{01}$ Selected from Group I

The pegylated folic acid (I1) can be obtained via the condensation reaction between the carboxyl group of folic acid and a polyethylene glycol or an alcohol derivative thereof (H1) or an amine derivative (C4). Wherein, the condensing agent is not particularly limited, preferably DCC, EDC.HCl, HATU or HBTU, and most preferably DCC. The molar equivalent of the condensing agent is usually 1 to 20 folds of folic acid, preferably 5 to 10 folds. Suitable catalysts, such as 4-dimethylaminopyridine, can be added to the reaction. The solvent can be no solvent or an aprotic solvent. The base is usually an organic base, preferably triethylamine or pyridine.

The pegylated cholesterol derivative (I2) can be obtained via the condensation reaction between the terminal hydroxyl group of polyethylene glycol and a corresponding cholesterol derivative in the form of a carboxylic acid (D1), an acyl halide (D4), a sulfonyl chloride (D5), an isocyanate (D9), an isothiocyanate (D10) or the like. The pegylated cholesterol can also be obtained via the coupling reaction between a cholesterol derivative and a compound with a suitable reactive group. Take cholesterol succinate for example, it can be obtained via the condensation reaction with the terminal hydroxyl group of polyethylene glycol.

The pegylated biotin derivative (I3) can be obtained via the condensation reaction between the carboxyl group of biotin and a polyethylene glycol or an alcohol derivative thereof (H1) or an amine derivative (C4). The reaction condition is in accordance with that disclosed hereinbefore for the reaction between the carboxyl group and a hydroxyl group. Biotin derivatives such as D-dethiobiotin and 2-iminobiotin can also be obtained via the condensation reaction between the carboxyl group and a polyethylene glycol or an alcohol derivative thereof (H1) or an amine derivative (C4).

The pegylated biotin derivative (I3) can also be obtained via the coupling reaction between any of the above-said biotin derivatives and a suitable polyethylene glycol or a derivative thereof selected from the group consisting of a polyethylene glycol, an amine derivative (C4), an alkyne derivative (F3, G1-G10), a carboxylic acid derivative (D1), an acyl halide derivative (D4), an aldehyde derivative (D6) and the like. Wherein, the amine derivative and the alcohol derivative of biotin can also be obtained via the alkylation reaction with a corresponding polyethylene glycol sulfonate or polyethylene glycol halide.

3.4.1.10. Group J: End-Functionalization into $R_{01}$ Selected from Group J

In this Group, fluorescein and derivatives thereof (including but not limited to J1 and J3), rhodamine and derivatives thereof (including but not limited to J2), anthracene and derivatives thereof (J4), pyrene and derivatives thereof (J5), coumarin and derivatives thereof (including but not limited to J6), fluorescent yellow 3G and derivatives thereof (including but not limited to J7), carbazole and derivatives thereof (J8), imidazole and derivatives thereof (J9), and indole and derivatives thereof (J10) can be obtained via the coupling reaction between the reactive group thereof and a functional polyethylene glycol to obtain a polyethylene glycol modified bio-related substance, wherein, the reactive group of the fluorescent groups can be a succinimidyl active ester group (A1, A6), a carboxyl group (D4), a primary amino group (C4), a secondary amino group (C5, C15), a hydrazino group or a substituted hydrazino group (C12, such as an N-aminocarbazole group), a cyano group (G23), the unsaturated bond of maleimide ($E_1$), a maleimido group (C21), an aldehyde group (D6), an acrylate group ($E_2$), a methacrylate group ($E_3$), an oxime group (G24) or a hydroxyl group (H1). The coupling reactions include but are not limited to the aforesaid coupling reactions. Wherein, reagents for functional groups (J1-J10) include but are not limited to fluorescent agents disclosed hereinbefore.

3.4.1.11. The Conversion Based on a Reactive Group into the Objective Functional Group The conversion can be achieved by any of the following approaches: Approach 1: direct modification based on a reactive group to get the objective functional group. For example, the conversion of a carboxyl group to an active ester group, an analog of the active ester group, an acyl halide group, a hydrazide group, an ester group, a thioester group or a dithioester group, the conversion of a hydroxyl group, a mercapto group, an alkynyl group, an amino group, a carboxyl group or the like to a corresponding protected form thereof, the modification to a hydroxyl group, an amino group or the like with an anhydride, etc. Approach 2: the coupling reaction between two reactive groups, using a heterofunctional reagent which contains a reactive group and the objective functional group to introduce the objective functional group via the reaction between said reactive group and the terminal reactive group of a polyethylene glycol chain. The reaction manner and reaction method between the aforesaid two reactive groups are not particularly limited, including but not limited to the aforesaid coupling methods, such as an alkylation reaction, the addition reaction of an α,β-unsaturated bond, the addition reaction of an alkyne, the combination of a Schiff base reaction and a reduction reaction, a condensation reaction, the cycloaddition reaction of an azide and an alkyne, a 1,3-dipolar cycloaddition reaction, a Diels-Alder reaction, a thiol-yne reaction, a thiol-ene reaction, a thiol-vinyl reaction and the like. Wherein, the alkylation reactions are preferably based on a hydroxyl group, a mercapto group or an amino group, corresponding to the formation of an ether bond, a thioether bond, a secondary amino group or a tertiary amino group, respectively. Wherein, the condensation reactions include but are not limited to the reactions to form an ester bond, a thioester bond, an amide bond, an imine bond (—C=N—), a hydrazone bond, a carbamate bond and the like. For another example, the objective functional group can be introduced via the click reaction between a heterofunctional reagent which contains a functional group (an azido group, an alkynyl group, an alkenyl group, a trithioester group, a mercapto group, a dienyl group, a furyl group, a 1,2,4,5-tetrazinyl group, a cyano oxide group or the like) and the objective functional group. The reaction between the two reactive groups brings the formation of a new bond. Representative examples of the newly formed divalent linking group include an amide bond, a urethane bond, an ester bond, a secondary amino bond, a thioether bond, a triazole linkage and the like. Approach 3: the combination of direct modification and a coupling reaction to obtain the objective functional group.

3.4.2. The Branched End-Functionalization for Polyethylene Glycol Chains

The branched end-functionalization refers to introducing an end-branching group to link multiple functional groups to the end of one polyethylene glycol chain. Herein, the number of functional groups at one polyethylene glycol chain terminal is greater than 1. The polyethylene glycol chain end to be connected with the end-branching group can be a hydroxyl group or a linearly end-functionalized reactive group selected from Groups A to H.

3.4.2.1. Methods for Branched End-Functionalization

The branched end-functionalization includes the following two processes: one process is the introduction of an end-branching group, and the other process is the introduction of multiple functional groups. The sequence of these two processes is no particularly limited. Herein, the branched end-functionalization can be achieved in the following manners: (1) direct reaction of a functionalized end-branching group with the terminal hydroxyl group of a polyethylene glycol chain; (2) functionalization of the terminal hydroxyl group of a polyethylene glycol chain in advance which is followed by the reaction with a functionalized end-branching group; (3) introduction of an end-branching group firstly followed by subsequent functionalization to the end-branching group. Wherein, the introduction of the end-branching group can form or do not form a linking group $L_0$. Take the terminal hydroxyl group of a polyethylene glycol chain for example: with respect to the introduction of an end-branching group to be connected via an alkylation reaction, the reagent that provides the end-branching group loses a leaving group, the hydroxyl group loses a hydrogen atom, and it can be regarded that no new linking group is generated, or be regarded that a new linking group of an ether bond is generated, wherein, $L_0$ contains a moiety of $CH_2CH_2O$. For another example, with respect to the reaction between the terminal hydroxyl group of a polyethylene glycol chain and a reactive group such as an isocyanato group, a carboxyl group or the like, the whole moiety of the newly formed bond such as —NHCOO—, —COO— or the like, or only part of moiety thereof such as —NHCO—, —CO— or the like are included in $L_0$. Further for another example, the reaction between a polyethylene glycol chain end functionalized with a succinic acid group and the end-branching reagent leads to the formation of a linking group containing a succinyl linkage. The modification methods for functionalizing the end-branching group are not particularly limited, including functionalization based on a hydroxyl group and the conversion of a non-hydroxyl reactive group into a new functional group.

The method for introducing the end-branching group is not particularly limited. The available techniques in the prior art in chemistry field can be applied as long as a covalent bond can be formed, including but not limited to the various aforesaid coupling reactions. For example, the production methods for comb-like structures in the literatures including "Macromolecules 2013, 46, 3280-3287", "Macromol. Chem. Phys. 2014, 215, 566-571", "Macromolecules, 2012, 45, 3039-3046", "Polym. Chem., 2012, 3, 1714-1721", U.S. Pat. Nos. 5,811,510, 7,790,150, 7,838,619 and the like, the production methods for hyperbranched structures in the literatures including "Journal of Polymer Science, Part A: Polymer Chemistry, 2013, 51, 995-1019", "Macromol. Biosci. 2011, 11, 1553-1562", "Macromol. Rapid Commun. 2010, 31, 1811-1815", "Langmuir 2010, 26(11), 8875-8881" and the like, the production methods for dendritic structures in the literatures including "Nanoscale Research Letters, 2014, 9:247", "J. Movellan et al. Biomaterials 35 (2014) 7940-7950", "Chem. Soc. Rev., 2011, 40, 2673-2703", "Macromolecules, Vol. 33, No. 12, 2000: 4496-4500", "Biomacromolecules 2012, 13, 4089-4097" and the like. Disclosed branched structures and production methods therefor in the above-said documents are all incorporated into the present invention by reference.

Functionalization methods for the terminus of the end-branching group are not particularly limited, including but not limited to the aforesaid linear end-functionalization methods.

3.4.2.1. Reagents for Branched End-Functionalization

With respect to terminal bifunctionalization, also referred to as end-bifunctionalization, applicable reagents preferably include aforesaid heterofunctional small molecule compounds (htriSM), aldehydes containing one epoxy group, alcohols containing one epoxy group (such as

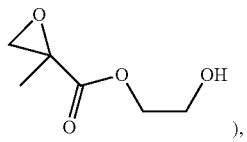

), sulfonates containing one epoxy group, halides containing one epoxy group, and compounds that contain one epoxy group and another different reactive group, and also include the combination by a primary amine and two molecules of acrylates for Michael addition reaction. Another example is that conducting termination with lipoic acid in advance, and then carrying out reduction/ring-opening reaction to the disulfide bond to obtain two terminal mercapto groups.

With respect to terminal trifunctionalization, applicable reagents include but are not limited to tetrafunctional small molecule compounds which contain three hydroxyl groups and another different kind of reactive group (htetraSM). Examples of the htetraSM include but are not limited to N-tris(hydroxymethyl)methyl-2-aminoethanesulfonic acid, 3-[tris(hydroxymethyl)methylamino]-1-propanesulfonic acid, methyl 6-O-tosyl-α-D-glucopyranoside, 2-(bromomethyl)-2-(hydroxymethyl)-1,3-propanediol, tris(hydroxymethyl)aminomethane, 2-amino-1,3,4-octadecanetriol, 3-aminopropylsilanetriol, 4-(2-amino-1-hydroxylethyl)-1,2-benzenediol, 4-[1-hydroxy-2-(propan-2-ylamino)ethyl]benzene-1,2-diol, 3,4-dihydroxy-α-(methylaminomethyl)benzyl alcohol, 2,5-anhydro-1-azido-1-deoxy-D-glucitol, 2,3,4-trihydroxybutanal (L-erythrose, D-erythrose, L-(+)-threose and D-(+)-threose), 2,3,4-trihydroxybenzaldehyde, 3,4,5-trihydroxybenzaldehyde, N-[tris(hydroxymethyl)methyl]glycine, 2,3,4-trihydroxybutyric acid (including but not limited to erythorbic acid and threonic acid), 2,4,6-trihydroxybenzoic acid, shikimic acid, 3,4,5-trihydroxybenzoic acid, 2,3,4-trihydroxybenzoic acid, arjunolic acid, 1,4,7-tris(tert-butoxycarbonyl)-1,4,7,10-tetraazacyclododecane, tris(t-butoxycarbonyl)spermine, the like, and hydroxyl-protected forms of above-said htetraSMs. The htetraSM can also be selected from the group consisting of citric acid, laricic acid, N-(2-hydroxyethyl)ethylenediamine-triacetic acid, pentaerythritol triacrylate, 4-amino-4-(2-carboxyehtyl)-heptanedioic acid (also aminomethane-tris(propionic acid)), di-tert-butyl 4-amino-4-(3-(tert-butoxy)-3-oxopropyl) heptanedioate (also aminomethane-tris(t-butyl propionate)) and the like. Examples also include the resulting compound formed via the reaction based on an alkene, trichlorosilane and allylmagnesium chloride, referring to the literature "Macromolecules, Vol. 33, No. 12, 2000, 4496-4500", wherein, a tetravalent silicon-branching center is formed. Examples also include the resulting compound formed via the reaction based on an alkene, trichlorosilane and allyl alcohol, wherein, a tetravalent silicon-branching center is formed. Trifunctional small molecules, such as 1,4,7-tris(t-butoxycarbonylmethyl)-1,4,7,10-azacyclotetradecane (NOTA), are also included, and reagents of such trifunctional small molecules require an excess amount for reaction.

With respect to terminal tetrafunctionalization, applicable reagents can be pentafunctional compounds such as xylitol, 1,5-anhydroglucitol, bis(2-hydroxyethyl)iminotris(hydroxymethyl)methane, miglitol, D-(+)-talose, arbutin, diethylenetriaminepentaacetic acid and the like, but preferably heteropentafunctional small molecules that contain two different kinds of functional groups, including but not limited to compounds with four protected hydroxyl groups and one reactive group such as 1,2:5,6-di-O-isopropylidene-α-D-isofuranose, 2,3:5,6-di-O-cyclohexylidene-α-D-mannofuranose, 2-azido-1,3-bis(2,2-dimethyl-1,3-dioxan-5-yl)oxy]propane and the like. The pentafunctional compounds also include but are not limited to molecules which contain two epoxy groups and one reactive group. The pentafunctional compounds can also be preferably pentafunctional small molecules (hpentSM) that contain two kinds of functional groups, wherein, one kind is four in quantities and the other kind is one, such as 2-(2-hydroxyethylamino)-2-(hydroxymethyl)-1,3-propanediol, 2-hydroxymethyl-piperidine-3,4,5-triol, 6-amino-4-(hydroxymethyl)-4-cyclohexane-[4H,5H]-1,2,3-triol, fenoterol, benserazide, 1-azido-1-deoxy-β-D-galactopyranoside, 2-azidoethyl β-D-glucopyranoside, 2,3,4,5-tetrahydroxypentanal (including but not limited to ribose, arabinose, xylose and lyxose), 2,3,4,5-tetrahydroxypentanoic acid (including but not limited to ribonucleic acid, arabinonic acid, lignic acid and lysuccinic acid), diethylenetriamine, N-(3-aminopropyl)-1,4-diaminebutane, the like, and protected forms of any above-said hpentSM in which the functional groups in quantities of four are protected.

With respect to terminal pentafunctionalization, applicable reagents are preferably a hexafunctional small molecule (hhexaSM) which contains two kinds of functional groups, wherein, one kind is five in quantities and the other kind is one, including but not limited to sorbitol, mannitol, D-talitol, D-glucamine, 1-mercapto-D-glucitol, N-methyl-D-glucamine, 2,3,4,5,6-pentahydroxyhexanal (including, but not limited to β-D-allose, D-altrose, D-glucose anhydrous, D-(+)-mannose, L-(−)-mannose, D-gluconose, idose, D-galactose, L(−)-talose and D-(+)-talose), 2,3,4,5,6-pentahydroxyhexanoic acid (including but not limited to allonic acid, altronic acid, gluconic acid, mannonic acid, gulonic acid, idonic acid, galactonic acid and talonic acid), D-sorbitol 3-phosphate, the like, and protected forms of any above-said hhexaSM in which the functional groups in quantities of five are protected.

Applicable reagents for providing dendritic end-branching groups can include but not limited to the group consisting of htriSMs, htetraSMs, hpentSMs, hhexaSMs, heterofunctional molecules containing one epoxy group and another kind of reactive group, htriSM molecules containing two unprotected or protected ethynyl groups and another kind of reactive group, diallyl(methyl)silane, the combination of acrylates and diamines (repeating Michael addition reaction between a primary amine and two molecules of acrylates and the amidation reaction of the ester group), the combination of glycidyl propargyl ether and mercaptoethylamine, mercaptoethylamine hydrochloride or amino-protected mercaptoethylamine (repeating the addition reaction between a primary amino group and an epoxy group and the click reaction between an alkynyl group and two mercapto groups), a diallylmethylsilyl group and the like. Specific examples include,

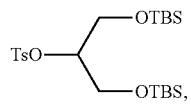

epichlorohydrin, lysine with two amino groups being protected, glutamic acid, aspartic acid, N,N-bis(2-hydroxyethyl)glycine and hydroxyl-protected form thereof with two hydroxyl groups being protected, dihydroxy monocarboxylic acids and hydroxyl-protected forms thereof, hydroxy dicarboxylic acids and hydroxyl-protected forms thereof, amino dicarboxylic acids and amino-protected forms thereof, mercaptodicarboxylic acids and mercapto-protected forms thereof, glyceraldehyde and hydroxyl-protected form thereof, methyl 6-O-tosyl-α-D-galactopyranoside, 3-aminopropylsilanetriol, 2,3,4-trihydroxybutanal, 2,3,4-trihydroxybutanoic acid, citric acid, N-(2-hydroxyethyl)ethylenediaminetriacetic acid,

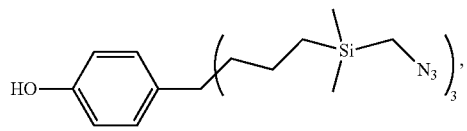

2-azido-1,3-bis[(2,2-dimethyl-1,3-dioxan-5-yl)oxo]propane, etc. Wherein, the dihydroxy monocarboxylic acid is preferably 2,2-bis(hydroxymethyl)propionic acid. The hydroxy dicarboxylic acid is preferably malic acid or 3-hydroxypentanedioic acid.

Applicable monomers used for preparing hyperbranched end-branching structures include but are not limited to those monomers disclosed in the literature "Journal of Polymer Science, Part A: Polymer Chemistry, 2013, 51, 995-1019", for example, glycidol,

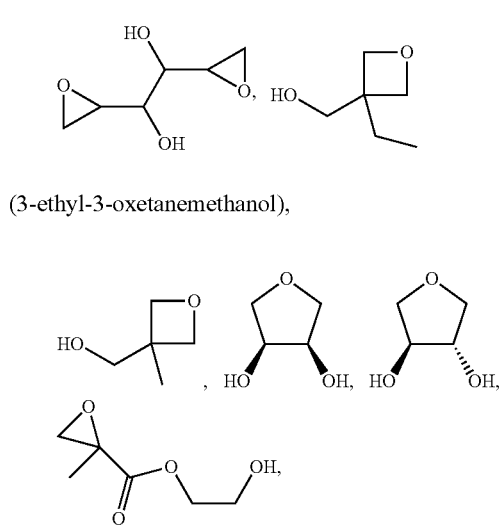

(3-ethyl-3-oxetanemethanol), the combination of acrylates and diamines and the like.

Applicable monomers used for preparing comb-like end-branching structures containing repeat units include but are not limited to glycerol with a protected 2-hydroxyl group which can form a multiglycidyl ether, pentaerythritol with two hydroxyl groups being protected (e.g., benzaldehyde monopentaerythritolacetel as a monomer to form polypentaerythritol),

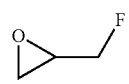

(the definition of F is the same as above, wherein, F is preferably a protected form, and one preferable form is a protected hydroxyl group $OPG_4$; e.g., 1-ethoxyethyl (2,3-epoxy)propyl ether, benzyl glycidyl ether butyl glycidyl ether, allyl glycidyl ether, glycidyl propargyl ether, glycidyl methacrylate,

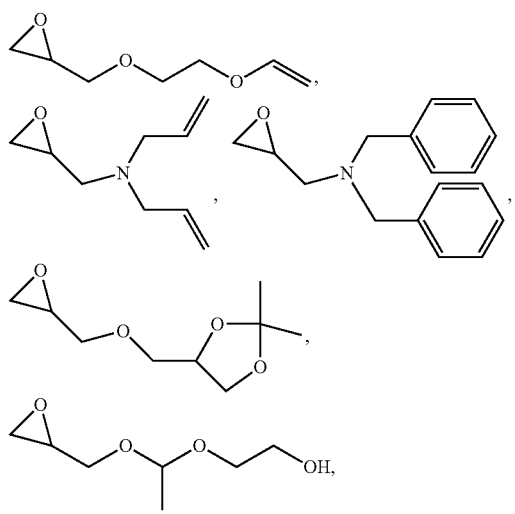

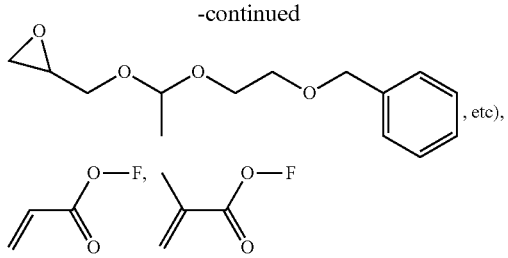

(e.g., azidopropyl methacrylate), the combination of carbon dioxide and

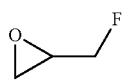

(e.g., "Macromolecules 2013, 46, 3280-3287"; e.g., the combination of carbon dioxide and

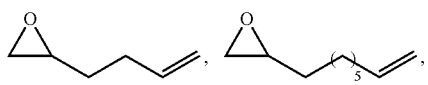

glycidyl propargyl ether or the like), the combination of a diisocyanate and a diol having one unprotected or protected reactive group),

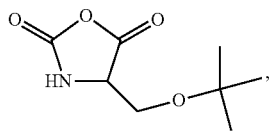

the combination of

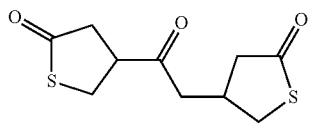 [SMILES: O=C1CC(CC(=O)C2CSC(=O)C2)CS1]

and a diamine (to form a comb-like structure with multiplependent mercapto groups, referring to "Macromol. Rapid Commun. 2014, 35, 1986-1993"), D-glucopyranose (to form glycan of an acetal structure, such as (1→6)polyhexose, (2→1)polyfructosan; specific examples include glucans disclosed in the literatures including U.S. Pat. Nos. 5,811,510, 7,790,150 and 7,838,619, oxidized structures of those glucans and polyfructose), lysine, aspartic acid, glutamic acid and the like. Other triols, tri- or tetra-ols with one hydroxyl group being protected, tetraols with two hydroxyl groups being protected, multiols with only two active hydroxyl groups and other hydroxyl groups being protected can also be used as reagents for preparing comb-like end-branching structures. In addition, the comb-like structure can be a non-repeated structure, e.g., polypeptide structures formed by using some amino acids such as glycine as the spacer group and using more than two amino acids selected from lysine, aspartic acid or/and glutamic acid as branching unit.

Moreover, the monomers including but not limited to 2,3,4,5-tetrahydroxy-petanal, 2,3,4,5-tetrahydroxy-pentanoic acid, 2,3,4,5,6-pentahydroxy-hexanal, 2,3,4,5,6-pentahydroxy-hexanoic acid, D-glucamine, 1-mercaptoglucitol, N-methyl-D-glucamine, D-sorbitol-3-phosphate and the like can directly be used as reagents for preparing comb-like branched terminals.

Applicable reagents for preparing cyclic end-branching structures include but are not limited to 2,5-anhydro-1-azido-1-deoxy-D-glucitol, 1,4,7-tris-(t-butoxycarbonyl)-1,4,7,10-tetraazacyclododecane, 2-hydroxymethyl-piperidine-3,4,5-triol, 6-amino-4-(hydroxymethyl)-4-cyclohexane-[4H,5H]-1,2,3-triol, 1-azido-1-deoxy-β-D-galactopyranoside, 2-azidoethyl β-D-glucopyranoside, propargyl α-D-mannopyranoside, propargyl α-L-fucopyranoside, propargyl β-D-lactoside, monofunctionalized cyclodextrin (e.g., mono-6-O-(azido)-6-deoxy-β-cyclodextrin, mono-6-O-(p-toluenesulfonyl)-γ-cyclodextrin, mono-2-O-(p-toluenesulfonyl)-γ-cyclodextrin, mono-6-O-(p-toluenesulfonyl)-β-cyclodextrin, mono-2-O-(p-toluenesulfonyl)-α-cyclodextrin and the like), etc.

3.5. The Formation of the Branching Centers in $CORE_8$ and Terminal G

The branching centers in $CORE_8$ and terminal G are each independently selected from but not limited to the group consisting of a carbon atom, a nitrogen atom, a phosphorus atom, a silicon atom, a cyclic structure and the combination of any two or two more kinds of the foregoing. The trivalent branching center can be of a symmetrical structure or of an asymmetric structure.

The branching centers can directly come from reagents, or be obtained via coupling reaction between reagents.

With respect to examples of reagents for direct sources, the symmetrical trivalent carbon-branching center can come from

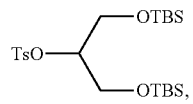

2-amino-1,3-propanediol (also serinol), 2,2-bis(hydroxymethyl)propionic acid (DMPA), etc; the asymmetrical trivalent carbon-branching center can come from epichlorohydrin, glycidol, 3-methylamino-1,2-propanediol, malic acid, 3-hydroxypentanedioic acid, lysine, glutamic acid, aspartic acid, etc; the symmetrical trivalent nitrogen-branching center can come from N,N-bis(2-hydroxyethyl)ethylenediamine, N,N-dihydroxyethylglycine, etc; the tetravalent carbon-branching center can come from pentaerythritol, citric acid, etc; the cyclic branching center can come from 3,6-diaminocarbazole, 2,5-anhydro-D-glucitol, α-methyl-D-mannopyranoside, dihydroxybenzoic acids (including various isomers at different substituted positions), dihydroxyphenylacetic acids (including various isomers at different substituted positions), aminoresorcinols (including various isomers at different substituted positions),

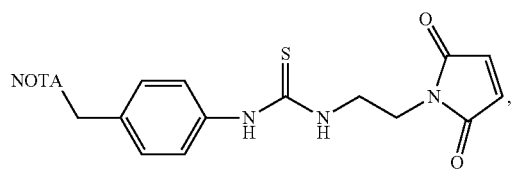

etc; the phosphorus-atom branching center can come from phosphoric acid, phosphate, thiophosphoric acid and thiophosphate.

With respect to examples of branching centers obtained via coupling reaction between reagents, the trivalent nitrogen-branching center can be obtained via the alkylation or amidation reaction of a secondary amine; the trivalent nitrogen-branching center can also be obtained via the reaction between a primary amine and two molecules of sulfonate, halide, epoxide or an α,β-unsaturated compound (such as acrylate); the asymmetrical trivalent carbon-branching center can be obtained via the reaction between an alkynyl group and two mercapto groups; the trivalent carbon-branching center can also be obtained via the reaction between a functional group from functional Group B5 or Group B6 and a disulfide bond; the tetravalent silicon-branching center can be obtained via the branched end-functionalization reaction based on an alkene, trichlorosilane and allylmagnesium chloride, or via the branched end-functionalization reaction based on an alkene, trichlorosilane and allyl alcohol; the trivalent silicon-branching center can be obtained via the reaction of diallylmethylsilane as repeat unit; the asymmetrical carbon-branching structure with two thioxy groups can be obtained via the reduction reaction of the disulfide bond in the five-membered ring of lipoic acid; the trivalent carbon-branching center of an acetalated structure, which can be degraded, can be obtained via the acetalation reaction of 4-(hydroxymethyl)benzaldehyde; the symmetrical trivalent carbon-branching center can be obtained via the reaction between a functional group from functional Group B5 or Group B6 and a disulfide bond.

3.6 Purification of Intermediates and Products

The intermediates and products involved in the present invention can be purified by a purification means such as, but not limited to, extraction, recrystallization, adsorption treatment, precipitation, reverse precipitation, membrane dialysis, supercritical extraction or the like. The characterization methods for the structure, molecular weight and molecular weight distribution of key intermediates and products include but are not limited to NMR, electrophoresis, UV-visible spectrophotometer, FTIR, AFM, GPC, HPLC, MALDI-TOF, circular dichroism and the like. With respect to a monodisperse eight-arm polyethylene glycol derivative, the molecular weight is preferably determined by MALDI-TOF. The identification methods for characteristic peaks in NMR spectra include but are not limited to those described and listed in the documents CN104877127A, CN104530413A, CN104530415A, CN104530417A and respective cited documents therein. The end-functionalization ratio (substitution ratio) of the functional eight-arm polyethylene glycol, i.e. the molar percentage of the functionalized terminal hydroxyl groups of the eight-arm polyethylene glycol, can be obtained via calculated conversion based on the integral ratio of peak area of terminal hydroxyl groups —CH$_2$CH$_2$OH relative to peak area of the EO segment —CH$_2$CH$_2$O— in the spectrum of the eight-arm polyethylene glycol compound, and the integral ratio of peak area of the functional group relative to peak area of the EO segment —CH$_2$CH$_2$O— in the spectrum of the functional eight-arm polyethylene glycol, wherein, the calculated conversion method is well known to those skilled in the art, and no more repeated here.

In the present invention, the molecular weight deviation is generally controlled within 10%, sometimes can be within 8%, and can even reach within 5%. The PDI value is generally controlled below 1.15, preferably below 1.10 to 1.08. For most molecular weights from 5 kDa to 40 kDa, the PDI value is stably controlled below 1.05, sometimes can be below 1.03, and can even reach below 1.02. For a monodisperse structure, PDI can achieve a value equal to 1 (PDI=1).

Hereinafter, the eight-arm polyethylene glycol derivative and production methods therefor are described more specifically with reference to EXAMPLES in the present invention. The specific embodiments and examples are provided to further illustrate the invention, and should not be regarded as limitation to the protection scope of the present invention. In some examples of preparing eight-arm polyethylene glycol derivatives, the molecular weight of monodisperse reagents, key intermediates and the resulting products are determined by MALDI-TOF. The identification methods for characteristic peaks in NMR test can use the analysis methods disclosed in the embodiments and examples of the documents CN104877127A, CN104530413A, CN104530415A, CN104530417A and respective cited documents therein. The yield of the eight-arm polyethylene glycol modified bio-related substance refers to the percentage of actual product weight relative to theoretical weight.

Example-1: Preparation of an Eight-Arm Polyethylene Glycol Succinimidyl Propionate Derivative (A1-1)

In this example, the structure of the eight-arm polyethylene glycol derivative was designed as follows: U=C(CH$_2$O—)$_4$,

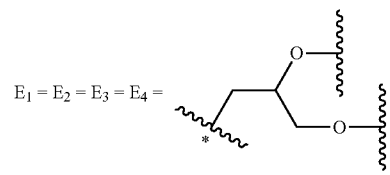 [SMILES: *CC(CO*)O*]

$E_1 = E_2 = E_3 = E_4 =$ (with a carbon-branching center of an asymmetrical type), $L_{11}=L_{12}=L_{21}=L_{22}=L_{31}=L_{32}=L_{41}=L_{42}=CH_2CH_2$, g=0, and F=CH$_2$CH$_2$CONHS (wherein, $Z_2$ is absent, $Z_1$ is CH$_2$CH$_2$, and $R_{01}$ is CONHS). The designed total molecular weight is approximately 21.5 kDa, wherein, the molecular weight of the eight PEG chains is approximately 8×2500=20000 Da, corresponding to $n_1 \approx n_2 \approx n_3 \approx n_4 \approx n_5 \approx n_6 \approx n_7 \approx n_8 = 56$.

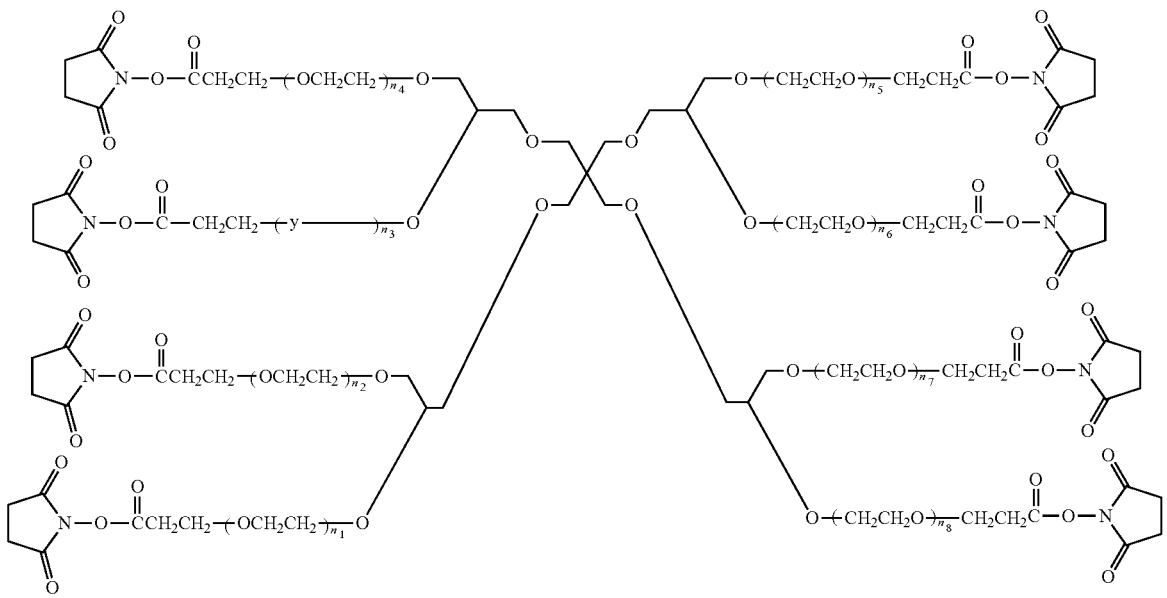

A1-1

Step (a): Into a clean and sealed reactor, 20% potassium hydroxide aqueous solution (250 mL) and pentaerythritol glycidyl ether (50 mmol) were added in sequence, followed by reaction for 4 hours. The product in the solvent was extracted, washed and purified via column chromatography, and then a small molecule initiator S1-2 containing eight hydroxyl groups (an octahydroxyl-containing small molecule initiator, OctaIN) was obtained.

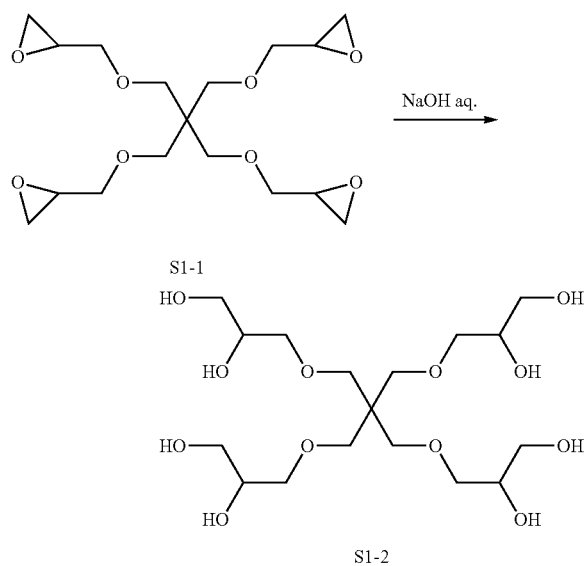

S1-1

S1-2

$^1$H NMR spectrum data of the initiator S1-2 were as follows: $^1$H NMR (CDCl$_3$) δ (ppm): 3.29 (C(CH$_2$O—)$_4$), 3.52 (—OCH$_2$CH—), 3.63 (—CH(OH)CH$_2$OH); 3.68 (—CH(OH)CH$_2$OH).

Step (b): Into a sealed reactor under an anhydrous and oxygen-free atmosphere, tetrahydrofuran (250 mL), the octahydroxyl-containing initiator S1-2 (1.266 mmol) and diphenylmethyl potassium (DPMK, 4.0 mmol) were added in sequence.

Step (c): After the addition of a calculated amount of ethylene oxide, the whole was heated stepwisely to 60° C., followed by reaction for 48 hours.

Step (d): Excess methanol as a proton source was added, thereafter the product in the solvent was concentrated and precipitated, and then an eight-arm polyethylene glycol H1-1 was obtained.

$^1$H NMR spectrum data of the eight-arm polyethylene glycol H1-1 were as follows: $^1$H NMR (CDCl$_3$) δ (ppm): 3.20-3.40 (C(CH$_2$O—)$_4$), 3.40-3.80 (—CH$_2$CH$_2$O—, —OCH$_2$CH—, —CH(OH)CH$_2$OH); M$_n$≈20 kDa, PDI=1.03.

H1-1

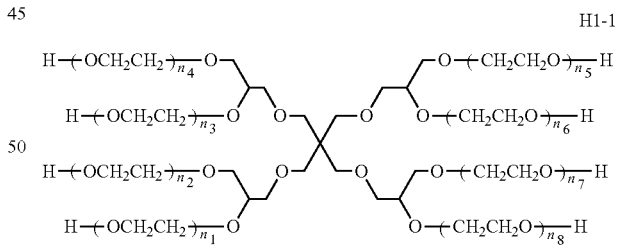

Step (e): Into a dry and clean 1 L round-bottom flask, 80 mmol of KOH and 400 mL of H$_2$O were added in sequence. The eight-arm polyethylene glycol intermediate (H1-1, treated by azeotropic removal of water with toluene) in an amount of 20 g (8 mmol equivalents relative to the hydroxyl group) was added slowly in an ice bath, followed by stirring at room temperature for 3 hours; thereafter, 80 mmol of acrylamide was added thereinto, and the reaction was carried out at room temperature for 24 hours, and then a small amount of concentrated hydrochloric acid was added to quench the reaction. The product in the solvent was concentrated, dissolved with dichloromethane (400 mL), washed with saturated salt solutions (100 mL trice), dried, concentrated and recrystallized, and then an eight-arm polyethylene glycol propionic acid derivative D1-1 in a white solid state was obtained.

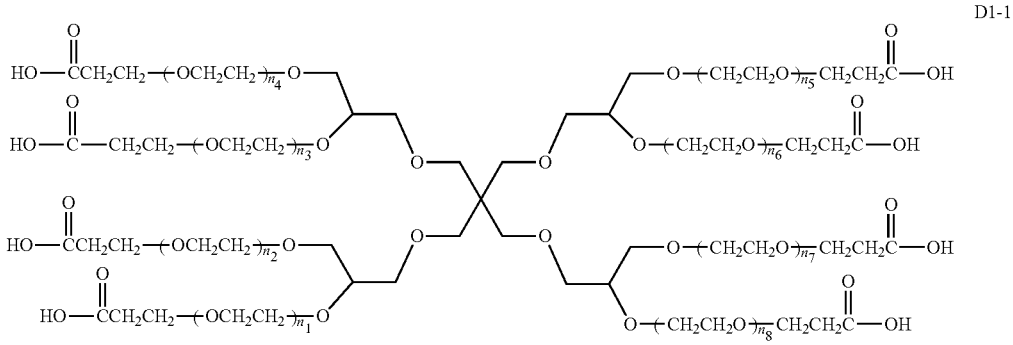

D1-1

$^1$H NMR spectrum data of the eight-arm polyethylene glycol propionic acid derivative D1-1 were as follows: $^1$H NMR (CDCl$_3$) δ (ppm): 2.40-2.60 (—CH$_2$CH$_2$COOH), 3.20-3.40 (C(CH$_2$O—)$_4$); 3.40-3.80 (—CH$_2$CH$_2$O—, —OCH$_2$CH(O—)CH$_2$O—, —CH$_2$CH$_2$COOH).

Step (f): Into a dry and clean 1 L round-bottom flask, 20 g of the eight-arm polyethylene glycol propionic acid derivative D1-1, 20 mL of triethylamine and 10 g of N-hydroxyl succinimide were added. Under nitrogen protection, dichloromethane (500 mL) was added, and the whole was stirred till dissolution. Subsequently, a solution of 20 g of dicyclohexylcarbodiimide (DCC) in dichloromethane was added thereinto, followed by reaction at room temperature for 24 hours. After completion of the reaction, the resulting mixture was filtrated to remove undissolved substances, concentrated and recrystallized from isopropanol, and then an eight-arm polyethylene glycol active ester derivative A1-1 in a white solid state was obtained.

$^1$H NMR spectrum data of the eight-arm polyethylene glycol active ester derivative A1-1 were as follows: $^1$H NMR (CDCl$_3$) δ (ppm): 2.40-2.60 (—CH$_2$CH$_2$COO—), 2.70-2.85 (—(O═)CCH$_2$CH$_2$C(═O)—), 3.20-3.40 (C(CH$_2$O—)$_4$), 3.40-3.80 (—CH$_2$CH$_2$O—, —OCH$_2$CH(O—)CH$_2$O—, —CH$_2$CH$_2$COO—); M$_n$≈21 kDa, PDI=1.03.

Example-2: Preparation of an Eight-Arm Polyethylene Glycol Thiazolidine-2-Thione Derivative, (A15-1)

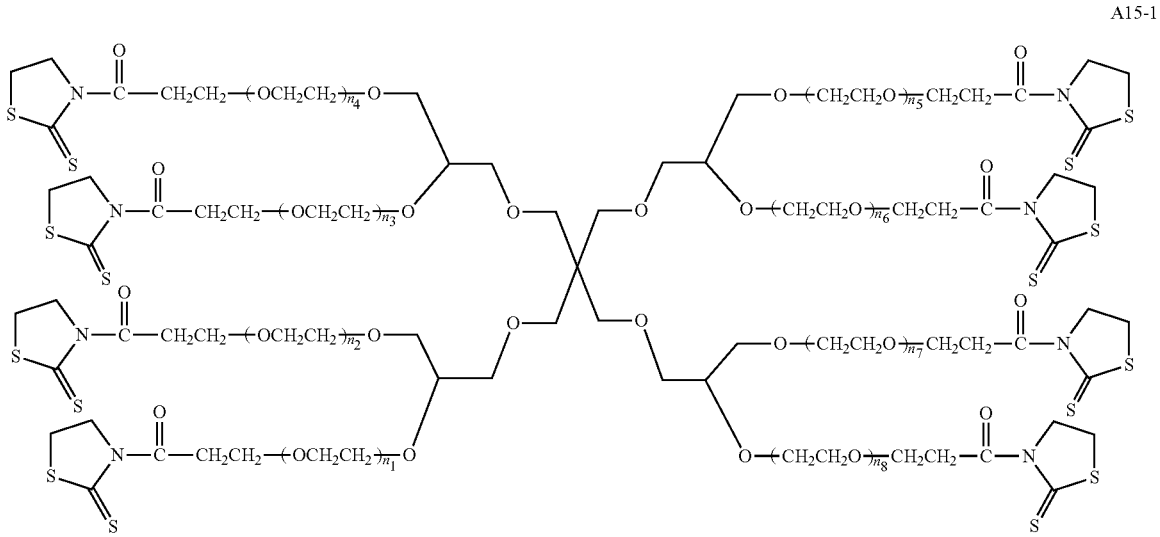

A15-1

Herein, the structure of the eight-armed polyethylene glycol derivative was designed as follows: U═C(CH$_2$O—)$_4$,

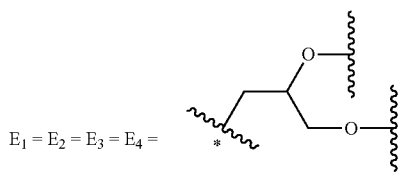 [SMILES: *CC(CO*)O*]

$E_1 = E_2 = E_3 = E_4 =$ (with a carbon-branching center of an asymmetrical type), g=0, $L_{11}=L_{12}=L_{21}=L_{22}=L_{31}=L_{32}=L_{41}=L_{42}=CH_2CH_2$, and

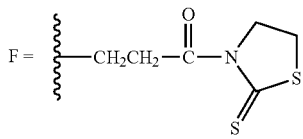

(wherein, $Z_2$ is absent, and $Z_1$ is $CH_2CH_2$). The designed total molecular weight is approximately 21.5 kDa, wherein, the molecular weight of the eight PEG chains is approximately 8×2500=20000 Da, corresponding to $n_1 \approx n_2 \approx n_3 \approx n_4 \approx n_5 \approx n_6 \approx n_7 \approx n_8 \approx 56$.

Into a dry and clean 1 L round-bottom flask, 20 g of the eight-arm polyethylene glycol propionic acid derivative D1-1 obtained in Example-1, 20 mL of triethylamine and 10 g of thiazolidine-2-thione were added. Under nitrogen protection, dichloromethane (500 mL) was added, and the whole was stirred till dissolution. Subsequently, a solution of 20 g of dicyclohexylcarbodiimide (DCC) in dichloromethane was added thereinto, followed by reaction at room temperature for 24 hours. After completion of the reaction, the resulting mixture was filtrated to remove undissolved substances, concentrated and recrystallized from isopropanol, and then an eight-arm polyethylene glycol thiazolidine-2-thione derivative A15-1 in a white solid state was obtained.

$^1$H NMR spectrum data of the eight-arm polyethylene glycol thiazolidine-2-thione derivative A15-1 were as follows: $^1$H NMR (CDCl$_3$) δ (ppm): 2.40-2.60 (—CH$_2$CH$_2$CO—), 3.20-3.40 (C(CH$_2$O—)$_4$); 3.40-3.80 (—CH$_2$CH$_2$O—, —NCH$_2$CH$_2$S—, —OCH$_2$CH(O—)CH$_2$O—, —CH$_2$CH$_2$CO—), 4.50-4.70 (—NCH$_2$CH$_2$S—); $M_n \approx 21$ kDa, PDI=1.03.

Example-3: Preparation of an Eight-Arm Polyethylene Glycol Sulfone Derivative (B5-1)

Herein, the structure of the eight-armed polyethylene glycol derivative was designed as follows:

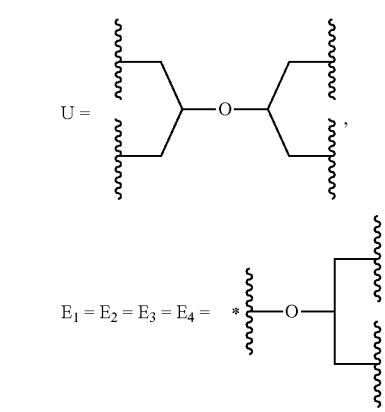

(with a carbon-branching center of a symmetrical type), the divalent linking groups $L_{11}$, $L_{12}$, $L_{21}$, $L_{22}$, $L_{31}$, $L_{32}$, $L_{41}$ and $L_{42}$ are all absent, g=0, and

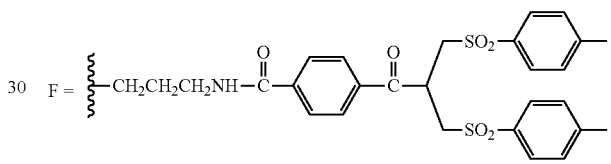

(wherein, $Z_2$ is $CH_2CH_2CH_2NH$, $Z_1$ is $COPh$, and $R_{01}$ is $COCH(CH_2S(=O)_2PhCH_3)_2$). The designed total molecular weight is approximately 68.5 kDa, wherein, the molecular weight of the eight PEG chains is approximately 8×8000=64000 Da, corresponding to $n_1 \approx n_2 \approx n_3 \approx n_4 \approx n_5 \approx n_6 \approx n_7 \approx n_8 \approx 181$.

B5-1

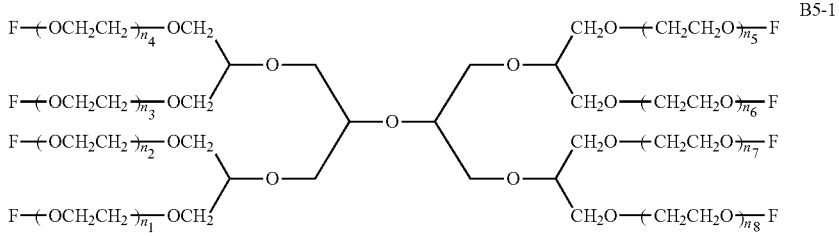

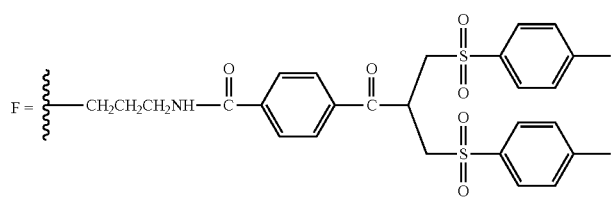

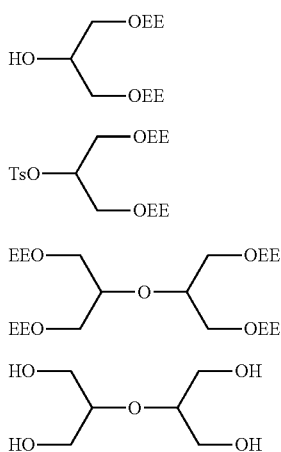

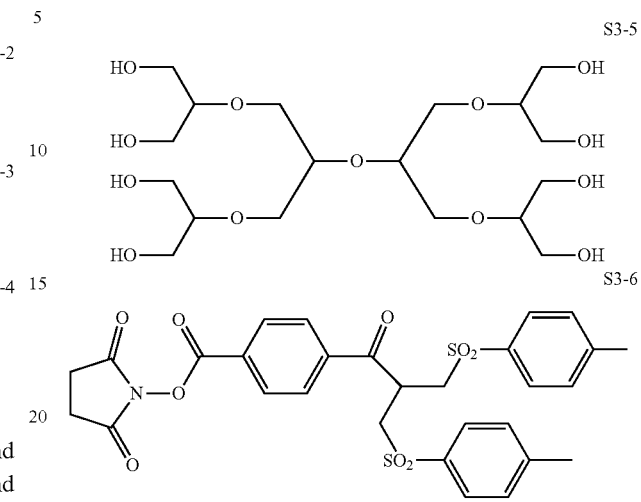

Step (a): Into a sealed reactor under an anhydrous and oxygen-free atmosphere, tetrahydrofuran (400 mL) and excess diphenylmethyl potassium (100 mmol) were added, then equal equivalents of a compound S3-1 and a compound S3-2 (50 mmol, OTs is a tosylate group) were added, followed by reaction at 30° C. for 12 hours. After completion of the reaction, open the reactor. The product in the solvent was concentrated, washed and purified via column chromatography, and then a small molecule compound S3-3 containing four protected hydroxyl groups was obtained.

Step (b): Into a dry and clean container, the intermediate S3-3 obtained in Step (a) was dissolved with methanol. The reaction solution was adjusted to pH 3.5 with the addition of hydrochloric acid (1 M), followed by reaction for 4 hours, and a small molecule compound S3-4 containing four unprotected hydroxyl groups was obtained.

Step (c): Into a sealed reactor under an anhydrous and oxygen-free atmosphere, tetrahydrofuran (400 mL), the compound S3-4 (10 mmol) and excess diphenylmethyl potassium (100 mmol) were added in sequence, then the compound S3-2 (100 mmol) was added, followed by reaction at 30° C. for 12 hours. After opening the reactor, the product in the solvent was washed, concentrated and then dissolved with methanol. The solution was adjusted to pH 3.5 with the addition of hydrochloric acid (1 M), followed by reaction for 4 hours. Thereafter, the product in the solvent was concentrated, washed and purified via column chroma-tography, and then a small molecule initiator S3-5 containing eight hydroxyl groups was obtained.

$^1$H NMR spectrum data of the octahydroxyl-containing small molecule initiator S3-5 were as follows: $^1$H NMR (CDCl$_3$) δ (ppm): 2.90-3.10 (—OCH(CH$_2$OH)$_2$), 3.40-3.50 (—OCH(CH$_2$O—)$_2$, —OCH(CH$_2$O—)$_2$, —OCH(CH$_2$OH)$_2$).

Step (d): Into a sealed reactor under an anhydrous and oxygen-free atmosphere, tetrahydrofuran (250 mL), the octahydroxyl-containing small molecule initiator S3-5 (1.266 mmol) and diphenylmethyl potassium (4.0 mmol) were added in sequence.

Step (e): After the addition of a calculated amount of ethylene oxide, the whole was heated stepwisely to 60° C., followed by reaction for 48 hours; thereafter, excess methanol as a proton source was added thereinto, and then an eight-arm polyethylene glycol H1-2 was obtained.

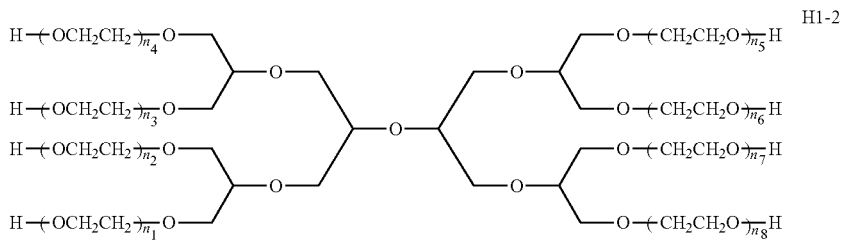

$^1$H NMR spectrum data of the eight-arm polyethylene glycol H1-2 were as follows: $^1$H NMR (CDCl$_3$) (ppm): 3.40-3.80 (—CH$_2$CH$_2$O—, —OCH(CH$_2$O—)$_2$). M$_n$≈64 kDa, PDI=1.06.

Step (f): Into a dry and clean 1 L round-bottom flask, 20 g of the eight-arm polyethylene glycol H1-2 was added. Under nitrogen protection, 500 mL of 1,4-dioxane was added, and the whole was stirred till dissolution. In an ice bath, 5 g of 50% potassium hydroxide solution was added thereinto, and then 3-chloropropionitrile was added dropwisely and in excess, followed by reaction at room temperature for 24 hours. Thereafter, the solution was adjusted to pH 7 with hydrochloric acid (1 mol/L) and then concentrated to remove 1,4-dioxane. The product was dissolved with 400 mL of deionized water, and then the aqueous phase was washed with dichloromethane (200 mL trice). The organic phase was combined, washed with saturated salt solutions, dried with anhydrous sodium sulfate, filtrated, concentrated and precipitated, and then an eight-arm polyethylene glycol propionitrile derivative G23-1 was obtained.

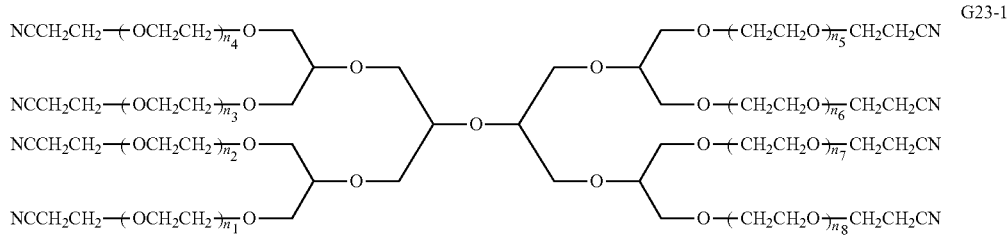

G23-1

$^1$H NMR spectrum data of the eight-arm polyethylene glycol propionitrile derivative G23-1 were as follows: H NMR (CDCl$_3$) δ (ppm): 2.60 (—CH$_2$CH$_2$CN), 3.40-3.80 (—CH$_2$CH$_2$—, —OCH(CH$_2$O—)$_2$, —OCH$_2$CH$_2$CN).

Step (g): Into a 1 L high-pressure reactor, 50 g of the eight-arm polyethylene glycol propionitrile derivative G23-1 obtained in Step (f) was added in advance, 500 mL of toluene was added subsequently, and then the whole was heated till dissolution. After the addition of 5.0 g of nickel, the reactor was pressurized with ammonia to 0.7 MPa and then with hydrogen to 4.5 MPa. The reaction was conducted at 130° C. overnight. After completion of the reaction, the product in the solution was filtrated, concentrated and recrystallized from isopropanol, and then an eight-arm polyethyleglycopropylamine derivative C4-1 was obtained.

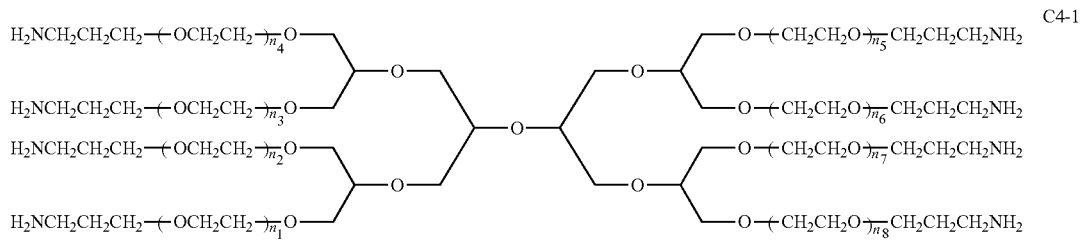

C4-1

$^1$H NMR spectrum data of the eight-arm polyethylene glycol propylamine derivative C4-1 were as follows: $^1$H NMR (CDCl$_3$) δ (ppm): 1.81 (—CH$_2$CH$_2$CH$_2$NH$_2$), 2.70-2.85 (—CH$_2$CH$_2$CH$_2$NH$_2$), 3.40-3.80 (—CH$_2$CH$_2$O—, —OCH(CH$_2$-)$_2$, —OCH$_2$CH$_2$CH$_2$NH$_2$).

Step (h): Into a dry and clean 1 L round-bottom flask, 20 g of the eight-arm polyethylene glycol propylamine derivative C4-1 obtained in Step (g), 500 mL of acetonitrile, 40 mL of triethylamine and 10 g of a compound S3-6 were added, followed by reaction at room temperature for 24 hours. Thereafter, the resulting solution was concentrated and recrystallized from isopropanol, and then an eight-arm polyethylene glycol sulfone derivative B5-1 in a white solid state was obtained.

$^1$H NMR spectrum data of the eight-arm polyethylene glycol sulfone derivative B5-1 were as follows: $^1$H NMR (CDCl$_3$) δ (ppm): 1.77 (—CH$_2$CH$_2$CH$_2$NH—), 2.35 (CH$_3$C$_6$H$_4$SO$_2$—), 3.0-3.20 (—C$_6$H4C(=O)CH(CH$_2$SO$_2$-)$_2$, —CH$_2$CH$_2$CH$_2$NH—), 3.40-3.80 (—OCH$_2$CH$_2$CH$_2$NH—, —CH$_2$CH$_2$O—, —C$_6$H4SO$_2$CH$_2$—, —OCH(CH$_2$O—)$_2$), 7.30-7.80 (CH$_3$C$_6$H$_4$SO$_2$—); M$_n$≈68 kDa, PDI=1.06.

Example-4: Preparation of an Eight-Arm Polyethylene Glycol Guanidine Derivative (D21-1)

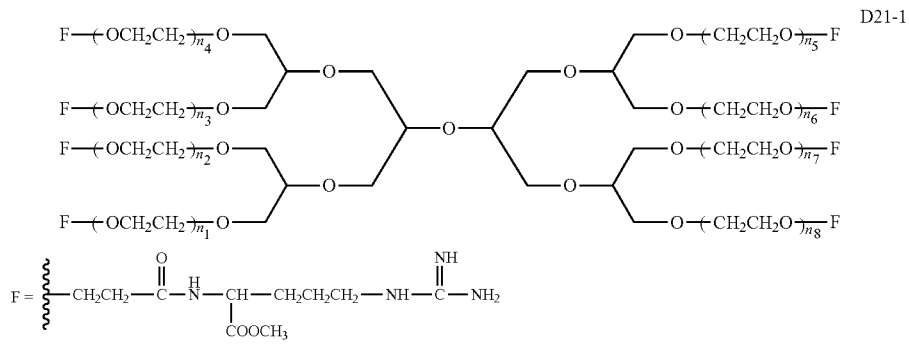

Herein, the structure of the eight-armed polyethylene glycol derivative was designed as follows:

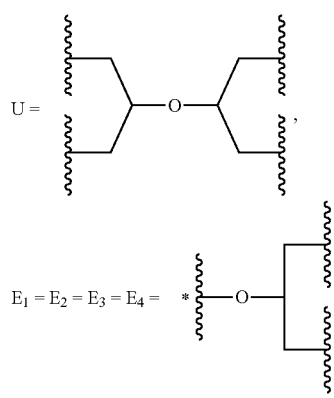

(with a carbon-branching center of a symmetrical type), the divalent linking groups $L_{11}$, $L_{12}$, $L_{21}$, $L_{22}$, $L_{31}$, $L_{32}$, $L_{41}$ and $L_{42}$ are all absent, g=0, and

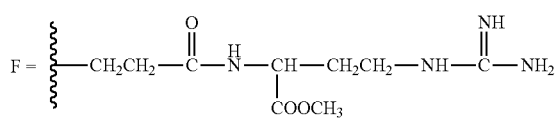

(wherein, $Z_2$ is $CH_2CH_2CO$, $Z_1$ is $NHCH(COOCH_3)CH_2CH_2$, and $R_{01}$ is $NHC(=NH)NH_2$). The designed total molecular weight is approximately 66.1 kDa, wherein, the molecular weight of the eight PEG chains is approximately 8×8000=64000 Da, corresponding to $n_1 \approx n_2 \approx n_3 \approx n_4 \approx n_5 \approx n_6 \approx n_7 \approx n_8 \approx 181$.

Step (a): Into a dry and clean 1 L round-bottom flask, 80 mmol of KOH and 400 mL of $H_2O$ were added in sequence, and then 20 g of the eight-arm polyethylene glycol (H1-2, treated by azeotropic removal of water with toluene) obtained in Example-3 was added slowly in an ice bath, followed by stirring at room temperature for 3 hours; then 80 mmol of acrylamide was added, followed by reaction at room temperature for 24 hours. Thereafter, a small amount of concentrated hydrochloric acid was added to quench the reaction. The product in the solution was concentrated, dissolved with dichloromethane (400 mL), washed with saturated salt solutions (100 mL trice), dried, concentrated and recrystallized, and then an eight-arm polyethylene glycol propionic acid derivative D1-2 in a white solid state was obtained.

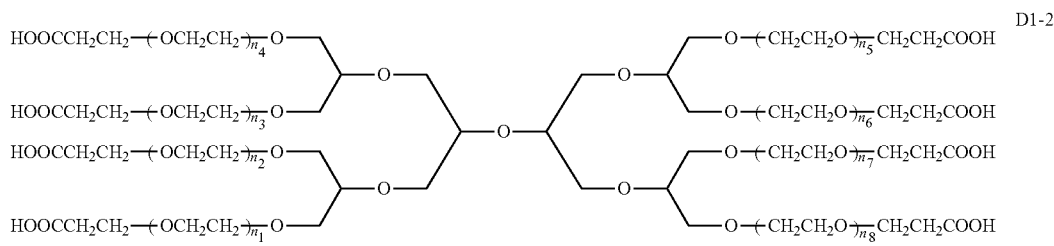

$^1$H NMR spectrum data of the eight-arm polyethylene glycol propionic acid derivative D1-2 were as follows: $^1$H NMR ($CDCl_3$) δ (ppm): 2.40-2.60 (—$CH_2CH_2COOH$), 3.40-3.80 (—$CH_2CH_2O$—, —$CH_2CH_2COOH$, —$OCH(CH_2O$—$)_2$).

Step (b): Into a dry and clean 1 L round-bottom flask, 20 g of the eight-arm polyethylene glycol propionic acid derivative D1-2, 20 mL of triethylamine and 10 g of arginine-methyl ester hydrochloride were added. Under nitrogen protection, a solvent DMF (200 mL) was added, and the whole was stirred till dissolution. Subsequently, a solution of 20 g of dicyclohexylcarbodiimide (DCC) in dichloromethane was added thereinto, followed by reaction at room temperature for 24 hours. After completion of the reaction, the resulting mixture was filtrated to remove undissolved substances, concentrated and recrystallized from isopropanol, and then an eight-arm polyethylene glycol guanidine derivative D21-1 in a white solid state was obtained.

$^1$H NMR spectrum data of the eight-arm polyethylene glycol guanidine derivative D21-1 were as follows: $^1$H NMR (CDCl$_3$) δ (ppm): 1.55 (—CH$_2$CH$_2$CH$_2$NH—), 1.90 (—CH$_2$CH$_2$CH$_2$NH—), 2.35-2.65 (—CH$_2$CH$_2$CONH—, —CH$_2$CH$_2$CH$_2$NH—), 3.40-3.80 (—CH$_2$CH$_2$O—, CH$_3$O—, —CH$_2$CH$_2$CONH—, —OCH(CH$_2$O—)$_2$), 4.15 (—CONHCH(COOCH$_3$)—); $M_n$≈66 kDa, PDI=1.07.

Example-5: Preparation of an Eight-Arm Protected PEG-Amine Derivative (C6-1)

Herein, the structure of the eight-armed polyethylene glycol derivative was designed as follows:

(with a carbon-branching center of a symmetrical type), the divalent linking groups $L_{11}$, $L_{12}$, $L_{21}$, $L_{22}$, $L_{31}$, $L_{32}$, $L_{41}$ and $L_{42}$ are all absent, g=1, k=8, $L_0$ is COCH$_2$NHOCH$_2$,

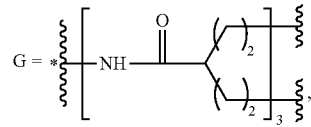

and the terminal functional groups are NHBoc (Boc is a t-butoxycarbonyl group). The designed total molecular weight is approximately 48.3 kDa, wherein, the molecular weight of the eight PEG chains is approximately 8×5000=40000 Da, corresponding to $n_1$≈$n_2$≈$n_3$≈$n_4$≈$n_5$≈$n_6$≈$n_7$≈$n_8$≈113.

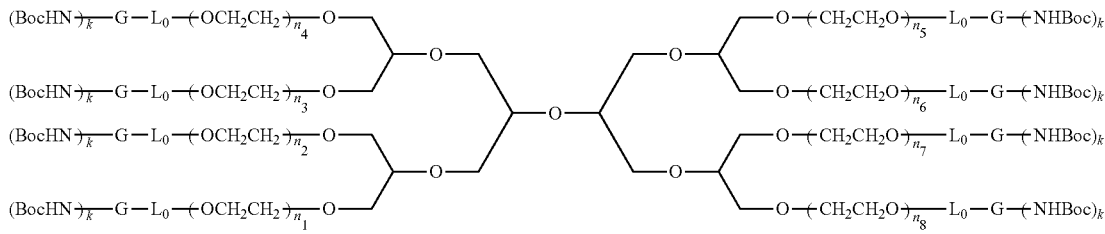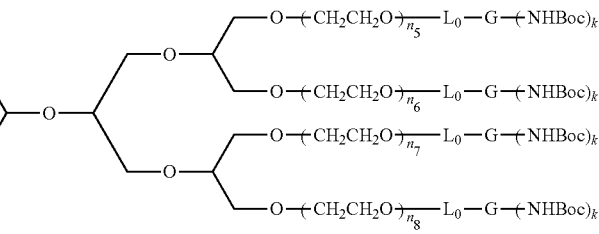

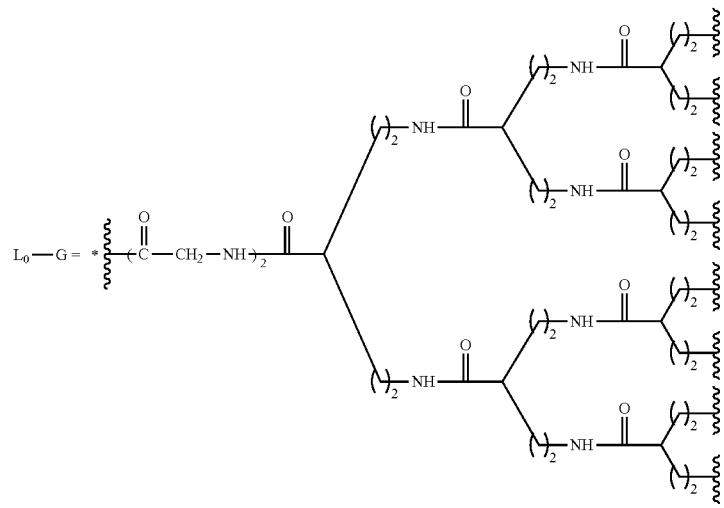

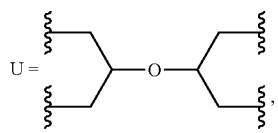

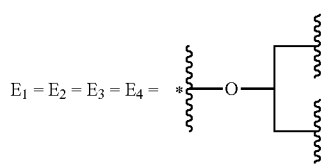

Step (a): Using the production method in Example-3 and adjusting the equivalent of ethylene oxide for polymerization to obtain an eight-arm polyethylene glycol H1-2b with a total molecular weight of 40 kDa. $M_n$=40 kDa, PDI=1.05.

S5-1

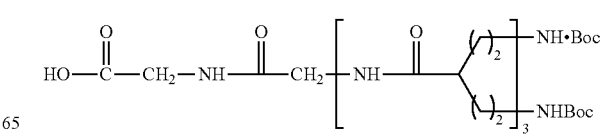

Step (b): Under nitrogen protection, into a dry and clean round-bottom flask, 1 mmol of the eight-arm polyethylene glycol H1-2b, 20 mmol of a dendritic molecule S5-1 (containing eight protected amino groups), 20 mmol of hydroxybenzotriazole and 20 mmol of 4-dimethylaminopyridine were added, followed by addition of anhydrous dichloromethane, and then the whole was stirred till dissolution. Subsequently, 20 mmol of dicyclohexylcarbodiimide (DCC) was added thereinto, and the whole was mixed. Under nitrogen protection, the reaction was conducted with stirring overnight. Thereafter, the resulting solution was concentrated by evaporation and precipitated with isopropanol. The precipitate was collected by filtration, washed with absolute diethyl ether and dried under vacuum; then an eight-arm protected PEG-amine derivative C6-1 with branched chain terminals was obtained.

$^1$H NMR spectrum data of the eight-arm protected PEG-amine derivative C6-1 were as follows: $^1$H NMR (CDCl$_3$) δ (ppm): 1.38 (OC(CH$_3$)$_3$), 1.79 (—CHCH$_2$CH$_2$NHCO—), 2.43 (—CHCH$_2$CH$_2$NHCO—), 3.20 (—CHCH$_2$CH$_2$NHCO—), 3.4-3.80 (—OCH$_2$CH$_2$O—, —OCH(CH$_2$O—)$_2$), 4.24-4.26 (OCOCH$_2$N—). M$_n$≈48 kDa, PDI=1.05. M$_n$≈48 kDa, PDI=1.05.

Example-6: Preparation of an Eight-Arm Polyethylene Glycol Isocyanate Derivative D9-1 in which the Chain Terminals have a Comb-Like End-Branched Structure

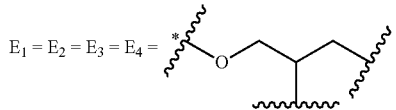

(with a carbon-branching center of an asymmetrical type), the divalent linking groups L$_{11}$, L$_{12}$, L$_{21}$, L$_{22}$, L$_{31}$, L$_{32}$, L$_{41}$ and L$_{42}$ are all absent, g=1, L$_0$ is absent,

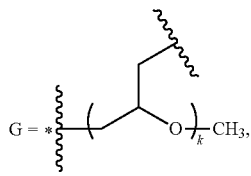

the mean value of k per PEG chain is about 16, and F is OCONH(CH$_2$)$_6$NCO (wherein, Z$_2$ is OCONH, Z$_1$ is (CH$_2$)$_6$, and R$_{01}$ is NCO). The designed total molecular weight is approximately 75.4 kDa, wherein, the molecular weight of the eight PEG chains is approximately 8×5000=40000 Da, corresponding to n$_1$≈n$_2$≈n$_3$≈n$_4$≈n$_5$≈n$_6$≈n$_7$≈n$_8$ or n$_1$≈113.

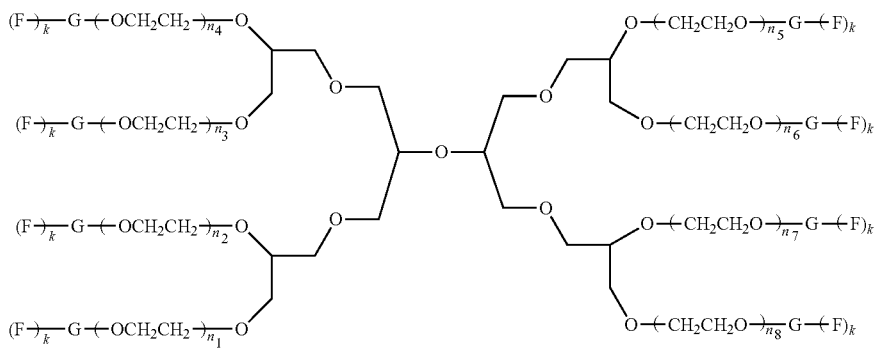

D9-1

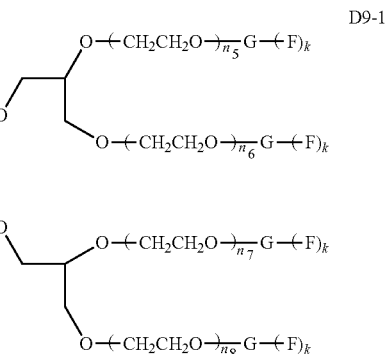

Herein, the structure of the eight-armed polyethylene glycol derivative was designed as follows:

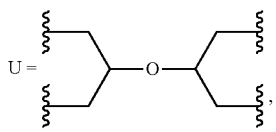

Step (a): Into a reactor, tetrahydrofuran, 10 mmol of a tetrahydroxyl-containing small molecule compound S3-4, and catalytic amount of boron trifluoride diethyl etherate were added in sequence, and then epichlorohydrin was added slowly, followed by reaction for 24 hours. After the addition of excess NaOH aqueous solution, the whole was refluxed overnight. Thereafter, the product in the solvent was neutralized, extracted, washed and purified via column chromatography, and then an octahydroxyl-containing small molecule compound S6-1 was obtained.

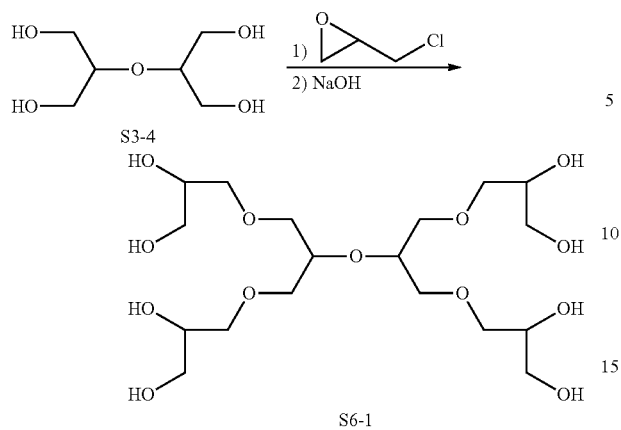

S3-4

S6-1

¹H NMR spectrum data of the octahydroxyl-containing small molecule initiator S6-1 were as follows: ¹H NMR (CDCl$_3$) δ (ppm): 3.40-3.50 (—OCH(CH$_2$O—)$_2$, —OCH$_2$CH(CH$_2$OH)$_2$).

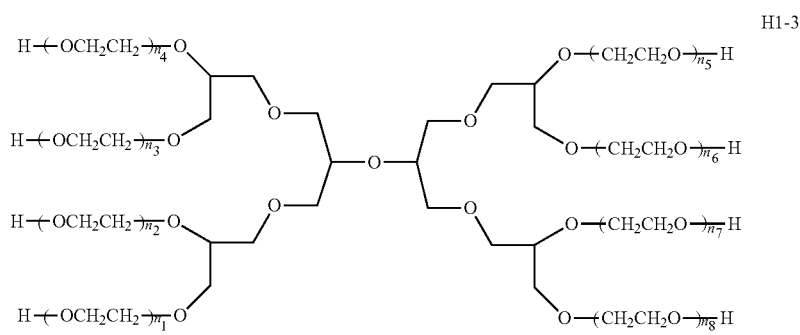

H1-3

Step (b): Into a sealed reactor under an anhydrous and oxygen-free atmosphere, tetrahydrofuran (250 mL), the compound S6-1 (1.266 mmol) and diphenylmethyl potassium (4.0 mmol) were added in sequence.

Step (c): After the addition of ethylene oxide in a calculated amount, the whole was heated stepwisely to 60° C., followed by reaction for 48 hours; thereafter, excess proton source (methanol) was added thereinto, and then an eight-arm polyethylene glycol H1-3 was obtained.

¹H NMR spectrum data of the eight-arm polyethylene glycol H1-3 were as follows: ¹H NMR (CDCl$_3$) δ (ppm): 3.40-3.90 (—OCH$_2$CH$_2$O—, —OCH(CH$_2$O—)$_2$, —OCH$_2$CH(CH$_2$O—)$_2$); $M_n$≈40 kDa, PDI=1.05.

Step (d): Into a sealed reactor under an anhydrous and oxygen-free atmosphere, tetrahydrofuran, 2.5 mmol of the eight-arm polyethylene glycol H1-3, and 16.0 mmol of diphenylmethyl potassium were added in sequence.

Step (e): After the addition of EEGE (ethoxy ethyl glycidyl ether) in a calculated amount, the whole was heated stepwisely to 60° C., followed by reaction for 48 hours;

Step (f): Thereafter, diphenylmethyl potassium (20 mmol) and methyl iodide (50 mmol) were added in sequence, followed by reaction at 30° C. for 12 hours. After opening the reactor, the product in the solvent was concentrated and precipitated with absolute diethyl ether at 0° C. The precipitate was collected by filtration and dried, and then an eight-arm polyethylene glycol derivative H2-1 was obtained.

¹H NMR spectrum data of the eight-arm polyethylene glycol derivative H2-1 were as follows: ¹H NMR (CDCl$_3$) δ (ppm): 1.22 (—OCH$_2$CH$_3$), 1.36 (—OCH(O)CH$_3$), 3.40-3.90 (—OCH$_2$CH$_2$O—, —OCH$_2$CH$_3$, —OCH(CH$_2$O—)$_2$, —OCH$_2$CH(CH$_2$O—)$_2$); $M_n$≈63 kDa, PDI=1.08.

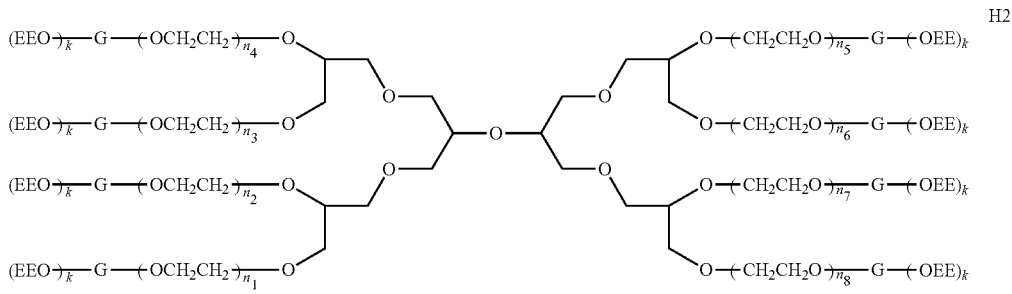

H2-1

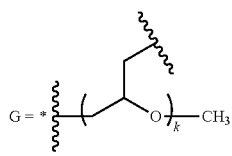

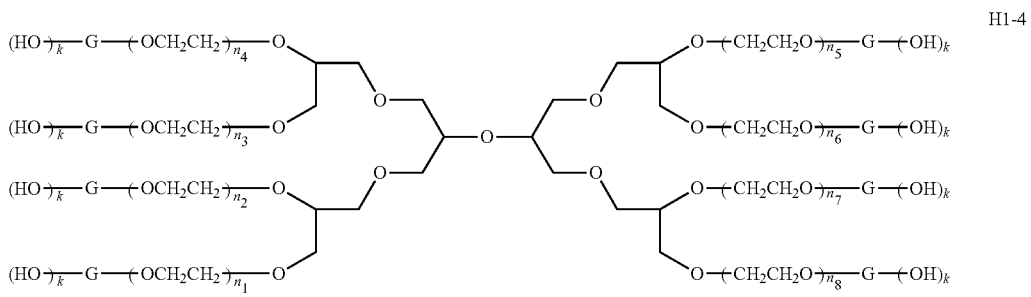

H1-4

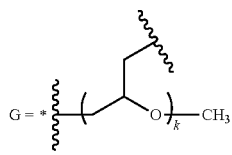

Step (g): Into a dry and clean container, the eight-arm polyethylene glycol derivative H2-1 was added and then dissolved with methanol. The solution was adjusted to pH 3.5 with hydrochloric acid (1 M), followed by reaction for 4 hours, and then an eight-arm polyethylene glycol H1-4 containing eight unprotected hydroxyl groups was obtained.

Step (h): Into a dry and clean 1 L round-bottom flask, 10 g of the eight-arm polyethylene glycol H1-4 and anhydrous dichloromethane (200 mL) were added in sequence, and the whole was stirred till dissolution. Thereafter, 5 mL of triethylamine and 4 g of hexamethylene diisocyanate were added in sequence, followed by reaction at room temperature for 8 hours. The resulting product was concentrated, precipitated with diethyl ether, and then an eight-arm polyethylene glycol isocyanate derivative D9-1 with comb-like branched chain-terminals in an off-white solid state was obtained.

In the $^1$H NMR spectrum of the eight-arm polyethylene glycol isocyanate derivative D9-1 with comb-like branched chain-terminals, besides the characteristic peaks of the chain backbone, the characteristic peaks of the isocyanate moiety also appeared as follows: $^1$H NMR (CDCl$_3$) δ (ppm): $^1$H NMR (CDCl$_3$) δ (ppm): 1.29-1.55 (—CH$_2$CH$_2$CH$_2$CH$_2$CH$_2$CH$_2$—), 3.15-3.47 (—CH$_2$NCO, —OCONHCH$_2$—), $M_n \approx 75$ kDa, PDI=1.08.

Example-7: Preparation of an Eight-Arm Fluorenylmethoxycarbonyl-Protected PEG-Amine Derivative (C6-2)

C6-2

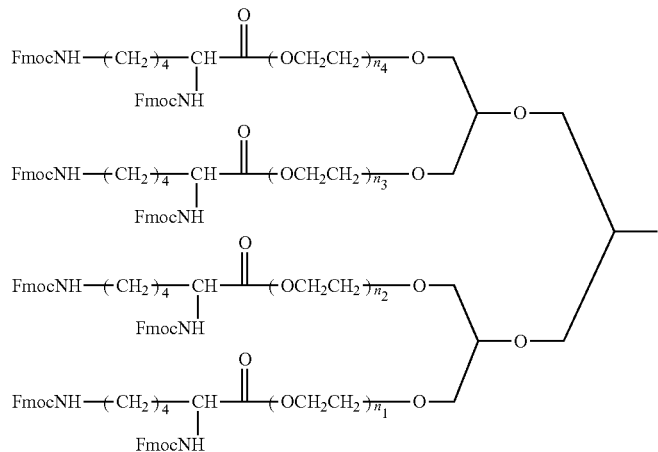

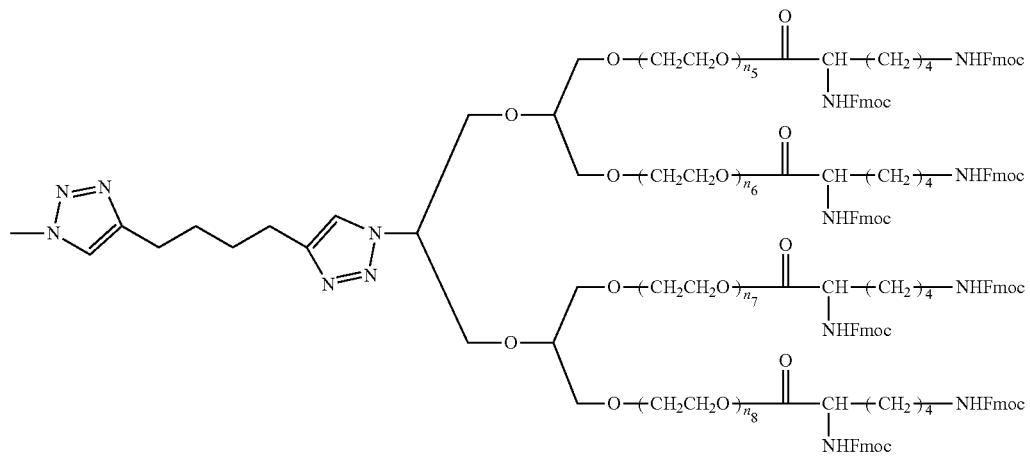

Herein, the structure of the eight-arm polyethylene glycol derivative was designed as follows:

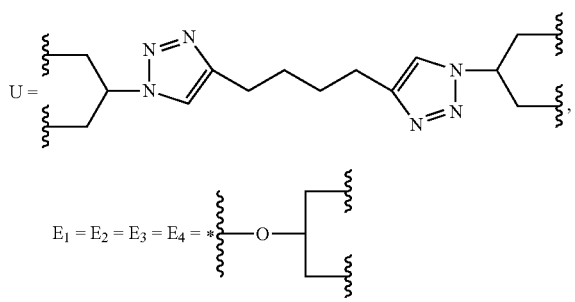

(with a carbon-branching center of a symmetrical type), the divalent linking groups $L_{11}$, $L_{12}$, $L_{21}$, $L_{22}$, $L_{31}$, $L_{32}$, $L_{41}$ and $L_{42}$ are all absent, g=1, $L_0$ is absent, G=

F=NHFmoc, and Fmoc is an N-fluorenylmethoxycarbonyl group (wherein, $Z_2$ and $Z_1$ are absent, and $R_{01}$ is $NPG_5$). The designed total molecular weight is approximately 45.0 kDa, wherein, the molecular weight of the eight PEG chains is approximately 8×5000=40000 Da, corresponding to $n_1 \approx n_2 \approx n_3 \approx n_4 \approx n_5 \approx n_6 \approx n_7 \approx n_8 \approx 113$.

Step (a): Into a reactor, tetrahydrofuran, a compound S7-1 (50 mmol) and 1,7-octadiyne (25 mmol) were added in sequence, followed by reaction for 4 hours. Thereafter, the solution was adjusted to pH 3.5 with the addition of hydrochloric acid (1 M), followed by reaction for 4 hours. The product was extracted, washed, concentrated and purified via column chromatography to obtain an initiator S7-2.

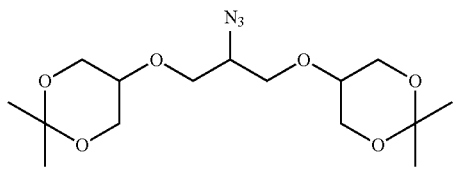

S7-1

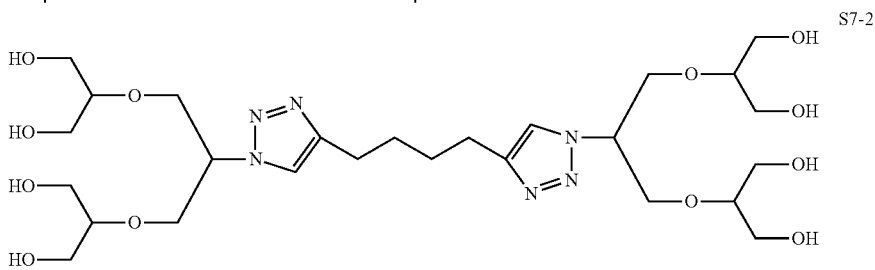

S7-2

¹H NMR spectrum data of the initiator S7-2 were as follows: ¹H NMR (CDCl₃) δ (ppm): 1.59 (—CH$_2$CH$_2$CH$_2$CH$_2$—), 2.44 (—CH$_2$CH$_2$CH$_2$CH$_2$—), 2.90-3.10 (—OCH(CH$_2$OH)$_2$), 3.40-3.50 (—NCH(CH$_2$O—)$_2$, —OCH(CH$_2$OH)$_2$), 3.78 (—NCH(CH$_2$O—)$_2$), 7.50 (NCH=C).

Thereafter, the resulting mixture was filtrated to remove undissolved substances, concentrated and recrystallized from isopropanol, and then an eight-arm Fmoc-protected PEG-amine derivative C6-2 in a white solid state was obtained.

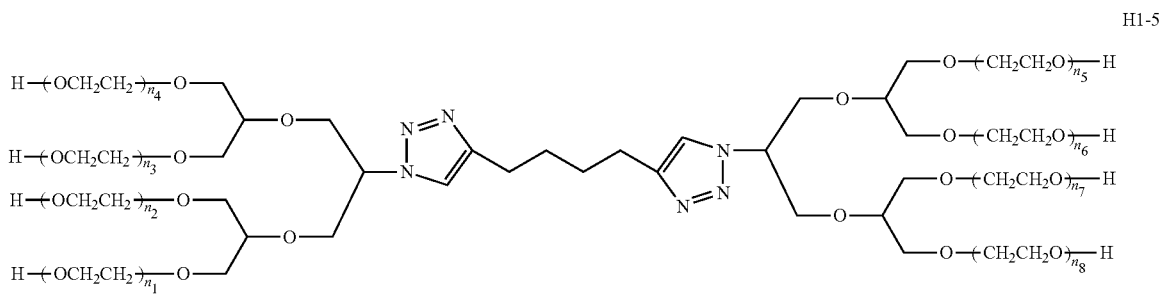

H1-5

Step (b): Into a sealed reactor under anhydrous and oxygen-free atmosphere, tetrahydrofuran (250 mL), the octahydroxyl-containing small molecule compound S7-2 (1.266 mmol) and diphenylmethyl potassium (4.0 mmol) were added in sequence.

Step (c): After the addition of a calculated amount of ethylene oxide, the whole was heated stepwisely to 60° C., followed by reaction for 48 hours.

Step (d): Thereafter, excess proton source (methanol) was added, and then the product in the solvent was concentrated and precipitated to obtain an eight-arm polyethylene glycol H1-5.

¹H NMR spectrum data of the eight-arm polyethylene glycol H1-5 were as follows: ¹H NMR (CDCl₃) δ (ppm): 1.59 (—CH$_2$CH$_2$CH$_2$CH$_2$—), 2.44 (—CH$_2$CH$_2$CH$_2$CH$_2$—), 3.40-3.80 (—NCH(CH$_2$O—)$_2$, —OCH$_2$CH$_2$O—, —OCH(CH$_2$O)$_2$), 3.78 (—NCH(CH$_2$O—)$_2$); $M_n \approx 40$ kDa, PDI=1.05.

Step (e): Into a dry and clean 1 L round-bottom flask, 20 g of the eight-arm polyethylene glycol H1-5, 20 mL of triethylamine and 10 g of lysine with amino groups being Fmoc-protected were added, and the whole was stirred till dissolution. Subsequently, a solution of 20 g of dicyclohexylcarbodiimide (DCC) in dichloromethane was added thereinto, followed by reaction at room temperature for 24 hours.

In the 1H NMR spectrum of the eight-arm Fmoc-protected PEG-amine derivative C6-2, besides the characteristic peaks of the chain backbone, characteristic peaks of the fluorenylmethoxycarbonyl group also appeared as follows: ¹H NMR (CDCl₃) δ (ppm): ¹H NMR (CDCl₃) δ (ppm): 4.25 (—NCOOCH$_2$CH$_2$O—), 4.45-4.70 (Ar—CH—CH$_2$—), 7.28-7.87 (—Ar—H). $M_n \approx 45$ kDa, PDI=1.05.

Example-8: Preparation of an Eight-Arm Polyethylene Glycol (H1-6)

Herein the structure of the eight-arm polyethylene glycol was designed as follows:

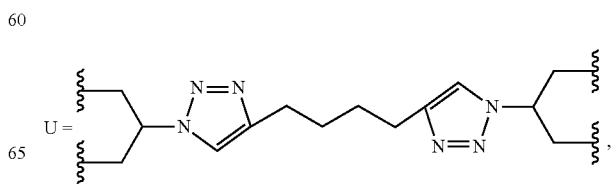

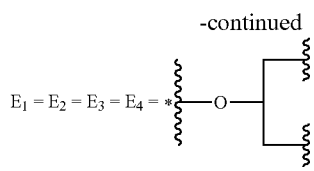

(with a carbon-branching center of a symmetrical type), the divalent linking groups $L_{11}$, $L_{12}$, $L_{21}$, $L_{22}$, $L_{31}$, $L_{32}$, $L_{41}$ and $L_{42}$ are all absent, g=1, $L_0$ contains a triazole moiety, G=

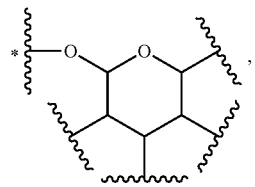 [SMILES: *OC1OC(*)C(*)C(*)C1*]

k=4 and F=OH (wherein, $Z_2$ and $Z_1$ are absent, and $R_{01}$ is OH). The designed total molecular weight is approximately 42.5 kDa, wherein, the molecular weight of the eight PEG chains is approximately 8×5000=40000 Da, corresponding to $n_1 \approx n_2 \approx n_3 \approx n_4 \approx n_5 \approx n_6 \approx n_7 \approx n_8 \approx 113$.

H1-6

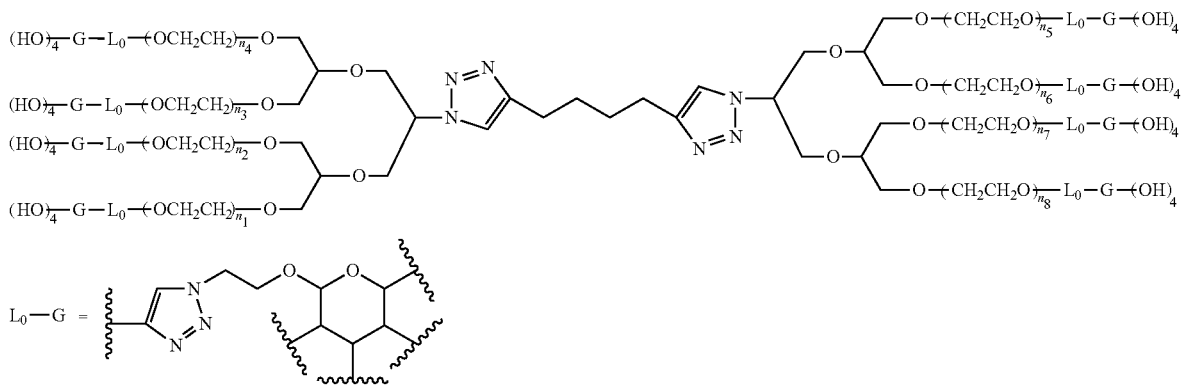

Step (a): Into a sealed reactor under an anhydrous and oxygen-free atmosphere, tetrahydrofuran (250 mL), an octahydroxyl-containing small molecule compound S7-2 (1.266 mmol) and diphenylmethyl potassium (20.0 mmol) were added in sequence.

S8-1

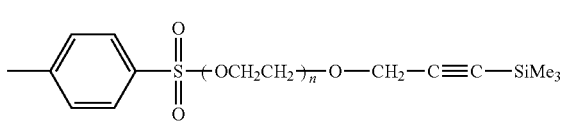

Step (b): A heterofunctional polyethylene glycol (S8-1, $M_n \approx 5000$ Da, PDI=1.04) was added thereinto, the whole was refluxed overnight. Thereafter, the resulting mixture was filtrated to remove undissolved substances, concentrated and recrystallized from isopropanol, and then a trimethylsilyl-protected alkyne derivative F4-1 in a white solid state was obtained.

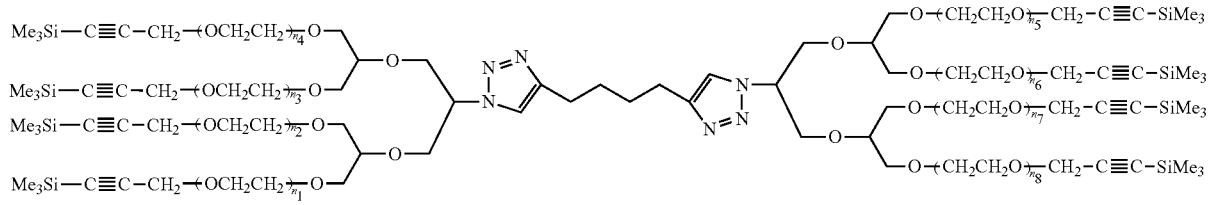

F4-1

In the $^1$H NMR spectrum of the trimethylsiyl-protected alkyne derivative F4-1, besides the characteristic peaks of the chain backbone, the characteristic peaks of the trimethylsiyl-protected alkynyl group also appeared as follows: $^1$H NMR (CDCl$_3$) δ (ppm): 0.08 (—Si(CH$_3$)$_3$), 4.15-4.35 (—C≡CCH$_2$O—).

Step (c): Into a reactor, 250 mL of tetrahydrofuran, 20 g of the trimethylsiyl-protected alkyne derivative F4-1 obtained in Step (b) and a small amount of tetrabutylammonium fluoride were added, followed by reaction at room temperature overnight. Thereafter, the reaction solution was concentrated and recrystallized from isopropanol, and then an eight-arm polyethylene glycol alkyne derivative F3-1 in a white solid state was obtained.

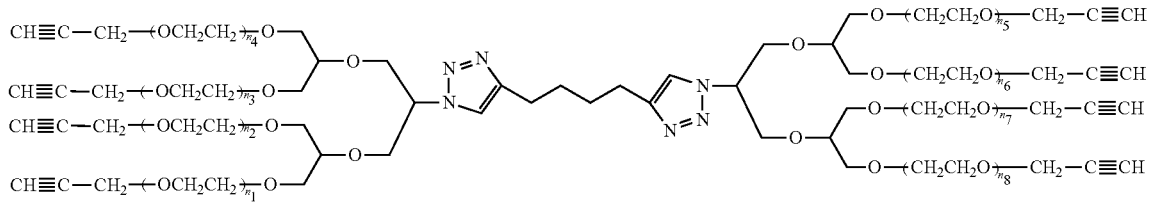

F3-1

In the $^1$H NMR spectrum of the polyethylene glycol alkyne derivative F3-1, besides the characteristic peaks of the chain backbone, the characteristic peaks of the trimethylsiyl protective group disappeared, and the characteristic peaks of the alkynyl group appeared as follows: $^1$H NMR (CDCl$_3$) δ (ppm): 2.40-2.60 (HC≡CCH$_2$O—), 4.15-4.35 (—C≡CCH$_2$O—); $M_n$≈41 kDa, PDI=1.03.

Step (d): Into a reactor, 250 mL of tetrahydrofuran, 8 g of the eight-arm polyethylene glycol alkyne derivative F3-1 obtained in Step (c) and 1 mmol of 2-azidoethyl β-D-glucopyranoside were added in sequence, followed by reaction at room temperature overnight. Thereafter, the reaction solution was concentrated and recrystallized from isopropanol, and then an eight-arm polyethylene glycol H1-6 in a white solid state was obtained.

In the $^1$H NMR spectrum of the eight-arm polyethylene glycol H1-6, besides the characteristic peaks of the chain backbone, the characteristic peaks of the alkynyl group disappeared, and the characteristic peaks of the glucopyranoside moiety appeared as follows: $^1$H NMR (CDCl$_3$) δ (ppm): 1.74-1.99 (—OCH(O)CH(O)CH$_2$CH(O)CH(O)), 3.27 (OCH(O)CH(O)CH$_2$CH(O)CH(O)), 5.27 (OCH(O)CH(O)CH$_2$CH(O)CH(O)); $M_n$≈41 kDa, PDI=1.03.

Example-9: Preparation of an Eight-Arm Polyethylene Glycol Aldehyde Derivative (D6-1)

Herein, the structure of the eight-armed polyethylene glycol derivative was designed as follows:

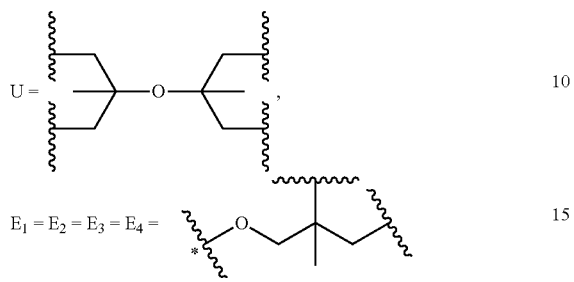

(with a carbon-branching center of an asymmetrical type), the divalent linking groups $L_{11}$, $L_{12}$, $L_{21}$, $L_{22}$, $L_{31}$, $L_{32}$, $L_{41}$ and $L_{42}$ are all absent, g=0, k=1, F=CH$_2$CH$_2$OphCHO (wherein, $Z_2$ is —CH$_2$CH$_2$—, $Z_1$ is —OPh-, and $R_{01}$ is CHO). The designed total molecular weight is approximately 41.5 kDa, wherein, the molecular weight of the eight PEG chains is approximately 8×500=40000 Da, corresponding to $n_1 \approx n_2 \approx n_3 \approx n_4 \approx n_5 \approx n_6 \approx n_7 \approx n_8 \approx 113$.

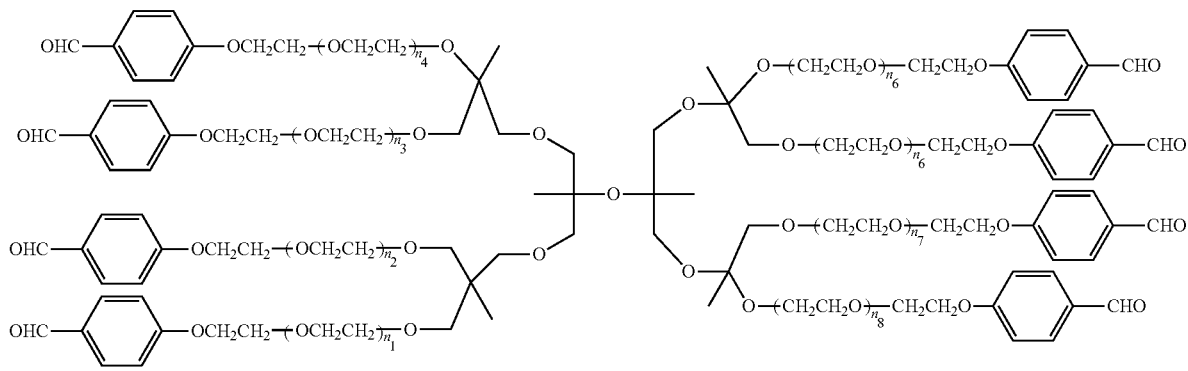

D6-1

Step (a): Into a sealed reactor under an anhydrous and oxygen-free atmosphere, tetrahydrofuran (400 mL) and excess diphenylmethyl potassium (100 mmol) were added, then equal equivalents of a dihydroxyl-protected compound S9-1 and a dihydroxyl-protected compound S9-2 (50 mmol, OTs is a tosylate group) were added, followed by reaction at 30° C. for 12 hours. After opening the reactor, the product in the solvent was concentrated, washed and purified via column chromatography, and then a small molecule compound S9-3 containing four protected hydroxyl groups was obtained.

Step (b): Into a dry and clean container, the small molecule compound S9-3 obtained in Step (a) was added and then dissolved with methanol. The solution was adjusted to pH 3.5 with the addition of hydrochloric acid (1 M), followed by reaction for 4 hours, and a small molecule compound S9-4 containing four hydroxyl groups was obtained.

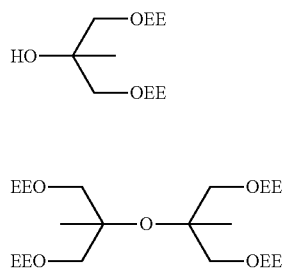

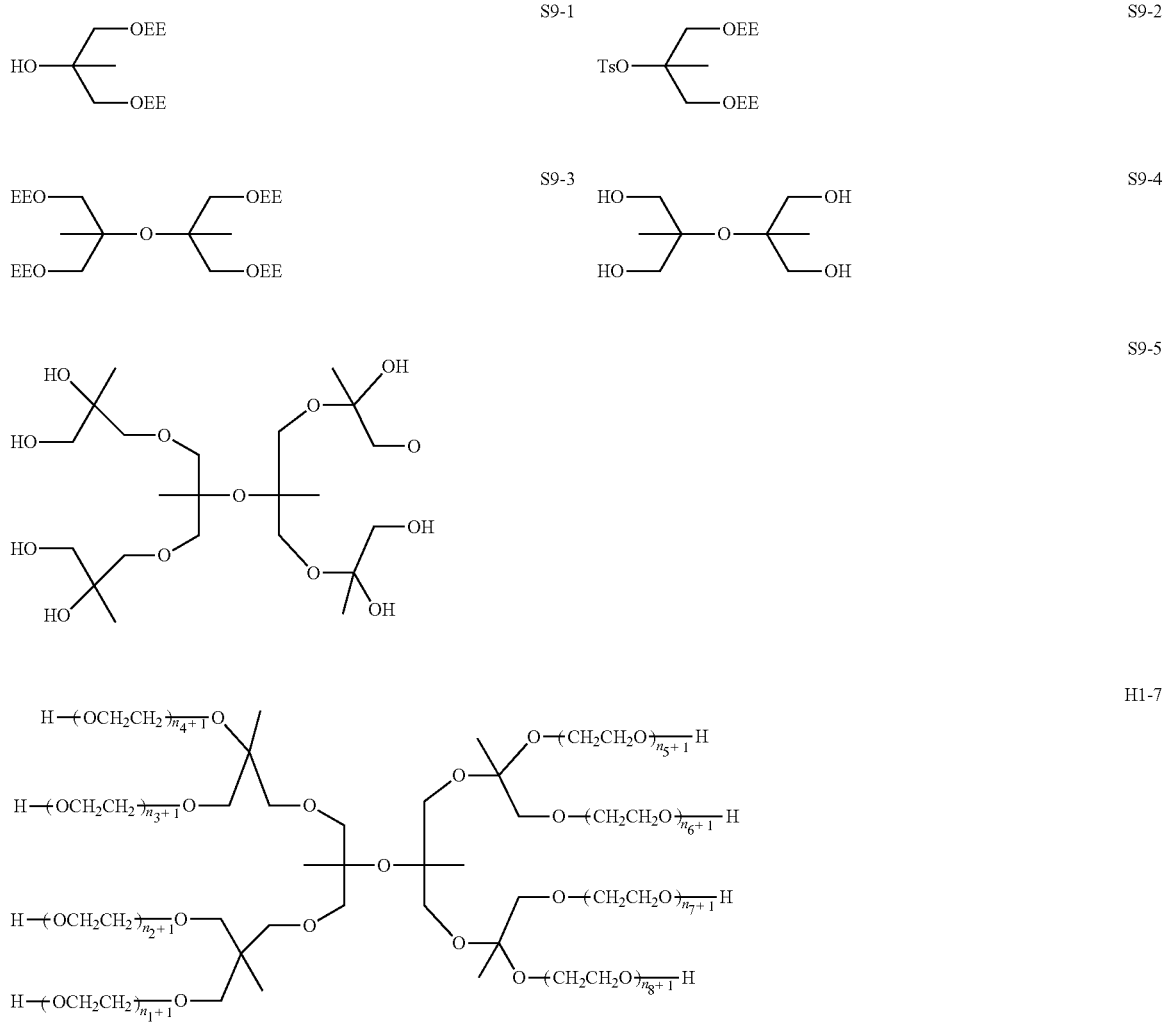

Step (c): Into a reactor, tetrahydrofuran, 10 mmol of the compound S9-4 and boron trifluoride diethyl etherate as a catalyst was added in sequence, and then 2-(chloromethyl)-2-methyloxirane was added slowly and in excess, followed by reaction for 24 hours. Thereafter, excess NaOH aqueous solution was added thereinto and the solution refluxed overnight. The product in the solvent was neutralized, extracted, washed and purified via column chromatography to obtain an octahydroxyl-containing initiator S9-5.

$^1$H NMR spectrum data of the octahydroxyl-containing initiator S9-5 were as follows: $^1$H NMR (CDCl$_3$) δ (ppm): 1.29 (CH$_3$—), 3.53 (CH$_2$OH), 3.72 (CCH$_2$OCH$_2$—).

Step (d): Into a sealed reactor under an anhydrous and oxygen-free atmosphere, tetrahydrofuran (250 mL), the octahydroxyl-containing initiator S9-5 (1.266 mmol) and diphenylmethyl potassium (4.0 mmol) were added in sequence.

Step (e): After the addition of a calculated amount of ethylene oxide, the whole was heated stepwise to 60° C., followed by reaction for 48 hours. After the addition of excess proton source (methanol), the product in the solvent was concentrated and precipitated, and then an eight-arm polyethylene glycol H1-7 was obtained.

$^1$H NMR spectrum data of the eight-arm polyethylene glycol H1-7 were as follows: $^1$H NMR (CDCl$_3$) δ (ppm): 1.29 (CH$_3$—), 3.40-3.80 (—OCH$_2$CH$_2$O—, —OC(CH$_3$)(CH$_2$OCH$_2$-)$_2$); $M_n$≈41 kDa, PDI=1.05.

Step (f): Into a dry and clean 1 L round-bottom flask, 10 g of the eight-arm polyethylene glycol H1-7 was added. Under nitrogen protection, 500 mL of dichloromethane, 20 mL of pyridine and 5 g of 4-toluenesulfonyl chloride were added thereinto, followed by reaction at room temperature for 24 hours. Thereafter, the solution was adjusted to a pH value less than 7 with the addition of hydrochloric acid (1 mol/L), and the aqueous phase was washed with dichloromethane (50 mL trice). The organic phase was combined, washed with saturated salt solutions, dried with anhydrous sodium sulfate, filtrated, concentrated and recrystallized, and then an eight-arm polyethylene glycol sulfonate derivative B1-1 was obtained.

In the $^1$H NMR spectrum of the eight-arm polyethylene glycol sulfonate derivative B1-1, besides the characteristic peaks of the chain backbone, the characteristic peaks of the tosylate moiety appeared as follows: $^1$H NMR (CDCl$_3$) δ (ppm): 2.35 (CH$_3$C$_6$H$_4$SO$_2$—), 4.20 (—OCH$_2$CH$_2$OSO$_2$—), 7.30 (CH$_3$C$_6$H$_4$SO$_2$—), 7.80 (CH$_3$C$_6$H$_4$SO$_2$—).

B1-1

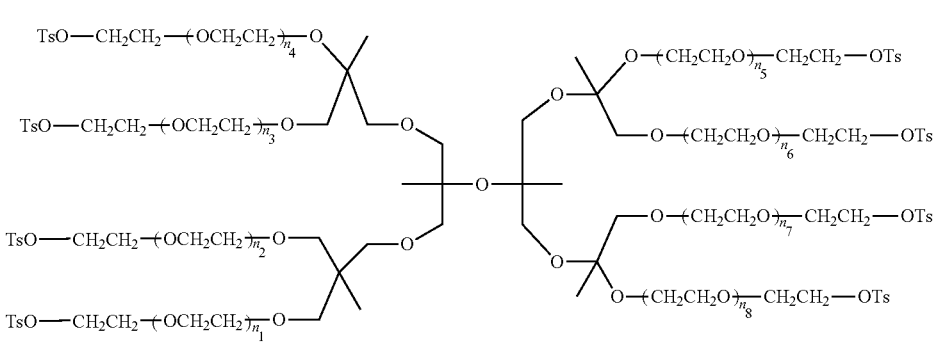

Step (g): Into a dry and clean 1 L round-bottom flask, 10 g of the eight-arm polyethylene glycol sulfonate derivative B1-1 obtained in Step (f) was added. Under nitrogen protection, 500 mL of dichloromethane, 5 g of potassium carbonate and 5 g of 4-hydroxybenzaldehyde were added thereinto, followed by reaction at room temperature for 24 hours. Thereafter, the mixture was filtrated and adjusted to a pH value less than 7 with the addition of hydrochloric acid (1 mol/L). The aqueous phase was washed with dichloromethane (50 mL trice). The organic phase was combined, washed with saturated salt solutions, dried with anhydrous sodium sulfate, filtrated, concentrated and recrystallized, and then an eight-arm polyethylene glycol benzaldehyde derivative D6-1 was obtained.

In the $^1$H NMR spectrum of the polyethylene glycol benzaldehyde derivative D6-1, besides the characteristic peaks of the chain backbone, the characteristic peaks of the tosylate moiety disappeared and the characteristic peaks of the benzaldehyde group appeared as follows: $^1$H NMR (CDCl$_3$) δ (ppm): 4.50-4.60 (—ArCH$_2$—), 7.30-7.80 (—Ar—H), 9.80 (—CHO); $M_n \approx$42 kDa, PDI=1.06.

Example-10: Preparation of an Eight-Arm Polyethylene Glycol Carboxylic Acid Derivative (D1-3)

D1-3
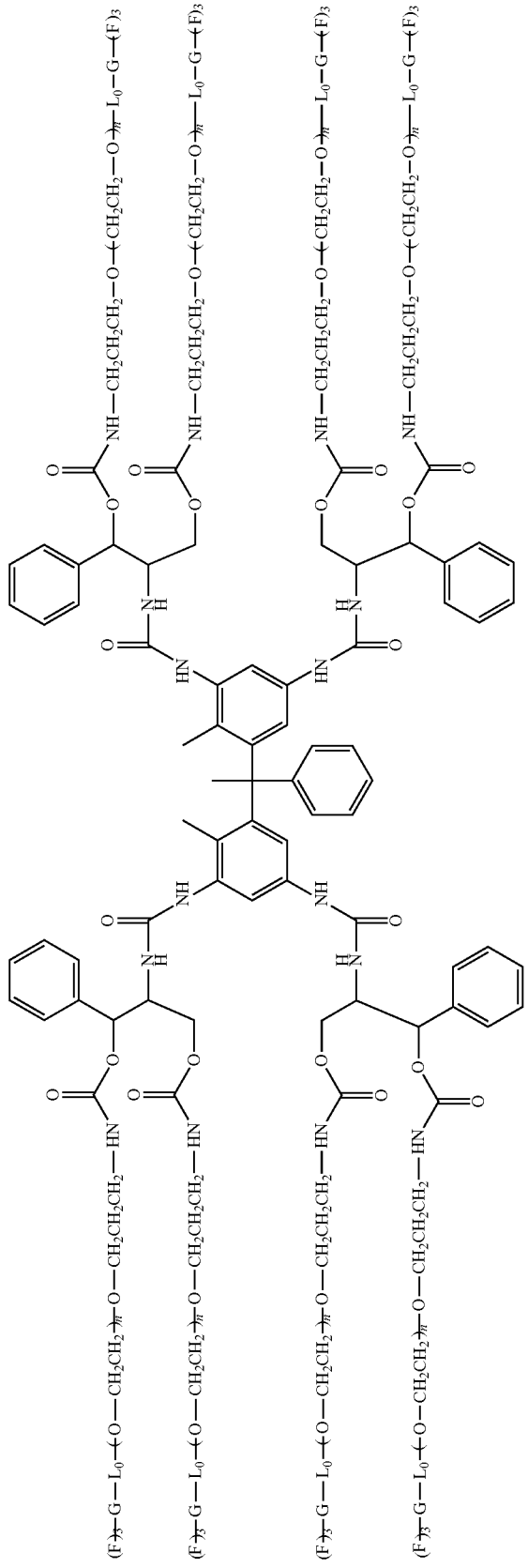
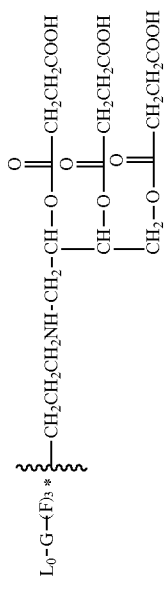

Herein, the structure of the eight-arm polyethylene glycol derivative was designed as follows:

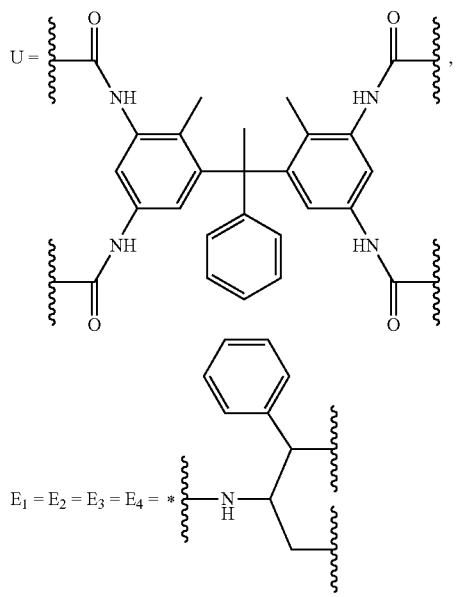

(with a carbon-branching center of an asymmetrical type), the divalent groups $L_{11}, L_{12}, L_{21}, L_{22}, L_{31}, L_{32}, L_{41}$ and $L_{42}$ are $OCONHCH_2CH_2CH_2$, $g=1$, $k=3$, $L_0=CH_2Cl_2CH_2NH$,

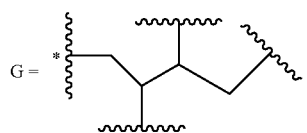 [SMILES: *CC(*)C(*)C*]

and F is $C(=O)CH_2CH_2COOH$ (wherein, $Z_2$ is a carbonyl group, $Z_1$ is an ethylene group, and $R_{01}$ is COOH). The designed total molecular weight is approximately 44.2 kDa, wherein, the molecular weight of the eight PEG chains is approximately $8 \times 5000 = 40000$ Da, corresponding to $n_1 \approx n_2 \approx n_3 \approx n_4 \approx n_5 \approx n_6 \approx n_7 \approx n_8 \approx 113$.

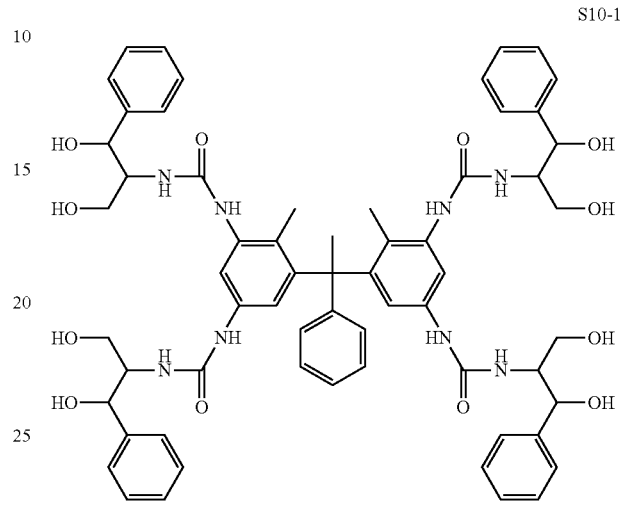

S10-1

Step (a): Into a dry and clean 1 L round-bottom flask, 50 mmol of 2,2'-dimethyldiphenylmethane-3,3',5,5'-tetraisocyanate, excess 2-amino-1-phenyl-1,3-propanediol and 500 mL of dichloromethane were added in sequence, followed by reaction for 0.5 hour. Thereafter, the product was concentrated, precipitated, collected by filtration, recrystallized and dried, and then an octahydroxyl-containing small molecule compound S10-1 was obtained.

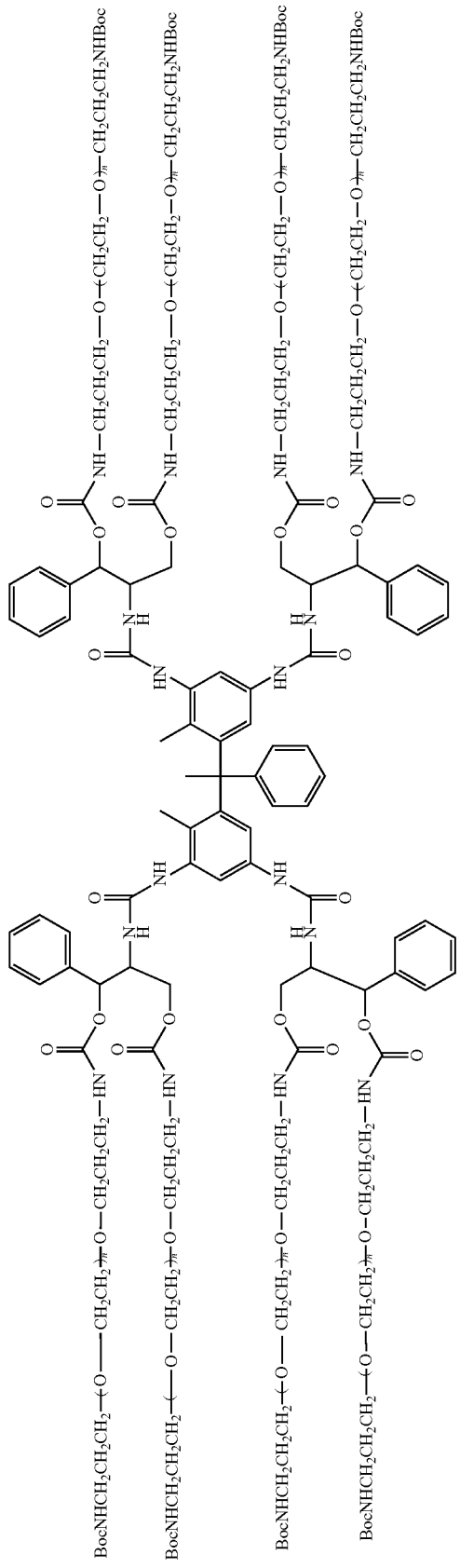

¹H NMR spectrum data of the octahydroxyl-containing small molecule compound S10-1 were as follows: ¹H NMR (CDCl₃) δ (ppm): 1.70 (—CH₂OH), 2.12 (CH₃—Ar), 2.28 (CH₃C), 3.47 (—CH(Ar)OH), 7.30-7.80 (Ar—H).

Step (b): Into a dry and clean 1 L round-bottom flask, a suitable amount of the octahydroxyl-containing small molecule compound S10-1, 0.01 mmol of dibutyltin dilaurate and 100 mL of tetrahydrofuran were added in sequence, the whole was dissolved, and then a solution of 25 mmol of a heterofunctional protected-amino polyethylene glycol isocyanate ($M_n$ was about 5 kDa, PDI=1.04) in dichloromethane was added dropwisely. Thereafter, the product was concentrated, precipitated, collected by filtration, recrystallized and dried, and then an eight-arm protected PEG-amine derivative S10-2 was obtained.

¹H NMR spectrum data of the eight-arm protected amine derivative S10-2 were as follows: ¹H NMR (CDCl₃) δ (ppm): 1.38 (OC(CH₃)₃), 1.70-1.76 (—CH₂CH₂CH₂NHCOO—, BocNHCH₂CH₂CH₂—), 2.12 (CH₃—Ar), 2.28 (CH₃C(Ar)₃), 3.06 (—CONHCH₂CH₂—), 3.10-3.20 (—CH₂CH₂CH₂NHCOO—, BocNHCH₂CH₂CH₂—), 3.40-3.80 (—OCH₂CH₂O—, —CH₂CH₂CH₂NHCOO—, BocNHCH₂CH₂CH₂—), 4.20 (—CH₂OC(=O)N), 5.85 (—CH(Ar)OC(=O)N), 7.30-7.80 (Ar—H); $M_n$≈42 kDa, PDI=1.03.

Step (c): Into a dry and clean container, the eight-arm protected PEG-amine derivative S10-2 was added and dissolved with dichloromethane. The solution was adjusted with trifluoroacetic acid (TFA) to 0.1 M, followed by reaction for 4 hours. Thereafter, the solution was adjusted to a neutral pH value, extracted and precipitated, and then an eight-arm polyethylene glycol amine derivative S10-3 with amino groups being unprotected was obtained.

In the ¹H NMR spectrum of S10-3, besides the characteristic peaks of the chain backbone, the characteristic peaks of the Boc group disappeared, and the characteristic peaks of the propylamine appeared as follows: ¹H NMR (CDCl₃) δ (ppm): 1.59 (—CH₂CH₂CH₂NH₂), 2.55 (—CH₂CH₂CH₂NH₂).

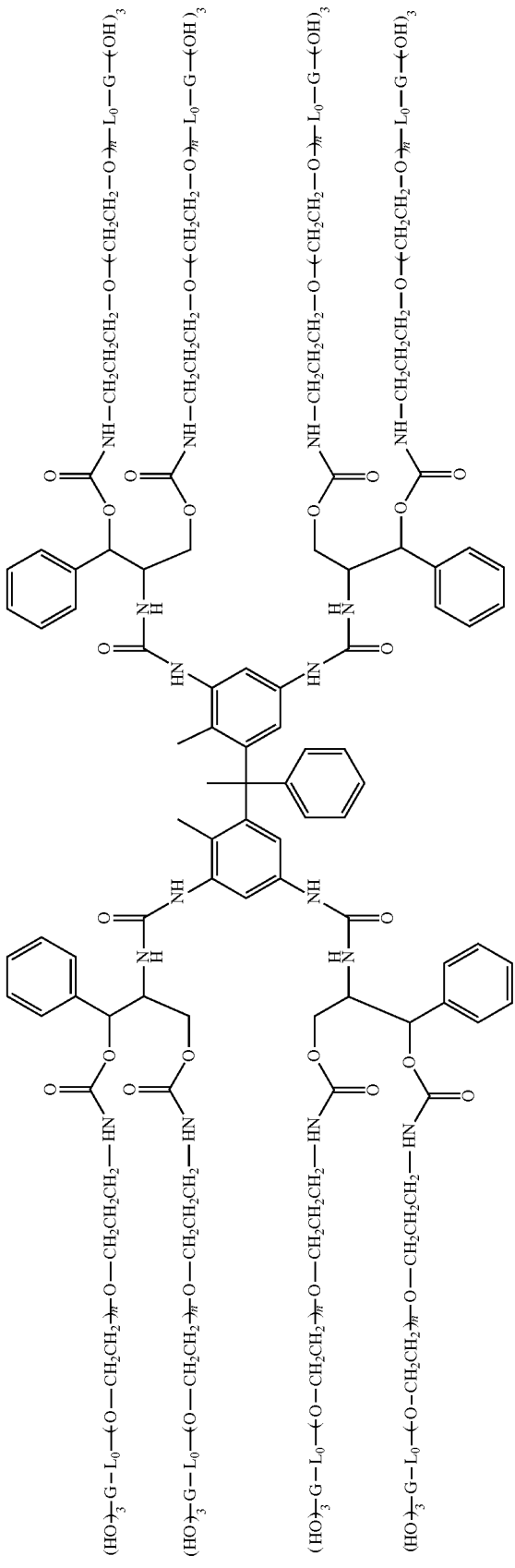
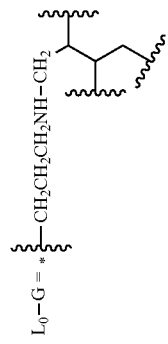

Into a dry and clean 1 L round-bottom flask, the eight-arm polyethylene glycol amine derivative S10-3 was added and dissolved with pH 8 buffer solution, and then excess 2,3,4-trihydroxybutanal was added thereinto, followed by stirring at room temperature for 3 hours. Thereafter, excess sodium cyanoborohydride was added thereinto, followed by reaction at room temperature for 24 hours. Thereafter, the resulting mixture was filtrated to remove undissolved substances, extracted with dichloromethane, dried, concentrated and recrystallized from isopropanol, and then an eight-arm end-trifunctionalized polyethylene glycol intermediate S10-4 was obtained.

In the $^1$H NMR spectrum of the eight-arm polyethylene glycol intermediate S10-4, besides the characteristic peaks of the chain backbone, other characteristic peaks also include as follows: $^1$H NMR (CDCl$_3$) δ (ppm): 1.55 (—CH$_2$CH$_2$CH$_2$NHCH$_2$—), 2.52 (—CH$_2$CH$_2$CH$_2$NHCH$_2$—), 2.75-2.90 (—NHCH$_2$CH(OH)—), 3.40-3.80 (—CH(OH)CH(OH)CH$_2$OH); $M_n$≈42 kDa PDI=1.03.

Step (d): Into a dry and clean reactor, the above-obtained eight-arm polyethylene glycol intermediate S10-4 with terminal hydroxyl groups being unprotected (2.5 mmol), toluene (500 mL) and excess butanedioic anhydride (400 mmol) were added in sequence, followed by reaction at 50° C. for 12 hours. After opening the reactor, the product in the solvent was concentrated, precipitated with absolute diethyl ether at 0° C., collected by filtration and dried, and then an eight-arm polyethylene glycol carboxylic acid derivative D1-3 was obtained.

In the $^1$H NMR spectrum of the eight-arm polyethylene glycol carboxylic acid derivative D1-3, besides the characteristic peaks of the chain backbone, the characteristic peaks of the carboxylic acid appeared as follows: 1H NMR (CDCl$_3$) δ (ppm): 2.40-2.70 (—OCOCH$_2$CH$_2$COO—), 4.15-4.35 (—OCH$_2$CH$_2$OCO—); $M_n$≈44 kDa, PDI=1.03.

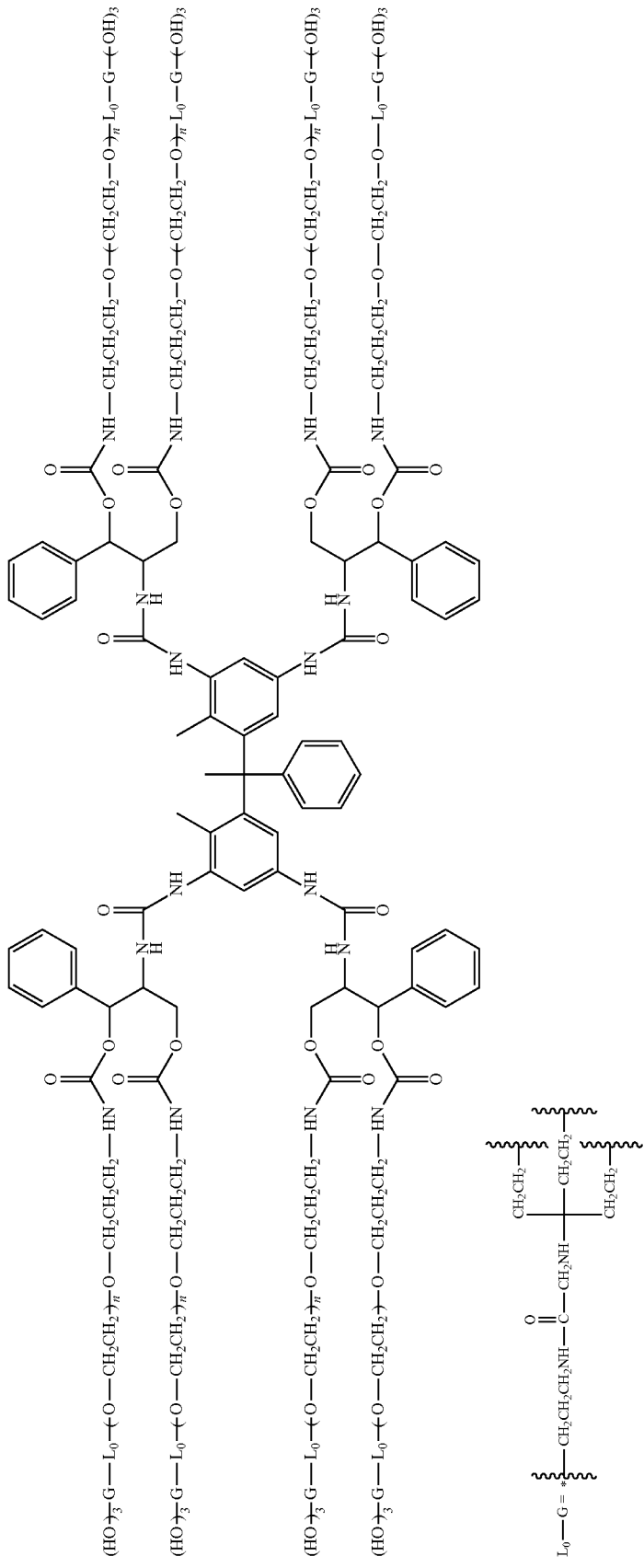

Herein, $U$, $E_1$, $E_2$, $E_3$, $E_4$, $L_{11}$, $L_{12}$, $L_{21}$, $L_{22}$, $L_{31}$, $L_{32}$, $L_{41}$, $L_{42}$, $n_1$, $n_2$, $n_3$, $n_4$, $n_5$, $n_6$, $n_7$ and $n_8$ in the eight-arm polyethylene glycol derivative are the same as those in Example-10, $g=1$, $k=3$, $L_0$ is $CH_2CH_2CH_2NH$, G is

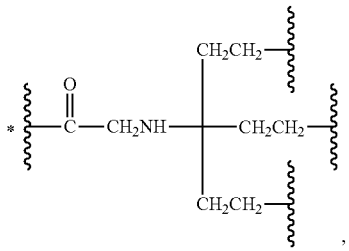

and F=OH. The designed total molecular weight is approximately 43.0 kDa, wherein, the molecular weight of the eight PEG chains is approximately $8 \times 5000 = 40000$ Da, corresponding to $n_1 \approx n_2 \approx n_3 \approx n_4 \approx n_5 \approx n_6 \approx n_7 \approx n_8 \approx 113$.

Step (a): Into a dry and clean 1 L round-bottom flask, 20 g of the eight-arm polyethylene glycol amine derivative S10-3 obtained in Example-10, 20 mL of triethylamine and 10 g of TBS-protected N-[tris(hydroxymethyl)methyl]glycine S11-1 were added in sequence, and the whole was stirred till dissolution. Subsequently, a solution of 20 g of dicyclohexylcarbodiimide (DCC) in dichloromethane was added thereinto, followed by reaction at room temperature for 24 hours. Thereafter, the resulting mixture was filtrated to remove undissolved substances, concentrated and recrystallized from isopropanol, and then an eight-arm polyethylene glycol intermediate S11-2 in a white solid state was obtained.

$^1$H NMR spectrum data of the eight-arm polyethylene glycol intermediate S11-2 were as follows: $^1$H NMR (CDCl$_3$) δ (ppm): 0.21 (—Si(CH$_3$)$_2$), 0.98 (—SiC(CH$_3$)$_3$), 1.73 (—CHCH$_2$CH$_2$NHCO—), 1.53 (—CH$_2$CH$_2$OSi—), 2.12 (CH$_3$—Ar), 3.06 (CONHCH$_2$CH$_2$), 3.20 (—CHCH$_2$CH$_2$NHCO—), 3.22 (—NHCOCH$_2$NH), 3.40-3.80 (—OCH$_2$CH$_2$O—, —CHCH$_2$CH$_2$NHCO—, —CH$_2$CH$_2$OSi—), 4.20 (—CH$_2$OC(=O)N), 5.85 (CH(Ar)OC(=O)N), 7.3-7.8 (Ar—H).

Step (b): Into a dry and clean container, the eight-arm polyethylene glycol intermediate S11-2 obtained in Step (a) was added and then dissolved with tetrahydrofuran, followed by the addition of tetra-t-butyl ammonium fluoride (TBAF); thereafter, the reaction was conducted overnight, and an eight-arm polyethylene glycol H1-8 with unprotected hydroxyl groups was obtained.

S11-1

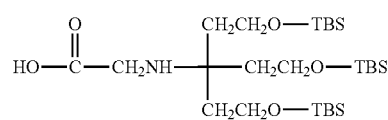

S11-2

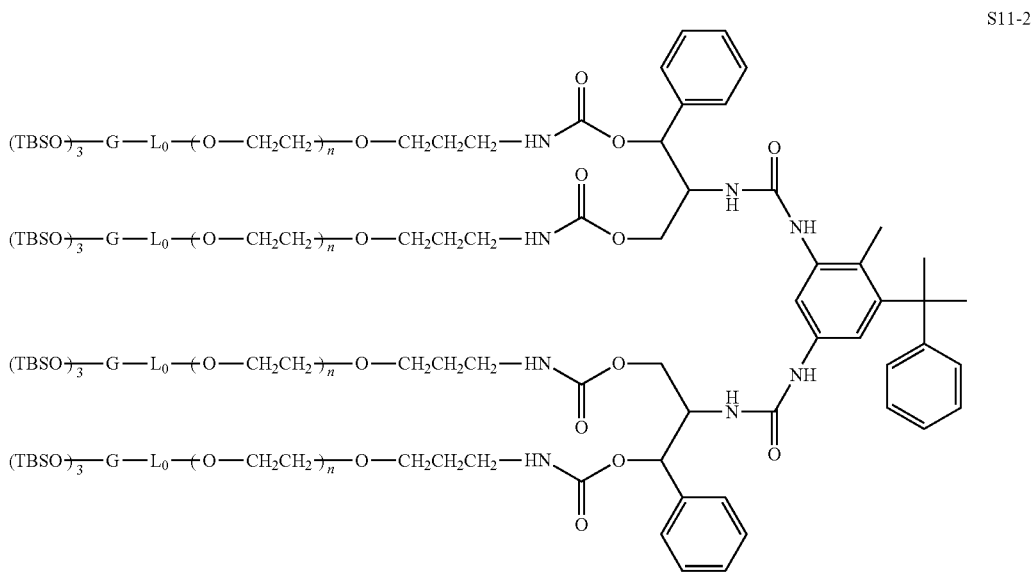

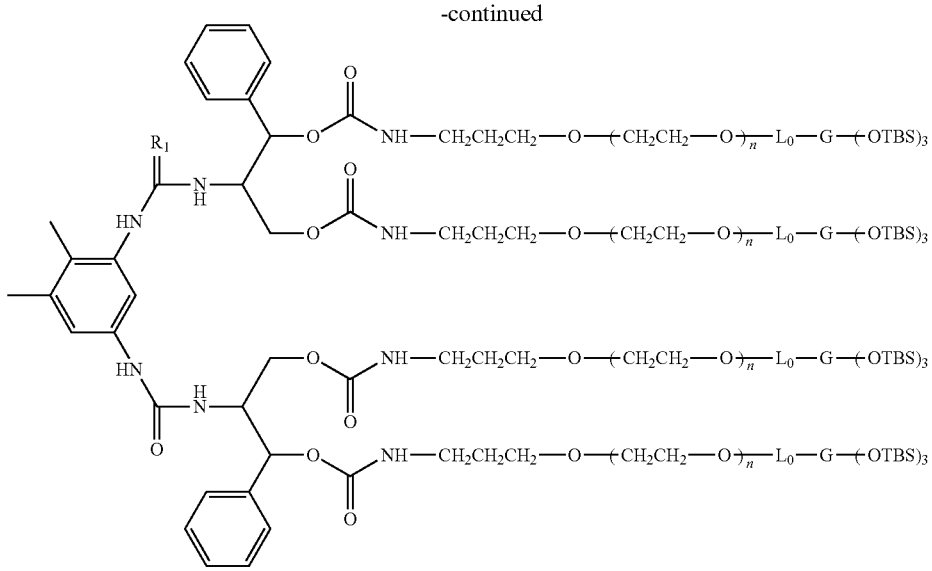

-continued

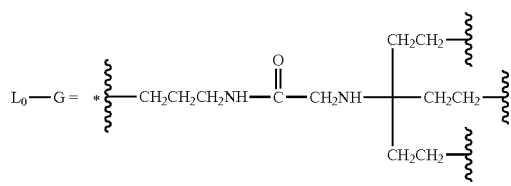

$^1$H NMR spectrum data of the eight-arm polyethylene glycol H1-8 were as follows: H NMR (CDCl$_3$) δ (ppm): 1.53 (—CH$_2$CH$_2$OH), 1.70-1.76 (—CH$_2$CH$_2$CH$_2$NHCOCH$_2$—, —CH$_2$CH$_2$CH$_2$NHCOO—), 2.12 (CH$_3$—Ar), 3.06 (—CONHCH$_2$CH$_2$—), 3.15-3.25 (—CH$_2$CH$_2$CH$_2$NHCOO—, —CH$_2$CH$_2$CH$_2$NHCOCH$_2$—, —NHCOCH$_2$NH), 3.40-3.80 (—OCH$_2$CH$_2$O—, —CH$_2$CH$_2$CH$_2$NHCOCH$_2$—, —CH$_2$CH$_2$CH$_2$NHCOO—, —CH$_2$CH$_2$OH), 4.20 (—CH$_2$OC(=O)N), 5.85 (—CH(Ar)OC(=O)N), 7.30-7.80 (Ar—H). $M_n \approx 43$ kDa, PDI=1.03.

Example-12: Preparation of an Eight-Arm Polyethylene Glycol Succinimidyl Carbonate Derivative (A6-1

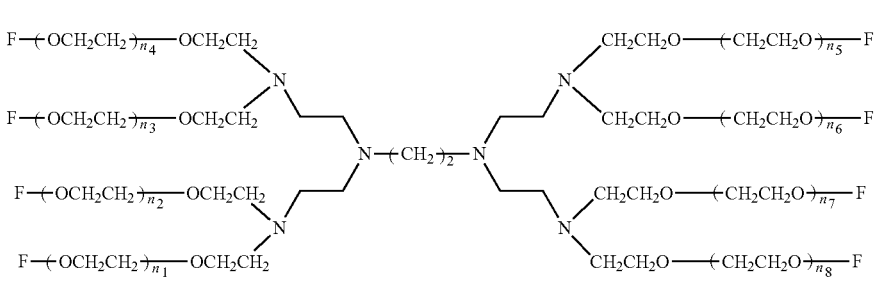

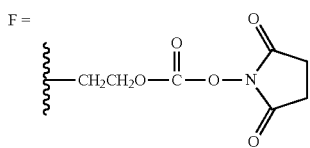

Herein, the structure of the eight-arm polyethylene glycol derivative was designed as follows:

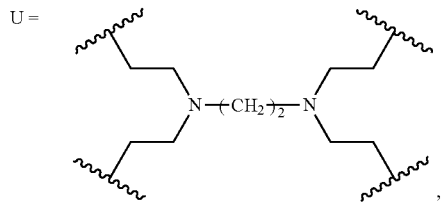

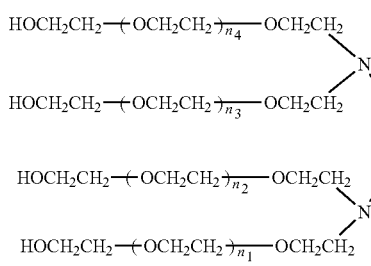

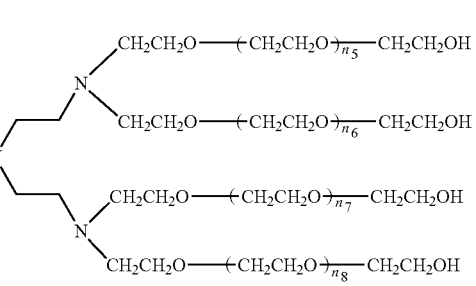

(with a nitrogen-atom-branching center of a symmetrical structure), the divalent linking groups $L_{11}$, $L_{12}$, $L_{21}$, $L_{22}$, $L_{31}$, $L_{32}$, $L_{41}$ and $L_{42}$ are all absent, g=0, k=1, and F=CH$_2$CH$_2$OCONHS (wherein, $Z_2$ is absent, $Z_1$ is an ethylene group, and $R_{01}$ is OCONHS). The designed total molecular weight is approximately 61.9 kDa, wherein, the molecular weight of the eight PEG chains is approximately 8×7500=60000 Da, corresponding to $n_1 \approx n_2 \approx n_3 \approx n_4 \approx n_5 \approx n_6 \approx n_7 \approx n_8 \approx 170$.

Step (a): Into a dry and sealed reactor, tetrahydrofuran (250 mL), a tetrasulfonate compound S12-2 (20 mmol) and excess diphenylmethyl potassium (120 mmol) were added, and then an excess amount of a secondary amine compound S12-1 with two protected hydroxyl groups (150 mmol) was added, followed by reaction at 30° C. for 12 hours. After opening the reactor, the product in the solvent was concentrated, dissolved in dichloromethane, washed and dried. Thereafter, the product was dissolved with tetrahydrofuran, added with tetra-t-butyl ammonium fluoride (TBAF), and then the reaction was conducted overnight. Thereafter, the product in the solvent was concentrated, dissolved in dichloromethane, washed, dried and purified via column chromatography, and then an octahydroxyl-containing initiator S12-3 was obtained.

$^1$H NMR spectrum data of the compound S12-3 were as follows: $^1$H NMR (CDCl$_3$) δ (ppm): 2.37 (NCH$_2$CH$_2$N), 2.55 (—NCH$_2$CH$_2$OH), 3.43-3.55 (—CH$_2$CH$_2$OH).

Step (b): Into a sealed reactor under an anhydrous and oxygen-free atmosphere, tetrahydrofuran (250 mL), the octahydroxyl-containing initiator S12-3 (1.266 mmol) and diphenylmethyl potassium (DPMK, 4.0 mmol) were added in sequence.

Step (c): After the addition of a calculated amount of ethylene oxide, the whole was heated stepwisely to 60° C., followed by reaction for 48 hours. After the addition of excess proton source (methanol), the product in the solvent was concentrated and precipitated, and then an eight-arm polyethylene glycol S12-4 was obtained.

$^1$H NMR spectrum data of the eight-arm polyethylene glycol S12-4 were as follows: H NMR (CDCl$_3$) δ (ppm): 2.37 (NCH$_2$CH$_2$N), 2.55 (—NCH$_2$CH$_2$O—), 3.40-3.80 (—OCH$_2$CH$_2$O—, —NCH$_2$CH$_2$O—); $M_n \approx 61$ kDa, PDI=1.06.

Step (d): Into a dry and clean 1 L round-bottom flask, 20 g of the eight-arm polyethylene glycol S12-4 obtained in Step (c), which was previously treated by azeotropic removal of water with toluene, was added, subsequently, 500 mL of acetonitrile, 40 mL of triethylamine and 10 g of N,N'-disuccinimidyl carbonate were added, and then the reaction was conducted at room temperature for 24 hours. Thereafter, the product in the solvent was concentrated and recrystallized from isopropanol, and then an eight-arm polyethylene glycol succinimidyl carbonate derivative A6-1 in a white solid state was obtained.

$^1$H NMR spectrum data of the eight-arm polyethylene glycol succinimidyl carbonate derivative A6-1 were as follows: $^1$H NMR (CDCl$_3$) δ (ppm): 2.30-2.45 (NCH$_2$CH$_2$N), 2.70-2.85 (—(O═)CCH$_2$CH$_2$C(═O)—, —NCH$_2$CH$_2$O—), 3.40-3.80 (—CH$_2$CH$_2$O—, —CH$_2$CH$_2$OC(═O)O—, —NCH$_2$CH$_2$O—), 4.30-4.40 (—CH$_2$OC(═O)O—); M$_n$≈62 kDa, PDI=1.06.

Example-13: Preparation of an Eight-Arm Polyethylene Glycol Halide Derivative (C7-1)

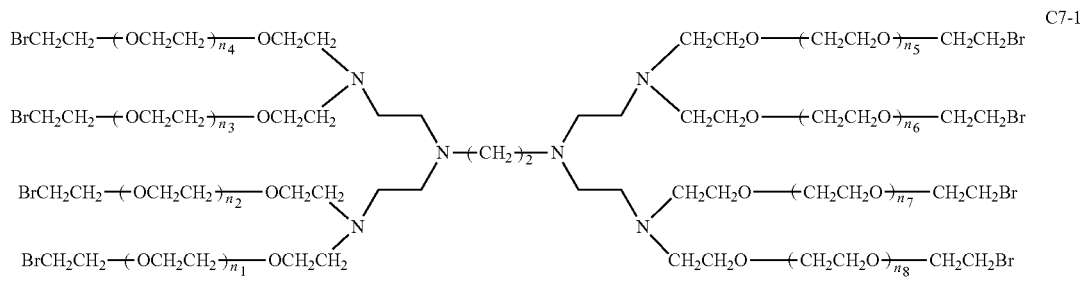

C7-1

Herein, U, E$_1$, E$_2$, E$_3$, E$_4$, L$_{11}$, L$_{12}$, L$_{21}$, L$_{22}$, L$_{31}$, L$_{32}$, L$_{41}$, L$_{42}$, n$_1$, n$_2$, n$_3$, n$_4$, n$_5$, n$_6$, n$_7$ and n$_8$ in the eight-arm polyethylene glycol derivative are the same as those in Example-12, g=0, k=1, and F=CH$_2$CH$_2$Br (wherein, Z$_2$ is absent, Z$_1$ is an ethylene group, and R$_{01}$ is Br). The designed total molecular weight is approximately 61.4 kDa.

Into a dry and clean 1 L round-bottom flask, 20 g of the eight-arm polyethylene glycol S12-4 obtained in Example-12, which was previously treated by azeotropic removal of water with toluene, was added. Subsequently, a solution of 7 g of bromosulfoxide in toluene (200 mL) was added slowly in an ice bath, followed by reaction at room temperature for 24 hours. Thereafter, the product was washed, concentrated and recrystallized from isopropanol, and then an eight-arm polyethylene glycol bromide C7-1 in a white solid state was obtained.

$^1$H NMR spectrum data of the eight-arm polyethylene glycol bromide C7-1 were as follows: $^1$H NMR (CDCl$_3$) δ (ppm): 2.30-2.45 (NCH$_2$CH$_2$N), 3.40-3.80 (—OCH$_2$CH$_2$O—, OCH$_2$CH$_2$Br); M$_n$≈61 kDa, PDI=1.06.

Example-14: Preparation of an Eight-Arm Polyethylene Glycol Azide Derivative (G21-1)

Herein, U, E$_1$, E$_2$, E$_3$, E$_4$, L$_{11}$, L$_{12}$, L$_{21}$, L$_{22}$, L$_{31}$, L$_{32}$, L$_{41}$, L$_{42}$, n$_1$, n$_2$, n$_3$, n$_4$, n$_5$, n$_6$, n$_7$, and n$_8$ in the eight-arm polyethylene glycol derivative are the same as those in Example-12, g=0, k=1, and F=CH$_2$CH$_2$N$_3$ (wherein, Z$_2$ is absent, Z$_1$ is an ethylene group, and R$_{01}$ is N$_3$). The designed total molecular weight is approximately 61.0 kDa.

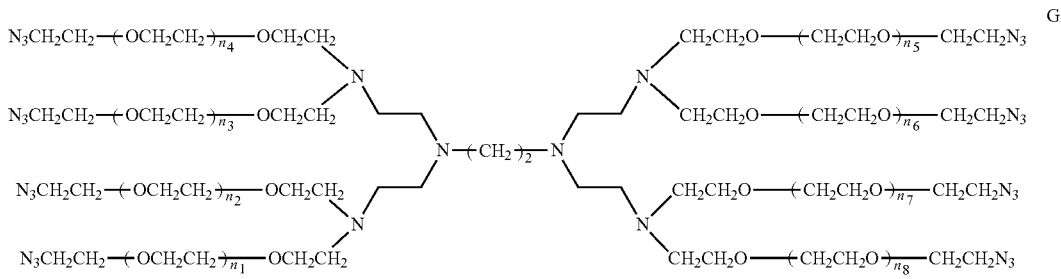

G21-1

Step (a): Into a dry and clean 1 L round-bottom flask, 10 g of the eight-arm polyethylene glycol S12-4 obtained in Example-12 was added. Under nitrogen protection, 500 mL of dichloromethane, 20 mL of pyridine and 5 g of 4-toluenesulfonyl chloride were added thereinto, followed by reaction at room temperature for 24 hours. Thereafter, the solution was adjusted to a pH value less than 7 with hydrochloric acid (1 mol/L), and the aqueous phase was washed with dichloromethane (50 mL trice). The organic phase was combined, washed with saturated salt solutions, dried with anhydrous sodium sulfate, filtrated, concentrated and recrystallized, and then an eight-arm polyethylene glycol sulfonate derivative B1-2 was obtained.

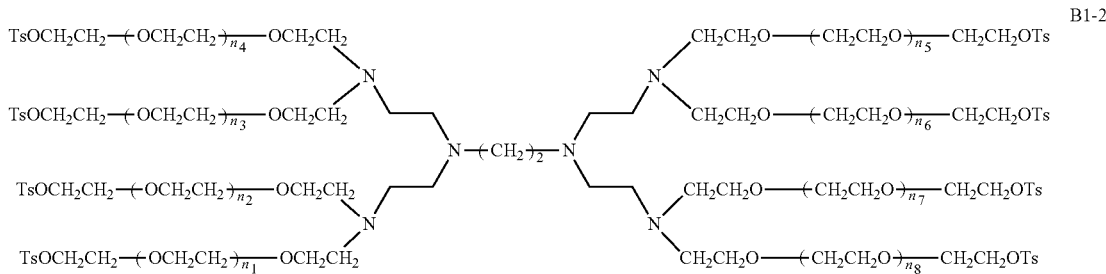

B1-2

$^1$H NMR spectrum data of the eight-arm polyethylene glycol sulfonate derivative B1-2 were as follows: $^1$H NMR (CDCl$_3$) δ (ppm): 2.30-2.45 (NCH$_2$CH$_2$N), 2.35 (CH$_3$C$_6$H$_4$SO$_2$—), 3.40-3.80 (—OCH$_2$CH$_2$O—), 4.20 (—OCH$_2$CH$_2$OSO$_2$—), 7.30 (CH$_3$C$_6$H$_4$SO$_2$—), 7.80 (CH$_3$C$_6$H$_4$O$_2$—).

Step (b): Into a dry and clean 1 L round-bottom flask, 10 g of the eight-arm polyethylene glycol sulfonate derivative B1-2 and 600 mL of tetrahydrofuran were added in sequence, and then the whole was stirred till all were dissolved. Subsequently, 4 g of sodium azide was added thereinto, and the reaction was conducted at room temperature for a week. Thereafter, the resulting product was extracted with dichloromethane (200 mL trice). The organic phase was combined, washed with saturated salt solutions, dried, filtrated, concentrated at low temperature and recrystallized, and then an eight-arm polyethylene glycol azide derivative G21-1 in a white solid state was obtained.

In the $^1$H NMR spectrum of the eight-arm polyethylene glycol azide derivative G21-1, besides the characteristic peaks of the chain backbone, the characteristic peaks of the tosylate moiety disappeared, and the characteristic peaks of the azide moiety appeared as follows: $^1$H NMR (CDCl$_3$) δ (ppm): 1.30-1.50 (—CH$_2$CH$_2$N$_3$); $M_n$≈61 kDa, PDI=1.06.

Example-15: Preparation of an Eight-Arm Polyethylene Glycol Cyanide Derivative (G23-1)

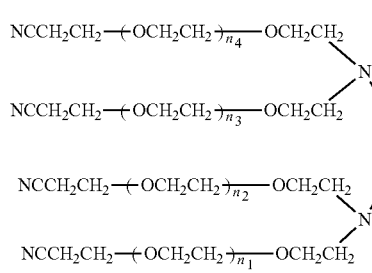
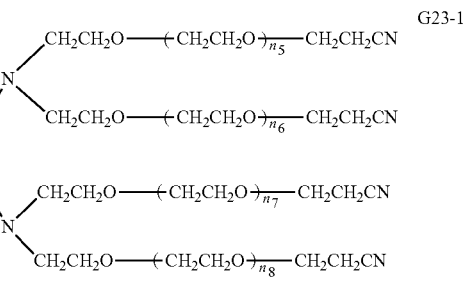

G23-1

Herein, U, $E_1$, $E_2$, $E_3$, $E_4$, $L_{11}$, $L_{12}$, $L_{21}$, $L_{22}$, $L_{31}$, $L_{32}$, $L_{41}$, $L_{42}$, $n_1$, $n_2$, $n_3$, $n_4$, $n_5$, $n_6$, $n_7$ and $n_8$ in the eight-arm polyethylene glycol derivative are the same as those in Example-12, g=0, k=1, and F=CH$_2$CH$_2$CN (wherein, $Z_2$ is absent, $Z_1$ is an ethylene group, and $R_{01}$ is CN). The designed total molecular weight is approximately 60.8 kDa.

Into a dry and clean 1 L round-bottom flask, 20 g of the eight-arm polyethylene glycol S12-4 obtained in Example-12 was added. Under nitrogen protection, 500 mL of 1,4-dioxane was added thereinto, and the whole was stirred till dissolution. Subsequently, 5 g of 50% potassium hydroxide solution was added in an ice bath, and then acrylonitrile was added dropwisely, followed by reaction at room temperature for 24 hours. Thereafter, the solution was adjusted to pH 7 with hydrochloric acid (1 mol/L) and then concentrated to remove 1,4-dioxane. The resulting substance was dissolved with 400 mL of deionized water, and the aqueous phase was washed with dichloromethane (200 mL trice). The organic phase was combined, washed with saturated salt solutions, dried with anhydrous sodium sulfate, filtrated, concentrated and precipitated, and then an eight-arm polyethylene glycol propionitrile derivative G23-1 was obtained.

$^1$H NMR spectrum data of the eight-arm polyethylene glycol propionitrile derivative G23-1 were as follows: $^1$H NMR (CDCl$_3$) δ (ppm): 2.30-2.45 (NCH$_2$CH$_2$N), 2.50-2.60 (—NCH$_2$CH$_2$O—, —CH$_2$CH$_2$CN), 3.40-3.80 (—OCH$_2$CH$_2$O—, —NCH$_2$CH$_2$O—, —OCH$_2$CH$_2$CN); $M_n$≈61 kDa, PDI=1.06.

Example-16: Preparation of an Eight-Arm Polyethylene Glycol Lipoic Acid Derivative Herein, the structure of the eight-arm polyethylene glycol derivative was designed as follows:

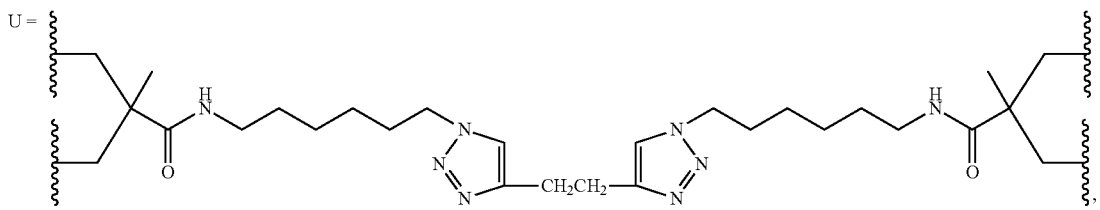

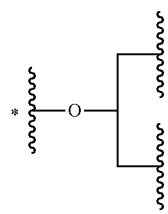

(with a carbon-branching center of a symmetrical type), the divalent linking groups $L_{11}$, $L_{12}$, $L_{21}$, $L_{22}$, $L_{31}$, $L_{32}$, $L_{41}$ and $L_{42}$ are OC(C=O), g=0, k=1, and

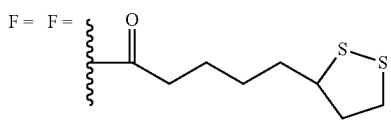

(wherein, $Z_2$ is absent, and $Z_1$ is $CO(CH_2)_6$). The designed total molecular weight is approximately 42.2 kDa, wherein, the molecular weight of the eight PEG chains is approximately 8×5000=40000 Da, corresponding to $n_1 \approx n_2 \approx n_3 \approx n_4 \approx n_5 \approx n_6 \approx n_7 \approx n_8 \approx 113$.

Step (a): Into a dry and clean 1 L round-bottom flask, 50 mmol of 1,5-hexadiyne and 50 mmol a heterofunctional protected-dihydroxyl polyethylene glycol azide compound S16-1 were added. Under nitrogen protection, 200 mL of tetrahydrofuran was added thereinto, and the whole was stirred till dissolution, followed by reaction at room temperature for 24 hours. Thereafter, the solution was concentrated and recrystallized from isopropanol, and then a dihydroxyl-protected compound S16-2 was obtained.

Step (b): Into a dry and clean 1 L round-bottom flask, the above-obtained dihydroxyl-protected compound S16-2 was added and then dissolved with methanol. The solution was adjusted to pH 3.5 with the addition of hydrochloric acid (1 M), followed by reaction for 4 hours, and then a compound S16-3 containing four unprotected hydroxyl groups was obtained.

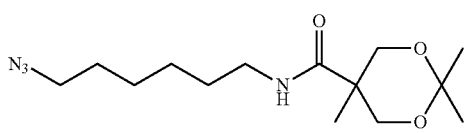

S16-1

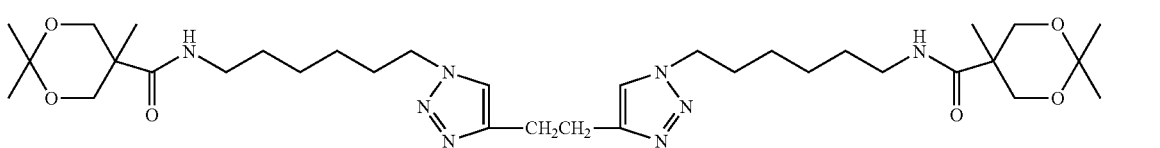

S16-2

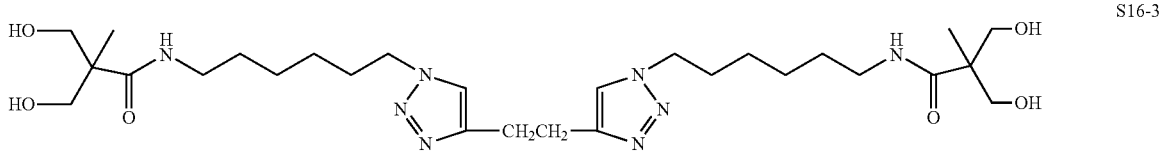

S16-3

Step (c): Into a sealed reactor under an anhydrous and oxygen-free atmosphere, tetrahydrofuran (400 mL), excess diphenylmethyl potassium (100 mmol) and the compound S16-3 containing four unprotected hydroxyl groups were added, and then excess dihydroxyl-protected compound S9-2 (50 mmol, OTs is a tosylate group) was added, followed by reaction at 30° C. for 12 hours. After opening the reactor, the mixture was washed, concentrated and then dissolved with methanol. The solution was adjusted to pH 3.5 with the addition of hydrochloric acid (1 M), followed by reaction for 4 hours. Thereafter, the product in the solvent was concentrated, washed and purified via column chromatography, and then an octahydroxyl-containing small molecule compound S16-4 was obtained.

$^1$H NMR spectrum data of the octahydroxyl-containing small molecule compound S16-4 were as follows: $^1$H NMR (CDCl$_3$) δ (ppm): 1.29-1.40 (—CONHCH$_2$CH$_2$CH$_2$CH$_2$CH$_2$CH$_2$—, —CH$_3$), 1.52-1.80 (—CONHCH$_2$CH$_2$CH$_2$CH$_2$CH$_2$CH$_2$), 3.0-3.3 (—CH(CH$_2$OH)$_2$—, —CH$_2$CH$_2$C(=CH)N=N—, —CONHCH$_2$CH$_2$CH$_2$CH$_2$CH$_2$CH$_2$—), 3.57 (—C(CH$_3$)(CH$_2$O—)$_2$), 4.46 (—CONHCH$_2$CCH$_2$CH$_2$CH$_2$CH$_2$CH$_2$—), 7.75 (—CH$_2$CH$_2$C(=CH)N=N—).

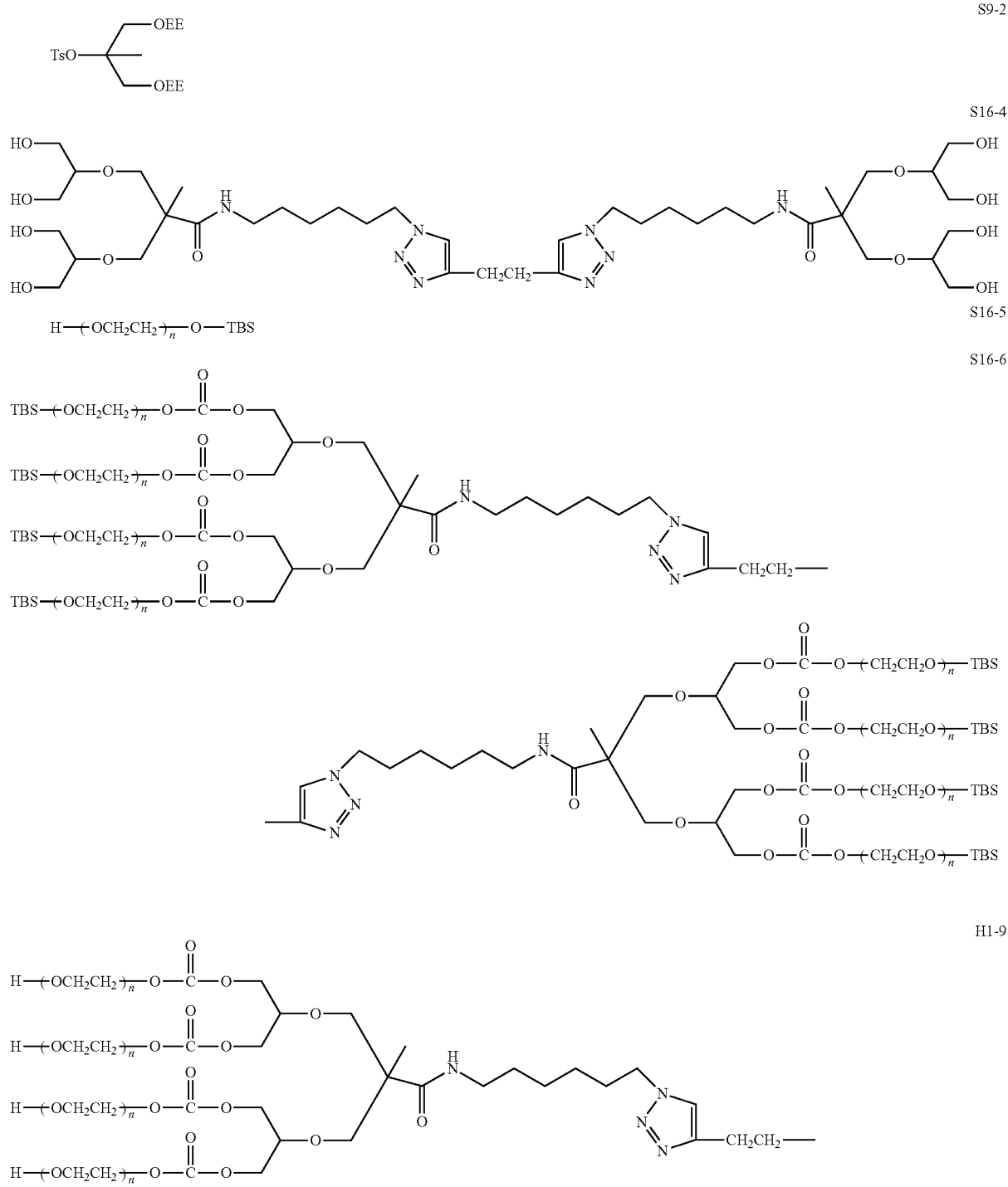

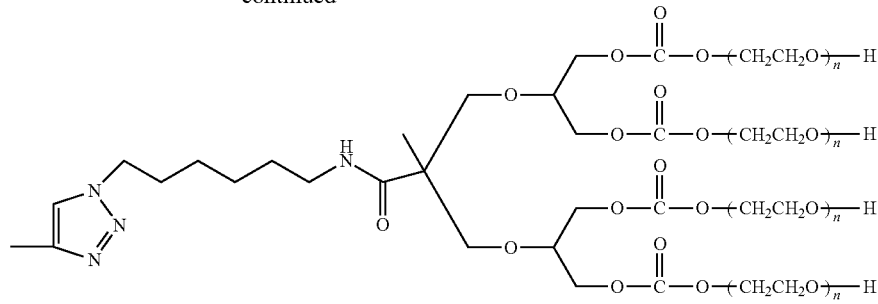

Step (d): Into a dry and clean 1000 mL round-bottom flask, 30 g of a heterofunctional polyethylene glycol (S16-5, $M_n$ was about 5 kDa, PDI=1.03), 12.2 g (100 mmol) of 4-dimethylaminopyridine and 200 mL of anhydrous dichloromethane were added, and the whole was stirred till dissolution. Subsequently, 18 mmol of triphosgene was added with stirring, followed by stirring for 20 minutes.

The above-obtained octahydroxyl-containing small molecule compound S16-4 (1 mmol) and a solution of DMAP (12.2 g, 100 mmol) in dichloromethane (200 mL) was added, and the whole was stirred till all were mixed, followed by reaction at room temperature for 2 hours. Thereafter, the resulting product was washed, dried and concentrated, and then an intermediate S16-6 was obtained.

The intermediate S16-6 was dissolved with tetrahydrofuran, followed by the addition of tetra-t-butyl ammonium fluoride (TBAF); thereafter, the reaction was conducted overnight, and then an eight-arm polyethylene glycol H1-9 with unprotected hydroxyl groups was obtained.

$^1$H NMR spectrum data of the eight-arm polyethylene glycol H1-9 were as follows: $^1$H NMR (CDCl$_3$) δ (ppm): 1.29-1.40 (—CONHCH$_2$CH$_2$CH$_2$CH$_2$CH$_2$CH$_2$—, —CH$_3$), 1.52-1.80 (—CONHCH$_2$CH$_2$CH$_2$CH$_2$CH$_2$CH$_2$), 3.0-3.3 (—CH(CH$_2$O—)$_2$—, —CH$_2$CH$_2$C(=CH)N=N—, —CONHCH$_2$CH$_2$CH$_2$CH$_2$CH$_2$CH$_2$—), 3.40-3.80 (—CH$_2$CH$_2$O—, —C(CH$_3$)(CH$_2$O—)$_2$), 4.20-4.30 (—CH$_2$OCOOCH$_2$—), 4.46 (—CONHCH$_2$CH$_2$CH$_2$CH$_2$CH$_2$CH$_2$—), 7.75 (—CH$_2$CH$_2$C(=CH)N=N—); $M_n$≈41 kDa, PDI=1.02.

Step (e): Into a dry and clean 1 L round-bottom flask, 40 g of the eight-arm polyethylene glycol with unprotected hydroxyl groups (H1-9, treated by azeotropic removal of water with toluene) obtained in the last step and 20 g of lipoic acid were added. Under nitrogen protection, dichloromethane (600 mL) was added thereinto, and the whole was stirred till dissolution. Subsequently, 40 mL of triethylamine and 40 g of dicyclohexylcarbodiimide (DCC) were added thereinto in sequence, followed by reaction at room temperature for 24 hours. Thereafter, the resulting mixture was filtrated to remove undissolved substances, concentrated and recrystallized from isopropanol, and then an eight-arm polyethylene glycol lipoic acid derivative C14-1 was obtained.

In the $^1$H NMR spectrum of the eight-arm polyethylene glycol disulfide derivative (cyclodisulfide), besides the characteristic peaks of the chain backbone, the characteristic peaks of a disulfide derivative also appeared as follows: $^1$H NMR (CDCl$_3$) δ (ppm): 1.20-1.70 (—CH$_2$CH$_2$CH$_2$CH$_2$CH$_2$CH$_2$—), 1.98 (—CH$_2$CH$_2$—S—S—), 2.32-2.60 (—CH(CH$_2$)—S—S—, —CH$_2$CH$_2$—S—S—, —CHC(=O)CH$_2$—); $M_n$≈42 kDa, PDI=1.02.

Example-17: Preparation of an Eight-Arm Protected PEG-Amine Derivative (C6-3)

C6-3

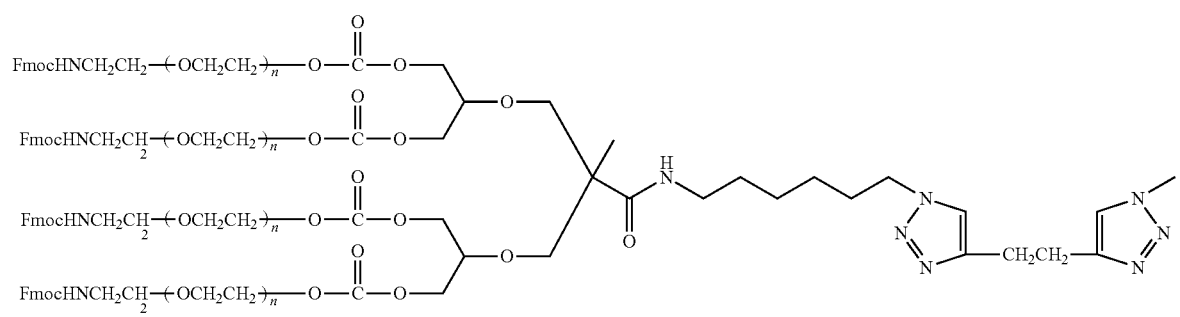

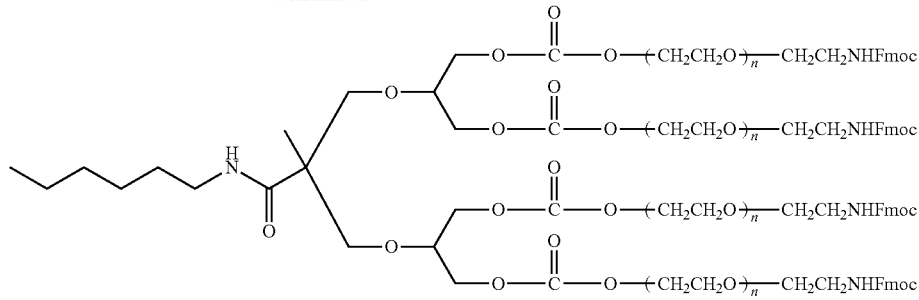

Herein, U, $E_1$, $E_2$, $E_3$, $E_4$, $L_{11}$, $L_{12}$, $L_{21}$, $L_{22}$, $L_{31}$, $L_{32}$, $L_{41}$ and $L_{42}$ in the eight-arm polyethylene glycol derivative are the same as those in Example-16, g=0, k=1, and F=$CH_2CH_2NH$—Fmoc (wherein, $Z_2$ is absent, $Z_1$ is an ethylene group, and $R_{01}$ is $NPG_5$). The designed total molecular weight is approximately 35.0 kDa, wherein, the molecular weight of the eight PEG chains is approximately 8×4000=32000 Da, corresponding to $n_1 \approx n_2 \approx n_3 \approx n_4 \approx n_5 \approx n_6 \approx n_7 \approx n_8 \approx 91$.

Into a dry and clean 1000 mL round-bottom flask, 30 g of a heterofunctional polyethylene glycol (S17-1, $M_n$ was about 4 kDa, PDI=1.03), 100 mmol of 4-dimethylaminopyridine and 200 mL of anhydrous dichloromethane were added in sequence, and the whole was stirred till dissolution.

Subsequently, 18 mmol of triphosgene was added with stirring, followed by stirring for 20 minutes. The above-obtained octahydroxyl-containing small molecule compound S16-4 (1 mmol) and a solution of DMAP (12.2 g, 100 mmol) in dichloromethane (200 mL) was added, and the whole was stirred till all were mixed, followed by reaction at room temperature for 2 hours. Thereafter, the resulting product was washed and precipitated, and then an eight-arm protected PEG-amine derivative C6-3 was obtained.

Fmoc-NHCH$_2$CH$_2$(-OCH$_2$CH$_2$-)$_n$OH      S17-1

$^1$H NMR spectrum data of the eight-arm protected PEG-amine derivative C6-3 were as follows: $^1$H NMR (CDCl$_3$) δ (ppm): 1.29-1.40 (—CONHCH$_2$CH$_2$CH$_2$CH$_2$CH$_2$CH$_2$—, —CH$_3$), 1.52-1.80 (—CONHCH$_2$CH$_2$CH$_2$CH$_2$CH$_2$CH$_2$), 3.0-3.3 (—CH(CH$_2$O—)$_2$—, —CH$_2$CH$_2$C(=CH)N=N—, —CONHCH$_2$CH$_2$CH$_2$CH$_2$CH$_2$CH$_2$—), 3.40-3.80 (—CH$_2$CH$_2$O—, —CONHCH$_2$CH$_2$—, —OCONHCH$_2$CH$_2$, —C(CH$_3$)(CH$_2$O—)$_2$), 4.20-4.30 (—CH$_2$OCOOCH$_2$—, —CH$_2$OCONHCH$_2$CH$_2$), 4.45-4.70 (—CONHCH$_2$CH$_2$CH$_2$CH$_2$CH$_2$CH$_2$—, Ar—CH—CH$_2$—), 7.75 (—CH$_2$CH$_2$C(=CH)N=N—), 7.28-7.87 (—Ar—H); $M_n \approx 35$ kDa, PDI=1.03.

Example-18: Preparation of an Eight-Arm Polyethylene Glycol Maleimide Derivative (E1-1)

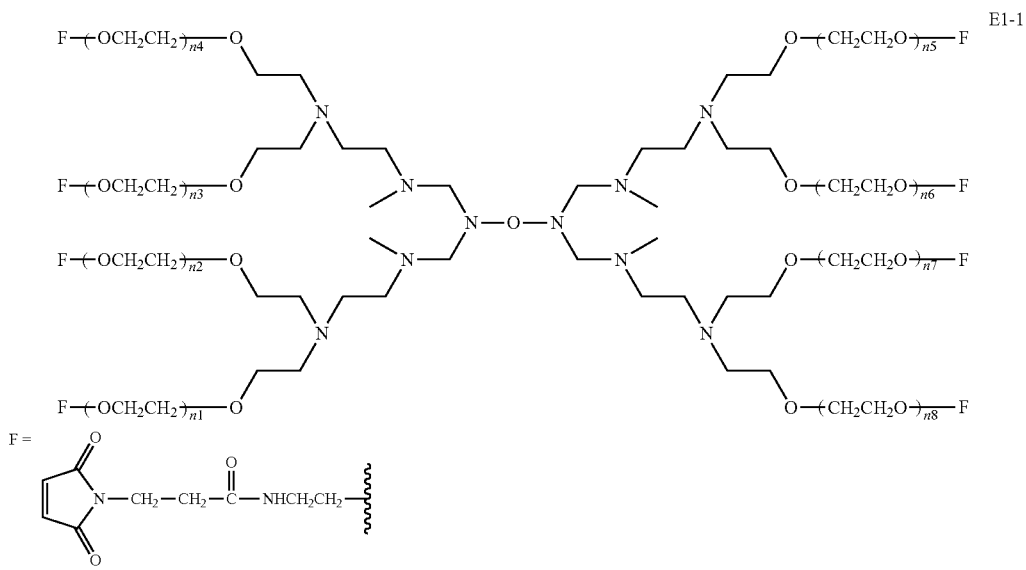

Herein, the structure of the eight-arm polyethylene glycol derivative was designed as follows:

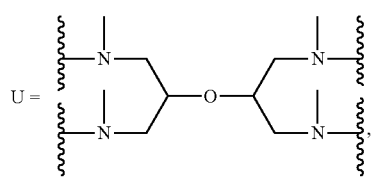

-continued

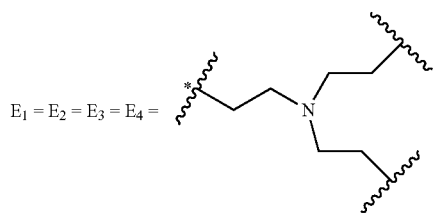

(with a nitrogen-branching center of a symmetrical type), the divalent linking groups $L_{11}$, $L_{12}$, $L_{21}$, $L_{22}$, $L_{31}$, $L_{32}$, $L_{41}$ and $L_{42}$ are all absent, g=0, k=1, and

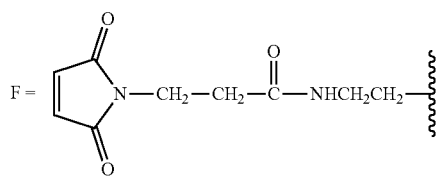

(wherein, $Z_2$ is an ethylene group, $Z_1$ is $NHCOCH_2CH_2$, and $R_{01}$ is a maleimido group abbreviated as a MAL group). The designed total molecular weight is approximately 42.1 kDa, wherein, the molecular weight of the eight PEG chains is approximately 8×5000=40000 Da, corresponding to $n_1 \approx n_2 \approx n_3 \approx n_4 \approx n_5 \approx n_6 \approx n_7 \approx n_8 \approx 113$.

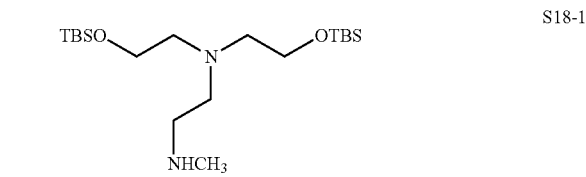

S18-1

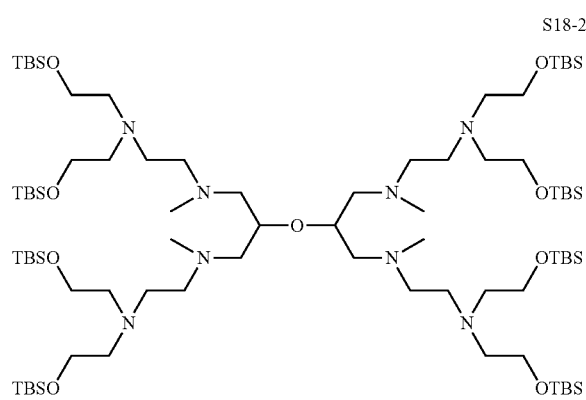

S18-2

-continued

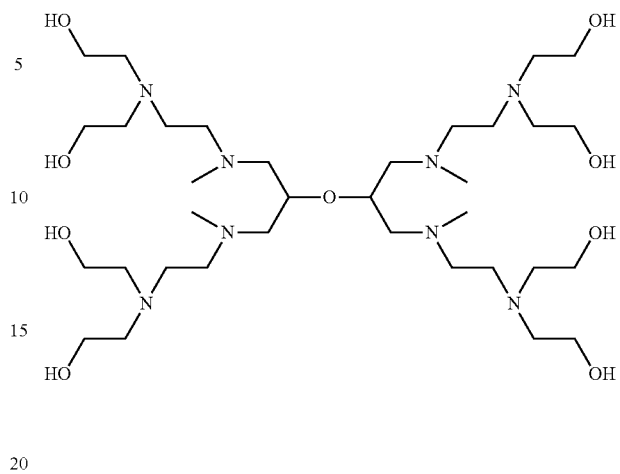

S18-3

Step (a): Into a reactor, 10 mmol of the tetrahydroxyl-containing small molecule compound S3-4 obtained in Example-3 was added. Under nitrogen protection, 500 mL of dichloromethane, 20 mL of pyridine and 10 g of 4-toluene-sulfonyl chloride were added thereinto, followed by reaction at room temperature for 24 hours. Thereafter, the solution was adjusted to a pH value less than 7 with hydrochloric acid (1 mol/L), and the aqueous phase was washed with dichloromethane (50 mL trice). The organic phase was combined, washed with saturated salt solutions, dried with anhydrous sodium sulfate and filtrated. Subsequently, 20 mL of pyridine and 50 mmol of a dihydroxyl-protected secondary-amine compound S18-1 were added thereinto.

Step (b): The reaction was conducted at room temperature for 24 hours. Thereafter, the solution was adjusted to a pH value less than 7 with hydrochloric acid (1 mol/L), and the aqueous phase was washed with dichloromethane (50 mL trice). The organic phase was combined, washed with saturated salt solutions, dried with anhydrous sodium sulfate, filtrated, concentrated and purified via column chromatography, and then a compound with eight protected hydroxyl groups S18-2 was obtained.

Step (c): The protected octaol compound S18-2 was dissolved with tetrahydrofuran, followed by the addition of tetra-t-butyl ammonium fluoride (TBAF); thereafter, the reaction was conducted overnight. The product was purified via column chromatography, and an octahydroxyl-containing small molecule compound S18-3 was obtained.

$^1$H NMR spectrum data of the octahydroxyl-containing small molecule compound S18-3 were as follows: $^1$H NMR ($CDCl_3$) δ (ppm): 2.26 (—$NCH_3$), 2.30-2.45 ($NCH_2CH_2N$), 2.55 (—$NCH_2CH_2OH$), 3.43-3.55 (—$CH_2CH_2OH$).

Step (d): Into a sealed reactor under an anhydrous and oxygen-free atmosphere, tetrahydrofuran (250 mL), the octahydroxyl-containing small molecule initiator S18-3 (1.266 mmol) and diphenylmethyl potassium (4.0 mmol) were added in sequence.

Step (e): After the addition of a calculated amount of ethylene oxide, the whole was heated stepwisely to 60° C., followed by reaction for 48 hours. Thereafter, excess proton source (methanol) was added thereinto, then the product in the solvent was concentrated and precipitated, and then an eight-arm polyethylene glycol S18-4 was obtained.

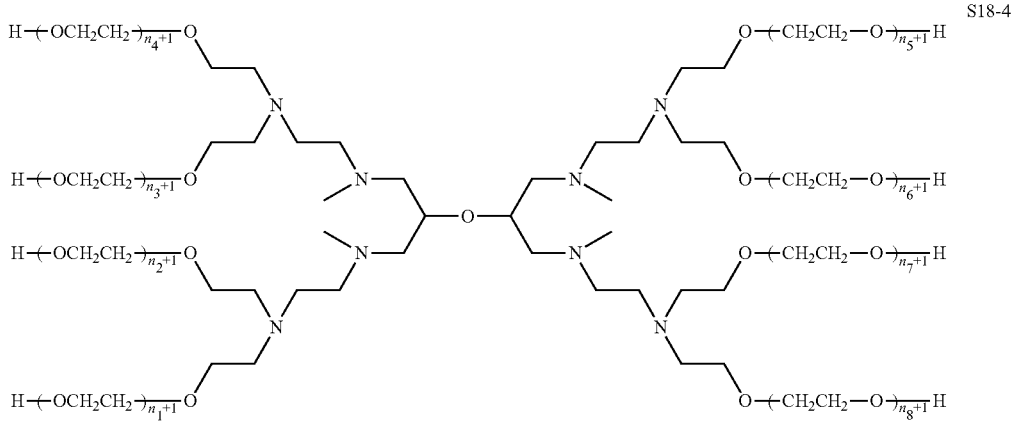

S18-4

$^1$H NMR spectrum data of the eight-arm polyethylene glycol S18-4 were as follows: $^1$H NMR (CDCl$_3$) δ (ppm): 2.26 (—NCH$_3$), 2.37 (NCH$_2$CH$_2$N), 2.55 (—NCH$_2$CH$_2$O—), 3.40-3.80 (—OCH$_2$CH$_2$O—, —NCH$_2$CH$_2$O—); $M_n$≈41 kDa, PDI=1.04.

Step (f): Into a dry and clean 1 L round-bottom flask, the above-obtained eight-arm polyethylene glycol S18-4 was added. Under nitrogen protection, 500 mL of anhydrous and oxygen-free dichloromethane, 40 mL of pyridine and 10 g of 4-toluenesulfonyl chloride were added thereinto, followed by reaction at room temperature for 24 hours. Thereafter, the solution was adjusted to a pH value less than 7 with hydrochloric acid (1 mol/L), and the aqueous phase was washed with dichloromethane (50 mL trice). The organic phase was combined and concentrated. Subsequently, 800 mL of ammonia water (40 wt %) was added thereinto, and the whole was stirred until all were dissolved. The reaction was conducted at room temperature for a week. Thereafter, the resulting product was extracted with dichloromethane (200 mL trice). The organic phase was combined, washed with saturated salt solutions, dried, filtrated, concentrated and recrystallized, and then an eight-arm polyethylene glycol amine derivative C4-2 was obtained.

$^1$H NMR spectrum data of the eight-arm polyethylene glycol amine derivative C4-2 were as follows: $^1$H NMR (CDCl$_3$) δ (ppm): 2.26 (—NCH$_3$), 2.37 (NCH$_2$CH$_2$N), 2.55 (—NCH$_2$CH$_2$O—), 2.70-2.85 (—CH$_2$CH$_2$NH$_2$), 3.40-3.80 (—OCH$_2$CH$_2$O—, —NCH$_2$CH$_2$O—).

Step (g): Into a dry and clean 1 L round-bottom flask, 20 g of the above-obtained polyethylene glycol amine derivative (C4-2, treated by azeotropic removal of water with toluene) and 10 g of β-maleimidopropionic acid were added. Under nitrogen protection, dichloromethane (600 mL) was added thereinto, and the whole was stirred till dissolution. Subsequently, 40 mL of triethylamine and 40 g of dicyclohexylcarbodiimide (DCC) were added thereinto in sequence, followed by reaction at room temperature for 24 hours. Thereafter, the resulting mixture was filtrated to remove undissolved substances, concentrated and recrystallized from isopropanol, and then an eight-arm polyethylene glycol maleimide derivative E1-1 in a white solid state was obtained.

In the $^1$H NMR spectrum of the eight-arm polyethylene glycol maleimide derivative E1-1, besides the characteristic peaks of the chain backbone, the characteristic peaks of the maleimide moiety also appeared as follows: $^1$H NMR (CDCl$_3$) δ (ppm): 2.70-2.80 (—NHC(=O)CH$_2$CH$_2$—), 3.92 (—NHCOCH$_2$CH$_2$N—), 6.81 (—CH=CH—); $M_n$≈42 kDa, PDI=1.04.

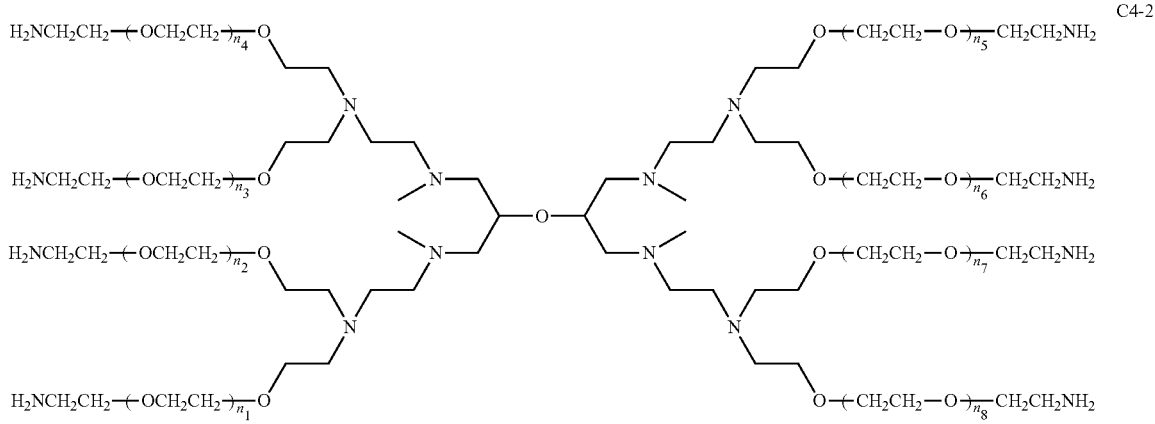

C4-2

Example-19: Preparation of an Eight-Arm Polyethylene Glycol Thiol Derivative (C2-1)

C2-1

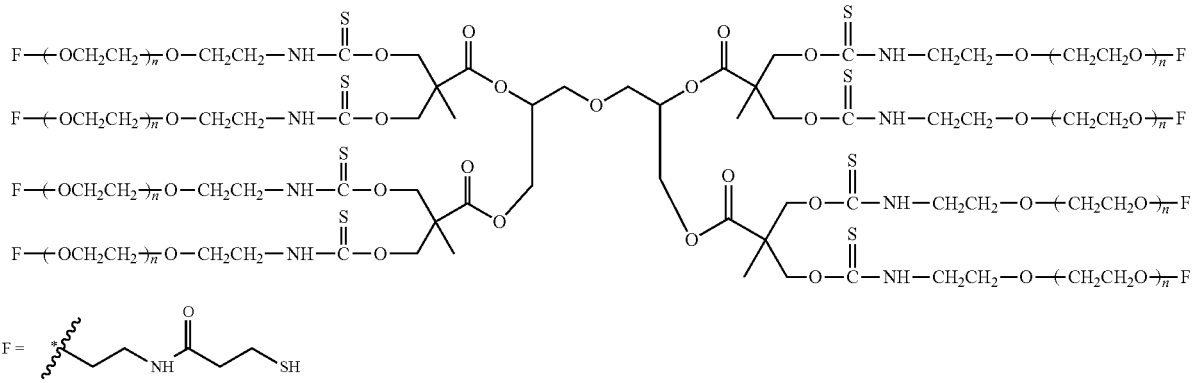

Herein, the structure of the eight-arm polyethylene glycol derivative was designed as follows:

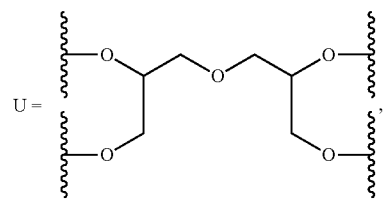

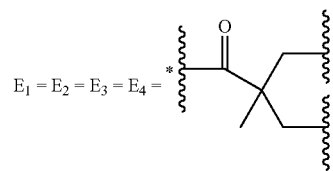

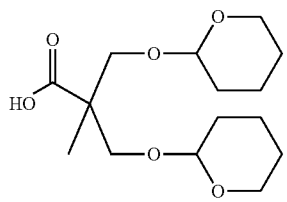

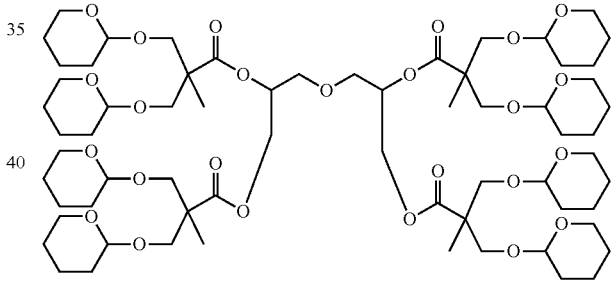

(with a carbon-branching center of a symmetrical type), the divalent linking groups $L_{11}$, $L_{12}$, $L_{21}$, $L_{22}$, $L_{31}$, $L_{32}$, $L_{41}$ and $L_{42}$ are OC(=S)NHCH$_2$CH$_2$, g=0, k=1, and F=CH$_2$CH$_2$NHCOCH$_2$CH$_2$SH. The designed total molecular weight is approximately 17.9 kDa, wherein, the molecular weight of the eight monodisperse PEG chains is approximately 8×2000=16000 Da, corresponding to $n_1=n_2=n_3=n_4=n_5=n_6=n_7=n_8=n=46$.

Step (a): Into a dry and clean 1 L round-bottom flask, 40 mmol of 2,2-dihydroxymethylpropionic acid, excess dihydropyran (100 mmol) and 4-toluenesulfonic acid were added, and then the reaction was conducted in a dichloromethane solution at 30° C. for 12 hours. After opening the reactor, the product in the solvent was washed with water, dried, concentrated, purified via column chromatography and dried, and then a compound S19-1 was obtained, in which the hydroxyl groups at the two terminals were protected by a tetrahydropyranyl group.

Step (b): Into a dry and clean 1 L round-bottom flask, 50 mmol of 2,2-dihydroxymethylpropionic acid, an excess amount of the compound S19-1 with terminal tetrahydropyranyl-protected hydroxyl groups and 20 mL of triethylamine were added. Under nitrogen protection, dichloromethane (500 mL) was added thereinto, and the whole was stirred till dissolution. Subsequently, a solution of 20 g of dicyclohexylcarbodiimide (DCC) in dichloromethane was added thereinto, followed by reaction at room temperature for 24 hours. Thereafter, the resulting mixture was filtrated to remove undissolved substances, concentrated, purified via column chromatography and concentrated, and then a small molecule compound S19-2 was obtained, in which the eight terminal hydroxyl groups were protected by tetrahydropyranyl groups. Subsequently, the small molecule compound S19-2 was added into a dry and clean reactor and then dissolved with methanol. The solution was adjusted to pH 3.0 with the addition of hydrochloric acid (1 M), followed by reaction for 4 hours. Thereafter, the product was concentrated, precipitated, collected by filtration, recrystallized and dried, and then an octahydroxyl-containing small molecule compound S19-3 was obtained.

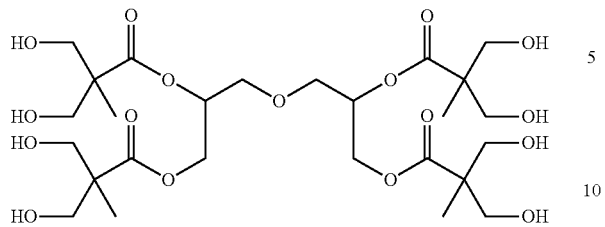

S19-3

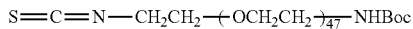

S19-4

¹H NMR spectrum data of the octahydroxyl-containing small molecule compound-S9-3 were as follows: ¹H NMR (CDCl₃) δ (ppm): 1.38 (—CH₃), 3.73 (—OCH₂CHOCO), 3.84 (—CCH₂OH), 4.20 (—CHCH₂OCO), 4.88 (—OCH₂CHOC(=O)).

Step (c): Into a round-bottom flask, the octahydroxyl-containing small molecule compound S19-3 was added and then dissolved with dichloromethane under nitrogen protection. Subsequently, a monodisperse heterofunctional polyethylene glycol isothiocyanate derivative (S19-4, the EO-unit number was 46) was added slowly and dropwisely in an ice bath. After the temperature is returned to room temperature, the reaction was conducted for 8 hours. After the addition of excess activated silicone gel, the mixture was filtrated, concentrated and recrystallized, and then an eight-arm protected PEG-amine derivative C6-3 was obtained.

¹H NMR spectrum data of the eight-arm protected PEG-amine derivative C6-3 were as follows: ¹H NMR (CDCl₃) δ (ppm): 1.38 (—CH₃), 2.73 (—OCSNHCH₂CH₂O), 3.00-3.20 (—OCH₂CH₂NH—), 3.40-3.80 (—CH₂CH₂O—, —OCSNHCH₂CH₂O, —OCH₂CH₂NH—), 4.20 (—CHCH₂O(C=O)), 4.88 (—OCH₂CHOC(=O)).

C6-3

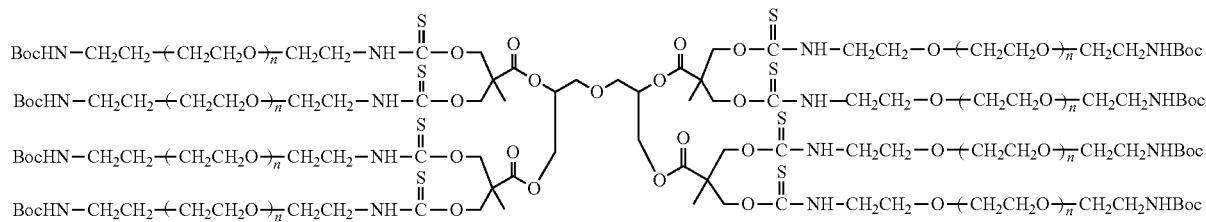

Step (d): Into a dry and clean container, the eight-arm protected PEG-amine derivative C6-3 was added and dissolved with dichloromethane. Subsequently, the solution was adjusted to 0.1 M with the addition of trifluoroacetic acid (TFA), followed by reaction for 4 hours. Thereafter, the solution was adjusted to a neutral pH value, extracted and precipitated, and then an eight-arm polyethylene glycol amine derivative C4-2 was obtained.

C4-2

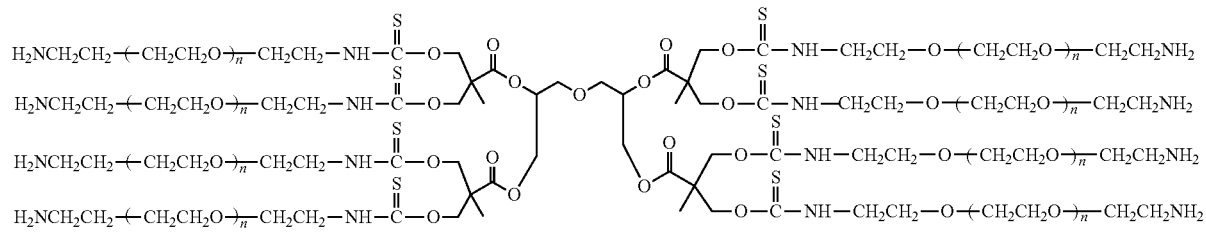

In the ¹H NMR spectrum of the eight-arm polyethylene glycol amine derivative C4-2, besides the characteristic peaks of the chain backbone, the characteristic peaks of the amino-protecting group disappeared, and the characteristic peaks of the ethylamino group appeared as follows: ¹H NMR (CDCl₃) δ (ppm): 2.70-2.85 (—CH₂CH₂NH₂).

Step (e): Into a dry and clean 1 L round-bottom flask, 20 g of the eight-arm polyethylene glycol amine derivative C4-2 obtained in Step (d) and 110 mL of triethylamine were added. Under nitrogen protection, dichloromethane (200 mL) was added thereinto, and the whole was stirred till dissolution. Subsequently, a solution of excess N-succinimidyl 3-(2-pyridyldithio)propionate in dichloromethane (500 mL) was added, followed by reaction at room temperature for 24 hours. After the addition of saturated ammonium chloride solution, the product was concentrated and dissolved with water (400 mL), and the mixture was washed with dichloromethane (150 mL trice). The organic phase was combined, washed with saturated salt solutions, dried, concentrated and recrystallized from isopropanol, and then an eight-arm protected PEG-thiol derivative C13-1 was obtained.

In the ¹H NMR spectrum of the eight-arm protected PEG-thiol derivative C13-1, besides the characteristic peaks of the chain backbone, the characteristic peaks of the pyridyldisulfide moiety also appeared as follows: ¹H NMR (CDCl₃) δ (ppm): 2.40-2.80 (—CH₂CH₂S—S—), 7.10-8.20 (—C₅H₄N—).

C13-1

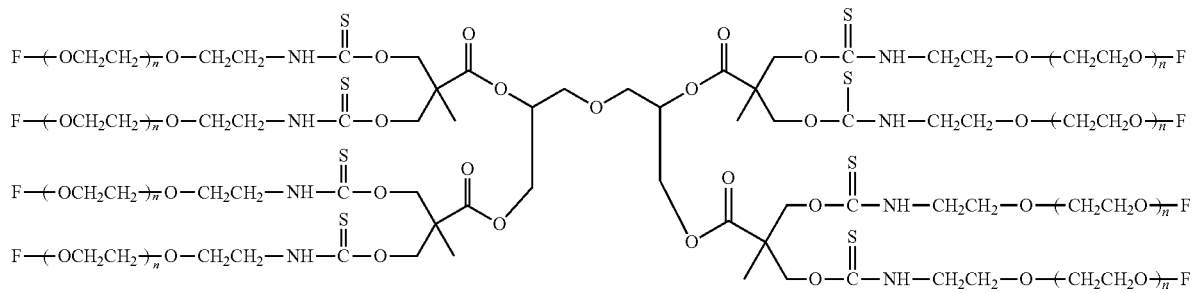

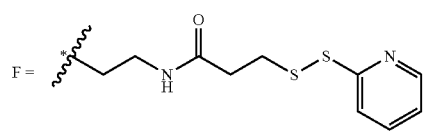

Step (f): Into a dry and clean 1 L round-bottom flask, 20 g of the eight-arm protected PEG-thiol derivative C13-1 obtained in Step (e) was added. Under nitrogen protection, tetrahydrofuran (400 mL) was added thereinto, and the whole was stirred till all were dissolved. Subsequently, 10 g of dithiothreitol was added, followed by reaction at room temperature for 24 hours. Thereafter, the mixture was concentrated, washed with saturated salt solutions (100 mL trice), dried, concentrated and recrystallized from isopropanol, and an eight-arm polyethylene glycol thiol derivative C2-1 was obtained.

In the $^1$H NMR spectrum of the eight-arm polyethylene glycol thiol derivative C2-1, besides the characteristic peaks of the chain backbone, the characteristic peaks of the pyridyldisulfide moiety as a protective group disappeared, and the characteristic peaks of the thiol derivative appeared as follows: $^1$H NMR (CDCl$_3$) δ (ppm): 1.60 (—SH), 2.85 (—OCH$_2$CH$_2$SH).

Example-20: Preparation of an Eight-Arm Polyethylene Glycol Thioester Derivative (C17-1)

tion, and then extracted with dichloromethane (250 mL trice). The organic phase was combined, washed with saturated salt solutions, dried, filtrated, concentrated and recrystallized, and then an eight-arm polyethylene glycol thioester derivative C17-1 was obtained.

1H NMR spectrum data of the eight-arm polyethylene glycol thioester derivative C17-1 were as follows: $^1$H NMR (CDCl$_3$) δ (ppm): 1.00-1.30 (CH$_3$C(=O)—), 1.38 (—CCH$_3$), 2.30-2.50 (CH$_3$CH$_2$C(=O)—), 2.73 (—OCSNHCH$_2$CH$_2$O—), 2.90-3.10 (—OCH$_2$CH$_2$S—), 3.40-3.80 (—CH$_2$CH$_2$O—, —OCSNHCH$_2$CH$_2$O—, —OCH$_2$CH$_2$NH), 3.90-4.10, (—SCH$_2$CH$_2$O—), 4.20 (—CHCH$_2$OCO—), 4.88 (—OCH$_2$CHOCO).

Example-21: Preparation of an Eight-Arm Polyethylene Glycol Thiocarbonate Derivative (C18-1)

Herein, U, $E_1$, $E_2$, $E_3$, $E_4$, $L_{11}$, $L_{12}$, $L_{21}$, $L_{22}$, $L_{31}$, $L_{32}$, $L_{41}$, $L_{42}$, $n_1$, $n_2$, $n_3$, $n_4$, $n_5$, $n_6$, $n_7$, $n_8$ and n in the eight-arm polyethylene glycol derivative are the same as those in Example-19, g=0, k=1, and

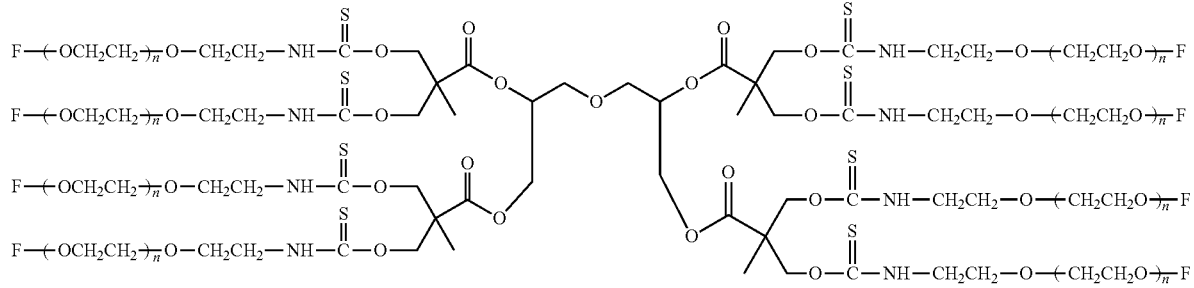

Herein, U, $E_1$, $E_2$, $E_3$, $E_4$, $L_{11}$, $L_{12}$, $L_{21}$, $L_{22}$, $L_{31}$, $L_{32}$, $L_{41}$, $L_{42}$, $n_1$, $n_2$, $n_3$, $n_4$, $n_5$, $n_6$, $n_7$, $n_8$ and n in the eight-arm polyethylene glycol derivative are the same as those in Example-19, g=0, k=1, and F=CH$_2$CH$_2$NHCOCH$_2$CH$_2$SCOCH$_3$ ($Z_2$ is CH$_2$CH$_2$NH, $Z_1$ is COCH$_2$CH$_2$, and $R_{01}$ is SCOCH$_3$). The designed total molecular weight is approximately 18.2 kDa, wherein, the molecular weight of each PEG chain is approximately 8×2000=16000 Da, corresponding to EO-unit number of $n_1$=$n_2$=$n_3$=$n_4$=$n_5$ $n_6$=$n_7$=$n_8$=n=46.

Into a dry and clean 1 L round-bottom flask, 20 g of the eight-arm polyethylene glycol thiol derivative C2-1 obtained in Example-19 and dichloromethane (500 mL) were added in sequence. The whole was stirred till dissolution, and subsequently 8 g of triethylamine and 10 g of acetyl chloride were added in sequence. The reaction was conducted at room temperature overnight; thereafter, the solution was added with saturated sodium bicarbonate solu- F=CH$_2$CH$_2$NHCOCH$_2$CH$_2$SCOCH$_3$ (wherein, $Z_2$ is CH$_2$CH$_2$NH, $Z_1$ is COCH$_2$CH$_2$, and $R_{01}$ is SFmoc). The designed total molecular weight is approximately 19.6 kDa, wherein, the molecular weight of each PEG chain is approximately 8×2000=16000 Da, corresponding to EO-unit number of $n_1$=$n_2$=$n_3$=$n_4$=$n_5$=$n_6$=$n_7$=$n_8$=n=46.

Into a dry and clean 1 L round-bottom flask, 20 g of the eight-arm polyethylene glycol thiol derivative C2-1 obtained in Example-19 and dichloromethane (500 mL) were added in sequence, and the whole was stirred till dissolution. Subsequently, 8 g of triethylamine and 20 g of 9-fluorenylmethyl chloroformate were added in sequence, and then the reaction was conducted at room temperature overnight. Thereafter, the solution was added with saturated sodium bicarbonate solution, and then extracted with dichloromethane (250 mL trice). The organic phase was combined, washed with saturated salt solutions, dried, filtrated, concentrated and recrystallized, and then an eight-arm polyethylene glycol thiocarbonate derivative C18-1 was obtained.

C18-1

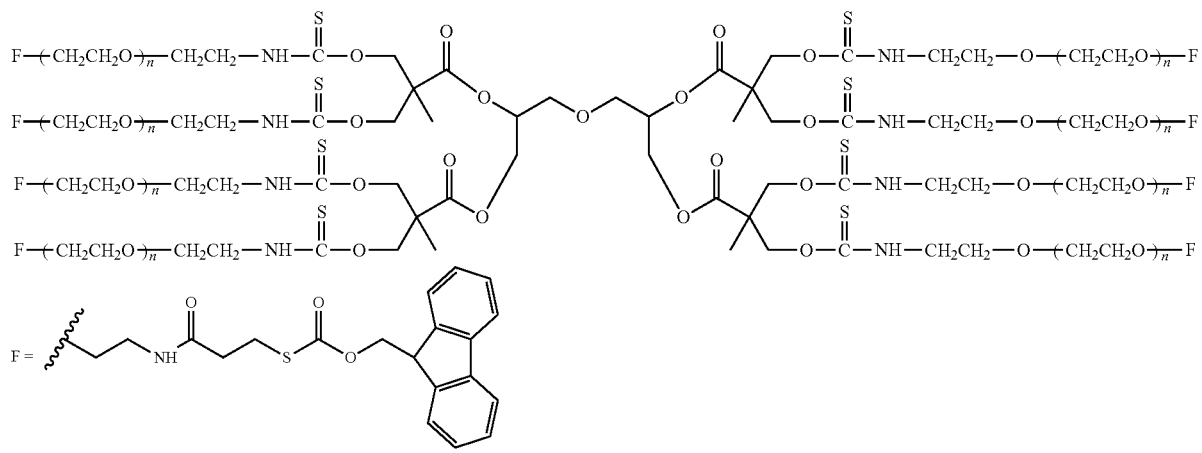

$^1$H NMR spectrum data of the eight-arm polyethylene glycol thiocarbonate derivative C18-1 were as follows: $^1$H NMR (CDCl$_3$) δ (ppm): 1.38 (—CCH$_3$), 2.30-2.50 (CH$_3$CH$_2$C(═O)—), 2.73 (—OCSNHCH$_2$CH$_2$O), 2.90-3.10 (—OCH$_2$CH$_2$S—), 3.40-3.80 (—CH$_2$CH$_2$O—, —CCH$_2$O, —OCH$_2$CH$_2$NH), 3.90-4.10 (—SCH$_2$CH$_2$O—), 4.20-4.46 (—CHCH$_2$O(C═O), —OCOOCH$_2$CH—Ar), 4.78-4.88 (—OCOOCH$_2$CH—Ar, —OCH$_2$CHO(C═O)), 7.28-7.87 (—Ar—H).

Example-22: Preparation of Eight-Arm Polyethylene Glycol Derivatives

Preparation of an Eight-Arm Polyethylene Glycol Cycloalkene Derivative (E9-1)

Herein, the structure of the eight-arm polyethylene glycol derivative was designed as follows:

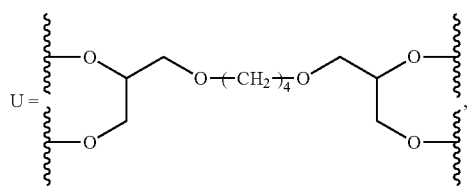

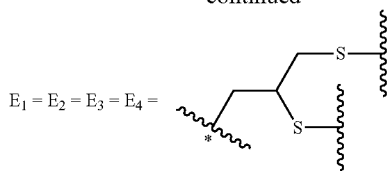

(with a carbon-branching center of an asymmetrical type), the divalent linking groups $L_{11}=L_{12}=L_{21}=L_{22}=L_{31}=L_{32}=L_{41}=L_{42}=CH_2CH_2$, g=0, k=1, and

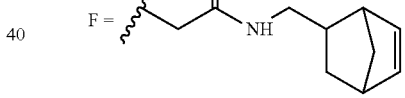

(wherein, $Z_2$ is $CH_2$, $Z_1$ is $CONHCH_2$, and $R_{01}$ is a norbornyl group). The designed total molecular weight is approximately 37.5 kDa, wherein, the molecular weight of the eight PEG chains is approximately 8×4400=35200 Da, corresponding to $n_1 \approx n_2 \approx n_3 \approx n_4 \approx n_5 \approx n_6 \approx n_7 \approx n_8 \approx 100$.

E9-1

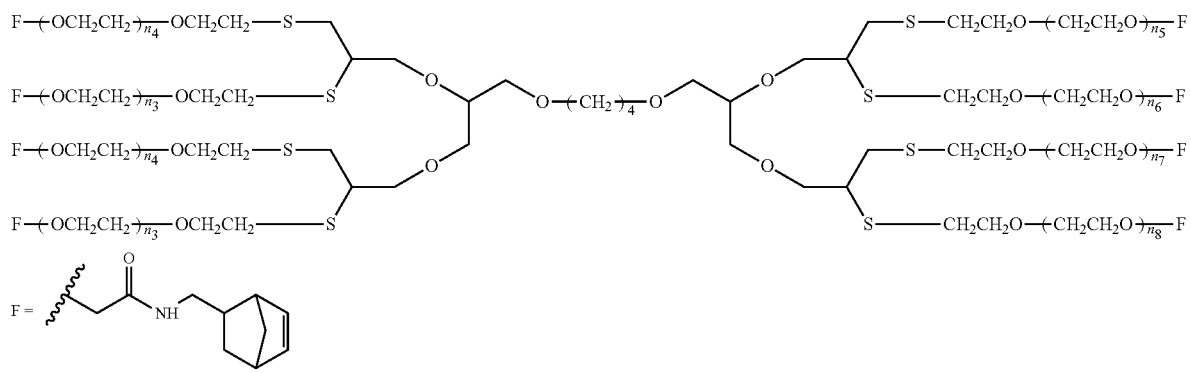

Step (a): Into a dry and clean 1 L round-bottom flask, 250 mL 20% potassium hydroxide solution and 50 mmol of 1,4-butanediol diglycidyl ether were added in sequence, and then the reaction was conducted for 4 hours. Thereafter, the intermediate was extracted, washed, dried, concentrated and transferred into a dry and clean 1 L round-bottom flask. Thereafter, 400 mL of tetrahydrofuran and 7.2 g of sodium hydride were added thereinto, and then excess propargyl bromide was added, followed by reaction at 30° C. for 12 hours. The reaction solution was concentrated and then dissolved with dichloromethane. The product was washed, dried and purified via column chromatography, and then a tetraalkyne compound S22-1 was obtained.

$^1$H NMR spectrum data of the tetraalkyne compound S22-1 were as follows: $^1$H NMR (CDCl$_3$) δ (ppm): 1.15 (—OCH$_2$CH$_2$CH$_2$CH$_2$O—), 2.40-2.60 (HC≡CCH$_2$O—), 3.27-3.63 (—OCH$_2$CH$_2$CH$_2$CH$_2$O—, —OCH$_2$CH(O)CH$_2$O—), 4.15-4.35 (HC≡CCH$_2$O—).

Step (b): Into a dry and clean 1 L round-bottom flask, 400 mL of tetrahydrofuran, 50 mmol of the tetraalkyne compound S22-1 and 500 mmol of 2-mercaptoethanol were added. Under nitrogen protection, a 3 wt % solution of DMAP in tetrahydrofuran (200 mL) was added thereinto, followed by reaction under UV-light at room temperature for 24 hours. Thereafter, the product in the solution was concentrated and purified via column chromatography, and then an octahydroxyl-containing compound S22-2 was obtained.

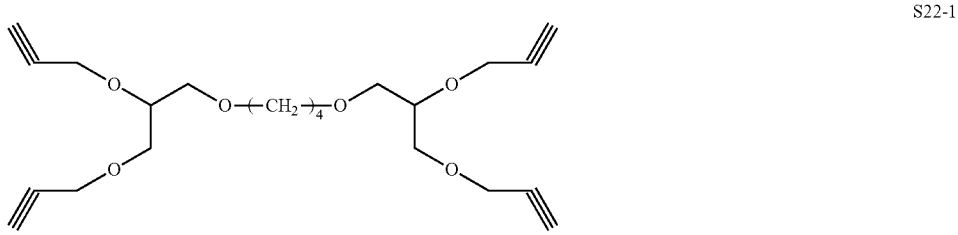

S22-1

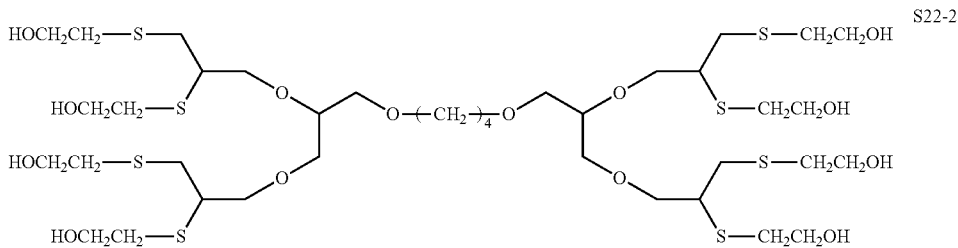

S22-2

Step (c): Into a sealed reactor under an anhydrous and oxygen-free atmosphere, tetrahydrofuran (250 mL), the octahydroxyl-containing initiator S22-2 (1.266 mmol) and diphenylmethyl potassium (4.0 mmol) were added in sequence.

Step (d): After the addition of a calculated amount of ethylene oxide, the whole was heated stepwisely to 60° C., followed by reaction for 48 hours. After the addition of excess proton source (methanol), the product in the solvent was concentrated and precipitated, and then an eight-arm polyethylene glycol H1-10 was obtained.

H1-10

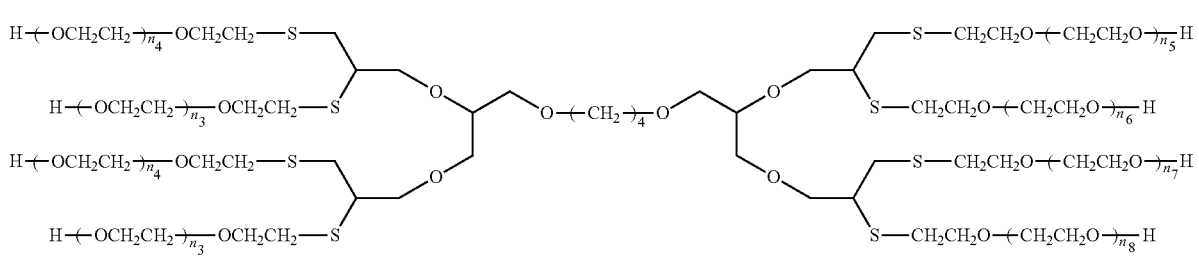

¹H NMR spectrum data of the eight-arm polyethylene glycol H1-10 were as follows: ¹H NMR (CDCl₃) δ (ppm): 1.15 (—OCH₂CH₂CH₂CH₂O—), 2.61-2.90 (—SCH₂CH₂—, —OCH₂CH(S)CH₂S—), 3.13 (—OCH₂CH(S)CH₂S—), 3.27-3.33 (—OCH₂CH₂CH₂CH₂O—), 3.40-3.80 (—OCH₂CH₂O—, —OCH₂CH(O)CH₂O—, OCH₂CH(S)CH₂S—); $M_n \approx 36$ kDa, PDI=1.04.

Step (e): The eight-arm polyethylene glycol H1-10 obtained in the last step was dissolved in water (500 mL). Thereafter, excess potassium hydroxide (20 mmol) and excess sodium bromoacetate (50 mmol) were added in sequence, followed by reaction at 30° C. for 12 hours. After completion of the reaction, open the reactor. The solution was adjusted to pH 1 with the addition of hydrochloric acid (3 M), followed by stirring at 30° C. for 1 hour. The product in the solvent was extracted with dichloromethane, concentrated, and then precipitated with absolute diethyl ether at 0° C. The precipitate was collected by filtration, recrystallized and dried, and then an eight-arm polyethylene glycol acetic acid derivative D1-4 was obtained.

D1-4

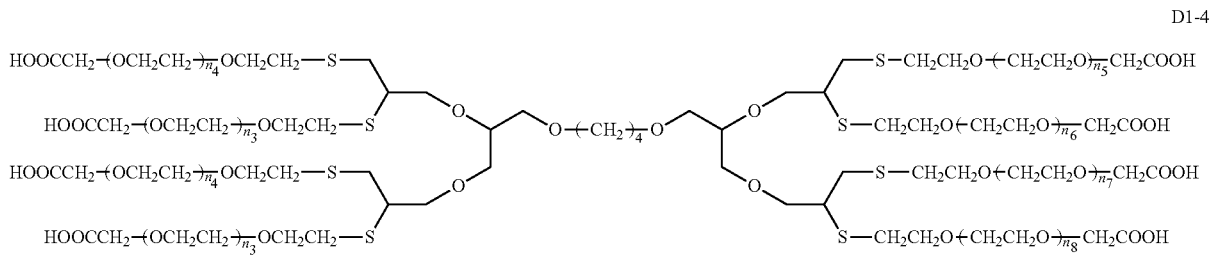

In the ¹H NMR spectrum of the eight-arm polyethylene glycol acetic acid derivative D1-4, besides the characteristic peaks of the chain backbone, the characteristic peaks of the carboxylic acid derivative also appeared as follows: ¹H NMR (CDCl₃) δ (ppm): 4.35 (—CH₂COOH).

Step (f): Into a dry and clean 1 L round-bottom flask, 10 g of the eight-arm polyethylene glycol acetic acid derivative (D1-4, treated by azeotropic removal of water with toluene), 10 mL of triethylamine and 5 g of 5-norbornene-2-methylamine were added. Under nitrogen protection, dichloromethane (160 mL) was added, and the whole was stirred till dissolution. Subsequently, 10 g of dicyclohexylcarbodiimide (DCC) was added thereinto, followed by reaction at room temperature for 24 hours. The resulting mixture was filtrated to remove undissolved substances, concentrated and recrystallized from isopropanol, and then an eight-arm polyethylene glycol cycloalkene derivative E9-1 in a white solid state was obtained.

In the $^1$H NMR spectrum of the eight-arm polyethylene glycol cycloalkene derivative E9-1, besides the characteristic peaks of the chain backbone, the characteristic peaks of the norbornene moiety appeared as follows: $^1$H NMR (CDCl$_3$) δ (ppm): 1.35-1.60 (—CH$_2$CH(CH$_2$)$_5$CH=CHCH—), 2.15-2.35 (—CH$_2$CH(CH$_2$)CH=CHCH—), 5.40-5.70 (—CH$_2$CH(CH$_2$)CH=CHCH—); $M_n$≈38 kDa, PDI=1.04.

Preparation of an Eight-Arm Polyethylene Glycol Cycloalkyne Derivative (G1-1)

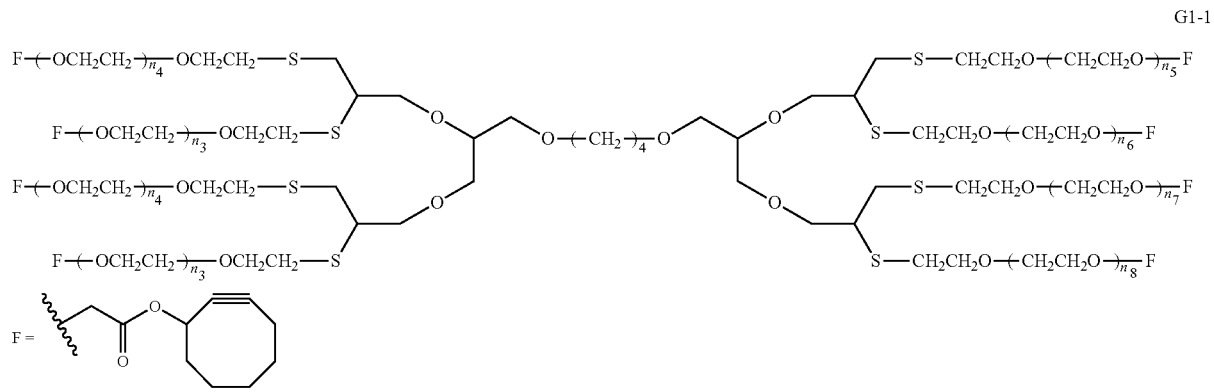

G1-1

Herein, U, $E_1$, $E_2$, $E_3$, $E_4$, $L_{11}$, $L_{12}$, $L_{21}$, $L_{22}$, $L_{31}$, $L_{32}$, $L_{41}$, $L_{42}$, $n_1$, $n_2$, $n_3$, $n_4$, $n_5$, $n_6$, $n_7$, $n_8$ and n in the eight-arm polyethylene glycol derivative are the same as those in Example E9-1, g=0, k=1, and

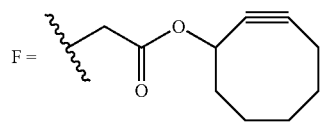 [SMILES: *CC(=O)OC1C#CCCCCC1]

(wherein, $Z_2$ is CH$_2$, $Z_1$ is an ester bond, and $R_{01}$ is a cyclooctynyl group). The designed total molecular weight is approximately 37.5 kDa, wherein, the molecular weight of the eight PEG chains is approximately 8×4400=3 5200 Da, corresponding to $n_1$≈$n_2$≈$n_3$≈$n_4$≈$n_5$≈$n_6$≈$n_7$≈$n_8$≈100.

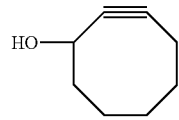

S22-3

Into a dry and clean 1 L round-bottom flask, 10 g of the eight-arm polyethylene glycol acetic acid derivative (D1-4, treated by azeotropic removal of water with toluene), 10 mL of triethylamine and 5 g of cyclooct-2-ynol S22-3 were added. Under nitrogen protection, dichloromethane (160 mL) was added thereinto, and the whole was stirred till dissolution. Subsequently, 10 g of dicyclohexylcarbodiimide (DCC) was added thereinto, followed by reaction at room temperature for 24 hours. The resulting mixture was filtrated to remove undissolved substances, concentrated and recrystallized from isopropanol, and then an eight-arm polyethylene glycol cycloalkyne derivative G1-1 in a white solid state was obtained.

In the $^1$H NMR spectrum of the eight-arm polyethylene glycol cycloalkyne derivative G1-1, besides the characteristic peaks of the chain backbone, the characteristic peaks of the cylcoalkynyl group also appeared as follows: $^1$H NMR (CDCl$_3$) δ (ppm): 1.28-1.98 (—CHC≡CCH$_2$CH$_2$CH$_2$CH$_2$CH$_2$CH$_2$—), 4.90-5.15 (—CHC≡CCH$_2$—); $M_n$≈38 kDa, PDI=1.04.

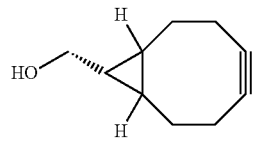

S22-4

Into a dry and clean 1 L round-bottom flask, 10 g of the eight-arm polyethylene glycol acetic acid derivative (D1-4, treated by azeotropic removal of water with toluene), 10 mL of triethylamine and 5 g of a hydroxyl-bearing cycloalkyne

Preparation of an Eight-Arm Polyethylene Glycol Cycloalkyne Derivative (G4-1)

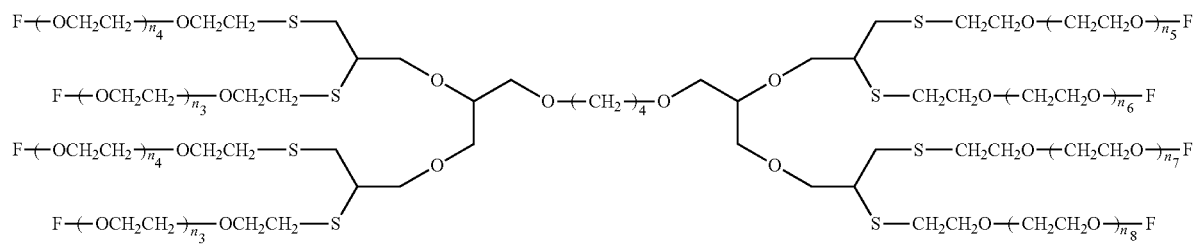

G4-1

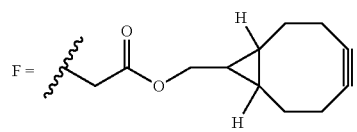

Herein, U, $E_1$, $E_2$, $E_3$, $E_4$, $L_{11}$, $L_{12}$, $L_{21}$, $L_{22}$, $L_{31}$, $L_{32}$, $L_{41}$, $L_{42}$, $n_1$, $n_2$, $n_3$, $n_4$, $n_5$, $n_6$, $n_7$, $n_8$ and n in the eight-arm polyethylene glycol derivative are the same as those in Example E9-1, g=0, k=1, and

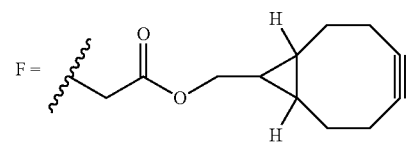 [SMILES: *CC(=O)OCC1C2CCC#CCCC21]

(wherein, $Z_2$ is CH$_2$, $Z_1$ is an ester bond, and $R_{01}$ is a cycloalkynyl group). The designed total molecular weight is approximately 37.7 kDa, wherein, the molecular weight of the eight PEG chains is approximately 8×4400=35200 Da, corresponding to $n_1$≈$n_2$≈$n_3$≈$n_4$≈$n_5$≈$n_6$≈$n_7$≈$n_8$≈100.

compound S22-4 were added. Under nitrogen protection, dichloromethane (160 mL) was added thereinto, and the whole was stirred till dissolution. Subsequently, 10 g of dicyclohexylcarbodiimide (DCC) was added thereinto, followed by reaction at room temperature for 24 hours. The resulting mixture was filtrated to remove undissolved substances, concentrated and recrystallized from isopropanol, and then an eight-arm polyethylene glycol cycloalkyne derivative G4-1 in a white solid state was obtained.

In the $^1$H NMR spectrum of the eight-arm polyethylene glycol cycloalkyne derivative G4-1, besides the characteristic peaks of the chain backbone, the characteristic peaks of the cylcoalkynyl group also appeared as follows: $^1$H NMR (CDCl$_3$) δ (ppm): 0.19 (—COOCH$_2$CH(CH)$_2$—), 0.79 (—COOCH$_2$CH—), 1.47 (—CH$_2$CH$_2$C≡C—), 2.03 (—CH$_2$CH$_2$C≡C—), 4.21 (—COOCH$_2$—); $M_n$=38 kDa, PDI=1.04.

Example-23: Preparation of Eight-Arm Polyethylene Glycol Derivatives

Preparation of an Eight-Arm Polyethylene Glycol Cycloalkyne Derivative (G9-1)

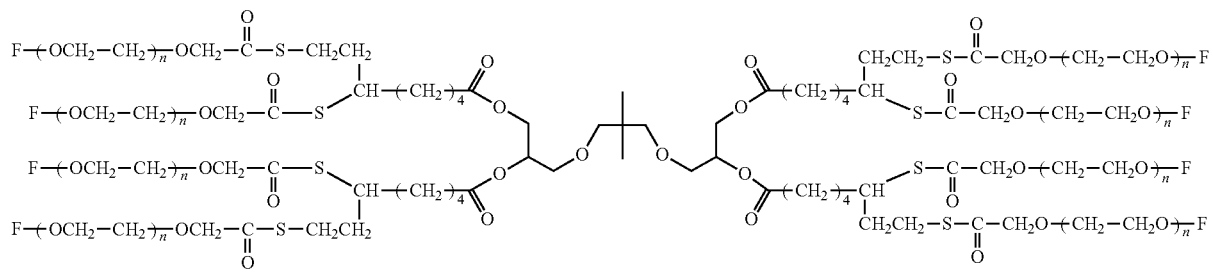

G9-1

Herein, the structure of the eight-arm polyethylene glycol derivative was designed as follows:

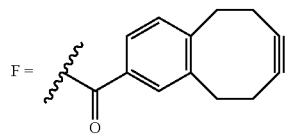

(with a carbon-branching center of an asymmetrical structure), the divalent linking groups $L_{11}=L_{12}=L_{21}=L_{22}=L_{31}=L_{32}=L_{41}=L_{42}=COCH_2$, g=0, k=1, and

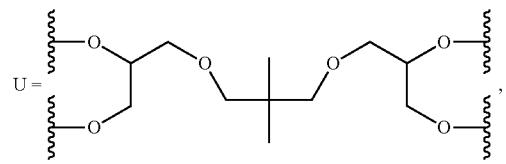

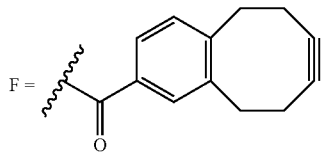 [SMILES: *C(=O)c1ccc2c(c1)CCC#CCC2]

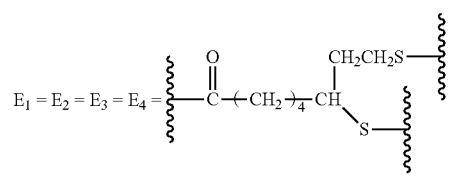

(wherein, $Z_2$ is absent, $Z_1$ is a carbonyl group, and $R_{01}$ is a benzocyclooctynyl group). The designed total molecular weight is approximately 10.6 kDa, wherein, the molecular weight of the eight monodisperse PEG chains is approximately 8×1000=8000 Da, corresponding to the EO-unit number of $n_1=n_2=n_3=n_4=n_5=n_6=n_7=n_8=n=22$.

Step (a): Into a dry and clean 500 mL round-bottom flask, a 20% aqueous solution of potassium hydroxide (250 mL) and 50 mmol of neopentyl glycol diglycidyl ether were added in sequence, followed by reaction for 4 hours. Thereafter, the intermediate was extracted, washed, dried, concentrated and transferred into a dry and clean 1 L round-bottom flask. Then, 10 mL of triethylamine and 5 g of protected 6,8-dimercaptooctanoic acid S23-1 were added thereinto. Under nitrogen protection, dichloromethane (160 mL) was added thereinto, and the whole was stirred till dissolution. Subsequently, 10 g of dicyclohexylcarbodiimide (DCC) was added thereinto, followed by reaction at room temperature for 24 hours. The resulting mixture was filtrated to remove undissolved substances, concentrated and recrystallized, and then a compound with eight mercapto groups being protected S23-2 was obtained.

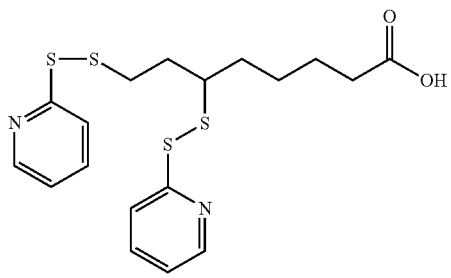

S23-1

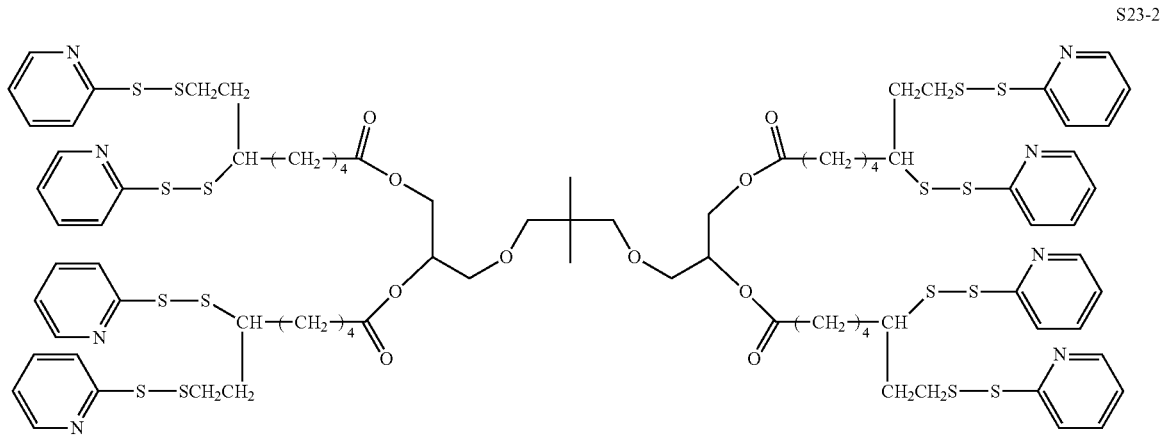

S23-2

Step (b): Into a dry and clean 1 L round-bottom flask, 10 g of the protected octathiol compound S23-2 was added. Under nitrogen protection, tetrahydrofuran (400 mL) was added thereinto, and the whole was stirred till all were dissolved. Subsequently, 10 g of dithiothreitol was added thereinto, followed by reaction at room temperature for 24 hours. The resulting mixture was concentrated, washed with saturated salt solutions (100 mL trice), dried, concentrated and recrystallized from isopropanol, and then an octathiol compound S23-3 was obtained.

Step (c): Into a dry and clean 1 L round-bottom flask, 1 mmol of the octathiol compound S23-3 and dichloromethane (500 mL) were added in sequence, and the whole was stirred till dissolution. Subsequently, 5 mL of triethylamine and 8 mmol of monodisperse heterofunctional protected-hydroxyl polyethylene glycol acyl chloride (S23-4, EO-unit number was 22) were added thereinto, followed by reaction at room temperature overnight. Thereafter, saturated sodium

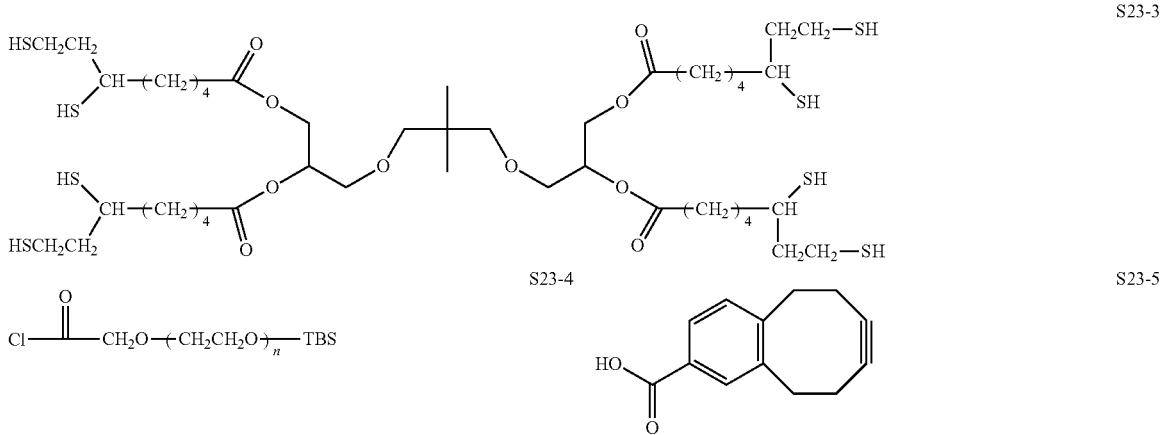

S23-3

S23-4

S23-5

$^1$H NMR spectrum data of the octathiol compound 523-3 were as follows: H NMR (CDCl$_3$) δ (ppm): 0.99 (—CH$_3$), 1.50-0.180 (HSCH$_2$CH$_2$CH(SH)CH$_2$CH$_2$CH$_2$—), 2.32 (—CH$_2$COO—), 2.50-2.60 (—CH$_2$CH$_2$SH, —CH$_2$CH (SH)—), 3.38-3.76 (—COOCH$_2$CH(O)CH$_2$O—, —OCH$_2$C (CH$_3$)$_2$—), 4.30 (—COOCH$_2$CH(O)CH$_2$O—).

bicarbonate solution was added thereinto, and the aqueous phase was extracted with dichloromethane (250 mL trice). The organic phase was combined, washed with saturated salt solutions, dried, filtrated, concentrated and recrystallized, and then an eight-arm polyethylene glycol derivative with protected hydroxyl groups H2-2 was obtained.

H2-2

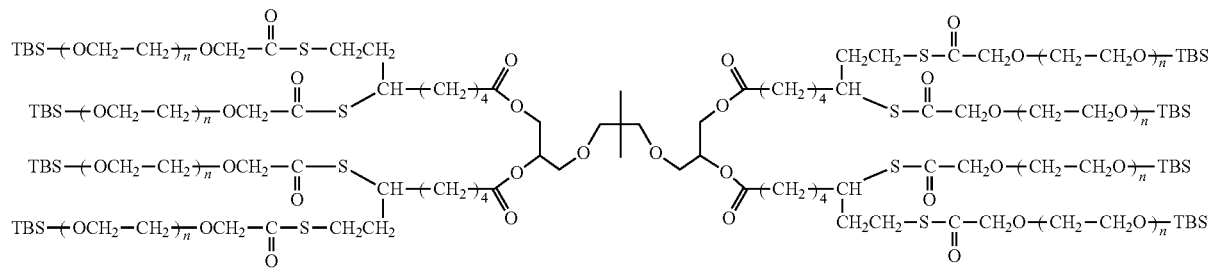

¹H NMR spectrum data of the eight-arm polyethylene glycol protected alcohol derivative H2-2 were as follows: ¹H NMR (CDCl$_3$) δ (ppm): 0.21 (—Si(CH$_3$)$_2$), 0.90-1.04 (—CH$_3$), 1.50-0.180 (—SCH$_2$CH$_2$CH(S)CH$_2$CH$_2$CH$_2$—), 2.32 (—CH$_2$COO—), 2.79-2.87 (—CH$_2$CH$_2$S—, —CH$_2$CH(S)—), 3.40-3.80 (—OCH$_2$CH$_2$O—, —COOCH$_2$CH(O)CH$_2$O—, —OCH$_2$CH$_2$OSi—, —OCH$_2$C(CH$_3$)$_2$—), 3.80-4.00 (—OCH$_2$CH$_2$OSi—), 4.30 (—COOCH$_2$CH(O)CH$_2$O—).

Step (d): Into a dry and clean container, the eight-arm polyethylene glycol protected alcohol derivative H2-2 was added and then dissolved with tetrahydrofuran, followed by the addition of tetra-t-butyl ammonium fluoride (TBAF); thereafter, the reaction was conducted overnight, and an eight-arm polyethylene glycol H1-11 with hydroxyl groups being unprotected was obtained.

(—CH$_2$CH$_2$S—, —CH$_2$CH(S)—), 3.40-3.80 (—OCH$_2$CH$_2$O—, —COOCH$_2$CH(O)CH$_2$O—, —OCH$_2$C(CH$_3$)$_2$—), 4.30 (—COOCH$_2$CH(O)CH$_2$O—).

Step (e): Into a dry and clean 1 L round-bottom flask, 16 g of the eight-arm polyethylene glycol H1-11 obtained in Step (d) and dichloromethane (500 mL) were added in sequence, and the whole was stirred till dissolution. Subsequently, 5 mL of triethylamine and a cycloalkyne compound S23-5 were added thereinto in sequence, followed by reaction at room temperature overnight. Thereafter, saturated sodium bicarbonate solution was added thereinto, and the mixture was extracted with dichloromethane (250 mL trice). The organic phase was combined, washed with saturated salt solutions, dried, filtrated, concentrated and recrystallized, and then an eight-arm polyethylene glycol benzocyclooctyne derivative G9-1 was obtained.

H1-11

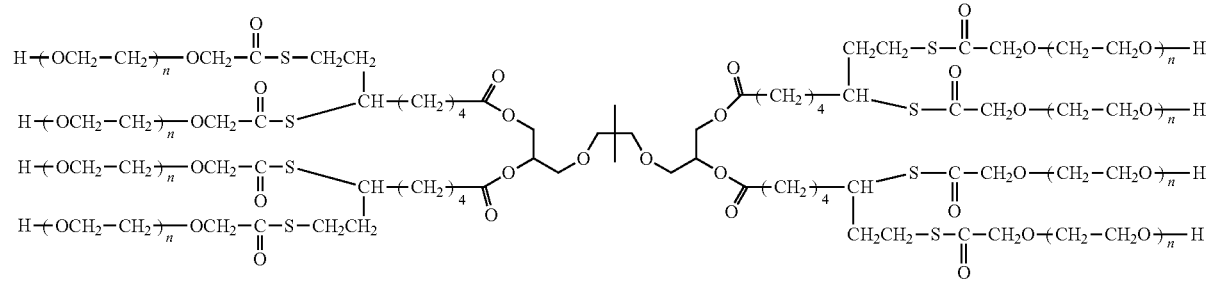

In the ¹H NMR spectrum of the eight-arm polyethylene glycol H1-11, besides the characteristic peaks of the chain backbone, the characteristic peaks of the t-butyldimethylsilyl group disappeared as follows: ¹H NMR (CDCl$_3$) δ (ppm): 0.90-1.04 (—CH$_3$), 1.50-0.180 (—SCH$_2$CH$_2$CH(S)CH$_2$CH$_2$CH$_2$—), 4.32 (—CH$_2$COO—), 2.79-2.87

In the ¹H NMR spectrum of the eight-arm polyethylene glycol benzocyclooctyne derivative G9-1, besides the characteristic peaks of the chain backbone, the characteristic peaks of the cycloalkynyl group appeared as follows: ¹H NMR (CDCl$_3$) δ (ppm): 2.32 (—CH$_2$CH$_2$CC—), 2.72 (—CH$_2$CH$_2$CC—), 7.35-7.82 (Ar—H).

Preparation of an Eight-Arm Polyethylene Glycol Cycloalkyne Derivative (E8-1)

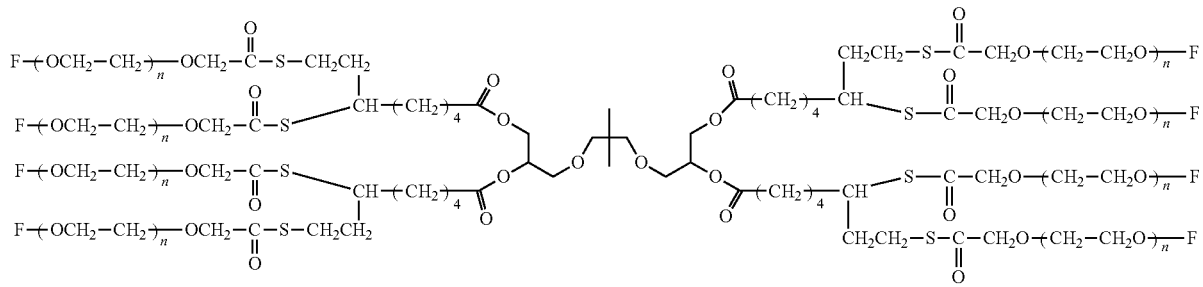

E6-1

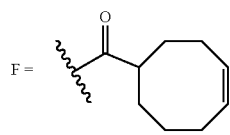

Herein, U, $E_1$, $E_2$, $E_3$, $E_4$, $L_{11}$, $L_{12}$, $L_{21}$, $L_{22}$, $L_3$, $L_{32}$, $L_{41}$, $L_{42}$, $n_1$, $n_2$, $n_3$, $L_4$, $n_5$, $n_6$, $n_7$, $n_8$ and n in the eight-arm polyethylene glycol derivative are the same as those in Example G9-1, g=0, k=1, and

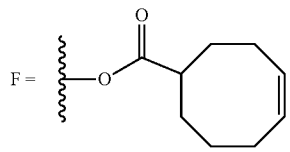

(wherein, $Z_2$ is absent, $Z_1$ is a carbonyl group, and $R_{01}$ is a cyclooctenyl group). The designed total molecular weight is approximately 10.3 kDa, wherein, the molecular weight of the eight PEG chains is approximately 8×1000=8000 Da, corresponding to the EO-unit number of $n_1=n_2=n_3=n_4=n_5=n_6=n_7=n_8=n=22$.

S23-5

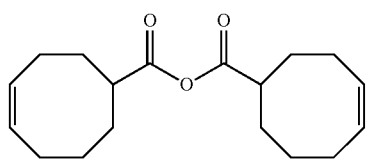

Into a dry and clean 1 L round-bottom flask, 16 g of the eight-arm polyethylene glycol H1-11 and toluene (500 mL) were added, followed by the addition of anhydride (400 mmol). Thereafter, the reaction was conducted at 50° C. for 12 hours. After completion of the reaction, open the reactor. The product in the solvent was concentrated and then precipitated with absolute diethyl ether at 0° C. The precipitates were collected by filtration and dried, and then an eight-arm polyethylene glycol cyclooctene derivative E8-1 was obtained.

$^1$H NMR spectrum data of the eight-arm polyethylene glycol cyclooctene derivative E8-1 were as follows: $^1$H NMR (CDCl$_3$) δ (ppm): 1.28-1.38 (—OC(=O)CH(CH$_2$)CH$_2$CH$_2$—); 1.51-1.80 (—OC(=O)CH(CH$_2$)CH$_2$—); 1.90-2.01 (—CH$_2$CH=CH—CH$_2$—), 2.31 (—OC(=O)CH(CH$_2$)$_2$—), 5.42 (—CH$_2$CH=CH—CH$_2$—).

Example-24: Preparation of an Eight-Arm Polyethylene Glycol Acetal Derivative (D7-1)

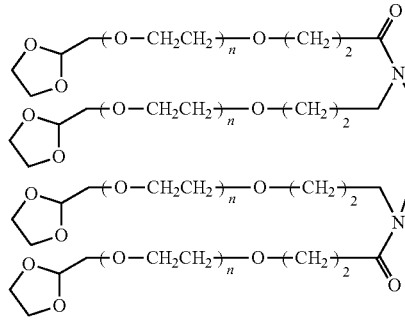
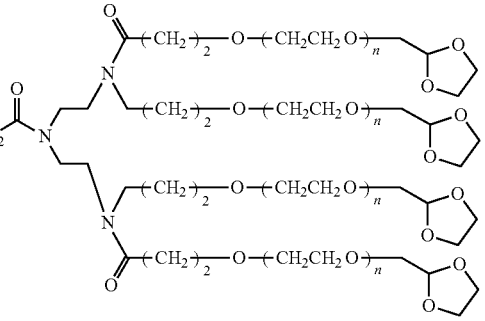

D7-1

Herein the structure of the eight-arm polyethylene glycol derivative was designed as follows:

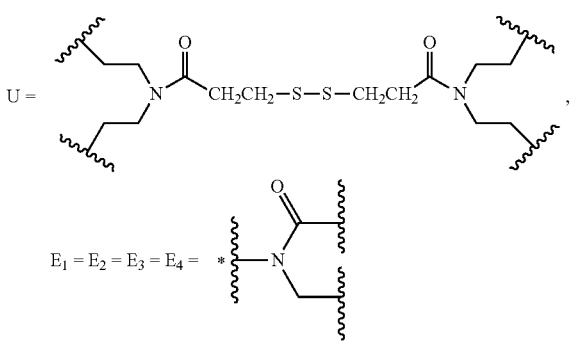

U =

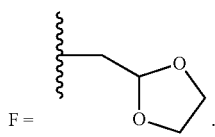

$E_1 = E_2 = E_3 = E_4 =$ (with a carbon-branching center of an asymmetrical structure), the divalent linking groups $L_{11}=L_{12}=L_{21}=L_{22}=L_{31}=L_{32}=L_{41}=L_{42}=CH_2CH_2$, g=0, k=1 and

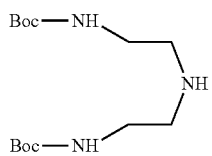

F =

The designed total molecular weight is approximately 5.8 kDa, wherein, the molecular weight of the eight monodisperse PEG chains is approximately 8×500=4000 Da, corresponding to the EO-unit number of $n_1=n_2=n_3=n_4=n_5=n_6=n_7=n_8=n=12$.

Step (a): Into a dry and clean 1 L round-bottom flask, 50 mmol of diethylenetriamine with the primary amino groups being protected S24-1 and 110 mL of triethylamine were added. Under nitrogen protection, dichloromethane (200 mL) was added thereinto, and the whole was stirred till dissolution. Thereafter, a solution of 20 mmol of 3,3'-dithioldipropionic acid bis(N-hydroxysuccinimide ester) in dichloromethane (500 mL) was added thereinto, followed by reaction at room temperature for 24 hours. After the addition of saturated ammonium chloride solution, the intermediate was concentrated, dissolved with water (400 mL), and then washed with dichloromethane (150 mL trice). The organic phase was combined, washed with saturated salt solutions, dried, concentrated and recrystallized from isopropanol. The crystals was dissolved with dichloromethane and adjusted to 0.1 M with TFA, followed by reaction for 4 hours. Thereafter, the solution was adjusted to a neutral pH value, extracted and precipitated, and then a quaternary primary amine compound S24-2 was obtained.

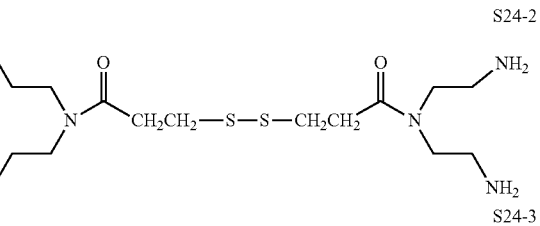

S24-1

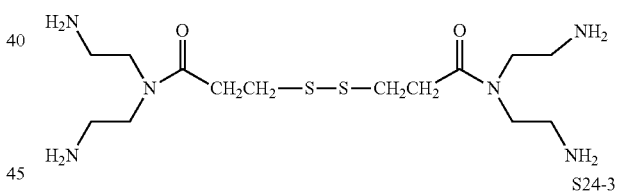

S24-2

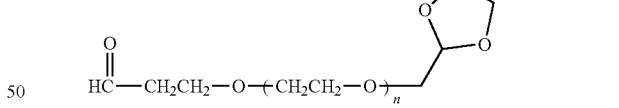

S24-3

$^1$H NMR spectrum data of the quaternary primary amine compound S24-2 were as follows: $^1$H NMR (CDCl$_3$) δ (ppm): 2.48 (—SCH$_2$CH$_2$C(═O)—), 2.76 (—CON(CH$_2$CH$_2$-)$_2$), 2.84 (—SCH$_2$CH$_2$C(═O)—), 3.46 (—CON(CH$_2$CH$_2$-)$_2$).

Step (b): Into a dry and clean 1 L round-bottom flask, the quaternary primary amine compound S24-2 was added and then dissolved with a buffer solution (pH 8); subsequently, a monodisperse heterofunctional polyethylene glycol aldehyde derivative (S24-3, EO-unit number was 12) was added, followed by stirring at room temperature for 3 hours. Thereafter, excess sodium cyanoborohydride was added thereinto, followed by reaction at room temperature for 24 hours. The resulting mixture was filtrated to remove undissolved substances, extracted with dichloromethane, dried, concentrated and recrystallized from isopropanol, and then a four-arm polyethylene glycol acetal derivative S24-4 was obtained.

¹H NMR spectrum data of the four-arm polyethylene glycol acetal derivative S24-4 were as follows: 1H NMR (CDCl₃) δ (ppm): 1.59 (—NHCH₂CH₂CH₂O—), 2.48-2.55 (—SCH₂CH₂C(=O)—, —NHCH₂CH₂CH₂O—), 2.66 (—CON(CH₂CH₂-)₂), 2.84 (—SCH₂CH₂C(=O)—), 3.32-3.37 (—CON(CH₂CH₂-)₂, —NHCH₂CH₂CH₂O—), 3.40-4.0 (—OCH₂CH₂O—, —OCH₂CH(O)O—), 5.20-5.25 (—OCH₂CHO(O)—).

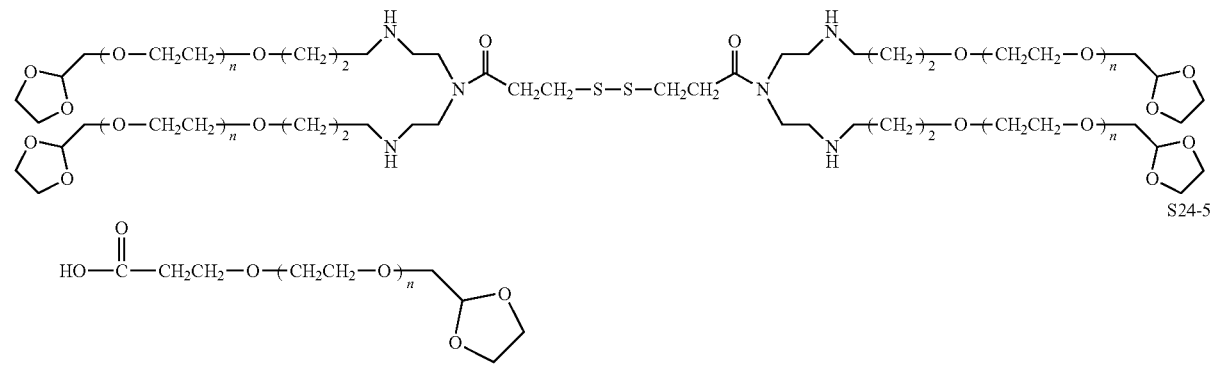

S24-4

S24-5

Step (c): Into a dry and clean 1 L round-bottom flask, 10 g of a monodisperse heterofunctional polyethylene glycol propionic acid derivative (S24-5, EO-unit number was 12, treated by azeotropic removal of water with toluene), 10 mL of triethylamine and 10 g of the four-arm polyethylene glycol acetal derivative S24-4 were added. Under nitrogen protection, dichloromethane (160 mL) was added thereinto, and the whole was stirred till dissolution. Subsequently, 10 g of dicyclohexylcarbodiimide (DCC) was added thereinto, followed by reaction at room temperature for 24 hours. The resulting mixture was filtrated to remove undissolved substances, extracted with dichloromethane, dried, concentrated and recrystallized from isopropanol, and then an eight-arm polyethylene glycol acetal derivative D7-1 was obtained.

¹H NMR spectrum data of the eight-arm polyethylene glycol acetal derivative D7-1 were as follows: ¹H NMR (CDCl₃) δ (ppm): 1.73 (—N(C=O)CH₂CH₂CH₂O—), 2.35 (—C(=O) CH₂CH₂O—), 2.48-2.55 (—SCH₂CH₂C (=O)—, —NCH₂CH₂CH₂O—), 2.66 (—CON(CH₂ CH₂-)₂), 2.84 (—SCH₂CH₂C(=O)—), 3.20-3.37 (—N (C=O)CH₂CH₂CH₂O—, —N(C=O)CH₂CH₂CH₂O—), 3.40-4.0 (—OCH₂CH₂O—, —OCH₂CH(O)O—, —CON (CH₂CH₂N)₂, —C(=O)CH₂CH₂O—), 5.20-5.25 (—OCH₂CHO(O)—).

Example-25: Preparation of an Eight-Arm Polyethylene Glycol Sulfonate Derivative (B1-3)

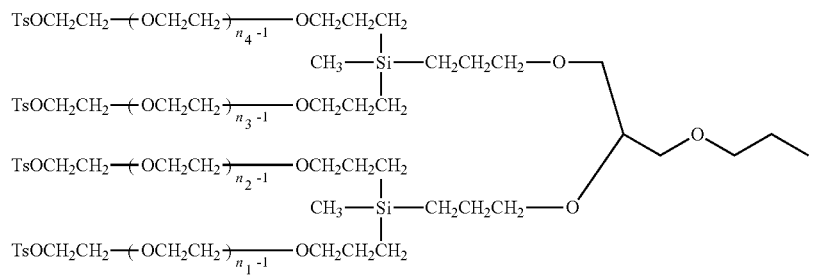

B1-3

-continued

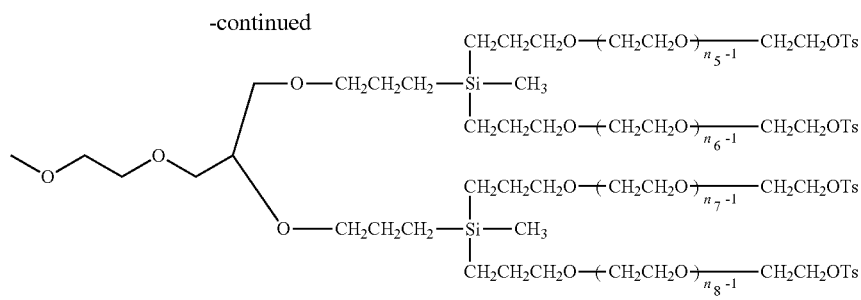

Herein, the structure of the eight-arm polyethylene glycol derivative was designed as follows:

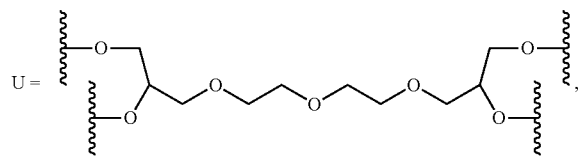

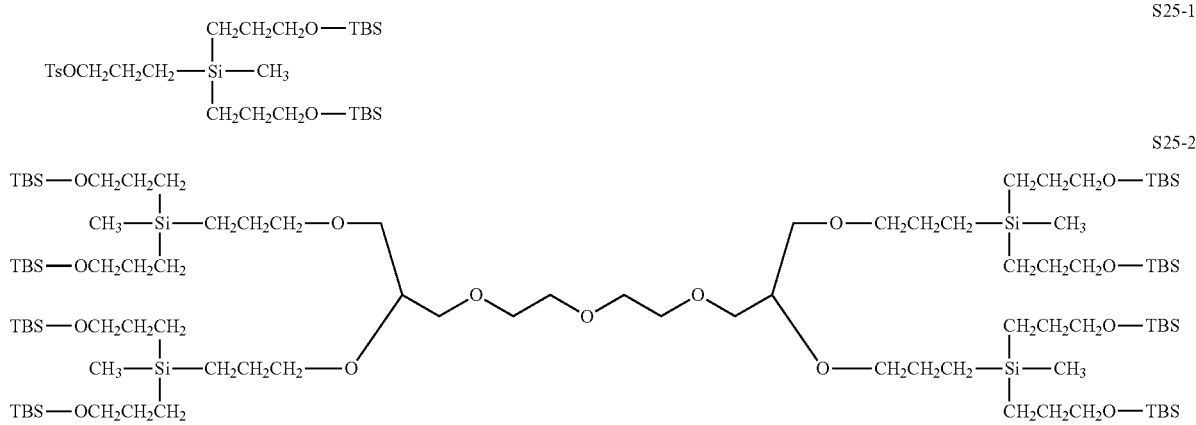

-continued

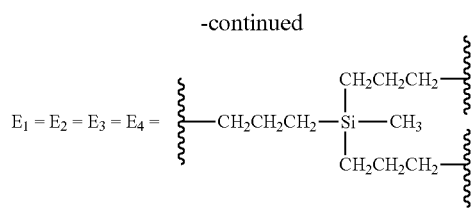

(with a silicon-atom-branching center of a symmetrical structure), the divalent linking groups $L_{11}$, $L_{12}$, $L_{21}$, $L_{22}$, $L_{31}$, $L_{32}$, $L_{41}$ and $L_{42}$ are all absent, g=0, k=1, and $F=CH_2CH_2OTs$. The designed total molecular weight is approximately 26.2 kDa, wherein, the molecular weight of the eight PEG chains is approximately 8×3000=24000 Da, corresponding to $n_1 \approx n_2 \approx n_3 \approx n_4 \approx n_5 \approx n_6 \approx n_7 \approx n_8 \approx 68$.

Step (a): Into a clean 1 L round-bottom flask, a 20% aqueous solution of potassium hydroxide (250 mL), 50 mmol of diethylene glycol diglycidyl ether were added in sequence, followed by reaction for 4 hours. Thereafter, the resulting intermediate was extracted, washed, dried, concentrated and transferred into a dry and clean 1 L round-bottom flask. Then, 400 mL of tetrahydrofuran and 7.2 g of sodium hydride was added, followed by the addition of an excess amount of a compound S25-1. The reaction was conducted at 30° C. for 12 hours. Thereafter, the reaction solution was concentrated and then dissolved in dichloromethane. The product was washed, dried and purified via column chromatography, and then a compound S25-2 with protected hydroxyl groups was obtained.

Step (b): Into a dry and clean container, the protected octaol compound S25-2 was added and then dissolved with tetrahydrofuran, followed by the addition of tetra-t-butyl ammonium fluoride (TBAF); thereafter, the reaction was conducted overnight, and an octahydroxyl-containing initiator S25-3 was obtained.

$^1$H NMR spectrum data of the octahydroxyl-containing initiator S25-3 were as follows: $^1$H NMR (CDCl$_3$) δ (ppm): 0.60 (—SiCH$_2$CH$_2$CH$_2$OH, —CH$_2$OCH$_2$CH$_2$CH$_2$Si—), 1.50 (—CH$_2$OCH$_2$CH$_2$CH$_2$Si—, —SiCH$_2$CH$_2$CH$_2$OH), 3.40-3.80 (—CH$_2$CH$_2$O—, —SiCH$_2$CH$_2$CH$_2$OH, —OCH$_2$CH(O)CH$_2$O—, —OCH(O)CH$_2$O—, —CH$_2$OCH$_2$CH$_2$CH$_2$Si—).

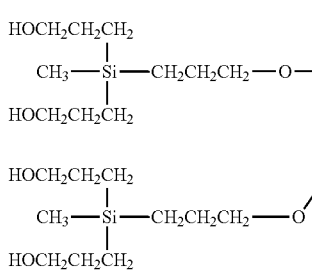 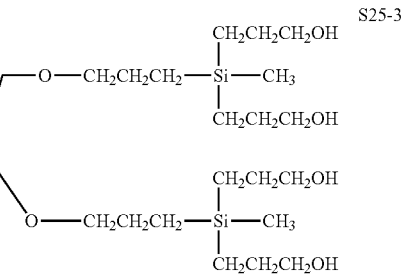

S25-3

Step (c): Into a sealed reactor under an anhydrous and oxygen-free atmosphere, tetrahydrofuran (250 mL), the octahydroxyl-containing initiator S25-3 (1.266 mmol) and diphenylmethyl potassium (DPMK, 4.0 mmol) were added in sequence.

Step (d): After the addition of a calculated amount of ethylene oxide, the whole was heated stepwisely to 60° C., followed by reaction for 48 hours.

Step (e): After the addition of excess proton source (methanol), the product in the solvent was concentrated and precipitated, and then an eight-arm polyethylene glycol H1-12 was obtained.

$^1$H NMR spectrum data of the eight-arm polyethylene glycol H1-12 were as follows: $^1$H NMR (CDCl$_3$) δ (ppm): 0.60 (—SiCH$_2$CH$_2$CH$_2$OH, —CH$_2$OCH$_2$CH$_2$CH$_2$Si—), 1.50 (—CH$_2$OCH$_2$CH$_2$CH$_2$Si—, —SiCH$_2$CH$_2$CH$_2$OH, 3.40-3.80 (—CH$_2$CH$_2$O—, —SiCH$_2$CH$_2$CH$_2$OH, —OCH$_2$CH(O)CH$_2$O—, —OCH$_2$CH(O)CH$_2$O—, —CH$_2$OCH$_2$CH$_2$CH$_2$Si—); $M_n$≈25 kDa, PDI=1.03.

added thereinto, followed by reaction at room temperature for 24 hours. Thereafter, the solution was adjusted to a pH value less than 7 with hydrochloric acid (1 mol/L), and the aqueous phase was washed with dichloromethane (50 mL trice). The organic phase was combined, washed with saturated salt solutions, dried with anhydrous sodium sulfate, filtrated, concentrated and recrystallized, and then an eight-arm polyethylene glycol sulfonate derivative B1-3 was obtained.

In the $^1$H NMR spectrum of the eight-arm polyethylene glycol sulfonate derivative B1-3, besides the characteristic peaks of the chain backbone, the characteristic peaks of the tosylate moiety appeared as follows: $^1$H NMR (CDCl$_3$) δ (ppm): 2.35 (CH$_3$C$_6$H$_4$SO$_2$—), 4.20 (—OCH$_2$CH$_2$OSO$_2$—), 7.30 (CH$_3$C$_6$H$_4$SO$_2$—), 7.80 (CH$_3$C$_6$H$_4$SO$_2$—); $M_n$≈26 kDa, PDI=1.03.

H1-12

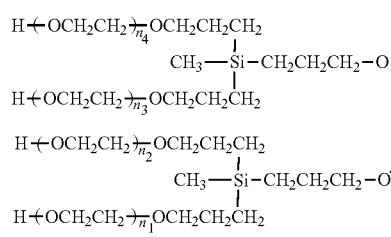 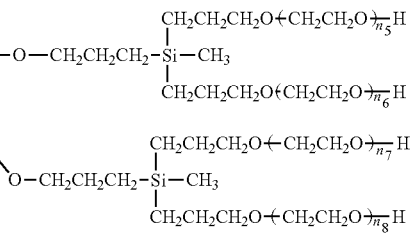

Step (f): Into a dry and clean 1 L round-bottom flask, 10 g of the eight-arm polyethylene glycol H1-12 was added. Under nitrogen protection, 500 mL of dichloromethane, 20 mL of pyridine and 5 g of 4-toluenesulfonyl chloride were Example-26: The Preparation Method for Modification of Biotin by an Eight-Arm Polyethylene Glycol Amine Derivative (I13-1)

I13-1

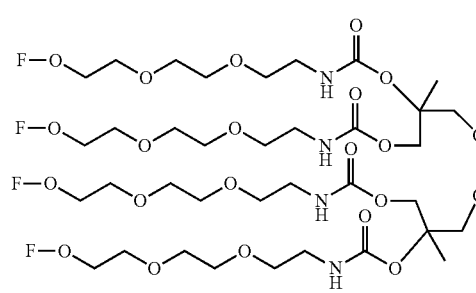 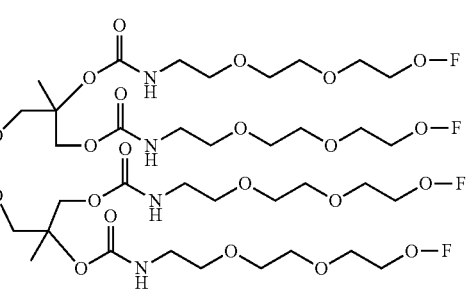

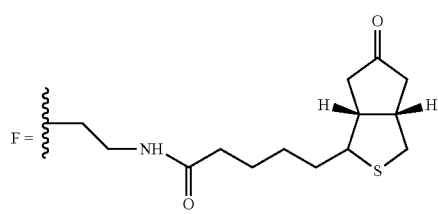

Herein, the structure of the eight-arm polyethylene glycol derivative was designed as follows:

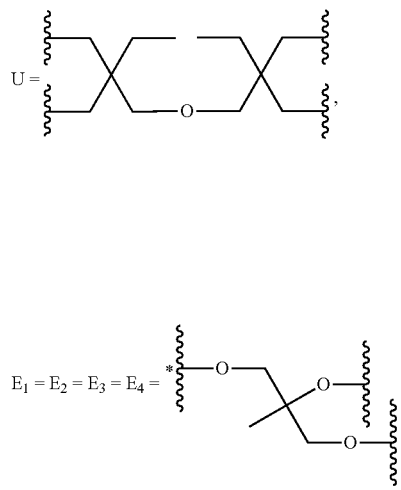

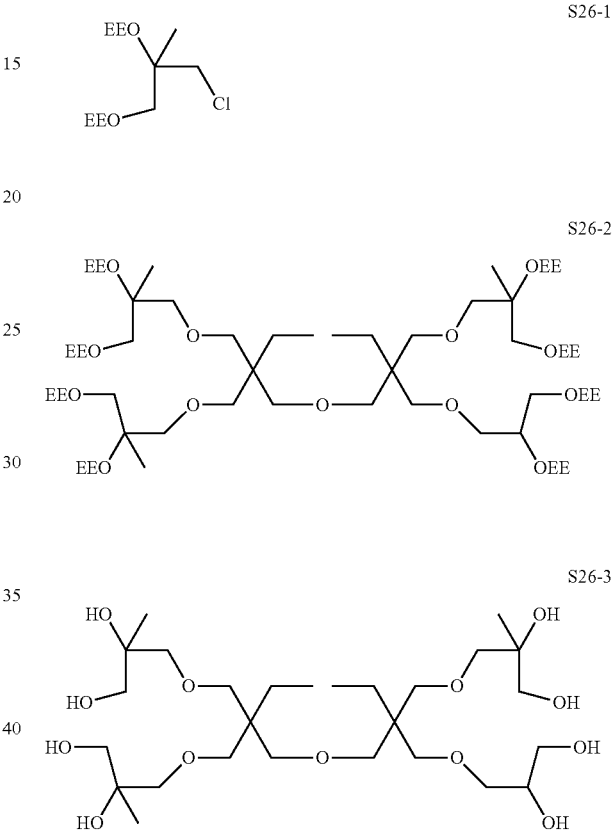

(with a carbon-branching center of an asymmetrical structure), the divalent linking groups $L_{11}=L_{12}=L_{21}=L_{22}=L_{31}=L_{32}=L_{41}=L_{42}=CONHCH_2CH_2$, $L_0$ is absent, $g=0$, $k=1$, $Z_2$ of F is $CH_2CH_2$, $Z_1$ is NH, and $R_{01}$ is a biotinyl group. The designed total molecular weight is approximately 4.5 kDa, wherein, the molecular weight of the eight monodisperse PEG chains is approximately 8×88=704 Da, corresponding to the EO-unit number of $n_1=n_2=n_3=n_4=n_5=n_6=n_7=n_8=n=2$.

Step (a): Into a reactor, tetrahydrofuran, 20 mmol of di(trimethylolpropane) and excess diphenylmethyl potassium (100 mmol) were added in sequence, and then a chloride with two protected hydroxyl groups S26-1 (100 mmol) was added, followed by an overnight reflux period. The resulting product was neutralized, extracted, washed and purified via column chromatography, and then a small molecule compound with eight hydroxyl groups being protected S26-2 was obtained.

Step (b): Into a dry and clean container, the protected-octahydroxyl small molecule compound S26-2 obtained in the last step was added and then dissolved with methanol. The solution was adjusted to pH 3.5 with the addition of hydrochloric acid (1 M), followed by reaction for 4 hours, and a small molecule compound S26-3 bearing eight unprotected hydroxyl groups was obtained.

$^1$H NMR spectrum data of the small molecule compound S26-3 bearing eight unprotected hydroxyl groups were as follows: $^1$H NMR (CDCl$_3$) δ (ppm): 0.90 (CH$_3$CH$_2$C(CH$_2$O—)$_3$—), 1.09 (CH$_3$C(CH$_2$OH)—), 1.25 (CH$_3$CH$_2$C(CH$_2$O—)$_3$—), 3.52 (CH$_3$C(CH$_2$OH)—), 3.61-3.77 (CH$_3$C(CH$_2$OCH$_2$)—), 5.67 (CH$_3$CH$_2$C(CH$_2$O—)$_3$—).

Step (c): Into a dry and clean 1 L round-bottom flask, 50 mmol of small molecule compound S26-3 bearing eight unprotected hydroxyl groups, which was previously treated by azeotropic removal of water with toluene, was added. Subsequently, 500 mL of acetonitrile, 40 mL of triethylamine and 500 mmol of N,N'-disuccinimidyl carbonate were added thereinto, followed by reaction at room temperature for 24 hours. The resulting product was concentrated and recrystallized from isopropanol, and then an active ester derivative S26-4 in a white solid state was obtained.

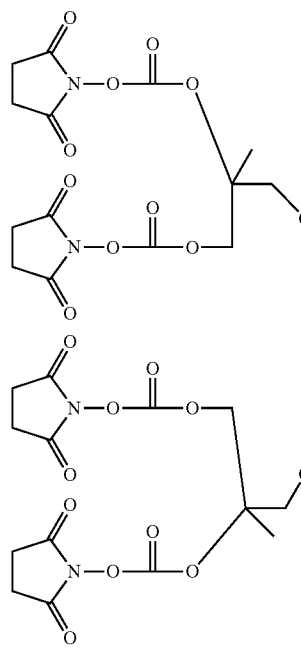

S26-4

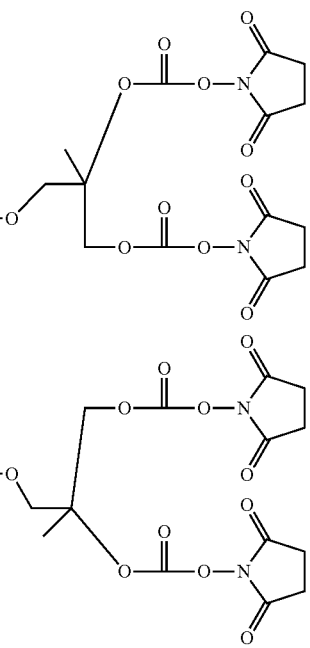

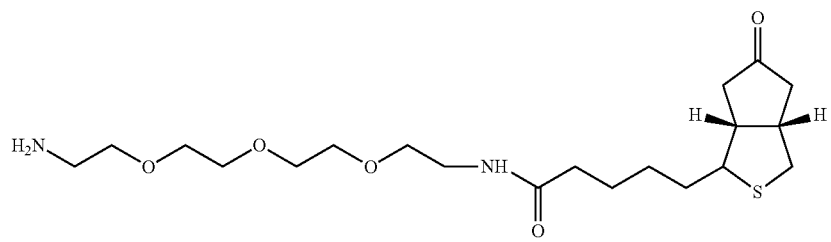

S26-5

¹H NMR spectrum data of the active ester derivative S26-4 were as follows: H NMR (CDCl₃) δ (ppm): 0.90 (CH₃CH₂C(CH₂O—)₃—), 1.48 (CH₃C(CH₂O)—), 1.25 (CH₃CH₂C(CH₂O—)₃—), 2.70-2.85 (—(O═)CCH₂CH₂C(═O)—), 3.40-3.80 (CH₃CH₂C(CH₂O—)₃—, CH₃C(CH₂O)—, CH₃C(CH₂OCH₂)—), 4.24-4.49 (CH₃C(CH₂OCH₂)—).

Step (d): Into a dry and clean 1 L round-bottom flask, 10 mmol of the active ester derivative S26-4 obtained in the last step, 500 mL of acetonitrile, 40 mL of triethylamine and 100 mmol of a biotin derivative S26-5 were added, followed by reaction at room temperature for 24 hours. The resulting product was concentrated and recrystallized from isopropanol, and then a biotin derivative I13-1 modified by an eight-arm polyethylene glycol amine in a white solid state was obtained.

¹H NMR spectrum data of the biotin derivative I13-1 modified by an eight-arm polyethylene glycol amine were as follows: ¹H NMR (CDCl₃) δ (ppm): 0.90 (CH₃CH₂C(CH₂O—)₃—), 1.25-1.62 ((CH₃CH₂C(CH₂O—)₃—, —CH₂CH₂CH₂CH₂CONH—, CH₃C(CH₂O)—)), 2.11 (—CH₂CONH—), 2.70-3.50 (—CHSCH₂—, —CH₂CH₂NH—), 3.40-3.80 (CH₃CH₂C(CH₂O—)₃—, —CH₂CH₂O—, CH₃C(CH₂O)—, CH₃C(CH₂OCH₂)—, —OCH₂CH₂NH), 4.24-4.49 (CH₃C(CH₂OCH₂)—), 4.55-4.60 (—CHNHC(═O)NHCH—).

Example-27: The Preparation Method for an Eight-Arm Polyethylene Glycol Alkyne Derivative (F3-2)

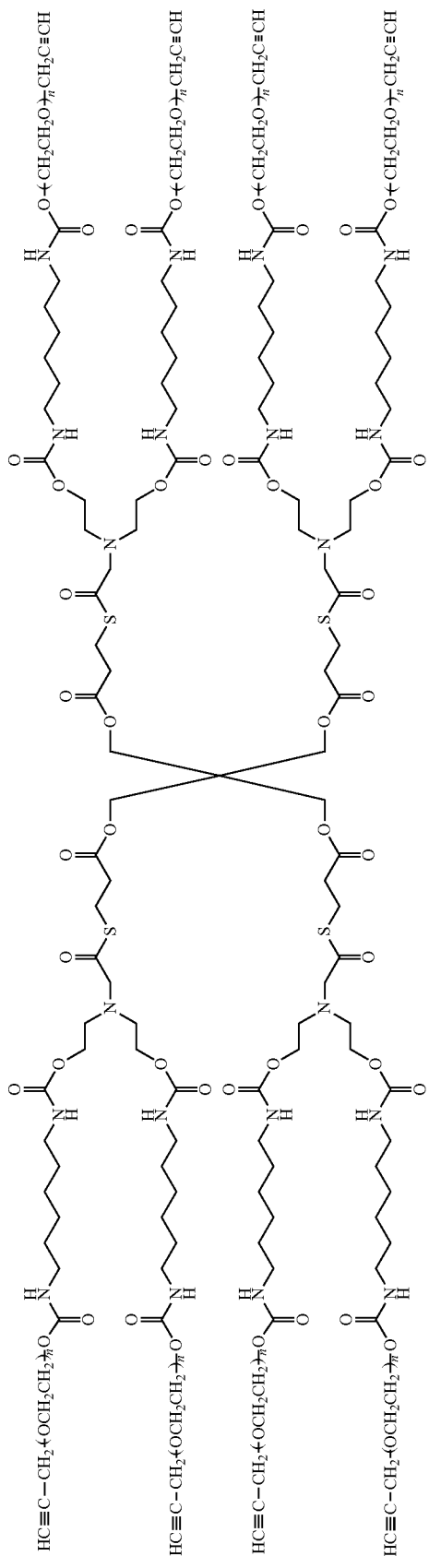
F3-2

Herein, the structure of the eight-arm polyethylene glycol derivative was designed as follows:

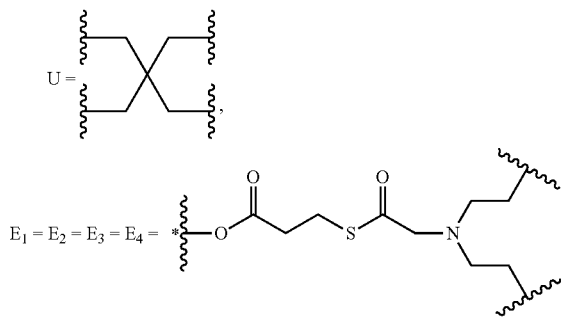

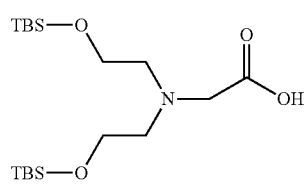

(with a nitrogen-atom-branching center of a symmetrical structure), the divalent linking groups $L_{11}=L_{12}=L_{21}=L_{22}=L_{31}=L_{32}=L_{41}=L_{42}=$OCONH$(CH_2)_6$NHCOO$(CH_2)_2$, $L_0$ is absent, $g=0$, $k=1$, and F is $CH_2C\equiv CH$ (wherein, $Z_2$ is absent, $Z_1$ is an ethylene group, and $R_{01}$ is an ethynyl group). The designed total molecular weight is approximately 26.8 kDa, wherein, the molecular weight of the eight PEG chains is approximately 8×3000=24000 Da, corresponding to $n_1 \approx n_2 \approx n_3 \approx n_4 \approx n_5 \approx n_6 \approx n_7 \approx n_8 \approx 68$.

Step (a): Into a dry and clean 1 L round-bottom flask, 100 mmol of pentaerythritol tetra(3-mercaptopropionate), 100 mL of triethylamine and 500 mmol of N,N-di(2-hydroxyethyl) glycine S27-1 with hydroxyl groups being protected were added. Under nitrogen protection, dichloromethane (600 mL) was added, and the whole was stirred till dissolution. Subsequently, a solution of 100 g of dicyclohexylcarbodiimide (DCC) in dichloromethane was added thereinto, followed by reaction at room temperature for 24 hours. The resulting mixture was filtrated to remove undissolved substances, concentrated and recrystallized from isopropanol, and then a compound with eight hydroxyl groups being protected S27-2 was obtained.

Step (b): Into a dry and clean container, the protected-octahydroxyl compound S27-2 was added and then dissolved with tetrahydrofuran, followed by the addition of tetra-t-butyl ammonium fluoride (TBAF); thereafter, the reaction was conducted overnight, and a compound S27-3 with eight unprotected hydroxyl groups was obtained.

$^1$H NMR spectrum data of the compound S27-3 with eight unprotected hydroxyl groups were as follows: $^1$H NMR (CDCl$_3$) δ (ppm): 2.53 (—CH$_2$CH$_2$OH), 2.91 (—CH$_2$CH$_2$S—), 3.26 (—CH$_2$CH$_2$S—), 3.41-3.47 (—CH$_2$CH$_2$OH, —SC(=O)CH$_2$—), 4.01 (C(CH$_2$O—)$_4$).

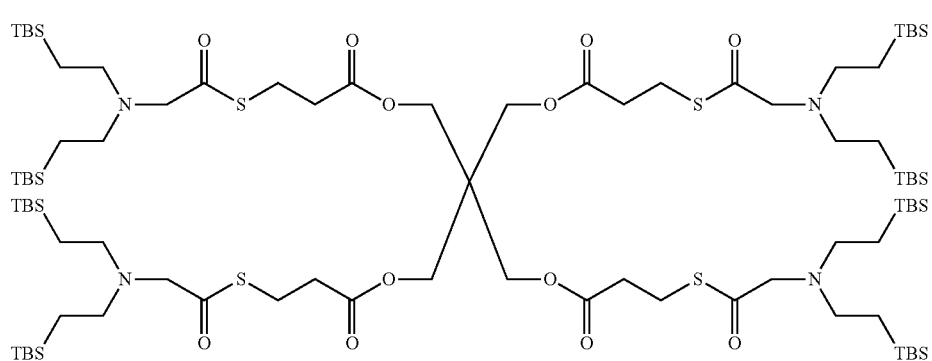

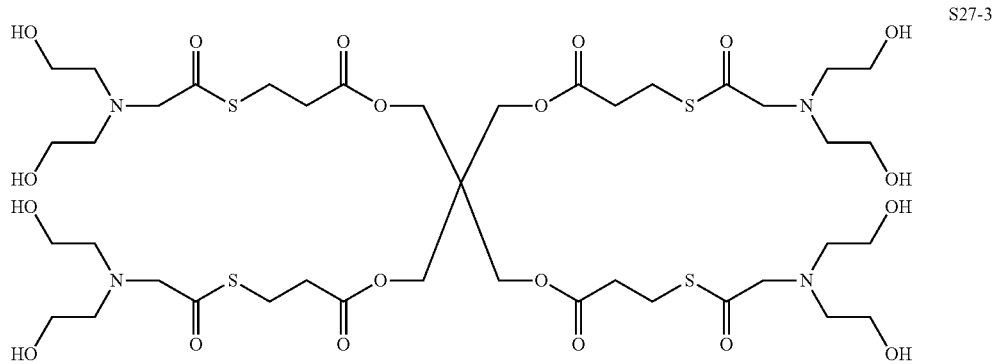

S27-4

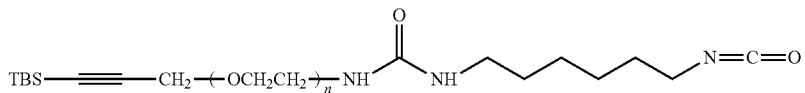

Step (c): Into a dry and clean 1 L round-bottom flask, the compound with eight unprotected hydroxyl groups S27-3 in a suitable amount and dibutyltin dilaurate (0.01 mmol) were added and then dissolved with 100 mL of DMSO. Subsequently, a solution of 25 mmol of a heterofunctional protected-alkynyl polyethylene glycol isocyanate (S27-4, $M_n$ was about 3 kDa, PDI=1.04) in dichloromethane was added dropwisely. The product was concentrated, precipitated, collected by filtration, recrystallized and dried, and then an eight-arm protected PEG-alkyne derivative F4-2 was obtained.

$^1$H NMR spectrum data of the eight-arm protected PEG-alkyne derivative F4-2 were as follows: $^1$H NMR (CDCl$_3$) δ (ppm): 0.21 (—Si(CH$_3$)$_2$), 0.98 (—SiC(CH$_3$)$_3$), 1.52 (—CH$_2$CH$_2$CH$_2$CH$_2$CH$_2$CH$_2$—), 1.29 (—CH$_2$CH$_2$CH$_2$CH$_2$CH$_2$CH$_2$—), 2.64 (—N(CH$_2$CH$_2$-)$_2$), 2.91 (—CH$_2$CH$_2$S—), 3.04-3.18 (CH$_2$CH$_2$CH$_2$CH$_2$CH$_2$CH$_2$—); 3.26 (—CH$_2$CH$_2$S—, —N(CH$_2$CH$_2$-)$_2$), 3.40-3.80 (—CH$_2$CH$_2$O—, —S(C=O)CH$_2$—, —OCH$_2$CH$_2$OSi—), 3.80-4.00 (—OCH$_2$CH$_2$OSi—, C(CH$_2$O—)$_4$), 4.15-4.35 (—C≡CCH$_2$O—).

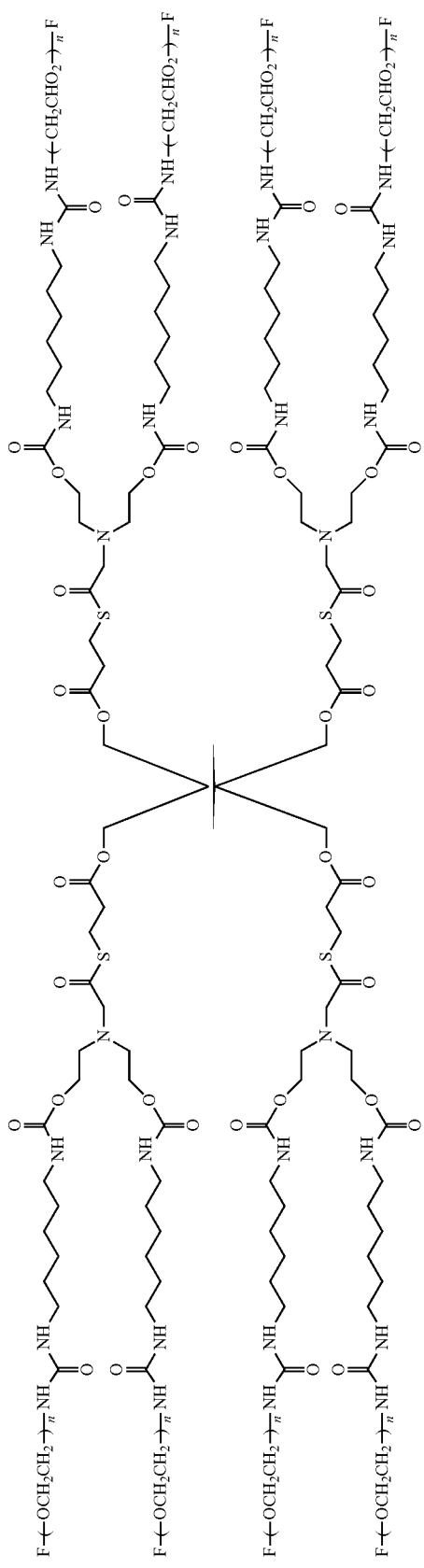

Step (d): Into a dry and clean container, the eight-arm protected PEG-alkyne derivative F4-2 was added and then dissolved with tetrahydrofuran, followed by the addition of tetra-t-butyl ammonium fluoride (TBAF); thereafter, the reaction was conducted overnight, and an eight-arm polyethylene glycol alkyne derivative F3-2 was obtained.

$^1$H NMR spectrum data of the eight-arm polyethylene glycol alkyne derivative F3-2 were as follows: $^1$H NMR (CDCl$_3$) δ (ppm): 1.52 (—CH$_2$CH$_2$CH$_2$CH$_2$CH$_2$CH$_2$—), 1.29 (—CH$_2$CH$_2$CH$_2$CH$_2$CH$_2$CH$_2$—), 2.40-2.70 (HC≡CCH$_2$O—, —N(CH$_2$CH$_2$-)$_2$), 2.91 (—CH$_2$CH$_2$S—), 3.04-3.18 (CH$_2$CH$_2$CH$_2$CH$_2$CH$_2$CH$_2$—); 3.26 (—CH$_2$CH$_2$S—, —N(CH$_2$CH$_2$-)$_2$), 3.40-3.80 (—CH$_2$CH$_2$O—, —SC(=O)CH$_2$—), 4.01 (C(CH$_2$O—)$_4$), 4.15-4.35 (—C—CCH$_2$O—); M$_n$≈27 kDa, PDI=1.04.

Example-28: The Preparation Method for an Eight-Arm Polyethylene Glycol Alcohol Derivative in which the Terminals are of a Cyclic End-Branched Type Herein, U, E$_1$, E$_2$, E$_3$, E$_4$, L$_{11}$, L$_{12}$, L$_{21}$, L$_{22}$, L$_{31}$, L$_{32}$, L$_{41}$, L$_{42}$, n$_1$, n$_2$, n$_3$, n$_4$, n$_5$, n$_6$, n$_7$, n$_8$ and n in the eight-arm polyethylene glycol derivative are the same as those in Example-27, g=1, k>1, L$_0$ contains a triazole ring, G is the β-CD skeleton, and F=OH (wherein, both Z$_2$ and Z$_1$ are absent, and R$_{01}$ is a hydroxyl group). The designed total molecular weight is approximately 36.1 kDa, wherein, the molecular weight of the eight PEG chains is approximately 8×3000=24000 Da, corresponding to n$_1$≈n$_2$≈n$_3$≈n$_4$≈n$_5$≈n$_6$≈n$_7$≈n$_8$≈68.

Into a dry and clean 1 L round-bottom flask, 10 g of the eight-arm polyethylene glycol alkyne derivative F3-2 obtained in Example-27 and 10 g of mono-6-azido-6-deoxy-β-cyclodextrin (S28-1, β-CD-N$_3$) were added. Under nitrogen protection, 200 mL of tetrahydrofuran was added thereinto, and the whole was stirred till dissolution, followed by reaction at room temperature for 24 hours. The resulting product was concentrated and recrystallized from isopropanol, and then an eight-arm polyethylene glycol alcohol derivative with cyclic branched terminals in a white solid state was obtained.

$^1$H NMR spectrum data of the eight-arm polyethylene glycol multihydroxylated derivative were as follows: $^1$H NMR (CDCl$_3$) δ (ppm): 1.52 (—CH$_2$CH$_2$CH$_2$CH$_2$CH$_2$CH$_2$—), 1.29 (—CH$_2$CH$_2$CH$_2$CH$_2$CH$_2$—), 2.40-2.70 (—N(CH$_2$CH$_2$-)$_2$), 2.90-3.18 ((—O)$_2$CHCHCHCH—, —CH$_2$CH$_2$S—, CH$_2$CH$_2$CH$_2$CH$_2$CH$_2$CH$_2$—); 3.26 (—CH$_2$CH$_2$S—, —N(CH$_2$CH$_2$-)$_2$), 3.40-4.10 (—CH$_2$CH$_2$O—, —SCOCH$_2$—, —NCH$_2$CH—, —OCHCH$_2$OH, (—O)$_2$CHCHCHCH—, C(CH$_2$O—)$_4$), 4.05-4.25 (—HC=CCH$_2$O—), 4.90-5.10 ((—O)$_2$CHCHCHCH—), 7.10-7.40 (—HC=CCH$_2$O—); M$_n$≈36 kDa, PDI=1.04.

Example-29: Preparation Methods for Eight-Arm Polyethylene Glycol Amine Derivatives Preparation of an Eight-Arm Polyethylene Glycol Amine Derivative (C4-3)

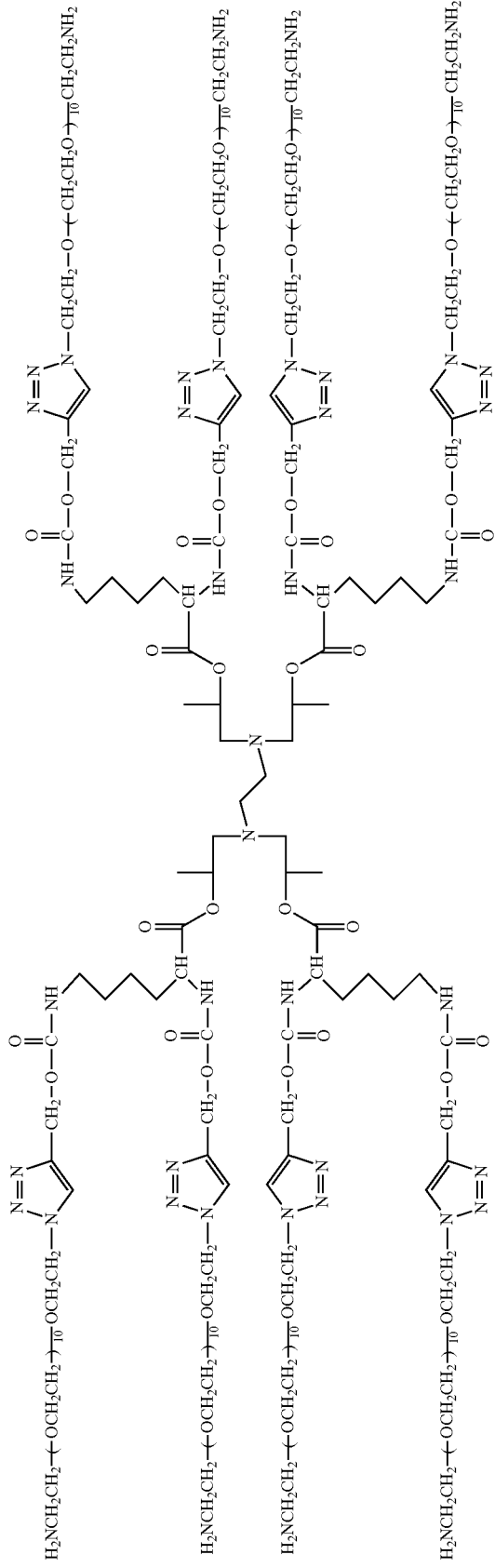
C4-3

Herein, the structure of the eight-arm polyethylene glycol derivative was designed as follows:

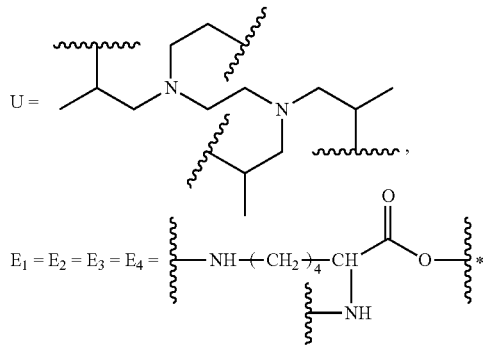

(with a carbon-branching center of an asymmetrical structure), the divalent linking groups $L_{11}=L_{12}=L_{21}=L_{22}=L_{31}=L_{32}=L_{41}=L_{42}=$

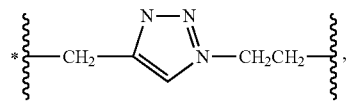

$g=0$, $k=1$, and $F=CH_2CH_2NH_2$ (wherein, $Z_2$ is absent, $Z_1$ is an ethylene group, and $R_{01}$ is $NH_2$). The designed total molecular weight is approximately 6.0 kDa, wherein, the molecular weight of the eight monodisperse PEG chains is approximately 8×450=3600 Da, corresponding to $n_1=n_2=n_3=n_4=n_5=n_6=n_7=n_8=n=10$.

Step (a): Into a dry and clean 1 L round-bottom flask, 50 mmol of N,N,N',N'-tetrakis(2-hydroxypropyl)ethylenediamine, 30 mL of triethylamine and excess alkynyl-containing lysine derivative S29-1 were added. Under nitrogen protection, dichloromethane (500 mL) was added thereinto, and the whole was stirred till dissolution. Subsequently, a solution of 20 g of dicyclohexylcarbodiimide (DCC) in dichloromethane was added thereinto, followed by reaction at room temperature for 24 hours. The resulting mixture was filtrated to remove undissolved substances, concentrated and recrystallized, and then an octaalkynyl-bearing lysine compound S29-2 was obtained.

$^1$H NMR spectrum data of the octaalkynyl-bearing lysine compound S29-2 were as follows: $^1$H NMR (CDCl$_3$) δ (ppm): 1.20-1.60 (—NCH$_2$CH$_2$CH$_2$CH$_2$CHCO—, CH$_3$CH(O)CH$_2$—), 1.70-1.90 (—NCH$_2$CH$_2$CH$_2$CH$_2$CHCO—), 2.40-2.73 (HC≡CCH$_2$O—, CH$_3$CH(O)CH$_2$—), 3.10-3.23 (—NCH$_2$CH$_2$CH$_2$CH$_2$CHCO—), 4.15-4.35 (—C≡CCH$_2$O—), 4.35-4.55 (CH$_3$CH(O)CH$_2$—, —NCH$_2$CH$_2$CH$_2$CH$_2$CHCO—).

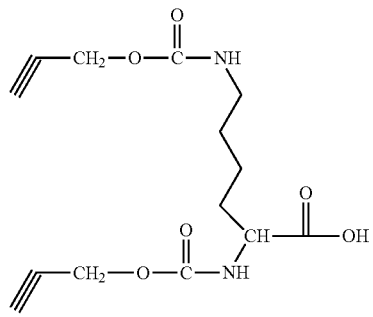

S29-1

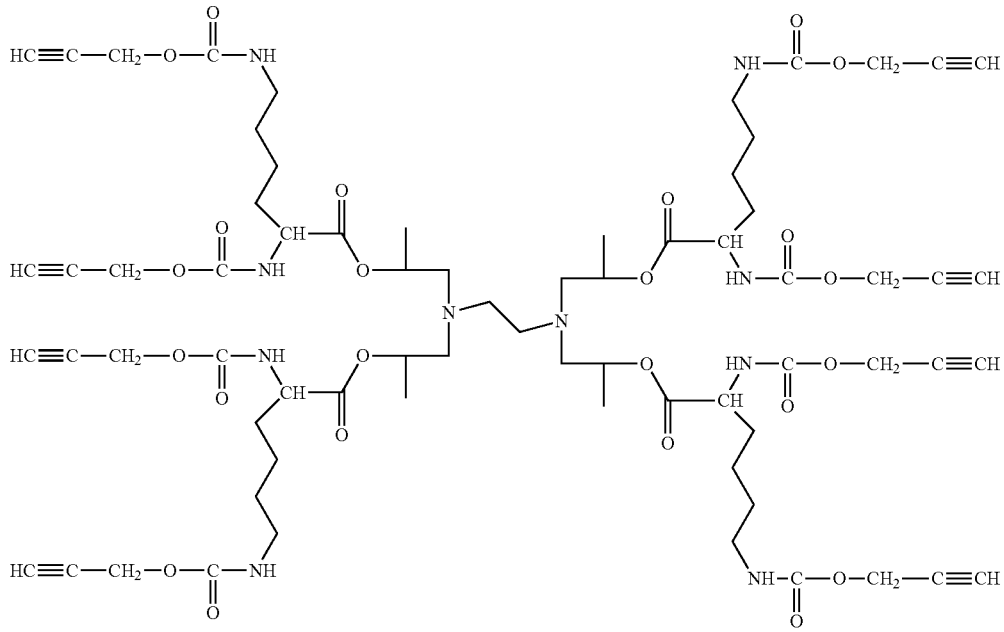

S29-2

Step (b): Into a dry and clean 1 L round-bottom flask, 10 g of the octaalkynyl-bearing lysine compound S29-2 and 10 g of O-(2-aminoethyl)-O'-(2-azidoethyl)nonaethylene glycol (containing nine EO units) were added. Under nitrogen protection, tetrahydrofuran (200 mL) was added, and the whole was stirred till dissolution, followed by reaction at room temperature for 24 hours. The resulting solution was concentrated and recrystallized from isopropanol, and then an eight-arm polyethylene glycol amine derivative C4-3 was obtained.

$^1$H NMR spectrum data of the eight-arm polyethylene glycol amine derivative C4-3 were as follows: $^1$H NMR (CDCl$_3$) δ (ppm): 1.20-1.60 (—NCH$_2$CH$_2$CH$_2$CH$_2$CHCO—, CH$_3$CH(O)CH$_2$—), 1.70-1.90 (—NCH$_2$CH$_2$CH$_2$CH$_2$CHCO—), 2.40-2.73 (CH$_3$CH(O)CH$_2$—, —OCH$_2$CH$_2$NH$_2$), 3.10-3.23 (—NCH$_2$CH$_2$CH$_2$CH$_2$CHCO—), 3.40-3.80 (—CH$_2$CH$_2$O—, —OCH$_2$CH$_2$NH$_2$), 3.85-4.11 (—NCH$_2$CH$_2$O—, —NHCOOCH$_2$—), 4.35-4.55 (CH$_3$CH(O)CH$_2$—, —NCH$_2$CH$_2$CH$_2$CHCO—), 7.75 (—CH$_2$CH$_2$C(≡CH)N═N—).

Preparation of an Eight-Arm Polyethylene Glycol Amine Hydrochloride Derivative (C11-1)

Herein, U, E$_1$, E$_2$, E$_3$, E$_4$, L$_{11}$, L$_{12}$, L$_{21}$, L$_{22}$, L$_{31}$, L$_{32}$, L$_{41}$, L$_{42}$, n$_1$, n$_2$, n$_3$, n$_4$, n$_5$, n$_6$, n$_7$, n$_8$, n, g and k in the eight-arm polyethylene glycol derivative are the same as those in Example C$_{4-3}$, g=0, k=1, and F=CH$_2$CH$_2$NH$_2$.HCl (wherein, Z$_2$ is absent, Z$_i$ is an ethylene group, and R$_{01}$ is NH$_2$.HCl). Wherein, the molecular weight of the eight monodisperse PEG chains is approximately 8×450=3600 Da, corresponding to n$_1$=n$_2$=n$_3$=n$_4$=n$_5$=n$_6$=n$_7$=n$_8$=n=10.

Into a dry and clean 1 L round-bottom flask, 10 g of the eight-arm polyethylene glycol amine derivative C4-3 was added. Under nitrogen protection, 200 mL of deionized water was added thereinto, and the whole was stirred till dissolution. The solution was adjusted to pH 1 with the addition of hydrochloric acid (3 M), followed by stirring at 30° C. for 1 hour. The product in the solvent was extracted with dichloromethane, concentrated, and precipitated with absolute diethyl ether at 0° C. The precipitate was collected by filtration and dried, and then an eight-arm polyethylene glycol amine hydrochloride derivative C11-1 was obtained.

$^1$H NMR spectrum data of the eight-arm polyethylene glycol amine hydrochloride derivative C11-1 were as follows: $^1$H NMR (CDCl$_3$) δ (ppm): 1.20-1.60 (—NCH$_2$CH$_2$CH$_2$CH$_2$CHCO—, CH$_3$CH(O)CH$_2$—), 1.70-1.90 (—NCH$_2$CH$_2$CH$_2$CH$_2$CHCO—), 2.40-2.73 (CH$_3$CH(O)CH$_2$—, —OCH$_2$CH$_2$NH$_2$), 3.10-3.23 (—NCH$_2$CH$_2$CH$_2$CH$_2$CHCO—), 3.40-3.80 (—CH$_2$CH$_2$O—, —OCH$_2$CH$_2$NH$_2$), 3.85-4.11 (—NCH$_2$CH$_2$O—, —NHCOOCH$_2$—), 4.35-4.55 (CH$_3$CH(O)CH$_2$—, —NCH$_2$CH$_2$CH$_2$CH$_2$CHCO—), 7.75 (—CH$_2$CH$_2$C(≡CH)N═N—).

Example-30: Preparation Methods for Eight-Arm Polyethylene Glycol Cycloalkyne Derivatives Preparation of an Eight-Arm Polyethylene Glycol Cycloalkyne Derivative (G1-2)

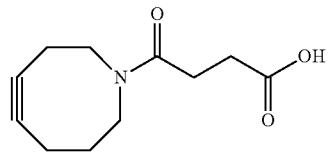

S30-1

Herein, U, E$_1$, E$_2$, E$_3$, E$_4$, L$_{11}$, L$_{12}$, L$_{21}$, L$_{22}$, L$_{31}$, L$_{32}$, L$_{41}$, L$_{42}$, n$_1$, n$_2$, n$_3$, n$_4$, n$_5$, n$_6$, n$_7$, n$_8$, n, g and k in the eight-arm polyethylene glycol derivative are the same as those in the Example C4-3, g=0, k=1, and

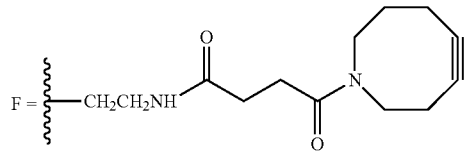

(wherein, Z$_2$ is CH$_2$CH$_2$NH, Z$_1$ is COCH$_2$CH$_2$, and R$_{01}$ is an azacyclooctynyl group). Wherein, the molecular weight of the eight monodisperse PEG chains is approximately 8×450=3600 Da, corresponding to n$_1$=n$_2$=n$_3$=n$_4$=n$_5$=n$_6$=n$_7$=n$_8$=n=10.

Into a dry and clean 1 L round-bottom flask, 8 g of the eight-arm polyethylene glycol amine derivative C4-3 (treated by azeotropic removal of water with toluene), 10 mL of triethylamine and 5 g of a compound S30-1 were added. Under nitrogen protection, dichloromethane (160 mL) was added thereinto, and the whole was stirred till dissolution. Subsequently, 10 g of dicyclohexylcarbodiimide (DCC) was added thereinto, followed by reaction at room temperature for 24 hours. The resulting mixture was filtrated to remove undissolved substances, concentrated and recrystallized from isopropanol, and then an eight-arm polyethylene glycol cycloalkyne derivative G1-2 in a white solid state was obtained.

G1-2
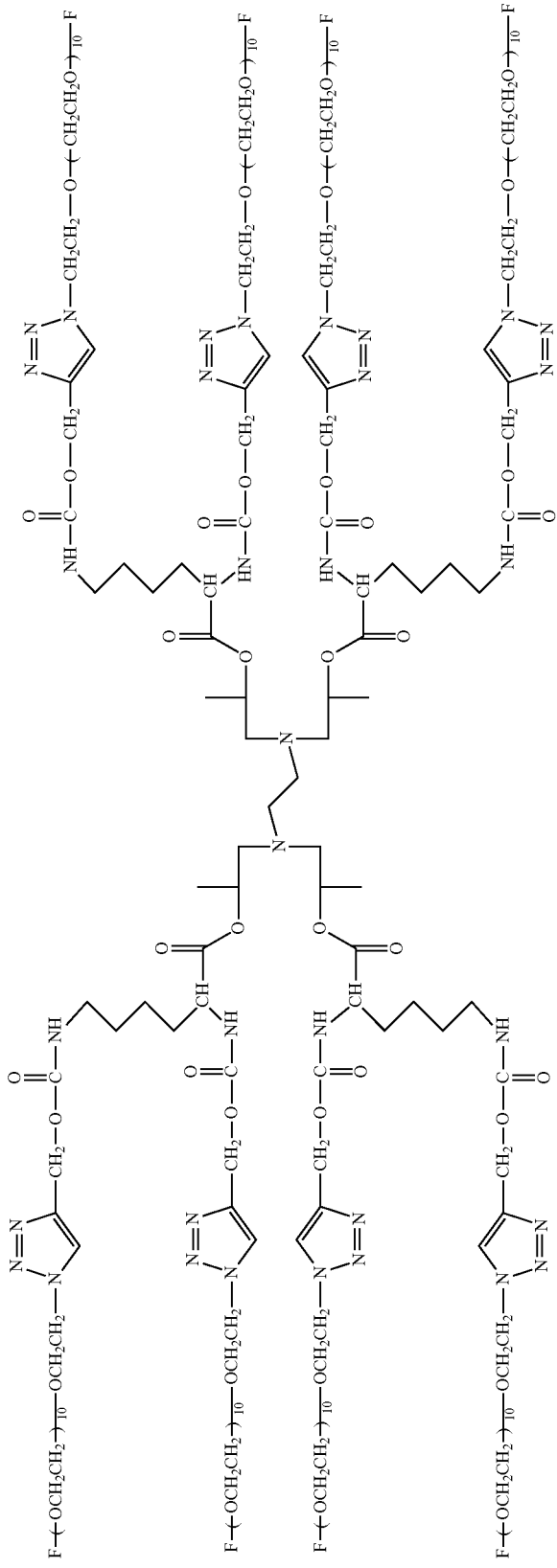
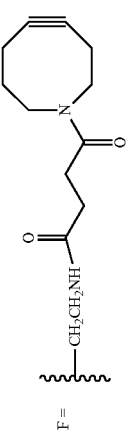

In the $^1$H NMR spectrum of the eight-arm polyethylene glycol cycloalkyne derivative G1-2, besides the characteristic peaks of chain backbone, the characteristic peaks of the cycloalkynyl group also appeared as follows: $^1$H NMR (CDCl$_3$) δ (ppm): 1.60-2.10 (—C≡CCH$_2$CH$_2$CH$_2$N—), 2.10-2.70 (—C≡CCH$_2$CH$_2$N—, —NC(=O)CH$_2$CH$_2$C(=O)O—), 3.10-3.50 (—C≡CCH$_2$CH$_2$N—, —C≡CCH$_2$CH$_2$CH$_2$N—).

Preparation of an Eight-Arm Polyethylene Glycol Cycloalkyne Derivative (G2-1)

G2-1
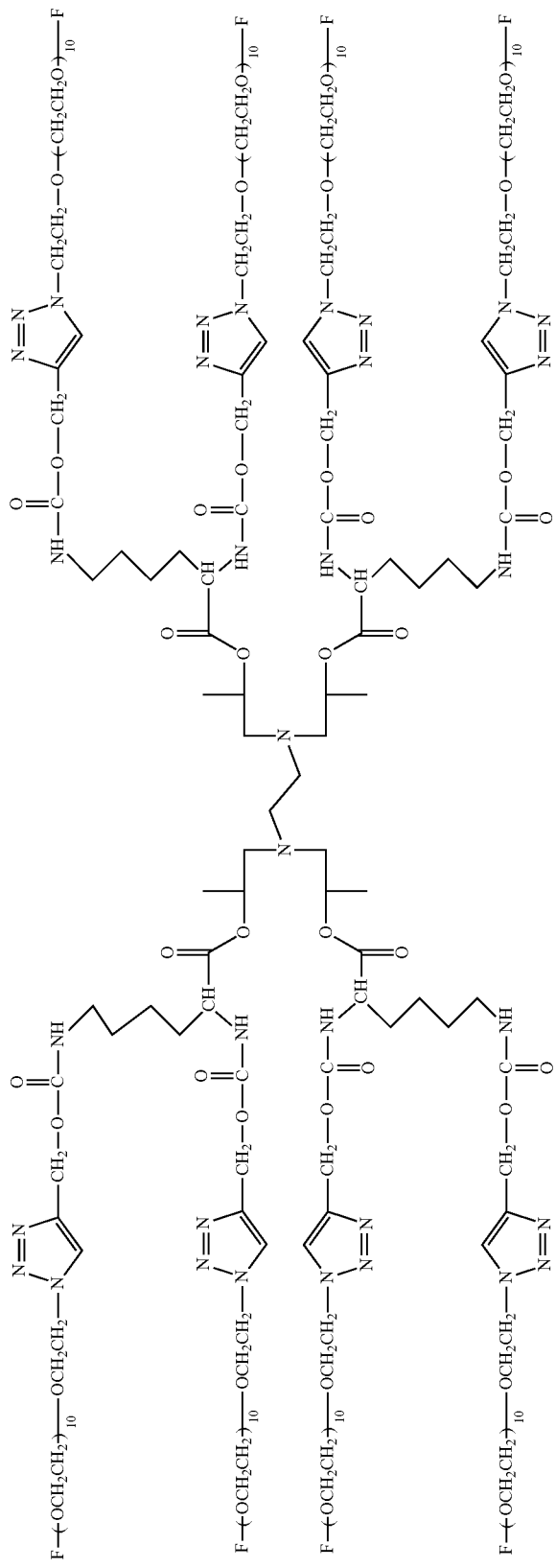
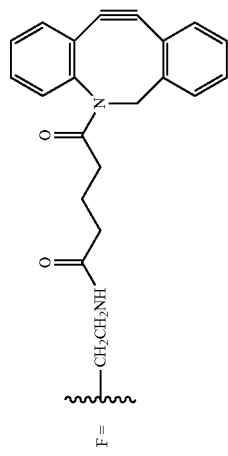

Herein, $U$, $E_1$, $E_2$, $E_3$, $E_4$, $L_{11}$, $L_{12}$, $L_{21}$, $L_{22}$, $L_{31}$, $L_{32}$, $L_{41}$, $L_{42}$, $n_1$, $n_2$, $n_3$, $n_4$, $n_5$, $n_6$, $n_7$, $n_8$, $n$, $g$ and $k$ in the eight-arm polyethylene glycol derivative are the same as those in Example $C_{4-3}$, $g=0$, $k=1$, $Z_2$ is $CH_2CH_2NH$, $Z_1$ is $COCH_2CH_2$, and $R_{01}$ is an azadibenzocyclooctynyl group. Wherein, the molecular weight of the eight monodisperse PEG chains is approximately 8×450=3600 Da, corresponding to $n_1=n_2=n_3=n_4=n_5=n_6=n_7=n_8=10$.

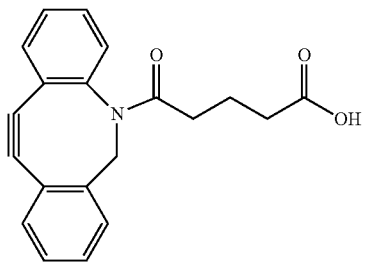

S30-2

Into a dry and clean 1 L round-bottom flask, 8 g of the eight-arm polyethylene glycol amine derivative C4-3 (treated by azeotropic removal of water with toluene), 10 mL of triethylamine and 5 g of a compound S30-2 were added. Under nitrogen protection, dichloromethane (160 mL) was added thereinto, and the whole was stirred till dissolution. Subsequently, 10 g of dicyclohexylcarbodiimide (DCC) was added thereinto, followed by reaction at room temperature for 24 hours. The resulting mixture was filtrated to remove undissolved substances, concentrated and recrystallized from isopropanol, and then an eight-arm polyethylene glycol cycloalkyne derivative G2-1 in a white solid state was obtained.

In the $^1H$ NMR spectrum of the eight-arm polyethylene glycol cycloalkyne derivative G2-1, besides the characteristic peaks of chain backbone, the characteristic peaks of the dibenzocyclooctynyl group also appeared as follows: $^1H$ NMR (CDCl$_3$) δ (ppm): 4.60-4.70 (ArCH$_2$—), 7.32-7.54 (Ar—H).

Preparation of an Eight-Arm Polyethylene Glycol Cycloalkyne Derivative (G7-1)

G7-1
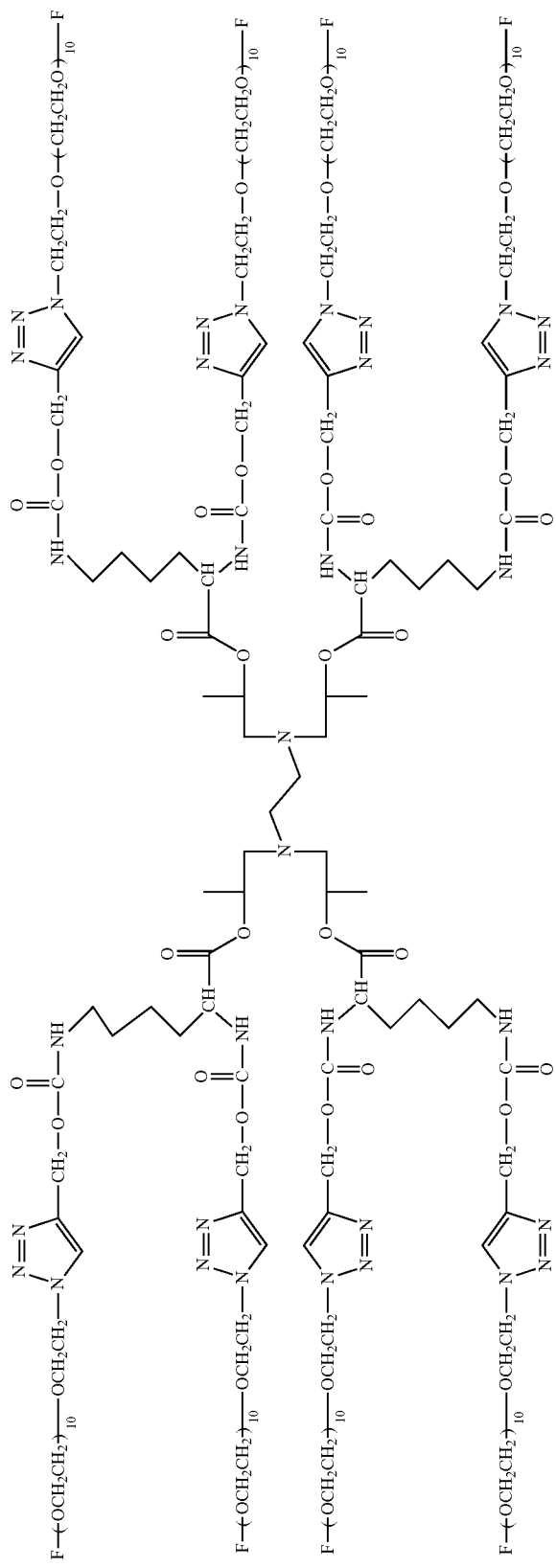
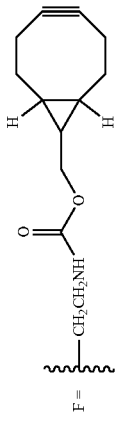

Herein, U, $E_1$, $E_2$, $E_3$, $E_4$, $L_{11}$, $L_{12}$, $L_{21}$, $L_{22}$, $L_{31}$, $L_{32}$, $L_{41}$, $L_{42}$, $n_1$, $n_2$, $n_3$, $n_4$, $n_5$, $n_6$, $n_7$, $n_8$, n, g and k in the eight-arm polyethylene glycol derivative are the same as those in Example C4-3, g=0, k=1, $Z_2$ is $CH_2CH_2NH$, $Z_1$ is $COCH_2CH_2$, and $R_{01}$ is a cycloalkynyl group. Wherein, the molecular weight of the eight monodisperse PEG chains is approximately 8×450=3600 Da, corresponding to $n_1=n_2=n_3=n_4=n_5=n_6=n_7=n_8=n=10$.

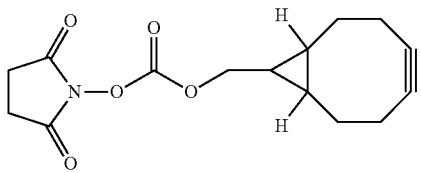

S30-3

Into a dry and clean 1 L round-bottom flask, 8 g of the eight-arm polyethylene glycol amine derivative C4-3 (treated by azeotropic removal of water with toluene) and 10 mL of triethylamine were added. Under nitrogen protection, a solution of 5 g of a compound S30-3 in dichloromethane (160 mL) was added thereinto, and the whole was stirred till dissolution. Subsequently, 10 g of dicyclohexylcarbodiimide (DCC) was added thereinto, followed by reaction at room temperature for 24 hours. The resulting mixture was filtrated to remove undissolved substances, concentrated and recrystallized from isopropanol, and then an eight-arm polyethylene glycol cycloalkyne derivative G7-1 in a white solid state was obtained.

In the $^1$H NMR spectrum of the eight-arm polyethylene glycol cycloalkyne derivative G7-1, besides the characteristic peaks of chain backbone, the characteristic peaks of the cyclooctynyl group also appeared as follows: $^1$H NMR ($CDCl_3$) δ (ppm): 0.19 (—$COOCH_2CH(CH)_2$—), 0.79 (—$COOCH_2CH$—), 1.30-1.50 (—C≡$CCH_2CH_2$—), 1.80-2.10 (—C≡$CCH_2CH_2$—), 4.21 (—$NHCOOCH_2$—).

Example-31: The Preparation Method for an Eight-Arm Polyethylene Glycol Iodoacetamide Derivative (C10-1)

Herein, U, $E_1$, $E_2$, $E_3$, $E_4$, $L_{11}$, $L_{12}$, $L_{21}$, $L_{22}$, $L_{31}$, $L_{32}$, $L_{41}$, $L_{42}$, $n_1$, $n_2$, $n_3$, $n_4$, $n_5$, $n_6$, $n_7$, $n_8$, n, g and k in the eight-arm polyethylene glycol derivative are the same as those in Example $C_{4-3}$, g=0, k=1, and F is $CH_2CH_2NHC(=O)CH_2I$ (wherein, $Z_2$ is absent, $Z_i$ is $CH_2CH_2$, and $R_{01}$ is $NHC(=O)CH_2I$). Wherein, the molecular weight of the eight monodisperse PEG chains is approximately 8×450=3600 Da, corresponding to $n_1=n_2=n_3=n_4=n_5=n_6=n_7=n_8=n=10$.

Into a dry and clean 1 L round-bottom flask, 40 g of the eight-arm polyethylene glycol amine derivative C4-3 obtained in Example-30 was added followed by the addition of dichloromethane (500 mL), and then the whole was stirred till dissolution. Subsequently, 20 mL of triethylamine, 10 g of iodoacetic acid and a solution of 20 g of dicyclohexylcarbodiimide (DCC) in dichloromethane were added thereinto in sequence, followed by a reaction away from light at room temperature for 24 hours. The resulting mixture was filtrated to remove undissolved substances, concentrated and recrystallized from isopropanol, and then an eight-arm polyethylene glycol iodoacetamide derivative C10-1 in an off-white solid state was obtained.

$^1$H NMR spectrum data of the eight-arm polyethylene glycol iodoacetamide derivative C10-1 were as follows: $^1$H NMR ($CDCl_3$) δ (ppm): 1.20-1.60 (—$NCH_2CH_2CH_2CH_2CHCO$—, $CH_3CH(O)CH_2$—), 1.70-1.90 (—$NCH_2CH_2CH_2CH_2CHCO$—), 2.40-2.73 ($CH_3CH(O)CH_2$—), 3.10-3.28 (—$NCH_2CH_2CH_2CH_2CHCO$—, —$OCH_2CH_2NHCOCH_2I$), 3.40-3.80 (—$CH_2CH_2O$—, —$OCH_2CH_2NH$—), 3.85-4.11 (—$NCH_2CH_2O$—, —$NHCOOCH_2$—, —$CH_2I$), 4.35-4.55 ($CH_3CH(O)CH_2$—, —$NCH_2CH_2CH_2CH_2CHCO$—), 7.75 (—$CH_2CH_2C(=CH)N=N$—).

Example-32: The Preparation Method for an Eight-Arm Polyethylene Glycol Acrylate Derivative (E2-1)

Herein, the structure of the eight-arm polyethylene glycol derivative was designed as follows:

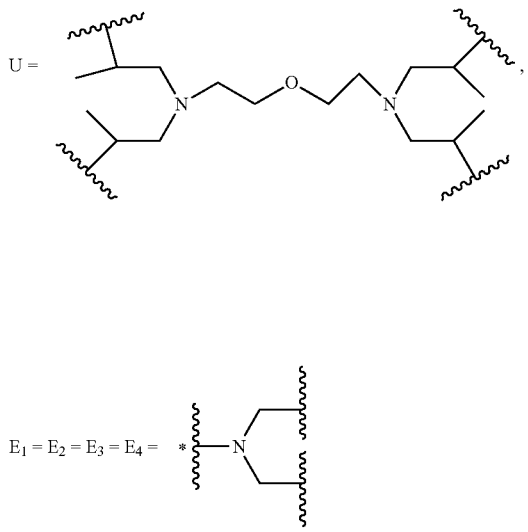

(with a nitrogen-branching center of a symmetrical type), the divalent linking groups $L_{11}$, $L_{12}$, $L_{21}$, $L_{22}$, $L_{31}$, $L_{32}$, $L_{41}$ and $L_{42}$ are all absent, g=0, k=1, and F is $COCH=CH_2$. The designed total molecular weight is approximately 25.7 kDa, wherein, the molecular weight of the eight PEG chains is approximately 8×3000=24000 Da, corresponding to $n_1 \approx n_2 \approx n_3 \approx n_4 \approx n_5 \approx n_6 \approx n_7 \approx n_8 \approx 68$.

E2-1

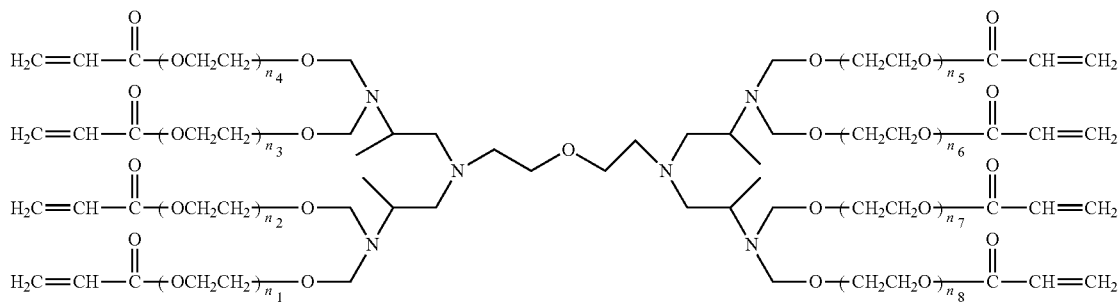

Step (a): Into a dry, clean and sealed reactor, tetrahydrofuran (400 mL) and dichlorodiethyl ether (100 mmol) were added, and then excess bis(2-hydroxypropyl)amine with hydroxyl groups being TBS-protected was added, followed by reaction at 30° C. for 12 hours. After completion of the reaction, open the reactor. The product in the solvent was concentrated, washed and purified via column chromatography, and then an intermediate with hydroxyl groups being TBS-protected was obtained. Into a dry and clean container, the resulting intermediate was added and then dissolved with tetrahydrofuran, followed by the addition of tetra-t-butyl ammonium fluoride (TBAF); thereafter, the reaction was conducted overnight, and then a small molecule compound S32-1 containing four hydroxyl groups was obtained.

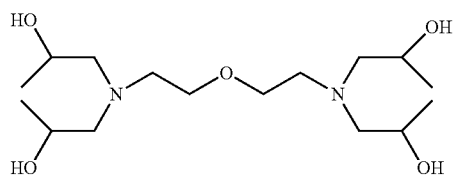

S32-1

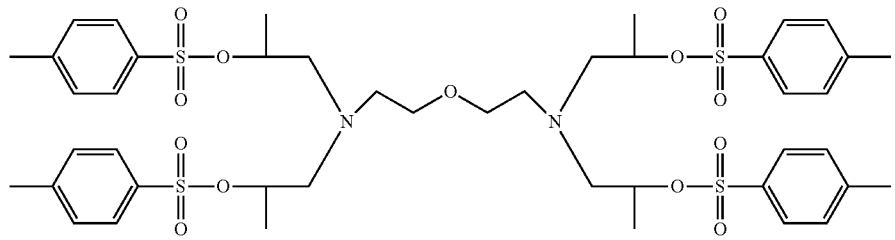

S32-2

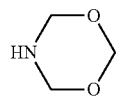

S32-3

Step (b): Into a dry and clean 1 L round-bottom flask, 50 mmol of the small molecule compound containing four hydroxyl groups S32-1 was added. Under nitrogen protection, 500 mL of anhydrous and oxygen-free dichloromethane, 20 mL of pyridine and excess 4-toluenesulfonyl chloride were added thereinto, followed by reaction at room temperature for 24 hours. The resulting solution was adjusted to a pH value less than 7 with hydrochloric acid (1 mol/L), and the aqueous phase was washed with dichloromethane (50 mL trice). The organic phase was combined, washed with saturated salt solutions, dried with anhydrous sodium sulfate, filtrated, concentrated and recrystallized, and then a tetratosylate compound S32-2 was obtained.

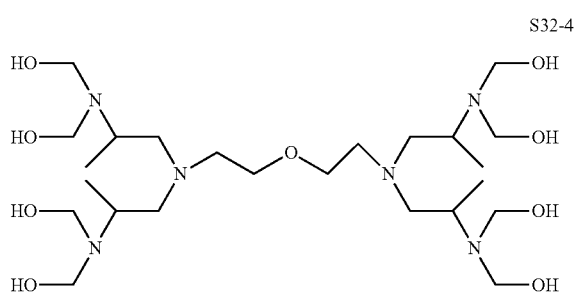 [SMILES: CC(CN(CCOCCN(CC(C)N(CO)CO)CC(C)N(CO)CO)CC(C)N(CO)CO)N(CO)CO]

S32-4

Step (c): Into a dry, clean and sealed reactor, tetrahydrofuran (400 mL) and tosylate (100 mmol) were added, and then excess 1,3,5-dioxazinane S32-3 was added, followed by reaction at 30° C. for 12 hours. After completion of the reaction, open the reactor. The product in the solvent was concentrated, dissolved with dichloromethane, washed, concentrated and then dissolved with HCl solution (1M), followed by stirring at room temperature overnight. Thereafter, the product was extracted, washed and purified via column chromatography, and then an octahydroxyl-containing small molecule compound S32-4 was obtained.

$^1$H NMR spectrum data of the octahydroxyl-containing small molecule compound S32-4 were as follows: $^1$H NMR (CDCl$_3$) δ (ppm): 1.12 (CH$_3$CH(N)CH$_2$—), 2.29-2.53 (CH$_3$CH(N)CH$_2$—, —OCH$_2$CH$_2$N—), 3.03 (CH$_3$CH(N)CH$_2$—); 3.60 (—OCH$_2$CH$_2$N—); 4.60 (—NCH$_2$OH).

calculated amount of ethylene oxide, the whole was heated stepwisely to 60° C., followed by reaction for 48 hours. After the addition of excess proton source (methanol), the product in the solvent was concentrated and precipitated, and then an eight-arm polyethylene glycol H1-13 was obtained.

$^1$H NMR spectrum data of the eight-arm polyethylene glycol H1-13 were as follows: $^1$H NMR (CDCl$_3$) δ (ppm): 1.10-1.15 (CH$_3$CH(N)CH$_2$—); 2.29-2.53 (CH$_3$CH(N)CH$_2$—, —OCH$_2$CH$_2$N—); 3.03 (CH$_3$CH(N)CH$_2$—); 3.40-3.80 (—OCH$_2$CH$_2$—, —OCH$_2$CH$_2$N—); 4.60 (—NCH$_2$O—); M$_n$≈25 kDa, PDI=1.03.

Step (e): Into a dry and clean 1 L round-bottom flask, the eight-arm polyethylene glycol H1-13 (treated by azeotropic removal of water with toluene) was added. Under nitrogen protection, 600 mL of anhydrous and oxygen-free tetrahydrofuran was added thereinto, and the whole was stirred at room temperature till dissolution. Subsequently, 10 mL of triethylamine and 2 mL of acryloyl chloride were added thereinto in sequence in an ice bath, followed by reaction at room temperature for 24 hours. Thereafter, the resulting product in the solvent was concentrated, dissolved with 200 mL of deionized water, and then extracted with dichloromethane (75 mL trice). The organic phase was combined, washed with saturated salt solutions (50 mL trice), dried, concentrated and recrystallized, and then an eight-arm polyethylene glycol acrylate derivative E2-1 was obtained.

$^1$H NMR spectrum data of the eight-arm polyethylene glycol acrylate derivative E2-1 were as follows: $^1$H NMR (CDCl$_3$) δ (ppm): 1.10-1.15 (CH$_3$CH(N)CH$_2$—); 2.29-2.53

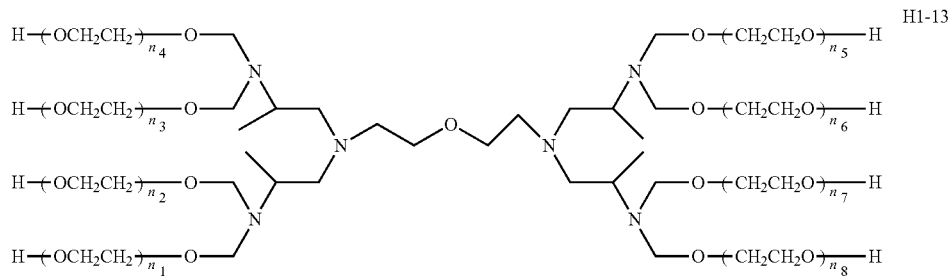

H1-13

Step (d): Into a sealed reactor under an anhydrous and oxygen-free atmosphere, tetrahydrofuran (250 mL), the octahydroxyl-containing small molecule compound S32-4 (1.266 mmol) and diphenylmethyl potassium (DPMK, 4.0 mmol) were added in sequence. After the addition of a (CH$_3$CH(N)CH$_2$—, —OCH$_2$CH$_2$N—); 3.00-3.05 (CH$_3$CH(N)CH$_2$—); 3.40-3.80 (—OCH$_2$CH$_2$—, —OCH$_2$CH$_2$N—, CH$_2$=CHCOOCH$_2$CH$_2$O—); 4.22-4.32 (CH$_2$=CHCOOCH$_2$CH$_2$O—); 4.60 (—NCH$_2$O—), 5.59-6.27 (CH$_2$=CHCOOCH$_2$CH$_2$O—); M$_n$≈26 kDa, PDI=1.03.

Example-33: The Preparation Method for an Eight-Arm Polyethylene Glycol Maleimide Derivative (E1-2)

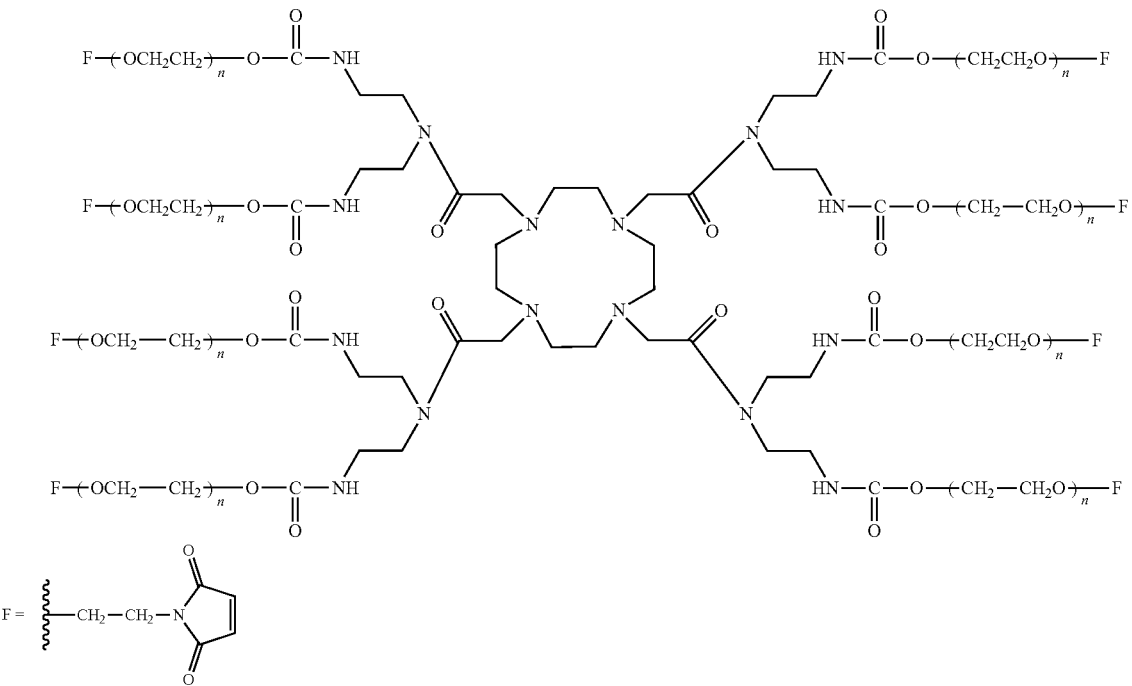

Herein, the structure of the eight-arm polyethylene glycol derivative was designed as follows:

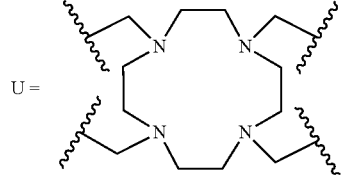

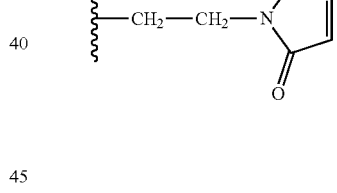

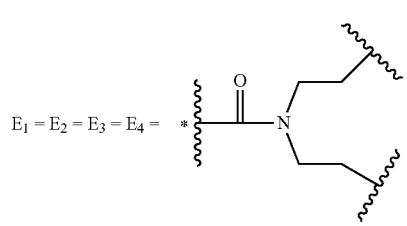

(with a nitrogen-branching center of a symmetrical type), the divalent linking groups $L_{11}=L_{12}=L_{21}=L_{22}=L_{31}=L_{32}=L_{41}=L_{42}=NHCO$, g=0, k=1, and F is (wherein, $Z_2$ is absent, $Z_1$ is an ethylene group, and $R_{01}$ is a maleimido group). The designed total molecular weight is approximately 25 kDa, wherein, the molecular weight of the eight monodisperse PEG chains is approximately 8×2816=22.5 kDa, corresponding to $n_1=n_2=n_3=n_4=n_5=n_6=n_7=n_8=n=65$.

Step (a): Into a dry and clean 1 L round-bottom flask, 10 mmol of 1,4,7,10-tetraazacyclododecane-N,N',N'',N'''-tetraacetic acid, 20 mL of triethylamine and 50 mmol of diethylenetriamine with terminal amino groups being Boc-protected S33-1 were added. Under nitrogen protection, dichloromethane (500 mL) was added thereinto, and the whole was stirred till dissolution. Subsequently, a solution of 20 g of dicyclohexylcarbodiimide (DCC) in dichloromethane was added thereinto, followed by reaction at room temperature for 24 hours. The resulting mixture was filtrated to remove undissolved substances, concentrated and recrystallized, and then A compound with terminal amino groups being Boc-protected S33-2 was obtained.

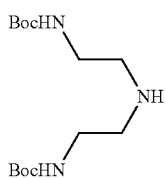

S33-1

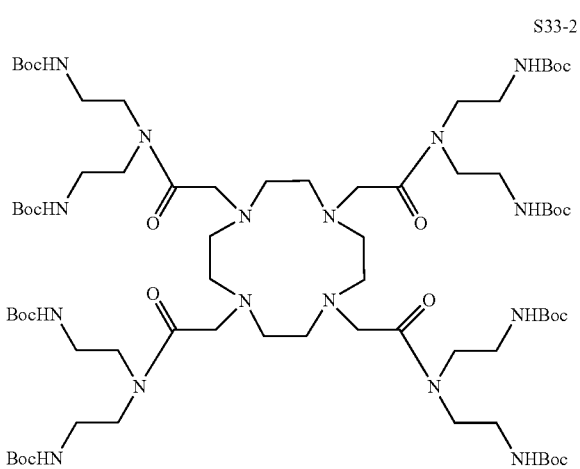

S33-2

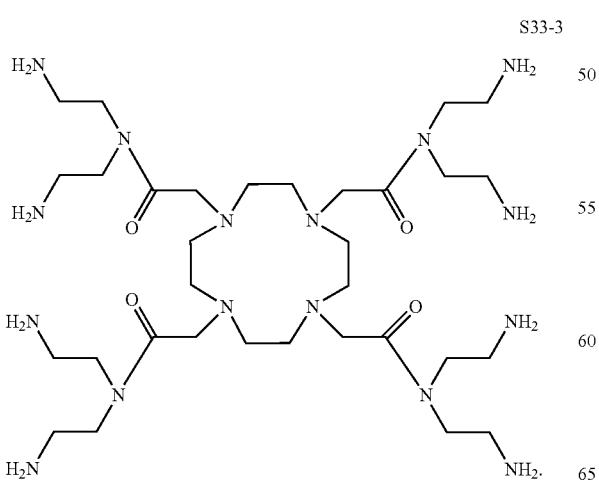

S33-3

¹H NMR spectrum data of the compound with terminal amino groups being tert-butoxycarbonyl-protected S33-2 were as follows: ¹H NMR (CDCl$_3$) δ (ppm): 1.39 (—C(CH$_3$)$_3$), 2.41-2.51 (—N(CH$_2$—)CH$_2$CH$_2$—), 3.29 (—N(CH$_2$—)CH$_2$CH$_2$—), 3.41-3.52 (—CON(CH$_2$CH$_2$NH—)$_2$, 3.60-3.71 (—CON(CH$_2$CH$_2$NH—)$_2$.

Step (b): Into a dry and clean container, the compound with terminal amino groups being Boc-protected S33-2 obtained in the last step was added and then dissolved with dichloromethane. The solution was adjusted to 0.1 M via the addition of trifluoroacetic acid (TFA), followed by reaction for 4 hours. Thereafter, the solution was adjusted to a neutral pH value, extracted and precipitated, and a compound with amino groups being unprotected S33-3 was obtained.

¹H NMR spectrum data of the compound with amino groups being unprotected S33-3 were as follows: ¹H NMR (CDCl$_3$) δ (ppm): 2.41-2.51 (—N(CH$_2$—)CH$_2$CH$_2$—), 2.71-2.81 (—CON(CH$_2$CH$_2$NH$_2$)$_2$, 3.29 (—N(CH$_2$—)CH$_2$CH$_2$—), 3.41-3.52 (—CON(CH$_2$CH$_2$NH$_2$)$_2$.

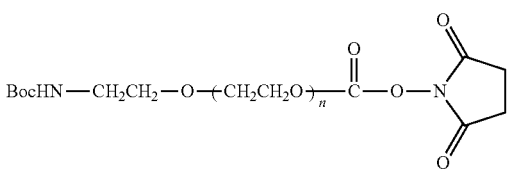

S33-4

Step (c): Into a dry and clean 1 L round-bottom flask, 10 mmol of the compound with amino groups being unprotected S33-3 obtained in the last step, 500 mL of acetonitrile, 40 mL of triethylamine and 80 mmol of a monodisperse heterofunctional polyethylene glycol derivative (SS-4, EO-unit number was n=65) were added, followed by reaction at room temperature for 24 hours. The resulting mixture was concentrated and recrystallized from isopropanol, and then an eight-arm polyethylene glycol derivative C6-4 with terminal amino groups being protected in a white solid state was obtained.

C6-4

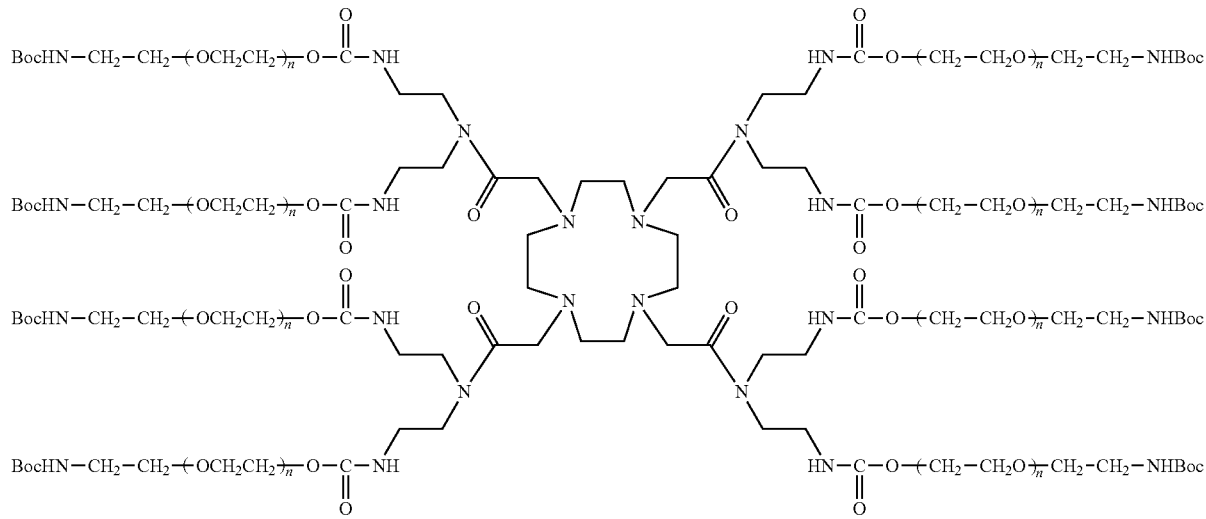

¹H NMR spectrum data of the eight-arm polyethylene glycol derivative C6-4 with terminal amino groups being protected were as follows: ¹H NMR (CDCl$_3$) δ (ppm): 1.38 (—C(CH$_3$)$_3$), 2.41-2.51 (—N(CH$_2$—)CH$_2$CH$_2$—), 3.29 (—N(CH$_2$—)CH$_2$CH$_2$—), 3.40-3.80 (—CH$_2$CH$_2$O—, —CON(CH$_2$CH$_2$NH—)$_2$, —CON(CH$_2$CH$_2$NH—)$_2$).

Step (d): Into a dry and clean container, the eight-arm polyethylene glycol derivative with terminal amino groups being protected C$_{6-4}$ obtained in the last step was added and then dissolved with dichloromethane. The solution was adjusted to 0.1 M with trifluoroacetic acid (TFA), followed by reaction for 4 hours. Thereafter, the solution was adjusted to a neutral pH value, extracted and precipitated, and then an eight-arm polyethylene glycol amine derivative C4-4 was obtained.

¹H NMR spectrum data of the eight-arm polyethylene glycol amine derivative C4-4 were as follows: ¹H NMR (CDCl$_3$) δ (ppm): 2.40-2.50 (—N(CH$_2$—)CH$_2$CH$_2$—), 2.70-2.85 (—CON(CH$_2$CH$_2$NH—)$_2$, (—OCH$_2$CH$_2$NH$_2$), 3.29 (—N(CH$_2$—)CH$_2$CH$_2$—); 3.40-3.80 (—CH$_2$CH$_2$O—, —CON(CH$_2$CH$_2$NH—)$_2$, —OCH$_2$CH$_2$NH$_2$); the molecular weight was about 24000 Da.

Step (e): Into a dry and clean 1 L round-bottom flask, 20 g of the eight-arm polyethylene glycol amine derivative C4-4 obtained in the last step (treated by azeotropic removal of water with toluene) and 10 g of β-maleimidopropionic acid were added. Under nitrogen protection, dichloromethane (600 mL) was added thereinto, and the whole was stirred till dissolution. Subsequently, 40 mL of triethylamine and 40 g of dicyclohexylcarbodiimide (DCC) were added in sequence, followed by reaction at room temperature for 24 hours. The resulting mixture was filtrated to remove undissolved substances, concentrated and recrystallized from isopropanol, and then an eight-arm polyethylene glycol maleimide derivative E1-2 in a white solid state was obtained.

In the ¹H NMR spectrum of the eight-arm polyethylene glycol maleimide derivative E1-2, besides the characteristic peaks of the chain backbone, the characteristic peaks of the maleimide moiety also appeared as follows: ¹H NMR (CDCl$_3$) δ (ppm): 2.70-2.80 (—NHC(=O)CH$_2$CH$_2$—), 3.92 (—NHCOCH$_2$CH$_2$N—), 6.81 (—CH=CH—).

Example-34: The Preparation Method for an Eight-Arm Polyethylene Glycol Maleimide Derivative (E1-3)

Herein, the structure of the eight-arm polyethylene glycol derivative was designed as follows:

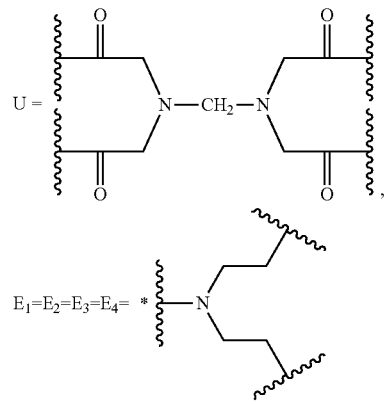

(with a nitrogen-branching center of a symmetrical type), the divalent linking groups $L_{11}=L_{12}=L_{21}=L_{22}=L_{31}=L_{32}=L_{41}=L_{42}$=NHCO, g=0, k=1, and F is

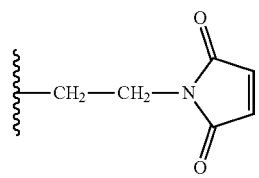 [SMILES: *CCN1C(=O)C=CC1=O]

(wherein, $Z_2$ is an ethylene group, $Z_1$ is absent, and $R_{01}$ is a maleimido group). The designed total molecular weight is approximately 24.8 kDa, wherein, the molecular weight of the eight monodisperse PEG chains is approximately 8×2816=22.5 kDa, corresponding to $n_1=n_2=n_3=n_4=n_5=n_6=n_7=n_8=n=65$.

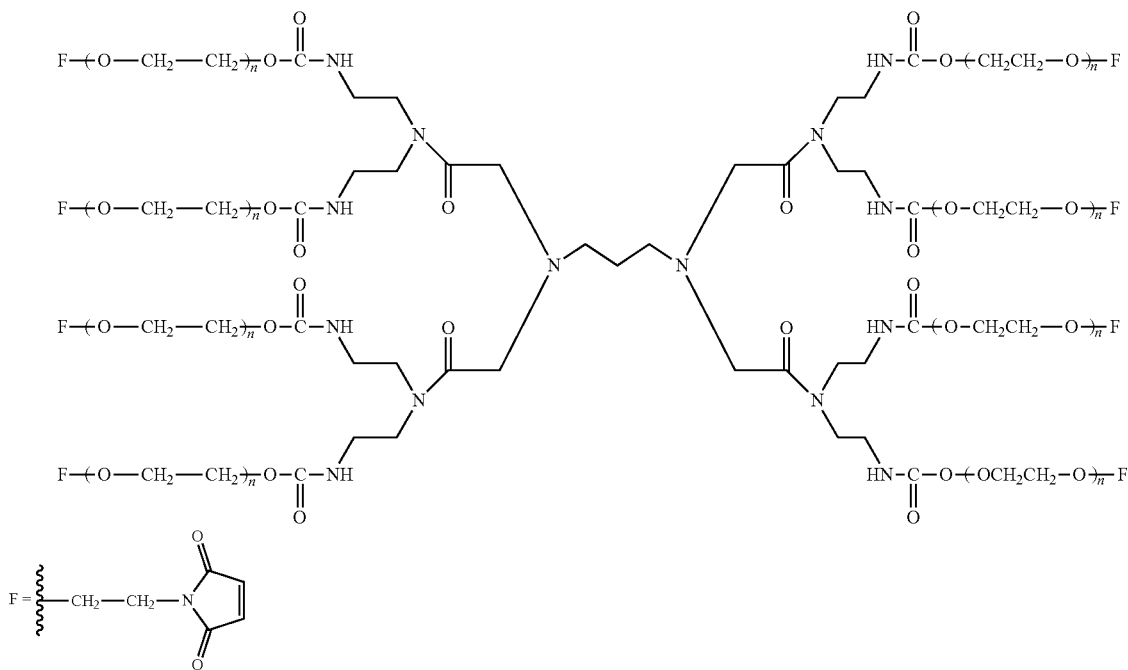

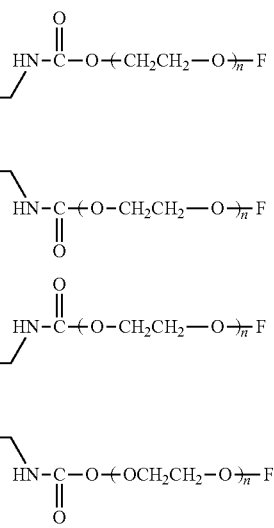

Step (a): Into a dry and clean 1 L round-bottom flask, 10 mmol of 1,3-propylenediaminetertaacetic acid, 20 mL of triethylamine and 50 mmol of diethylenetriamine with terminal amino groups being Boc-protected S33-1 were added. Under nitrogen protection, dichloromethane (500 mL) was added, and the whole was stirred till dissolution. Subsequently, a solution of 20 g of dicyclohexylcarbodiimide (DCC) in dichloromethane was added thereinto, followed by reaction at room temperature for 24 hours. The resulting mixture was filtrated to remove undissolved substances, concentrated and recrystallized, and then a compound with terminal amino groups being Boc-protected S34-1 was obtained.

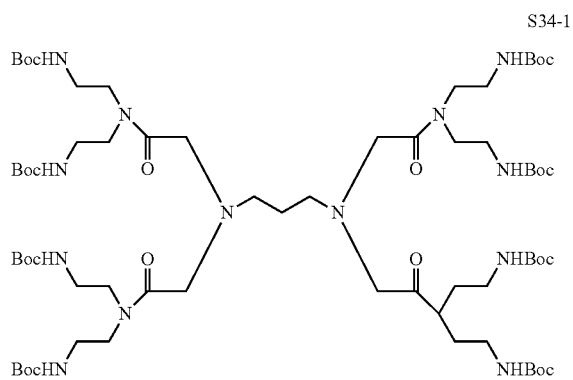

S34-1

-continued

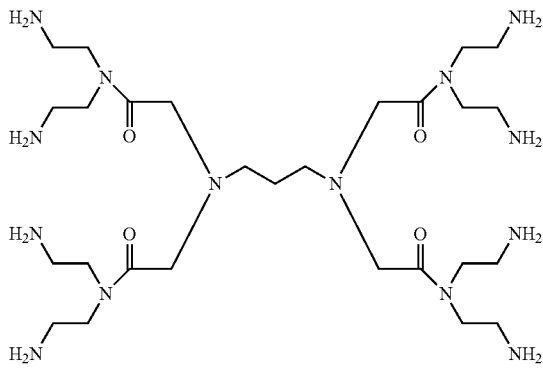

S34-2

$^1$H NMR spectrum data of the compound with terminal amino groups being Boc-protected S34-1 were as follows: $^1$H NMR (CDCl$_3$) δ (ppm): 1.39 (—C(CH$_3$)$_3$), 1.46-1.55 (—CH$_2$CH$_2$CH$_2$N(CH$_2$-)$_2$), 2.40-2.50 (—CH$_2$CH$_2$CH$_2$N(CH$_2$-)$_2$), 3.29 (—CH$_2$CH$_2$CH$_2$N(CH$_2$-)$_2$), 3.40-3.52 (—CON(CH$_2$CH$_2$NH—)$_2$), 3.60-3.71 (—CON(CH$_2$CH$_2$NH—)$_2$).

Step (b): Into a dry and clean container, the compound with terminal amino groups being Boc-protected S34-1 obtained in the last step was added and then dissolved with dichloromethane. The solution was adjusted to 0.1 M with trifluoroacetic acid (TFA), followed by reaction for 4 hours. Thereafter, the solution was adjusted to a neutral pH value, extracted and precipitated, and an octary primary amine compound with amino groups being unprotected S34-2 was obtained.

$^1$H NMR spectrum data of the octary primary amine compound with amino groups being unprotected S34-2 were as follows: $^1$H NMR (CDCl$_3$) δ (ppm): 1.46-1.55 (—CH$_2$CH$_2$CH$_2$N(CH$_2$-)$_2$), 2.40-2.50 (—CH$_2$CH$_2$CH$_2$N (CH$_2$-)$_2$), 2.70-2.80 (—CON(CH$_2$CH$_2$NH$_2$)$_2$); 3.29 (—CH$_2$CH$_2$CH$_2$N(CH$_2$-)$_2$), 3.41-3.52 (—CON(CH$_2$CH$_2$NH$_2$)$_2$).

$^1$H NMR spectrum data of the eight-arm polyethylene glycol amine derivative C4-5 were as follows: $^1$H NMR (CDCl$_3$) δ (ppm): 1.46-1.55 (—CH$_2$CH$_2$CH$_2$N(CH$_2$-)$_2$),

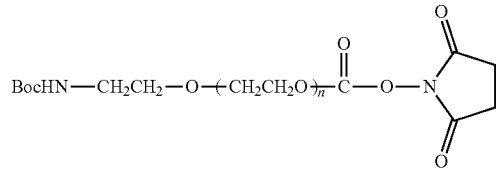

S34-3

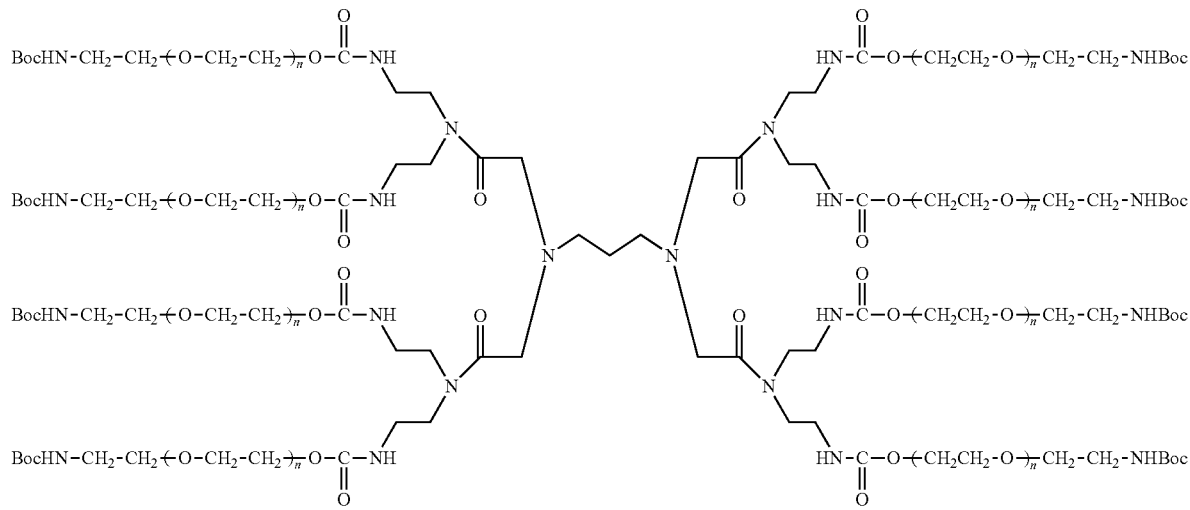

C6-5

Step (c): Into a dry and clean 1 L round-bottom flask, 10 mmol of the compound with amino groups being unprotected S34-2, 500 mL of acetonitrile, 40 mL of triethylamine and 80 mmol of a monodisperse heterofunctional polyethylene glycol derivative (S34-3, EO-unit number was n=65) were added, followed by reaction at room temperature for 24 hours. The resulting mixture was concentrated and recrystallized from isopropanol, and then an eight-arm polyethylene glycol derivative with terminal amino groups being protected C$_{6-5}$ in a white solid state was obtained.

$^1$H NMR spectrum data of the eight-arm polyethylene glycol derivative with terminal amino groups being protected C$_{6-5}$ were as follows: $^1$H NMR (CDCl$_3$) δ (ppm): 1.38 (OC(CH$_3$)$_3$), 1.46-1.55 (—CH$_2$CH$_2$CH$_2$N(CH$_2$-)$_2$), 2.41-2.51 (—CH$_2$CH$_2$CH$_2$N(CH$_2$-)$_2$), 2.71-2.85 (—CON(CH$_2$CH$_2$NH—)$_2$, —OCH$_2$CH$_2$NH), 3.29 (—CH$_2$CH$_2$CH$_2$N(CH$_2$-)$_2$), 3.40-3.80 (—CH$_2$CH$_2$O—, —CON(CH$_2$CH$_2$NH—)$_2$, —OCH$_2$CH$_2$NH—).

Step (d): Into a dry and clean container, the eight-arm polyethylene glycol derivative with terminal amino groups being protected C$_{6-5}$ was added and then dissolved with dichloromethane.

The solution was adjusted to 0.1 M with the addition of trifluoroacetic acid (TFA), followed by reaction for 4 hours. Thereafter, the solution was adjusted to a neutral pH value, extracted and precipitated, and then an eight-arm polyethylene glycol amine derivative C4-5 was obtained.

2.41-2.51 (—CH$_2$CH$_2$CH$_2$N(CH$_2$-)$_2$), 2.71-2.85 (—CON(CH$_2$CH$_2$NH—)$_2$, —OCH$_2$CH$_2$NH$_2$), 3.29 (—CH$_2$CH$_2$CH$_2$N(CH$_2$-)$_2$), 3.40-3.80 (—CH$_2$CH$_2$O—, —CON(CH$_2$CH$_2$NH—)$_2$, —OCH$_2$CH$_2$NH$_2$).

Step (e): Into a dry and clean 1 L round-bottom flask, 20 g of the eight-arm polyethylene glycol amine derivative C4-5 (treated by azeotropic removal of water with toluene) and 10 g of β-maleimidopropionic acid were added. Under nitrogen protection, dichloromethane (600 mL) was added thereinto, and the whole was stirred till dissolution. Subsequently, 40 mL of triethylamine and 40 g of dicyclohexylcarbodiimide (DCC) were added thereinto in sequence, followed by reaction at room temperature for 24 hours. The resulting mixture was filtrated to remove undissolved substances, concentrated and recrystallized from isopropanol, and then an eight-arm polyethylene glycol maleimide derivative E1-3 in a white solid state was obtained.

In the $^1$H NMR spectrum of the eight-arm polyethylene glycol maleimide derivative E1-3, besides the characteristic peaks of the chain backbone, the characteristic peaks of the maleimide moiety also appeared as follows: $^1$H NMR (CDCl$_3$) δ (ppm): 2.70-2.80 (—NHC(=O)CH$_2$CH$_2$N—), 3.92 (—NHCOCH$_2$CH$_2$N—), 6.81 (—CH=CH—).

Example-35: The Preparation Method for an Eight-Arm Polyethylene Glycol Carboxylic Acid Derivative (D1-4)

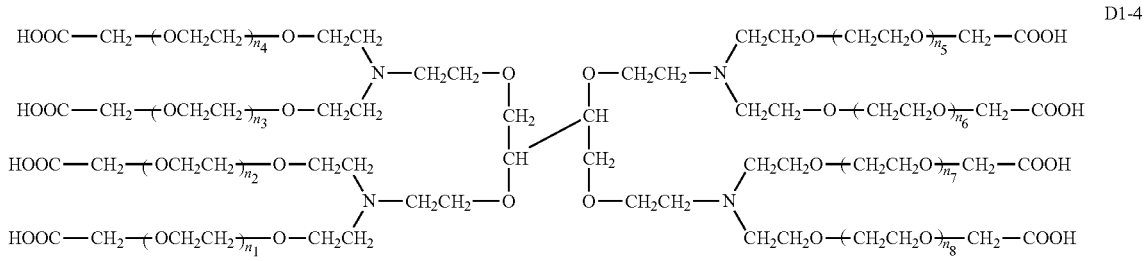

D1-4

Herein, the structure of the eight-arm polyethylene glycol derivative was designed as follows:

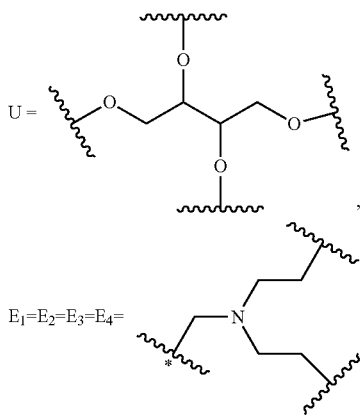

(with a nitrogen-branching center of a symmetrical type), the divalent linking groups $L_{11}$, $L_{12}$, $L_{21}$, $L_{22}$, $L_{31}$, $L_{32}$, $L_{41}$ and $L_{42}$ are all absent, $g=0$, $k=1$, and F is $CH_2COOH$ (wherein, $Z_2$ is absent, $Z_1$ is an ethylene group, and $R_{01}$ is COOH). The designed total molecular weight is approximately 20.8 kDa, wherein, the molecular weight of the eight PEG chains is approximately $8\times 2500 = 20000$ Da, corresponding to $n_1 \approx n_2 \approx n_3 \approx n_4 \approx n_5 \approx n_6 \approx n_7 \approx n_8 \approx 56$.

Step (a): Into a sealed reactor under an anhydrous and oxygen-free atmosphere, tetrahydrofuran (400 mL), erythritol (2.5 mmol) and diphenylmethyl potassium (20.0 mmol) were added in sequence, and then a compound S35-1 (30 mmol) in an excess amount was added, followed by reaction at 30° C. for 12 hours. After completion of the reaction, open the reactor. The product in the solvent was concentrated and then precipitated with absolute diethyl ether at 0° C. The precipitate was collected by filtration and dried, and then a compound S35-2 with terminal hydroxyl groups being protected as a silyl ether was obtained.

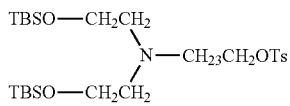

S35-1

-continued

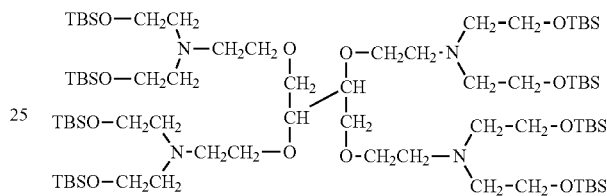

S35-2

$^1$H NMR spectrum data of the compound S35-2 with terminal hydroxyl groups being silyl-protected were as follows: $^1$H NMR (CDCl$_3$) δ (ppm): 0.21 (—Si(CH$_3$)$_2$), 0.98 (—SiC(CH$_3$)$_3$), 2.45-2.65 (—NCH$_2$CH$_2$OSi—, —NCH$_2$CH$_2$OCH—), 3.90 (—NCH$_2$CH$_2$OSi—), 3.40-3.60 (—NCH$_2$CH$_2$OCH—, —OCH(CH)CH$_2$—, —OCH(CH)CH$_2$—).

Step (b): Into a dry and clean container, the compound with terminal hydroxyl groups being silyl-protected S35-2 was added and then dissolved with tetrahydrofuran, followed by the addition of tetra-t-butyl ammonium fluoride (TBAF); thereafter, the reaction was conducted overnight, and an octahydroxyl-containing initiator S35-3 was obtained.

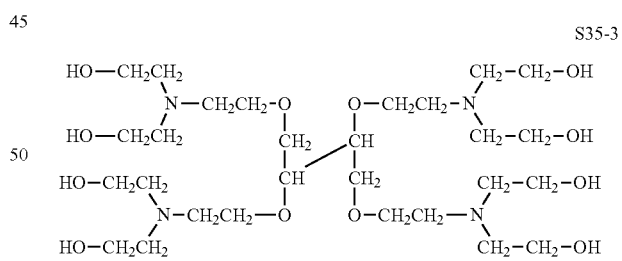

S35-3

$^1$H NMR spectrum data of the octahydroxyl-containing initiator S35-3 were as follows: $^1$H NMR (CDCl$_3$) δ (ppm): 2.45-2.65 (—NCH$_2$CH$_2$OH, —NCH$_2$CH$_2$O—), 3.90 (—NCH$_2$CH$_2$OH), 3.40-3.60 (—NCH$_2$CH$_2$O—, —(CH(O)CH$_2$-)$_2$).

Step (c): Into a sealed reactor under an anhydrous and oxygen-free atmosphere, tetrahydrofuran (250 mL), the octahydroxyl-containing initiator S35-3 (1.266 mmol) and diphenylmethyl potassium (4.0 mmol) were added in sequence. After the addition of a calculated amount of ethylene oxide, the whole was heated stepwisely to 60° C., followed by reaction for 48 hours.

Step (d): After the addition of excess proton source (methanol), the product in the solvent was concentrated and precipitated, and then an eight-arm polyethylene glycol H1-14 was obtained.

$^1$HNMR (CDCl$_3$) δ (ppm): 2.45-2.65 (—NCH$_2$CH$_2$O), 3.30-3.90 (—OCH$_2$CH$_2$O—, —NCH$_2$CH$_2$O—, —(CH(O)CH$_2$—)$_2$), 4.53 (—OCH$_2$COO—); M$_n$≈21 kDa, PDI=1.03.

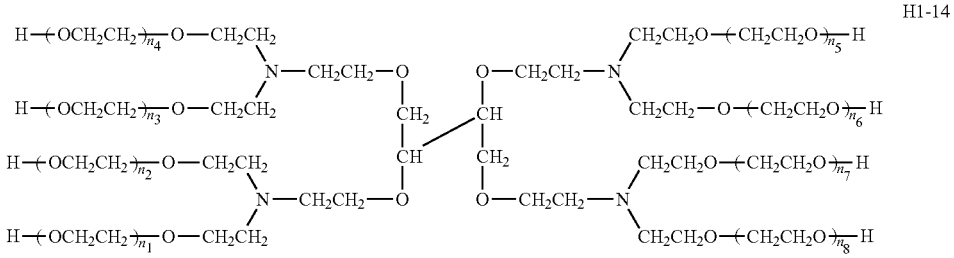

H1-14

$^1$H NMR spectrum data of the eight-arm polyethylene glycol H1-14 were as follows: $^1$H NMR (CDCl$_3$) δ (ppm): 2.45-2.65 (—NCH$_2$CH$_2$OH, —NCH$_2$CH$_2$OCH—), 3.30-3.90 (—OCH$_2$CH$_2$O—, —NCH$_2$CH$_2$OCH—, —OCH(CH)CH$_2$—, —OCH(CH)CH$_2$—, —NCH$_2$CH$_2$OH); M$_n$≈20 kDa, PDI=1.03.

Step (e): The eight-arm polyethylene glycol H111-14 (20 g) was dissolved with water (500 mL); subsequently, excess potassium hydroxide (20 mmol) and excess sodium bromoacetate (50 mmol) were added in sequence, followed by reaction at 30° C. for 12 hours. After completion of the reaction, open the reactor. The solution was adjusted to pH 1 with hydrochloric acid (3 M) at an ice bath, followed by stirring at 30° C. for 1 hour. The product in the solvent was extracted with dichloromethane, concentrated, and precipitated with absolute diethyl ether at 0° C. The precipitate was collected by filtration and dried, and then an eight-arm polyethylene glycol carboxylic acid derivative D1-4 was obtained.

$^1$H NMR spectrum data of the eight-arm polyethylene glycol carboxylic acid derivative D1-4 were as follows:

Example-36: The Preparation Method for an Eight-Arm Polyethylene Glycol Acyl Chloride Derivative (D4-1)

Herein, U, E$_1$, E$_2$, E$_3$, E$_4$, L$_{11}$, L$_{12}$, L$_{21}$, L$_{22}$, L$_{31}$, L$_{32}$, L$_{41}$, L$_{42}$, n$_1$, n$_2$, n$_3$, n$_4$, n$_5$, n$_6$, n$_7$, n$_8$, g and k in the eight-arm polyethylene glycol derivative are the same as those in Example-35, g=0, k=1, and F is CH$_2$COCl (wherein, Z$_2$ is absent, Z$_1$ is an ethylene group, and R$_{01}$ is COCl). The designed total molecular weight is approximately 21.0 kDa, wherein, the molecular weight of the eight PEG chains is approximately 8×2500=20000 Da, corresponding to n$_1$≈n$_2$≈n$_3$≈n$_4$≈n$_5$≈n$_6$≈n$_7$≈n$_8$≈56.

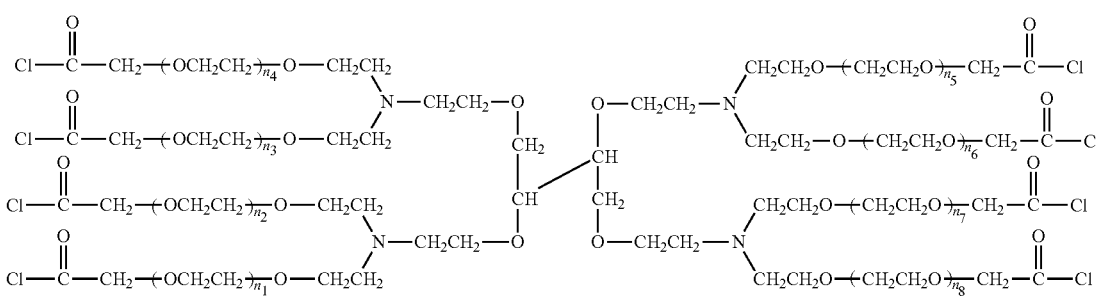

D4-1

20 g of the eight-arm polyethylene glycol carboxylic acid derivative D1-4 obtained in Example-35 was dissolved in dichloromethane, and then excess thionyl chloride was added, followed by an overnight reflux. Thereafter, the product in the solvent was concentrated and precipitated with absolute diethyl ether at 0° C. The precipitate was collected by filtration and dried, and then an eight-arm polyethylene glycol acyl chloride derivative D4-1 was obtained.

$^1$H NMR spectrum data of the eight-arm polyethylene glycol acyl chloride derivative D4-1 were as follows: $^1$HNMR (CDCl$_3$) δ (ppm): 2.45-2.65 (—NCH$_2$CH$_2$O—), 2.45-2.65 (—NCH$_2$CH$_2$O), 3.30-3.90 (—OCH$_2$CH$_2$O—, —NCH$_2$CH$_2$O—, —(CH(O)CH$_2$-)$_2$), 4.80-5.0 (—OCH$_2$COCl); $M_n$≈21 kDa, PDI=1.03.

Example-37: The Preparation Method for an Eight-Arm Polyethylene Glycol Acyl Hydrazide Derivative (D22-1)

Herein, U, E$_1$, E$_2$, E$_3$, E$_4$, L$_{11}$, L$_{12}$, L$_{21}$, L$_{22}$, L$_{31}$, L$_{32}$, L$_{41}$, L$_{42}$, n$_1$, n$_2$, n$_3$, n$_4$, n$_5$, n$_6$, n$_7$, n$_8$, g and k in the eight-arm polyethylene glycol derivative are the same as those in Example-35, g=0, k=1, and F is CH$_2$CONHNH$_2$ (wherein, Z$_2$ is absent, Z$_1$ is CH$_2$, and R$_{01}$ is CONHNH$_2$). The designed total molecular weight is approximately 21.0 kDa, wherein, the molecular weight of the eight PEG chains is approximately 8×2500=20000 Da, corresponding to n$_1$≈n$_2$≈n$_3$≈n$_4$≈n$_5$≈n$_6$≈n$_7$≈n$_8$≈56.

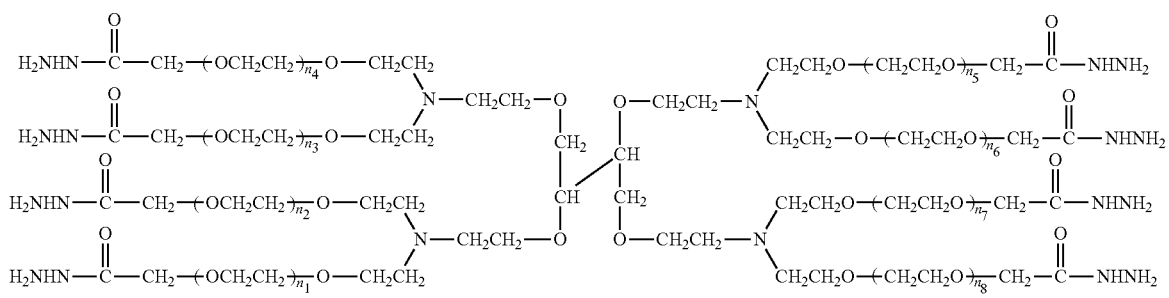

D22-1

20 g of the eight-arm polyethylene glycol acyl chloride derivative D4-1 obtained in Example-35 was dissolved in tetrahydrofuran, and then excess hydrazine hydrate was added, followed by reaction at 30° C. for 4 hours. After completion of the reaction, the product in the solvent was concentrated and precipitated with absolute diethyl ether at 0° C. The precipitate was collected by filtration and dried, and then an eight-arm polyethylene glycol acyl hydrazine derivative D22-1 was obtained.

$^1$H NMR spectrum data of the eight-arm polyethylene glycol acyl hydrazine derivative D22-1 were as follows: $^1$HNMR (CDCl$_3$) δ (ppm): 2.45-2.65 (—NCH$_2$CH$_2$O), 3.30-3.90 (—OCH$_2$CH$_2$O—, —NCH$_2$CH$_2$O—, —(CH(O)CH$_2$—)$_2$), 4.20-4.30 (—OCH$_2$CONH—); $M_n$≈21 kDa, PDI=1.03.

Example-38: The Preparation Method for an Eight-Arm Polyethylene Glycol Propionaldehyde Derivative (D6-2)

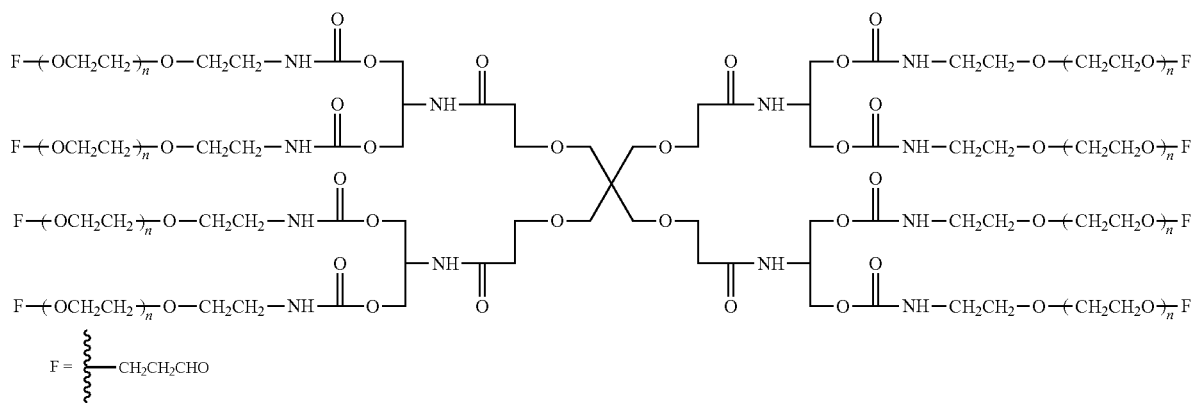

D6-2

Herein, the structure of the eight-arm polyethylene glycol derivative was designed as follows: U=C(CH$_2$OCH$_2$CH$_2$C(=O)—)$_4$, E$_1$=E$_2$=E$_3$=E$_4$=NHCH(OC(=O)NHCH$_2$CH$_2$-)$_2$ (with a carbon-branching center of a symmetrical type), the divalent linking groups L$_{11}$, L$_{12}$, L$_{21}$, L$_{22}$, L$_{31}$, L$_{32}$, L$_{41}$ and L$_{42}$ are all absent, g=0, k=1, and F is CH$_2$CH$_2$CHO (wherein, Z$_2$ is absent, Z$_1$ is CH$_2$CH$_2$, and R$_{01}$ is CHO). The designed total molecular weight is approximately 21.5 kDa, wherein, the molecular weight of the eight PEG chains is approximately 8×2500=20000 Da, corresponding to n$_1$≈n$_2$≈n$_3$≈n$_4$≈n$_5$≈n$_6$≈n$_7$≈n$_8$≈56.

Step (a): Into a reactor, deionized water (200 mL), pentaerythritol (2.5 mmol), acrylonitrile (20 mmol) and catalytic amount of tetraethylammonium hydroxide were added and then the solution was stirred at 25° C. overnight. Thereafter, the reaction solution was extracted, washed, dried and concentrated, and then a tetranitrile S38-1 in a colorless viscous state was obtained.

S38-1

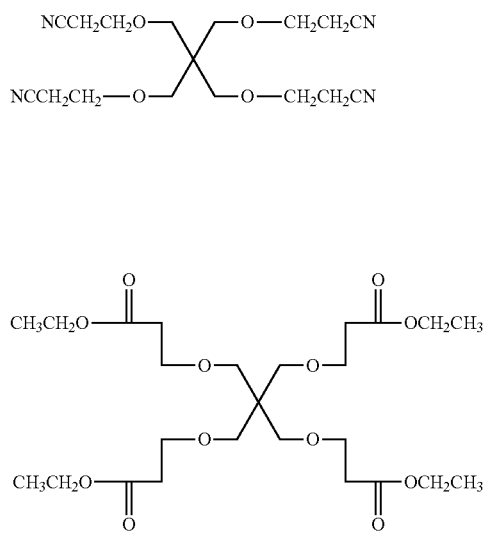

S38-2

$^1$H NMR spectrum data of the tetranitrile S38-1 were as follows: $^1$H NMR (CDCl$_3$) δ (ppm): 2.61 (—OCH$_2$CH$_2$CN), 3.66 (—OCH$_2$CH$_2$CN), 3.48 (C(CH$_2$O—)$_4$).

Step (b): Into a dry and clean reactor, anhydrous ethanol (100 mL) was added, and then concentrated sulfuric acid (40.8 mL) was added slowly with stirring. After completion of heat release, the tetranitrile intermediate S38-1 (20 mmol) was added slowly, and then the solution was heated under reflux for 6 hours. Thereafter, the reaction mixture was treated to obtain a carboxylate compound S38-2.

$^1$H NMR spectrum data of the carboxylate compound S38-2 were as follows: $^1$H NMR (CDCl$_3$) δ (ppm): 1.25 (—OCH$_2$CH$_3$), 2.53 (—CH$_2$C(=O)O—), 3.34 (C(CH$_2$-)$_4$), 3.64 (—OCH$_2$CH$_2$—); 4.10-4.18 (—OCH$_2$CH$_3$).

Step (c): Into a reactor, the carboxylate intermediate S38-2 (28 mmol), serinol (112 mmol), 17.0 g of potassium carbonate and DMSO (70 mL) were added in sequence, and the reaction was conducted at 25° C. for 12 hours; thereafter, the whole was heated to 40° C., followed by reaction for 36 hours. The reaction mixture was treated to obtain an octahydroxyl-containing compound S38-3.

-continued

S38-3

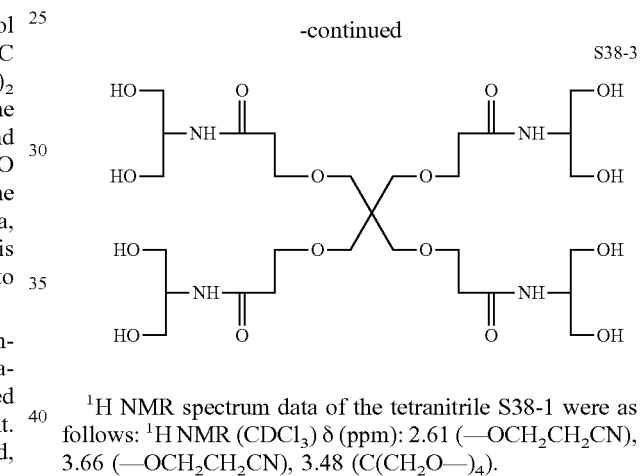

$^1$H NMR spectrum data of the octahydroxyl-containing compound S38-3 were as follows: $^1$H NMR (CDCl$_3$) δ (ppm): 2.43 (—CH$_2$CH$_2$C(=O)NH—), 3.34 (C(CH$_2$-)$_4$), 3.64 (—CH$_2$CH$_2$C(=O)NH—); 3.70-3.90 (—NHCH(CH$_2$OH)$_2$).

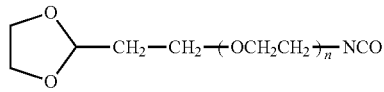
S38-4

Step (d): Into a dry and clean reactor, 25 mmol of a solution of a heterofunctional polyethylene glycol derivative (S38-4, $M_n \approx 2500$ Da, PDI=1.04) in dichloromethane was added. The above-obtained octahydroxyl-containing compound S38-3 (2.5 mmol) and dibutyltin dilaurate (0.01 mmol) were dissolved in DMSO (100 mL), and then dropwisely added to the PEG/CH$_2$Cl$_2$ solution. The intermediate was concentrated, precipitated, collected by filtration, recrystallized and dried, and then an eight-arm polyethylene glycol acetal intermediate S38-5 was obtained. Into a dry and clean 1 L round-bottom flask, 400 mL of deionized water was added thereinto, and the whole was stirred till all were dissolved. The solution was adjusted to pH 1.0 with 1 mol/L HCl solution in an ice bath, followed by reaction at room temperature for 4 hours. Thereafter, the product was extracted with dichloromethane (200 mL trice). The organic phase was combined, washed with saturated salt solutions, dried, filtrated, concentrated and recrystallized, and then an eight-arm polyethylene glycol aldehyde derivative D6-2 in a white solid state was obtained.

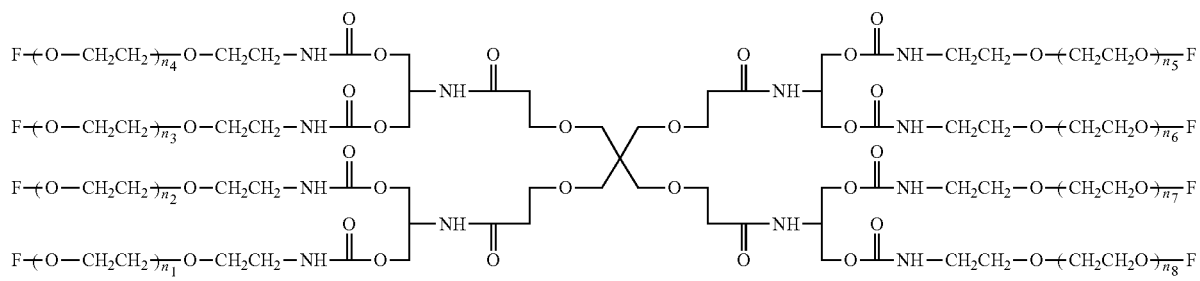
S38-5

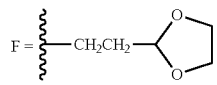

$^1$H NMR spectrum data of the eight-arm polyethylene glycol aldehyde derivative D6-2 were as follows: $^1$H NMR (CDCl$_3$) δ (ppm): 1.91 (—OCH$_2$CH$_2$CHO), 2.43 (—CH$_2$CH$_2$C(=O)NH—), 3.34 (C(CH$_2$-)$_4$), 3.40-3.90 (—CH$_2$CH$_2$O—, —OCH$_2$CH$_2$CHO, —CH$_2$CH$_2$C(=O)NH—, —NHCH(CH$_2$-)$_2$), 9.75 (—OCH$_2$CH$_2$CHO); $M_n \approx 22$ kDa, PDI=1.03.

Example-39: The Preparation Method for an Eight-Arm Polyethylene Glycol Aldoxime Derivative (D24-1)

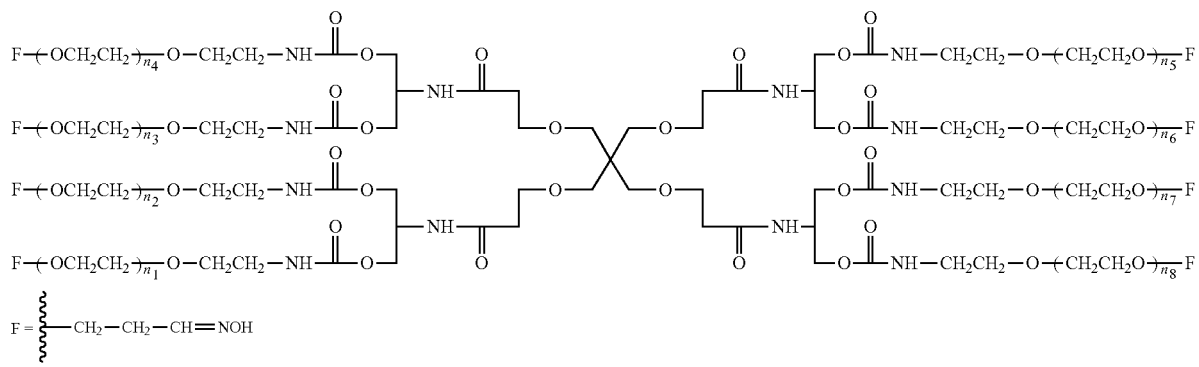

D24-1

Herein, U, $E_1, E_2, E_3, E_4, L_{11}, L_{12}, L_{21}, L_{22}, L_{31}, L_{32}, L_{41}, L_{42}, n_1, n_2, n_3, n_4, n_6, n_7, n_8$, g and k in the eight-arm polyethylene glycol derivative are the same as those in Example-38, g=0, k=1, and F is $CH_2CH_2CH=NOH$ (wherein, $Z_2$ is absent, $Z_1$ is $CH_2CH_2$, and $R_{01}$ is $CH=NOH$). The designed total molecular weight is approximately 21.6 kDa, wherein, the molecular weight of the eight PEG chains is approximately 8×2500=20000 Da, corresponding to $n_1 \approx n_2 \approx n_3 \approx n_4 \approx n_5 \approx n_6 \approx n_7 \approx n_8 \approx 56$.

Into a dry and clean 1 L round-bottom flask, 40 g of the eight-arm polyethylene glycol aldehyde derivative D6-2 and acetonitrile were added in sequence, and the whole was stirred till all were dissolved. Thereafter, the atmosphere was replaced by a nitrogen atmosphere. After the addition of hydroxylamine hydrochloride (100 mmol), the solution was adjusted to pH 8 with sodium acetate, and then the reaction was conducted at room temperature overnight. The resulting product was concentrated and precipitated with diethyl ether, and then an eight-arm polyethylene glycol aldoxime derivative D24-1 was obtained.

$^1$H NMR spectrum data of the eight-arm polyethylene glycol aldoxime derivative D24-1 were as follows: $^1$H NMR (CDCl$_3$) δ (ppm): 1.70 (—OCH$_2$CH$_2$CH=NOH), 2.43 (—CH$_2$CH$_2$C(=O)NH—), 3.34 (C(CH$_2$-)$_4$), 3.40-3.90 (—CH$_2$CH$_2$O—, —OCH$_2$CH$_2$CH=NOH, —CH$_2$CH$_2$C(=O)NH—, —NHCH(CH$_2$-)$_2$, —NHCH(CH$_2$-)$_2$), 7.10 (—OCH$_2$CH$_2$CH=NOH); $M_n$≈22 kDa, PDI=1.03.

Example-40: The Preparation Method for an Eight-Arm Polyethylene Glycol Nitrile Oxide Derivative (D22-1)

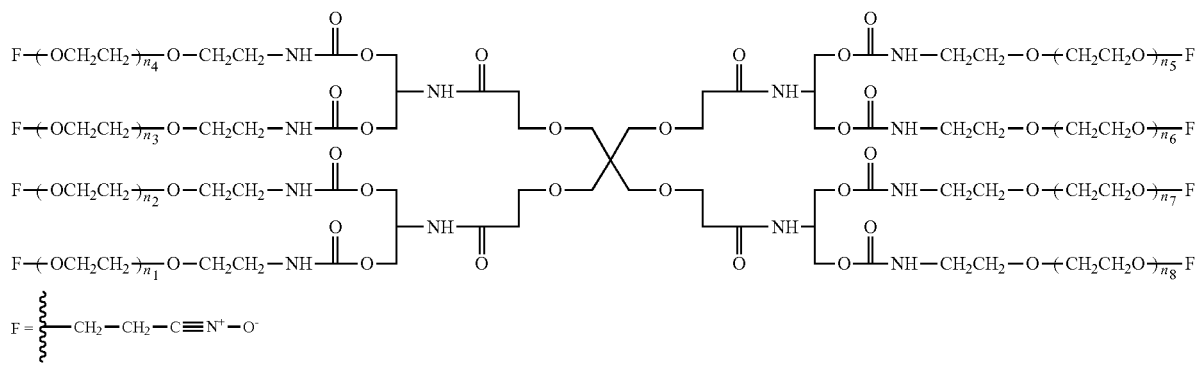

D22-1

Herein, U, $E_1, E_2, E_3, E_4, L_{11}, L_{12}, L_{21}, L_{22}, L_{31}, L_{32}, L_{41}, L_{42}, n_1, n_2, n_3, n_4, n_5, n_6, n_7, n_8$, g and k in the eight-arm polyethylene glycol derivative are the same as those in Example-38, g=0, k=1, and

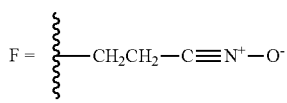

(wherein, $Z_2$ is absent, $Z_1$ is $CH_2CH_2$, and $R_{01}$ is $C\equiv N^+O^-$). The designed total molecular weight is approximately 21.6 kDa, wherein, the molecular weight of the eight PEG chains is approximately 8×2500=20000 Da, corresponding to $n_1 \approx n_2 \approx n_3 \approx n_4 \approx n_5 \approx n_6 \approx n_7 \approx n_8 \approx 56$.

Into a dry and clean round-bottom flask, 20 g of the eight-arm polyethylene glycol aldoxime derivative D24-1 obtained in Example-39 and N,N-dimethylformamide (160 mL) were added and then dissolved. Thereafter, the atmosphere was replaced by a nitrogen atmosphere. After the addition of solid NCS (32 mmol), the reaction was conducted at room temperature overnight. Thereafter, saturated sodium bicarbonate solution (160 mL) was added thereinto, followed by stirring at room temperature for 4 hours. Thereafter, the product was diluted with a large amount of dichloromethane, washed with saturated salt solutions, dried, concentrated and precipitated with diethyl ether, and then an eight-arm polyethylene glycol nitrile oxide D22-1 was obtained.

The structure of the eight-arm polyethylene glycol nitrile oxide D22-1 was determined by $^1$H NMR test. $M_n \approx 22$ kDa, PDI=1.03.

Example-41: Preparation of an Eight-Arm Polyethylene Glycol Amine Derivative with Branched Terminals (C4-6)

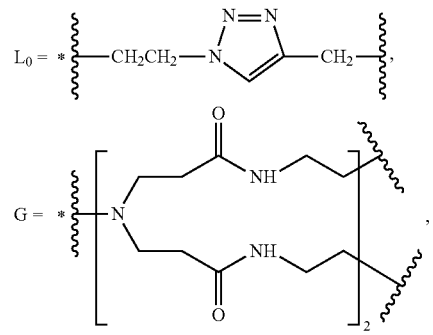

and F=$NH_2$ (wherein, $Z_2$ and $Z_1$ are absent, and $R_{01}$ is $NH_2$). The designed total molecular weight is approximately 38.0 kDa, wherein, the molecular weight of the eight PEG chains is approximately 8×3500=28000 Da, corresponding to $n_1 \approx n_2 \approx n_3 \approx n_4 \approx n_5 \approx n_6 \approx n_7 \approx n_8 \approx 79$.

Step (a): Into a clean 1 L round-bottom flask, 500 mL of dichloromethane, 50 mmol of ethylenediamine and excess glycidol were added in sequence, followed by reaction for 4 hours. Thereafter, the product was extracted, washed, dried, concentrated and purified via column chromatography, and then an octahydoxyl-containing compound S41-1 was obtained.

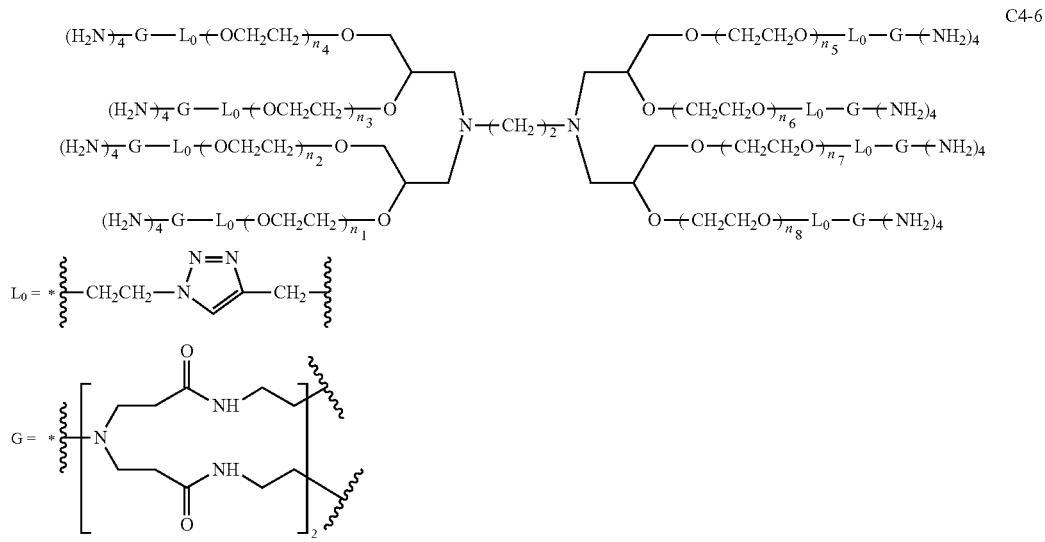

Herein, the structure of the eight-arm polyethylene glycol derivative was designed as follows:

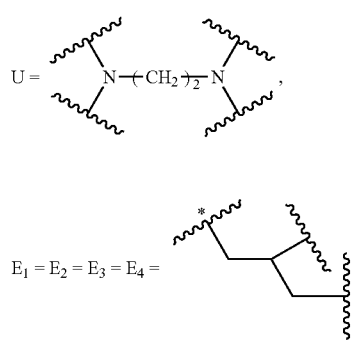

(with a carbon-branching center of an asymmetrical structure), the divalent linking groups $L_{11}$, $L_{12}$, $L_{21}$, $L_{22}$, $L_{31}$, $L_{32}$, $L_{41}$ and $L_{42}$ are all absent, g=1, k=4,

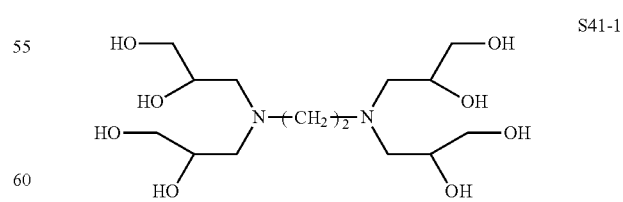

$^1$H NMR spectrum data of the octahydroxyl-containing compound S41-1 were as follows: $^1$H NMR (CDCl$_3$) δ (ppm): 2.37 (NCH$_2$CH$_2$N), 2.38-2.63 (—NCH$_2$CH(CH$_2$OH)OH), 3.50-3.56 (—NCH$_2$CH(—CH$_2$OH)OH), 3.56-3.81 (—NCH$_2$CH(CH$_2$OH)OH).

Step (b): Into a sealed reactor under an anhydrous and oxygen-free atmosphere, tetrahydrofuran (250 mL), the octahydroxyl-containing compound S41-1 (1.266 mmol) and diphenylmethyl potassium (4.0 mmol) were added in sequence. After the addition of a calculated amount of ethylene oxide, the whole was heated stepwisely to 60° C., followed by reaction for 48 hours. After the addition of excess proton source (methanol), the product in the solvent was concentrated and precipitated, and then an eight-arm polyethylene glycol H1-15 was obtained.

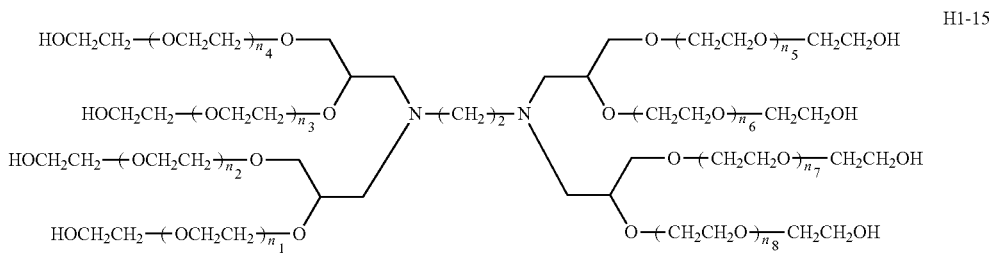

H1-15

$^1$H NMR spectrum data of the eight-arm polyethylene glycol H1-15 were as follows: $^1$H NMR (CDCl$_3$) δ (ppm): 2.37 (—NCH$_2$CH$_2$N—), 2.38-2.63 (—NCH$_2$CH—), 3.40-3.80 (—CH$_2$CH$_2$O—, —NCH$_2$CH—, —NCH$_2$CH(CH$_2$O—)). $M_n$≈28 kDa, PDI=1.03.

Step (c): Into a dry and clean 1 L round-bottom flask, 20 g of the eight-arm polyethylene glycol H1-15 was added. Under nitrogen protection, 500 mL of anhydrous and oxygen-free dichloromethane, 20 mL of pyridine and excess 4-toluenesulfonyl chloride were added thereinto, followed by reaction at room temperature for 24 hours. Thereafter, the solution was adjusted to a pH value less than 7 with hydrochloric acid (1 mol/L), and then the aqueous phase was washed with dichloromethane (50 mL trice). The organic phase was combined, washed with saturated salt solutions, dried with anhydrous sodium sulfate, filtrated, concentrated and recrystallized, and then an eight-arm polyethylene glycol sulfonate derivative B1-4 was obtained.

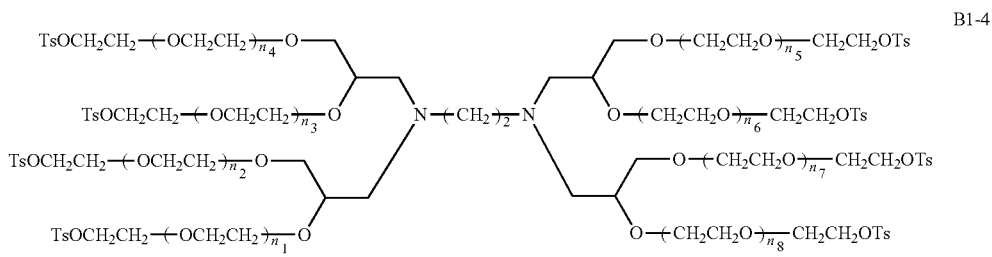

B1-4

In the $^1$H NMR spectrum of the eight-arm polyethylene glycol sulfonate derivative B1-4, besides the characteristic peaks of the chain backbone, the characteristic peaks of the tosylate moiety also appeared as follows: $^1$H NMR (CDCl$_3$) δ (ppm): 2.35 (CH$_3$C$_6$H$_4$SO$_2$—), 4.20 (—OCH$_2$CH$_2$OSO$_2$—), 7.30 (CH$_3$CH$_4$SO$_2$—), 7.80 (CH$_3$C$_6$H$_4$SO$_2$—).

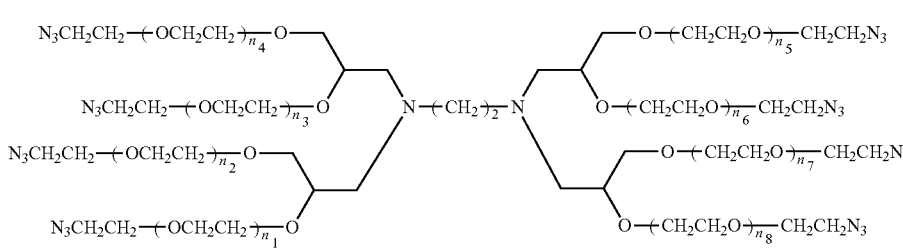

G21-2

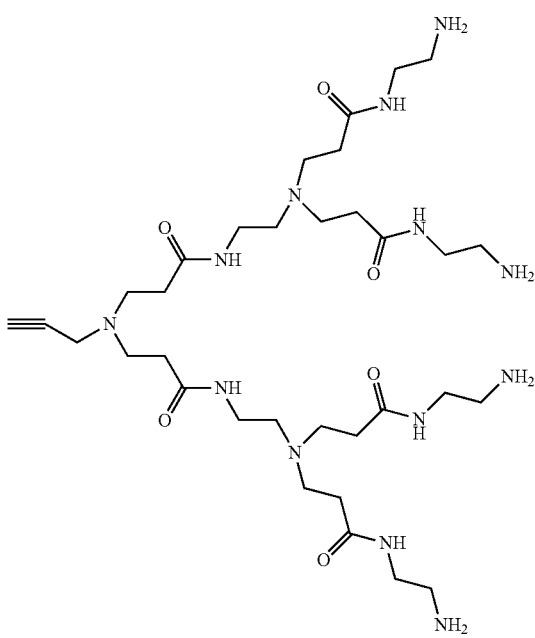

S41-2

Step (d): Into a dry and clean 1 L round-bottom flask, 10 g of the eight-arm polyethylene glycol sulfonate derivative B1-4 and 600 mL of tetrahydrofuran were added in sequence, and then the whole was stirred till all were dissolved. Subsequently, 4 g of sodium azide was added thereinto, and then the reaction was conducted at room temperature for a week. The resulting product was extracted with dichloromethane (200 mL trice). The organic phase was combined, washed with saturated salt solutions, dried, filtrated, concentrated at low temperature and recrystallized, and then an eight-arm polyethylene glycol azide derivative G21-2 in a white solid state was obtained.

In the $^1$H NMR spectrum of the eight-arm polyethylene glycol azide derivative G21-2, besides the characteristic peaks of the chain backbone, the characteristic peaks of the tosylate moiety disappeared, and the characteristic peaks of the azide derivative appeared as follows: $^1$H NMR (CDCl$_3$) δ (ppm): 1.30-1.50 (—CH$_2$Cl$_2$N$_3$).

Step (e): Into a reactor, 250 mL of tetrahydrofuran, 8 g of the eight-arm polyethylene glycol azide derivative G21-2 and 1 mmol of an alkynyl-modified dendritic small molecule compound S41-2 were added, and then the reaction was conducted at room temperature overnight. Thereafter, the product was concentrated and recrystallized from isopropanol, and then an eight-arm polyethylene glycol amine derivative with branched terminals C4-6 in a white solid state was obtained.

In the $^1$H NMR spectrum of the eight-arm polyethylene glycol amine derivative with branched terminals C4-6, besides the characteristic peaks of the chain backbone, the characteristic peaks of the alkynyl group disappeared, and the characteristic peaks of the pyrazole and amine moiety appeared as follows: $^1$HNMR (CDCl$_3$) δ (ppm): 2.50 (—CH$_2$CONHCH$_2$—); 2.70-80 (CONHCH$_2$CH$_2$NH$_2$); 3.0-3.3 (—CH$_2$CH$_2$C(=CH)N=N—, —CH$_2$CONHCH$_2$—), 7.75 (—CH$_2$CH$_2$C(=CH)N=N—); $M_n$≈38 kDa, PDI=1.03.

Example-42: Preparation of an Eight-Arm Polyethylene Glycol Alcohol Derivative with Branched Terminals (H-16)

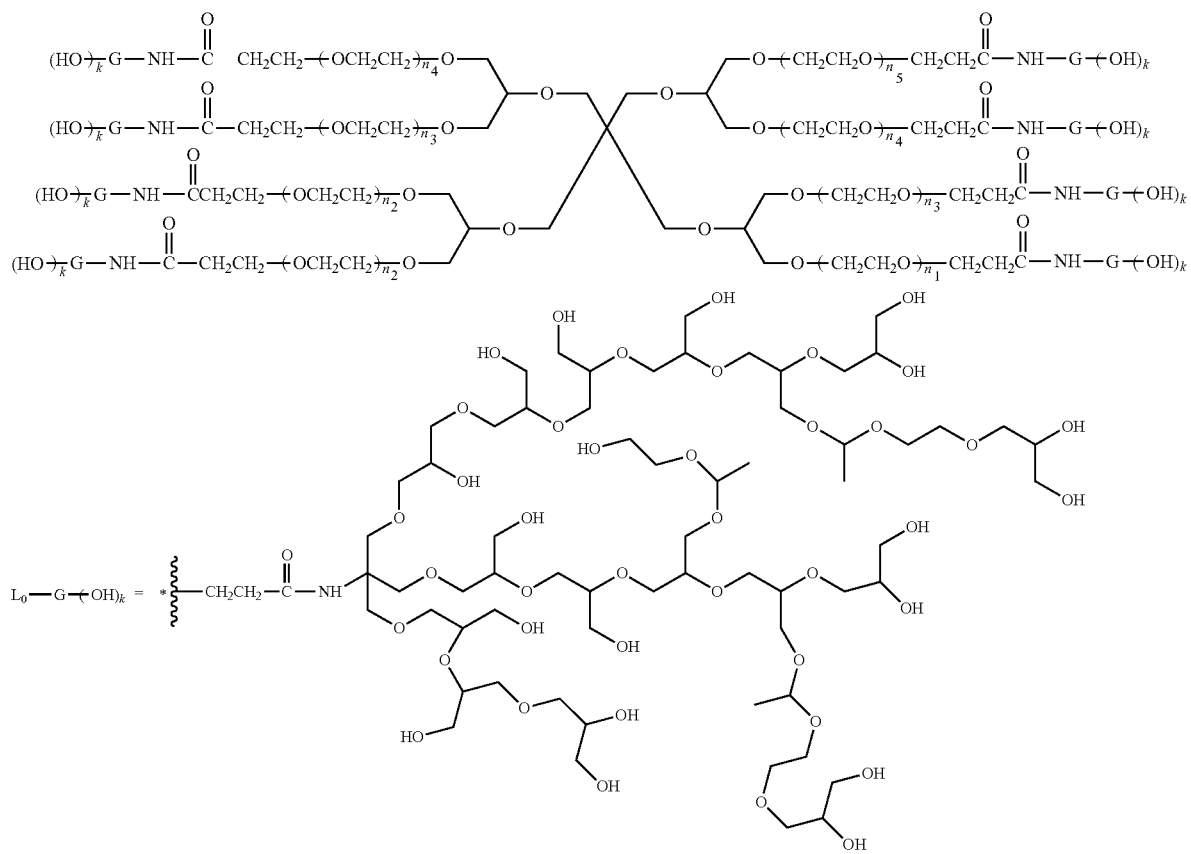

H1-16

Herein, the structure of the eight-arm polyethylene glycol derivative was designed as follows: $U=C(CH_2-)_4$,

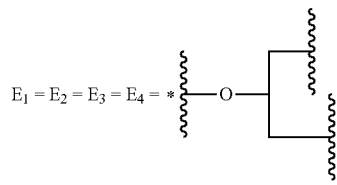 [SMILES: *CC(C*)O*]

(with a carbon-branching center of a symmetrical type), the divalent linking groups $L_{11}$, $L_{12}$, $L_{21}$, $L_{22}$, $L_{31}$, $L_{32}$, $L_{41}$ and $L_{42}$ are all absent, g=1, k≈18, $L_0$ is $CH_2CH_2CONH$, G is a hyperbranched structure combined by glycidol and ethylene oxide (wherein, the above-shown structural formula is just a schematic structure, and the ratio of epoxyethane and epoxy acetal is 5:1), and F=OH. The designed total molecular weight is approximately 54.8 kDa, wherein, the molecular weight of the eight PEG chains is approximately 8×5000=40000 Da, corresponding to $n_1 \approx n_2 \approx n_3 \approx n_4 \approx n_5 \approx n_6 \approx n_7 \approx n_8 \approx 113$.

Step (a): Into a sealed reactor under an anhydrous and oxygen-free atmosphere, tetrahydrofuran (400 mL), pentaerythritol (10 mmol) and excess diphenylmethyl potassium (100 mmol) were added in sequence, and then a compound S3-2 in an excess amount (100 mmol) was added, followed by reaction at 30° C. for 12 hours. After completion of the reaction, open the reactor. The product in the solvent was washed, concentrated and dissolved with methanol. The solution was adjusted to pH 3.5 with the addition of hydrochloric acid (1 M), followed by reaction for 4 hours. The product in the solvent was concentrated, washed and purified via column chromatography, and then an octahydroxyl-containing small molecule initiator S42-1 was obtained.

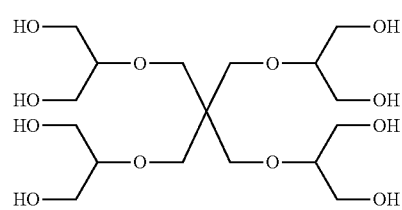

S42-1

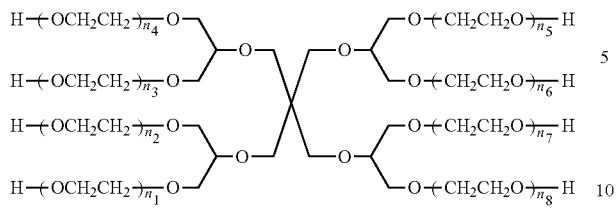

H1-17

$^1$H NMR spectrum data of the octahydroxyl-containing small molecule initiator S42-1 were as follows: $^1$H NMR (CDCl$_3$) δ (ppm): 2.90-3.10 (—OCH(CH$_2$OH)$_2$), 3.20-3.40 (C(C$_2$O—)$_4$), 3.40-3.50 (—OCH(CH$_2$OH)$_2$).

Step (b): Into a sealed reactor under an anhydrous and oxygen-free atmosphere, tetrahydrofuran (250 mL), the octahydroxyl-containing small molecule initiator S42-1 (1.266 mmol) and diphenylmethyl potassium (4.0 mmol) were added in sequence.

Step (c): After the addition of a calculated amount of ethylene oxide, the whole was heated stepwisely to 60° C., followed by reaction for 48 hours. Finally, excess proton source (methanol) was added to obtain an eight-arm polyethylene glycol H1-17.

$^1$H NMR spectrum data of the eight-arm polyethylene glycol H1-17 were as follows: $^1$H NMR (CDCl$_3$) δ (ppm): 2.90-3.10 (—OCH(CH$_2$O—)$_2$), 3.20-3.40 (C(CH$_2$O—)$_4$), 3.40-3.80 (—CH$_2$CH$_2$O—, —OCH(CH$_2$O—)$_2$); $M_n$≈40 kDa, PDI=1.05.

Step (d): Into a dry and clean 1 L round-bottom flask, 80 mmol of KOH and 400 mL of water were added in sequence. Subsequently, 20 g (8 mmol equivalents relative to the hydroxyl group) of the eight-arm polyethylene glycol H1-17 (treated by azeotropic removal of water with toluene) was added slowly in an ice bath, followed by stirring at room temperature for 3 hours; subsequently, 80 mmol of acrylamide was added thereinto, followed by reaction at room temperature for 24 hours. After the addition of a small amount of concentrated hydrochloric acid to quench the reaction, the product was concentrated, dissolved with dichloromethane (400 mL), washed with saturated salt solutions (100 mL trice), dried, concentrated and recrystallized, and then an eight-arm polyethylene glycol propionic acid derivative D1-5 in a white solid state was obtained.

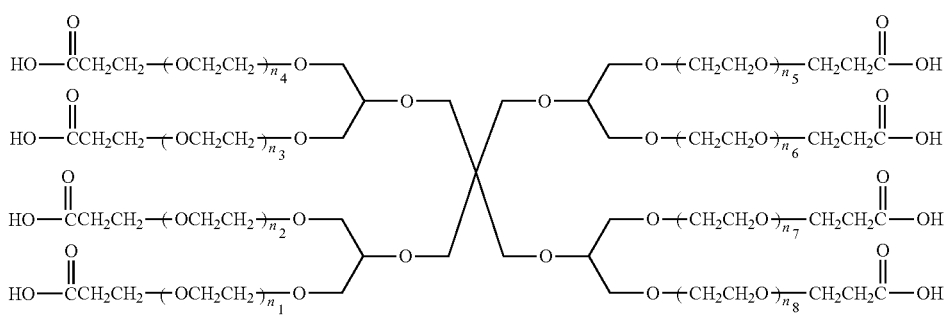

D1-5

$^1$H NMR spectrum data of the eight-arm polyethylene glycol propionic acid derivative D1-5 were as follows: $^1$H NMR (CDCl$_3$) δ (ppm): 2.40-2.60 (—CH$_2$CH$_2$COOH), 3.20-3.40 (C(CH$_2$O—)$_4$), 3.40-3.80 (—CH$_2$CH$_2$O—, —OCH(CH$_2$O—)$_2$, —CH$_2$CH$_2$COOH).

Step (e): Into a dry and clean 1 L round-bottom flask, 20 g of the eight-arm polyethylene glycol propionic acid derivative D1-5, 20 mL of triethylamine and 10 g of N-hydroxyl succinimide were added. Under nitrogen protection, dichloromethane (500 mL) was added thereinto, and the whole was stirred till dissolution. Subsequently, a solution of 20 g of dicyclohexylcarbodiimide (DCC) in dichloromethane was added thereinto, followed by reaction at room temperature for 24 hours. The resulting mixture was filtrated to remove undissolved substances, concentrated and recrystallized from isopropanol, and then an eight-arm polyethylene glycol succinimidyl propionate derivative A1-2 in a white solid state was obtained.

$^1$H NMR spectrum data of the eight-arm polyethylene glycol succinimidyl propionate derivative A1-2 were as follows: $^1$H NMR (CDCl$_3$) δ (ppm): 2.40-2.60 (—CH$_2$CH$_2$COO—), 2.70-2.85 (—(O═)CCH$_2$CH$_2$C(═O)—), 3.20-3.40 (C(CH$_2$O—)$_4$), 3.40-3.80 (—CH$_2$CH$_2$O—, —OCH(CH$_2$O—)$_2$, —CH$_2$CH$_2$COO—).

and glycidyl ether, the molar ratio is 1:5, and the average hydroxyl-group number k per PEG chain per molecule was about 18) were added thereinto, and the whole was stirred till dissolution, followed by reaction at room temperature for 24 hours. The resulting mixture was filtrated to remove undissolved substances, concentrated and recrystallized from isopropanol, and then a hyperbranched eight-arm polyethylene glycol H1-16 in a white solid state was obtained.

$^1$H NMR spectrum data of the hyperbranched eight-arm polyethylene glycol H1-16 were as follows: $^1$H NMR (CDCl$_3$) δ (ppm): 2.40-2.60 (—CH$_2$CH$_2$COO—), 3.20-3.40 (C(CH$_2$O—)$_4$), 3.40-3.80 (—CH$_2$CH$_2$O—, —OCH(CH$_2$O—)$_2$, —OCH$_2$CH(CH$_2$O—)—, —CH$_2$CH$_2$CON—, —NHC(CH$_2$O—)$_3$); $M_n$≈55 kDa, PDI=1.08.

Preparation of an Eight-Arm Polyethylene Glycol Active Succinate Derivative (A1-3)

Step (a): Into a dry and clean reactor, 10 g of the eight-arm polyethylene glycol H1-17 prepared with the above method, toluene (500 mL) and excess butanedioic anhydride (40 mmol) were added in sequence, followed by reaction at 50° C. for 12 hours. After completion of the reaction, open the reactor. The product in the solvent was concentrated and

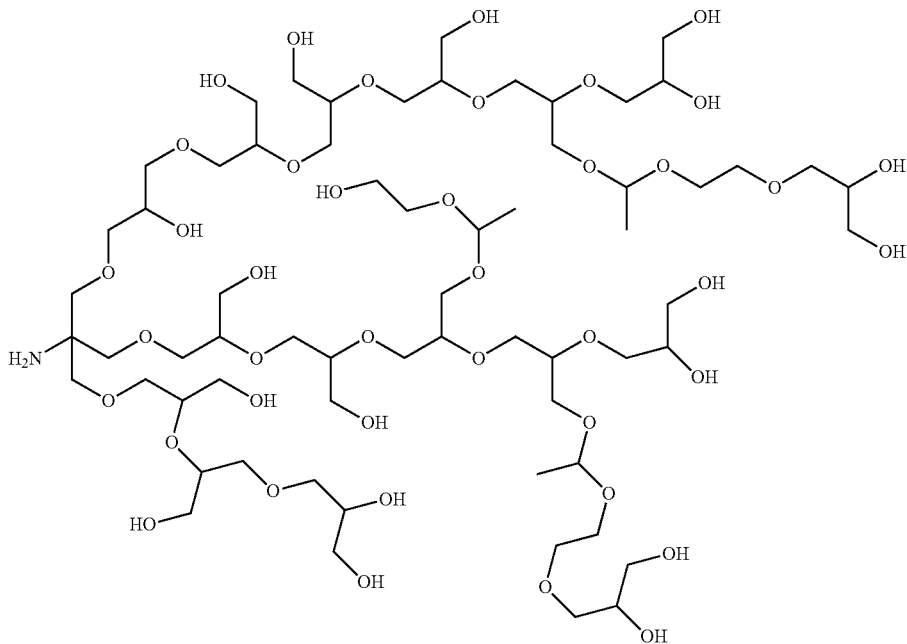

S42-2

Step (f): Into a dry and clean 1 L round-bottom flask, 20 g of the eight-arm polyethylene glycol active ester derivative A1-2 was added. Under nitrogen protection, dichloromethane (500 mL) and a degradable branched multihydroxyl-bearing compound S42-2 in an excess amount (wherein, the branching units are the combination of

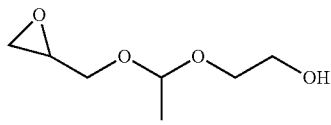

then precipitated with absolute diethyl ether at 0° C. The precipitate was collected by filtration and dried, and then an eight-arm polyethylene glycol succinic acid derivative D1-6 was obtained.

$^1$H NMR spectrum data of the eight-arm polyethylene glycol carboxylic acid derivative D1-6 were as follows: $^1$H NMR (CDCl$_3$) δ (ppm): 2.40-2.70 (—OCOCH$_2$CH$_2$COOH), 3.20-3.40 (C(CH$_2$O—)$_4$), 3.40-3.80 (—CH$_2$CH$_2$O—, —OCH$_2$CH$_2$OCO—, —OCH(CH$_2$O—)$_2$), 4.15-4.35 (—OCH$_2$CH$_2$OCO—).

D1-6

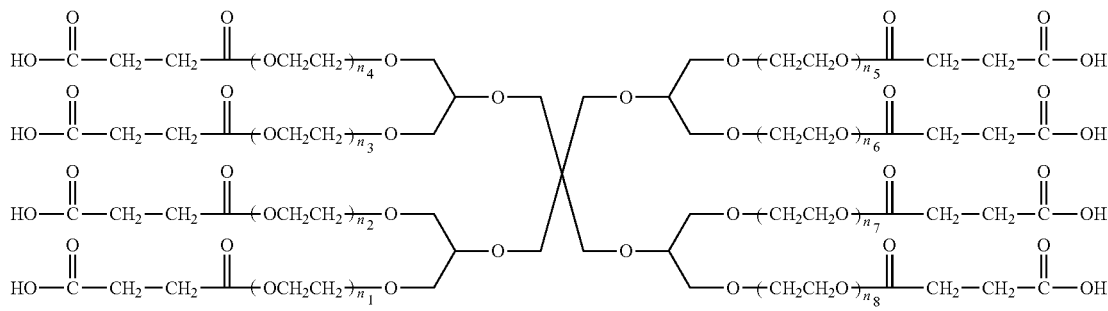

Step (b): Into a dry and clean 1 L reactor, 8 g of the above-obtained eight-arm polyethylene glycol carboxylic acid derivative D1-6, 10 mL of triethylamine and 10 g of N-hydroxyl succinimide (NHS) were added. Under nitrogen protection, dichloromethane (600 mL) was added thereinto, and the whole was stirred till dissolution. Subsequently, a solution of 20 g of dicyclohexylcarbodiimide (DCC) in dichloromethane was added thereinto, followed by reaction at room temperature for 24 hours. The resulting mixture was filtrated to remove undissolved substances, concentrated and recrystallized from isopropanol, and then an eight-arm polyethylene glycol succinimidyl succinate derivative A1-3 in a white solid state was obtained.

$^1$H NMR spectrum data of the eight-arm polyethylene glycol active ester derivative A1-3 were as follows: $^1$H NMR (CDCl$_3$) δ (ppm): 2.40-2.70 (—OCOCH$_2$CH$_2$COO—), 2.70-2.85 (—(O)CCH$_2$CH$_2$C(=O)N—), 3.20-3.40 (C(CH$_2$O—)$_4$), 3.40-3.80 (—CH$_2$CH$_2$O—, —OCH$_2$CH$_2$OCO—, —OCH(CH$_2$O—)$_2$), 4.15-4.35 (—OCH$_2$CH$_2$OCO—); the molecular weight $M_n \approx 42$ kDa, PDI=1.05.

By using the production method for 111-17 in the present Example, having a designed structure with $n_1 \approx n_2 \approx n_3 \approx n_4 \approx n_5 \approx n_6 \approx n_7 \approx n_8 \approx 227$, using the same reagents and only changing the calculated amount of ethylene oxide, an eight-arm polyethylene glycol D1-19, which had the same structure as the compound H1-17, was obtained. $M_n \approx 83$ kDa and PDI=1.09.

By using the production method for H1-17 in the present Example, having a designed structure with $n_1 \approx n_2 \approx n_3 \approx n_4 \approx n_5 \approx n_6 \approx n_7 \approx n_8 \approx 272$, using the same reagents and only changing the calculated amount of ethylene oxide, an eight-arm polyethylene glycol D1-20, which had the same structure as the compound H1-17, was obtained. $M_n \approx 96$ kDa and PDI=1.14.

A1-3

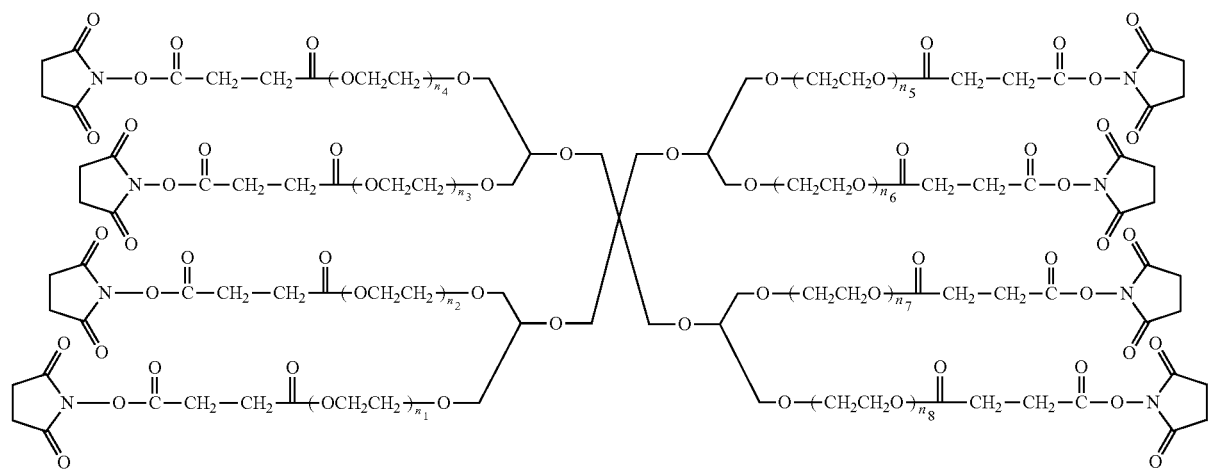

Example-43: Preparation of an Eight-Arm Polyethylene Glycol Carboxylic Acid Derivative (D1-7)

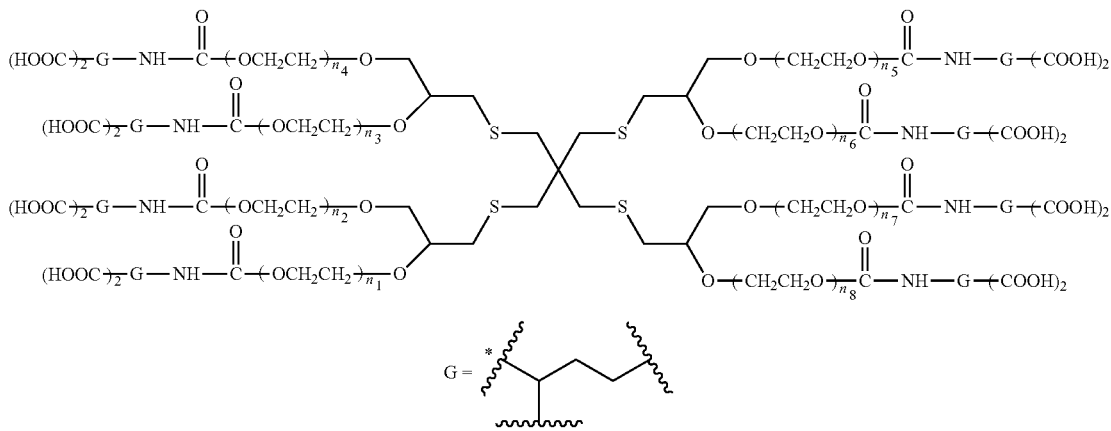

D1-7

Herein, the structure of the eight-arm polyethylene glycol derivative was designed as follows: $U=C(CH_2S-)_4$,

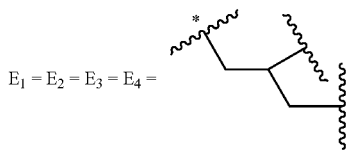 [SMILES: *CC(*)C*]

(with a carbon-branching center of an asymmetrical type), the divalent linking groups $L_{11}$, $L_{12}$, $L_{21}$, $L_{22}$, $L_{31}$, $L_{32}$, $L_{41}$ and $L_{42}$ are all absent, $g=1$, $k=2$,

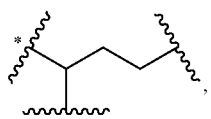 [SMILES: *CCC(*)*]

and F=COOH. The designed total molecular weight is approximately 41.7 kDa, wherein, the molecular weight of the eight PEG chains is approximately 8×5000=40000 Da, corresponding to $n_1 \approx n_2 \approx n_3 \approx n_4 \approx n_5 \approx n_6 \approx n_7 \approx n_8 \approx 113$.

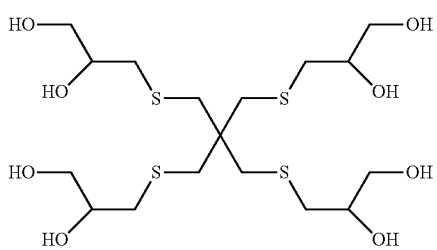

S43-1

Step (a): Into a clean and sealed rector, dichloromethane (500 mL), 2,2-bis(mercaptomethyl)propane-1,3-dithiol (neopentanetetrathiol, 50 mmol), trimethylbenzylammonium hydroxide in a catalytic amount and glycidyl ether (250 mmol) were added in sequence, followed by reaction for 4 hours. Thereafter, the product was extracted, washed and purified via column chromatography, and then an octahydroxyl-containing small molecule initiator S43-1 was obtained.

$^1$H NMR spectrum data of the octahydroxyl-containing small molecule initiator S43-1 were as follows: $^1$H NMR (CDCl$_3$) δ (ppm): 2.36 (C(CH$_2$S—)$_4$), 2.43-2.71 (—SCH$_2$CH—), 3.63 (—CH(OH)CH$_2$OH), 3.68 (—CH(OH)CH$_2$OH).

Step (b): Into a sealed reactor under an anhydrous and oxygen-free atmosphere, tetrahydrofuran (250 mL), the octahydroxyl-containing initiator S43-1 (1.266 mmol) and diphenylmethyl potassium (DPMK, 4.0 mmol) were added in sequence. After the addition of a calculated amount of ethylene oxide, the whole was heated stepwisely to 60° C., followed by reaction for 48 hours. After the addition of excess proton source (methanol), the product in the solvent was concentrated and precipitated, and then an eight-arm polyethylene glycol H1-18 was obtained.

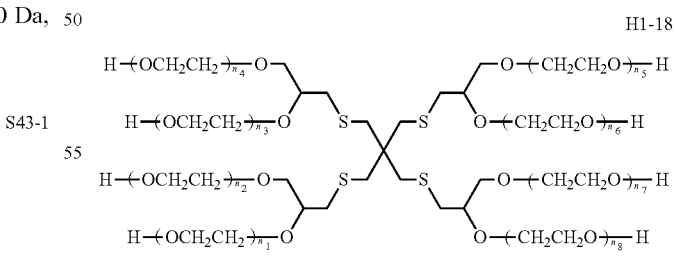

H1-18

$^1$H NMR spectrum data of the eight-arm polyethylene glycol H1-18 were as follows: $^1$H NMR (CDCl$_3$) δ (ppm): 2.36 (C(CH$_2$S—)$_4$), 2.43-2.71 (—SCH$_2$CH—), 3.40-3.80 (—CH$_2$CH$_2$O—, —CH(O)CH$_2$O—); $M_{n,z}$ 40 kDa, PDI=1.05.

Step (c): Into a dry and clean 1 L round-bottom flask, 20 g of the eight-arm polyethylene glycol H1-18 obtained in Step (b) (treated by azeotropic removal of water with toluene) was added, and then 500 mL of acetonitrile, 40 mL of triethylamine and 10 g of N,N'-disuccinimidyl carbonate were added, followed by reaction at room temperature for 24 hours. Thereafter, the product in the solvent was concentrated and recrystallized from isopropanol, and then an eight-arm polyethylene glycol succinimidyl carbonate derivative A6-2 in a white solid state was obtained.

a cysteine moiety was introduced to the C-terminus of the non-active domain) in PBS was added. Under nitrogen protection, the solution was adjusted to pH 7.2, and 21.0 mg (the maleimido functional group was in an amount of about 0.5 folds by mole relative to exenatide) of the eight-arm polyethylene glycol maleimide derivative (E1-1, the molecular weight was about 42 kDa, and k=1) obtained in Example-18 was added thereinto, followed by reaction at 4°

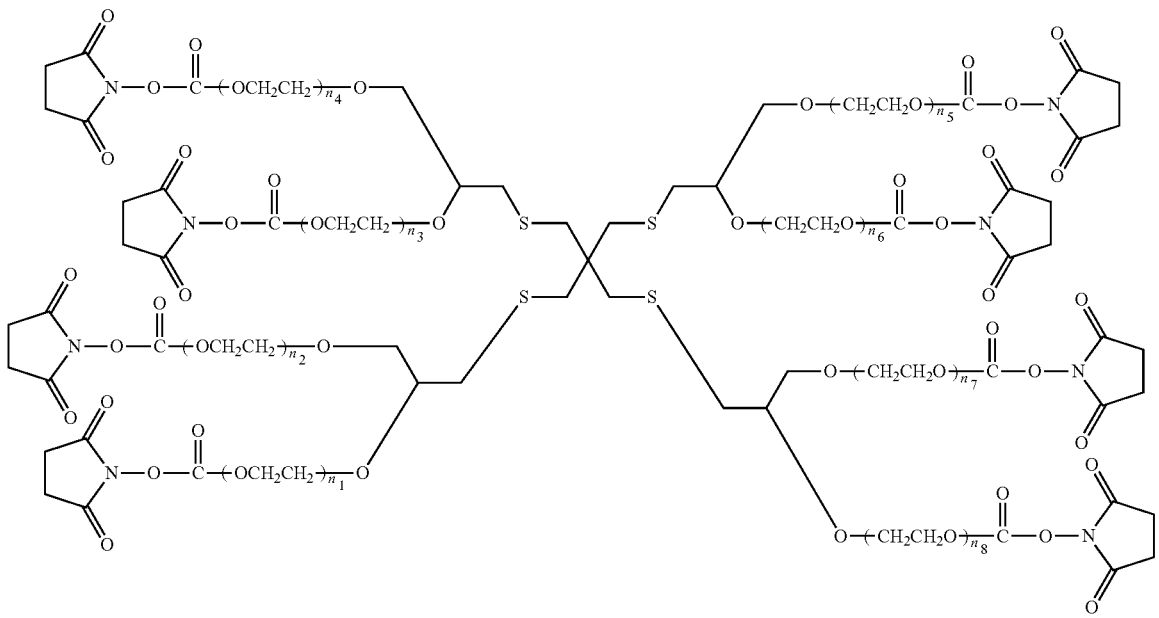

A6-2

$^1$H NMR spectrum data of the eight-arm polyethylene glycol succinimidyl carbonate derivative A6-2 were as follows: $^1$H NMR (CDCl$_3$) δ (ppm): 2.36 (C(CH$_2$S—)$_4$), 2.43-2.70 (—SCH$_2$CH—), 2.70-2.85 (—(O=)CCH$_2$CH$_2$C(=O)—), 3.40-3.80 (—CH$_2$CH$_2$O—, —CH$_2$CH$_2$OCOO—, —CH(O)CH$_2$O—), 4.30-4.40 (—CH$_2$CH$_2$OCOO—).

Step (d): Into a dry and clean 1 L round-bottom flask, 500 mL of a pH 8.0 buffer solution and 50 mmol of 2-aminoglutaric acid were added in sequence. After dissolution, a solution (200 mL) of dichloromethane containing 10 g of the eight-arm polyethylene glycol succinimidyl carbonate derivative A6-2 was added slowly, and then the reaction was conducted with stirring overnight. Thereafter, the mixture was separated, washed, concentrated and recrystallized from isopropanol, and then an eight-arm polyethylene glycol carboxylic acid derivative D1-7 in a white solid state was obtained.

$^1$H NMR spectrum data of the eight-arm polyethylene glycol carboxylic acid derivative D1-7 were as follows: $^1$H NMR (CDCl$_3$) δ (ppm): 2.05 (—NHCHCH$_2$CH$_2$COOH), 2.30-2.36 (—NHCHCH$_2$CH$_2$COOH, C(CH$_2$S—)$_4$), 2.43-2.70 (—SCH$_2$CH—), 3.40-3.80 (—CH$_2$CH$_2$O—, —CH$_2$CH$_2$OCOO—, —CH(O)CH$_2$O—), 4.15-4.30 (—CH$_2$CH$_2$OCON—), 4.50-4.60 (—NHCHCH$_2$CH$_2$COOH); $M_n$≈42 kDa, PDI=1.05.

Example-44: Preparation of an Eight-Arm Polyethylene Glycol Maleimide Derivative Modified Exenatide (Via a Thioether Bond)

Into a dry and clean 100 mL round-bottom flask, 10 mL of a mutant analogue of exenatide (exenatide-Cys, in which C. for 24 hours; thereafter, the solution was diluted with a cysteine solution, followed by reaction at room temperature for 2 hours, and then diluted with distilled water. The resulting product was purified by means of column chromatography using MacroCap SP (GE) ion exchange column. The column was equilibrated with a 20 mM pH 4.0 NaAc buffer solution and then gradiently eluted with a 20 mM pH 4.0 NaAc buffer solution comprising 1 M NaCl. Thereafter, different pegylated exenatide components were collected respectively, and the solution was treated by chromatography desalination with Sephadex G25 and then by ultrafiltration. The components were tested by SDS-PAGE and high performance liquid chromatography (HPLC). The results showed that the weight-average molecular weight of the pegylated product of exenatide P-1 was about 73 kDa, and the purity exceeded 96%, and one eight-arm polyethylene glycol derivative molecule was attached with 7.3 exenatide molecules on average.

Herein, the linking group L formed via the reactions contains

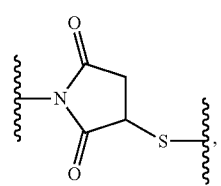 [SMILES: *SC1CC(=O)N(*)C1=O]

and D=Exanatide-Cys.

Example-45: Preparation of an Eight-Arm Polyethylene Glycol Carboxylic Acid Derivative Modified Small Molecule Drug SN38 (PEG-Amide Bond-Glycine-Ester Bond-D)

Step (a): Preparation of TBDPS-(10)-(7-ethyl-10-hydroxycamptothecin) (compound S45-2): Into a dry and clean 500 mL round-bottom flask, a suspension of 3.92 g (10.0 mmol, 1 equivalent; in the present invention, the term "equivalent" is also abbreviated as "eq.") of 7-ethyl-10-hydroxycamptothecin (SN38, compound S45-1) in 200 mL of anhydrous dichloromethane (DCM) was added, and then 60 mmol (6 eq.) of triethylamine and 60 mmol (6 eq.) of tert-butylchlorodiphenylsilane (TBDPSCl) were added in sequence; subsequently, the reaction mixture was heated to reflux overnight. Thereafter, the resulting product was washed with a 0.2 N HCl solution (80 mL trice), a saturated NaHCO$_3$ solution (150 mL) and a 20 mM NaCl solution (150 mL) in sequence. The organic phase was dried over MgSO$_4$, filtrated and evaporated under vacuum. The residue was dissolved in anhydrous dichloromethane, and precipitated with hexanes followed by collection of the precipitate. Steps including dissolution with dichloromethane and precipitation with hexanes were repeated to remove excess TBDPSCl. Thereafter, the product was collected by filtration and dried under vacuum, and then a compound S45-2 was obtained. The structure was determined by NMR test.

Step (b): Preparation of TBDPS-(10)-(7-ethyl-10-hydroxycamptothecin)-(20)-glycine-Boc (compound S45-3, TBDPS-SN38-Gly-Boc): Into a dry and clean 500 mL round-bottom flask, a solution of 5.04 g (about 8 mmol, 1 equivalent) of the compound S45-2 and 2.10 g (12 mmol, 1.5 eq.) of N-(t-butoxycarbonyl)glycine (Boc-glycine, Boc-Gly) in 200 mL of anhydrous dichloromethane was added at an ice bath, and then 12 mmol (1.5 eq.) of dichloroethane (EDC), 488 mg (4 mmol, 0.5 eq.) of 4-dimethylaminopyridine (DMAP) were added. The reaction solution was stirred for about 2 hours at an ice bath, and then the characteristic peak shown in the HPLC spectrum of the compound S45-2 disappeared completely. Subsequently, the mixture was washed with a saturated NaHCO$_3$ solution (80 mL trice), ultrapure water (80 mL), a 0.1 N HCl solution (80 mL twice) and a 20 mM NaCl solution (150 mL) in sequence. The organic phase was dried over MgSO$_4$, filtrated, and concentrated by vacuum evaporation, and then a compound S45-3 was obtained. The compound S45-3 was directly used in the next step without further purification. The structure was determined by NMR test.

Step (c): Preparation of TBDPS-(10)-(7-ethyl-10-hydroxycamptothecin)-(20)-Gly-HCl (compound S45-4): Into a dry and clean 250 mL round-bottom flask, 4.72 g (6 mmol) of the compound S45-3, 20 mL of anhydrous dioxane and 20 mL of a solution of 4 N HCl in dioxane were added, and the whole was stirred till all were mixed, followed by reaction at room temperature for about 1.5 hours. Then, the characteristic peak shown in the HPLC spectrum of the compound S45-3 disappeared completely. Thereafter, the reaction mixture was precipitated with 100 mL of diethyl ether. The precipitate was collected by filtration, dissolved in 100 mL of dichloromethane, and then washed with a pH 2.5 solution of HCl adjusted by a saturated NaHCO$_3$ solution. The organic phase was dried over MgSO$_4$, filtrated, and concentrated by vacuum evaporation. The concentrated residue was dissolved in 10 mL of DCM, precipitated with anhydrous diethyl ether and followed by collection of the precipitate. Steps including dissolution and precipitation with anhydrous diethyl ether were repeated; thereafter, the product was collected by filtration and concentrated by vacuum evaporation, and then a compound S45-4 was obtained. The structure was determined by NMR test.

Step (d): Preparation of an eight-arm polyethylene glycol derivative modified Gly-SN38-TBDPS (8arm-PEG-Gly-SN38-TBDPS, S45-5): Into a dry and clean 200 mL round-bottom flask, a solution of 1.05 g (about 0.05 mmol, 1 equivalent per active site) of the eight-arm polyethylene glycol carboxylic acid (D1-1, about 21 kDa, prepared in Example-1) in anhydrous dichloromethane (30 mL) was added, and then 870 mg (1.2 mmol, 3 eq.) of the compound S45-4, 488 mg (4 mmol, 10 eq.) of DMAP and a solution of 50% ethyl acetate (10 eq.) were added. The reaction mixture was stirred at room temperature overnight. Thereafter, the mixture was concentrated by vacuum evaporation. The resulting residue was dissolved in dichloromethane and precipitated with anhydrous diethyl ether. The precipitate was collected by filtration and recrystallized with a dimethylformamide/isopropanol mixed solution, and then a compound S45-5 was obtained. The structure was determined by NMR test.

Step (e): Preparation of an eight-arm polyethylene glycol derivative modified Gly-SN38 (8arm-PEG-Gly-SN38, compound P-2): Into a dry and clean 100 mL round-bottom flask, 782 mg (about 0.03 mmol) of the compound S45-5, 0.80 mmol of tetrabutylammonium fluoride, 15 mL of a 1:1 (v/v) mixed solution of tetrahydrofuran and a 0.05 N hydrochloric acid were added, and the whole was stirred till all were mixed, followed by reaction at room temperature for 4 hours. Thereafter, the mixture was extracted with dichloromethane twice. The organic phase was combined, dried over MgSO$_4$, filtrated and concentrated by vacuum evaporation. The resulting residue was dissolved in dimethylformamide, precipitated with isopropanol, collected by filtration and precipitated with isopropanol again. Steps including dissolution and precipitation were repeated, and the resulting residue was dissolved in dichloromethane and precipitated with anhydrous diethyl ether. The precipitate was collected by filtration, further dried under vacuum at 37° C. for 16 hours, and then a compound P-2 was obtained. The yield was higher than 95%, and the structure was determined by NMR test. The product was also characterized by means of HPLC; one eight-arm polyethylene glycol derivative molecule was loaded with about 7.4 SN38 molecules on average.

The synthesis route including the above steps from step (a) to step (e) is as follows:

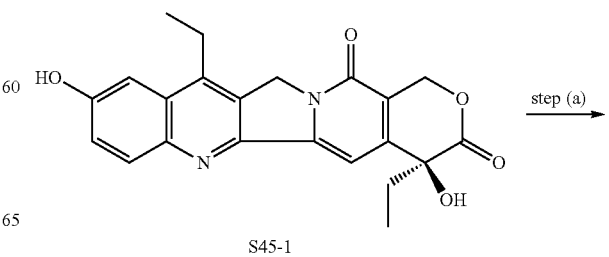

S45-1

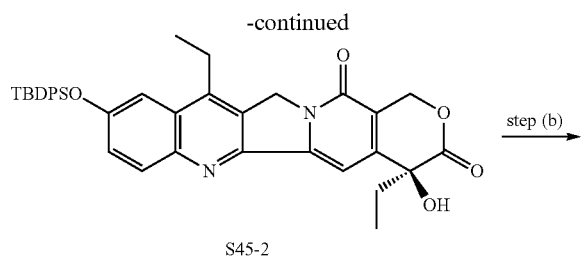

S45-2

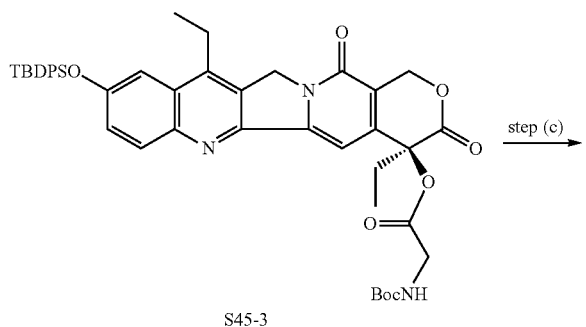

S45-3

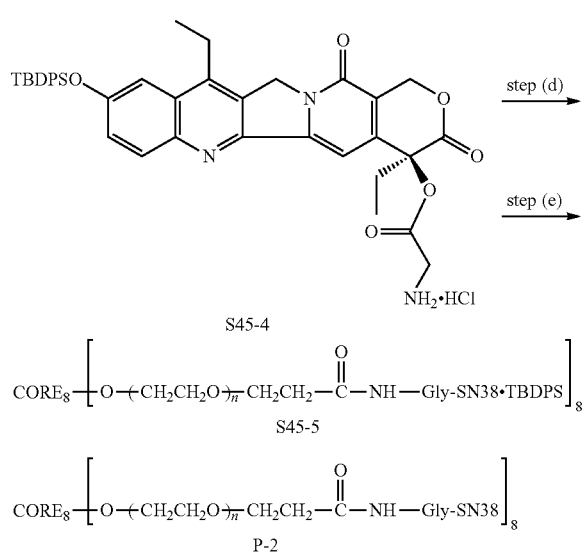

S45-4

$$CORE_8 \left[ O\!-\!(CH_2CH_2O)_{\overline{n}}\!-\!CH_2CH_2\!-\!\overset{O}{\underset{\|}{C}}\!-\!NH\!-\!Gly\text{-}SN38\!\cdot\!TBDPS \right]_8$$

S45-5

$$CORE_8 \left[ O\!-\!(CH_2CH_2O)_{\overline{n}}\!-\!CH_2CH_2\!-\!\overset{O}{\underset{\|}{C}}\!-\!NH\!-\!Gly\text{-}SN38 \right]_8$$

P-2

In this Example, the linking group L formed via the reactions contains an amide bond, and D is SN38-Gly.

Example-46: Preparation of an Eight-Arm Polyethylene Glycol Succinimidyl Carbonate Derivative Modified Small Molecule Drug Irinotecan (Via a Carbamate Linkage, i.e. a Urethane Bond)

Step (a): Preparation of irinotecan-glycine-Boc (compound S46-2, IRES-Gly-Boc): Into a dry and clean 1 L round-bottom flask, 2.35 g of irinotecan (compound S46-1, 4 mmol, 1 eq.), 1.4 g of Boc-glycine (8 mmol, 2 eq.), 488 mg of 4-dimethylaminopyridine (4 mmol, 1 eq.) and 300 mL of anhydrous dichloromethane were added in sequence, and the whole was stirred till dissolution. Subsequently, a solution of dicyclohexylcarbodiimide (DCC, 8 mmol, 2 eq.) in anhydrous dichloromethane (50 mL) was added thereinto, and the whole was stirred till all were mixed. The reaction mixture was stirred at room temperature for 16 hours. The solid impurities were removed through a coarse filter, and the solution was washed with 150 mL of a 0.1 N HCl solution and 250 mL of ultrapure water in sequence in a separatory funnel. The collected organic phase was dried with $Na_2SO_4$ and then concentrated by using rotary evaporation to remove the solvent. The product was further dried under vacuum, and then a compound S46-2 was obtained. The structure was determined by $^1H$ NMR test, and the molecular weight was measured by HPLC as 744 Da.

Step (b): Preparation of irinotecan-glycine (compound 46-3, IRES-Gly): Into a dry and clean 250 mL round-bottom flask, 1.49 g of the compound S46-2 (2 mmol, 1 eq.) was dissolved in 75 mL of anhydrous dichloromethane, followed by the addition of 16 mmol of trifluoroacetic acid (5 eq.), and then the whole was stirred till all were mixed. The reaction mixture was stirred at room temperature for 1 hour. The solvent was removed by rotary evaporation. Thereafter, the crude product was dissolved in a minimum amount of methanol, precipitated with 200 mL of anhydrous diethyl ether. The suspension was rotated for 30 minutes in an ice bath. Thereafter, the product was collected by filtration and dried under vacuum, and then a compound S46-3 was obtained. The structure was determined by $^1H$ NMR, and the yield was about 96%.

Step (c): Preparation of an eight-arm polyethylene glycol derivative modified glycine-irinotecan (8arm-PEG-Gly-IRES, P-3): Into a dry and clean 50 mL round-bottom flask, 1.29 g of the compound S46-3 (2 mmol, 5 eq.), 3.1 g of the eight-arm polyethylene glycol succinimidyl carbonate derivative (A6-1, obtained in Example-12, $M_n$ was about 62 kDa, 0.05 mmol, 1 equivalent per active site), 122 mg of 4-dimethylaminopyridine (1 mmol, 2.5 eq.) and 20 mL of anhydrous dichloromethane were added, and the whole was stirred till dissolution. Subsequently, 577 mg of DCC (2.8 mmol, 7 eq.) was added, and the whole was stirred till all were mixed. The reaction was conducted at room temperature for 12 hours. The mixture was filtrated through a coarse filter to remove solid impurities, and the solvent was removed by rotary evaporation. The syrup was precipitated in an ice bath with the addition of 200 mL of isopropanol. The product was collected by filtration and dried under vacuum, and then a product P-3 was obtained. The yield was higher than 95%. The structure was determined by NMR test. According to result of HPLC test, one eight-arm polyethylene glycol derivative molecule was loaded with about 7.6 irinotecan molecules on average.

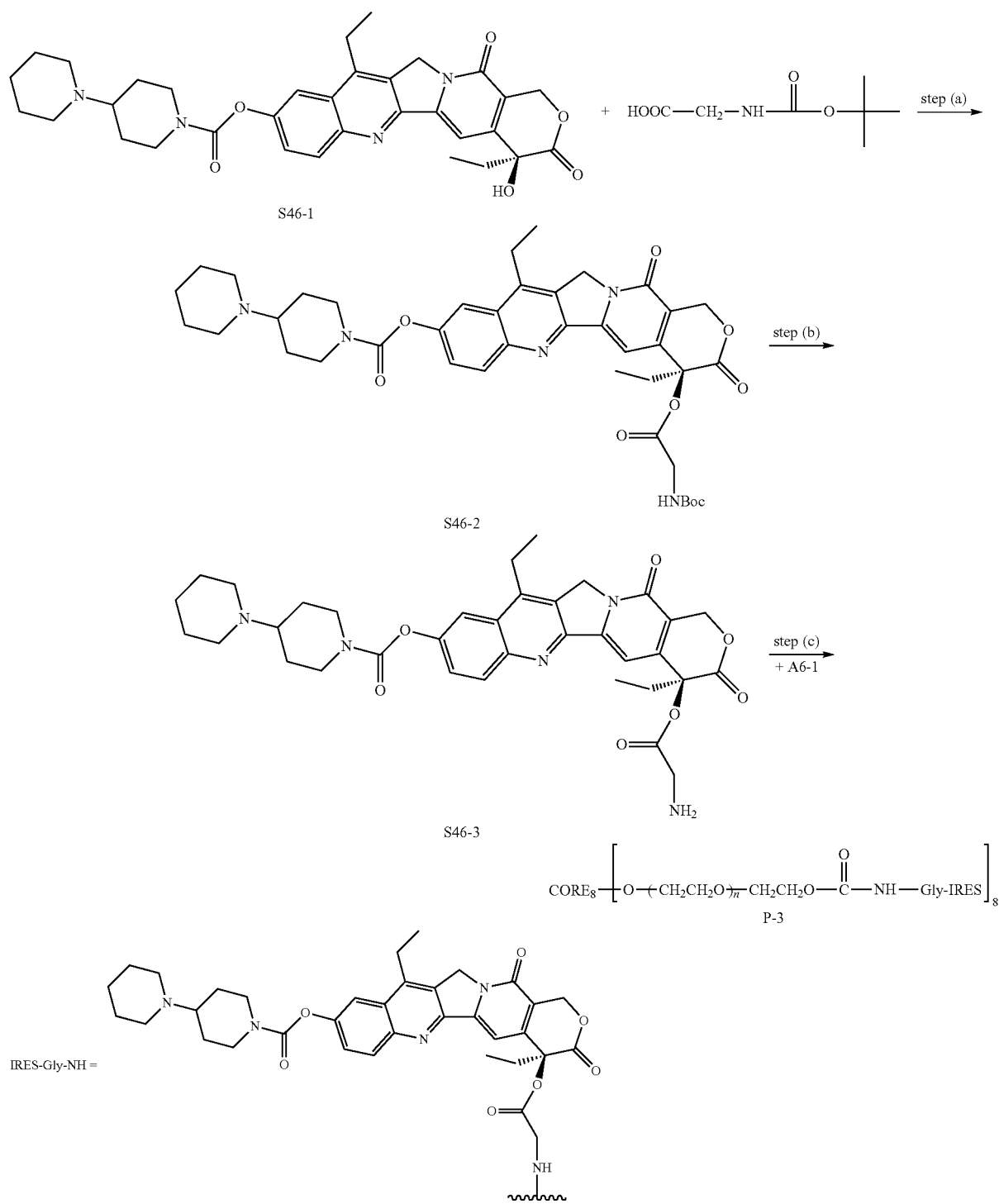

In this Example, the linking group L formed by the reactions contains a urethane bond, and D is IRES-Gly.

Example-47: Preparation of an Eight-Arm Polyethylene Glycol Succinimidyl Active Ester Derivative Modified Small Molecule Drug Irinotecan (D-(Carbonate Bond)-Spacer-(Amide Bond)-PEG)

Step (a): Preparation of 2-(2-Boc-aminoethoxy)ethanol (compound S47-1): Into a dry and clean 500 mL round-bottom flask, 21.5 g (0.2 mol) of 2-(2-aminoethoxy)ethanol, 25.2 g (0.3 mol) of NaHCO₃, 150 mL of dichloromethane and 150 mL of ultrapure water were added in sequence, followed by stirring for 15 minutes. Subsequently, 43.6 g (0.2 mol) of di-t-butyl dicarbonate was added thereinto, and the whole was stirred till all were mixed. The reaction was conducted at room temperature for 10 hours. Thereafter, the product was precipitated with anhydrous dichloromethane (100 mL trice). The organic phase was combined, dried with Na₂SO₄ and by vacuum evaporation in sequence, and then a compound S47-1 was obtained. The structure was determined via NMR test.

Step (b): Preparation of 2-(2-Boc-aminoethoxy)ethoxycarbonyl-irinotecan (compound S47-2): Into a dry and clean 1000 mL round-bottom flask, 10.25 g (50 mmol) of the compound S47-1, 12.2 g (100 mmol) of 4-dimethylaminopyridine and 200 mL of anhydrous dichloromethane were added in sequence, and the whole was stirred till dissolution. Subsequently, 18 mmol of triphosgene was added with stirring and followed by stirring for 20 minutes. Thereafter, a solution of irinotecan (5.87 g, 10 mmol) and DMAP (12.2 g, 100 mmol) in dichloromethane (200 mL) was added thereinto, and the whole was stirred till all were mixed. The reaction was conducted at room temperature for 2 hours. Thereafter, the product was washed with a pH 3.2 HCl solution (200 mL trice). The organic phase was combined, dried with Na₂SO₄ and concentrated by vacuum evaporation, and then a compound S47-2 was obtained. The structure was determined by NMR test.

Step (c): Preparation of 2-(2-aminoethoxy)ethoxycarbonyl-irinotecan trifluoroacetate (compound S47-3): Into a dry and clean 200 mL round-bottom flask, 4.9 g (6 mmol) of the compound S47-2 and 60 mL of anhydrous dichloromethane were added in sequence, and the whole was stirred till dissolution. Subsequently, 20 mL of trifluoroacetic acid was added thereinto at room temperature, and the reaction mixture was stirred for 2 hours. Thereafter, the solvent was removed by vacuum distillation. The residue was precipitated with anhydrous diethyl ether. The precipitate was collected by filtration and dried, and then a compound S47-3 was obtained. The structure was determined by ¹H NMR test.

Step (d): Preparation of an eight-arm polyethylene glycol derivative modified 2-(2-aminoethoxy)ethoxycarbonyl-irinotecan (8arm-PEG-IRES, P-4): Into a dry and clean 500 mL round-bottom flask, a solution of the compound S47-3 (1.96 g, 2.4 mmol, 1.2 eq.) in dimethylformamide (12 mL) and 0.6 mL of triethylamine were added in sequence and mixed. Subsequently, a solution of the eight-arm polyethylene glycol succinimidyl propionate derivative (compound A1-1, obtained in Example-1, $M_n$ was about 21 kDa, 0.25 mmol, 1 equivalent per active site) in dichloromethane (200 mL) was added thereinto, and the whole was stirred till all were mixed. The reaction was conducted at room temperature for 12 hours. Thereafter, the resulting product was precipitated with anhydrous diethyl ether, recrystallized with isopropanol, collected by filtration and dried. The yield was about 95%, and the structure was determined by means of NMR and HPLC. According to the HPLC results, one eight-arm polyethylene glycol derivative molecule was loaded with about 7.5 irinotecan molecules on average.

The synthesis route including steps from step (a) to step (d) is as follows:

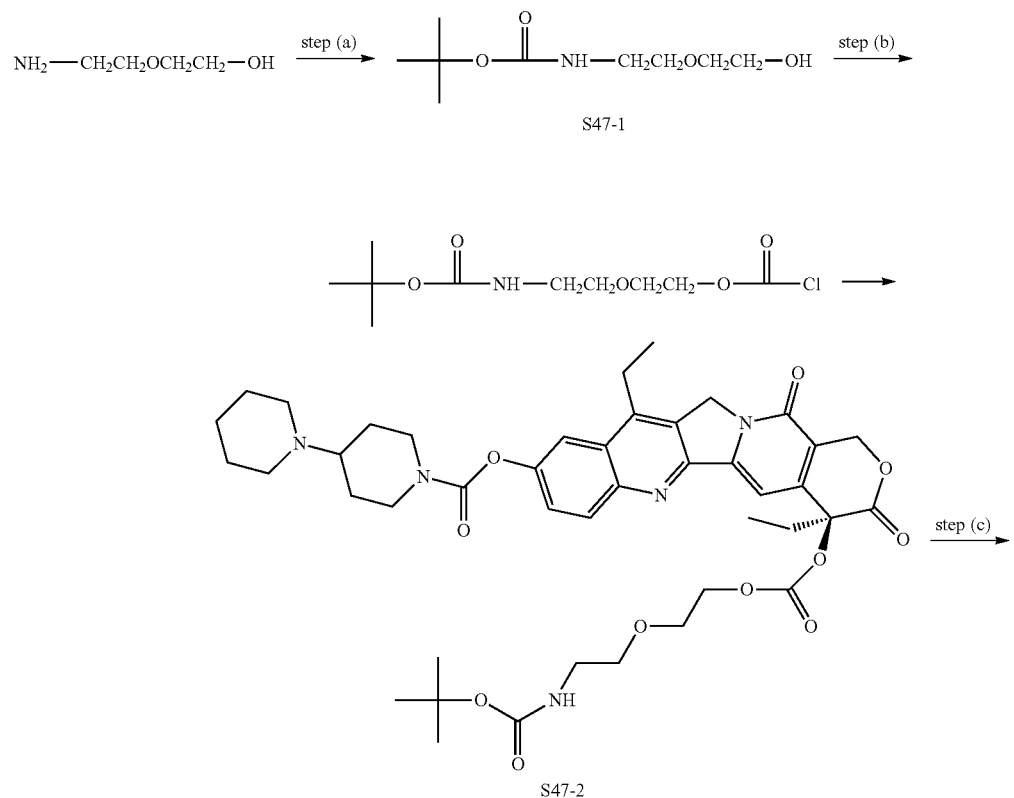

-continued

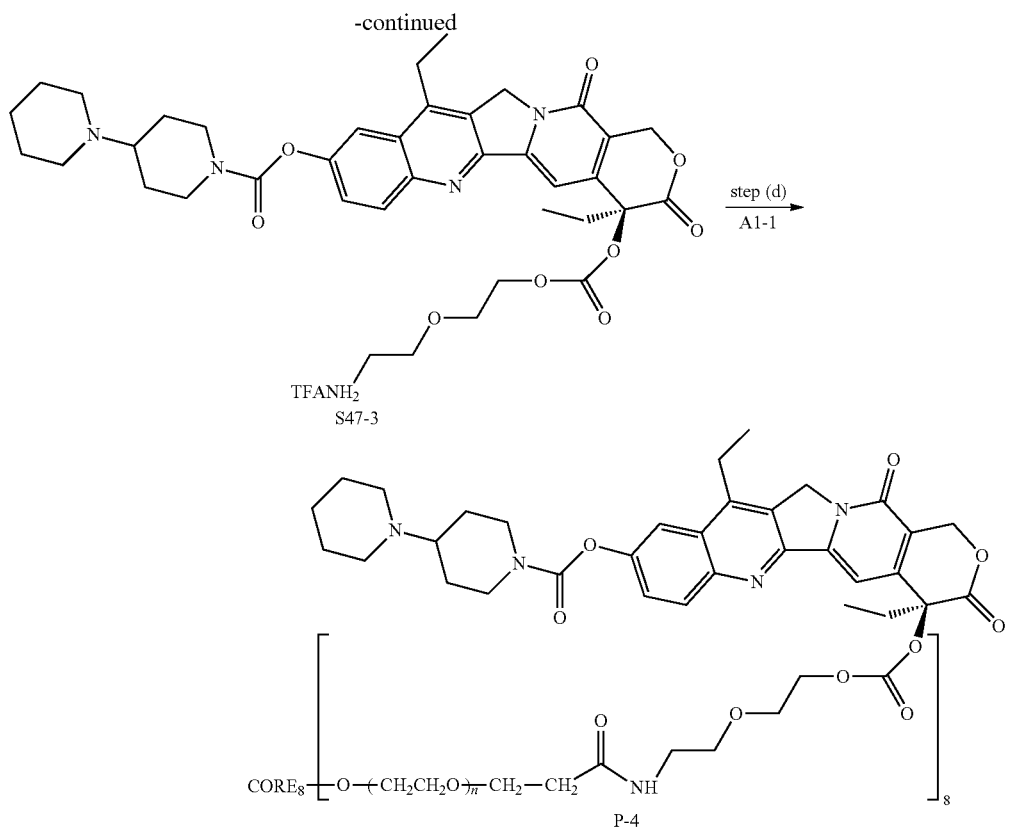

TFANH₂
S47-3 step (d)
A1-1

P-4

In this Example, the linking group L formed by the reactions contains an amide bond, and D is 2-(2-aminoethoxy)ethoxycarbonyl-irinotecan.

Example-48: Preparation of an Eight-Arm Polyethylene Glycol Carboxylic Acid Derivative Modified Small Molecule Drug Irinotecan (P-5) (Via an Amide Bond)

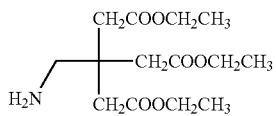

S48-1

Step (a): Into a dry and clean 1 L round-bottom flask, 10 g of the eight-arm polyethylene glycol acetic acid derivative (D1-4, treated by azeotropic removal of water with toluene) obtained in Example-22, triethylamine (10 mL) and aminomethanetrispropionic acid (S48-1) were added. Under nitrogen protection, dichloromethane (160 mL) was added, and the whole was stirred till dissolution. Subsequently, 10 g of dicyclohexylcarbodiimide (DCC) was added thereinto, followed by reaction at room temperature for 24 hours. The resulting mixture was filtrated to remove undissolved substances and concentrated. Thereafter, a 1 mol/L aqueous solution of sodium hydroxide (200 mL) was added thereinto, and the whole was stirred till all were dissolved, followed by reaction at 80° C. for 24 hours. Thereafter, the solution was adjusted to pH 3 with a 3 mol/L HCl solution in an ice bath. The aqueous phase was extracted with dichloromethane (100 mL trice). The organic phase was combined, washed with saturated salt solutions, dried, filtrated, concentrated and recrystallized, and then a carboxylic acid derivative D1-8 in a white solid state was obtained. The structure was determined by NMR test. The molecular weight was measured as about 38 kDa, and PDI=1.04.

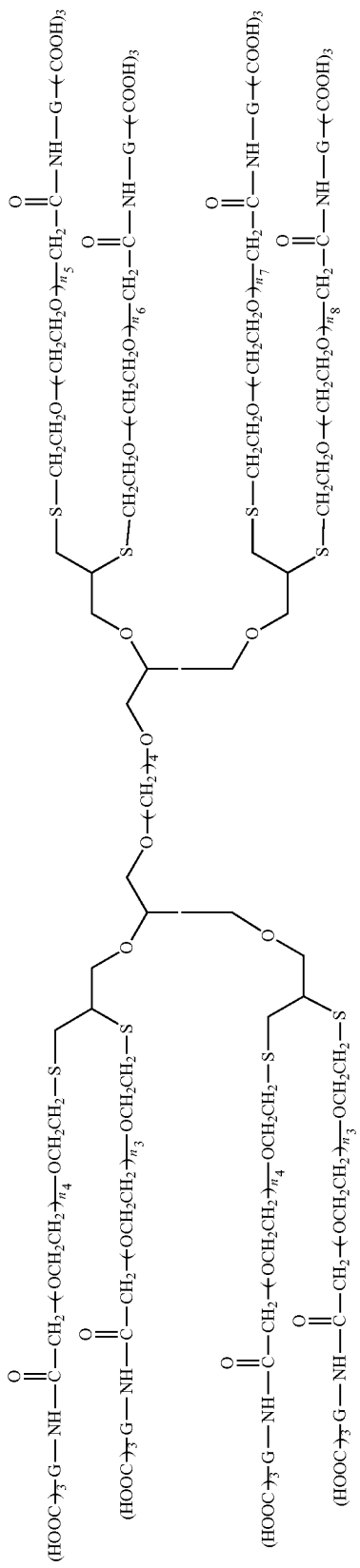
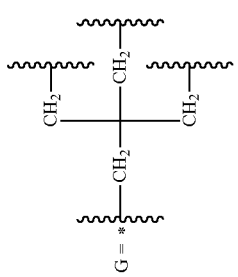

Step (b): Preparation of irinotecan-glycine hydrochloride (compound S48-3, IRES-Gly.HCl): Irinotecan-glycine-Boc was prepared by repeating Step (a) of Example-46. Into a dry and clean 100 mL round-bottom flask, 2.23 g (3 mmol) of irinotecan-glycine-Boc (the compound S46-2, IRES-Gly-Boc), 10 mL of anhydrous dioxane and 10 mL of a solution of 4 N HCl in dioxane were added, and the whole was stirred till all were mixed. The reaction was conducted at room temperature for about 1.5 hours. The characteristic peak shown in the HPLC spectrum of the compound S46-2 disappeared completely. Thereafter, the product was precipitated with 50 mL of diethyl ether. The precipitate was collected by filtration, dissolved in 50 mL of DCM, and then washed with a pH 2.5 solution of HCl adjusted by a saturated $NaHCO_3$ solution. The organic phase was dried over $MgSO_4$, filtrated and concentrated by vacuum evaporation. Thereafter, the concentrated product was dissolved in 5 mL of DCM, and then precipitated with anhydrous diethyl ether. Steps including dissolution and precipitation with anhydrous diethyl ether were repeated. The product was collected by filtration and concentrated by vacuum evaporation, and then a compound S48-3 was obtained. The structure was determined by NMR test.

Step (c): Preparation of an eight-arm polyethylene glycol derivative modified glycine-irinotecan (8arm-PEG-Gly-IRES, compound P-5): Into a dry and clean 100 mL round-bottom flask, a solution of 957 mg (the compound D1-8, about 38 kDa, 0.025 mmol, 1 equivalent per active site) of the eight-arm polyethylene glycol carboxylic acid in anhydrous DCM (50 mL) was added, and then 817 mg of the compound S48-3 (1.2 mmol, 2 eq.), 732 mg (6 mmol, 10 eq.) of DMAP and a 50% ethyl acetate solution (10 eq.) were added in sequence. The reaction mixture was stirred at room temperature overnight. Thereafter, the mixture was concentrated by vacuum evaporation. The residue was dissolved in dichloromethane and then precipitated with anhydrous diethyl ether. The precipitate was collected by filtration and recrystallized from a mixed solution of dimethylformamide and isopropanol. The resulting product was dissolved in dichloromethane, precipitated with anhydrous diethyl ether, collected by filtration and dried at 37° C. under vacuum, and then a compound P-5 was obtained. The yield was higher than 95%, and the structure was determined by NMR test. The product was also characterized by means of HPLC; one eight-arm polyethylene glycol derivative molecule was loaded with about 22.6 irinotecan molecules on average.

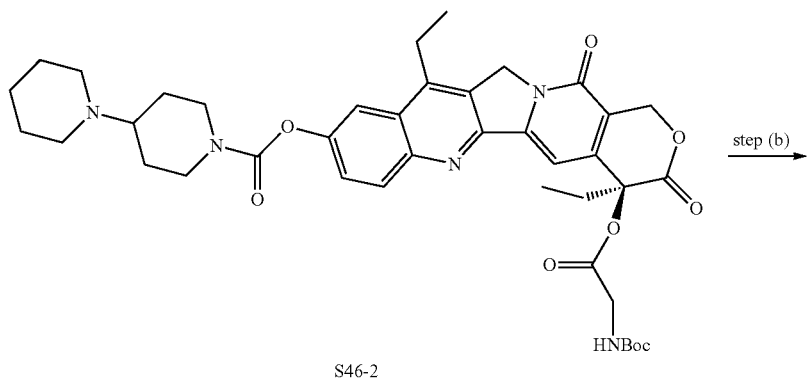

S46-2 step (b) →

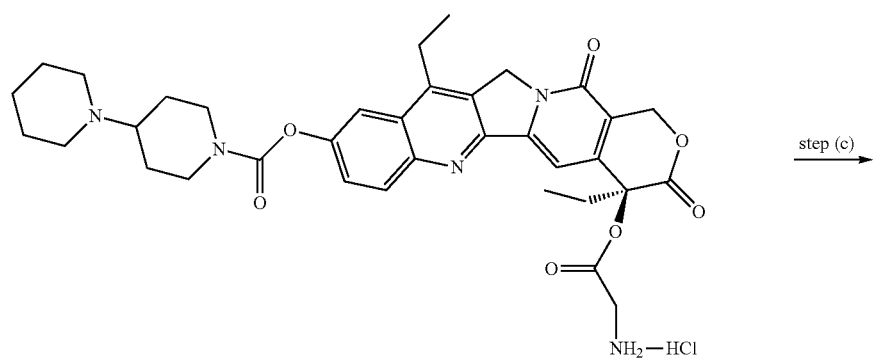

S48-3 step (c) →

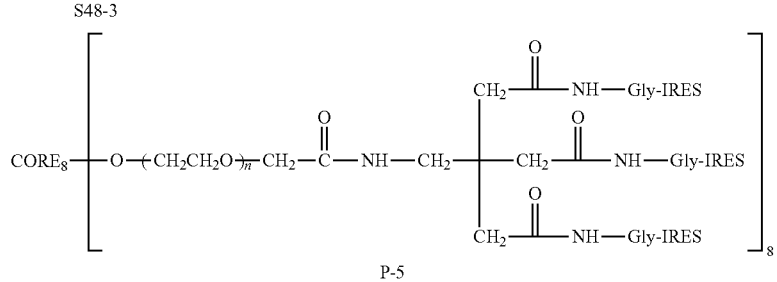

P-5

Wherein, IRES-Gly-NH is the same as that in Example-46. In this Example, L contains an amide bond, and D is IRES-Gly.

Example-49: Preparation of an Eight-Arm Polyethylene Glycol Derivative Modified Cyclovirobuxine D (P-6, Via a Urethane Bond)

Step (a): Preparation of N,N'-di-t-butoxycarbonyl-cyclovirobuxine D (compound S49-2): Into a dry and clean 100 mL round-bottom flask, 1.21 g of cyclovirobuxine D (3 mmol), 1 mL of trifluoroethylamine and 12 mL of anhydrous dichloromethane were added, and the whole was stirred till all were mixed. Subsequently, a solution of 1.64 g (7.5 mmol) of di-tert-butyl dicarbonate ($Boc_2O$) in dichloromethane (12 mL) was added dropwisely in an ice bath within about 15 minutes. Thereafter, the ice bath was removed, and the mixture was returned to room temperature. The reaction was conducted with stirring for 4 hours. The mixture was concentrated under reduced pressure and then precipitated with isopropanol. The product was collected by filtration, washed with isopropanol twice and dried under vacuum, and then a compound S49-2 was obtained. The structure was determined by NMR test.

Step (b): Preparation of an eight-arm polyethylene glycol derivative modified N,N'-di-tert-butoxycarbonyl-cyclovirobuxine D (compound S49-3): Into a dry and clean 500 mL round-bottom flask, 900 mg (D9-1, obtained in Example-6, the molecular weight was about 75 kDa, 0.012 mmol, 1 equivalent per active site) of the eight-arm polyethylene glycol isocyanate derivative, 1.39 g of the compound S49-2 (2.30 mmol, 1.5 eq.) obtained in Step (a), 188 mg (1.536 mmol, 2 eq.) of 4-dimethylaminopyridine (DMAP) and 100 mL of anhydrous dichloromethane were added in sequence, and the whole was stirred to dissolve. Subsequently, 1.26 g (6.14 mmol, 2.4 eq.) of DCC was added thereinto, and the whole was stirred till all were mixed. The reaction was conducted at room temperature for 12 hours. The resulting mixture was filtrated through a coarse filter to remove solid impurities, and then concentrated by evaporation. The residue was precipitated with a 1:6 (v/v) mixed solution of isopropanol and anhydrous diethyl ether. The precipitate was collected by filtration, washed and dried under vacuum, and then a compound S49-3 was obtained. The structure was determined by NMR test. The molecular weight was measured as about 152 kDa according to HPLC test.

Step (c): Preparation of an eight-arm polyethylene glycol derivative modified cyclovirobuxine D (compound P-6): Into a dry and clean 100 mL round-bottom flask, 1.20 g (0.015 mmol) of the compound S49-3 and 7.5 mL of chloroform were added and stirred to dissolve. Subsequently, 2.4 mL of trifluoroacetic acid was added thereinto, and the whole was stirred till all were mixed. The reaction was conducted at room temperature for 3 hours. The solution changed from colorless to light green. The mixture was concentrated under reduced pressure, and precipitated with anhydrous diethyl ether. The precipitate was collected by filtration and dried under vacuum, and then a compound P-6 was obtained. The structure is determined by NMR test. The yield was higher than 90%.

The synthesis route including steps from step (a) to step (c) is as follows:

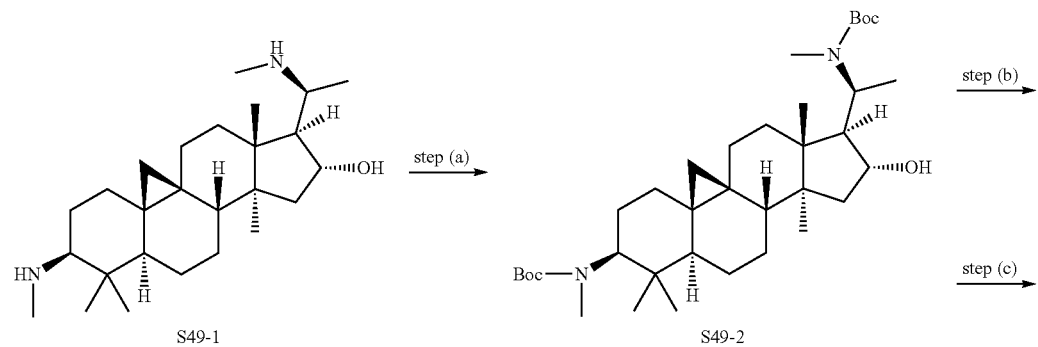

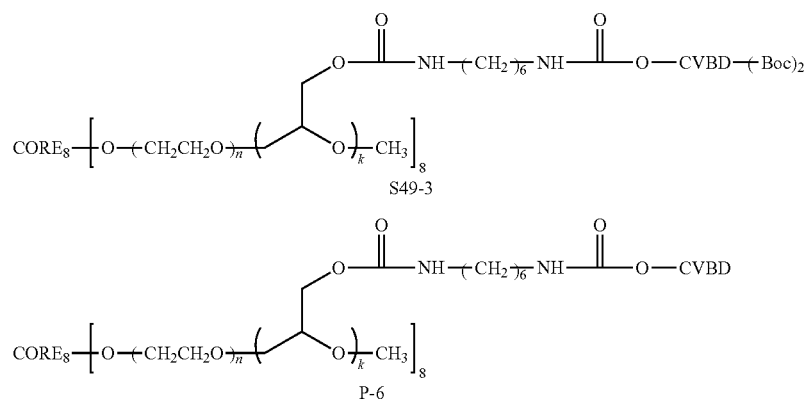

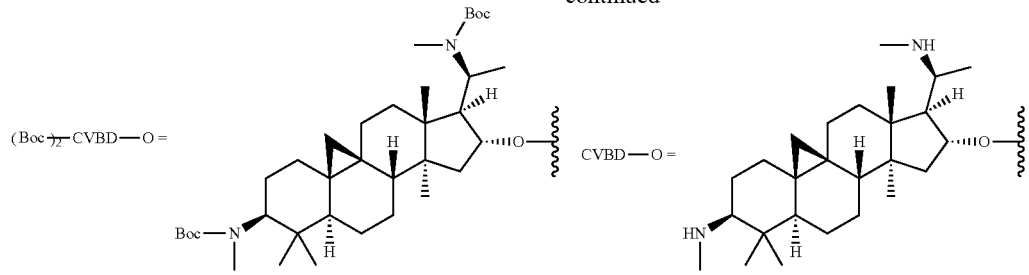

In this Example, the linking group L formed by the reactions contains a urethane bond, and D is CVBD.

Example-50: Preparation of an Eight-Arm Polyethylene Glycol Derivative Modified Cycloprotobuxamine C (P-7) (Via an Amide Bond)

Preparation of an eight-arm polyethylene glycol derivative modified cycloprotobuxamine C (8arm-PEG-CPBC, compound P-7): Into a dry and clean 100 mL round-bottom flask, 1.60 g (compound S50-1, 4 mmol, 5 eq.) of cycloprotobuxamine C, 2.10 g (A1-3, about 42 kDa, 0.1 mmol, 1 equivalent per active site) of the eight-arm polyethylene glycol succinimidyl succinate obtained in Example-42, 98 mg (2 mmol, 2.5 eq.) of 4-dimethylaminopyridine and 60 mL of anhydrous dichloromethane were added, and the whole was stirred till dissolution. Subsequently, 989 mg (4.8 mmol, 6 eq.) of DCC was added thereinto, and the whole was stirred till all were mixed. The reaction was conducted at room temperature for 12 hours. The resulting mixture was filtrated through a coarse filter to remove solid impurities, and the solvent was removed by rotary evaporation. The residue was precipitated in an ice bath with the addition of 200 mL of isopropanol, collected by filtration and dried under vacuum, and then a compound P-7 was obtained. The structure was determined by NMR test. The yield was about 90%.

Wherein, the structures of the compound S50-1 and the product P-7 are as follows:

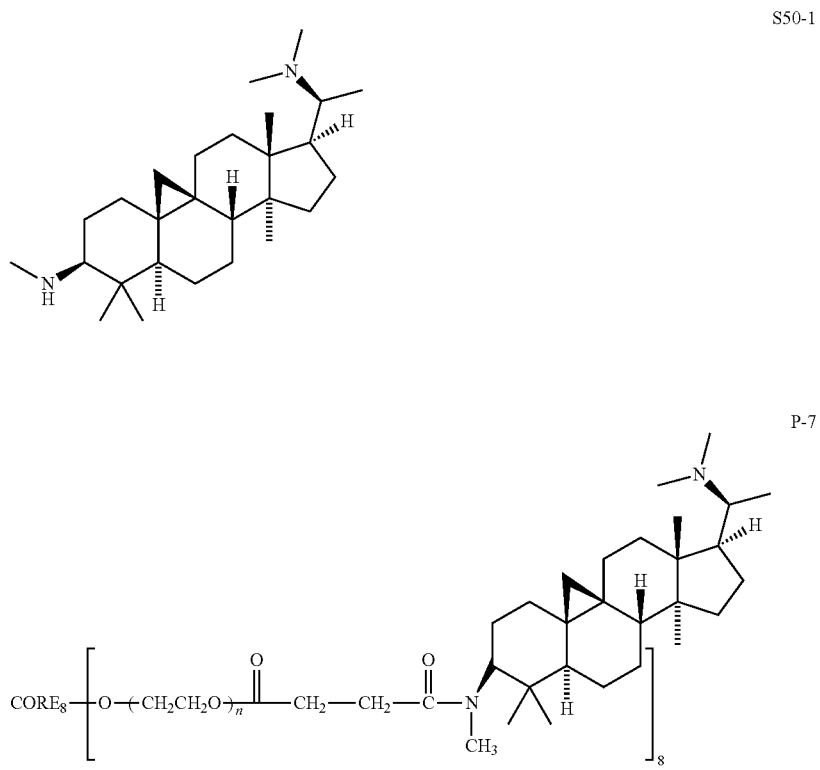

In this Example, the linking group L formed by the reactions contains an amide bond, and D is CPBC.

Example-51: Preparation of an Eight-Arm Polyethylene Glycol Derivative Modified N-diglycine-norcantharidimide (P-9) (Via a Triazole Linkage)

Step (a): Preparation of cycloalkynyl-modified N-diglycine-norcantharidimide S51-3: Into a dry and clean 100 mL round-bottom flask, 1.34 g of a compound S51-2 (5 mmol, 1 eq.), 1.42 g (S51-1, 10 mmol, 2 eq.) of N-diglycinenorcantharidimide, 1.22 g (DMAP, 10 mmol, 2 eq.) of 4-dimethylaminopyridine and 40 mL of anhydrous dichloromethane were added, and the whole was stirred till all were mixed. Subsequently, 2.06 g (10 mmol, 2 eq.) of DCC was added thereinto, and the whole was stirred till all were mixed. Under nitrogen protection and at room temperature, the reaction was conducted with stirring for 12 hours. The resulting mixture was filtrated to remove solid impurities, and concentrated by rotary evaporation. The residue was precipitated with isopropanol, collected by filtration and dried under vacuum, and then a compound S51-3 was obtained. The structure was determined by $^1$H NMR test.

Step (b): Preparation of an eight-arm polyethylene glycol derivative modified N-diglycine-norcantharidimide (8arm-PEG-Gly-Gly-NCN, compound P-9): Into a dry and clean 100 mL round-bottom flask, a solution of 2.35 g (6 mmol, 1.5 eq.) of the compound S51-3 in dichloromethane (24 mL) and a solution of the eight-arm polyethylene glycol azide derivative G21-1 (the molecular weight was about 61 kDa, 0.25 mmol, 1 equivalent per active site) obtained in Example-14 in dichloromethane (20 mL) were added and then stirred for 15 minutes. The resulting mixture was filtrated to remove solid impurities, and concentrated by rotary evaporation. The residue was precipitated with isopropanol, collected by filtration and dried under vacuum, and then a compound P-6 was obtained. The structure was determined by NMR test. The yield was about 98%.

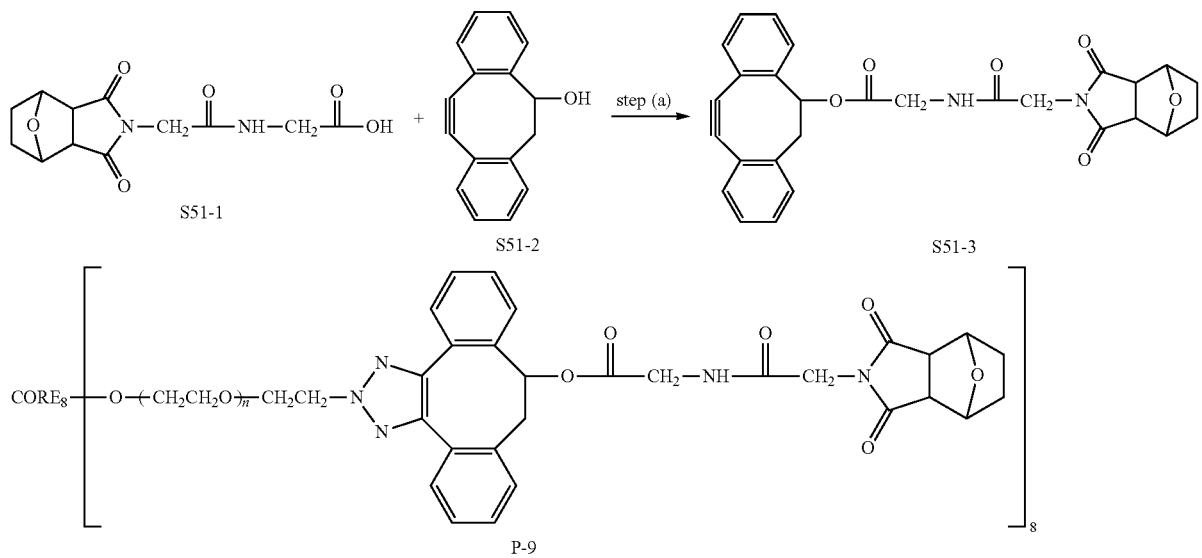

In this Example, the linking group L formed by the reactions contains a triazole ring, and D is NCN-Gly-Gly.

Example-52: Preparation of an Eight-Arm Polyethylene Glycol Derivative Modified Biotin (P-10, Via a Triazole Linkage)

Preparation of an eight-arm polyethylene glycol derivative modified biotin (8arm-PEG-Gly-Gly-NCN, compound P-10): Into a dry and clean 100 mL round-bottom flask, a solution of 1.55 g (4.8 mmol, 1.2 eq.) of a compound S52-1 in dichloromethane (24 mL) and a solution of the eight-arm polyethylene glycol alkyne derivative F3-2 (the molecular weight was about 24 kDa, 0.5 mmol, 1 equivalent per active site) obtained in Example-27 in dichloromethane (20 mL) were added and then stirred for 15 minutes. The resulting mixture was filtrated to remove solid impurities, and concentrated by rotary evaporation. The residue was precipitated with isopropanol, collected by filtration and dried under vacuum, and then a compound P-10 was obtained. The structure was determined by $^1$H NMR test. The yield was about 98%.

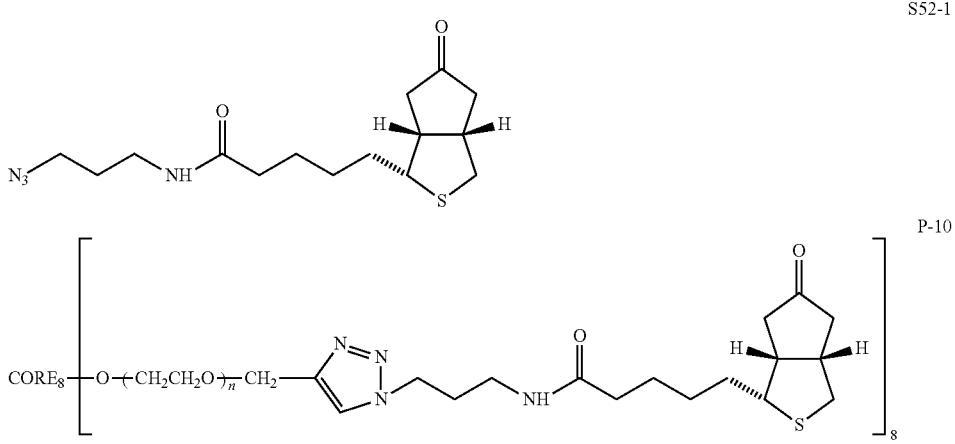

S52-1

P-10

In this Example, the linking group L formed by the reactions is

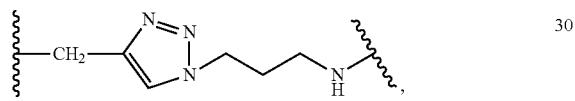

and D is

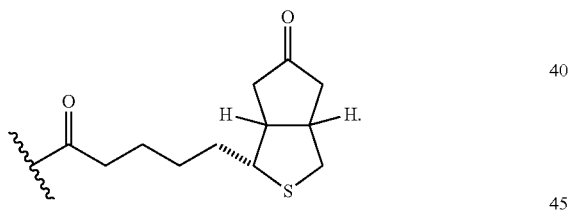

Example-53: Preparation of an Eight-Arm Polyethylene Glycol Derivative Modified Rhodamine (P-11, Via an Amide Bond)

Into a dry and clean 150 mL round-bottom flask, 2 g of the eight-arm polyethylene glycol amino derivative C4-3 (the molecular weight was about 6 kDa, 0.5 mmol, 1 equivalent per active site) obtained in Example-29, 3.83 g (8 mmol, 2 eq.) of rhodamine B and 480 mg of DMAP were added. Under nitrogen protection, anhydrous dichloromethane (50 mL) was added, and the whole was stirred till dissolution. Subsequently, 164 mg of dicyclohexylcarbodiimide (DCC, 8 mmol, 2 eq.) was added thereinto, and the reaction was conducted at room temperature for 24 hours. The resulting mixture was filtrated to remove undissolved substances, concentrated and recrystallized from isopropanol, and then an eight-arm polyethylene glycol derivative modified rhodamine B (P-11) was obtained. The structure was determined by NMR test. The yield was about 96%.

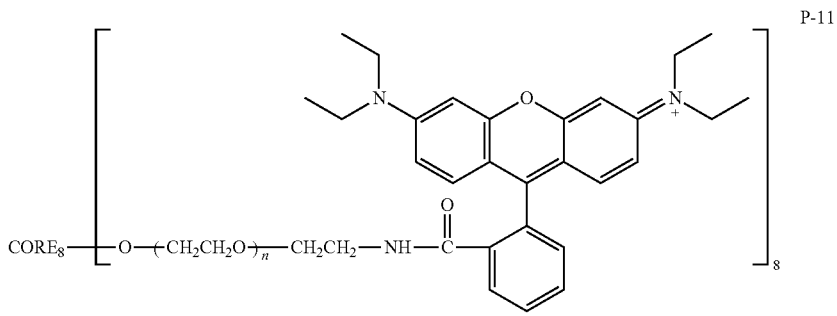

Using the eight-arm polyethylene glycol amine derivative with branched terminals C4-6 obtained in Example-41 as a reagent, and keeping the same equivalents of reagents, the above steps were carried out, and then a compound P1-12 was obtained. The yield was about 93%.

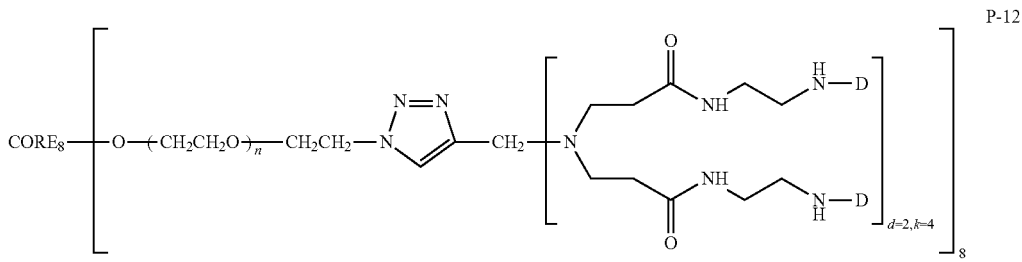

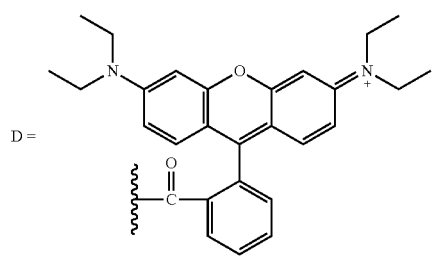

Wherein, the linkage formed by the reactions is an amide bond, and D is tetramethylrhodamine.

Example-54: Preparation of an Eight-Arm Polyethylene Glycol Derivative Modified Triptolide (P-13, Via a Carbonate Linkage)

Step (a): Preparation of an eight-arm polyethylene glycol acyl chloride derivative: Under nitrogen protection, into a dry and clean 100 mL round-bottom flask, 1 g (the molecular weight was about 20 kDa, 0.5 mmol, 1 equivalent per active site) of the eight-arm polyethylene glycol H1-14 obtained in Example-35 and 475 mg (1.6 mmol, 4 eq.) of triphosgene were dissolved in 30 mL of acetonitrile. Subsequently, 1.2 mL of anhydrous pyridine was added dropwisely thereinto, and the reaction was conducted with stirring for 3 hours. The resulting product was concentrated by rotary evaporation to remove redundant solvent, and then precipitated with anhydrous diethyl ether. The precipitate was collected and dried under vacuum, and then a compound D12-1 was obtained. The structure was determined by NMR test.

Step (b): Preparation of an eight-arm polyethylene glycol derivative modified triptolide (P-13): Under nitrogen protection, into a dry and clean reactor, the compound D12-1 obtained in Step (a) was dissolved in 15 mL of dichloromethane; thereafter, 288 mg (0.8 mmol, 2 eq.) of triptolide and 489 mg (4 mmol, 10 eq.) of 4-dimethylaminopyridine were added. The reaction mixture was stirred for 5 hours. The resulting mixture was filtrated to remove solid impurities, and the redundant solvent was removed by rotary evaporation. The residue was precipitated with a 1:2 (v/v) mixed solution of isopropanol and anhydrous diethyl ether. The precipitate was collected by filtration, washed and dried under vacuum, and then a compound P-13 was obtained. The structure was determined by NMR test. The yield was about 85%.

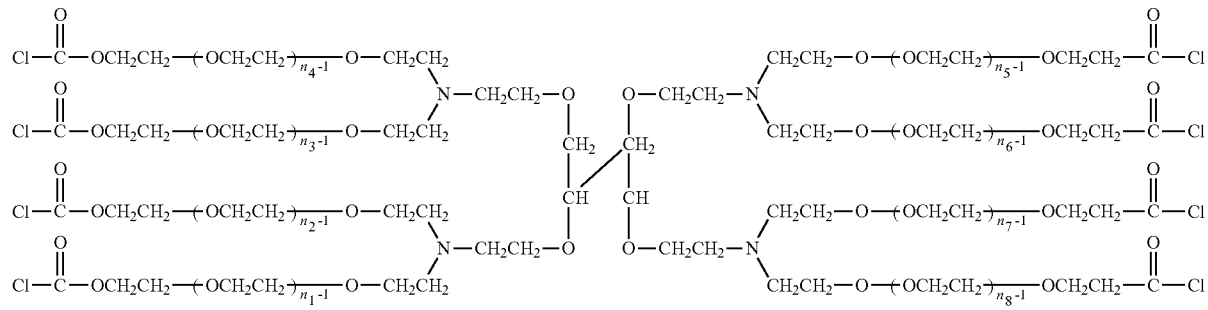

Wherein, the structure of the compound P-13 is as follows:

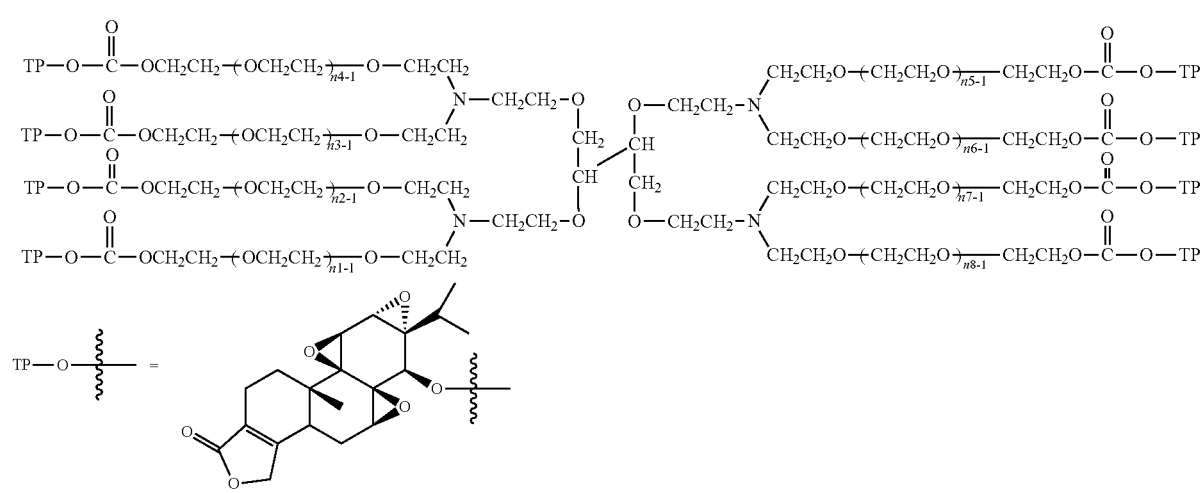

P-13

In this Example, the linking group formed by the reactions is a carbonate linkage, and D is triptolide.

Example-55: Preparation of an Eight-Arm Polyethylene Glycol Derivative Modified Tanshinone IIa (Via an Imine Linkage)

Into a dry and clean 250 mL round-bottom flask, 8 g of the eight-arm protected PEG-amine derivative ($C_{6-2}$) and 150 mL of a 50% solution of piperidine in dichloromethane were added in sequence. After completion of the reaction, the resulting mixture was washed, concentrated and recrystallized, and then an eight-arm polyethylene glycol amine derivative C4-7 with amino groups being unprotected was obtained.

Preparation of an eight-arm polyethylene glycol derivative modified tanshinone IIa (compound P-14): Into a dry and clean 100 mL round-bottom flask, 2.08 g (the molecular weight was about 41 kDa, 0.05 mmol, 1 equivalent per active site) of the eight-arm polyethylene glycol amine derivative C4-7 obtained by reference with Example-7, and 235 mg (a compound S55-1, 0.8 mmol, 1 eq.) of tanshinone IIa were added, and then 25 mL of anhydrous methanol and 0.15 mL of trifluoroacetic acid were added in sequence. Away from light, the reaction under reflux was conducted for 2 hours. The redundant solvent was removed by rotary evaporation. The residue was precipitated with isopropanol. The precipitate was collected and dried under vacuum. The product was purified via an ion-exchange resin and further dried under vacuum. Then, a compound P-14 was obtained. The structure was determined by NMR test. The yield was about 92%.

Preparation of an eight-arm polyethylene glycol derivative modified tanshinone IIa (compound P-15): Into a dry and clean 100 mL round-bottom flask, 2.55 g (the molecular weight was about 24 kDa, 0.05 mmol, 1 equivalent per active site) of the eight-arm polyethylene glycol amine derivative $C_{4-5}$ obtained in Example-34 and 118 mg (the compound S55-1, 0.4 mmol, 1 eq.) of tanshinone IIa were added; subsequently, 20 mL of anhydrous methanol and 0.1 mL of trifluoroacetic acid were added in sequence. Away from light, the reaction under reflux was conducted for 2 hours. The redundant solvent was removed by rotary evaporation. The residue was precipitated with isopropanol. The precipitate was collected and dried under vacuum. The product was purified via an ion-exchange resin and further dried under vacuum. Then, a compound P-15 was obtained. The structure was determined by NMR test. The yield was about 91%.

Wherein, the main components of the product P-14 and product P-15 are as follows respectively:

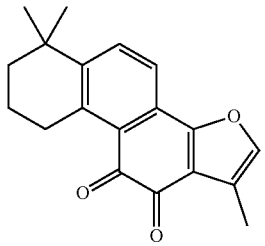

S55-1

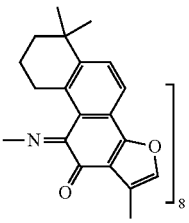

P-15

In this Example, an imine bond was formed after the reactions.

Example-56: Preparation of an Eight-Arm Polyethylene Glycol Derivative Modified Cholesterol (Via an Ester Bond)

By using the production method in Example-4 for producing the polyethylene glycol carboxylic acid derivative D1-2, employing the same reagents, only changing the feed amount of ethylene oxide, and having a designed structure with $n_1 \approx n_2 \approx n_3 \approx n_4 \approx n_5 \approx n_6 \approx n_7 \approx n_8 \approx 90$, an eight-arm polyethylene glycol carboxylic acid derivative D1-9 was obtained. $M_n \approx 25$ kDa and PDI=1.02.

Preparation of an eight-arm poly(ethylene glycol) cholesteryl ester (compound P-16): Under nitrogen protection, into a dry and clean 100 mL round-bottom flask, the eight-arm polyethylene glycol propionic acid derivative (D1-9, 1.4 g, 0.05 mmol, 1 equivalent per active site), cholesterol (S56-1, 309 mg, 0.8 mmol, 2 eq.), benzotriazole (0.8 mmol, 2 eq.) and 98 mg (0.8 mmol, 2 eq.) of 4-dimethylaminopyridine were added, and then 50 mL of anhydrous dichloromethane was added. The whole was stirred till dissolution. Subsequently, 164 mg (0.8 mmol, 2 eq.) of DCC was added thereinto, and the whole was stirred till all were mixed. Under nitrogen protection, the reaction mixture was stirred overnight. The resulting mixture was concentrated by evaporation. The residue was added with 20 mL of 1,4-dioxane and then filtrated to remove the precipitate. The resulting mixture was concentrated by evaporation and precipitated with isopropanol. The precipitate was collected by filtration, washed with anhydrous diethyl ether and dried under vacuum, and then a compound P-16 was obtained. The structure was determined by NMR test.

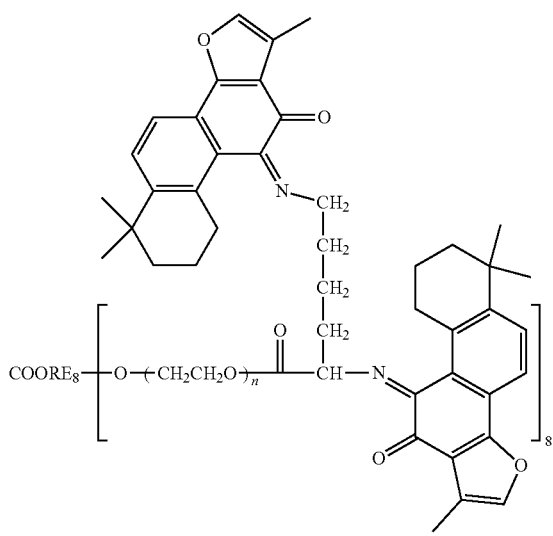

P-14

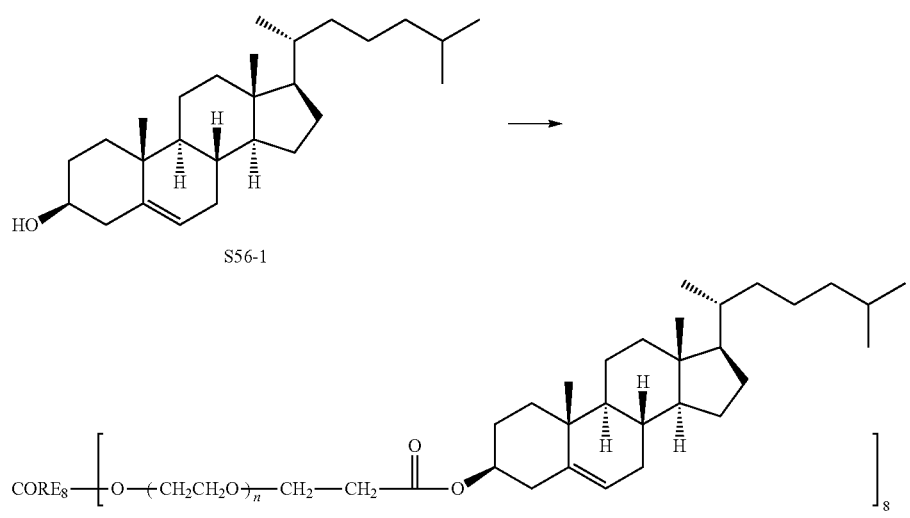

S56-1

P-16

In this Example, the linkage formed by the reactions is an ester bond, and D is cholesterol.

Example-57: Preparation of an Eight-Arm Polyethylene Glycol Derivative Modified Cantharidin (P-17, Via an Imide Bond)

S57-1

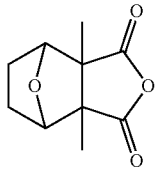

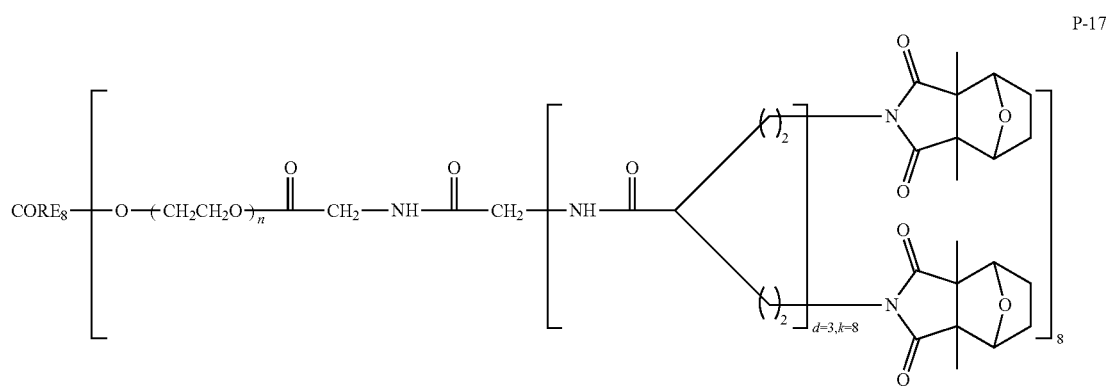

P-17

Into a dry and clean container, 10.0 g of the eight-arm Boc-protected PEG-amine derivative with dendritic branched terminals (C6-1, the molecular weight was about 48 kDa) obtained in Example-5 was added and then dissolved with dichloromethane. The solution was adjusted to 0.1M with the addition of TFA, followed by reaction for 4 hours. Thereafter, the solution was adjusted to a neutral pH value, extracted and precipitated, and then a polyethylene glycol amine derivative with amino groups being unprotected C4-8 was obtained. Into a dry and clean 500 mL round-bottom flask, 480 mg (0.01 mmol, 1 equivalent per active site) of the compound C4-8, 376 mg (1.92 mmol, 3 eq.) of cantharidin and 235 mg (1.92 mmol, 3 eq.) of 4-dimethylaminopyridine (DMAP) were added, and then a mixed solution of 100 mL of anhydrous dichloromethane and 20 mL of dimethylformamide was added. The whole was stirred till all were mixed. Subsequently, 198 mg (0.96 mmol, 1.5 eq.) of DCC was added thereinto, and the whole was stirred till all were mixed. The reaction was conducted at room temperature for 12 hours and then terminated with the addition of glycine. The resulting mixture was filtrated, concentrated by evaporation and then precipitated with a 1:6 (v/v) mixed solution of isopropanol and anhydrous diethyl ether. The precipitate was collected by filtration, washed and dried under vacuum, and then a compound P-17 was obtained. The structure was determined by NMR test.

Wherein, an imide bond was formed after the reactions.

Example-58: Preparation of an Eight-Arm Polyethylene Glycol Derivative Modified Norcantharidimide (P-18)

Into a dry and clean 200 mL round-bottom flask, 80 mg of sodium hydride (60% by weight in oil, 2 mmol, 10 eq.) was added. Under nitrogen protection, 500 mL of anhydrous tetrahydrofuran was added thereinto, and then a solution of hydroxyethyl-norcantharidimide (S58-1, 844 mg, 0.4 mmol, 2 eq.) in tetrahydrofuran was added slowly and dropwisely in an ice bath. The reaction mixture was stirred at room temperature for 3 hours. Thereafter, 1.06 g (about 42 kDa, 0.025 mmol, 1 equivalent per active site) of the eight-arm polyethylene glycol sulfonate B1-1 (Example-9) was added thereinto, followed by reaction at room temperature for 24 hours. The reaction was quenched with the addition of a small amount of saturated ammonium chloride solution, concentrated and added with 400 mL of dichloromethane. The product was washed with saturated salt solutions (120 mL trice), dried, concentrated and recrystallized, and then a compound P-18 was obtained. The structure was determined by NMR test. The yield was about 92%.

S58-1

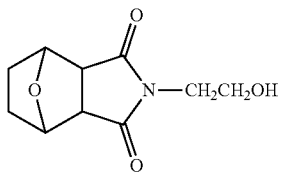

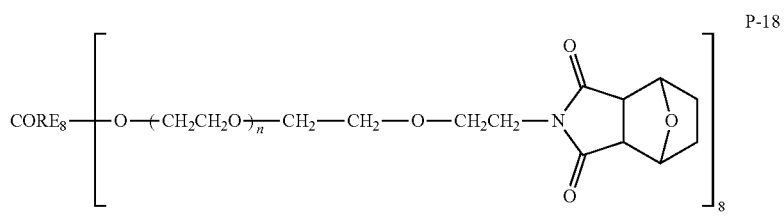

In this Example, L contains an ether bond, and D is hydroxyethyl-norcantharidimide.

Example-59: Biological Tests of Pegylated Exenatide

TABLE 1

| No. | modified product $M_w$ (kDa) | PEG structure | Production method | PEG $M_n$ (kDa) | PDI | EO-unit number per PEG chain (n) |
|---|---|---|---|---|---|---|
| T1 P-1 | 75 | E1-1 | S18 | 42 | 1.04 | 113 |
| T2 P-22 | 56 | E1-1 | S18 | 25 | 1.03 | 65 |
| T3 P-23 | 122 | E1-1 | S18 | 82 | 1.09 | 227 |
| T4 P-24 | 55 | E1-3 | S34 | 25 | 1 | 65 |
| T5 P-25 | 61 | E1-3 | S34 | 30 | 1.03 | 80 |
| T6 P-26 | 74 | E1-3 | S34 | 42 | 1.02 | 113 |
| C1 P-27 | 42 | CE-1 | S18 | 24 | 1.03 | 137 |
| C2 P-28 | 55 | CE-2 | S18 | 25 | 1.05 | 65 |
| C3 | exenatide | | | | | |
| C4 | saline solution | | | | | |

By using the production method in Example-18, eight-arm polyethylene glycol maleimide derivatives P-22 and P-23 which have the same structure as the compound E1-1 was prepared, wherein, the feed amount of ethylene oxide in the polymerization process was calculated according to the n value in Table 1. The molecular weight and polydispersity index of the eight-arm products are shown in Table 1.

By using the production method in Example-34, eight-arm polyethylene glycol maleimide derivatives P-24, P-25 and P-26 which have the same structure as the compound E1-3 were prepared, wherein, the molecular weight of the heterofunctional polyethylene glycol reagents for coupling was selected according to the n value in Table 1. The molecular weight and polydispersity index of the eight-arm products are shown in Table 1.

By using the production method in Example-18, using pentaerythritol and tripentaerythritol as initiators respectively, and adjusting the feed amount of ethylene oxide for polymerization according to the n value in Table 1, four-arm and eight-arm polyethylene glycol maleimide derivatives CE-1 and CE-2 were obtained, respectively. The molecular weight and polydispersity index of the products are shown in Table 1.

By using the production method in Example-44, not changing the equivalent ratios to feed, the pegylated exenatide products as shown in Table 1 were obtained, respectively. The molecular weights of the modified products are shown in Table 1.

Adult male Swiss mice were selected as the research object to carry out blood glucose test. Adult male Swiss mice with a weight from 20 g to 30 g were selected, and each group has 24 mice. The mice were starved for 24 hours in advance and then administered glucose by intraperitoneal injection at a dose of 20 mmol/kg. The mice in experimental groups and in control groups of Table 1 were treated as follows respectively: the mice in the group P-1, groups P-22 to P-28 and the group C3 were administered glucose by intraperitoneal injection at the same dose of 6 nmol/kg, and the mice in the group C4 were administered a saline solution of the same volume as blank control. Blood samples were taken from the tail vein at 15 min, 30 min, 1 h, 4 h, 12 h, 24 h, 48 h and 72 h after administration. Blood glucose levels were determined by the glucose-oxidase method (GOD method). According to the results, at 15 min after-administration, the experimental groups T1~T6 and the control groups C1~C3 showed a decrease in blood glucose level compared with the blank control. The most significant hypoglycemic effect in experimental groups T1~T6 and the control group C2 happened within 30 min, the blood glucose level decreased by about 40% to 65%, and the hypoglycemic effect was maintained for more than 12 hours. The most significant hypoglycemic effect of the control group C1 began to appear at about 1 h after-administration. In the experimental groups, the larger the molecular weight was, the longer the hypoglycemic effect was maintained. Compared with the experimental groups with the same molecular weight and with an E1-3 structure, the experimental groups with an E1-1 structure had longer maintenance time. Wherein, the maintenance time of the group T3 was the longest, and can be maintained up to 72 h. The hypoglycemic effect was maintained for a slightly shorter time in the group T4 than in the group T2, while longer in the group T2 than in the group C2.

Example-60: Biological Test of Pegylated Irinotecan (1) Preparation of Polyethylene Glycol-Modified Irinotecan Drug Molecules

TABLE 2

| No. | modified product $M_w$ (kDa) | PEG structure | Production Method | PEG $M_n$ (kDa) | PDI | EO-unit number per PEG chain (n) | $k_D$ mean value | Irinotecan content (%) |
|---|---|---|---|---|---|---|---|---|
| T7  | P-31 | 25 | D1-1 | S1       | 21 | 1.03 | 56  | 7.2  | 17.9 |
| T8  | P-5  | 53 | D1-8 | S48      | 38 | 1.04 | 100 | 22.6 | 26.9 |
| T9  | P-32 | 50 | D1-5 | S42      | 40 | 1.05 | 113 | 15.2 | 18.9 |
| T10 | P-33 | 46 | D1-6 | S42      | 40 | 1.05 | 113 | 7.5  | 10.3 |
| T11 | P-34 | 51 | D1-7 | S43      | 42 | 1.05 | 113 | 15.2 | 18.6 |
| T12 | P-35 | 70 | D1-2 | S4       | 64 | 1.06 | 181 | 7.6  | 6.8  |
| T13 | P-3  | 66 | A6-1 | S12, S46 | 62 | 1.06 | 170 | 7.6  | 6.1  |
| C3  | P36  | 43 | CD-1 |          | 40 | 1.07 | 227 | 3.8  | 5.6  |
| C4  | P37  | 45 | CD-2 |          | 41 | 1.06 | 113 | 7.4  | 10.2 |

By using the production methods in Examples-46 and Examples-48, a sufficient amount of pegylated irinotecan products for testing were prepared, corresponding to structures P-3 (A6-1) and P-5 (D1-8), respectively.

By using the same reagents, equivalents and production methods, polyethylene glycol derivatives including D1-1 in Example-1, D1-5 in Example-42, D1-6 in Example-42, D1-7 in Example-43 and D1-2 in Example-4 were prepared.

By using the production method for D1-1, keeping the same equivalents, using pentaerythritol and tripentaerythritol as initiators respectively, and adjusting the feed amount of ethylene oxide for polymerization according to the n value in Table 2, four-arm and eight-arm polyethylene glycol carboxylic acid derivatives CD-1 and CD-2 were prepared, respectively. The molecular weight and polydispersity index of the products are shown in Table 2.

By using the production method in Example-48, not changing the equivalent ratio to feed, pegylated irinotecan products shown in Table 2 other than T8 and T13 were prepared, and the properties of the modified products are shown in Table 2. Herein, $k_D$ is the average number of irinotecan molecules grafted by one eight-arm polyethylene glycol molecule, wherein, $k_D$ is calculated according to the results of HPLC test. The irinotecan content refers to the weight percentage of irinotecan per unit weight of pegylated irinotecan.

Wherein, P-32 and P-34 are end-bifunctionalized, P-5 is end-trifunctionalized, and the others are end-monofunctionalized. P-33 and P-3 contain an ester bond and a urethane bond at the position of $Z_2$, respectively; P-34 contains a degradable ester bond at the position of $L_0$. Those irinotecan molecules in Table 2 are all linked to a glycine spacer via an ester bond.

(2) Cytotoxicity Test

Human colon cancer COLO205 cells, human colon carcinoma HT29 cells, human lung carcinoma A549 cells, pancreatic cancer MiaPaCa-2 cells, human ovarian cancer A2780 cells and human ovarian carcinoma OVCAR-3 cells, six cell lines in total, were used. Cells were plated into 12-well plates at a density of 10,000 cells per well, and cultured with supplement of pegylated irinotecan drugs as shown in Table 1 respectively and at the same mass concentration.

The cytotoxicity test of each cell line was performed by using four samples in each group, and a blank control group without drug was supplemented. Cells were cultured in a cell incubator at 37° C. with 4% $CO_2$. The MTT assay was used to evaluate the cytotoxicity at 72 h post-seeding, wherein, cells were incubated with a 0.5 mg/mL MTT solution in pH 7.4 PBS for 4 hours. Thereafter, the purple crystals were dissolved with DMSO, and the absorbance at 490 nm was measured by using a microplate reader. The results showed that, for the six cell lines, the pegylated irinotecan products corresponding to the groups in Table 2 reveal significant inhibition against cell proliferation. The higher the irinotecan content per unit was, the better the cytotoxic activity was.

(3) Maximum Tolerated Dose (MTD)

The nude mouse model was used to evaluate the maximum tolerated dose of each group. When the body weight of a nude mouse decreased by 20%, the death/survival was monitored and counted. For single-dose studies, the maximum tolerated dose was from about 35 to about 80 mg/kg. With respect to the maximum tolerated dose, T12 and C3 showed the highest MTD, followed by T13, while T8 and T11 the lowest.

(4) Pharmacokinetics

Tumor-free Adult SD rats were administrated a single dose of 25 mg/kg, and four rats were used for each experimental point. The rats were sacrificed at different time points within 7 days, and the concentrations of pegylated irinotecan and its metabolite SN38 were measured and analyzed by HPLC. The analysis of pharmacokinetics was carried out by using a non-compartmental model. The higher the molecular weight was, the longer the apparent elimination half-life of pegylated irinotecan was. With respect to the metabolite SN38, the pegylated irinotecan products in T8 showed the longest apparent elimination half-life, followed by T9; while T13 the shortest, followed by T10 and C3.

(5) Anti-Tumor Effect

An animal model of transplanted tumor was used. Mouse hepatoma H22 cells were transplanted subcutaneously into the right axillary region of mice to form solid tumors. After transplantation for 2 days and 7 days, drugs were administered intravenously via the tail vein as a single dose. Two weeks after transplantation, the mice were sacrificed by cervical dislocation, and the tumors were isolated and weighed. The results showed that, for the six cell lines, compared with the blank control group, the pegylated irinotecan products corresponding to the groups in Table 2 all reveal significant anti-tumor effect, wherein, the tumor-inhibition ratios reached near 100%, and the survival ratios were more than 92%. T8 and T11 showed the highest tumor-inhibition ratio, followed by T7, T9 and T10, further followed by C4, while C3 the lowest. The profile of tumor-inhibition time was consistent with the pharmacokinetic data.

The foregoing descriptions of the embodiments in the present invention are provided for illustration only, and not for the purpose of limiting the scope of the present invention. The equivalent structures and equivalent routes according to the description of the present invention, which can be applied in other related arts in a direct or an indirect way, are also incorporated into the scope of protection of the present invention.

What is claimed is:

1. An eight-arm functional polyethylene glycol, wherein, the eight-arm functional polyethylene glycol has eight PEG chains and one octavalent central group $CORE_8$ as represented by $CORE_8$

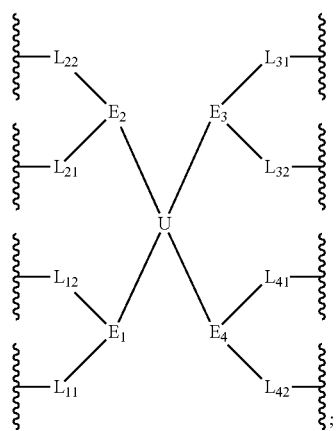

is denoted as "CORE" and consists of one tetravalent central group U and four trivalent branching groups $E_1$, $E_2$, $E_3$ and $E_4$; wherein, $E_1$, $E_2$, $E_3$ and $E_4$ are each independently identical or not identical in one molecule;

wherein, $L_{11}$, $L_{12}$, $L_{21}$, $L_{12}$, $L_{31}$, $L_{32}$, $L_{41}$, and $L_{42}$ are divalent linking groups that respectively attaches a PEG chain to one of the eight ends of CORE; $L_{11}$, $L_{12}$, $L_{21}$, $L_{12}$, $L_{31}$, $L_{32}$, $L_{41}$, and $L_{42}$, can be each independently identical or not identical in one molecule;

wherein, each PEG chain bears at least one terminal functional group F as represented by

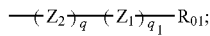

wherein, q and $q_1$ are each independently equal to 0 or 1; $Z_1$ and $Z_2$ are each independently a divalent linking group; $R_{01}$ is a functional end-group capable of interacting with a bio-related substance to generate a covalent bond, a dynamic covalent bond, dihydrogen-bonding, multiple hydrogen-bonding, therapeutic targeting binding or photoreactive response.

2. The eight-arm functional polyethylene glycol according to claim 1, wherein, the eight-arm functional polyethylene glycol has a structure represented by the general formula (1):

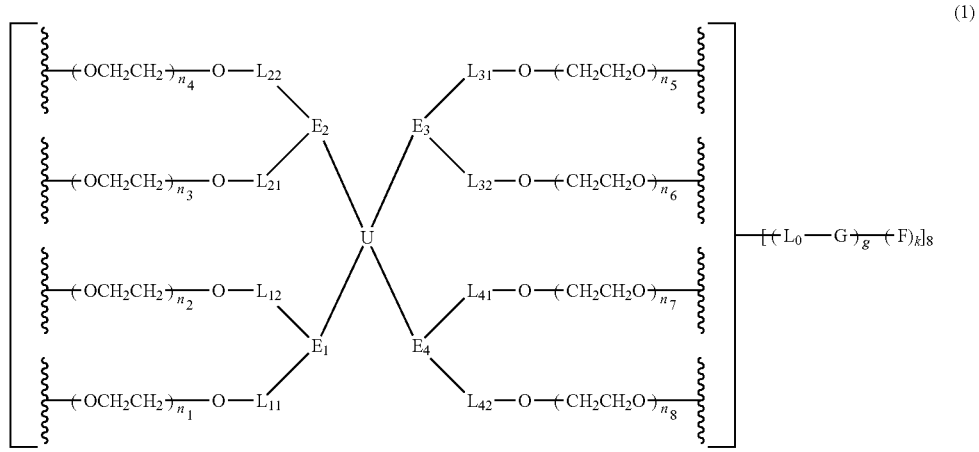

(1)

wherein, the moiety

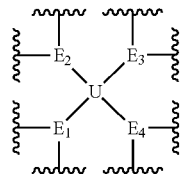

wherein, $n_1$, $n_2$, $n_3$, $n_4$, $n_5$, $n_6$, $n_7$ and $n_8$ are each independently a value from 2 to about 2000, and can be each independently identical or not identical in one molecule; wherein, the term "about" refers to a range within ±10% of the value;

wherein, g is 0 or 1; k is 1 or an integer from 2 to 250;

when g is 0, k is equal to 1, and both $L_0$ and G are absent; the eight-arm functional polyethylene glycol has a structure represented by the general formula (3);

(3)

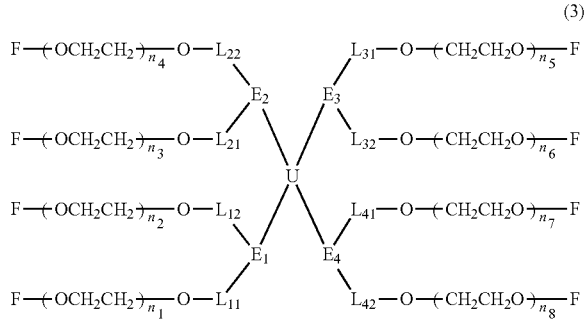

when g is 1, G is present, $L_0$ can be present or absent, and k is an integer from 2 to 250; when the k values of the eight PEG chain terminals are all greater than 2, those k values can be each independently equal or different; wherein, $L_0$ is a divalent linking group which connects the PEG chain with an end-branching group G, and G is a (k+1)-valent end-branching group which connects one PEG chain with terminal functional F groups in quantities of k; wherein, the eight-arm functional polyethylene glycol has a structure represented by the general formula (4)

(4)

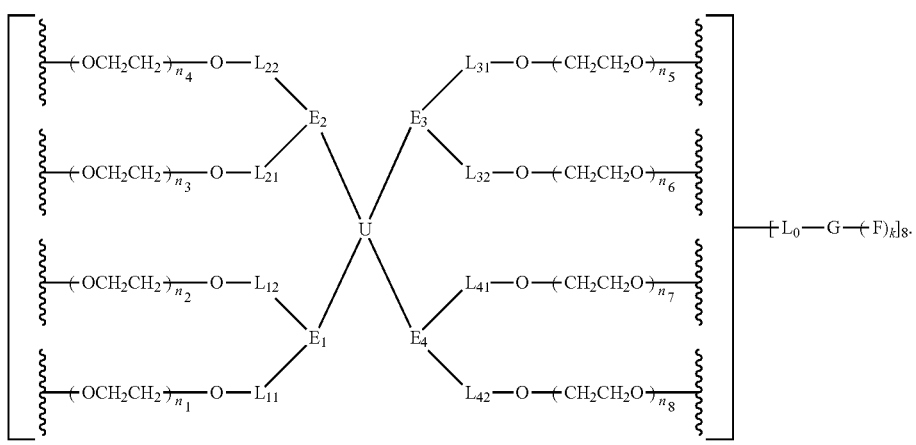

3. The eight-arm functional polyethylene glycol according to claim 2, wherein, the combination of $D_{Emax}$, $d_{DE}$ and $d_{E2}$ satisfies at least one of the following formulas: $D_{Emax} \leq 15$, $d_{DE} \leq 2$ and $d_{E2} \leq 1$;
wherein, $D_{Emax}$ represents "maximum chain length", and refers to the largest number of skeleton atoms between any two trivalent branching centers of the four trivalent branching groups $E_i$ (i=1, 2, 3 and 4), wherein, the skeleton atoms between two trivalent branching centers cross U, but exclude the two branching points;
wherein, $D_{Emin}$ refers to the minimum chain length between any two trivalent branching centers of $E_i$ (i=1, 2, 3 and 4);
wherein, $d_{DE}$ refers to the difference between $D_{Emax}$ and $D_{Emin}$;
wherein, $d_{E2}$ refers to the length difference between the two branches which respectively starts from one branching center of $E_i$ (i=1, 2, 3 or 4) to two oxygen atoms of the two corresponding PEG chains.

4. The eight-arm functional polyethylene glycol according to claim 3, wherein, the combination of $D_{Emax}$, $d_{DE}$ and $d_{E2}$ is selected from the group consisting of (7, 0, 1), (5, 0, 0), (6, 2, 0), (8, 2, 1), (11, 4, 1), (9, 4, 0), (11, 5, 1), (9, 5, 0), (7, 2, 0), (9, 2, 1), (9, 2, 0), (11, 5, 0), (10, 3, 0), (14, 7, 0) and (17, 11, 0).

5. The eight-arm functional polyethylene glycol according to claim 2, wherein, any linking group of U, $E_1$, $E_2$, $E_3$, $E_4$, $L_{11}$, $L_{12}$, $L_{21}$, $L_{22}$, $L_{31}$, $L_{32}$, $L_{41}$, $L_{42}$, $L_0$, G and $(Z_2)_q$—$(Z_1)q_1$ is independently a STAG group or a DEGG group, and the joint linking group formed by any aforesaid group with its adjacent group is independently a STAG group or a DEGG group; wherein, said STAG group is a linking group which keeps covalently linking with adjacent groups along the backbone therein under a condition of light illumination, heat, an enzymatic condition, an oxidation-reduction condition, a neutral condition, an acidic condition, a basic condition, a physiological condition or a simulated physiological environment in vitro, and said DEGG group is a linking group which can be degraded into at least two separate individual submoieties under a condition of light illumination, heat, an enzymatic condition, an oxidation-reduction condition, an acidic condition, a basic condition, a physiological condition or a simulated physiological environment in vitro.

6. The eight-arm functional polyethylene glycol according to claim 5, wherein, the eight-arm functional polyethylene glycol has at least one DEGG group; the distribution of the DEGG linkages is selected from the following Groups:
Group (a): wherein, g is equal to 0 or 1, U contains at least one DEGG group and the other positions are composed of STAG groups;
Group (b): wherein, g is equal to 0 or 1, the connections between U and $E_i$ (i=1, 2, 3 or/and 4) contain at least one DEGG group and the other positions are composed of STAG groups;
Group (c): wherein, g is equal to 0 or 1, $E_i$ (i=1, 2, 3 or/and 4) contain at least one DEGG group and the other positions are composed of STAG groups;
Group (d): wherein, g is equal to 0 or 1, $E_i$-$L_{i1}$-O (i=1, 2, 3 or/and 4) and $E_i$-$L_{i2}$-O (i=1, 2, 3 or/and 4) contain at least one DEGG group and the other positions are composed of STAG groups;
Group (e): wherein, g is equal to 0 or 1, —$(Z_2)_q$—$(Z_1)_{q1}$— or the connection between —$(Z_2)_q$—$(Z_1)_{q1}$— and its adjacent group towards the PEG side contains at least one DEGG group and the other positions are composed of STAG groups;

Group (f): wherein, g is equal to 1, O-$L_0$ or the connection between $L_0$ and G contains at least one DEGG group and the other positions are composed of STAG groups;

Group (g): wherein, g is equal to 1, G contains at least one DEGG group and the other positions are composed of STAG groups;

Group (h): wherein, the octavalent center $CORE_8(O\text{---})_8$ and the functional terminals are composed of STAG groups;

Group (i): wherein, the octavalent center $CORE_8(O\text{---})_8$ is composed of STAG groups and the functional terminals contain at least one DEGG group;

Group (j): wherein, the octavalent center $CORE_8(O\text{---})_8$ contains at least one DEGG group and the functional terminals are composed of STAG groups; and Group (k): wherein, the octavalent center $CORE_8(O\text{---})_8$ and the functional terminals contain at least one DEGG group;

wherein, when g is equal to 0, the functional terminals have a non-branched divalent structure —$O(Z_2)_q(Z_1)_{q1}$—; when g is equal to 1, the functional terminals have a branched structure —O-$L_0$-G-$((Z_2)q(Z_1)_{q1}\text{-})_k$.

7. The eight-arm functional polyethylene glycol according to claim 1, wherein, the eight-arm functional polyethylene glycol has a structure represented by the general formula (5), wherein, n is a value from 2 to about 2000 and the eight PEG chains all have a polydispersity or all have a monodispersity; wherein, $L_0$, G, g and k are defined the same as those in the general formula (1).

8. The eight-arm functional polyethylene glycol according to claim 1, wherein, the eight PEG chains have a polydispersity, and the number average molecular weight of each PEG chain is from about 2 kDa to about 40 kDa; wherein the term "about" refers to a range within ±10% of the value.

9. The eight-arm functional polyethylene glycol according to claim 1, wherein, the eight PEG chains have a polydispersity, and the number average molecular weight of each PEG chain is about 500, 600, 700, 800, 900, 1000, 1500, 2000, 2500, 3000, 3350, 3500, 4000, 5000, 5500, 6000, 6500, 7000,7500, 8000, 8500, 9000, 9500, 10000, 11000, 12000, 13000, 14000, 15000, 16000, 17000, 18000, 19000 or about 20000 Da; wherein, the term "about" refers to a range within ±10% of the value.

10. The eight-arm functional polyethylene glycol according to claim 1, wherein, the oxyethylene-unit number of the eight PEG chains are equal, and the oxyethylene-unit number of each PEG chain is from 2 to 70.

11. The eight-arm functional polyethylene glycol according to claim 10, wherein, the oxyethylene-unit number of each PEG chain is 2, 3, 4, 5, 6, 7, 8, 9, 10, 11, 12, 13, 14, 15, 16, 18, 20, 22, 24, 26, 27, 28, 29, 30, 32, 34, 36, 38, 40, 42, 44, 45, 46, 48, 50, 52, 54, 56, 58, 60, 62, 64, 66, 67, 68 or 70.

12. The eight-arm functional polyethylene glycol according to claim 2, wherein, $n_1$, $n_2$, $n_3$, $n_4$, $n_5$, $n_6$, $n_7$ and $n_8$ are each independently a value from 5 to about 500.

13. The eight-arm functional polyethylene glycol according to claim 2, wherein, $n_1$, $n_2$, $n_3$, $n_4$, $n_5$, $n_6$, $n_7$ and $n_8$ are each independently a value from 11 to about 500.

14. The eight-arm functional polyethylene glycol according to claim 2, wherein, $n_1$, $n_2$, $n_3$, $n_4$, $n_5$, $n_6$, $n_7$ and $n_8$ are each independently a value from 22 to about 500.

15. The eight-arm functional polyethylene glycol according to claim 1, wherein, U has a branched structure or a ring-containing structure.

16. The eight-arm functional polyethylene glycol according to claim 1, wherein, $E_1$, $E_2$, $E_3$ and $E_4$ contain identical trivalent cores selected from the group consisting of a trivalent atom core, a trivalent unsaturated bond core and a trivalent cyclic core.

17. The eight-arm functional polyethylene glycol according to claim 1, wherein, each of $E_1$, $E_2$, $E_3$ and $E_4$ is a trivalent group $E_0$ or each contains a trivalent group $E_0$; wherein, $E_0$ contains a trivalent core selected from the group consisting of an atom core $CM_3$, an unsaturated bond core $CB_3$ and a cyclic core $CC_3$; wherein, said $CM_3$ is a carbon atom core, a nitrogen atom core, a silicon atom core or a phosphorus atom core;

(5)

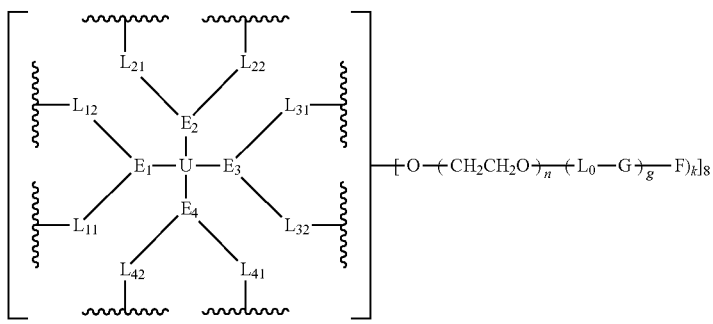

said $CB_3$ is a trivalent imine bond, a trivalent carbon-carbon double bond or >C=C=N—;

said $CC_3$ is derived from a cyclic structure selected from the group consisting of a furanose ring, a pyranose ring, benzene, tetrahydrofuran, pyrrolidine, thiazolidine, cyclohexane, cyclohexene, tetrahydropyran, piperidine, 1,4-dioxane, pyridine, pyridazine, pyrimidine, pyrazine, 1,3,5-triazine, 1,4,7-triazacyclononane, cyclotripeptides, indene, indane, indole, isoindole, purine, naphthalene, dihydroanthracene, xanthene, thioxanthene, dihydrophenanthrene, 10,11-dihydro-5H-dibenzo[a,d]cycloheptane, dibenzocycloheptene, 5-dibenzosuberenone, quinoline, isoquinoline, fluorene, carbazole, iminodibenzyl, acenaphthene, dibenzocyclooctyne, aza-dibenzocyclooctyne, the substituted form of any aforesaid cyclic structure and the heterosubstituted form of any aforesaid cyclic structure.

18. The eight-arm functional polyethylene glycol according to claim 17, wherein, $E_O$ contains one trivalent structure selected from the group consisting of
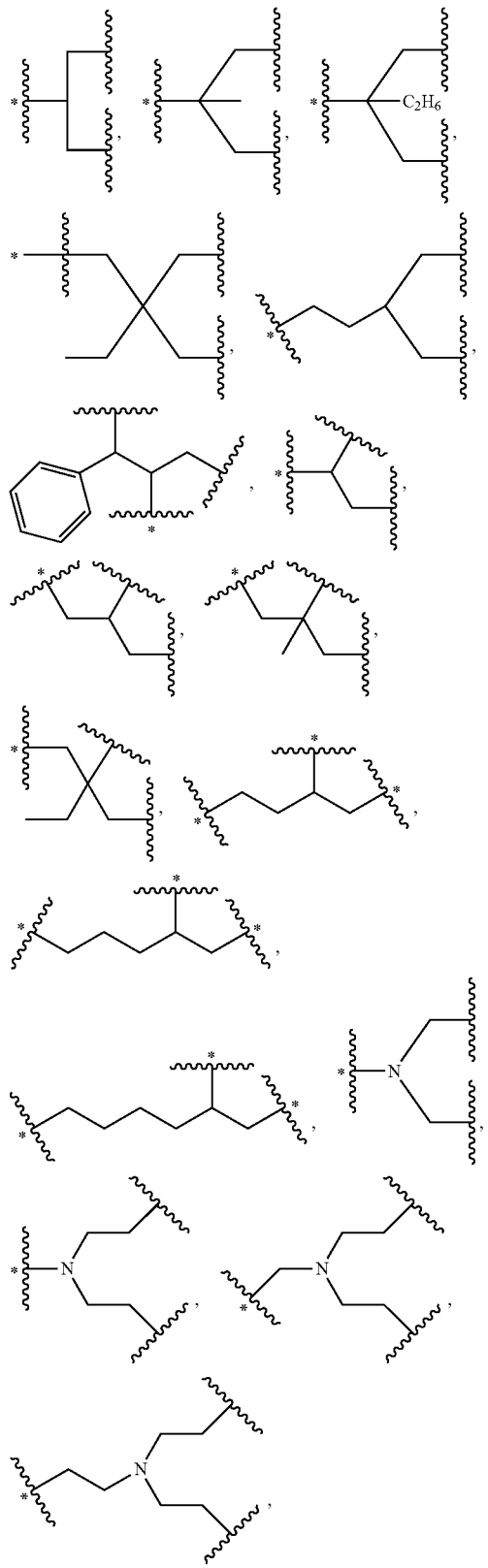
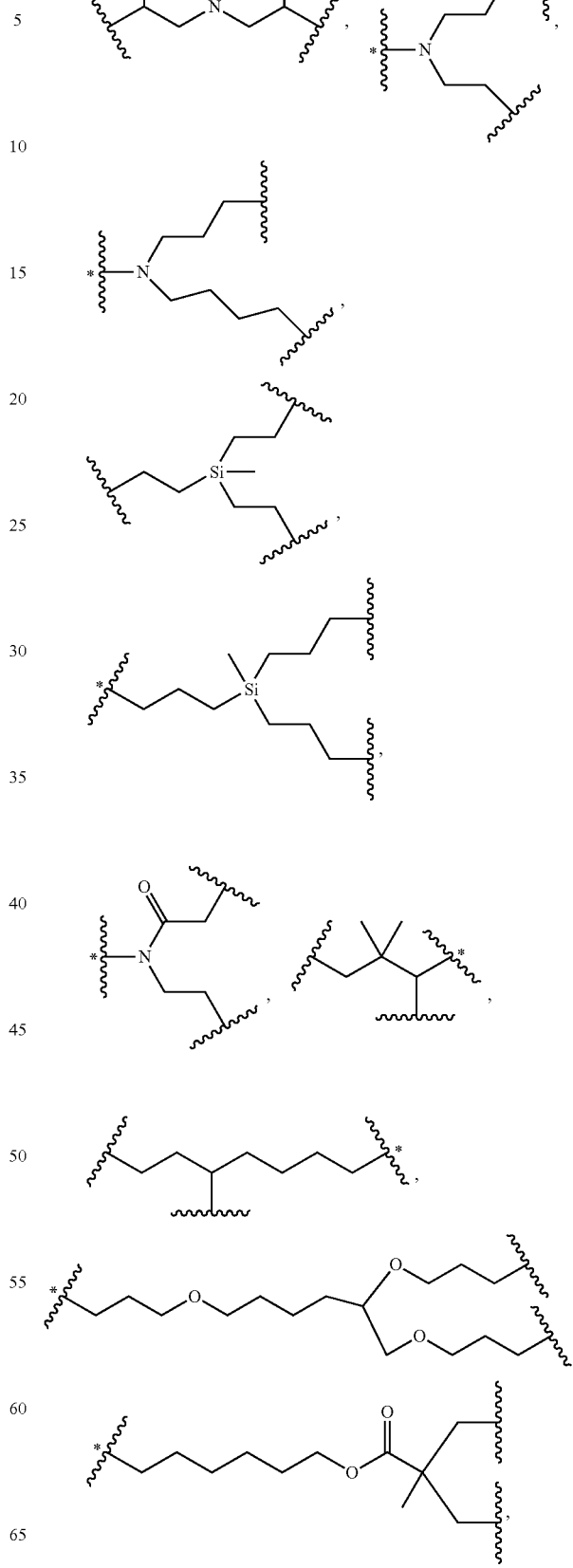

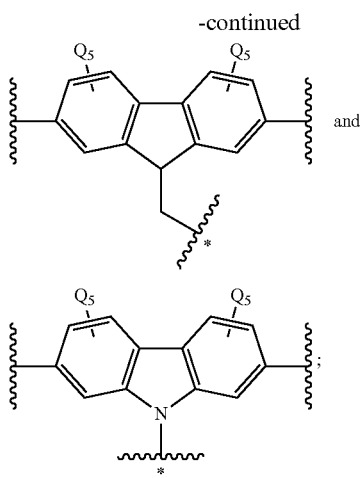

wherein, $Q_5$ is a hydrogen atom or a substituent of the ring; the number of $Q_5$ is one or more; when the number of $Q_5$ is greater than one, the $Q_5$ groups are identical or not identical; wherein, any said trivalent structure is independently end-capped or not; wherein, the number of the end-groups for end-capping is one, two or three, the end-groups are selected from the group consisting of an oxy group, a thioxy group, a secondary amino group, a divalent t-amino group and a carbonyl group, and the end-groups can be identical or not identical when more than one; wherein, the asterisk symbol "*" in the structural formulas indicates the direction towards U.

19. The eight-arm functional polyethylene glycol according to claim 17, wherein, $E_0$ is a trivalent structure selected from one of the following Groups:

Group (1) consisting of:

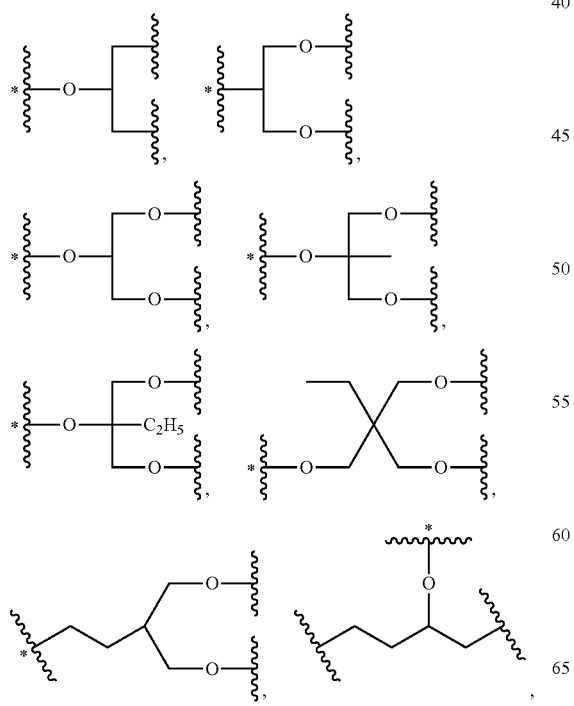

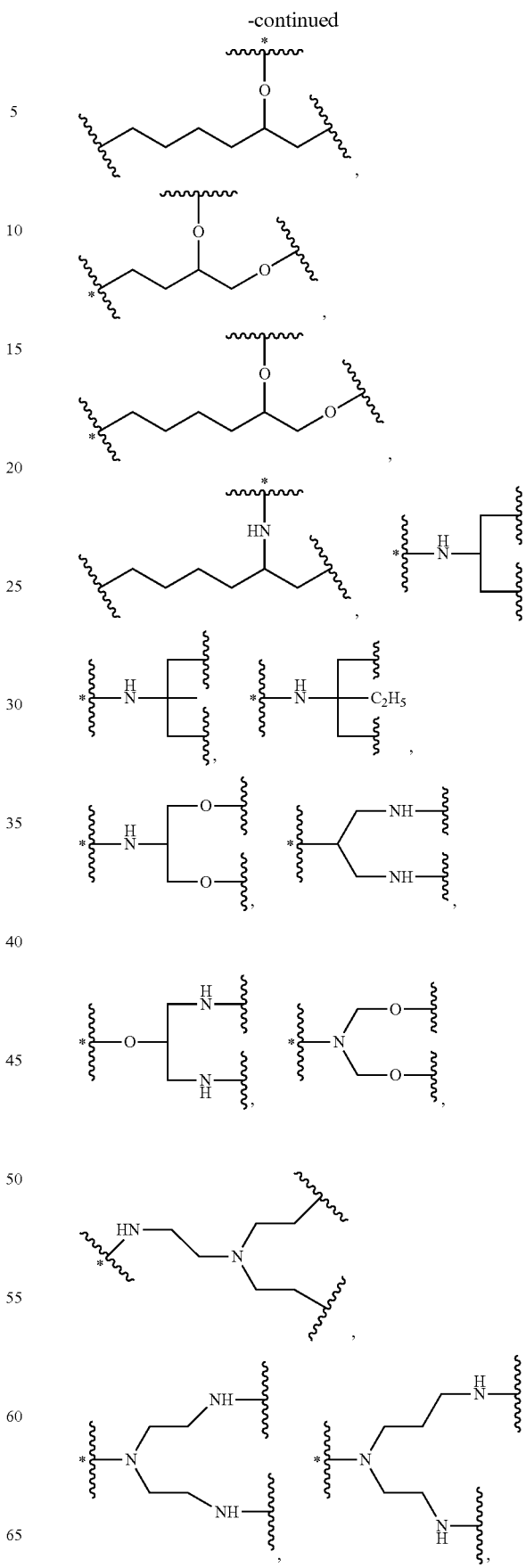

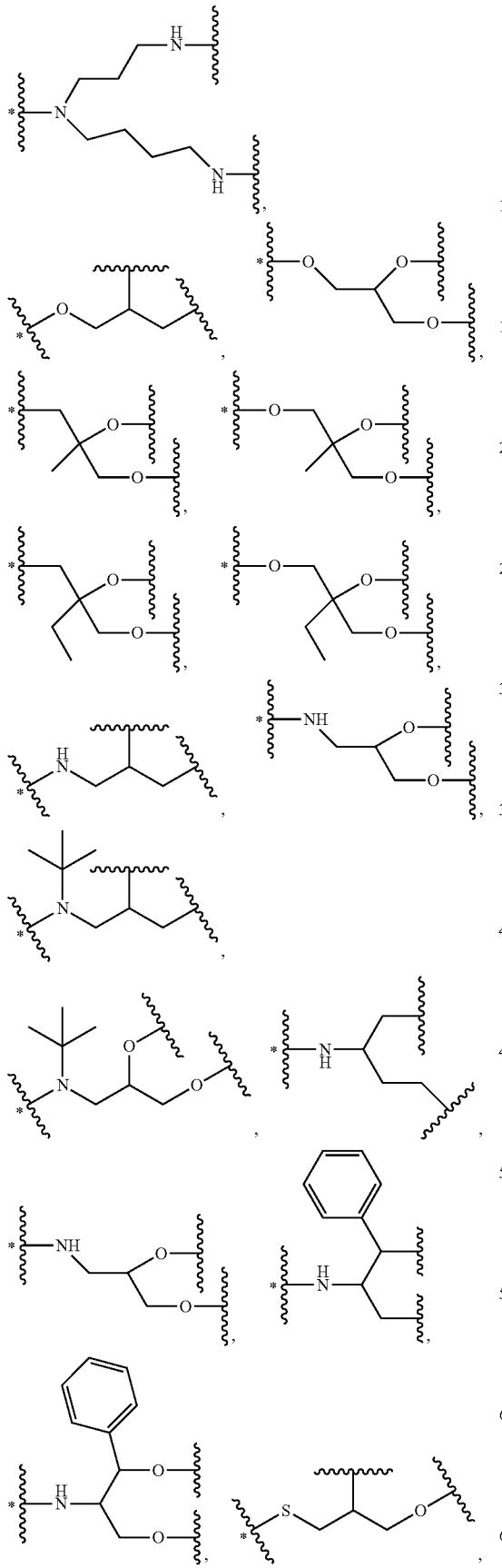
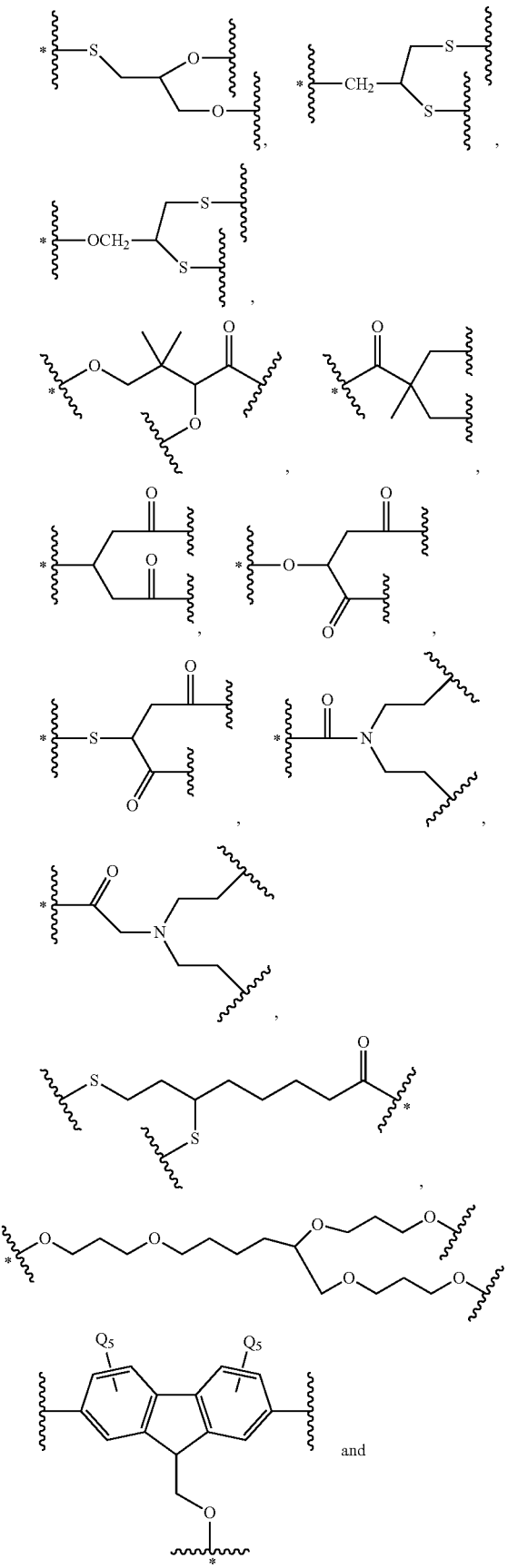

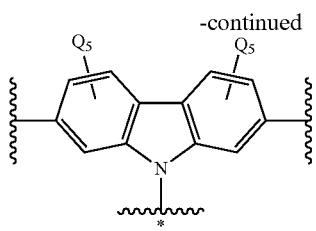

wherein, $Q_5$ is a hydrogen atom or a substituent located on the ring; the number of $Q_5$ is one or more; when the number of $Q_5$ is greater than one, the $Q_5$ groups are identical or not identical; wherein, the asterisk symbol "*" in the structural formulas indicates the direction towards U; and Group (2) consisting of trivalent skeleton structures of amino acids and derivatives thereof.

20. The eight-arm functional polyethylene glycol according to claim 1, wherein, the tetravalent central group U contains a tetravalent core selected from the group consisting of an atom core $CM_4$, an unsaturated bond core $CB_4$ and a cyclic core $CC_4$, or contains two trivalent cores.

21. The eight-arm functional polyethylene glycol according to claim 1, wherein, U is selected from one of the following Groups:

Group (1): wherein, U contains a tetravalent silicon atom core, a tetravalent carbon-carbon double bond or >C=C=C< or a cyclic core $CC_4$; wherein, $CC_4$ is derived from a cylcic structure selected from the group consisting of a furanose ring, a pyranose ring, cycleanine, a cyclic tetrapeptide, tetrahydrofuran, pyrrolidine, thiazolidine, cyclohexane, benzene, cyclohexene, tetrahydropyran, piperidine, 1,4-dioxane, pyridine, pyridazine, pyrimidine, pyrazine, indene, indane, indole, isoindole, purine, naphthalene, dihydroanthracene, xanthene, thioxanthene, dihydrophenanthrene, 10,11-5H-dihydro-dibenzo[a,d]cycloheptane, dibenzocycloheptene, 5-dibenzosuberenone, quinoline, isoquinoline, fluorene, carbazole, iminodibenzyl, tetramethyl tetrahydroindene, dipyridamole skeleton, the tetravalent skeleton of triethanedial dihydrate, the tetravalent six-membered ring of D-sorbitol skeleton with 2-hydroxyl group and 4-hydroxyl group being protected, the substituted form of any aforesaid cyclic structure and the heterosubstituted form of any aforesaid cyclic structure;

Group (2): wherein, U is a tetravalent group $U_0$ or contains a tetravalent group $U_0$, wherein, $U_0$ is a tetravalent group selected from the group consisting of

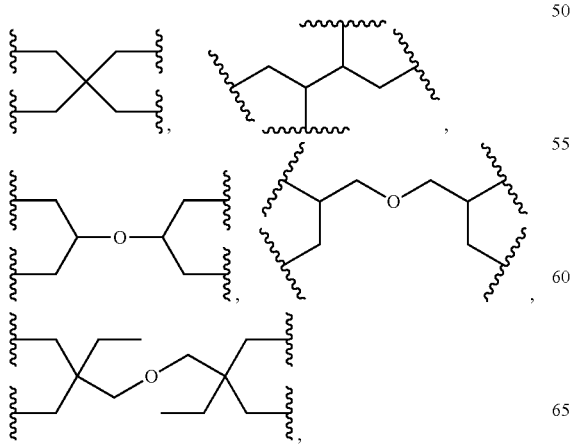

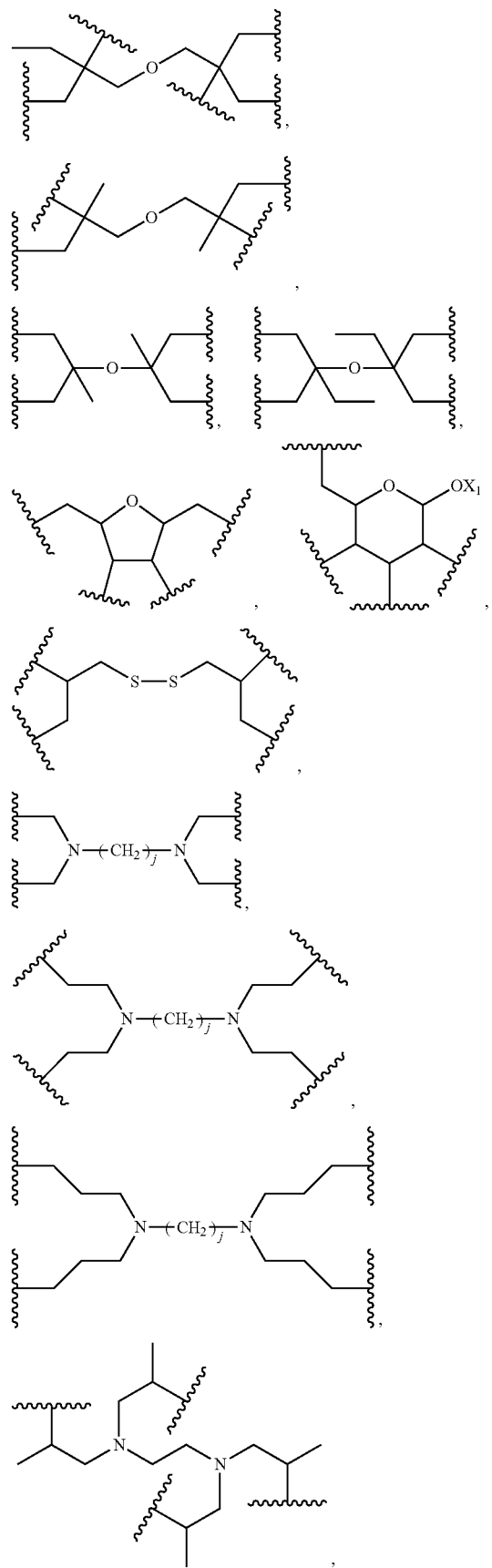

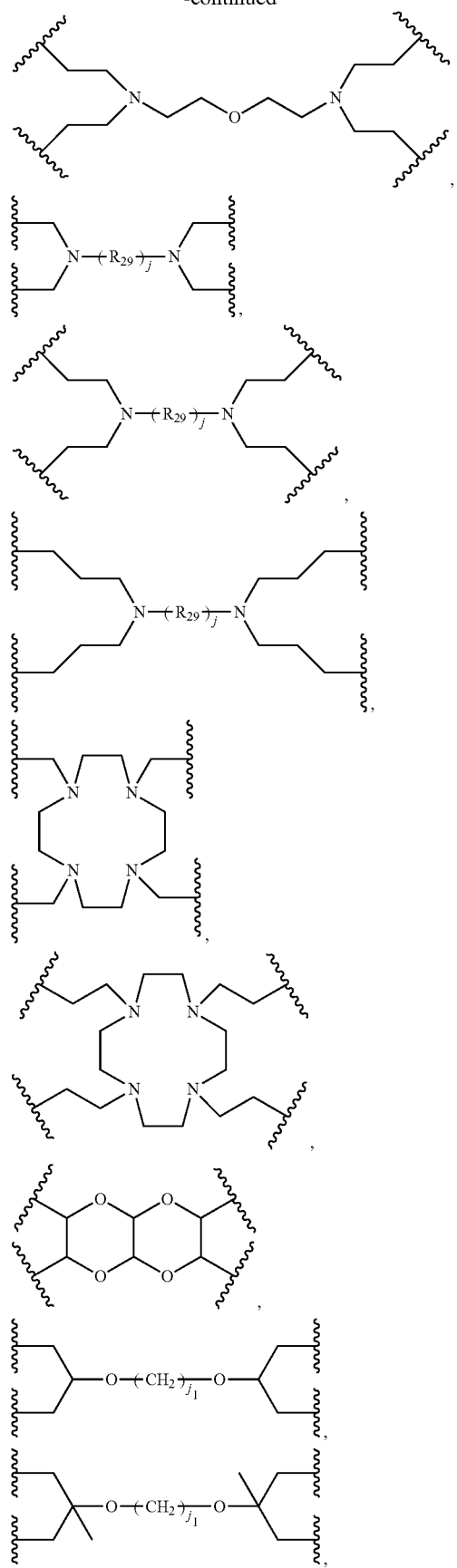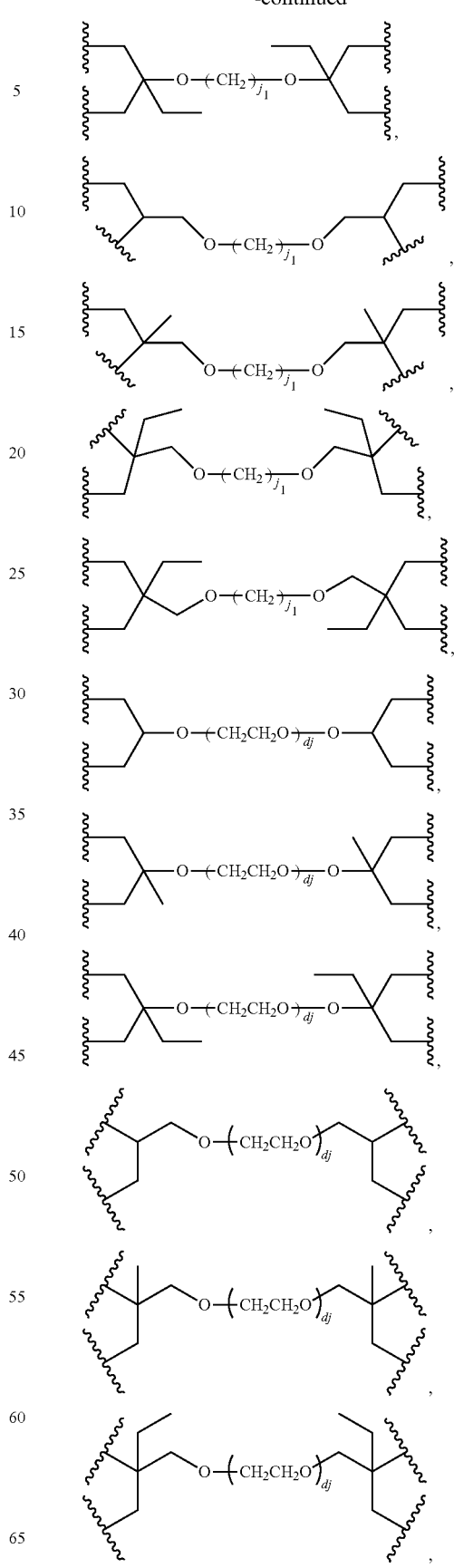

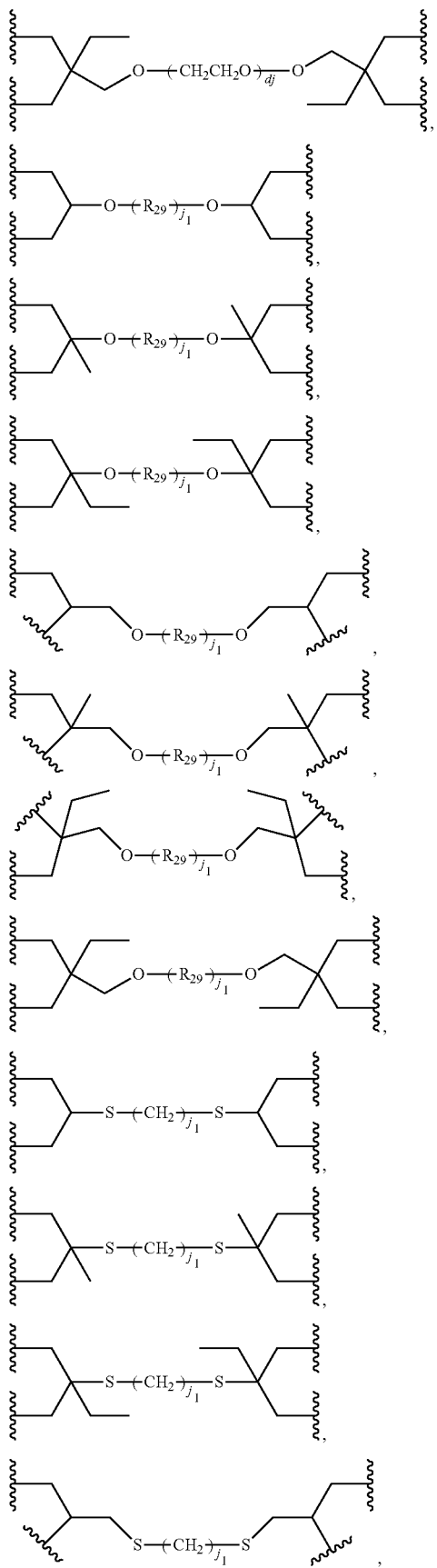

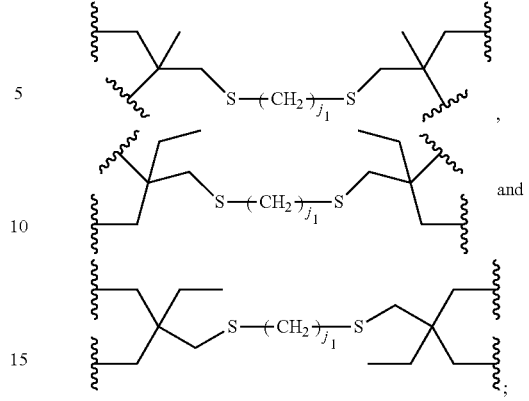

wherein, j is an integer from 2 to 20;
wherein, $j_1$ is an integer from 2 to 20;
wherein, dj is a value from 1 to 70;
wherein, $R_{29}$ is a $C_{3-20}$ alkylene group;
wherein, $X_1$ is selected from the group consisting of a $C_{1-10}$ alkyl group, an allyl group, a trityl group, a phenyl group, a benzyl group, a methylbenzyl group, a 1-ethoxyethyl group, a 2-ethoxyethyl group, a methoxyethoxymethyl group, a benzyloxymethyl group, a (methylthio)methyl group, a tetrahydropyranyl group, a nitrobenzyl group, a 4-methoxybenzyl group, a trifluoromethyl benzyl group, a t-butoxycarbonyl group, a phenoxycarbonyl group, a benzyloxycarbonyl group, an acetyl group and a trifluoroacetyl group;
Group (3): wherein, U is constructed by terminating a $U_0$ group with four identical or different divalent linking groups selected from the group consisting of an oxy group, a thioxy group, a secondary amino group and a divalent t-amino group;
Group (4): wherein, U is constructed by terminating a $U_0$ group with four carbonyl groups;
Group (5): wherein, U is constructed by terminating a $U_0$ group with four identical divalent skeletons derived from glycine, alanine, valine, leucine, isoleucine, phenylalanine, proline, sarcosine, β-alanine or $H_2N(CH_2)_{j_1}COOH$; and
Group (6): wherein, U is constructed by a bifunctional small molecule and two identical $E_0$ groups via a direct or indirect combination, wherein, the bifunctional small molecule is selected from the group consisting of a diol, a diamine, a dithiol, a dicarboxylic acid, a diisocyanate, a disuccinimidyl active diester, a dihalide, a diazide, a diacyl halide, a dihydrazide, a dialdehyde, a compound with two dichloroformate groups, a dimaleimide, a disuccinate, a dicyanide, a dialkyne, a dialkene and a dialdoxime; wherein, the indirect combination is achieved by using a spacer group $L_{10}$, and $L_{10}$ is a single-atom divalent group, a hydrocarbylene group or a heteroatom-containing divalent group; the number of $L_{10}$ is one or more; when the number of $L_{10}$ is greater than one, the $L_{10}$ groups are the same or different; wherein, $E_0$ is defined the same as that in claim 19.

22. The eight-arm functional polyethylene glycol according to claim 21,
Group (1): wherein, the branching center of U and branching centers of $E_1$, $E_2$, $E_3$ and $E_4$ are selected from the group consisting of a tetravalent carbon-atom center, a tetravalent silicon-atom center, a trivalent carbon-atom center, a trivalent nitrogen-atom center, a trivalent active-hydrogen-free silicon-atom center, a trivalent fluorene core, a trivalent carbazole core, a trivalent saturated six-membered carbon ring, a trivalent phenyl group, a trivalent naphthyl group, a trivalent azaphenyl group, a trivalent five-membered oxa-ring, a trivalent quinolyl group, a tetravalent five-membered oxa-ring, a tetravalent D-furanose ring, a tetravalent D-pyranose ring, a tetravalent saturated six-membered dioxa-ring, a tetravalent skeleton of triethanedial dihydrate, a tetravalent six-membered ring of D-sorbitol skeleton with 2- and 4-hydroxyl groups being protected, and substituted forms of the aforesaid branching centers substituted by active-hydrogen-free monovalent end-groups;

Group (2): wherein, CORE is combined by a U group and four trivalent amino acid skeletons, wherein, the trivalent amino acid skeletons are selected from the group consisting of lysine skeletons, aspartic acid skeletons and glutamic acid skeletons;

Group (3): wherein, U is a $U_0$ group, and $E_1$, $E_2$, $E_3$ and $E_4$ have the same structure; CORE is combined by $U_0$ and $E_1$, $E_2$, $E_3$ and $E_4$ via four identical divalent skeletons derived from glycine, alanine, valine, leucine, isoleucine, phenylalanine, proline, sarcosine, β-alanine or $H_2N(CH_2)_{j1}COOH$;

Group (4): wherein, U is a $U_0$ group, and $E_1$, $E_2$, $E_3$ and $E_4$ have the same structure selected from the group consisting of

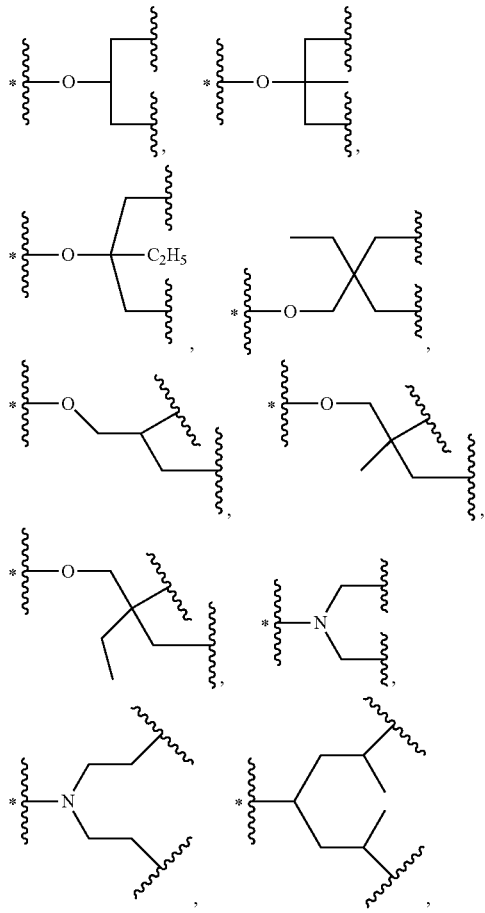

-continued

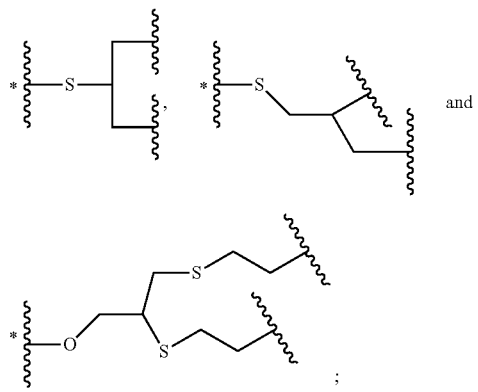

Group (5): wherein, CORE is combined by a U group and four identical trivalent groups respectively via a divalent linking group; wherein, U is selected from the group consisting of

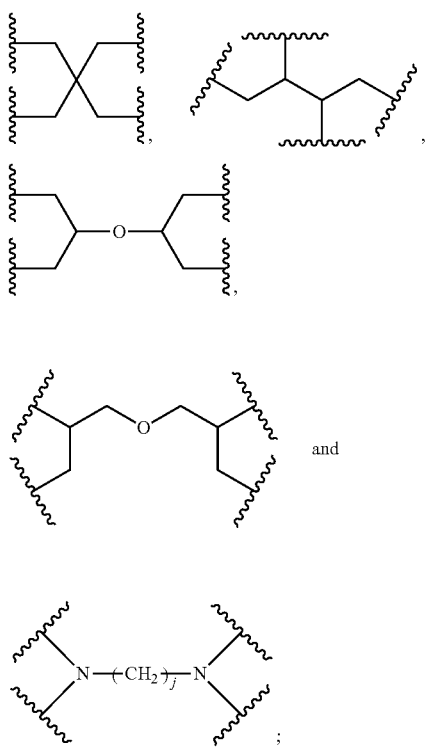

wherein, the trivalent group is selected from the group consisting of

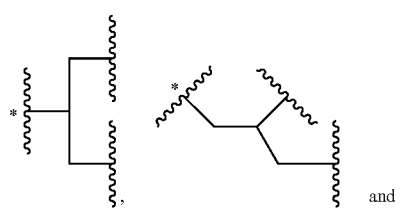

563
-continued

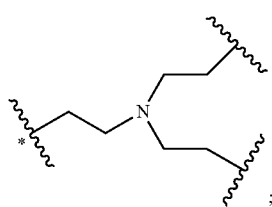

wherein, the divalent linking group is selected from the group consisting of an oxy group, a thioxy group, an amino group, an ester bond, an amide bond, a urethane bond, a urea bond, a carbonate bond, a thioester bond, a thiocarboxylate bond, an acetal linkage, a thioacetal linkage, an oxime bond, a dithioester bond and a trithioester bond;

Group (6): wherein, U is

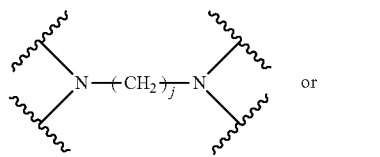 or

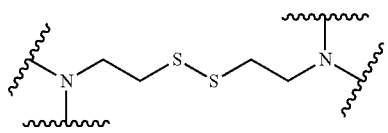, and $E_1$, $E_2$, $E_3$ and $E_4$ have the same structure selected from the group consisting of

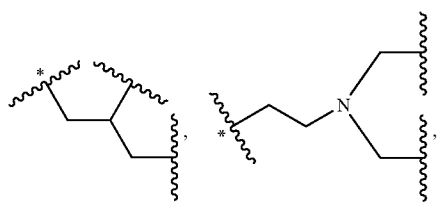

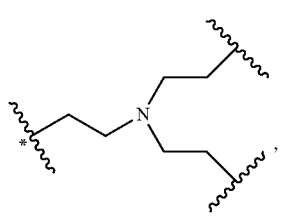

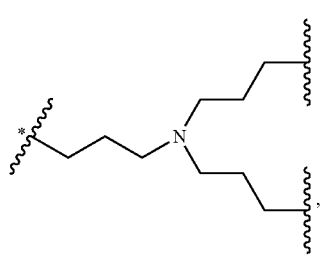

564
-continued

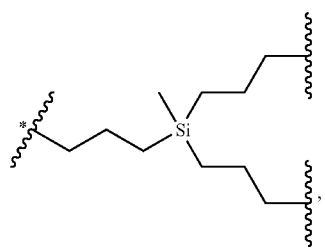

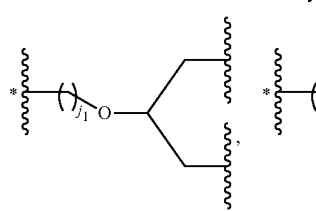

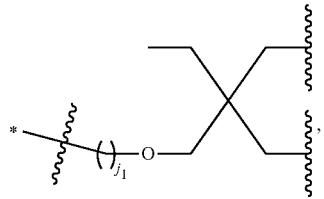

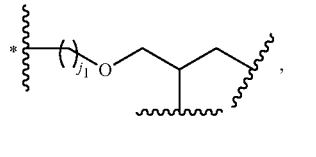

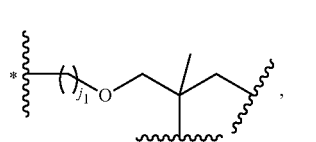

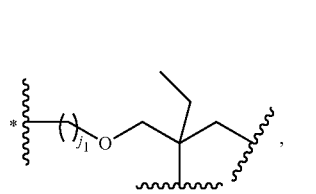

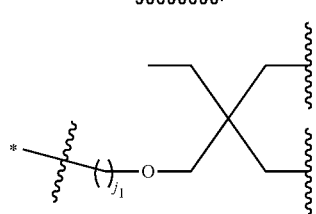

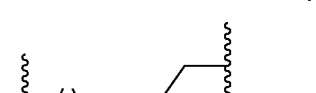

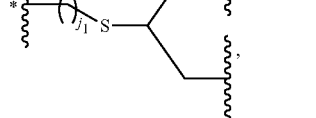

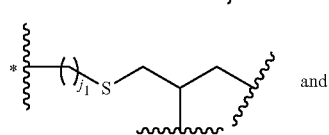 and

-continued
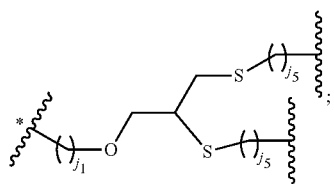
wherein, $j_5$ is an integer from 2 to 20, and $j_1$ and $j_5$ are the same or different in one molecule;
Group (7): wherein, U is selected from the group consisting of
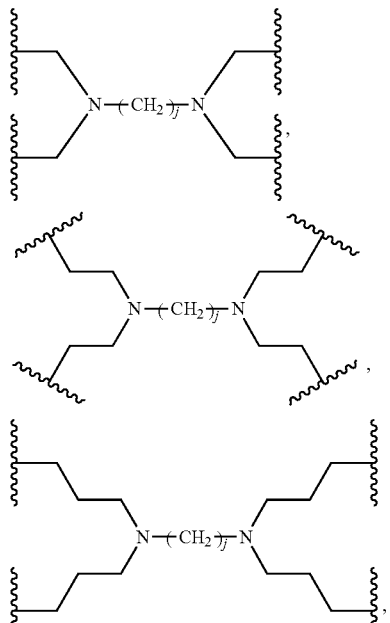
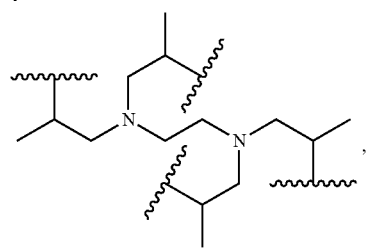
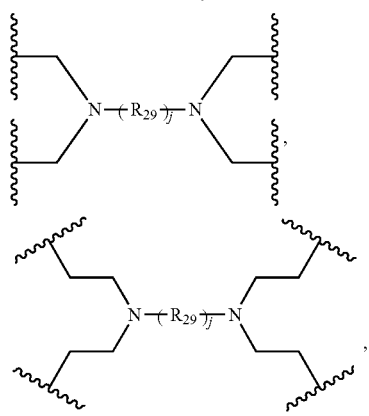
-continued
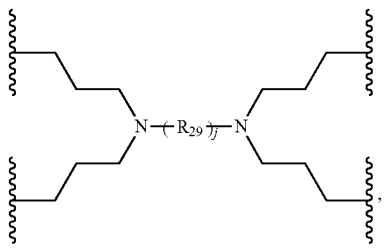
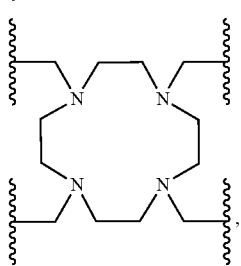
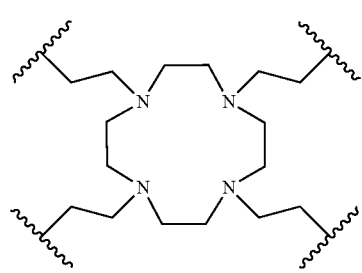
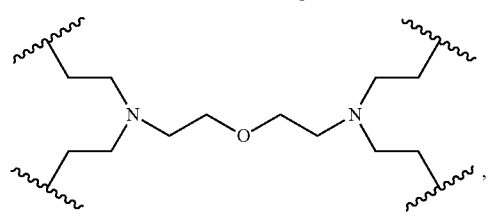
and $E_1$, $E_2$, $E_3$ and $E_4$ have the same structure selected from the group consisting of
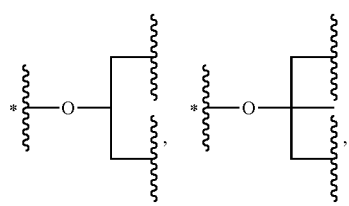
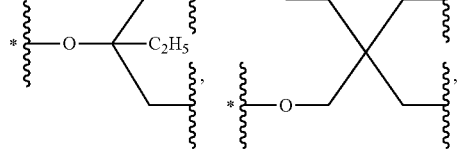
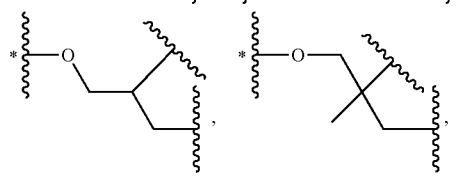

-continued

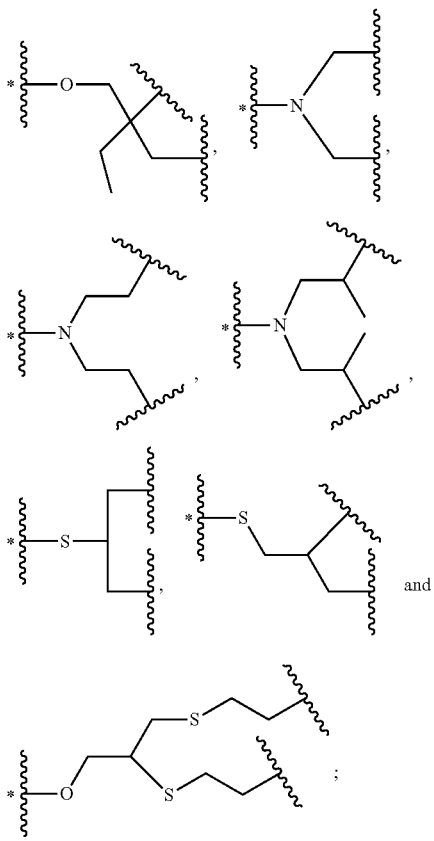

Group (8): wherein, U is constructed by connecting a diol with two trivalent groups having the same structure selected from the group consisting of

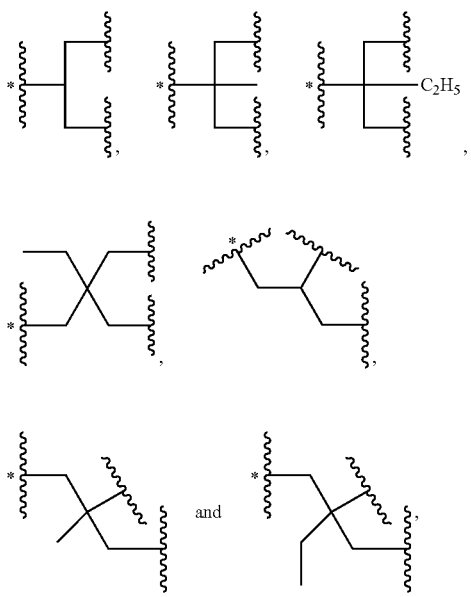

and $E_1$, $E_2$, $E_3$ and $E_4$ have the same structure selected from the group consisting of

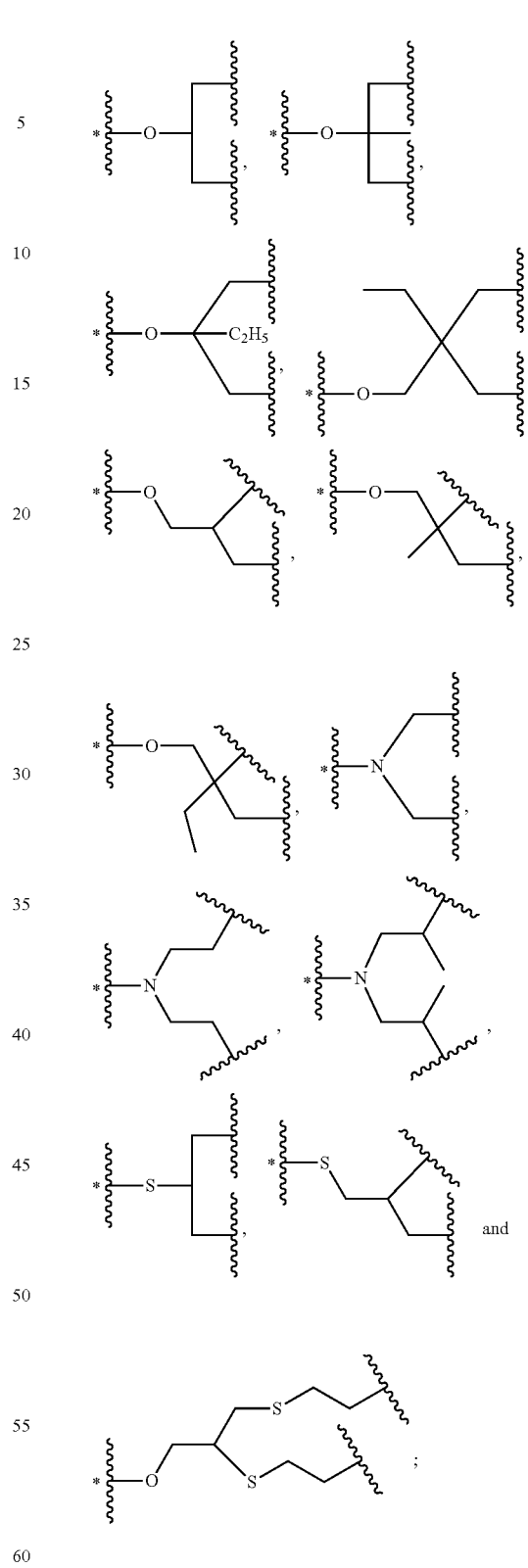

wherein, the diol is a $C_{2-20}$ hydrocarbondiol or an oligomer or polymer of small molecule diols;

Group (9): wherein, U is a tetravalent residue group of a hydrocarbon-bis(primary amine), and $E_1$, $E_2$, $E_3$ and $E_4$ have the same structure of

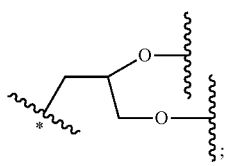 [SMILES: *CC(CO*)O*]

and

Group (10): wherein, $CORE_8$ contains no $O(CH_2CH_2O)_{j3}$ segment, wherein, $j_3$ is greater than or equal to 10.

23. The eight-arm functional polyethylene glycol according to claim 1, wherein, $L_{11}$, $L_{12}$, $L_{21}$, $L_{22}$, $L_{31}$, $L_{32}$, $L_{41}$ and $L_{42}$ are all absent, or $L_{11}$, $L_{12}$, $L_{21}$, $L_{22}$, $L_{31}$, $L_{32}$, $L_{41}$ and $L_{42}$ are all present with the same structure in one molecule.

24. The eight-arm functional polyethylene glycol according to claim 22, wherein, $CORE_8$ is selected from one of the following Groups:

Group (1): wherein, $CORE_8$ is selected from the group consisting of:

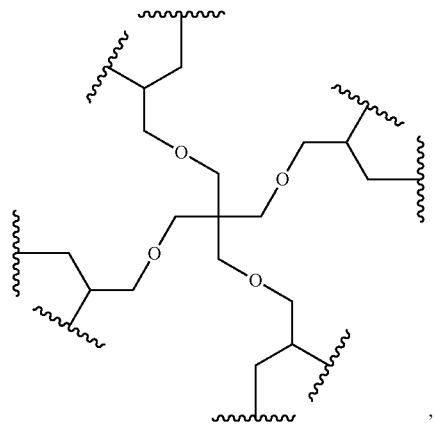

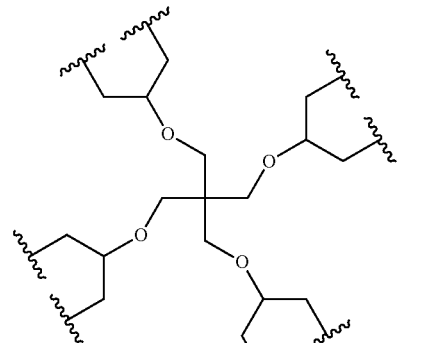

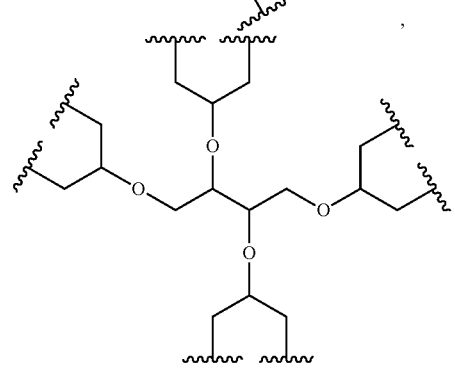

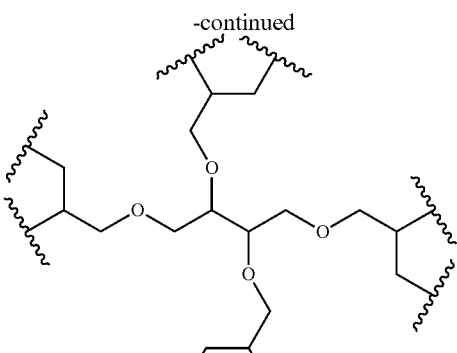

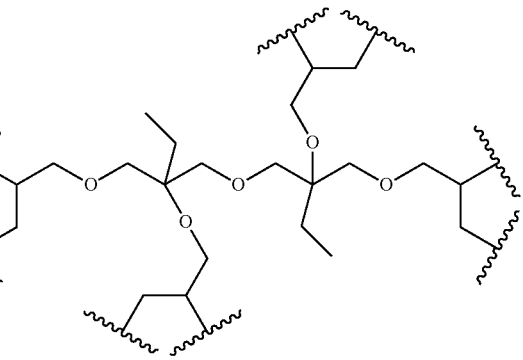

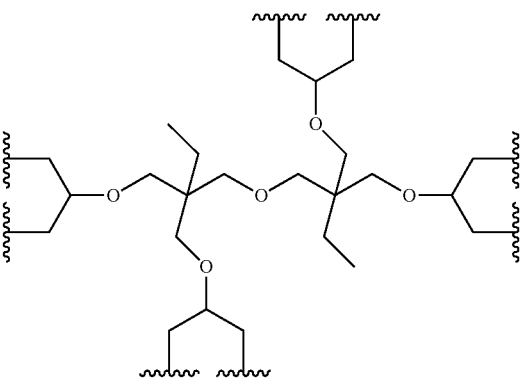

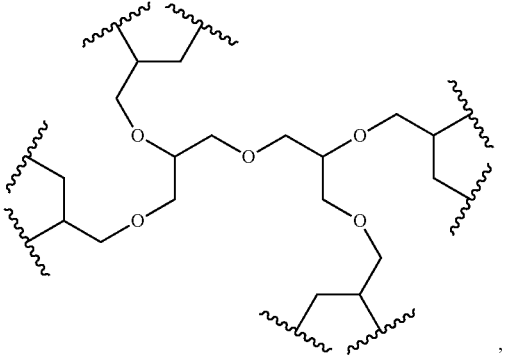

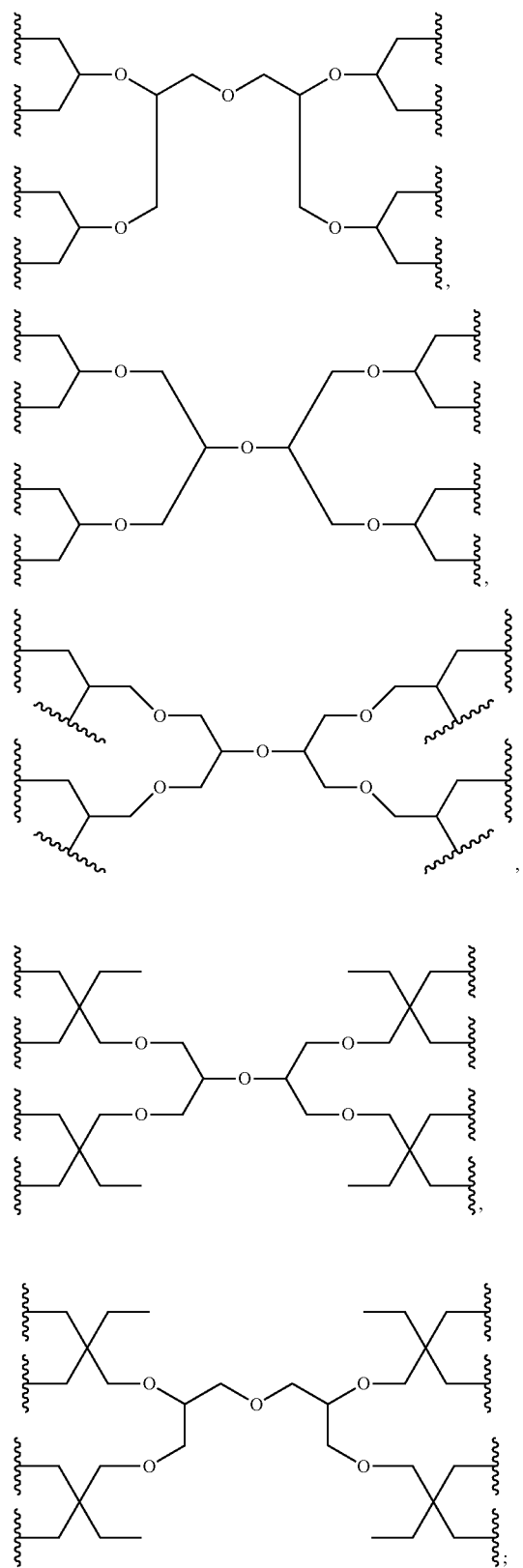
Group (2): wherein, U is constructed by —O(CH₂CH₂O)$_{dj}$— and two identical trivalent groups selected from the group consisting of
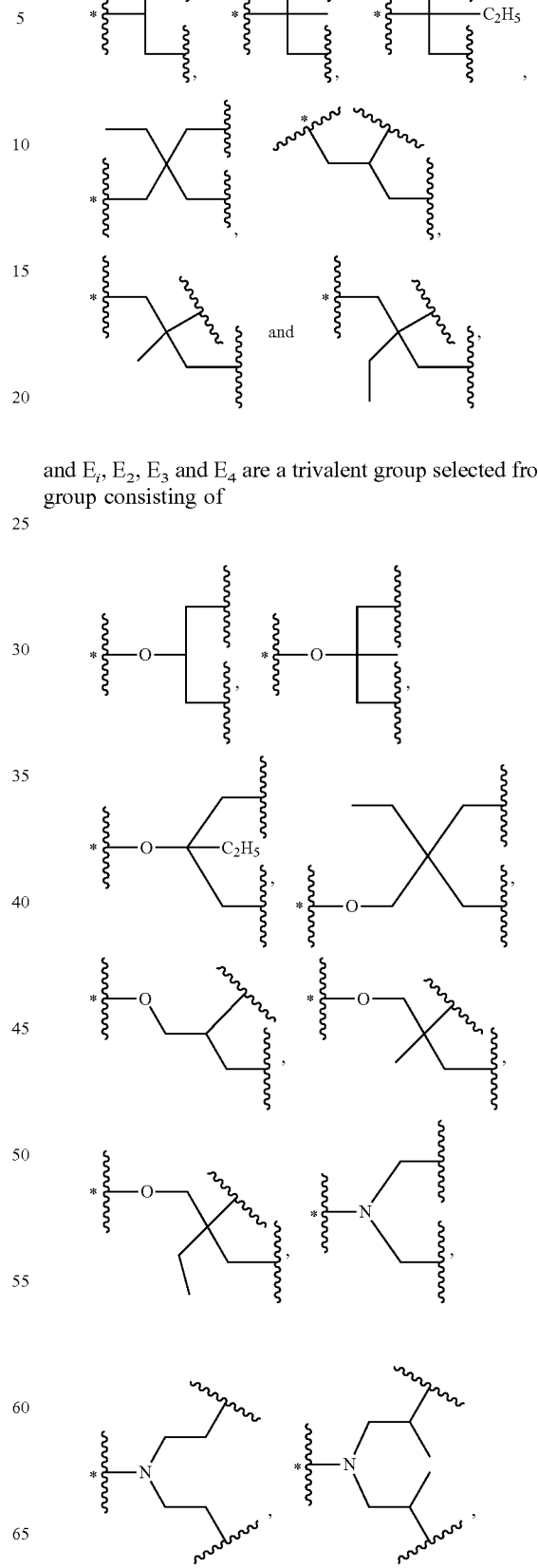
and $E_i$, $E_2$, $E_3$ and $E_4$ are a trivalent group selected from the group consisting of -continued

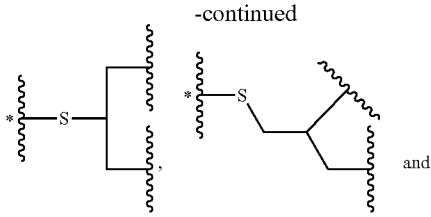
and

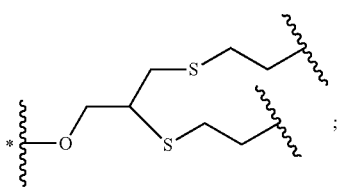

Group (3): wherein, U is

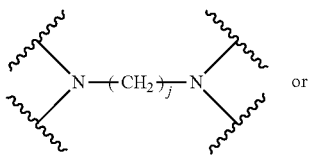 or

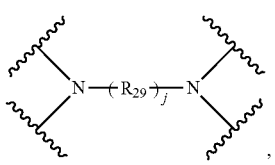

$E_1$, $E_2$, $E_3$ and $E_4$ have the same structure of

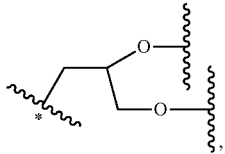 [SMILES: *CC(CO*)O*]

and $L_{11}$, $L_{12}$, $L_{21}$, $L_{22}$, $L_{31}$, $L_{32}$, $L_{41}$ and $L_{42}$ are all absent; and Group (4): wherein, heteroatom-containing linking groups in $CORE_8$ are independently selected from the group consisting of an oxy group, a thioxy group, a trivalent t-amino group, a divalent t-amino group, a secondary amino group, a divalent active-hydrogen-free silyl group and a trivalent active-hydrogen-free silyl group; the species of heteroatom-containing linking groups in $CORE_8$ is one or more, and the quantity of each species is one or more.

25. The eight-arm functional polyethylene glycol according to claim 2, wherein, g is equal to 1, and G has a branched structure, a ring-containing structure, a comb-like structure, a dendritic structure or a hyperbranched structure.

26. The eight-arm functional polyethylene glycol according to claim 2, wherein, g is equal to 1, and G is a (k+1)-valent group selected from one of the following Groups:

Group (1): wherein, all the k values are equal to 2, and $L_0$-G is a trivalent group;

Group (2): wherein, all the k values are equal to 3, and G contains a tetravalent core selected from the group consisting of an atom core $CM_4$, an unsaturated bond core $CB_4$ and a cyclic core $CC_4$, or contains two trivalent cores; wherein;

said $CM_4$ is a tetravalent carbon atom core or a tetravalent silicon atom core;

said $CB_4$ is a tetravalent carbon-carbon double bond or >C=C=C<;

said $CC_4$ is derived from a cylcic structure selected from the group consisting of a furanose ring, a pyranose ring, cycleanine, a cyclic tetrapeptide, tetrahydrofuran, pyrrolidine, thiazolidine, cyclohexane, benzene, cyclohexene, tetrahydropyran, piperidine, 1,4-dioxane, pyridine, pyridazine, pyrimidine, pyrazine, indene, indane, indole, isoindole, purine, naphthalene, dihydroanthracene, xanthene, thioxanthene, dihydrophenanthrene, 10,11-5H-dihydro-dibenzo[a,d]cycloheptane, dibenzocycloheptene, 5-dibenzosuberenone, quinoline, isoquinoline, fluorene, carbazole, iminodibenzyl, tetramethyl tetrahydroindene, dipyridamole skeleton, the tetravalent skeleton of triethanedial dihydrate, the tetravalent six-membered ring of D-sorbitol skeleton with 2- and 4-hydroxyl groups being protected, the substituted form of any aforesaid cyclic structure and the heterosubstituted form of any aforesaid cyclic structure;

Group (3): wherein, k is equal to or greater than 3, and G is combined directly by lower-valent groups with a valence from 3 to k in quantities of 2 to k−1, or is combined indirectly via one or more divalent spacer groups $L_{10}$; the lower-valent groups of 3- to k-valence are identical or not identical in structure, and identical or not identical in valence; wherein, $L_{10}$ is a single-atom divalent group, a hydrocarbylene group or a heteroatom-containing divalent group; the number of $L_{10}$ is one or more; when the number of $L_{10}$ is greater than one, the $L_{10}$ groups are the same or different;

Group (4): wherein, k is equal to or greater than 3, and G contains a (k+1)-valent cyclic core structure; and Group (5): wherein, k is equal to or greater than 4, and G is constructed via a direct or indirect combination, wherein, the combination manner is a comb-like manner, a dendritic manner, a branched manner, a hyperbranched manner or a cyclic manner.

27. The eight-arm functional polyethylene glycol according to claim 2, wherein, g is equal to 1, and G is selected from one of the following Groups:

Group (1): wherein, k is equal to 2, and $L_0$-G contains one structure selected from the group consisting of

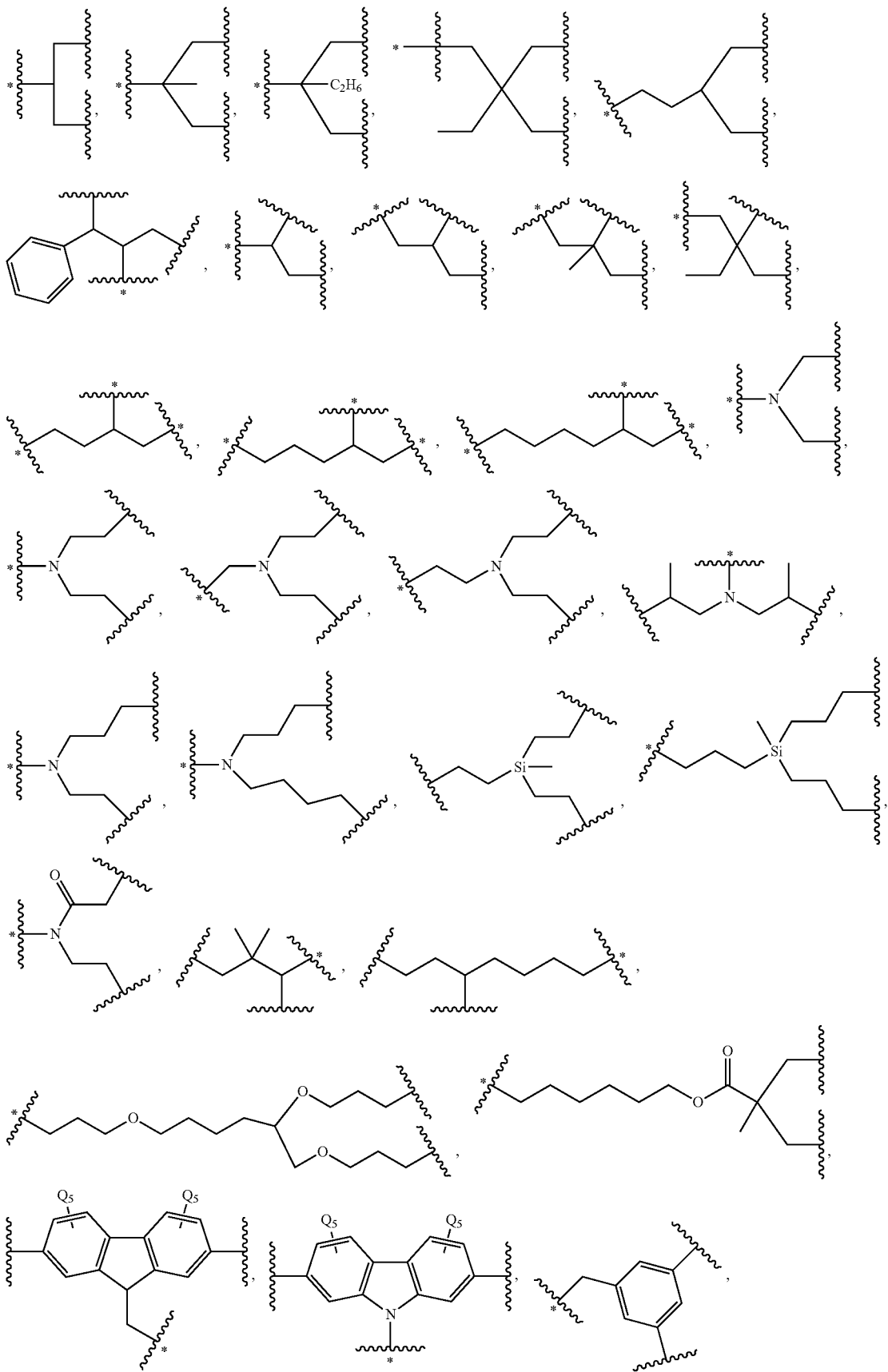

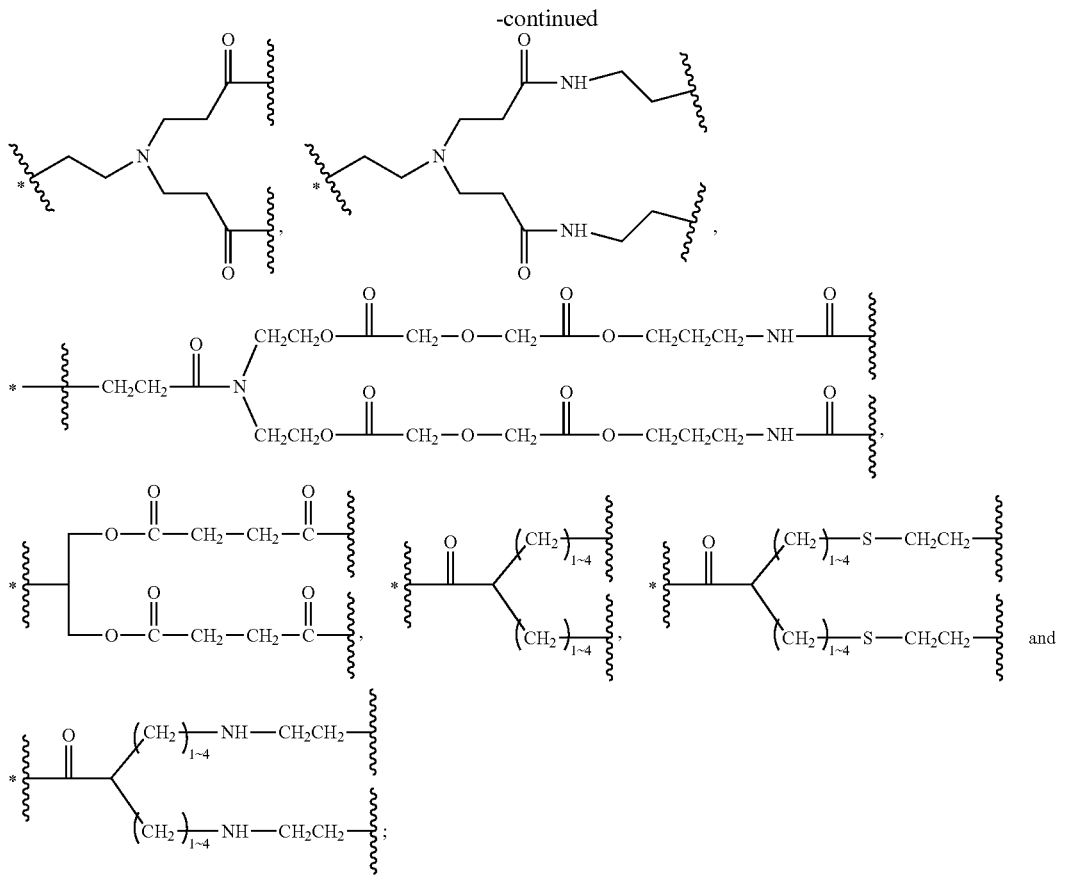

wherein, $Q_5$ is a hydrogen atom or a substituent of the ring; the number of $Q_5$ is one or more; when the number of $Q_5$ is greater than one, the $Q_5$ groups are identical or not identical; wherein, any said trivalent structure is independently end-capped or not; wherein, the number of the end-groups for end-capping is one, two or three, the end-groups are selected from the group consisting of an oxy group, a thioxy group, a secondary amino group, a divalent t-amino group and a carbonyl group, and the end-groups can be identical or not identical when more than one; wherein, the asterisk symbol "*" in the structural formulas indicates the direction towards U;

Group (2): wherein, k is equal to 3, and $L_0$-G contains one structure selected from the group consisting of:

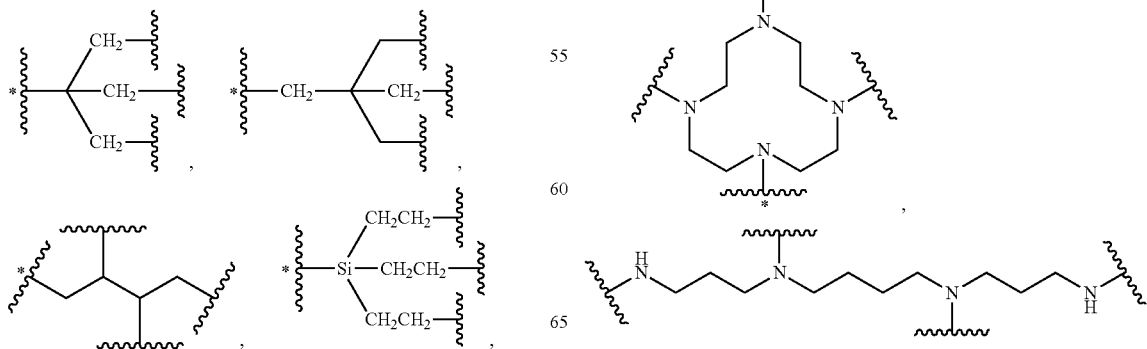

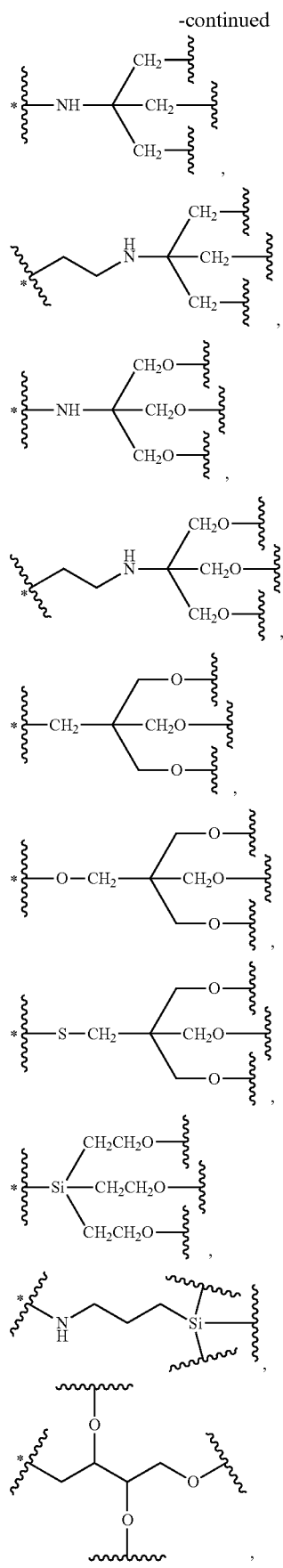
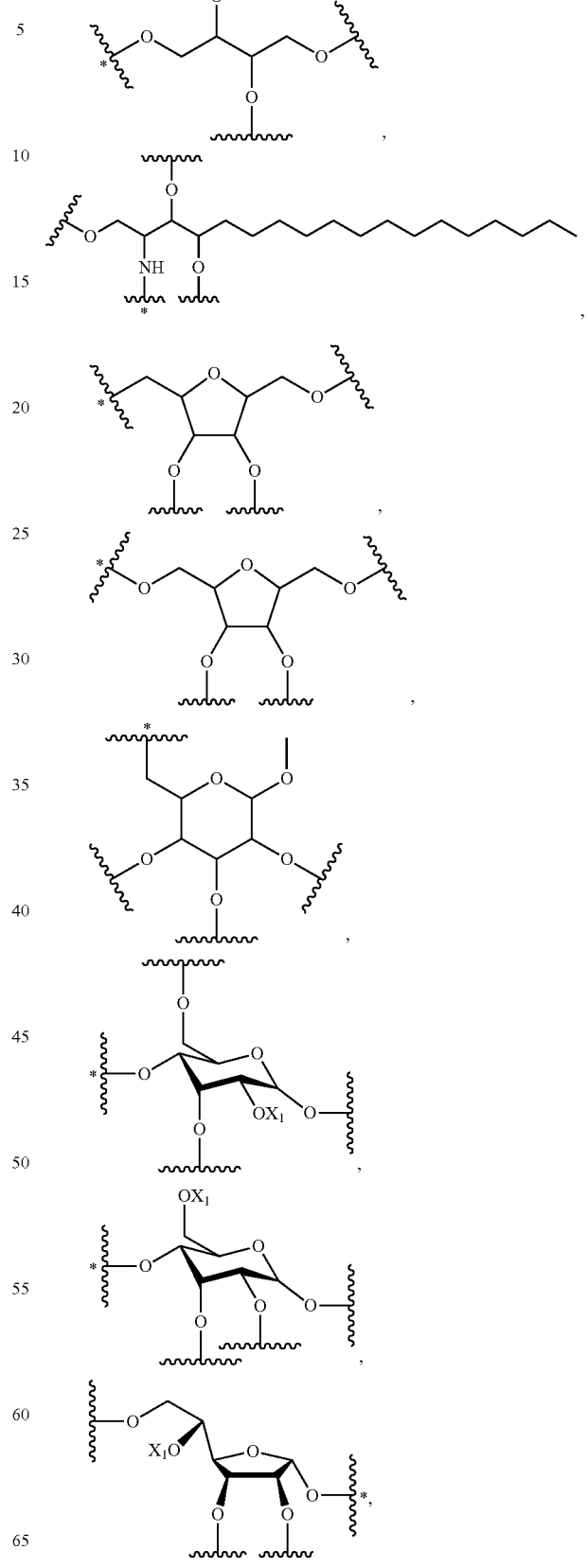

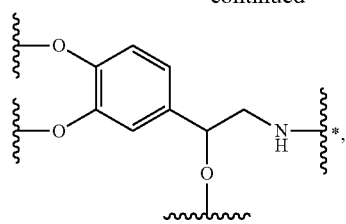
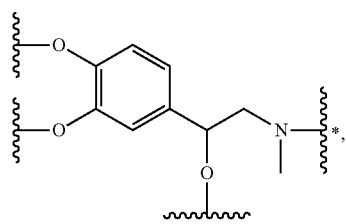
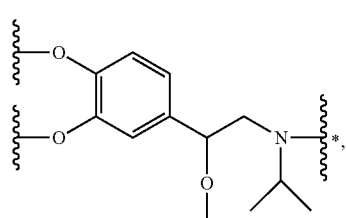
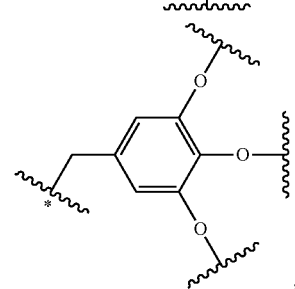
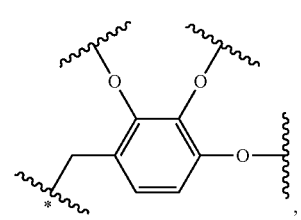
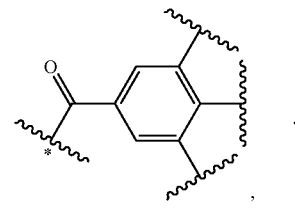
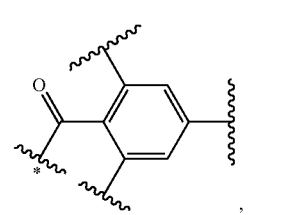
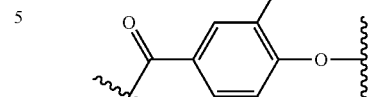
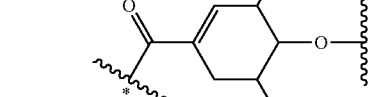
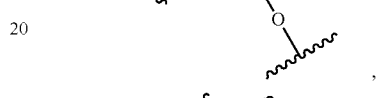
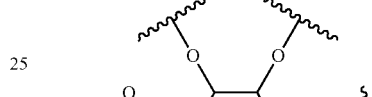
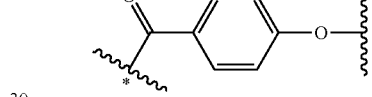
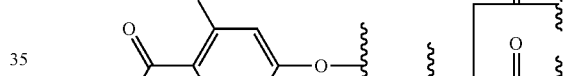
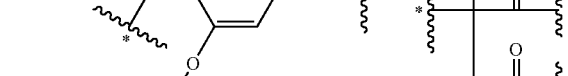
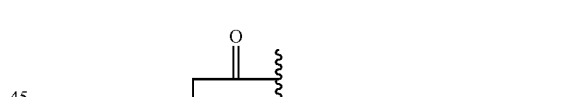
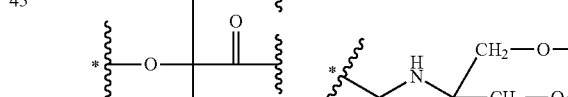
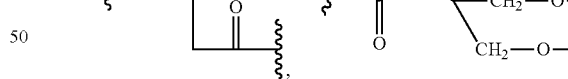
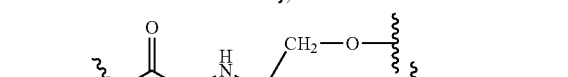
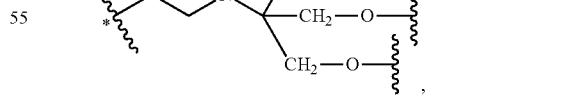
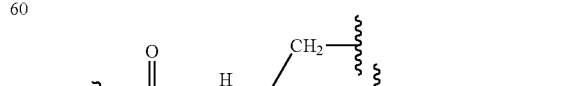

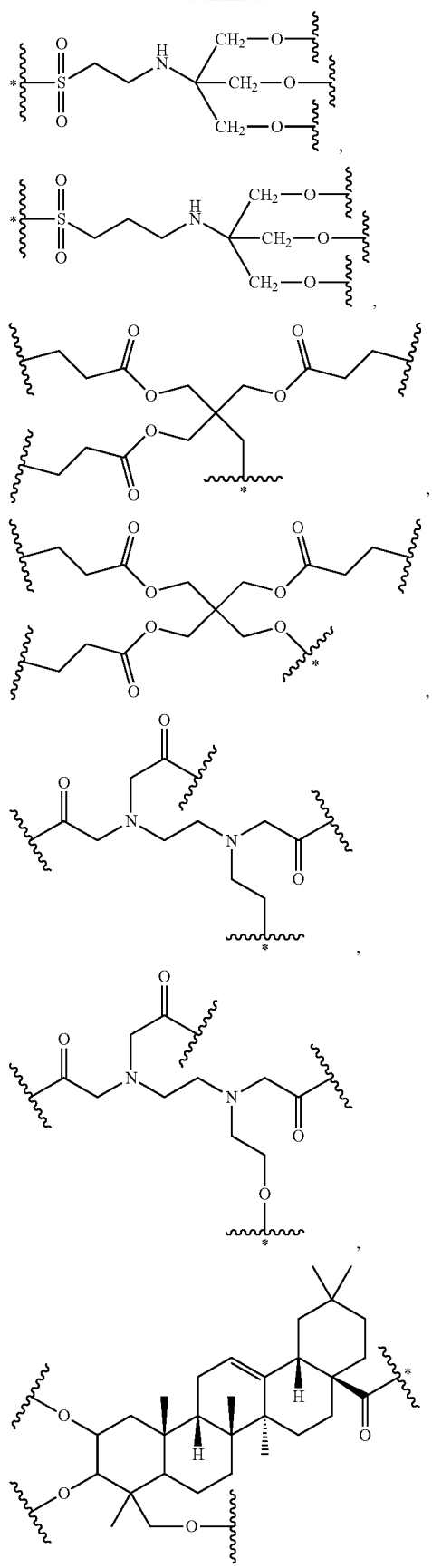

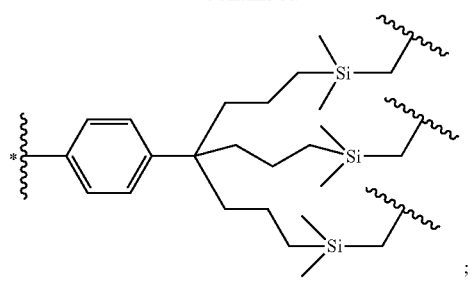

wherein, $X_1$ is selected from the group consisting of a $C_{1-10}$ alkyl group, an allyl group, a trityl group, a phenyl group, a benzyl group, a methylbenzyl group, a 1-ethoxyethyl group, a 2-ethoxyethyl group, a methoxyethoxymethyl group, a benzyloxymethyl group, a (methylthio)methyl group, a tetrahydropyranyl group, a nitrobenzyl group, a 4-methoxybenzyl group, a trifluoromethyl benzyl group, a t-butoxycarbonyl group, a phenoxycarbonyl group, a benzyloxycarbonyl group, an acetyl group and a trifluoroacetyl group; and Group (3): wherein, k is equal to or greater than 4, and $L_0$-G contains one structure selected from the group consisting of:

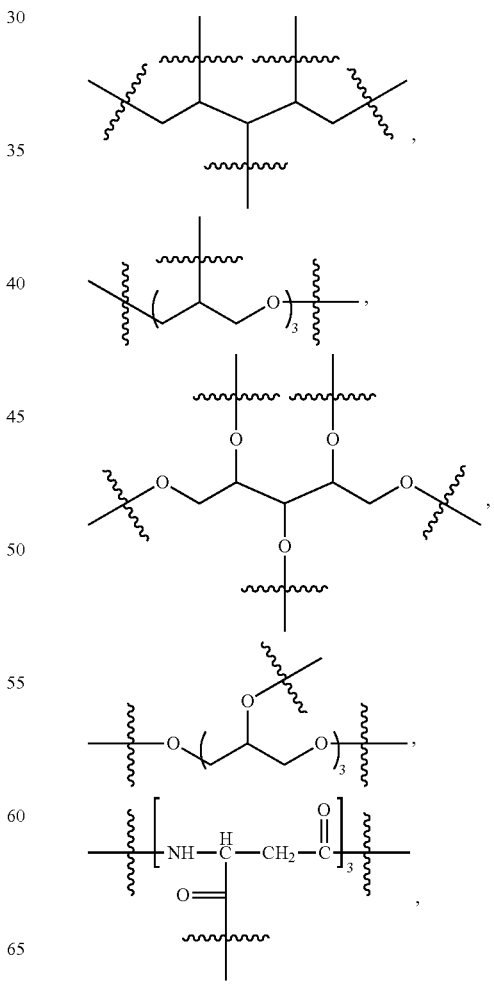

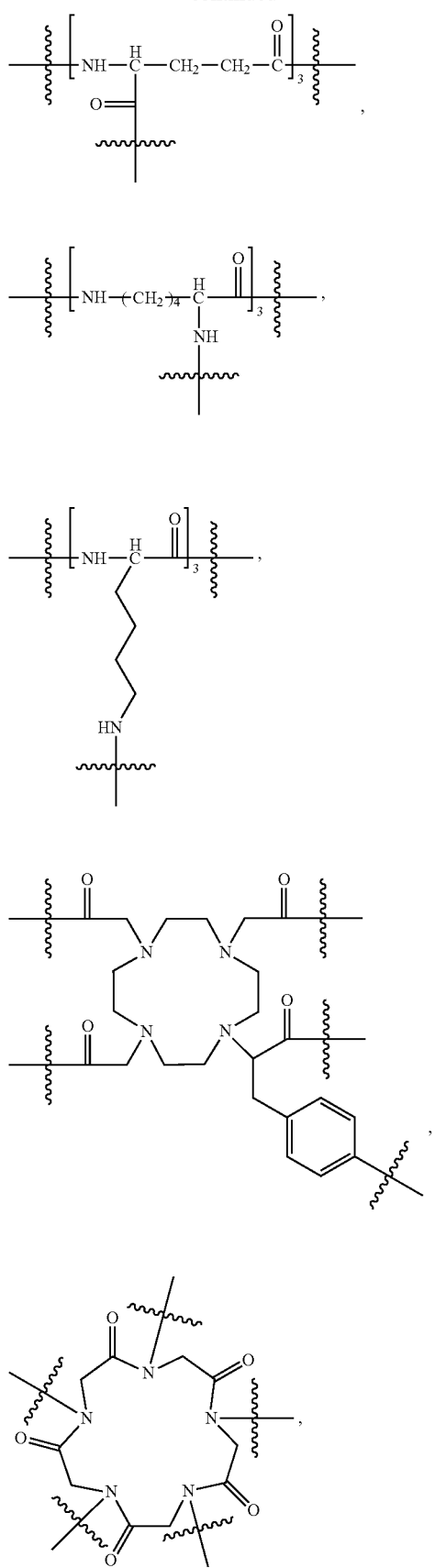

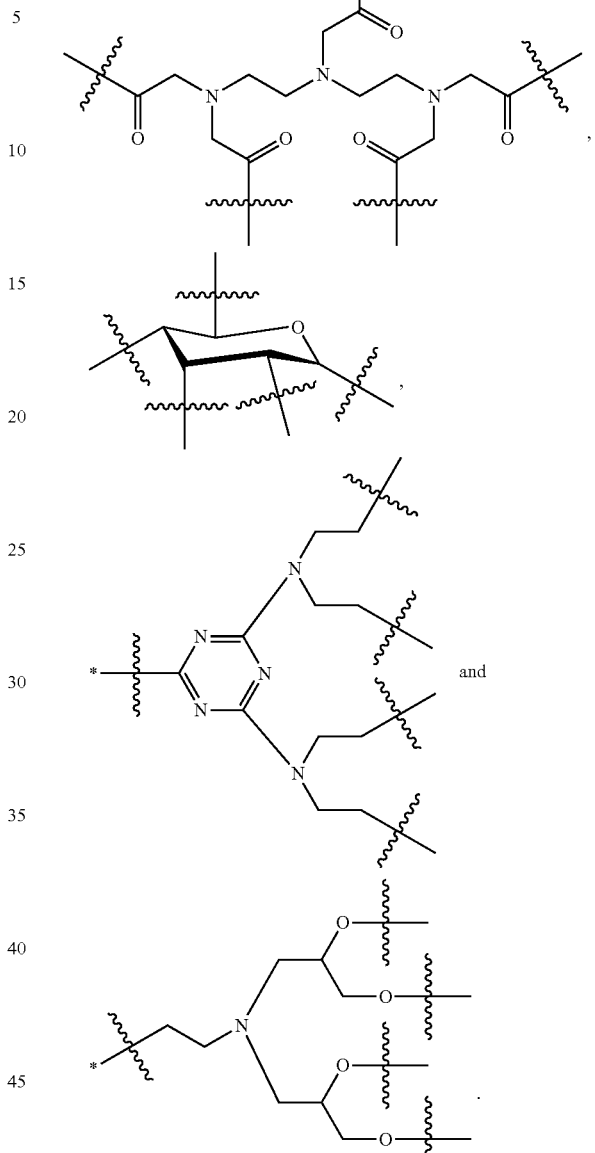

28. The eight-arm functional polyethylene glycol according to claim 2, wherein, g is equal to 1, and $L_0$ contains an oligopeptide or polypeptide segment.

29. The eight-arm functional polyethylene glycol according to claim 1, wherein, $R_{01}$ is selected from the group consisting of a reactive group, a variant form of a reactive group, a therapeutic targeting functional group and a fluorescent functional group;

wherein, the reactive group is a functional group capable of forming a covalent bond, a dynamic covalent bond, dihydrogen-bonding or multiple hydrogen bonding;

wherein, the variant form of a reactive group is selected from the group consisting of a precursor of a reactive group, an active form as the precursor of a reactive group, a substituted active form, a protected form and a deprotected form;

wherein, the precursor of a reactive group refers to a structure that can be converted into said reactive group after at least one process selected from the group consisting of oxidation, reduction, hydration, dehydration, electronic rearrangement, structural rearrangement, salt complex and decomplexation, ionization, protonation and deprotonation.

30. The eight-arm functional polyethylene glycol according to claim 29, wherein, $R_{01}$ is selected from the group consisting of functional groups in Groups A to H, variant forms of functional groups in Groups A to H, functional groups in Groups I to J, functional derivatives of functional groups in Groups I to J and pharmaceutically acceptable salts of targeting groups in Group I;

Group A: active ester groups and analogs of active ester groups; wherein, the active ester groups include a succinimidyl ester group, a 4-nitrophenyl ester group, a 2-nitrophenyl ester group, a benzotriazole ester group, a 1,3,5-trichlorophenyl ester group, a 1,3,5-trifluorophenyl ester group, a pentafluorophenyl ester group and an imidazole ester group, and the analogs of active ester groups include a 2-thioxothiazolidin-3-yl-carbonyl group, 2-thioxothiazolidin-3-yl-formate group, a 2-thioxopyrrolidin-1-yl-carbonyl group, a 2-thioxopyrrolidin-1-yl-formate group, a 2-thioxobenzothiazol-3-yl-carbonyl group, a 2-thioxobenzothiazol-3-yl-formate group, a 3-oxo-thioxoisoindolin-N-carbonyl group and a 3-oxo-thioxoisoindolin-N-formate group;

Group B: a sulfonate group, a sulfinate group, a sulfonyl group, a sulfoxide group, a 1,3-disulfonyl-2-propylcarbonylphenyl group and a (2-sulfonylmethyl)acryl group;

Group C: a hydroxylamino group, a mercapto group, a protected mercapto group, a primary or secondary amino group, a protected amino group, a halogen atom, a haloacetylamino group, a tetramethylpiperidinyloxy group, a dioxapiperidinyloxy group, an ammonia salt group, a hydrazino group, a disulfide group, an ester group, a thioester group, a thiocarboxylate group, a carbonate group, a thiocarbonate group, a dithiocarbonate group, a trithiocarbonate group, a xanthate group, a perthiocarbonate group, a dithiobis(thionoformate) group, an O-carbonylhydroxylamino group, an amido group, an imide group, a hydrazino-carbonyl group, a sulfonylhydrazino group, a hydrazone group, an imino group, an enamine group, an alkynylamino group, a carbamate group, a thiocarbamate group and a dithiocarbamate group;

Group D: a carboxyl group, a sulfonic acid group, a sulfenic acid group, a hydroxamic acid group, a thiohydroxamic acid group, a xanthogenic acid group, an acylhalide group, a chlorosulfonyl group, an aldehyde group, a glyoxal group, an acetal group, a hemiacetal group, a hydrated aldehyde group, a ketone group, a ketal group, a hemiketal group, a hydrated ketone group, an orthoacid group, an orthoester group, a cyanate group, a thiocyanate group, an isocyanato group, an isothiocyanato group, a carboxylate group, an oxycarbonyl halide group, a dihydrooxazole group, a thioaldehyde group, a thione group, a thioacetal group, a thione hydrate group, a thioketal group, a dithioketal group, a thiohemiketal group, a thioester group, a thioate group, a dithioester group, a thiohemiacetal group, a monothiohydrate group, a dithiohydrate group, a thiol hydrate group, a monothiocarboxylic acid group, a dithiocarboxylic acid group, a guanidino group and the protonated form thereof, an amidino group and the protonated form thereof, an anhydride group, a squaric acid group, a squarate group, a semi-squaric acid group, a semi-squarate group, an N-carbamoyl-3-imidazole group, an N-carbamoyl-3-methylimidazolium iodide group, an imidic acid group, an imidic ester group, a nitrone group, an oxime group, a urea group, a thiourea group and a pseudourea group;

Group E: a maleimido group, an acrylate group, an N-acrylamide group, a methacrylate group, an N-methacrylamide group, a protected maleimido group, a maleamic acid group, a 1,2,4-triazoline-3,5-dione group, an azo group in a linear structure, an azo group in a cyclic structure and a cycloalkenyl group;

Group F: an epoxy group, an alkenyl group, an alkenylhydrocarbyl group, an alkynyl group and an alkynylhydrocarbyl group;

Group G:

Group Ga: a cycloalkynyl group, a heterosubstituted cycloalkynyl group, a conjugated dienyl group, a heterosubstituted conjugated dienyl group with a skeleton-membering heteroatom and a 1,2,4,5-tetrazinyl group;

Group Gb: an azido group, a nitrile oxide group, a cyano group, an isocyano group, an aldoxime group, a diazo group, a diazonium group, an azoxy group, a nitrilimine group, an N-aldimine oxide group, a tetrazole group, a 4-acetyl-2-methoxy-5-nitrophenoxy group and its diazo form, and other functional groups for 1,3-dipolar cycloaddition reactions;

Group H: a hydroxyl group, a protected hydroxyl group, a siloxy group, a protected dihydroxyl group, a trihydroxysilyl group and a protected trihydroxysilyl group;

Group I: targeting groups: residues of folic acid and derivatives thereof, cholesterol and derivatives thereof, biotins and derivatives thereof and functional derivatives of any aforesaid targeting group; and Group J: fluorescent groups: residues of phthalocyanine coordiation compound, a fluorescein group, a rhodamine group, an anthracenyl group, a pyrenyl group, a coumarin group, a fluorescent yellow 3G group, a carbazole group, an imidazole group, an indole group, a galleinmonohydrate group and functional derivatives of any aforesaid fluorescent group.

31. The eight-arm functional polyethylene glycol according to claim 29, wherein, $R_{01}$ is selected from the group consisting of functional groups in Groups A to H, variant forms of functional groups in Groups A to H, functional groups in Groups I to J, functional derivatives of functional groups in Groups I to J and pharmaceutically acceptable salts of targeting groups in Group I;

Group A:

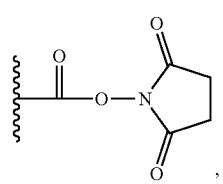

A1

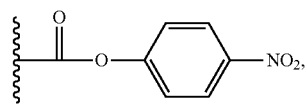

A2

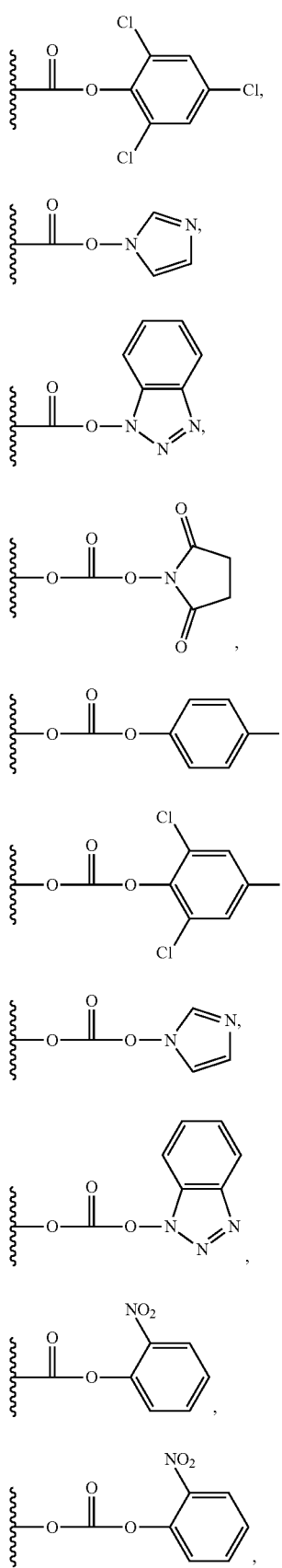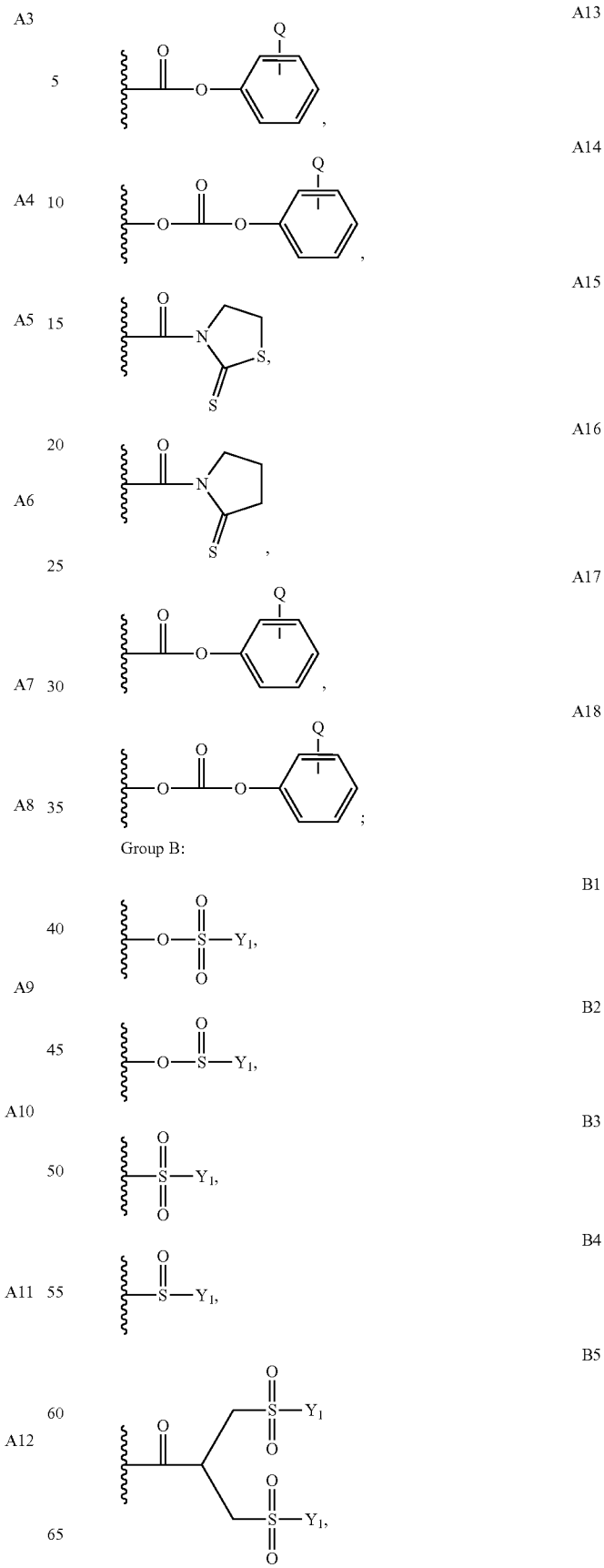

591
-continued
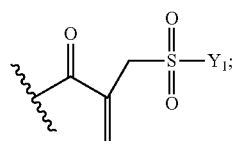
Group C:
C1
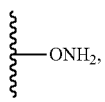
—ONH₂,
C2
—SH,
C3
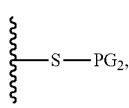
—S—PG₂,
C4
—NH₂,
C5
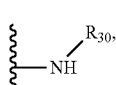
—NH—R₃₀,
C6
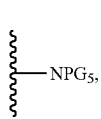
—NPG₅,
C7
—W,
C8
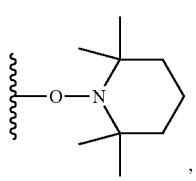
C9
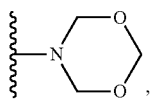
C10
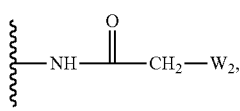
—NH—C(O)—CH₂—W₂,
C11
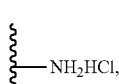
—NH₂HCl,
C12
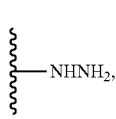
—NHNH₂,
592
-continued
B6
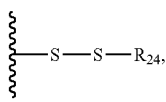
—S—S—R₂₄,
C13
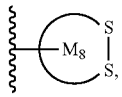
C14
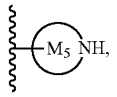
C15
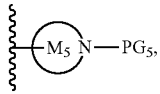
C16
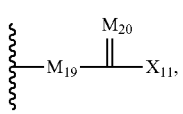
C17
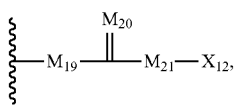
C18
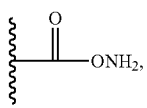
—C(O)—ONH₂,
C19
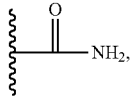
—C(O)—NH₂,
C20
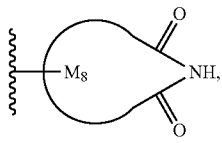
C21
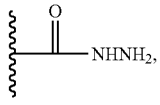
—C(O)—NHNH₂,
C22
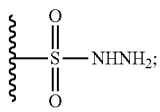
—S(O)₂—NHNH₂;
Group D:
D1
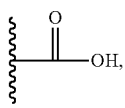
—C(O)—OH,
D2
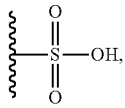
—S(O)₂—OH,

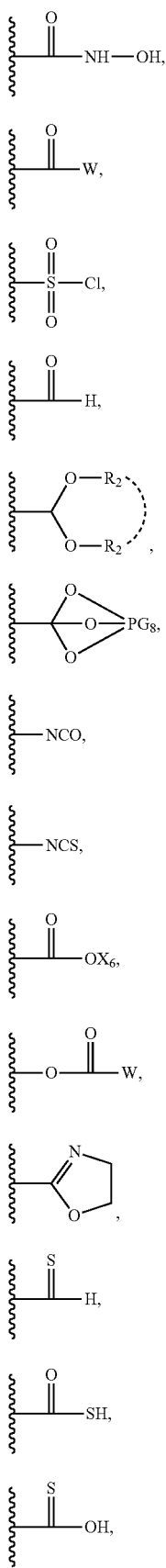
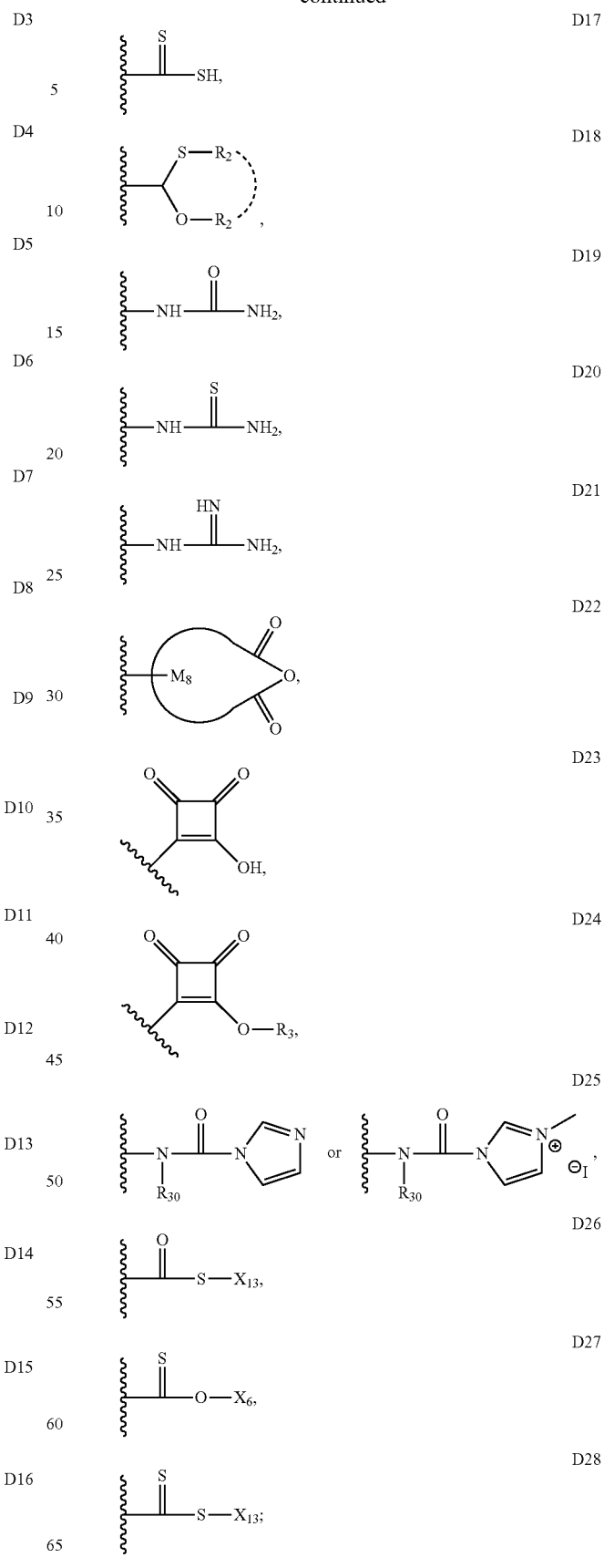

Group E:
E1 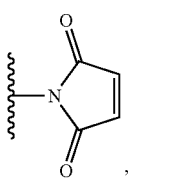,
E2 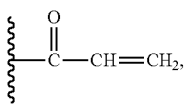,
E3 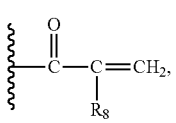,
E4 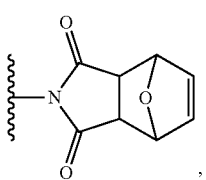,
E5 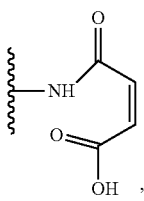,
E6 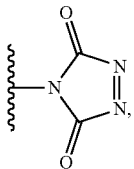,
E7 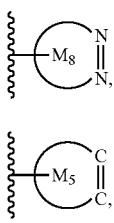,
E8 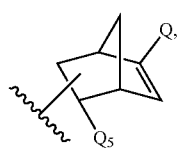,
E9 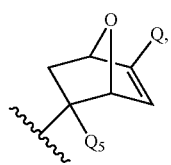,
E10 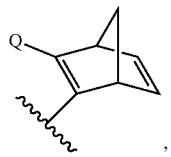,
E11 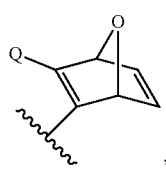,
E12 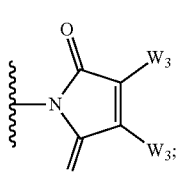;
Group F:
F1 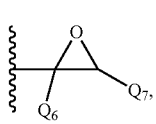,
F2 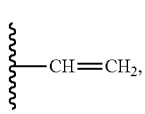,
F3 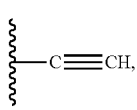,
F4 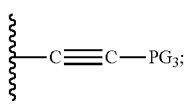;
Group G:
Group Ga:
G1 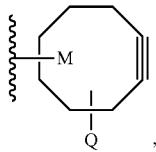,
G2 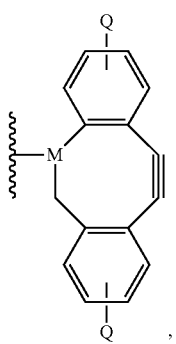, 597
-continued
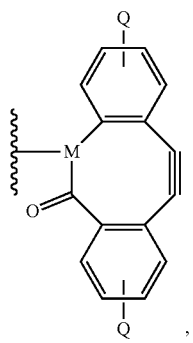
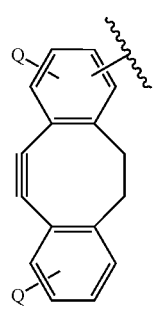
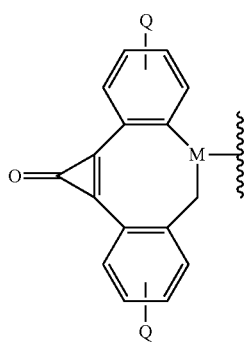
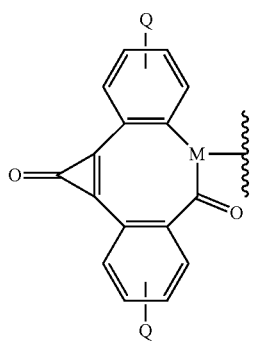
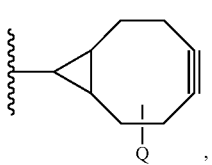
598
-continued
G3 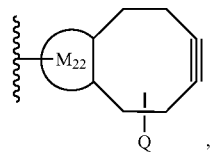
G4 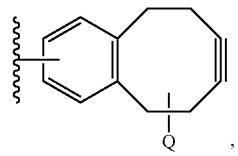
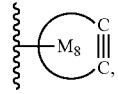
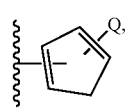
G5 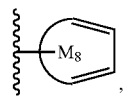
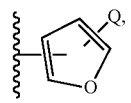
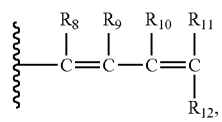
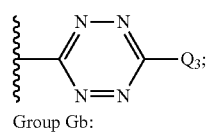
Group Gb:
G21 
G22 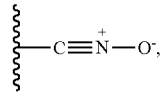
G23 
G24 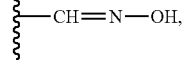
G25 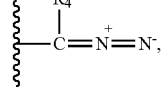
G8
G9
G10
G11
G12
G13
G14
G15
G6
G7

-continued
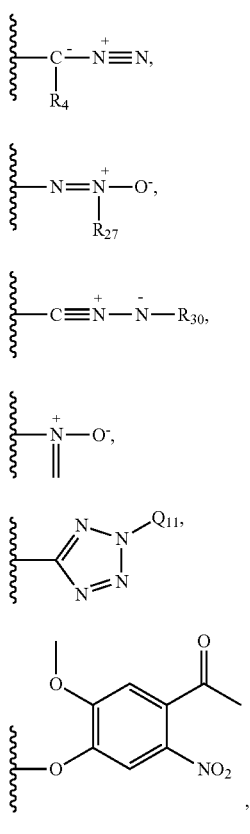
Group H:
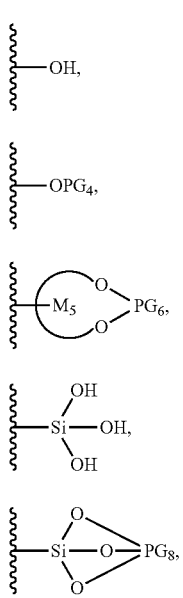
-continued
G26
G27 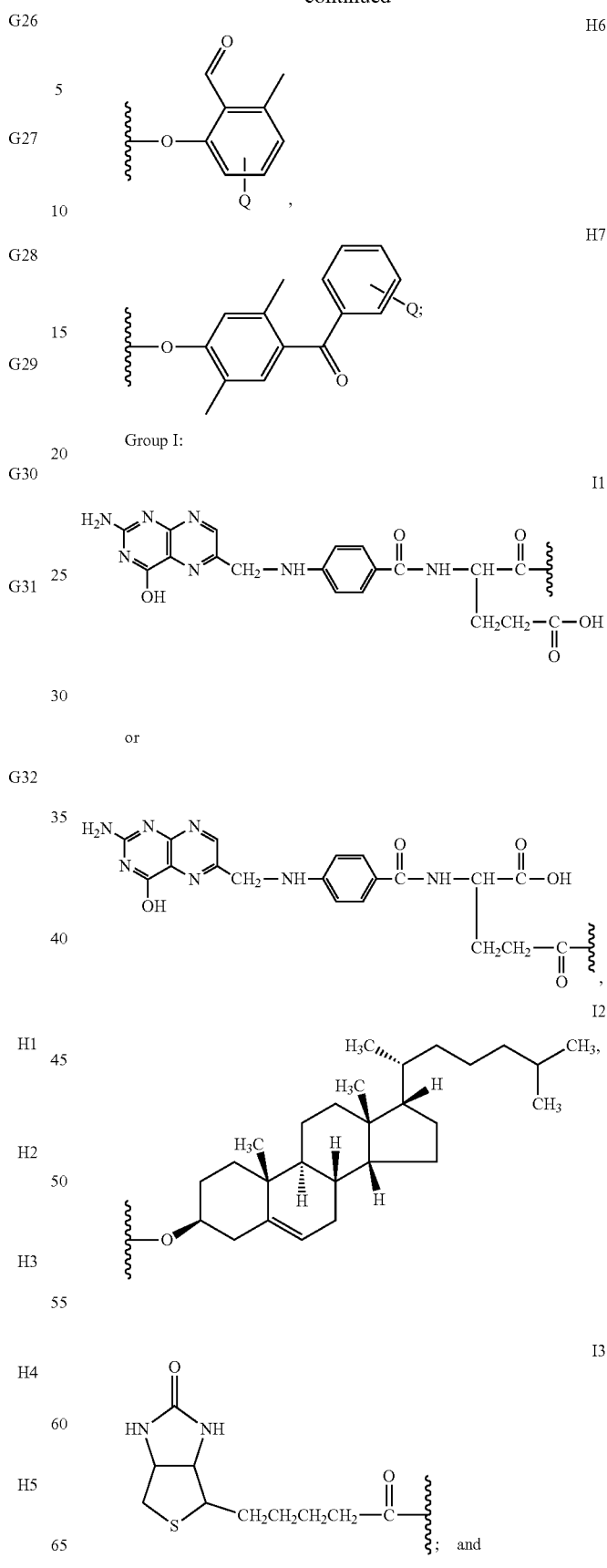
G28
G29
Group I:
G30
G31
I1
or
G32
I2
H1
H2
H3
H4
H5 ; and
H6
H7
I3

Group J:
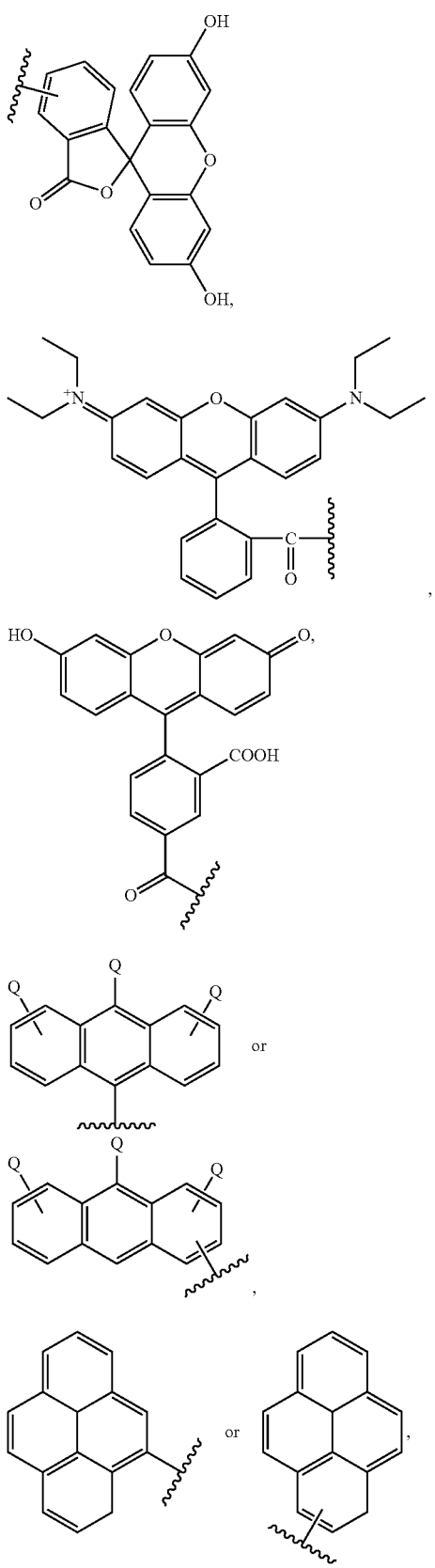
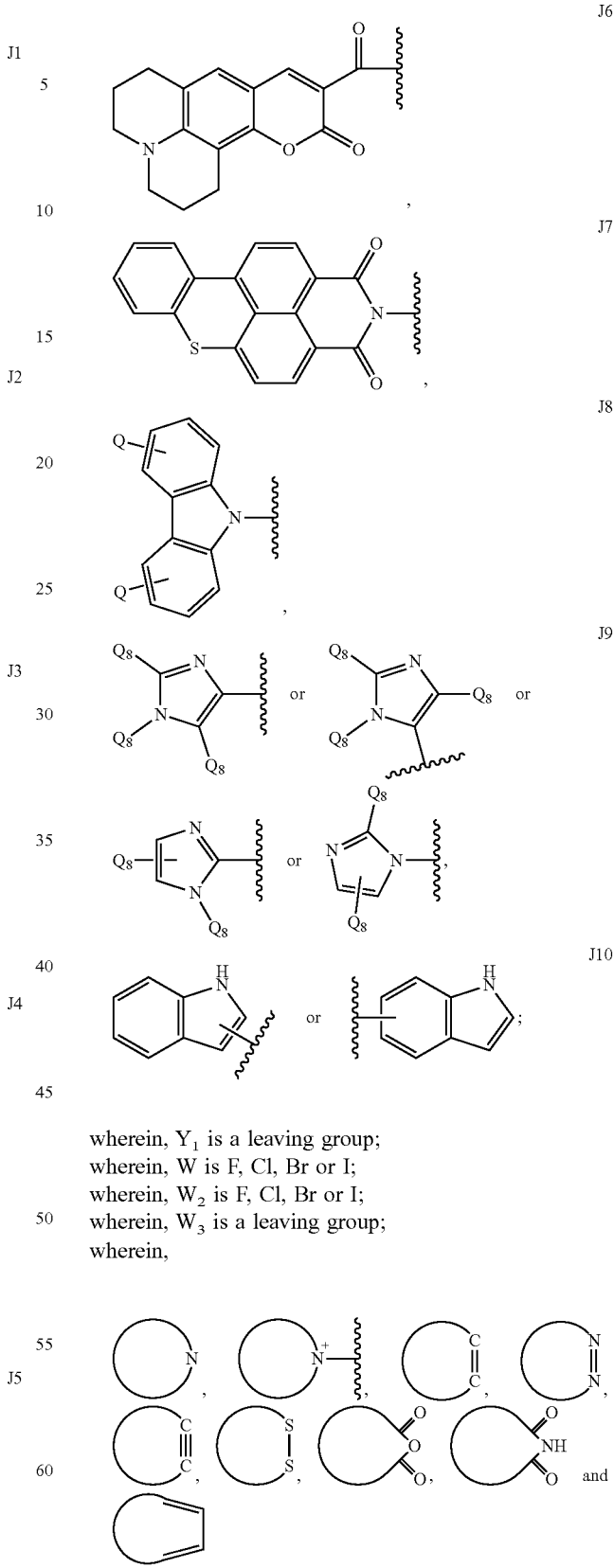
wherein, $Y_1$ is a leaving group;
wherein, W is F, Cl, Br or I;
wherein, $W_2$ is F, Cl, Br or I;
wherein, $W_3$ is a leaving group;
wherein,
are cyclic structures in which the ring skeletons contain a nitrogen atom, a nitrogen cation, a carbon-carbon double bond, an azo bond, a carbon-carbon triple bond, a disulfide bond, an anhydride moiety, an imide moiety and a dienylene moiety, respectively;

wherein, M is a ring-membering atom, and selected from the group consisting of a carbon atom and a heteroatom;

wherein, $M_5$ is a ring-membering atom, selected from the group consisting of a carbon atom, a nitrogen atom, a phosphorus atom and a silicon atom, and the $M_5$-membered ring is 3- to 50-membered;

wherein, $M_8$ is a ring-membering atom, selected from the group consisting of a carbon atom, a nitrogen atom, a phosphorus atom and a silicon atom, and the $M_8$-membered ring is 4- to 32-membered;

wherein, $M_{19}$, $M_{20}$ and $M_{21}$ are each independently an oxygen atom or a sulfur atom, and in one molecule $M_{19}$, $M_{20}$ and $M_{21}$ can be identical or not identical;

wherein, $M_{22}$ is a ring-membering atom, selected from the group consisting of a carbon atom, a nitrogen atom, a phosphorus atom and a silicon atom, and the $M_{22}$-membered ring is 4-, 5-, 6-, 7- or 8-membered;

wherein, $R_2$ is a monovalent group or a divalent linking group that connects with an oxygen atom or a sulfur atom, and $R_2$ is selected from the group consisting of a hydrogen atom, a divalent group $R_{21}$ or a monovalent group $R_3$;

said $R_{21}$ is a ring-membering divalent linking group, and selected from the group consisting of a $C_{1-20}$ alkylene group, a 1,2-phenylene group, a benzylene group, a $C_{1-20}$ oxa-alkylene group, a $C_{1-20}$ thia-alkylene group, a $C_{1-20}$ aza-alkylene group, an aza-arylhydrocarbylene group, the substituted form of any aforesaid group and the combination of any two or two more identical or different aforesaid groups or/and substituted forms;

said $R_3$ is a monovalent group, and selected from the group consisting of a $C_{1-20}$ alkyl group, a benzyl group, an allyl group and the substituted form of any aforesaid group;

wherein, $R_4$ is selected from the group consisting of a $C_{1-20}$ alkyl group, an allyl group, a propenyl group, an ethenyl group, a phenyl group, a methylphenyl group, a butylphenyl group and a benzyl group;

wherein, $R_8$, $R_9$, $R_{10}$, $R_{11}$ and $R_{12}$ are each independently a hydrogen atom, a fluorine atom or a methyl group; in one molecule, $R_8$, $R_9$, $R_{10}$, $R_{11}$ and $R_{12}$ can be identical or not identical; and in the group $E_3$, $R_8$ is a methyl group;

wherein, $R_{24}$ is a monovalent group, and selected from the group consisting of a $C_{1-20}$ alkyl group, an aryl group, an arylhydrocarbyl group and a heterosubstituted phenyl group;

wherein, $R_{27}$ is a group substituent, and selected from the group consisting of a phenyl group, a substituted phenyl group and a heterosubstituted phenyl group;

wherein, $R_{30}$ is a hydrocarbyl group;

wherein, $X_{13}$ is a monovalent group, and selected from the group consisting of a mercapto protecting group and a group $LG_2$;

said $LG_2$ is selected from the group consisting of a $C_{1-20}$ alkyl group, an aryl group, an arylalkyl group, a $C_{1-20}$ heteroalkyl group, a heteroaryl group, a heteroarylalkyl group, a $C_{1-20}$ alkylthio group, an arylthio group, an arylalkylthio group, a $C_{1-20}$ heteroalkylthio group, a heteroarylthio group, a heteroarylalkylthio group, a $C_{1-20}$ alkylcarbonyl group, an arylcarbonyl group, an arylalkylcarbonyl group, a $C_{1-20}$ heteroalkylcarbonyl group, a heteroarylcarbonyl group, a heteroarylalkylcarbonyl group, a $C_{1-20}$ alkoxycarbonyl group, an aryloxycarbonyl group, an arylalkoxycarbonyl group, a $C_{1-20}$ (alkylthio)carbonyl group, an (arylthio)carbonyl group, an (arylalkylthio)carbonyl group, a $C_{1-20}$ alkylaminocarbonyl group, an arylaminocarbonyl group, an arylalkylaminocarbonyl group, a $C_{1-20}$ heteroalkoxycarbonyl group, a heteroaryloxycarbonyl group, a heteroarylalkoxycarbonyl group, a $C_{1-20}$ hetero(alkylthio)carbonyl group, a hetero(arylthio)carbonyl group, a hetero(arylalkylthio)carbonyl group, a $C_{1-20}$ heteroalkylaminocarbonyl group, a heteroarylaminocarbonyl group, a heteroarylalkylaminocarbonyl group, a $C_{1-20}$ alkyl-thiocarbonyl group, an aryl-thiocarbonyl group, an arylalkyl-thiocarbonyl group, a $C_{1-20}$ heteroalkyl-thiocarbonyl group, a heteroaryl-thiocarbonyl group, a heteroarylalkyl-thiocarbonyl group, a $C_{1-20}$ alkoxy-thiocarbonyl group, an aryloxy-thiocarbonyl group, an arylalkoxy-thiocarbonyl group, a $C_{1-20}$ (alkylthio)thiocarbonyl group, an (arylthio)thiocarbonyl group, an (arylalkylthio)thiocarbonyl group, a $C_{1-20}$ alkylaminothiocarbonyl group, an arylaminothiocarbonyl group, an arylalkylaminothiocarbonyl group, a $C_{1-20}$ heteroalkoxy-thiocarbonyl group, a heteroaryloxy-thiocarbonyl group, a heteroarylalkoxy-thiocarbonyl group, a $C_{1-20}$ hetero(alkylthio)thiocarbonyl group, a hetero(arylthio)thiocarbonyl group, a hetero(arylalkylthio)thiocarbonyl group, a $C_{1-20}$ heteroalkylaminothiocarbonyl group, a heteroarylaminothiocarbonyl group, a heteroarylalkylaminothiocarbonyl group and the substituted form of any aforesaid group;

wherein, $X_6$ is a monovalent group, and selected from the group consisting of a hydroxyl protecting group and a group $LG_4$;

said $LG_4$ is selected from the group consisting of a $C_{1-20}$ alkyl group, a $C_{3-20}$ alkenylhydrocarbyl group, an aryl group, an arylalkyl group, a $C_{1-20}$ heteroalkyl group, a heteroaryl group, a heteroarylalkyl group, a $C_{1-20}$ alkylcarbonyl group, an arylcarbonyl group, an arylalkylcarbonyl group, a $C_{1-20}$ heteroalkylcarbonyl group, a heteroarylcarbonyl group, a heteroarylalkylcarbonyl group, a $C_{1-20}$ alkoxycarbonyl group, an aryloxycarbonyl group, an arylalkoxycarbonyl group, a $C_{1-20}$ (alkylthio)carbonyl group, an (arylthio)carbonyl group, an (arylalkylthio)carbonyl group, a $C_{1-20}$ alkylaminocarbonyl group, an arylaminocarbonyl group, an arylalkylaminocarbonyl group, a $C_{1-20}$ heteroalkoxycarbonyl group, a heteroaryloxycarbonyl group, a heteroarylalkoxycarbonyl group, a $C_{1-20}$ hetero(alkylthio)carbonyl group, a hetero(arylthio)carbonyl group, a hetero(arylalkylthio)carbonyl group, a $C_{1-20}$ heteroalkylaminocarbonyl group, a heteroarylaminocarbonyl group, a heteroarylalkylaminocarbonyl group, a $C_{1-20}$ alkyl-thiocarbonyl group, an aryl-thiocarbonyl group, an arylalkyl-thiocarbonyl group, a $C_{1-20}$ heteroalkyl-thiocarbonyl group, a heteroaryl-thiocarbonyl group, a heteroarylalkyl-thiocarbonyl group, a $C_{1-20}$ alkoxy-thiocarbonyl group, an aryloxy-thiocarbonyl group, an arylalkoxy-thiocarbonyl group, a $C_{1-20}$ (alkylthio)thiocarbonyl group, an (arylthio)thiocarbonyl group, an (arylalkylthio)thiocarbonyl group, a $C_{1-20}$ alkylaminothiocarbonyl group, an arylaminothiocarbonyl group, an arylalkylaminothiocarbonyl group, a $C_{1-20}$ heteroalkoxy-thiocarbonyl group, a heteroaryloxy-thiocarbonyl group, a heteroarylalkoxy-thiocarbonyl group, a $C_{1-20}$ hetero(alkylthio)thiocarbonyl group, a hetero(arylthio)thiocarbonyl group, a hetero(arylalkylthio)thiocarbonyl group, a $C_{1-20}$ heteroalkylaminothiocarbonyl group, a heteroarylaminothiocarbonyl group, a heteroarylalkylaminothiocarbonyl group and substituted forms of any aforesaid group;

wherein, $X_{11}$ is a $C_{1-20}$ alkyl group;

wherein, $X_{12}$ is a $C_{1-20}$ hydrocarbyl group;

wherein, Q is a hydrogen atom or a substituent of ring; the number of Q is one or more; when the number of Q is greater than one, the Q groups are identical or not identical;

wherein, $Q_3$ is a hydrogen atom or a substituent of ring, and selected from the group consisting of a hydrogen atom, a halogen atom, a $C_{1-20}$ alkyl group, a $C_{2-20}$ alkenyl group, a $C_{3-20}$ open-chain alkenyl-hydrocarbyl group, a $C_{3-20}$ cycloalkenyl group, an aryl group, an arylhydrocarbyl group, a $C_{1-20}$ heteroalkyl group, a heteroaryl group, a heteroarylalkyl group, a $C_{1-20}$ alkoxy group, an aryloxy group, an arylhydrocarbyloxy group, a $C_{1-20}$ heteroalkoxy group, a heteroaryloxy group, a heteroarylhydrocarbyloxy group, a $C_{1-20}$ heteroalkylthio group, a heteroarylthio group, a heteroarylhydrocarbylthio group, a $C_{1-20}$ haloalkyl group and the substituted form of any aforesaid group;

wherein, $Q_5$ is a hydrogen atom, a methyl group, an ethyl group or a propyl group;

wherein, $Q_6$ is a hydrogen atom or a methyl group, and $Q_7$ is a hydrogen atom, a methyl group, a phenyl group or a substituted phenyl group; in one molecule, $Q_6$ and $Q_7$ can be identical or different from each other;

wherein, $Q_8$ is a hydrogen atom, a methyl group, an ethyl group, a propyl group, a butyl group or a phenyl group; the number of $Q_8$ is one or more; when $Q_8$ is more than one, the $Q_8$ groups are identical or not identical;

wherein, $Q_{11}$ is a phenyl group, a substituted phenyl group or an azaphenyl group;

wherein, $PG_2$ is a mercapto protecting group;

wherein, $PG_3$ is an alkynyl protecting group;

wherein, $PG_4$ is a hydroxyl protecting group;

wherein, $PG_5$ is an amino protecting group;

wherein, $PG_6$ is a dihydroxyl protecting group;

wherein, $PG_8$ is a protecting group for orthocarbonic acid or orthosilicic acid.

32. The eight-arm functional polyethylene glycol according to claim 2, wherein, divalent linking groups $L_{11}$, $L_{12}$, $L_{21}$, $L_{22}$, $L_{31}$, $L_{32}$, $L_{41}$, $L_{42}$, $L_0$ (g=1), $Z_1$ and $Z_2$ are each independently identical or not identical in one molecule; any aforesaid divalent linking group or the joint linking group formed by any aforesaid group with its adjacent heterosubstituted group is independently a STAG group or a DEGG group.

33. The eight-arm functional polyethylene glycol according to claim 5, wherein, said STAG group is selected from the group consisting of an alkylene group, a divalent heteroalkyl group, a carbon-carbon double bond, a divalent dienyl group, a divalent cycloalkyl group, a divalent cycloalkenyl group, a divalent cycloalkenylhydrocarbyl group, a divalent cycloalkynyl group, an arylene group, an aliphatic-derived heteroring linkage, a heterophenylene group, an aryloheterороring linkage, a heterocondensed heteroring linkage, a substituted alkylene group, a substituted heteroalkylene group, a substituted double bond, a substituted divalent dienyl group, a substituted divalent cycloalkyl group, a substituted divalent cycloalkenyl group, a substituted divalent cycloalkenylhydrocarbyl group, a substituted divalent cycloalkynyl group, a substituted arylene group, a substituted aliphatic-derived heteroring linkage, a substituted heterophenylene group, a substituted aryloheteroring linkage, a substituted heterocondensed heteroring linkage, an ether bond, a thioether bond, a urea bond, a thiourea bond, a carbamate bond, a thiocarbamate bond, a linkage containing a —P(=O)— moiety, a linkage containing a —P(=S)— moiety, a divalent active-hydrogen-free silyl group, a boron-containing divalent linking group, a secondary amino bond, a tertiary amino bond, a carbonyl group, a thiocarbonyl group, a S(=O)$_2$— linkage, a —S(=O)— linkage, a divalent 1,1-ring linkage, an amide bond, a thioamide bond, a sulfonamide bond, an enamino group, a triazole linkage, a 4,5-dihydroisoxazole linkage, the skeleton of an ω-amino acid, the skeleton of an amino acid or an amino acid derivative, and a divalent linking group combined by any two or two more linkages of the foregoing; and independently, said DEGG group contains at least one divalent linkage selected from the group consisting of a disulfide bond, a vinylether bond, an ester bond, a thioester bond, a thioate bond, a dithioester bond, a carbonate bond, a thiocarbonate bond, a dithiocarbonate bond, a trithiocarbonate bond, a carbamate bond, a thiocarbamate bond, a dithiocarbamate bond, an acetal linkage, a cycloacetal linkage, a mercaptal linkage, an azaacetal linkage, an azacycloacetal linkage, an azathiaacetal linkage, a dithioacetal linkage, a hemiacetal linkage, a thiohemiacetal linkage, an azahemiacetal linkage, a ketal linkage, a thioketal linkage, an azaketal linkage, an azacycloketal linkage, an azathiaketal linkage, an imine bond, a hydrazone bond, an acylhydrazone bond, an oxime bond, a thiooxime bond, a semicarbazone bond, a thiosemicarbazone bond, a hydrazino bond, an acylhydrazino bond, a thiocarbonyl-hydrazino bond, an azocarbonyl-hydrazino linkage, an azo-thiocarbonyl-hydrazino linkage, a hydrazino formate linkage, a hydrazino thioformate linkage, a carbohydrazide bond, a thiocarbohydrazide bond, an azo bond, an isourea bond, an isothiourea bond, an allophanate linkage, a thioallophanate linkage, a guanidino linkage, an amidino linkage, an aminoguanidino linkage, an aminoamidino linkage, an iminocarbonyl-oxy linkage, an iminocarbonyl-thioxy linkage, a sulfonate linkage, a sulfinate linkage, a sulfonylhydrazino linkage, a sulfonylureido linkage, a maleimide linkage, an orthoester linkage, a phosphate linkage, a phosphirate linkage, a phosphinate linkage, a phosphonate linkage, a phosphosilicate linkage, a silicate linkage, an amide bond, a thioamide bond, a sulfonamide bond, a polyamide linkage, a phosphamide linkage, a phosphiramide linkage, a phosphinamide linkage, a phosphonamide linkage, a pyrophosphamide linkage, a cyclophosphamide linkage, an ifosfamide linkage, a thiophosphamide linkage, an aconityl linkage, a benzyloxycarbonyl linkage, a peptide bond, a polypeptide fragment, the skeleton of a nucleotide or a nucleotide derivative, the skeleton of a deoxynucleotide or a deoxynucleotide derivative, and the divalent linking groups containing any two or two more divalent linkages of the foregoing.

34. The eight-arm functional polyethylene glycol according to claim 5, wherein, said DEGG group contains at least one linkage selected from the group consisting of —S—S—, CH=CH—O—, —O—CH=CH—, —C(=O)—O—, —O—C(=O)—, —C(=O)—O—CH$_2$—, —CH$_2$—O—C(=O)—, —C(=O)—O—CH$_2$—O—C(=O)—, —C(=O)—O—CH$_2$—NH—C(=O)—, —O—C(=O)—R$_5$—C(=O)—O—, —C(=O)—S—, —S—C(=O)—, —C(=S)—O—, —O—C(=S)—, —C(=S)—S—, —S—C(=S)—, —O—C(=O)—O—, —S—C(=O)—O—, —O—C(=S)—O—, —O—C(=O)—S—, —S—C (=S)—O—, —O—C(=S)—S—, —S—C(=O)—S—, —S—C(=S)—S—, —NH—C(=O)—O—, —O—C(=O)—NH—, —NH—C(=S)—O—, —O—C(=S)—NH—, —NH—C(=O)—S—, —S—C(=O)—NH—, —NH—C(=S)—S—, —S—C(=S)—NH—, —CH(OR$_3$)—O—, —O—CH(OR$_3$)—, —CH(OR$_3$)—S—, —S—CH(OR$_3$)—, —CH(SR$_3$)—O—, —O—CH(SR$_3$)—, —CH(SR$_3$)—S—, —S—CH(SR$_3$)—, —CH(OR$_3$)—NH—, —NH—CH(OR$_3$)—, —CH(NPG$_5$)-O—, —O—CH(NH$_2$)—, —CH(NH$_2$)—NH—, —NH—CH(NH$_2$)—, —(NH$_2$)C(SR$_3$)—, —CH(SR$_3$)—NH—, —NH—CH(SR$_3$)—, —CH(NH$_2$)—S—, —S—CH(NH$_2$)—, —CH(OH)—NH—, —NH—CH(OH)—, —CH(NH$_2$)—O—, —CH(OH)—O—, —O—CH(OH)—, —CH(OH)—S—, —S—CH(OH)—, —HC=N—, —N=CH—, —HC=N—NH—, —NH—N=CH—, —HC=N—NH—C(=O)—, —C(=O)—NH—N=CH—, —HC=N—O—, —O—N=CH—, —HC=N—S—, —S—N=CH—, —NH—C(=O)—NH—N=CH—, —HC=N—NH—C(=O)—NH—, —NH—C(=S)—NH—N=CH—, —HC=N—NH—C(=S)—NH—, —NH—NH—, —NH—NH—C(=O)—, —C(=O)—NH—NH—, —NH—NH—C(=S)—, —C(=S)—NH—NH—, —NH—NH—C(=O)—N=N—, —N=N—C(=O)—NH—NH—, —NH—NH—C(=S)—N=N—, —N=N—C(=S)—NH—NH—, —NH—NH—C(=O)—O—, —O—C(=O)—NH—NH—, —NH—NH—C(=S)—O—, —O—C(=S)—NH—NH—, —NH—NH—C(=O)—S—, —S—C(=O)—NH—NH—, —NH—NH—C(=S)—S—, —S—C(=S)—NH—NH—, —NH—NH—C(=O)—NH—NH—, —NH—NH—C(=S)—NH—NH—, —N=N—, —O—C(=NH)—NH—, —NH—C(=NH)—O—, —O—C(=NH$_2^+$)—NH—, —NH—C(=NH$_2^+$)—O—, —NH—C(=NH)—S—, —S—C(=NH)—NH—, —NH—C(=NH$_2^+$)—S—, —S—C(=NH$_2^+$)—NH—, —NH—C(=O)—NH—C(=O)—O—, —O—C(=O)—NH—C(=O)—NH—, —NH—C(=S)—NH—C(=O)—O—, —O—C(=O)—NH—C(=S)—NH—, —NH—C(=NH)—NH—, —NH—C(=NH$_2^+$)—NH—, —C(=NH)—NH—, —NH—C(=NH)—, —NH—C(=NH$_2^+$)—, —C(=NH$_2^+$)—NH—, —NH—NH—C(=NH)—NH—, —NH—C(=NH)—NH—NH—, —NH—NH—C(=NH)—NH—NH—, —NH—NH—C(=NH$_2^+$)—NH—, —NH—C(=NH$_2^+$)—NH—NH—, —C(=NH)—NH—NH—, —NH—NH—C(=NH$_2^+$)—, —C(=NH$_2^+$)—NH—NH—, —C(=NH)—O—, —O—C(=NH)—, —O—C(=NH$_2$+)—, —C(=NH$_2^+$)—O—, —C(=NH)—S—, —S—C(=NH)—, —S—C(=NH$_2^+$)—, —C(=NH$_2^+$)—S—, —S(=O)$_2$—O—, —O—S(=O)$_2$—, —S(=O)—O—, —O—S(=O)—, —S(=O)$_2$—NH—, —NH—S(=O)$_2$—, —NH—S(=O)$_2$—NH—, —S(=O)$_2$—NH—NH—, —NH—NH—S(=O)$_2$—, —S(=O)$_2$—NH—C(=O)—NH—, —NH—C(=O)—NH—S(=O)$_2$—, —NH—(CH$_2$)$_{r3}$—O—C(=O)—, —N(CH$_3$)—(CH$_2$)$_{r3}$—O—C(=O)—, —O—Si(R$_{41}$R$_{42}$)—O—, an orthocarbonate linkage, an orthosilicate linkage, an orthophosphate linkage, an orthosulfate linkage, an orthotellurate linkage, a phosphate linkage, a phosphirate linkage, a phosphinate linkage, a phosphonate linkage, a phosphosilicate linkage, a silicate linkage, an amide bond, a thioamide bond, a sulfonamide bond, a polyamide linkage, a phosphamide linkage, a phosphiramide linkage, a phosphinamide linkage, a phosphonamide linkage, a pyrophosphamide linkage, a cyclophosphamide linkage, an ifosfamide linkage, a thiophosphamide linkage, an aconityl linkage, a benzyloxycarbonyl linkage, a peptide bond, a polypeptide fragment, the divalent linkages deriving from a nucleotide and derivatives thereof, the divalent linkages deriving from a deoxynucletide and derivatives thereof a lactide ring linkage,

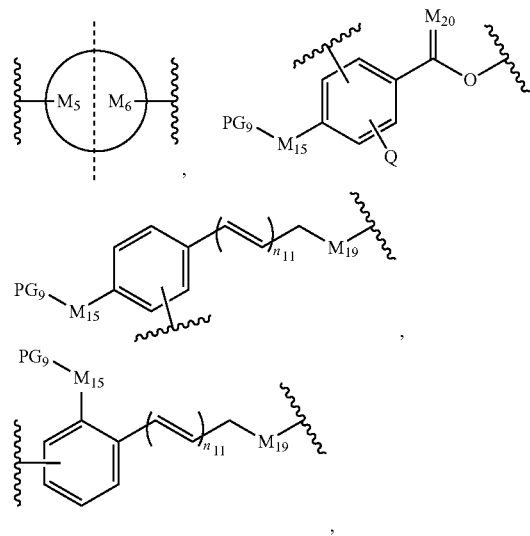

the substituted form of any aforesaid divalent linkage, and the divalent linking groups containing any two or two more divalent linkages of the foregoing;

wherein, r3 is 2, 3, 4, 5 or 6;

wherein, $R_5$ is a hydrocarbylene group or a substituted hydrocarbylene group;

wherein, $R_3$ is a $C_{1-20}$ alkyl group, a benzyl group, an allyl group or the substituted form of any aforesaid group;

wherein, $PG_5$ is an amino protecting group;

wherein, $R_{41}$ and $R_{42}$ are each independently a $C_{1-20}$ alkyl group, a phenyl group, a benzyl group, a $C_{1-20}$ alkyl-substituted phenyl group, a $C_{1-20}$ alkyl-substituted benzyl group or a $C_{1-20}$ alkoxy group; $R_{41}$ and $R_{42}$ attached to a common silicon atom are the same or different;

wherein,

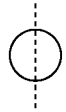

is a cyclic structure that can be degraded into at least two individual fragments; wherein, $M_5$ and $M_6$ are ring-membering atoms, and are each independently a carbon atom, a nitrogen atom, a phosphorus atom or a silicon atom; the ring structure containing $M_5$ or $M_6$ is a 3- to 50-membered ring;

wherein, $M_{15}$ is a heteroatom selected from the group consisting of an oxygen atom, a sulfur atom and a nitrogen atom; $PG_9$ is the protecting group for $M_{15}$, corresponding to a hydroxyl protecting group, a mercapto protecting group or an amino protecting group, respectively;

wherein, $M_{19}$ and $M_{20}$ are each independently an oxygen atom or a sulfur atom, and in one linkage, they can be identical or different;

wherein, $n_{11}$ is zero or an integer from 1 to 10.

35. A substance comprising the eight-arm functional polyethylene glycol according to claim 1, wherein, the PDI value of the whole substance is equal to or greater than 1.

36. A bio-related derivative of the eight-arm functional polyethylene glycol according to claim 1, wherein, the eight-arm functional polyethylene glycol also binds a bio-related substance to form a linkage L, and the number of the bio-related substance residue D in one molecule is at least one;

wherein, L is a covalent linkage or a non-covalent linkage, wherein the non-covalent linkage is a dihydrogen bond or a multiple hydrogen bond;

wherein, the bio-related substance is selected from the group consisting of drugs, proteins, peptides, oligopeptides, protein mimetics, fragments and analogs of proteins, fragments and analogs of peptides, enzymes, antigens, antibodies and fragments thereof, receptors, small molecule drugs, nucleosides, nucleotides, oligonucleotides, antisense oligonucleotides, polynucleotides, nucleic acids, aptamers, polysaccharides, proteoglycans, glycoproteins, steroids, lipids, hormones, vitamins, vesicles, liposomes, phospholipids, glycolipids, dyes, fluorescent substances, targeting factors, cytokines, neurotransmitters, extracellular matrix substances, plant or animal extracts, viruses, vaccines, cells and micelles.

37. The bio-related derivative of the eight-arm functional polyethylene glycol according to claim 36, wherein, the bio-related substance is selected from the group consisting of the bio-related substance itself, a dimer or multimer thereof, a subunit or fragment thereof, a related form selected from the group consisting of precursors, active forms, derivatives, isomers, mutants, analogs, mimetics, polymorphs, pharmaceutically acceptable salts, fusion proteins, chemically modified substances and genetic recombinant substances, and respective related forms selected from the group consisting of agonists, activating agents, activators, inhibitors, antagonists, modulators, receptors, ligands, aptamers, antibodies and antibody fragments, enzymes and substrates for enzymes.

38. The bio-related derivative of the eight-arm functional polyethylene glycol according to claim 36, wherein, the bio-related substance is selected from the group consisting of anticancer drugs, antitumor drugs, drugs for treating liver diseases, drugs for treating diabetes, drugs for treating gout, drugs for treating rheumatism, drugs for treating rheumatoid, anti-allergic drugs, anti-infective agents, antibiotics, antiviral agents, antifungal agents, vaccines, central nervous system depressants, central nervous system stimulants, psychotropic drugs, respiratory drugs, peripheral nervous system drugs, drugs acting on synaptic connections or effector connections, drugs acting on smooth muscle activities, histamine agents, antihistamine agents, blood drugs, drugs on hematopoietic system, gastrointestinal drugs, steroid agents, cell growth inhibitors, anthelmintics, antiprotozoal agents, antimicrobials, anti-inflammatory drugs, immunosuppressants, drugs or compounds for Alzheimer's disease, imaging agents, antidotes, anticonvulsants, muscle relaxants, antiphlogistic drugs, appetite suppressants, antimigraine agents, muscle contractants, antimalarial agents, antiemetics, bronchodilators, antithrombotic drugs, antihypertensive drugs, cardiovascular drugs, antiarrhythmic drugs, antioxicants, anti-asthmatic drugs, diuretics, lipid-regulating agents, antiandrogens, anti-parasitic drugs, anticoagulants, neoplastic agents, hypoglycaemic drugs, nutritional agents and supplements, growth supplements, antienteritis agents, antibodies, diagnostic agents, contrast agents, contrasting agents, hypnotic agents, sedatives, psychostimulants, tranquilizers, antiparkinson drugs, analgesics, anti-anxiety drugs, anti-myositis drugs and inhibitors for auditory diseases; wherein, the anticancer or anti-tumor drugs are used for treating diseases selected from the group consisting of breast cancer, ovarian cancer, cervical cancer, uterine cancer, endometrial cancer, gastrointestinal cancer, intestinal cancer, metastatic colorectal cancer, rectal cancer, colon cancer, colorectal cancer, gastric cancer, squamous cell cancer, laryngeal cancer, esophageal cancer, lung cancer, small cell lung cancer, non-small cell lung cancer, liver cancer, thyroid cancer, kidney cancer, bile duct cancer, brain cancer, skin cancer, pancreatic cancer, prostate cancer, bladder cancer, testicular cancer, nasopharyngeal cancer, head and neck cancer, gallbladder and bile duct cancer, retinal cancer, renal cell cancer, gallbladder cancer, multidrug resistance in cancer, melanoma, lymphoma, non-Hodgkin's lymphoma, adenoma, leukemia, chronic lymphocytic leukemia, multiple myeloma, brain tumor, Wilms' tumor, liposarcoma, endometrial sarcoma, rhabdomyosarcoma, neuroblastoma and AIDS-related cancers, wherein, the tumor or cancer is selected from the group consisting of primary or secondary cancers, sarcomas and carcinosarcomas.

39. The bio-related derivative of the eight-arm functional polyethylene glycol according to claim 36, wherein, the average number of D per molecule is greater than or equal to 8, or the average D content per molecule is greater than 75%, wherein, the D content is the fraction of the number of D relative to the number of terminal functional groups.

40. The bio-related derivative of the eight-arm functional polyethylene glycol according to claim 36, wherein, L is selected from one of the following Groups:

Group (1): wherein, L is selected from the group consisting of an ether bond, a thioether bond, a urea bond, a thiourea bond, a carbamate bond, a thiocarbamate bond, a secondary amino bond, a tertiary amino bond, an amide bond, an imide bond, a thioamide bond, a sulfonamide bond, an enamino bond, a triazole linkage, an isoxazole linkage and the optional combination of the foregoing;

Group (2): wherein, L contains a linking group selected from the group consisting of a disulfide bond, a vinylether bond, an ester bond, a thioester bond, a thioate bond, a dithioester bond, a carbonate bond, a thiocarbonate bond, a dithiocarbonate bond, a trithiocarbonate bond, a carbamate bond, a thiocarbamate bond, a dithiocarbannate bond, an acetal linkage, a cycloacetal linkage, a mercaptal linkage, an azaacetal linkage, an azacycloacetal linkage, an azathiaacetal linkage, a dithioacetal linkage, a hemiacetal linkage, a thiohemiacetal linkage, an azahemiacetal linkage, a ketal linkage, a thioketal linkage, an azaketal linkage, an azacycloketal linkage, an azathiaketal linkage, an imine bond, a hydrazone bond, an acylhydrazone bond, an oxime bond, a thiooxime bond, a semicarbazone bond, a thiosemicarbazone bond, a hydrazino bond, an acylhydrazino bond, a thiocarbonyl-hydrazino bond, an azocarbonyl-hydrazino linkage, an azo-thiocarbonyl-hydrazino linkage, a hydrazino formate linkage, a hydrazino thioformate linkage, a carbohydrazide bond, a thiocarbohydrazide bond, an azo bond, an isourea bond, an isothiourea bond, an allophanate linkage, a thioallophanate linkage, a guanidino linkage, an amidino linkage, an aminoguanidino linkage, an aminoamidino linkage, an iminocarbonyl-oxy linkage, an iminocarbonyl-thioxy linkage, a sulfonate linkage, a sulfinate linkage, a sulfonamide bond, a sulfonylhydrazino linkage, a sulfonylureido linkage, a maleimide linkage, an orthoester linkage, a phosphate linkage, a phosphirate linkage, a phosphinate linkage, a phosphonate linkage, a phosphosilicate linkage, a silicate linkage, an amide bond, a thioamide bond, a phosphamide linkage, a phosphiramide linkage, a phosphinamide linkage, a phosphonamide linkage, a pyrophosphamide linkage, a cyclophosphamide linkage, an ifosfamide linkage, a thiophosphamide linkage, an aconityl linkage, a peptide bond and a divalent linking group containing any two or two more divalent linkages of the foregoing; and Group (3) consisting of optional combinations of the linkages from Group (1) and the linkages from Group (2).

\* \* \* \* \*

UNITED STATES PATENT AND TRADEMARK OFFICE
CERTIFICATE OF CORRECTION

PATENT NO. : 10,434,182 B2
APPLICATION NO. : 15/738761
DATED : October 8, 2019
INVENTOR(S) : Wengui Weng et al.

It is certified that error appears in the above-identified patent and that said Letters Patent is hereby corrected as shown below:

In the Claims

Column 544, Line 5, in Claim 1, "$L_{12}$" should read "$L_{22}$."
Column 544, Line 8, in Claim 1, "$L_{12}$" should read "$L_{22}$."
Column 544, Line 23, in Claim 1, "divalentlinking" should read "divalent linking."

Signed and Sealed this
Thirty-first Day of December, 2019

Andrei Iancu
*Director of the United States Patent and Trademark Office*